(12) United States Patent
Freier et al.

(10) Patent No.: US 11,118,183 B2
(45) Date of Patent: *Sep. 14, 2021

(54) MODULATION OF ANGIOPOIETIN-LIKE 3 EXPRESSION

(71) Applicant: Ionis Pharmaceuticals, Inc., Carlsbad, CA (US)

(72) Inventors: Susan M. Freier, San Diego, CA (US); Mark J. Graham, San Clemente, CA (US); Rosanne M. Crooke, Carlsbad, CA (US)

(73) Assignee: Ionis Pharmaceuticals, Inc., Carlsbad, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/125,584

(22) Filed: Sep. 7, 2018

(65) Prior Publication Data

US 2019/0062755 A1    Feb. 28, 2019

Related U.S. Application Data

(63) Continuation of application No. 15/108,099, filed as application No. PCT/US2014/072303 on Dec. 24, 2014, now abandoned.

(60) Provisional application No. 61/920,652, filed on Dec. 24, 2013.

(51) Int. Cl.
C12N 15/113    (2010.01)

(52) U.S. Cl.
CPC ........ *C12N 15/1136* (2013.01); *C12N 15/113* (2013.01); *C12N 2310/11* (2013.01); *C12N 2310/315* (2013.01); *C12N 2310/321* (2013.01); *C12N 2310/3231* (2013.01); *C12N 2310/3341* (2013.01); *C12N 2310/346* (2013.01); *C12N 2310/351* (2013.01); *C12N 2320/30* (2013.01); *C12N 2320/53* (2013.01)

(58) Field of Classification Search
CPC .............. C12N 15/1136; C12N 15/113; C12N 2310/315; C12N 2310/321; C12N 2310/3231; C12N 2310/3341; C12N 2310/351; C12N 2320/30; C12N 2310/11; C12N 2310/346; C12N 2320/53; C12N 2310/341; C12N 2310/322; C12N 2310/3525; A61P 9/00; A61P 43/00; A61P 3/04; A61P 3/00; A61K 31/7105; A61K 31/7115; A61K 31/712; A61K 31/7125

See application file for complete search history.

(56) References Cited

U.S. PATENT DOCUMENTS

| | | |
|---|---|---|
| 4,981,957 A | 1/1991 | Lebleu et al. |
| 5,034,506 A | 7/1991 | Summerton et al. |
| 5,118,800 A | 6/1992 | Smith et al. |
| 5,166,315 A | 11/1992 | Summerton et al. |
| 5,185,444 A | 2/1993 | Summerton et al. |
| 5,319,080 A | 6/1994 | Leumann |
| 5,359,044 A | 10/1994 | Cook et al. |
| 5,393,878 A | 2/1995 | Leumann |
| 5,446,137 A | 8/1995 | Maag et al. |
| 5,466,786 A | 11/1995 | Buhr et al. |
| 5,514,785 A | 5/1996 | Van Ness et al. |
| 5,519,134 A | 5/1996 | Acevedo et al. |
| 5,567,811 A | 10/1996 | Mistura et al. |
| 5,576,427 A | 11/1996 | Cook et al. |
| 5,591,722 A | 1/1997 | Montgomery et al. |
| 5,597,909 A | 1/1997 | Urdea et al. |
| 5,610,300 A | 3/1997 | Altmann et al. |
| 5,627,053 A | 5/1997 | Usman et al. |
| 5,639,873 A | 6/1997 | Barascut et al. |
| 5,646,265 A | 7/1997 | McGee |
| 5,670,633 A | 9/1997 | Cook et al. |
| 5,698,685 A | 12/1997 | Summerton et al. |
| 5,700,920 A | 12/1997 | Altmann et al. |
| 5,792,847 A | 8/1998 | Buhr et al. |
| 5,801,154 A | 9/1998 | Baracchini et al. |
| 6,268,490 B1 | 7/2001 | Imanishi et al. |
| 6,525,191 B1 | 2/2003 | Ramasamy |
| 6,582,908 B2 | 6/2003 | Fodor et al. |
| 6,600,032 B1 | 7/2003 | Manoharan et al. |
| 6,670,461 B1 | 12/2003 | Wengel et al. |
| 6,673,661 B1 | 1/2004 | Liu et al. |
| 6,770,748 B2 | 8/2004 | Imanishi et al. |
| 6,794,499 B2 | 9/2004 | Wengel et al. |
| 7,034,133 B2 | 4/2006 | Wengel et al. |

(Continued)

FOREIGN PATENT DOCUMENTS

| | | |
|---|---|---|
| CA | 2450022 A1 | 12/2002 |
| WO | 9839352 A1 | 9/1998 |

(Continued)

OTHER PUBLICATIONS

Extended European Search Report for 18174926.8 dated Nov. 23, 2018.

(Continued)

*Primary Examiner* — J. E. Angell

(74) *Attorney, Agent, or Firm* — Arnold & Porter Kaye Scholer LLP

(57) ABSTRACT

Provided herein are methods, compounds, and compositions for reducing expression of an ANGPTL3 mRNA and protein in an animal. Also provided herein are methods, compounds, and compositions for reducing lipids and/or glucose in an animal. Such methods, compounds, and compositions are useful to treat, prevent, delay, or ameliorate any one or more of cardiovascular disease and/or metabolic disease, or a symptom thereof, in an individual in need thereof.

16 Claims, No Drawings

Specification includes a Sequence Listing.

(56) References Cited

U.S. PATENT DOCUMENTS

| | | |
|---|---|---|
| 7,053,207 B2 | 5/2006 | Wengel |
| 7,267,819 B2 | 9/2007 | Ferrara et al. |
| 7,399,845 B2 | 7/2008 | Seth et al. |
| 7,427,672 B2 | 9/2008 | Imanishi et al. |
| 8,278,283 B2 | 10/2012 | Seth et al. |
| 8,278,425 B2 | 10/2012 | Prakash et al. |
| 8,278,426 B2 | 10/2012 | Seth et al. |
| 8,501,805 B2 | 8/2013 | Seth et al. |
| 8,546,556 B2 | 10/2013 | Seth et al. |
| 8,653,047 B2 | 2/2014 | Crooke et al. |
| 9,139,831 B2 | 9/2015 | Crooke et al. |
| 9,322,018 B2 | 4/2016 | Bettencourt et al. |
| 2001/0053519 A1 | 12/2001 | Fodor et al. |
| 2003/0017488 A1 | 1/2003 | Koishi et al. |
| 2003/0228597 A1 | 12/2003 | Cowsert et al. |
| 2004/0171570 A1 | 9/2004 | Allerson et al. |
| 2004/0214325 A1 | 10/2004 | Crooke et al. |
| 2005/0130923 A1 | 6/2005 | Bhat et al. |
| 2005/0255487 A1 | 11/2005 | Khvorova et al. |
| 2007/0031844 A1 | 2/2007 | Khvorova et al. |
| 2007/0054856 A1 | 3/2007 | Gerber et al. |
| 2007/0287831 A1 | 12/2007 | Seth et al. |
| 2008/0039618 A1 | 2/2008 | Allerson et al. |
| 2008/0113351 A1 | 5/2008 | Nalto et al. |
| 2008/0177045 A1 | 7/2008 | Lee et al. |
| 2008/0255030 A1 | 10/2008 | Yu et al. |
| 2009/0012281 A1 | 1/2009 | Swayze et al. |
| 2009/0098117 A1 | 4/2009 | Ferrara et al. |
| 2009/0318536 A1 | 12/2009 | Freier et al. |
| 2011/0086342 A1 | 4/2011 | Esumi et al. |
| 2011/0117609 A1 | 5/2011 | Kurosawa et al. |
| 2011/0243948 A1 | 10/2011 | Lee et al. |
| 2013/0023579 A1 | 1/2013 | Crooke et al. |
| 2015/0057329 A1 | 2/2015 | Bhanot et al. |
| 2016/0060626 A1 | 3/2016 | Crooke et al. |
| 2017/0037409 A1 | 2/2017 | Freier et al. |

FOREIGN PATENT DOCUMENTS

| | | |
|---|---|---|
| WO | 9914226 A2 | 3/1999 |
| WO | 0063364 A2 | 10/2000 |
| WO | 0105825 A2 | 1/2001 |
| WO | WO 2002/101039 | 12/2002 |
| WO | 03004602 A2 | 1/2003 |
| WO | 03044172 A2 | 5/2003 |
| WO | 2003/100101 | 12/2003 |
| WO | 2004011624 A2 | 2/2004 |
| WO | 2004035765 A2 | 4/2004 |
| WO | 2004072046 A2 | 8/2004 |
| WO | 2004106356 A1 | 12/2004 |
| WO | 2005021570 A1 | 3/2005 |
| WO | 2005121371 A2 | 12/2005 |
| WO | 2006006948 A2 | 1/2006 |
| WO | WO 2006/014729 | 2/2006 |
| WO | 2006/034348 | 3/2006 |
| WO | 2007134181 A2 | 11/2007 |
| WO | 2008073300 A2 | 6/2008 |
| WO | 2008101157 A1 | 8/2008 |
| WO | 2008150729 A2 | 12/2008 |
| WO | 2008154401 A2 | 12/2008 |
| WO | 2009006478 A2 | 1/2009 |
| WO | 2011/085271 A2 | 7/2011 |
| WO | 2012177784 A2 | 12/2012 |
| WO | 2013142571 A2 | 9/2013 |

OTHER PUBLICATIONS

Yilmaz et al., "Serum concentrations of human angiopoietin-like protein 3 in patients with nonalcoholic fatty liver disease: association with insulin resistance" Eur J Gastroenterol Hepatol (2009) 21(11): 1247-1251.

Extended European Search Report for EP 14874081.4, Jul. 19, 2017, 10 pages.

Gao et al., "Angiopoietin-like protein 3 regulates the motility and permeability of podocytes by altering nephrin expression in vitro," Biochem. Biophys. Res. Comm. 399, 31-36, 2010.

Graham et al., "Cardiovascular and Metabolic Effects of ANGPTL3 Antisense Oligonucleotides," New Engl. J. Med. 2017.

Graham et al., "Cardiovascular and Metabolic Effects of ANGPTL3 Antisense Oligonucleotides," Supplementary Appendix, New Engl. J. Med. 2017.

Norata et al., "Gene silencing approaches for the management of dyslipidaemia," Trends in Pharmacol. Sci. 34, 198-205, 2013.

Sehgal et al., "Liver as a target for oligonucleotide therapeutics," J. Hepatology 59, 1354-59, 2013.

Yu et al., "Effects of ANGPTL3 antisense oligodeoxynucleotide transfection on the cell growth and invasion of human hepatocellular carcinoma cells," Hepato-Gastroenterology 58, 1742-46, 2011.

New England Biolabs 1998/99 Catalog (cover page and pp. 121 and 284).

Noto et al., "Prevalence of ANGPTL3 and APOB gene mutations in subjects with combined hypolipidemia" Arterioscler. Thromb. Vasc. Biol. (2012) 32(3):805-809.

Orum et al., "Locked nucleic acids: A promising molecular family for gene-function analysis and antisense drug development" Curr. Opinion Mol. Ther. (2001) 3:239-243.

Pisciotta et al., "Characterization of three kindreds with familial combined hypolipidemia caused by loss-of-function mutations of ANGPTL3." Circulation Cardiovasc Genet (2012) 5: 42-50.

Reynolds et al., "Rational siRNA design for RNA interference" Nature Biotechnology (2004) 22(3):326-330.

Romeo et al. "Rare loss-of-function mutations in ANGPTL family members contribute to plasma triglyceride levels in humans" J Clin Invest, 119(1): 70-79.

Sanan et al., "Low density lipoprotein receptor-negative mice expressing human apolipoprotein B-100 develop complex atherosclerotic lesions on a chow diet: No accentuation by apolipoprotein(a)" PNAS (1998) 95:4544-4549.

Sanghvi et al., "Heterocyclic Base Modifications in Nucleic Acids and Their Applications in Antisense Oligonucleotides" Antisense Research and Applications (1993) pp. 273-288.

Shimamura et al., "Angiopoietin-like protein3 regulates plasma HDL cholesterol through suppression of endothelial lipase" Arterioscler Thromb Vasc Biol. (2007) 27(2):366-372.

Shimamura et al., "Leptin and insulin down-regulate angiopoietin-like protein 3, a plasma triglyceride-increasing factor" Biochem. Biophys. Res. Commun. (2004) 322:1080-1085.

Shimamura et al., Biochem. Biophys. Res. Commun. (2003) 301:604-609.

Shimizugawa et al., "ANGPTL3 decreases very low density lipoprotein triglyceride clearance by inhibition of lipoprotein lipase" J. Biol. Chem. (2002) 277:33742-33748.

Sindelka et al., "Association of Obesity, Diabetes, Serum Lipids and Blood Pressure Regulates Insulin Action" Physiol. Res. (2002) 51:85-91.

Singh et al., "LNA (locked nucleic acids): synthesis and high-affinity nucleic acid recognition" Chem. Commun. (1998) 455-456.

Singh et al., "Synthesis of 2'-amino-LNA: A novel conformationally restricted high-affinity oligonucleotide analogue with a handle" J. Org. Chem. (1998) 63: 10035-10039.

Sonnenburg et al., "GPIHBP1 stabilizes lipoprotein lipase and prevents its inhibition by angiopoietin-like 3 and angiopoietin-like 4" The Journal of Lipid Research (2009) 50(12): 2421-2429.

Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.

Thomas et al., "Development of Apolipoprotein B antisense Molecules as a Therapy for Hyperlipidemia," Current Atherosclerosis Reports (2009) 12: 58-65.

Valdivielso et al., "Association of moderate and severe hypertriglyceridemia with obesity, diabetes mellitus and vascular disease in the Spanish working population: Results of the ICARIA study" Atherosclerosis (2009) 207 (2):573-578.

Verdel et al., "RNAi-mediated targeting of heterochromatin by the RITS complex." Science (2004) 303(5658): 672-676.

(56) References Cited

OTHER PUBLICATIONS

Volpe et al., "Regulation of heterochromatic silencing and histone H3 lysine-9 methylation by RNAi" Science (2002) 297(5588):1833:1837.
Wahlestedt et al., "Potent and nontoxic antisense oligonucleotide containing locked nucleic acids" Proc. Natl. Acad. Sci. USA (2000) 97: 5633-5638.
Willer et al., "Newly identified loci that influence lipid concentrations and risk of coronary artery disease" Nature Genetics (2008) 40(2):161-169.
Woolf et al. "Specificity of antisense oligonucleotides in vivo" PNAS (1992) 89:7305-7309.
Zhang et al., "Spontaneous atherosclerosis in aged lipoprotein lipase-deficient mice with severe hypertriglyceridemia on a normal chow diet" Circ. Res. (2008) 102(2):250-256.
Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.
Akdim et al., "Antisense apolipoprotein B therapy: where do we stand?" Current Opinion in Lipidology (2007) 18:397-400.
Albaek et al., "Analogues of a Locked Nucleic Acid with Three-Carbon 2',4'-Linkages: Synthesis by Ring-Closing Metathesis and Influence of Nucleic AcidDuplex Stability" J. Org. Chem. (2006) 71:7731-7740.
Allshire, "RNAi and Heterochromatin—a Hushed-Up Affair" Science (2003) 297: 1818-1819.
Altmann et al., "Second Generation Antisense Oligonucleotides— Inhibition of PKC-a and c-RAF Kinase Expression by Chimeric Oligonucleotides Incorporating 6'-Substituted Carbocyclic Nucleosides and 2'-O-Ethylene Glycol Substituted Ribonucleosides" Nucleosides Nucleotides (1997) 16: 917-926.
Altmann et al., "Second Generation of Antisense Oligonucleotides: From Nuclease Resistance to Biological Efficacy in Animals" Biochem. Soc. Trans. (1996) 24: 630-637.
Altmann et al., "Second-generation antisense oligonucleotides: structure-activity relationships and the design of improved signal-transduction inhibitors" Chimia (1996) 50: 168-176.
Ando et al., "A decreased expression of angiopoietin-like 3 is protective against atherosclerosis in apoE-deficient mice" Journal o Lipid Research (2003) 44(6):1215-1223.
Angelakopoulou et al., "Comparative analysis of genome-wide association studies signals for lipids, diabetes, and coronary heart disease: Cardiovascular Biomarker Genetics Collaboration" Eur Heart J. (2012) 33(3):393-407.
Baker et al., "2'-O-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J. Biol. Chem. (1997) 272: 11944-12000.
Braasch et al., "Locked nucleic acid (LNA): fine-tuning the recognition of DNA and RNA" Chem. Biol. (2001) 8:1-7.
Braasch et al., "Novel Antisense and Peptide Nucleic Acid Strategies for Controlling Gene Expression" Biochemistry (2002) 41: 4503-4510.
Branch et al., "A good antisense molecule is hard to find," TIBS (1998) 23:45-50.
Browning et al., "Molecular mediators of hepatic steatosis and liver injury" J. Clin. Invest. (2004) 114:147-152.
Camenisch et al., "ANGPTL3 stimulates endothelial cell adhesion and migration via integrin alpha vbeta 3 and induces blood vessel formation in vivo." J. Biol. Chem. (2002) 277(19)17281-17290.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Conklin et al., "Identification of a mammalian angiopoietin-related protein expressed specifically in liver." Genomics (1999) 62(3):477-482.

Crooke et al., "Basic Principles of Antisense Therapeutics" Antisense Research and Application (1998) Chapter 1:1-50.
Elayadi et al., "Application of PNA and LNA oligomers to chemotherapy" Curr. Opinion Invens. Drugs (2001) 2:558-561.
EMBL Accession No. BG400407, Homo sapiens cDNA clone, Mar. 17, 2001, retrieved from the Internet, Apr. 3, 2013 <http://www.ebi.ac.uk/Tools/dbfetch/emblfetch?id=BG400407&Submit=Go>.
European Search Report for application EP 11732249.5 dated Aug. 7, 2014.
Freier et al., "The ups and downs of nucleic acid duplex stability: structure-stability studies on chemically-modified DNA:RNA duplexes" Nucleic Acids Research (1997) 25(22):4429-4443.
Frieden et al., "Expanding the design horizon of antisense oligonucleotides with alpha-L-LNA" Nucleic Acids Research (2003) 31(21):6365-6372.
Fujimoto et al., "Angptl3-null mice show low plasma lipid concentrations by enhanced lipoprotein lipase activity" Exp. Anim (2006) 55(1):27-34.
Gautschi et al., "Activity of a Novel bcl-2/bcl-xL-Bispecific Antisense Oligonucleotide Against Tumors of Diverse Histologic Origins" J. Natl. Cancer Inst. (2001) 93:463-471.
GenBank Accession No. NM_014495.1. Homo sapiens angiopoietin-like 3 (ANGPTL3) mRNA, retrieved from the Internet on Apr. 18, 2013, downloaded from http://www.ncbi.nlm.nih.gov/nuccore/NM_014495.1.
Hall et al., "Establishment and maintenance of a heterochromatin domain" Science (2002) 297(5590):2232-2237.
Hatsuda et al., "Association between Plasma Angiopoietin-Like Protein 3 and Arterial Wall Thickness in Healthy Subjects" J Vasc Res (2007) 44:61-66.
Hooper et al., "Recent developments in the genetics of LDL deficiency" Curr Opin Lipidol (2013) 24(2):111-115.
Ichimura et al., "Serum Angiopoietin-like Protein 3 Levels: Possible Correlation with Progressive Skin Sclerosis, Digital Ulcers and Pulmonary Vascular Involvement in Patients with Systemic Sclerosis" Acta Derma Venereol (2013) 1-6.
Inaba et al., "Angiopoietin-like protein 3 mediates hypertriglyceridemia induced by the liver X receptor." J. Biol. Chem. (2003) 278(24):21344-21351.
International Search Report for application PCT/US11/20606 dated Jun. 27, 2011.
Inukai et al., "ANGPTL3 is increased in both insulin-deficient and -resistant diabetic states." Biochem. Biophys. Res. Commun. (2004) 317(4):1075-1079.
Ishibashi et al., "Hypercholesterolemia in low density lipoprotein receptor knockout mice and its reversal by adenovirus-mediated gene delivery." J. Clin. Invest. (1993) 92(2):883-893.
Kaplan et al., "Regulation of the angiopoietin-like protein 3 gene by LXR" J. Lipid Res. (2003) 44(1):136-143.
Koishi et al., "Angptl3 regulates lipid metabolism in mice" Nat. Genet. (2002) 30(2):151-157.
Korstanje et al., "Locating Ath8, a locus for murine atherosclerosis susceptibility and testing several of its candidate genes in mice and humans" Atherosclerosis (2004) 177:443-450.
Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.
Koster et al., "Transgenic angiopoietin-like (angptl)4 overexpression and targeted disruption of angptl4 and angptl3: regulation of triglyceride metabolism" Endocrinology (2005) 146(11): 4943-4950.
Kumar et al., "The first analogues of LNA (locked nucleic acids): phosphorothioate-LNA and 2'-thio-LNA" Bioorg Med Chem Lett. (1998) 8:2219-2222.
Lee et al., "Identification of a New Functional Domain in Angiopoietin-like 3 (ANGPTL3) and Angiopoietin-like 4 (ANGPTL4) Involved in Binding and Inhibition of Lipoprotein Lipase (LPL)" Journal of Biological Chemistry (2009) 284 (20): 13735-13745.
Leumann et al., "DNA Analogues: From Supramolecular Principles to Biological Properties" Bioorganic & Medicinal Chemistry (2002) 10:841-854.

(56) References Cited

OTHER PUBLICATIONS

Lichtenstein et al., "Modulation of plasma TG lipolysis by Angiopoietin-like proteins and GPIHBP1" Biochimica and Biophysica Acta (2010) 1804(4): 415-420.

Linton et al., "Transgenic mice expressing high plasma concentrations of human apolipoprotein B100 and lipoprotein (a)." J. Clin. Invest. (1993) 92: 3029-3037.

Maher et al., "Comparative hybrid arrest by tandem antisense oligodeoxyribonucleotides or oligodeoxyriboncleoside methylphosphonates in a cell-free system" Nuc. Acid. Res. (1988) 16:3341-3358.

Martin-Campos et al., "Identification of a novel mutation in the ANGPTL3 gene in two families diagnosed of familial hypobetalipoproteinemia without APOB mutation." Clin Chim Acta (2012) 413: 552-555.

Minicocci et al., "Clinical characteristics and plasma lipids in subjects with familial combined hypolipidemia: a pooled analysis" J of Lipid Research (2013) 54: 3481-3490.

Minicocci et al., "Mutations in the ANGPTL3 gene and familial combined hypolipidemia: a clinical and biochemical characterization" J. Clin. Endocrinol. Metab. (2012) 97(7):E1266-E1275.

Monia et al., "Selective Inhibition of Mutant Ha-ras mRNA Expression by Antisense Oligonucleotides," J. Biol. Chem. 267, 19954-62, 1992.

Musunuru et al., "Exome sequencing, ANGPTL3 mutations, and familial combined hypolipidemia" N. Engl. J. Med. (2010) 363(23):2220-2227.

Naoumova et al., A new drug target for treatment of dyslipidaemia associated with type 2 diabetes and the metabolic syndrome? Lancet (2002) 359(9325):2215-2216.

Fei Jai (ed.), Military Medical Science Press, siRNA Drug Development Technology, pp. 18-24 (Aug. 31, 2011).

International Search Report for application PCT/US14/072303 dated Apr. 28, 2015.

Kallanthottathil, "Conjugation Strategies for In Vivo siRNA Delivery," Oct. 29, 2012, 8th Annual meeting of the Oligonucleotide Therapeutics Society, presentation.

Li et al., "Research Development of ANGLPTL3," *Journal of Third Military Medical University*, 27(5):461-463 (2005).

Robciuc et al., "Angptl3 Deficiency is Associated with Increased Insulin Sensitivity, Lipoprotein Lipase Activity, and Decreased Serum Free Fatty Acids," *Arterioscler. Thromb. Vasc. Biol.*, 33:1706-1713 (2013).

Yilmaz et al., "Serum Concentrations of Human Angiopoietin-Like Protein 3 in Patients with Nonalcoholic Fatty Liver Disease: Association with Insulin Resistance," *Obesity Reviews*, 10:496-497 (2009).

MODULATION OF ANGIOPOIETIN-LIKE 3 EXPRESSION

SEQUENCE LISTING

The present application is being filed along with a Sequence Listing in electronic format. The Sequence Listing is provided as a file entitled BIOL0179USC1_ST25.txt, created on Sep. 5, 2018 which is 0.98 MB in size. The information in the electronic format of the sequence listing is incorporated herein by reference in its entirety.

FIELD OF THE INVENTION

Provided herein are methods, compounds, and compositions for reducing expression of angiopoietin-like 3 (ANGPTL3) mRNA and protein in an animal. Also, provided herein are methods, compounds, and compositions having an ANGPTL3 inhibitor for reducing ANGPTL3 related diseases or conditions in an animal. Such methods, compounds, and compositions are useful, for example, to treat, prevent, delay or ameliorate any one or more of cardiovascular disease or metabolic syndrome, or a symptom thereof, in an animal.

BACKGROUND

Diabetes and obesity (sometimes collectively referred to as "diabesity") are interrelated in that obesity is known to exacerbate the pathology of diabetes and greater than 60% of diabetics are obese. Most human obesity is associated with insulin resistance and leptin resistance. In fact, it has been suggested that obesity may have an even greater impact on insulin action than diabetes itself (Sindelka et al., *Physiol Res.*, 2002, 51, 85-91). Additionally, several compounds on the market for the treatment of diabetes are known to induce weight gain, a very undesirable side effect to the treatment of this disease.

Cardiovascular disease is also interrelated to obesity and diabetes. Cardiovascular disease encompasses a wide variety of etiologies and has an equally wide variety of causative agents and interrelated players. Many causative agents contribute to symptoms such as elevated plasma levels of cholesterol, including non-high density lipoprotein cholesterol (non-HDL-C), as well as other lipid-related disorders. Such lipid-related disorders, generally referred to as dyslipidemia, include hyperlipidemia, hypercholesterolemia and hypertriglyceridemia among other indications. Elevated non-HDL cholesterol is associated with atherogenesis and its sequelae, including cardiovascular diseases such as arteriosclerosis, coronary artery disease, myocardial infarction, ischemic stroke, and other forms of heart disease. These rank as the most prevalent types of illnesses in industrialized countries. Indeed, an estimated 12 million people in the United States suffer with coronary artery disease and about 36 million require treatment for elevated cholesterol levels.

Epidemiological and experimental evidence has shown that high levels of circulating triglyceride (TG) can contribute to cardiovascular disease and a myriad of metabolic disorders (Valdivielso et al., 2009, *Atherosclerosis* Zhang et al., 2008, *Circ Res.* 1; 102(2):250-6). TG derived from either exogenous or endogenous sources is incorporated and secreted in chylomicrons from the intestine or in very low density lipoproteins (VLDL) from the liver. Once in circulation, TG is hydrolyzed by lipoprotein lipase (LpL) and the resulting free fatty acids can then be taken up by local tissues and used as an energy source. Due to the profound effect LpL has on plasma TG and metabolism in general, discovering and developing compounds that affect LpL activity are of great interest.

Metabolic syndrome is a combination of medical disorders that increase one's risk for cardiovascular disease and diabetes. The symptoms, including high blood pressure, high triglycerides, decreased HDL and obesity, tend to appear together in some individuals. It affects a large number of people in a clustered fashion. In some studies, the prevalence in the USA is calculated as being up to 25% of the population. Metabolic syndrome is known under various other names, such as (metabolic) syndrome X, insulin resistance syndrome, Reaven's syndrome or CHAOS. With the high prevalence of cardiovascular disorders and metabolic disorders there remains a need for improved approaches to treat these conditions The angiopoietins are a family of secreted growth factors. Together with their respective endothelium-specific receptors, the angiopoietins play important roles in angiogenesis. One family member, angiopoietin-like 3 (also known as angiopoietin-like protein 3, ANGPT5, ANGPTL3, or angiopoietin 5), is predominantly expressed in the liver, and is thought to play a role in regulating lipid metabolism (Kaplan et al., *J. Lipid Res.*, 2003, 44, 136-143). Genome-wide association scans (GWAS) surveying the genome for common variants associated with plasma concentrations of HDL, LDL and triglyceride found an association between triglycerides and single-nucleotide polymorphisms (SNPs) near ANGPTL3 (Willer et al., Nature Genetics, 2008, 40(2): 161-169). Individuals with homozygous ANGPTL3 loss-of-function mutations present with low levels of all atherogenic plasma lipids and lipoproteins, such as total cholesterol (TC) and TG, low density lipoprotein cholesterol (LDL-C), apolipoprotein B (apoB), non-HDL-C, as well as HDL-C (Romeo et al. 2009, *J Clin Invest,* 119(1):70-79; Musunuru et al. 2010 *N Engl J Med,* 363:2220-2227; Martin-Campos et al. 2012, *Clin Chim Acta,* 413:552-555; Minicocci et al. 2012, *J Clin Endocrinol Metab,* 97:e1266-1275; Noto et al. 2012, *Arterioscler Thromb Vasc Biol,* 32:805-809; Pisciotta et al. 2012, *Circulation Cardiovasc Genet,* 5:42-50). This clinical phenotype has been termed familial combined hypolipidemia (FHBL2). Despite reduced secretion of VLDL, subjects with FHBL2 do not have increased hepatic fat content. They also appear to have lower plasma glucose and insulin levels, and importantly, both diabetes and cardiovascular disease appear to be absent from these subjects. No adverse clinical phenotypes have been reported to date (Minicocci et al. 2013, *J of Lipid Research*, 54:3481-3490). Reduction of ANGPTL3 has been shown to lead to a decrease in TG, cholesterol and LDL levels in animal models (U.S. Ser. No. 13/520,997; PCT Publication WO 2011/085271). Mice deficient in ANGPTL3 have very low plasma triglyceride (TG) and cholesterol levels, while overexpression produces the opposite effects (Koishi et al. 2002; Koster 2005; Fujimoto 2006). Accordingly, the potential role of ANGPTL3 in lipid metabolism makes it an attractive target for therapeutic intervention.

To date, therapeutic strategies to treat cardiometabolic disease by directly targeting ANGPTL3 levels have been limited. ANGPTL3 polypeptide fragments (U.S. Ser. No. 12/128,545), anti-ANGPTL3 antibodies (U.S. Ser. No. 12/001,012) and ANGPTL3 nucleic acid inhibitors including antisense oligonucleotides (U.S. Ser. No. 13/520,997; PCT Publication WO 2011/085271; incorporated by reference herein, in their entirety) have previously been suggested or developed, but none of the compounds directly targeting ANGPTL3 have been approved for treating cardiometabolic disease. Accordingly, there is an unmet need for highly potent and tolerable compounds to inhibit ANGPTL3. The invention disclosed herein relates to the discovery of novel, highly potent inhibitors of ANGPTL3 expression and their use in treatment.

SUMMARY OF THE INVENTION

Provided herein are compositions and methods for modulating expression of ANGPTL3 mRNA and protein. In certain embodiments, the composition is an ANGPTL3 specific inhibitor. In certain embodiments, the ANGPTL3 specific inhibitor decreases expression of ANGPTL3 mRNA and protein.

In certain embodiments, the composition is an ANGPTL3 specific inhibitor. In certain embodiments, the ANGPTL3 specific inhibitor is a nucleic acid. In certain embodiments, the nucleic acid is an antisense compound. In certain embodiments, the antisense compound is a modified oligonucleotide.

In certain embodiments, the ANGPTL3 specific inhibitor is a modified oligonucleotide consisting of 12 to 30 linked nucleosides and having a nucleobase sequence comprising at least 8, least 9, least 10, least 11, at least 12, least 13, at least 14, at least 15, at least 16, least 17, least 18, least 19, or 20 contiguous nucleobases of the nucleobase sequence of SEQ ID NO: 77.

In certain embodiments, the ANGPTL3 specific inhibitor is a modified oligonucleotide consisting of 12 to 30 linked nucleosides and comprising a nucleobase sequence comprising a portion of at least 8 contiguous nucleobases complementary to an equal length portion of nucleobases 1140-1159 of SEQ ID NO: 1, wherein the nucleobase sequence of the modified oligonucleotide is at least 80% complementary to SEQ ID NO: 1.

In certain embodiments, the ANGPTL3 specific inhibitor is a modified oligonucleotide consisting of 12 to 30 linked nucleosides and comprising a nucleobase sequence comprising a portion of at least 8 contiguous nucleobases complementary to an equal length portion of nucleobases 9715-9734 of SEQ ID NO: 2, wherein the nucleobase sequence of the modified oligonucleotide is at least 80% complementary to SEQ ID NO: 2.

In certain embodiments, the ANGPTL3 specific inhibitor is a modified oligonucleotide consisting of 20 linked nucleosides and having a nucleobase sequence comprising at least 8 contiguous nucleobases of SEQ ID NO: 77, wherein the modified oligonucleotide comprises: (a) a gap segment consisting of ten linked deoxynucleosides; (b) a 5' wing segment consisting of five linked nucleosides; (c) a 3' wing segment consisting of five linked nucleosides; and wherein the gap segment is positioned between the 5' wing segment and the 3' wing segment, wherein each nucleoside of each wing segment comprises a 2'-O-methoxyethyl sugar, wherein each internucleoside linkage is a phosphorothioate linkage and wherein each cytosine residue is a 5-methylcytosine.

In certain embodiments, the ANGPTL3 specific inhibitor is a modified oligonucleotide consisting of 20 linked nucleosides and having a nucleobase sequence consisting of at least 8 contiguous nucleobases of SEQ ID NO: 77, wherein the modified oligonucleotide consists of: (a) a gap segment consisting of ten linked deoxynucleosides; (b) a 5' wing segment consisting of five linked nucleosides; (c) a 3' wing segment consisting of five linked nucleosides; and wherein the gap segment is positioned between the 5' wing segment and the 3' wing segment, wherein each nucleoside of each wing segment comprises a 2'-O-methoxyethyl sugar, wherein each internucleoside linkage is a phosphorothioate linkage and wherein each cytosine residue is a 5-methylcytosine.

In certain embodiments, the ANGPTL3 specific inhibitor is a modified oligonucleotide represented by the following structure and the designation ISIS 563580. In certain embodiments, the ANGPTL3 specific inhibitor comprises the modified oligonucleotide ISIS 563580 represented by the following structure having SEQ ID NO: 77.

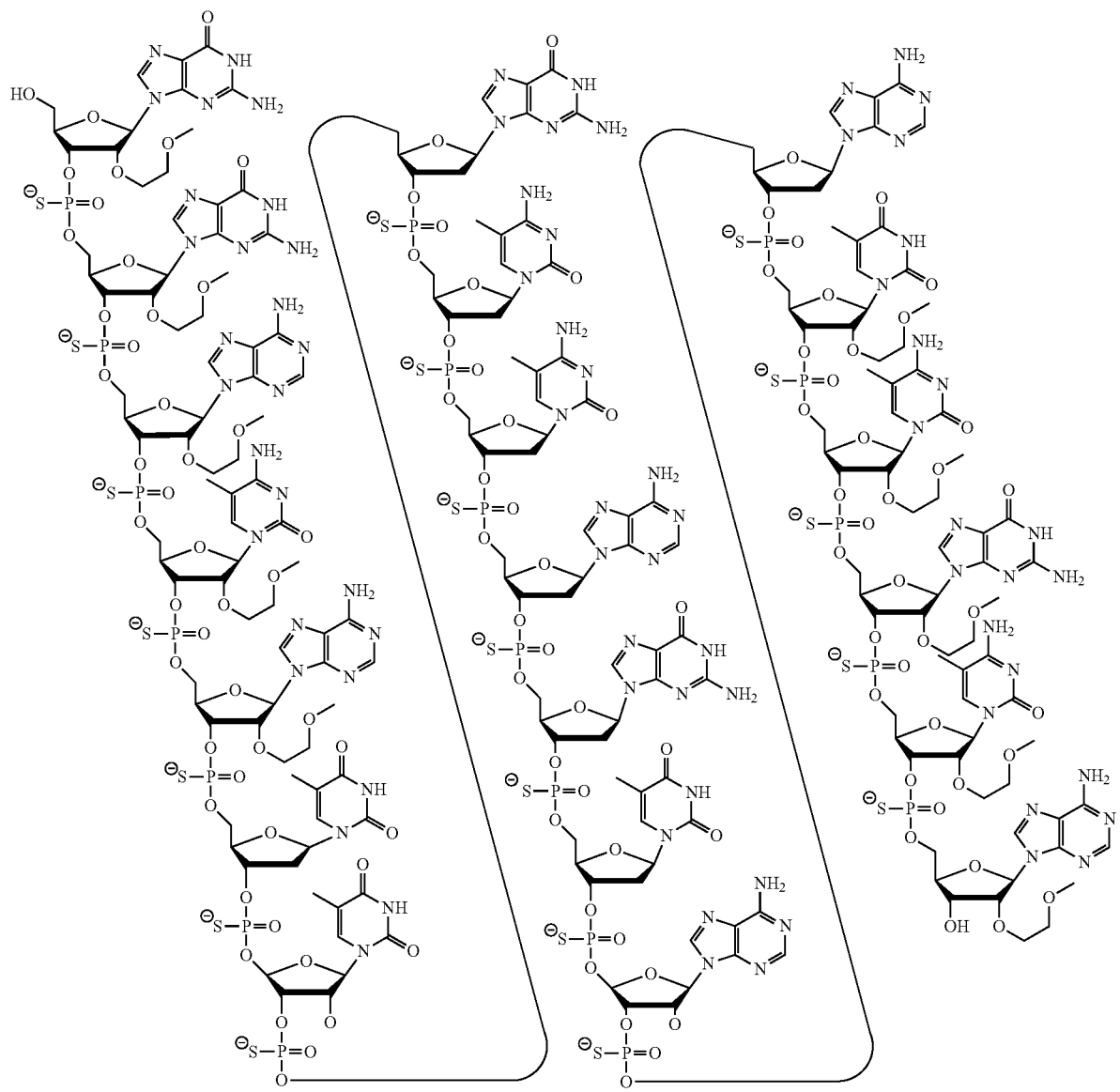

Certain embodiments provide a composition comprising a compound described herein, or a salt thereof, and a pharmaceutically acceptable carrier or diluent.

In certain embodiments, the modulation of ANGPTL3 expression occurs in a cell or tissue. In certain embodiments, the modulations occur in a cell or tissue in an animal. In certain embodiments, the animal is a human. In certain embodiments, the modulation is a reduction in ANGPTL3 mRNA level. In certain embodiments, the modulation is a reduction in ANGPTL3 protein level. In certain embodiments, both ANGPTL3 mRNA and protein levels are reduced. Such reduction may occur in a time-dependent or in a dose-dependent manner.

Certain embodiments provide compositions and methods for use in therapy. Certain embodiments provide compositions and methods for preventing, treating, delaying, slowing the progression and/or ameliorating ANGPTL3 related diseases, disorders, and conditions. In certain embodiments, such diseases, disorders, and conditions are cardiovascular and/or metabolic diseases, disorders, and conditions. In certain embodiments, the compositions and methods for therapy include administering an ANGPTL3 specific inhibitor to an individual in need thereof. In certain embodiments, the ANGPTL3 specific inhibitor is a nucleic acid. In certain embodiments, the nucleic acid is an antisense compound. In certain embodiments, the antisense compound is a modified oligonucleotide.

DETAILED DESCRIPTION OF THE INVENTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component"

encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated-by-reference for the portions of the document discussed herein, as well as in their entirety.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques can be used for chemical synthesis, and chemical analysis. Where permitted, all patents, applications, published applications and other publications, GENBANK Accession Numbers and associated sequence information obtainable through databases such as National Center for Biotechnology Information (NCBI) and other data referred to throughout in the disclosure herein are incorporated by reference for the portions of the document discussed herein, as well as in their entirety.

Unless otherwise indicated, the following terms have the following meanings:

"2'-O-methoxyethyl" (also 2'-MOE and 2'-O(CH$_2$)$_2$—OCH$_3$) refers to an O-methoxy-ethyl modification of the 2' position of a furosyl ring. A 2'-O-methoxyethyl modified sugar is a modified sugar.

"2'-O-methoxyethyl nucleotide" means a nucleotide comprising a 2'-O-methoxyethyl modified sugar moiety.

"3' target site" or "3' stop site" refers to the nucleotide of a target nucleic acid which is complementary to the 3'-most nucleotide of a particular antisense compound.

"5' target site" or "5 start site" refers to the nucleotide of a target nucleic acid which is complementary to the 5'-most nucleotide of a particular antisense compound.

"5-methylcytosine" means a cytosine modified with a methyl group attached to the 5' position. A 5-methylcytosine is a modified nucleobase.

"About" means within ±10% of a value. For example, if it is stated, "a marker may be increased by about 50%", it is implied that the marker may be increased between 45%-55%

"Active pharmaceutical agent" means the substance or substances in a pharmaceutical composition that provide a therapeutic benefit when administered to an individual. For example, in certain embodiments an antisense oligonucleotide targeted to ANGPTL3 is an active pharmaceutical agent.

"Active target region" or "target region" means a region to which one or more active antisense compounds is targeted.

"Active antisense compounds" means antisense compounds that reduce target nucleic acid levels or protein levels.

"Adipogenesis" means the development of fat cells from preadipocytes. "Lipogenesis" means the production or formation of fat, either fatty degeneration or fatty infiltration.

"Adiposity" or "Obesity" refers to the state of being obese or an excessively high amount of body fat or adipose tissue in relation to lean body mass. The amount of body fat includes concern for both the distribution of fat throughout the body and the size and mass of the adipose tissue deposits. Body fat distribution can be estimated by skin-fold measures, waist-to-hip circumference ratios, or techniques such as ultrasound, computed tomography, or magnetic resonance imaging. According to the Center for Disease Control and Prevention, individuals with a body mass index (BMI) of 30 or more are considered obese. The term "Obesity" as used herein includes conditions where there is an increase in body fat beyond the physical requirement as a result of excess accumulation of adipose tissue in the body. The term "obesity" includes, but is not limited to, the following conditions: adult-onset obesity; alimentary obesity; endogenous or metabolic obesity; endocrine obesity; familial obesity; hyperinsulinar obesity; hyperplastic-hypertrophic obesity; hypogonadal obesity; hypothyroid obesity; lifelong obesity; morbid obesity and exogenous obesity.

"Administered concomitantly" refers to the co-administration of two agents in any manner in which the pharmacological effects of both are manifest in the patient at the same time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

"Administering" means providing an agent to an animal, and includes, but is not limited to, administering by a medical professional and self-administering.

"Agent" means an active substance that can provide a therapeutic benefit when administered to an animal. "First Agent" means a therapeutic compound of the invention. For example, a first agent can be an antisense oligonucleotide targeting ANGPTL3. "Second agent" means a second therapeutic compound of the invention (e.g. a second antisense oligonucleotide targeting ANGPTL3) and/or a non-ANGPTL3 therapeutic compound.

"Amelioration" refers to a lessening of at least one indicator, sign, or symptom of an associated disease, disorder, or condition. The severity of indicators can be determined by subjective or objective measures, which are known to those skilled in the art.

"ANGPTL3" means any nucleic acid or protein of ANGPTL3.

"ANGPTL3 expression" means the level of mRNA transcribed from the gene encoding ANGPTL3 or the level of protein translated from the mRNA. ANGPTL3 expression can be determined by art known methods such as a Northern or Western blot.

"ANGPTL3 nucleic acid" means any nucleic acid encoding ANGPTL3. For example, in certain embodiments, an ANGPTL3 nucleic acid includes a DNA sequence encoding ANGPTL3, a RNA sequence transcribed from DNA encoding ANGPTL3 (including genomic DNA comprising introns and exons), and a mRNA sequence encoding ANGPTL3. "ANGPTL3 mRNA" means a mRNA encoding an ANGPTL3 protein.

"Animal" refers to a human or non-human animal, including, but not limited to, mice, rats, rabbits, dogs, cats, pigs, and non-human primates, including, but not limited to, monkeys and chimpanzees.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding.

"Antisense inhibition" means reduction of target nucleic acid levels or target protein levels in the presence of an antisense compound complementary to a target nucleic acid compared to target nucleic acid levels or target protein levels in the absence of the antisense compound.

"Antisense oligonucleotide" means a single-stranded oligonucleotide having a nucleobase sequence that permits hybridization to a corresponding region or segment of a target nucleic acid.

"ApoB-containing lipoprotein" means any lipoprotein that has apolipoprotein B as its protein component, and is understood to include LDL, VLDL, IDL, and lipoprotein(a) and can be generally targeted by lipid lowering agent and therapies. "ApoB-100-containing LDL" means ApoB-100 isoform containing LDL.

"Atherosclerosis" means a hardening of the arteries affecting large and medium-sized arteries and is characterized by the presence of fatty deposits. The fatty deposits are called "atheromas" or "plaques," which consist mainly of cholesterol and other fats, calcium and scar tissue, and damage the lining of arteries.

"Bicyclic sugar" means a furosyl ring modified by the bridging of two non-geminal ring atoms. A bicyclic sugar is a modified sugar.

"Bicyclic nucleic acid" or "BNA" refers to a nucleoside or nucleotide wherein the furanose portion of the nucleoside or nucleotide includes a bridge connecting two carbon atoms on the furanose ring, thereby forming a bicyclic ring system.

"Cap structure" or "terminal cap moiety" means chemical modifications, which have been incorporated at either terminus of an antisense compound.

"Cardiovascular disease" or "cardiovascular disorder" refers to a group of conditions related to the heart, blood vessels, or the circulation. Examples of cardiovascular diseases or disorders include, but are not limited to, aneurysm, angina, arrhythmia, atherosclerosis, cerebrovascular disease (stroke), coronary heart disease, hypertension, dyslipidemia, hyperlipidemia, and hypercholesterolemia.

"Cardiometabolic disease" or "cardiometabolic disorder" are diseases or disorders concerning both the cardiovascular system and the metabolic system. Examples of cardiometabolic diseases or disorders include, but are not limited to, diabetes and dyslipidemias.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-O-methoxyethyl modifications.

"Chimeric antisense compound" means an antisense compound that has at least two chemically distinct regions.

"Co-administration" means administration of two or more agents to an individual. The two or more agents can be in a single pharmaceutical composition, or can be in separate pharmaceutical compositions. Each of the two or more agents can be administered through the same or different routes of administration. Co-administration encompasses parallel or sequential administration.

"Cholesterol" is a sterol molecule found in the cell membranes of all animal tissues. Cholesterol must be transported in an animal's blood plasma by lipoproteins including very low density lipoprotein (VLDL), intermediate density lipoprotein (IDL), low density lipoprotein (LDL), and high density lipoprotein (HDL). "Plasma cholesterol" refers to the sum of all lipoproteins (VDL, IDL, LDL, HDL) esterified and/or non-estrified cholesterol present in the plasma or serum.

"Cholesterol absorption inhibitor" means an agent that inhibits the absorption of exogenous cholesterol obtained from diet.

"Complementarity" means the capacity for pairing between nucleobases of a first nucleic acid and a second nucleic acid. In certain embodiments, complementarity between the first and second nucleic acid may be between two DNA strands, between two RNA strands, or between a DNA and an RNA strand. In certain embodiments, some of the nucleobases on one strand are matched to a complementary hydrogen bonding base on the other strand. In certain embodiments, all of the nucleobases on one strand are matched to a complementary hydrogen bonding base on the other strand. In certain embodiments, a first nucleic acid is an antisense compound and a second nucleic acid is a target nucleic acid. In certain such embodiments, an antisense oligonucleotide is a first nucleic acid and a target nucleic acid is a second nucleic acid.

"Contiguous nucleobases" means nucleobases immediately adjacent to each other.

"Coronary heart disease (CHD)" means a narrowing of the small blood vessels that supply blood and oxygen to the heart, which is often a result of atherosclerosis.

"Deoxyribonucleotide" means a nucleotide having a hydrogen at the 2' position of the sugar portion of the nucleotide. Deoxyribonucleotides may be modified with any of a variety of substituents.

"Diabetes mellitus" or "diabetes" is a syndrome characterized by disordered metabolism and abnormally high blood sugar (hyperglycemia) resulting from insufficient levels of insulin or reduced insulin sensitivity. The characteristic symptoms are excessive urine production (polyuria) due to high blood glucose levels, excessive thirst and increased fluid intake (polydipsia) attempting to compensate for increased urination, blurred vision due to high blood glucose effects on the eye's optics, unexplained weight loss, and lethargy.

"Diabetic dyslipidemia" or "type 2 diabetes with dyslipidemia" means a condition characterized by Type 2 diabetes, reduced HDL-C, elevated triglycerides, and elevated small, dense LDL particles.

"Diluent" means an ingredient in a composition that lacks pharmacological activity, but is pharmaceutically necessary or desirable. For example, the diluent in an injected composition can be a liquid, e.g. saline solution.

"Dyslipidemia" refers to a disorder of lipid and/or lipoprotein metabolism, including lipid and/or lipoprotein overproduction or deficiency. Dyslipidemias may be manifested by elevation of lipids such as cholesterol and triglycerides as well as lipoproteins such as low-density lipoprotein (LDL) cholesterol.

"Dosage unit" means a form in which a pharmaceutical agent is provided, e.g. pill, tablet, or other dosage unit known in the art. In certain embodiments, a dosage unit is a vial containing lyophilized antisense oligonucleotide. In certain embodiments, a dosage unit is a vial containing reconstituted antisense oligonucleotide.

"Dose" means a specified quantity of a pharmaceutical agent provided in a single administration, or in a specified time period. In certain embodiments, a dose can be administered in one, two, or more boluses, tablets, or injections. For example, in certain embodiments where subcutaneous administration is desired, the desired dose requires a volume not easily accommodated by a single injection, therefore, two or more injections can be used to achieve the desired dose. In certain embodiments, the pharmaceutical agent is administered by infusion over an extended period of time or continuously. Doses can be stated as the amount of pharmaceutical agent per hour, day, week, or month. Doses can be expressed as mg/kg or g/kg.

"Effective amount" or "therapeutically effective amount" means the amount of active pharmaceutical agent sufficient to effectuate a desired physiological outcome in an individual in need of the agent. The effective amount can vary among individuals depending on the health and physical condition of the individual to be treated, the taxonomic group of the individuals to be treated, the formulation of the composition, assessment of the individual's medical condition, and other relevant factors.

"Fully complementary" or "100% complementary" means each nucleobase of a nucleobase sequence of a first nucleic acid has a complementary nucleobase in a second nucleobase sequence of a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region can be referred to as a "gap segment" and the external regions can be referred to as "wing segments."

"Gap-widened" means a chimeric antisense compound having a gap segment of 12 or more contiguous 2'-deoxyribonucleosides positioned between and immediately adjacent to 5' and 3' wing segments having from one to six nucleosides.

"Glucose" is a monosaccharide used by cells as a source of energy and metabolic intermediate. "Plasma glucose" refers to glucose present in the plasma.

"High density lipoprotein-C(HDL-C)" means cholesterol associated with high density lipoprotein particles. Concentration of HDL-C in serum (or plasma) is typically quantified in mg/dL or nmol/L. "serum HDL-C" and "plasma HDL-C" mean HDL-C in serum and plasma, respectively.

"HMG-CoA reductase inhibitor" means an agent that acts through the inhibition of the enzyme HMG-CoA reductase, such as atorvastatin, rosuvastatin, fluvastatin, lovastatin, pravastatin, and simvastatin.

"Hybridization" means the annealing of complementary nucleic acid molecules. In certain embodiments, complementary nucleic acid molecules include an antisense compound and a target nucleic acid.

"Hypercholesterolemia" means a condition characterized by elevated cholesterol or circulating (plasma) cholesterol, LDL-cholesterol and VLDL-cholesterol, as per the guidelines of the Expert Panel Report of the National Cholesterol Educational Program (NCEP) of Detection, Evaluation of Treatment of high cholesterol in adults (see, *Arch. Int. Med.* (1988) 148, 36-39).

"Hyperlipidemia" or "hyperlipemia" is a condition characterized by elevated serum lipids or circulating (plasma) lipids. This condition manifests an abnormally high concentration of fats. The lipid fractions in the circulating blood are cholesterol, low density lipoproteins, very low density lipoproteins and triglycerides.

"Hypertriglyceridemia" means a condition characterized by elevated triglyceride levels.

"Identifying" or "selecting a subject having a metabolic or cardiovascular disease" means identifying or selecting a subject having been diagnosed with a metabolic disease, a cardiovascular disease, or a metabolic syndrome; or, identifying or selecting a subject having any symptom of a metabolic disease, cardiovascular disease, or metabolic syndrome including, but not limited to, hypercholesterolemia, hyperglycemia, hyperlipidemia, hypertriglyceridemia, hypertension, increased insulin resistance, decreased insulin sensitivity, above normal body weight, and/or above normal body fat content or any combination thereof. Such identification may be accomplished by any method, including but not limited to, standard clinical tests or assessments, such as measuring serum or circulating (plasma) cholesterol, measuring serum or circulating (plasma) blood-glucose, measuring serum or circulating (plasma) triglycerides, measuring blood-pressure, measuring body fat content, measuring body weight, and the like.

"Identifying" or "selecting a diabetic subject" means identifying or selecting a subject having been identified as diabetic or identifying or selecting a subject having any symptom of diabetes (type 1 or type 2) such as, but not limited to, having a fasting glucose of at least 110 mg/dL, glycosuria, polyuria, polydipsia, increased insulin resistance, and/or decreased insulin sensitivity.

"Identifying" or "selecting an obese subject" means identifying or selecting a subject having been diagnosed as obese or identifying or selecting a subject with a BMI over 30 and/or a waist circumference of greater than 102 cm in men or greater than 88 cm in women.

"Identifying" or "selecting a subject having dyslipidemia" means identifying or selecting a subject diagnosed with a disorder of lipid and/or lipoprotein metabolism, including lipid and/or lipoprotein overproduction or deficiency. Dyslipidemias may be manifested by elevation of lipids such as cholesterol and triglycerides as well as lipoproteins such as low-density lipoprotein (LDL) cholesterol.

"Identifying" or "selecting" a subject having increased adiposity" means identifying or selecting a subject having an increased amount of body fat (or adiposity) that includes concern for one or both the distribution of fat throughout the body and the size and mass of the adipose tissue deposits. Body fat distribution can be estimated by skin-fold measures, waist-to-hip circumference ratios, or techniques such as ultrasound, computer tomography, or magnetic resonance imaging. According to the Center for Disease Control and Prevention, individuals with a body mass index (BMI) of 30 or more are considered obese.

"Improved cardiovascular outcome" means a reduction in the occurrence of adverse cardiovascular events, or the risk thereof. Examples of adverse cardiovascular events include, without limitation, death, reinfarction, stroke, cardiogenic shock, pulmonary edema, cardiac arrest, and atrial dysrhythmia.

"Immediately adjacent" means there are no intervening elements between the immediately adjacent elements.

"Individual" or "subject" or "animal" means a human or non-human animal selected for treatment or therapy.

"Inhibiting the expression or activity" refers to a reduction or blockade of the expression or activity and does not necessarily indicate a total elimination of expression or activity.

"Insulin resistance" is defined as the condition in which normal amounts of insulin are inadequate to produce a normal insulin response from cells, e.g., fat, muscle and/or liver cells. Insulin resistance in fat cells results in hydrolysis of stored triglycerides, which elevates free fatty acids in the blood plasma. Insulin resistance in muscle reduces glucose uptake whereas insulin resistance in liver reduces glucose storage, with both effects serving to elevate blood glucose. High plasma levels of insulin and glucose due to insulin resistance often leads to metabolic syndrome and type 2 diabetes.

"Insulin sensitivity" is a measure of how effectively an individual processes glucose. An individual having high insulin sensitivity effectively processes glucose whereas an individual with low insulin sensitivity does not effectively process glucose.

"Internucleoside linkage" refers to the chemical bond between nucleosides.

"Intravenous administration" means administration into a vein.

"Linked nucleosides" means adjacent nucleosides which are bonded together.

"Lipid-lowering" means a reduction in one or more lipids in a subject. Lipid-lowering can occur with one or more doses over time.

"Lipid-lowering agent" means an agent, for example, an ANGPTL3-specific modulator, provided to a subject to achieve a lowering of lipids in the subject. For example, in certain embodiments, a lipid-lowering agent is provided to a subject to reduce one or more of apoB, apoC-III, total cholesterol, LDL-C, VLDL-C, IDL-C, non-HDL-C, triglycerides, small dense LDL particles, and Lp(a) in a subject.

"Lipid-lowering therapy" means a therapeutic regimen provided to a subject to reduce one or more lipids in a subject. In certain embodiments, a lipid-lowering therapy is provided to reduce one or more of apoB, apoC-III, total cholesterol, LDL-C, VLDL-C, IDL-C, non-HDL-C, triglycerides, small dense LDL particles, and Lp(a) in a subject.

"Lipoprotein", such as VLDL, LDL and HDL, refers to a group of proteins found in the serum, plasma and lymph and are important for lipid transport. The chemical composition of each lipoprotein differs in that the HDL has a higher proportion of protein versus lipid, whereas the VLDL has a lower proportion of protein versus lipid.

"Low density lipoprotein-cholesterol (LDL-C)" means cholesterol carried in low density lipoprotein particles. Concentration of LDL-C in serum (or plasma) is typically quantified in mg/dL or nmol/L. "Serum LDL-C" and "plasma LDL-C" mean LDL-C in the serum and plasma, respectively.

"Major risk factors" refers to factors that contribute to a high risk for a particular disease or condition. In certain embodiments, major risk factors for coronary heart disease include, without limitation, cigarette smoking, hypertension, low HDL-C, family history of coronary heart disease, age, and other factors disclosed herein.

"Metabolic disorder" or "metabolic disease" refers to a condition characterized by an alteration or disturbance in metabolic function. "Metabolic" and "metabolism" are terms well known in the art and generally include the whole range of biochemical processes that occur within a living organism. Metabolic disorders include, but are not limited to, hyperglycemia, prediabetes, diabetes (type I and type 2), obesity, insulin resistance, metabolic syndrome and dyslipidemia due to type 2 diabetes.

"Metabolic syndrome" means a condition characterized by a clustering of lipid and non-lipid cardiovascular risk factors of metabolic origin. In certain embodiments, metabolic syndrome is identified by the presence of any 3 of the following factors: waist circumference of greater than 102 cm in men or greater than 88 cm in women; serum triglyceride of at least 150 mg/dL; HDL-C less than 40 mg/dL in men or less than 50 mg/dL in women; blood pressure of at least 130/85 mmHg; and fasting glucose of at least 110 mg/dL. These determinants can be readily measured in clinical practice (JAMA, 2001, 285: 2486-2497).

"Mismatch" or "non-complementary nucleobase" refers to the case when a nucleobase of a first nucleic acid is not capable of pairing with the corresponding nucleobase of a second or target nucleic acid.

"Mixed dyslipidemia" means a condition characterized by elevated cholesterol and elevated triglycerides.

"Modified internucleoside linkage" refers to a substitution or any change from a naturally occurring internucleoside bond (i.e. a phosphodiester internucleoside bond).

"Modified nucleobase" refers to any nucleobase other than adenine, cytosine, guanine, thymidine, or uracil. An "unmodified nucleobase" means the purine bases adenine (A) and guanine (G), and the pyrimidine bases thymine (T), cytosine (C), and uracil (U).

"Modified nucleoside" means a nucleoside having, independently, one or more modified sugar moiety or modified nucleobase.

"Modified nucleotide" means a nucleotide having, independently, one or more modified sugar moiety, modified internucleoside linkage, or modified nucleobase. A "modified nucleoside" means a nucleoside having, independently, one or more modified sugar moiety or modified nucleobase.

"Modified oligonucleotide" means an oligonucleotide comprising at least one modified nucleotide.

"Modified sugar" refers to a substitution or change from a natural sugar.

"Motif" means the pattern of chemically distinct regions in an antisense compound.

"MTP inhibitor" means an agent inhibits the enzyme microsomal triglyceride transfer protein.

"Naturally occurring internucleoside linkage" means a 3' to 5' phosphodiester linkage.

"Natural sugar moiety" means a sugar found in DNA (2'-H) or RNA (2'-OH).

"Non-alcoholic fatty liver disease" or "NAFLD" means a condition characterized by fatty inflammation of the liver that is not due to excessive alcohol use (for example, alcohol consumption of over 20 g/day). In certain embodiments, NAFLD is related to insulin resistance and metabolic syndrome. NAFLD encompasses a disease spectrum ranging from simple triglyceride accumulation in hepatocytes (hepatic steatosis) to hepatic steatosis with inflammation (steatohepatitis), fibrosis, and cirrhosis.

"Nonalcoholic steatohepatitis" (NASH) occurs from progression of NAFLD beyond deposition of triglycerides. A "second hit" capable of inducing necrosis, inflammation, and fibrosis is required for development of NASH. Candidates for the second-hit can be grouped into broad categories: factors causing an increase in oxidative stress and factors promoting expression of proinflammatory cytokines. It has been suggested that increased liver triglycerides lead to increased oxidative stress in hepatocytes of animals and humans, indicating a potential cause-and-effect relationship between hepatic triglyceride accumulation, oxidative stress, and the progression of hepatic steatosis to NASH (Browning and Horton, *J Clin Invest,* 2004, 114, 147-152). Hypertriglyceridemia and hyperfattyacidemia can cause triglyceride accumulation in peripheral tissues (Shimamura et al., *Biochem Biophys Res Commun,* 2004, 322, 1080-1085).

"Nucleic acid" refers to molecules composed of monomeric nucleotides. A nucleic acid includes ribonucleic acids (RNA), deoxyribonucleic acids (DNA), single-stranded nucleic acids, double-stranded nucleic acids, small interfering ribonucleic acids (siRNA), and microRNAs (miRNA). A nucleic acid can also comprise a combination of these elements in a single molecule.

"Nucleobase" means a heterocyclic moiety capable of pairing with a base of another nucleic acid.

"Nucleobase sequence" means the order of contiguous nucleobases independent of any sugar, linkage, or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo or tricyclo sugar mimetics e.g. non furanose sugar units.

"Nucleotide" means a nucleoside having a phosphate group covalently linked to the sugar portion of the nucleoside.

"Nucleotide mimetic" includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage).

"Oligomeric compound" or "oligomer" refers to a polymeric structure comprising two or more sub-structures and capable of hybridizing to a region of a nucleic acid molecule. In certain embodiments, oligomeric compounds are oligonucleosides. In certain embodiments, oligomeric compounds are oligonucleotides. In certain embodiments, oligomeric compounds are antisense compounds. In certain embodiments, oligomeric compounds are antisense oligonucleotides. In certain embodiments, oligomeric compounds are chimeric oligonucleotides.

"Oligonucleotide" means a polymer of linked nucleosides each of which can be modified or unmodified, independent one from another.

"Parenteral administration" means administration by a manner other than through the digestive tract. Parenteral administration includes topical administration, subcutaneous administration, intravenous administration, intramuscular administration, intraarterial administration, intraperitoneal administration, or intracranial administration, e.g. intrathecal or intracerebroventricular administration. Administration can be continuous, or chronic, or short or intermittent.

"Peptide" means a molecule formed by linking at least two amino acids by amide bonds. Peptide refers to polypeptides and proteins.

"Pharmaceutical agent" means a substance that provides a therapeutic benefit when administered to an individual. For example, in certain embodiments, an antisense oligonucleotide targeted to ANGPTL3 is pharmaceutical agent.

"Pharmaceutical composition" means a mixture of substances suitable for administering to an individual. For example, a pharmaceutical composition can comprise one or more active agents and a sterile aqueous solution.

"Pharmaceutically acceptable carrier" means a medium or diluent that does not interfere with the structure or function of the oligonucleotide. Certain, of such carries enable pharmaceutical compositions to be formulated as, for example, tablets, pills, dragees, capsules, liquids, gels, syrups, slurries, suspension and lozenges for the oral ingestion by a subject. Certain of such carriers enable pharmaceutical compositions to be formulated for injection or infusion. For example, a pharmaceutically acceptable carrier can be a sterile aqueous solution.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e. linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" refers to delaying or forestalling the onset or development of a disease, disorder, or condition for a period of time from minutes to indefinitely. Prevent also means reducing risk of developing a disease, disorder, or condition.

"Prodrug" means a therapeutic agent that is prepared in an inactive form that is converted to an active form within the body or cells thereof by the action of endogenous enzymes or other chemicals or conditions.

"Side effects" means physiological responses attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum can indicate liver toxicity or liver function abnormality. For example, increased bilirubin can indicate liver toxicity or liver function abnormality.

"Single-stranded oligonucleotide" means an oligonucleotide which is not hybridized to a complementary strand.

"Specifically hybridizable" refers to an antisense compound having a sufficient degree of complementarity with a target nucleic acid to induce a desired effect, while exhibiting minimal or no effects on non-target nucleic acids under conditions in which specific binding is desired, i.e. under physiological conditions in the case of in vivo assays and therapeutic treatments.

"Statin" means an agent that inhibits the activity of HMG-CoA reductase.

"Subcutaneous administration" means administration just below the skin.

"Targeting" or "targeted" means the process of design and selection of an antisense compound that will specifically hybridize to a target nucleic acid and induce a desired effect.

"Target nucleic acid," "target RNA," and "target RNA transcript" all refer to a nucleic acid capable of being targeted by antisense compounds.

"Target region" is defined as a portion of the target nucleic acid having at least one identifiable structure, function, or characteristic.

"Target segment" means the sequence of nucleotides of a target nucleic acid to which one or more antisense compound is targeted. "5' target site" or "5' start site" refers to the 5'-most nucleotide of a target segment. "3' target site" or "3' stop site" refers to the 3'-most nucleotide of a target segment.

"Therapeutically effective amount" means an amount of an agent that provides a therapeutic benefit to an individual.

"Therapeutic lifestyle change" means dietary and lifestyle changes intended to lower fat/adipose tissue mass and/or cholesterol. Such change can reduce the risk of developing heart disease, and may include recommendations for dietary intake of total daily calories, total fat, saturated fat, polyunsaturated fat, monounsaturated fat, carbohydrate, protein, cholesterol, insoluble fiber, as well as recommendations for physical activity.

"Triglyceride" means a lipid or neutral fat consisting of glycerol combined with three fatty acid molecules.

"Type 2 diabetes" (also known as "type 2 diabetes mellitus" or "diabetes mellitus, type 2", and formerly called "diabetes mellitus type 2", "non-insulin-dependent diabetes (NIDDM)", "obesity related diabetes", or "adult-onset diabetes") is a metabolic disorder that is primarily characterized by insulin resistance, relative insulin deficiency, and hyperglycemia.

"Treat" refers to administering a pharmaceutical composition to effect an alteration or improvement of a disease, disorder, or condition.

"Unmodified nucleotide" means a nucleotide composed of naturally occurring nucleobases, sugar moieties, and internucleoside linkages. In certain embodiments, an unmodified nucleotide is a RNA nucleotide (i.e. β-D-ribonucleosides) or a DNA nucleotide (i.e. β-D-deoxyribonucleoside).

CERTAIN EMBODIMENTS

In certain embodiments disclosed herein, ANGPTL3 has the sequence as set forth in GenBank Accession No. NM_014495.2 (incorporated herein as SEQ ID NO: 1). In certain embodiments, ANGPTL3 has the sequence as set forth in GenBank Accession No. NT_032977.9 nucleotides 33032001 to 33046000 (incorporated herein as SEQ ID NO: 2).

Certain embodiments disclosed herein provide compounds or compositions comprising a modified oligonucleotide consisting of 12 to 30 nucleosides having a nucleobase sequence comprising at least 8 contiguous nucleobases complementary to an equal length portion of SEQ ID NOs: 1-2.

Certain embodiments disclosed herein provide compounds or compositions comprising a modified oligonucleotide 12 to 30 linked nucleosides in length targeted to ANGPTL3. The ANGPTL target can have a sequence selected from any one of SEQ ID NOs: 1-2.

Certain embodiments disclosed herein provide compounds or compositions comprising a modified oligonucleotide consisting of 12 to 30 linked nucleosides and comprising a nucleobase sequence comprising a portion of at least 8 contiguous nucleobases complementary to an equal length portion of nucleobases 1140 to 1159 of SEQ ID NO: 1, wherein the nucleobase sequence of the modified oligonucleotide is at least 80% complementary to SEQ ID NO: 1. In certain embodiments, the modified oligonucleotide is at least 8, least 9, least 10, least 11, at least 12, least 13, at least 14, at least 15, at least 16, least 17, least 18, least 19, or 20 contiguous nucleobases complementary to an equal length portion of nucleobases 1140 to 1159 of SEQ ID NO: 1.

Certain embodiments disclosed herein provide compounds or compositions comprising a modified oligonucleotide consisting of 12 to 30 linked nucleosides and comprising a nucleobase sequence complementary to nucleobases 1140 to 1159 of SEQ ID NO: 1, wherein the nucleobase sequence of the modified oligonucleotide is at least 80% complementary to SEQ ID NO: 1.

Certain embodiments disclosed herein provide compounds or compositions comprising a modified oligonucleotide consisting of 12 to 30 linked nucleosides and comprising a nucleobase sequence comprising a portion of at least 8 contiguous nucleobases complementary to an equal length portion of nucleobases 1907 to 1926 of SEQ ID NO: 1, wherein the nucleobase sequence of the modified oligonucleotide is at least 80% complementary to SEQ ID NO: 1. In certain embodiments, the modified oligonucleotide is at least 8, least 9, least 10, least 11, at least 12, least 13, at least 14, at least 15, at least 16, least 17, least 18, least 19, or 20 contiguous nucleobases complementary to an equal length portion of nucleobases 1907 to 1926 of SEQ ID NO: 1.

Certain embodiments disclosed herein provide compounds or compositions comprising a modified oligonucleotide consisting of 12 to 30 linked nucleosides and comprising a nucleobase sequence complementary to nucleobases 1907 to 1926 of SEQ ID NO: 1, wherein the nucleobase sequence of the modified oligonucleotide is at least 80% complementary to SEQ ID NO: 1.

Certain embodiments disclosed herein provide compounds or compositions comprising a modified oligonucleotide consisting of 12 to 30 linked nucleosides and comprising a nucleobase sequence comprising a portion of at least 8 contiguous nucleobases complementary to an equal length portion of nucleobases 147 to 162 of SEQ ID NO: 1, wherein the nucleobase sequence of the modified oligonucleotide is at least 80% complementary to SEQ ID NO: 1. In certain embodiments, the modified oligonucleotide is at least 8, least 9, least 10, least 11, at least 12, least 13, at least 14, at least 15, or 16 contiguous nucleobases complementary to an equal length portion of nucleobases 147 to 162 of SEQ ID NO: 1.

Certain embodiments disclosed herein provide compounds or compositions comprising a modified oligonucleotide consisting of 12 to 30 linked nucleosides and comprising a nucleobase sequence complementary to nucleobases 147 to 162 of SEQ ID NO: 1, wherein the nucleobase sequence of the modified oligonucleotide is at least 80% complementary to SEQ ID NO: 1.

In certain embodiments, the modified oligonucleotide consists of 12 to 30, 15 to 30, 18 to 24, 19 to 22, 13 to 25, 14 to 25, 15 to 25 or 16 to 24 linked nucleosides. In certain embodiments, the modified oligonucleotide consists of 8, 9, 10, 11, 12, 13, 14, 15, 16, 17, 18, 19, 20, 21, 22, 23, 24, 25, 26, 27, 28, 29 or 30 linked nucleosides or a range defined by any two of these values. In certain embodiments, the modified oligonucleotide is 16 linked nucleosides in length. In certain embodiments, the modified oligonucleotide is 20 linked nucleosides in length.

In certain embodiments, the modified oligonucleotide comprises a nucleobase sequence comprising a portion of at least 8, least 9, least 10, least 11, at least 12, least 13, at least 14, at least 15, at least 16, least 17, least 18, least 19, or 20 contiguous nucleobases complementary to an equal length portion of SEQ ID NO: 1 or 2.

Certain embodiments disclosed herein provide compounds or compositions comprising a modified oligonucleotide consisting of 12 to 30 linked nucleosides and having a nucleobase sequence comprising at least 8, least 9, least 10, least 11, at least 12, least 13, at least 14, at least 15, at least 16, least 17, least 18, least 19, or 20 contiguous nucleobases of a nucleobase sequence selected from any one of SEQ ID NOs: 15-27, 30-73, 75-85, 87-232, 238, 240-243, 245-247, 249-262, 264-397, 399-469, 471-541, 543-600, 604-760, 762-819, 821-966, 968-971, 973-975, 977-990, 992-1110, 1112-1186, 1188-1216, 1218-1226, 1228-1279, 1281-1293, 1295-1304, 1306-1943, 1945-1951, 1953-1977, 1979-1981, 1983-2044, 2046-2097, 2099-2181, 2183-2232, 2234-2238, 2240-2258, 2260-2265, 2267-2971, 2973-2976, 2978-4162, 4164-4329, 4331-4389, 4391-4394, 4396-4877.

Certain embodiments disclosed herein provide compounds or compositions comprising a modified oligonucleotide consisting of 12 to 30 linked nucleosides and having a nucleobase sequence comprising at least 8, least 9, least 10, least 11, at least 12, least 13, at least 14, at least 15, at least 16, least 17, least 18, least 19, or 20 contiguous nucleobases of the nucleobase sequences of SEQ ID NOs: 77.

Certain embodiments disclosed herein provide compounds or compositions comprising a modified oligonucleotide consisting of 12 to 30 linked nucleosides and having a nucleobase sequence comprising at least 8, least 9, least 10, least 11, at least 12, least 13, at least 14, at least 15, at least 16, least 17, least 18, least 19, or 20 contiguous nucleobases of the nucleobase sequence of SEQ ID NO: 20.

Certain embodiments disclosed herein provide compounds or compositions comprising a modified oligonucleotide consisting of 12 to 30 linked nucleosides and having a nucleobase sequence comprising at least 8, least 9, least 10, least 11, at least 12, least 13, at least 14, at least 15, or 16 contiguous nucleobases of the nucleobase sequence of SEQ ID NO: 110.

In certain embodiments, the nucleobase sequence of the modified oligonucleotide is at least 70%, 75%, 80%, 85%, 90%, 95% or 100% complementary to any one of SEQ ID NO: 1-2 as measured over the entirety of the modified oligonucleotide.

In certain embodiments, the compound disclosed herein is a single-stranded oligonucleotide. In certain embodiments, the compound disclosed herein is a single-stranded modified oligonucleotide.

In certain embodiments, at least one internucleoside linkage of said modified oligonucleotide is a modified internucleoside linkage. In certain embodiments, each internucleoside linkage is a phosphorothioate internucleoside linkage.

In certain embodiments, at least one nucleoside of the modified oligonucleotide comprises a modified sugar. In certain embodiments, at least one modified sugar is a bicyclic sugar. In certain embodiments, at least one modified sugar comprises a 2'-O-methoxyethyl, a constrained ethyl, a 3'-fluoro-HNA or a 4'-(CH$_2$)$_n$—O-2' bridge, wherein n is 1 or 2.

In certain embodiments, at least one nucleoside of said modified oligonucleotide comprises a modified nucleobase. In certain embodiments, the modified nucleobase is a 5-methylcytosine.

Certain embodiments disclosed herein provide compounds or compositions comprising a modified oligonucleotide with: a) a gap segment consisting of linked deoxynucleosides; b) a 5' wing segment consisting of linked nucleosides; and c) a 3' wing segment consisting of linked nucleosides. The gap segment is positioned between the 5' wing segment and the 3' wing segment and each nucleoside of each wing segment comprises a modified sugar.

In certain embodiments, the modified oligonucleotide consists of 12 to 30 linked nucleosides and comprises: a gap segment consisting of linked deoxynucleosides; a 5' wing segment consisting of linked nucleosides; a 3' wing segment consisting of linked nucleosides; wherein the gap segment is positioned between the 5' wing segment and the 3' wing segment and wherein each nucleoside of each wing segment comprises a modified sugar.

In certain embodiments, the compounds or compositions disclosed herein comprise a modified oligonucleotide consisting of 20 linked nucleosides having a nucleobase sequence comprising at least 8 contiguous nucleobases complementary to an equal length portion of SEQ ID NO: 1-2, wherein the modified oligonucleotide comprises: a gap segment consisting of ten linked deoxynucleosides; a 5' wing segment consisting of five linked nucleosides; and a 3' wing segment consisting of five linked nucleosides; wherein the gap segment is positioned between the 5' wing segment and the 3' wing segment; wherein each nucleoside of each wing segment comprises a 2'-O-methoxyethyl sugar; wherein each internucleoside linkage is a phosphorothioate linkage and wherein each cytosine residue is a 5-methylcytosine.

In certain embodiments, the modified oligonucleotide consists of 20 linked nucleosides and comprises: a gap segment consisting of ten linked deoxynucleosides; a 5' wing segment consisting of five linked nucleosides; a 3' wing segment consisting of five linked nucleosides; wherein the gap segment is positioned between the 5' wing segment and the 3' wing segment; wherein each nucleoside of each wing segment comprises a 2'-O-methoxyethyl sugar; wherein each internucleoside linkage is a phosphorothioate linkage and wherein each cytosine residue is a 5-methylcytosine.

In certain embodiments, the compounds or compositions disclosed herein comprise a modified oligonucleotide consisting of 20 linked nucleosides having a nucleobase sequence comprising at least 8 contiguous nucleobases of a nucleobase sequence selected of SEQ ID NO: 77, wherein the modified oligonucleotide comprises: a gap segment consisting of ten linked deoxynucleosides; a 5' wing segment consisting of five linked nucleosides; and a 3' wing segment consisting of five linked nucleosides; wherein the gap segment is positioned between the 5' wing segment and the 3' wing segment; wherein each nucleoside of each wing segment comprises a 2'-O-methoxyethyl sugar; wherein each internucleoside linkage is a phosphorothioate linkage and wherein each cytosine residue is a 5-methylcytosine.

In certain embodiments, the modified oligonucleotide consists of 20 linked nucleosides with the nucleobase sequence of SEQ ID NO: 77 and comprises: a gap segment consisting of ten linked deoxynucleosides; a 5' wing segment consisting of five linked nucleosides; a 3' wing segment consisting of five linked nucleosides; wherein the gap segment is positioned between the 5' wing segment and the 3' wing segment; wherein each nucleoside of each wing segment comprises a 2'-O-methoxyethyl sugar; wherein each internucleoside linkage is a phosphorothioate linkage and wherein each cytosine residue is a 5-methylcytosine.

In certain embodiments, the modified oligonucleotide is ISIS 563580. In certain embodiments, ISIS 563580 is characterized as a 5-10-5 MOE gapmer, having a sequence of (from 5' to 3') GGACATTGCCAGTAATCGCA (incorporated herein as SEQ ID NO: 77), wherein each internucleoside linkage is a phosphorothioate linkage, each cytosine is a 5'-methylcytosine, each of nucleosides 1-5 and 16-20 are 2'-O-methoxyethyl modified nucleosides, and each of nucleosides 6-15 are 2'-deoxynucleosides.

In certain embodiments, ISIS 563580 is described by the following chemical notation having SEQ ID NO: 77: Ges Ges Aes mCes Aes Tds Tds Gds mCds mCds Ads Gds Tds Ads Ads Tes mCes Ges mCes Ae; wherein, A=an adenine,
mC=a 5'-methylcytosine
G=a guanine,
T=a thymine,
e=a 2'-O-methoxyethyl modified nucleoside,
d=a 2'-deoxynucleoside, and
s=a phosphorothioate internucleoside linkage.

In certain embodiments, ISIS 563580 is described by the following chemical structure having SEQ ID NO: 77:

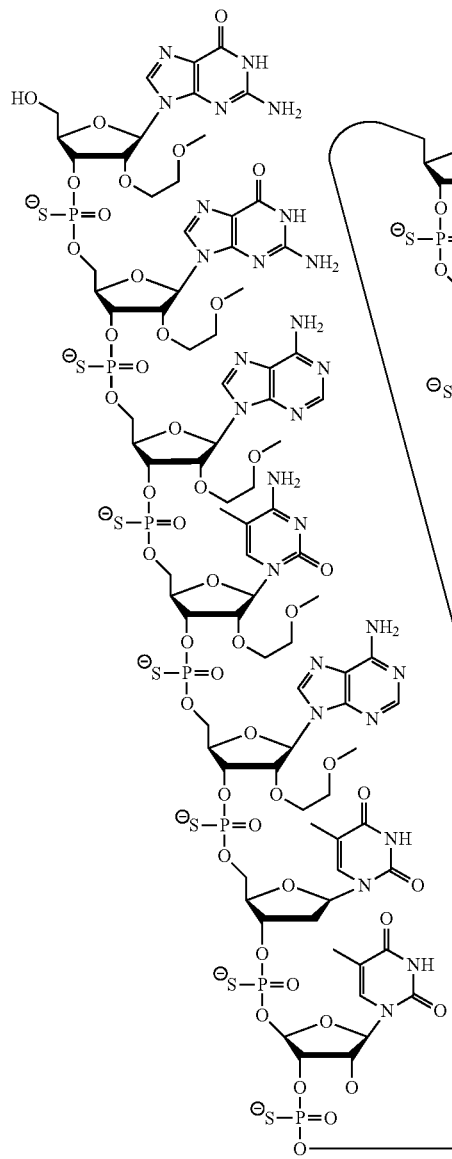
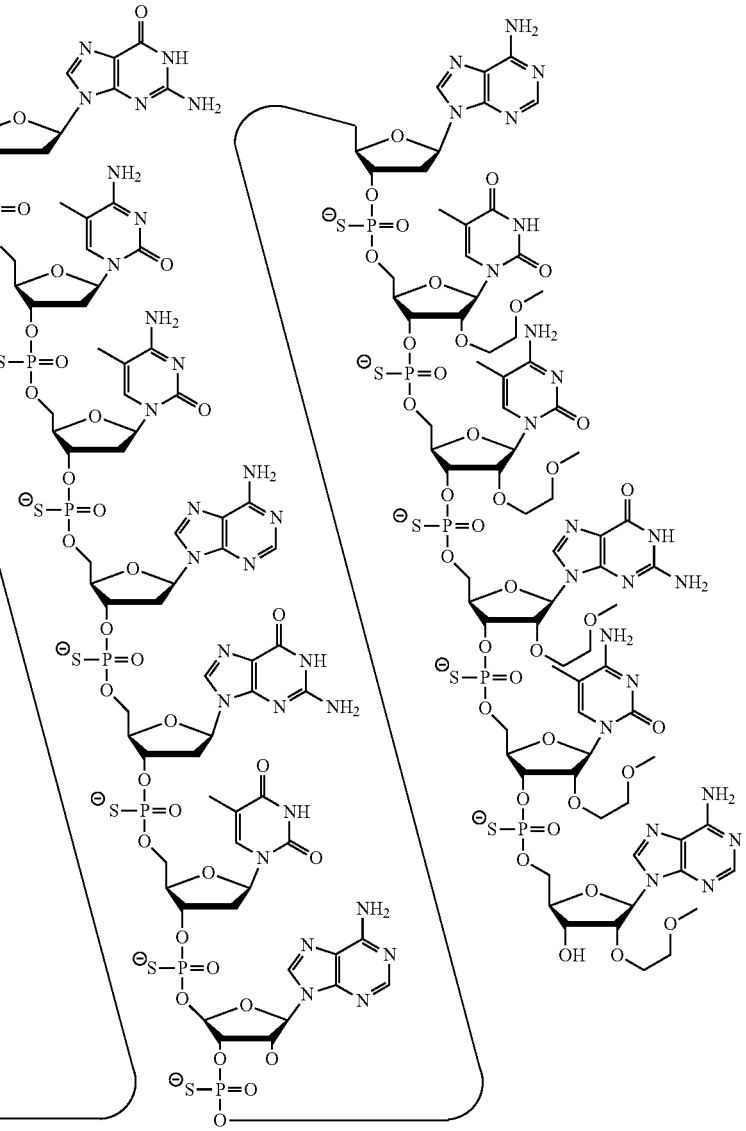

In certain embodiments, the modified oligonucleotide comprises ISIS 563580 represented by the preceeding chemical structure.

In certain embodiments, the compounds or compositions disclosed herein comprise a modified oligonucleotide consisting of 20 linked nucleosides having a nucleobase sequence comprising at least 8 contiguous nucleobases of a nucleobase sequence selected of SEQ ID NO: 20, wherein the modified oligonucleotide comprises: a gap segment consisting of ten linked deoxynucleosides; a 5' wing segment consisting of five linked nucleosides; and a 3' wing segment consisting of five linked nucleosides; wherein the gap segment is positioned between the 5' wing segment and the 3' wing segment; wherein each nucleoside of each wing segment comprises a 2'-O-methoxyethyl sugar; wherein each internucleoside linkage is a phosphorothioate linkage and wherein each cytosine residue is a 5-methylcytosine.

In certain embodiments, the modified oligonucleotide consists of 20 linked nucleosides with the nucleobase sequence of SEQ ID NO: 20 and comprises: a gap segment consisting of ten linked deoxynucleosides; a 5' wing segment consisting of five linked nucleosides; a 3' wing segment consisting of five linked nucleosides; wherein the gap segment is positioned between the 5' wing segment and the 3' wing segment; wherein each nucleoside of each wing segment comprises a 2'-O-methoxyethyl sugar; wherein each internucleoside linkage is a phosphorothioate linkage and wherein each cytosine residue is a 5-methylcytosine.

In certain embodiments, the compounds or compositions disclosed herein comprise a modified oligonucleotide consisting of 16 linked nucleosides having a nucleobase sequence comprising at least 8 contiguous nucleobases of a nucleobase sequence of SEQ ID NO: 110, wherein the modified oligonucleotide comprises: a gap segment consisting of ten linked deoxynucleosides; a 5' wing segment consisting of three linked nucleosides; and a 3' wing segment consisting of three linked nucleosides; wherein the gap segment is positioned between the 5' wing segment and the 3' wing segment; wherein each wing segment comprises at least one 2'-O-methoxyethyl sugar and at least one cEt sugar; wherein each internucleoside linkage is a phosphorothioate linkage and wherein each cytosine residue is a 5-methylcytosine.

In certain embodiments, the modified oligonucleotide consists of 16 linked nucleosides with the nucleobase sequence of SEQ ID NO: 110 and comprises: a gap segment consisting of ten linked deoxynucleosides; a 5' wing segment consisting of three linked nucleosides; a 3' wing segment consisting of three linked nucleosides; wherein the gap segment is positioned between the 5' wing segment and the 3' wing segment; wherein each wing segment comprises at least one 2'-O-methoxyethyl sugar and at least one cEt sugar; wherein each internucleoside linkage is a phosphorothioate linkage and wherein each cytosine residue is a 5-methylcytosine.

Certain embodiments provide methods of using the compounds and compositions described herein for inhibiting ANGPTL3 expression. In certain embodiments, the compounds or compositions inhibit ANGPTL3 by at least 5%, at least 10%, at least 20%, at least 30%, at least 35%, at least 40%, at least 45%, at least 50%, at least 55%, at least 60%, at least 65%, at least 70%, at least 75%, at least 80%, at least 85%, at least 90% or at least 95%. In a preferred embodiment, the antisense compound comprising a modified oligonucleotide decreases ANGPTL3 by at least 50%. In a preferred embodiment, the antisense compound comprising a modified oligonucleotide decreases ANGPTL3 by at least 55%. In a preferred embodiment the antisense compound comprising a modified oligonucleotide decreases ANGPTL3 by at least 60%. In a preferred embodiment, the antisense compound comprising a modified oligonucleotide decreases ANGPTL3 by at least 65%. In a preferred embodiment, the antisense compound comprising a modified oligonucleotide decreases ANGPTL3 by at least 70%. In a preferred embodiment, the antisense compound comprising a modified oligonucleotide decreases ANGPTL3 by at least 75%. In a preferred embodiment, the antisense compound comprising a modified oligonucleotide decreases ANGPTL3 by at least 80%. In a preferred embodiment, the antisense compound comprising a modified oligonucleotide decreases ANGPTL3 by at least 85%. In a preferred embodiment, the antisense compound comprising a modified oligonucleotide decreases ANGPTL3 by at least 90%. In a preferred embodiment, the antisense compound comprising a modified oligonucleotide decreases ANGPTL3 by at least 95%.

Certain embodiments provide methods of using the compounds and compositions described herein for reducing one or more of triglycerides, LDL-cholesterol, non-HDL cholesterol, VLDL-cholesterol, total cholesterol, ApoB and ApoC-III. In certain embodiments, the compounds or compositions reduce one or more of triglycerides, LDL-cholesterol, non-HDL cholesterol, VLDL-cholesterol, total cholesterol, ApoB and ApoC-III by at least 5%, at least 10%, at least 20%, at least 30%, at least 35%, at least 40%, at least 45%, at least 50%, at least 55%, at least 60%, at least 65%, at least 70%, at least 75%, at least 80%, at least 85%, at least 90% or at least 95%.

In certain embodiments, the compounds or compositions disclosed herein have an $IC_{50}$ of less than 20 Ian less than 10 µM, an less than 8 µM, less than 5 µM, less than 2 µM, less than 1 µM, or less than 0.8 µM, when tested human cells, for example, in the Hep3B cell line as described in Examples 2-3 and 7-10.

In certain embodiments, the compounds or compositions disclosed herein are efficacious by virtue of having a viscosity of less than 40 cP, less than 35 cP, less than 30 cP, less than 25 cP, less than 20 cP or less than 15 cP when measured by the parameters as described in Example 13.

In certain embodiments, the compounds or compositions disclosed herein are highly tolerable, as demonstrated by the in vivo tolerability measurements described in the examples. In certain embodiments, the antisense compounds as described herein are highly tolerable, as demonstrated by having an increase in ALT and/or AST value of no more than 4 fold, 3 fold, 2 fold or 1.5 fold over saline treated animals.

In certain embodiments, the compounds or compositions disclosed herein comprise a salt of the modified oligonucleotide.

In certain embodiments, the compounds or compositions disclosed herein further comprise a pharmaceutically acceptable carrier or diluent.

In certain embodiments, the animal is a human.

Certain embodiments provide methods of using the compounds and compositions described herein in therapy. In certain embodiments, the therapy is used in treating, preventing, or slowing progression of a disease related to elevated ANGPTL3. In certain embodiments, the disease is a cardiovascular and/or metabolic disease, disorder or condition. In certain embodiments, the metabolic and/or cardiovascular disease includes, but is not limited to, obesity, diabetes, atherosclerosis, dyslipidemia, lipodystrophy, coronary heart disease, non-alcoholic fatty liver disease (NAFLD), nonalcoholic steatohepatitis (NASH) hyperfattyacidemia or metabolic syndrome, or a combination thereof. The dyslipidemia can be hyperlipidemia. The hyperlipidemia can be combined hyperlipidemia, familial combined hyperlipidemia (FCHL), hypercholesterolemia, hypertriglyceridemia, or both hypercholesterolemia and hypertriglyceridemia. The hypercholesterolemia can be familial homozygous hypercholesterolemia (HoFH), familial heterozygous hypercholesterolemia (HeFH). The hypertriglyceridemia can be familial chylomicronemia syndrome (FCS) or hyperlipoproteinemia Type IV. The NAFLD can be hepatic steatosis or steatohepatitis. The diabetes can be type 2 diabetes or type 2 diabetes with dyslipidemia.

In certain embodiments, the compounds or compositions disclosed herein are designated as a first agent and the methods or uses disclosed herein further comprise administering a second agent. In certain embodiments, the first agent and the second agent are co-administered. In certain embodiments the first agent and the second agent are co-administered sequentially or concomitantly.

In certain embodiments, the second agent is a glucose-lowering agent. The glucose lowering agent can include, but is not limited to, a therapeutic lifestyle change, PPAR agonist, a dipeptidyl peptidase (IV) inhibitor, a GLP-1 analog, insulin or an insulin analog, an insulin secretagogue, a SGLT2 inhibitor, a human amylin analog, a biguanide, an alpha-glucosidase inhibitor, or a combination thereof. The glucose-lowering agent can include, but is not limited to metformin, sulfonylurea, rosiglitazone, meglitinide, thiazolidinedione, alpha-glucosidase inhibitor or a combination thereof. The sulfonylurea can be acetohexamide, chlorpropamide, tolbutamide, tolazamide, glimepiride, a glipizide, a glyburide, or a gliclazide. The meglitinide can be nateglinide or repaglinide. The thiazolidinedione can be pioglitazone or rosiglitazone. The alpha-glucosidase can be acarbose or miglitol.

In certain embodiments, the second agent is a lipid-lowering therapy. In certain embodiments the lipid lowering therapy can include, but is not limited to, a therapeutic lifestyle change, HMG-CoA reductase inhibitor, cholesterol absorption inhibitor, MTP inhibitor (e.g., a small molecule, polypeptide, antibody or antisense compound targeted to MTP), ApoB inhibitor (e.g., a small molecule, polypeptide, antibody or antisense compound targeted to ApoB), ApoC3 inhibitor (e.g., a small molecule, polypeptide, antibody or antisense compound targeted to ApoC3), PCSK9 inhibitor (e.g., a small molecule, polypeptide, antibody or antisense compound targeted to PCSK9), CETP inhibitor (e.g., a small molecule, polypeptide, antibody or antisense compound targeted to CETP), fibrate, beneficial oil (e.g., krill or fish oils (e.g., Vascepa®), flaxseed oil, or other oils rich in omega-3 fatty acids such as α-linolenic acid (ALA), docosahexaenoic acid (DHA) or eicosapentaenoic acid (EPA)), or any combination thereof. The HMG-CoA reductase inhibitor can be atorvastatin, rosuvastatin, fluvastatin, lovastatin, pravastatin, or simvastatin. The cholesterol absorption inhibitor can be ezetimibe. The fibrate can be fenofibrate, bezafibrate, ciprofibrate, clofibrate, gemfibrozil and the like.

In certain embodiments, administration comprises parenteral administration.

In certain embodiments, administering a compound disclosed herein results in a reduction of lipid levels, including triglyceride levels, cholesterol levels, insulin resistance, glucose levels or a combination thereof. One or more of the levels can be independently reduced by at least 5%, at least 10%, at least 20%, at least 30%, at least 35%, at least 40%, at least 45%, at least 50%, at least 55%, at least 60%, at least 65%, at least 70%, at least 75%, at least 80%, at least 85%, at least 90% or at least 95%. Administering the compound can result in improved insulin sensitivity or hepatic insulin sensitivity. Administering the compound disclosed herein can result in a reduction in atherosclerotic plaques, obesity, glucose, lipids, glucose resistance, cholesterol, or improvement in insulin sensitivity or any combination thereof.

Certain embodiments provide the use of a compound as described herein in the manufacture of a medicament for treating, ameliorating, delaying or preventing one or more of a metabolic disease or a cardiovascular disease.

Certain embodiments provide a kit for treating, preventing, or ameliorating one or more of a metabolic disease or a cardiovascular disease as described herein wherein the kit comprises: a) a compound as described herein; and optionally b) an additional agent or therapy as described herein. The kit can further include instructions or a label for using the kit to treat, prevent, or ameliorate one or more of a metabolic disease or a cardiovascular disease.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound can be "antisense" to a target nucleic acid, meaning that is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to ANGPTL3 nucleic acid is 10 to 30 nucleotides in length. In other words, antisense compounds are from 10 to 30 linked nucleobases. In other embodiments, the antisense compound comprises a modified oligonucleotide consisting of 8 to 80, 10 to 80, 12 to 50, 12 to 30, 15 to 30, 18 to 24, 19 to 22, or 20 linked nucleobases. In certain such embodiments, the antisense compound comprises a modified oligonucleotide consisting of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked nucleobases in length, or a range defined by any two of the above values.

In certain embodiments, the antisense compound comprises a shortened or truncated modified oligonucleotide. The shortened or truncated modified oligonucleotide can have a single nucleoside deleted from the 5' end (5' truncation), or alternatively from the 3' end (3' truncation). A shortened or truncated oligonucleotide can have two or more nucleosides deleted from the 5' end, or alternatively can have two or more nucleosides deleted from the 3' end. Alternatively, the deleted nucleosides can be dispersed throughout the modified oligonucleotide, for example, in an antisense compound having one or more nucleoside deleted from the 5' end and one or more nucleoside deleted from the 3' end.

When a single additional nucleoside is present in a lengthened oligonucleotide, the additional nucleoside can be located at the 5', 3' end or central portion of the oligonucleotide. When two or more additional nucleosides are present, the added nucleosides can be adjacent to each other, for example, in an oligonucleotide having two nucleosides added to the 5' end (5' addition), or alternatively to the 3' end (3' addition) or the central portion, of the oligonucleotide. Alternatively, the added nucleoside can be dispersed throughout the antisense compound, for example, in an oligonucleotide having one or more nucleoside added to the 5' end, one or more nucleoside added to the 3' end, and/or one or more nucleoside added to the central portion.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Certain Antisense Compound Motifs and Mechanisms

In certain embodiments, antisense compounds have chemically modified subunits arranged in patterns, or motifs, to confer to the antisense compounds properties such as enhanced inhibitory activity, increased binding affinity for a target nucleic acid, or resistance to degradation by in vivo nucleases. Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may confer another desired property e.g., serve as a substrate for the cellular endonuclease RNase H, which cleaves the RNA strand of an RNA:DNA duplex.

Antisense activity may result from any mechanism involving the hybridization of the antisense compound (e.g., oligonucleotide) with a target nucleic acid, wherein the hybridization ultimately results in a biological effect. In certain embodiments, the amount and/or activity of the target nucleic acid is modulated. In certain embodiments, the amount and/or activity of the target nucleic acid is reduced. In certain embodiments, hybridization of the antisense compound to the target nucleic acid ultimately results in target nucleic acid degradation. In certain embodiments, hybridization of the antisense compound to the target nucleic acid does not result in target nucleic acid degradation. In certain such embodiments, the presence of the antisense compound hybridized with the target nucleic acid (occupancy) results in a modulation of antisense activity. In certain embodiments, antisense compounds having a particular chemical motif or pattern of chemical modifications are particularly suited to exploit one or more mechanisms. In certain embodiments, antisense compounds function through more than one mechanism and/or through mechanisms that have not been elucidated. Accordingly, the antisense compounds described herein are not limited by particular mechanism.

Antisense mechanisms include, without limitation, RNase H mediated antisense; RNAi mechanisms, which utilize the RISC pathway and include, without limitation, siRNA, ssRNA and microRNA mechanisms; and occupancy based mechanisms. Certain antisense compounds may act through more than one such mechanism and/or through additional mechanisms.

RNase H-Mediated Antisense

In certain embodiments, antisense activity results at least in part from degradation of target RNA by RNase H. RNase H is a cellular endonuclease that cleaves the RNA strand of an RNA:DNA duplex. It is known in the art that single-stranded antisense compounds which are "DNA-like" elicit RNase H activity in mammalian cells. Accordingly, antisense compounds comprising at least a portion of DNA or DNA-like nucleosides may activate RNase H, resulting in cleavage of the target nucleic acid. In certain embodiments, antisense compounds that utilize RNase H comprise one or more modified nucleosides. In certain embodiments, such antisense compounds comprise at least one block of 1-8 modified nucleosides. In certain such embodiments, the modified nucleosides do not support RNase H activity. In certain embodiments, such antisense compounds are gapmers, as described herein. In certain such embodiments, the gap of the gapmer comprises DNA nucleosides. In certain such embodiments, the gap of the gapmer comprises DNA-like nucleosides. In certain such embodiments, the gap of the gapmer comprises DNA nucleosides and DNA-like nucleosides.

Certain antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE and 2'-O—CH$_3$, among others), and bicyclic sugar modified nucleosides (such bicyclic sugar modified nucleosides may include those having a constrained ethyl). In certain embodiments, nucleosides in the wings may include several modified sugar moieties, including, for example 2'-MOE and bicyclic sugar moieties such as constrained ethyl or LNA. In certain embodiments, wings may include several modified and unmodified sugar moieties. In certain embodiments, wings may include various combinations of 2'-MOE nucleosides, bicyclic sugar moieties such as constrained ethyl nucleosides or LNA nucleosides, and 2'-deoxynucleosides.

Each distinct region may comprise uniform sugar moieties, variant, or alternating sugar moieties. The wing-gap-wing motif is frequently described as "X—Y—Z", where "X" represents the length of the 5'-wing, "Y" represents the length of the gap, and "Z" represents the length of the 3'-wing. "X" and "Z" may comprise uniform, variant, or alternating sugar moieties. In certain embodiments, "X" and "Y" may include one or more 2'-deoxynucleosides. "Y" may comprise 2'-deoxynucleosides. As used herein, a gapmer described as "X—Y—Z" has a configuration such that the gap is positioned immediately adjacent to each of the 5'-wing and the 3' wing. Thus, no intervening nucleotides exist between the 5'-wing and gap, or the gap and the 3'-wing. Any of the antisense compounds described herein can have a gapmer motif. In certain embodiments, "X" and "Z" are the same; in other embodiments they are different. In certain embodiments, "Y" is between 8 and 15 nucleosides. X, Y, or Z can be any of 1, 2, 3, 4, 5, 6, 7, 8, 9, 10, 11, 12, 13, 14, 15, 16, 17, 18, 19, 20, 25, 30 or more nucleosides.

In certain embodiments, the antisense compound targeted to an ANGPTL3 nucleic acid has a gapmer motif in which the gap consists of 6, 7, 8, 9, 10, 11, 12, 13, 14, 15, or 16 linked nucleosides.

In certain embodiments, the antisense oligonucleotide has a sugar motif described by Formula A as follows: $(J)_m\text{-}(B)_n\text{-}(J)_p\text{-}(B)_r\text{-}(A)_t\text{-}(D)_g\text{-}(A)_v\text{-}(B)_w\text{-}(J)_x\text{-}(B)_y\text{-}(J)_z$.

wherein:
each A is independently a 2'-substituted nucleoside;
each B is independently a bicyclic nucleoside;
each J is independently either a 2'-substituted nucleoside or a 2'-deoxynucleoside;
each D is a 2'-deoxynucleoside;
m is 0-4; n is 0-2; p is 0-2; r is 0-2; t is 0-2; v is 0-2; w is 0-4; x is 0-2; y is 0-2; z is 0-4; g is 6-14; provided that:
at least one of m, n, and r is other than 0;
at least one of w and y is other than 0;
the sum of m, n, p, r, and t is from 2 to 5; and
the sum of v, w, x, y, and z is from 2 to 5.

RNAi Compounds

In certain embodiments, antisense compounds are interfering RNA compounds (RNAi), which include double-stranded RNA compounds (also referred to as short-interfering RNA or siRNA) and single-stranded RNAi compounds (or ssRNA). Such compounds work at least in part through the RISC pathway to degrade and/or sequester a target nucleic acid (thus, include microRNA/microRNA-mimic compounds). In certain embodiments, antisense compounds comprise modifications that make them particularly suited for such mechanisms.

i. ssRNA Compounds

In certain embodiments, antisense compounds including those particularly suited for use as single-stranded RNAi compounds (ssRNA) comprise a modified 5'-terminal end. In certain such embodiments, the 5'-terminal end comprises a modified phosphate moiety. In certain embodiments, such modified phosphate is stabilized (e.g., resistant to degradation/cleavage compared to unmodified 5'-phosphate). In certain embodiments, such 5'-terminal nucleosides stabilize the 5'-phosphorous moiety. Certain modified 5'-terminal nucleosides may be found in the art, for example in WO/2011/139702.

In certain embodiments, the 5'-nucleoside of an ssRNA compound has Formula IIc:

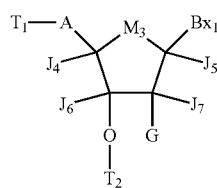

wherein:

$T_1$ is an optionally protected phosphorus moiety;

$T_2$ is an internucleoside linking group linking the compound of Formula IIc to the oligomeric compound;

A has one of the formulas:

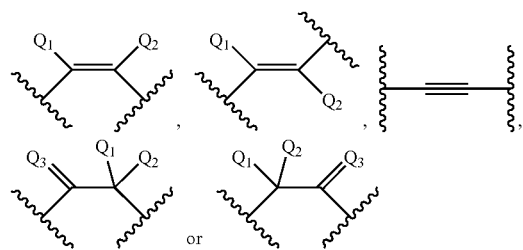

$Q_1$ and $Q_2$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, substituted $C_2$-$C_6$ alkynyl or $N(R_3)(R_4)$;

$Q_3$ is O, S, $N(R_5)$ or $C(R_6)(R_7)$;

each $R_3$, $R_4$ $R_5$, $R_6$ and $R_7$ is, independently, H, $C_1$-$C_6$ alkyl, substituted $C_1$-$C_6$ alkyl or $C_1$-$C_6$ alkoxy;

$M_3$ is O, S, $NR_{14}$, $C(R_{15})(R_{16})$, $C(R_{15})(R_{16})C(R_{17})(R_{18})$, $C(R_{15})$=$C(R_{17})$, $OC(R_{15})(R_{16})$ or $OC(R_{15})(Bx_2)$;

$R_{14}$ is H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

$R_{15}$, $R_{16}$, $R_{17}$ and $R_{18}$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

$Bx_1$ is a heterocyclic base moiety;

or if $Bx_2$ is present then $Bx_2$ is a heterocyclic base moiety and $Bx_1$ is H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

$J_4$, $J_5$, $J_6$ and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

or $J_4$ forms a bridge with one of $J_5$ or $J_7$ wherein said bridge comprises from 1 to 3 linked biradical groups selected from O, S, $NR_{19}$, $C(R_{20})(R_{21})$, $C(R_{20})$=$C(R_{21})$, g=$C(R_{20})(R_{21})$] and C(=O) and the other two of $J_5$, $J_6$ and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

each $R_{19}$, $R_{20}$ and $R_{21}$ is, independently, H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

G is H, OH, halogen or O—$[C(R_8)(R_9)]_n$—$[(C$=$O)_m$—$X_1]_j$—Z;

each $R_8$ and $R_9$ is, independently, H, halogen, $C_1$-$C_6$ alkyl or substituted $C_1$-$C_6$ alkyl;

$X_1$ is O, S or $N(E_1)$;

Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to about 6;

m is 0 or 1;

j is 0 or 1;

each substituted group comprises one or more optionally protected substituent groups independently selected from halogen, $OJ_1$, $N(J_1)(J_2)$, =$NJ_1$, $SJ_1$, $N_3$, CN, $OC$(=$X_2$)$J_1$, $OC$(=$X_2$)$N(J_1)(J_2)$ and C(=$X_2$)$N(J_1)(J_2)$;

$X_2$ is O, S or $NJ_3$;

each $J_1$, $J_2$ and $J_3$ is, independently, H or $C_1$-$C_6$ alkyl;

when j is 1 then Z is other than halogen or N(E2)(E3); and wherein said oligomeric compound comprises from 8 to 40 monomeric subunits and is hybridizable to at least a portion of a target nucleic acid.

In certain embodiments, $M_3$ is O, CH=CH, $OCH_2$ or $OC(H)(Bx_2)$. In certain embodiments, $M_3$ is O.

In certain embodiments, $J_4$, $J_5$, $J_6$ and $J_7$ are each H. In certain embodiments, $J_4$ forms a bridge with one of $J_5$ or $J_7$.

In certain embodiments, A has one of the formulas:

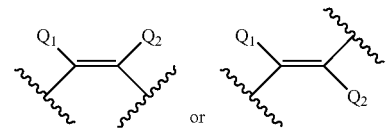

wherein:

$Q_1$ and $Q_2$ are each, independently, H, halogen, $C_1$-$C_6$ alkyl, substituted $C_1$-$C_6$ alkyl, $C_1$-$C_6$ alkoxy or substituted $C_1$-$C_6$ alkoxy. In certain embodiments, $Q_1$ and $Q_2$ are each H. In certain embodiments, $Q_1$ and $Q_2$ are each, independently, H or halogen. In certain embodiments, $Q_1$ and $Q_2$ is H and the other of $Q_1$ and $Q_2$ is F, $CH_3$ or $OCH_3$.

In certain embodiments, $T_1$ has the formula:

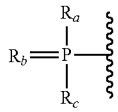

wherein:

$R_a$ and $R_c$ are each, independently, protected hydroxyl, protected thiol, $C_1$-$C_6$ alkyl, substituted $C_1$-$C_6$ alkyl, $C_1$-$C_6$ alkoxy, substituted $C_1$-$C_6$ alkoxy, protected amino or substituted amino; and $R_b$ is O or S. In certain embodiments, $R_b$ is O and $R_a$ and $R_b$ are each, independently, $OCH_3$, $OCH_2CH_3$ or $CH(CH_3)_2$.

In certain embodiments, G is halogen, $OCH_3$, $OCH_2F$, $OCHF_2$, $OCF_3$, $OCH_2CH_3$, $O(CH_2)_2F$, $OCH_2CHF_2$, $OCH_2CF_3$, $OCH_2$—$CH$=$CH_2$, $O(CH_2)_2$—$OCH_3$, $O(CH_2)_2$—$SCH_3$, $O(CH_2)_2$—$OCF_3$, $O(CH_2)_3$—$N(R_{10})(R_{11})$, $O(CH_2)_2$—$ON(R_{10})(R_{11})$, $O(CH_2)_2$—$O(CH_2)_2$—$N(R_{10})(R_{11})$, $OCH_2C$(=O)—$N(R_{10})(R_{11})$, $OCH_2C$(=O)—$N(R_{12})$—$(CH_2)_2$—$N(R_{10})(R_{11})$ or $O(CH_2)_2$—$N(R_{12})$—$C$(=$NR_{13}$)[$N(R_{10})(R_{11})$] wherein $R_{10}$, $R_{11}$, $R_{12}$ and $R_{13}$ are each, independently, H or $C_1$-$C_6$ alkyl. In certain embodiments, G is halogen, $OCH_3$, $OCF_3$, $OCH_2CH_3$, $OCH_2CF_3$, $OCH_2$—$CH$=$CH_2$, $O(CH_2)_2$—$OCH_3$, $O(CH_2)_2$—$O(CH_2)_2$—$N(CH_3)_2$, $OCH_2C$(=O)—$N(H)CH_3$, $OCH_2C$(=O)—$N(H)$—$(CH_2)_2$—$N(CH_3)_2$ or $OCH_2$—$N(H)$—$C$(=$NH$)$NH_2$. In certain embodiments, G is F, $OCH_3$ or $O(CH_2)_2$—$OCH_3$. In certain embodiments, G is $O(CH_2)_2$—$OCH_3$.

In certain embodiments, the 5'-terminal nucleoside has Formula IIe:

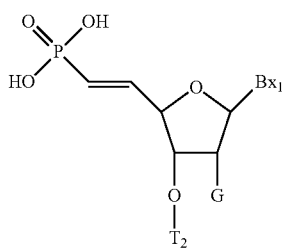

In certain embodiments, antisense compounds, including those particularly suitable for ssRNA comprise one or more type of modified sugar moieties and/or naturally occurring sugar moieties arranged along an oligonucleotide or region thereof in a defined pattern or sugar modification motif. Such motifs may include any of the sugar modifications discussed herein and/or other known sugar modifications.

In certain embodiments, the oligonucleotides comprise or consist of a region having uniform sugar modifications. In certain such embodiments, each nucleoside of the region comprises the same RNA-like sugar modification. In certain embodiments, each nucleoside of the region is a 2'-F nucleoside. In certain embodiments, each nucleoside of the region is a 2'-OMe nucleoside. In certain embodiments, each nucleoside of the region is a 2'-MOE nucleoside. In certain embodiments, each nucleoside of the region is a cEt nucleoside. In certain embodiments, each nucleoside of the region is an LNA nucleoside. In certain embodiments, the uniform region constitutes all or essentially all of the oligonucleotide. In certain embodiments, the region constitutes the entire oligonucleotide except for 1-4 terminal nucleosides.

In certain embodiments, oligonucleotides comprise one or more regions of alternating sugar modifications, wherein the nucleosides alternate between nucleotides having a sugar modification of a first type and nucleotides having a sugar modification of a second type. In certain embodiments, nucleosides of both types are RNA-like nucleosides. In certain embodiments the alternating nucleosides are selected from: 2'-OMe, 2'-F, 2'-MOE, LNA, and cEt. In certain embodiments, the alternating modifications are 2'-F and 2'-OMe. Such regions may be contiguous or may be interrupted by differently modified nucleosides or conjugated nucleosides.

In certain embodiments, the alternating region of alternating modifications each consist of a single nucleoside (i.e., the pattern is $(AB)_xA_y$ wherein A is a nucleoside having a sugar modification of a first type and B is a nucleoside having a sugar modification of a second type; x is 1-20 and y is 0 or 1). In certain embodiments, one or more alternating regions in an alternating motif includes more than a single nucleoside of a type. For example, oligonucleotides may include one or more regions of any of the following nucleoside motifs:

AABBAA;

ABBABB;

AABAAB;

ABBABAABB;

ABABAA;

AABABAB;

ABABAA;

ABBAABBABABAA;

BABBAABBABABAA;
or

ABABBAABBABABAA;

wherein A is a nucleoside of a first type and B is a nucleoside of a second type. In certain embodiments, A and B are each selected from 2'-F, 2'-OMe, BNA, and MOE.

In certain embodiments, oligonucleotides having such an alternating motif also comprise a modified 5' terminal nucleoside, such as those of formula IIc or IIe.

In certain embodiments, oligonucleotides comprise a region having a 2-2-3 motif. Such regions comprises the following motif:

-(A)_2-(B)_x-(A)_2-(C)_y-(A)_3- wherein: A is a first type of modified nucleoside;

B and C, are nucleosides that are differently modified than A, however, B and C may have the same or different modifications as one another;

x and y are from 1 to 15.

In certain embodiments, A is a 2'-OMe modified nucleoside. In certain embodiments, B and C are both 2'-F modified nucleosides. In certain embodiments, A is a 2'-OMe modified nucleoside and B and C are both 2'-F modified nucleosides.

In certain embodiments, oligonucleosides have the following sugar motif:

wherein:

Q is a nucleoside comprising a stabilized phosphate moiety. In certain embodiments, Q is a nucleoside having Formula IIc or IIe;

A is a first type of modified nucleoside;

B is a second type of modified nucleoside;

D is a modified nucleoside comprising a modification different from the nucleoside adjacent to it.

Thus, if y is 0, then D must be differently modified than B and if y is 1, then D must be differently modified than A. In certain embodiments, D differs from both A and B.

X is 5-15;

Y is 0 or 1;

Z is 0-4.

In certain embodiments, oligonucleosides have the following sugar motif:

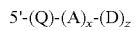

wherein:

Q is a nucleoside comprising a stabilized phosphate moiety. In certain embodiments, Q is a nucleoside having Formula IIc or IIe;

A is a first type of modified nucleoside;

D is a modified nucleoside comprising a modification different from A.

X is 11-30;

Z is 0-4.

In certain embodiments A, B, C, and D in the above motifs are selected from: 2'-OMe, 2'-F, 2'-MOE, LNA, and cEt. In certain embodiments, D represents terminal nucleosides. In certain embodiments, such terminal nucleosides are not designed to hybridize to the target nucleic acid (though one or more might hybridize by chance). In certain embodiments, the nucleobase of each D nucleoside is adenine, regardless of the identity of the nucleobase at the corresponding position of the target nucleic acid. In certain embodiments the nucleobase of each D nucleoside is thymine.

In certain embodiments, antisense compounds, including those particularly suited for use as ssRNA comprise modified internucleoside linkages arranged along the oligonucleotide or region thereof in a defined pattern or modified internucleoside linkage motif. In certain embodiments, oligonucleotides comprise a region having an alternating internucleoside linkage motif. In certain embodiments, oligonucleotides comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate internucleoside linkages. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least one block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

Oligonucleotides having any of the various sugar motifs described herein, may have any linkage motif. For example, the oligonucleotides, including but not limited to those described above, may have a linkage motif selected from non-limiting the table below:

| 5' most linkage | Central region | 3'-region |
| --- | --- | --- |
| PS | Alternating PO/PS | 6 PS |
| PS | Alternating PO/PS | 7 PS |
| PS | Alternating PO/PS | 8 PS | ii. siRNA Compounds

In certain embodiments, antisense compounds are double-stranded RNAi compounds (siRNA). In such embodiments, one or both strands may comprise any modification motif described above for ssRNA. In certain embodiments, ssRNA compounds may be unmodified RNA. In certain embodiments, siRNA compounds may comprise unmodified RNA nucleosides, but modified internucleoside linkages.

Several embodiments relate to double-stranded compositions wherein each strand comprises a motif defined by the location of one or more modified or unmodified nucleosides. In certain embodiments, compositions are provided comprising a first and a second oligomeric compound that are fully or at least partially hybridized to form a duplex region and further comprising a region that is complementary to and hybridizes to a nucleic acid target. It is suitable that such a composition comprise a first oligomeric compound that is an antisense strand having full or partial complementarity to a nucleic acid target and a second oligomeric compound that is a sense strand having one or more regions of complementarity to and forming at least one duplex region with the first oligomeric compound.

The compositions of several embodiments modulate gene expression by hybridizing to a nucleic acid target resulting in loss of its normal function. In some embodiments, the target nucleic acid is ANGPTL3. In certain embodiment, the degradation of the targeted ANGPTL3 is facilitated by an activated RISC complex that is formed with compositions disclosed herein.

Several embodiments are directed to double-stranded compositions wherein one of the strands is useful in, for example, influencing the preferential loading of the opposite strand into the RISC (or cleavage) complex. The compositions are useful for targeting selected nucleic acid molecules and modulating the expression of one or more genes. In some embodiments, the compositions of the present invention hybridize to a portion of a target RNA resulting in loss of normal function of the target RNA.

Certain embodiments are drawn to double-stranded compositions wherein both the strands comprises a hemimer motif, a fully modified motif, a positionally modified motif or an alternating motif. Each strand of the compositions of the present invention can be modified to fulfil a particular role in for example the siRNA pathway. Using a different motif in each strand or the same motif with different chemical modifications in each strand permits targeting the antisense strand for the RISC complex while inhibiting the incorporation of the sense strand. Within this model, each strand can be independently modified such that it is enhanced for its particular role. The antisense strand can be modified at the 5'-end to enhance its role in one region of the RISC while the 3'-end can be modified differentially to enhance its role in a different region of the RISC.

The double-stranded oligonucleotide molecules can be a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. The double-stranded oligonucleotide molecules can be assembled from two separate oligonucleotides, where one strand is the sense strand and the other is the antisense strand, wherein the antisense and sense strands are self-complementary (i.e. each strand comprises nucleotide sequence that is complementary to nucleotide sequence in the other strand; such as where the antisense strand and sense strand form a duplex or double-stranded structure, for example wherein the double-stranded region is about 15 to about 30, e.g., about 15, 16, 17, 18, 19, 20, 21, 22, 23, 24, 25, 26, 27, 28, 29 or 30 base pairs; the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof (e.g., about 15 to about 25 or more nucleotides of the double-stranded oligonucleotide molecule are complementary to the target nucleic acid or a portion thereof). Alternatively, the double-stranded oligonucleotide is assembled from a single oligonucleotide, where the self-complementary sense and antisense regions of the siRNA are linked by means of a nucleic acid based or non-nucleic acid-based linker(s).

The double-stranded oligonucleotide can be a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof. The double-stranded oligonucleotide can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNAi.

In certain embodiments, the double-stranded oligonucleotide comprises separate sense and antisense sequences or regions, wherein the sense and antisense regions are covalently linked by nucleotide or non-nucleotide linkers molecules as is known in the art, or are alternately non-covalently linked by ionic interactions, hydrogen bonding, van der waals interactions, hydrophobic interactions, and/or stacking interactions. In certain embodiments, the double-stranded oligonucleotide comprises nucleotide sequence that is complementary to nucleotide sequence of a target gene. In another embodiment, the double-stranded oligonucleotide interacts with nucleotide sequence of a target gene in a manner that causes inhibition of expression of the target gene.

As used herein, double-stranded oligonucleotides need not be limited to those molecules containing only RNA, but further encompasses chemically modified nucleotides and non-nucleotides. In certain embodiments, the short interfering nucleic acid molecules lack 2'-hydroxy (2'-OH) containing nucleotides. In certain embodiments short interfering nucleic acids optionally do not include any ribonucleotides (e.g., nucleotides having a 2'—OH group). Such double-stranded oligonucleotides that do not require the presence of ribonucleotides within the molecule to support RNAi can however have an attached linker or linkers or other attached or associated groups, moieties, or chains containing one or more nucleotides with 2'—OH groups. Optionally, double-stranded oligonucleotides can comprise ribonucleotides at about 5, 10, 20, 30, 40, or 50% of the nucleotide positions. As used herein, the term siRNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically modified siRNA, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetics. For example, double-stranded oligonucleotides can be used to epigenetically silence genes at both the post-transcriptional level and the pre-transcriptional level. In a non-limiting example, epigenetic regulation of gene expression by siRNA molecules of the invention can result from siRNA mediated modification of chromatin structure or methylation pattern to alter gene expression (see, for example, Verdel et al., 2004, Science, 303, 672-676; Pal-Bhadra et al., 2004, Science, 303, 669-672; Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237).

It is contemplated that compounds and compositions of several embodiments provided herein can target ANGPTL3 by a dsRNA-mediated gene silencing or RNAi mechanism, including, e.g., "hairpin" or stem-loop double-stranded RNA effector molecules in which a single RNA strand with self-complementary sequences is capable of assuming a double-stranded conformation, or duplex dsRNA effector molecules comprising two separate strands of RNA. In various embodiments, the dsRNA consists entirely of ribonucleotides or consists of a mixture of ribonucleotides and deoxynucleotides, such as the RNA/DNA hybrids disclosed, for example, by WO 00/63364, filed Apr. 19, 2000, or U.S. Ser. No. 60/130,377, filed Apr. 21, 1999. The dsRNA or dsRNA effector molecule may be a single molecule with a region of self-complementarity such that nucleotides in one segment of the molecule base pair with nucleotides in another segment of the molecule. In various embodiments, a dsRNA that consists of a single molecule consists entirely of ribonucleotides or includes a region of ribonucleotides that is complementary to a region of deoxyribonucleotides. Alternatively, the dsRNA may include two different strands that have a region of complementarity to each other.

In various embodiments, both strands consist entirely of ribonucleotides, one strand consists entirely of ribonucleotides and one strand consists entirely of deoxyribonucleotides, or one or both strands contain a mixture of ribonucleotides and deoxyribonucleotides. In certain embodiments, the regions of complementarity are at least 70, 80, 90, 95, 98, or 100% complementary to each other and to a target nucleic acid sequence. In certain embodiments, the region of the dsRNA that is present in a double-stranded conformation includes at least 19, 20, 21, 22, 23, 24, 25, 26, 27, 28, 29, 30, 50, 75, 100, 200, 500, 1000, 2000 or 5000 nucleotides or includes all of the nucleotides in a cDNA or other target nucleic acid sequence being represented in the dsRNA. In some embodiments, the dsRNA does not contain any single stranded regions, such as single stranded ends, or the dsRNA is a hairpin. In other embodiments, the dsRNA has one or more single stranded regions or overhangs. In certain embodiments, RNA/DNA hybrids include a DNA strand or region that is an antisense strand or region (e.g, has at least 70, 80, 90, 95, 98, or 100% complementarity to a target nucleic acid) and an RNA strand or region that is a sense strand or region (e.g, has at least 70, 80, 90, 95, 98, or 100% identity to a target nucleic acid), and vice versa.

In various embodiments, the RNA/DNA hybrid is made in vitro using enzymatic or chemical synthetic methods such as those described herein or those described in WO 00/63364, filed Apr. 19, 2000, or U.S. Ser. No. 60/130,377, filed Apr. 21, 1999. In other embodiments, a DNA strand synthesized in vitro is complexed with an RNA strand made in vivo or in vitro before, after, or concurrent with the transformation of the DNA strand into the cell. In yet other embodiments, the dsRNA is a single circular nucleic acid containing a sense and an antisense region, or the dsRNA includes a circular nucleic acid and either a second circular nucleic acid or a linear nucleic acid (see, for example, WO 00/63364, filed Apr. 19, 2000, or U.S. Ser. No. 60/130,377, filed Apr. 21, 1999.) Exemplary circular nucleic acids include lariat structures in which the free 5' phosphoryl group of a nucleotide becomes linked to the 2' hydroxyl group of another nucleotide in a loop back fashion.

In other embodiments, the dsRNA includes one or more modified nucleotides in which the 2' position in the sugar contains a halogen (such as fluorine group) or contains an alkoxy group (such as a methoxy group) which increases the half-life of the dsRNA in vitro or in vivo compared to the corresponding dsRNA in which the corresponding 2' position contains a hydrogen or an hydroxyl group. In yet other embodiments, the dsRNA includes one or more linkages between adjacent nucleotides other than a naturally-occurring phosphodiester linkage. Examples of such linkages include phosphoramide, phosphorothioate, and phosphorodithioate linkages. The dsRNAs may also be chemically modified nucleic acid molecules as taught in U.S. Pat. No. 6,673,661. In other embodiments, the dsRNA contains one or two capped strands, as disclosed, for example, by WO 00/63364, filed Apr. 19, 2000, or U.S. Ser. No. 60/130,377, filed Apr. 21, 1999.

In other embodiments, the dsRNA can be any of the at least partially dsRNA molecules disclosed in WO 00/63364, as well as any of the dsRNA molecules described in U.S. Provisional Application 60/399,998; and U.S. Provisional Application 60/419,532, and PCT/US2003/033466, the teaching of which is hereby incorporated by reference. Any of the dsRNAs may be expressed in vitro or in vivo using the methods described herein or standard methods, such as those described in WO 00/63364.

Occupancy

In certain embodiments, antisense compounds are not expected to result in cleavage or the target nucleic acid via RNase H or to result in cleavage or sequestration through the RISC pathway. In certain such embodiments, antisense activity may result from occupancy, wherein the presence of the hybridized antisense compound disrupts the activity of the target nucleic acid. In certain such embodiments, the antisense compound may be uniformly modified or may comprise a mix of modifications and/or modified and unmodified nucleosides.

Target *Nucleic Acids, Target Regions and Nucleotide Sequences*

Nucleotide sequences that encode ANGPTL3 include, without limitation, the following: the human sequence as set forth in GenBank Accession No. NM_014495.2 (incorporated herein as SEQ ID NO: 1) or GenBank Accession No. NT_032977.9 nucleotides 33032001 to 33046000 (incorporated herein as SEQ ID NO: 2). It is understood that the sequence set forth in each SEQ ID NO in the Examples contained herein is independent of any modification to a sugar moiety, an internucleoside linkage, or a nucleobase. As such, antisense compounds defined by a SEQ ID NO can comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region can encompass a 3' UTR, a 5' UTR, an exon, an intron, an exon/intron junction, a coding region, a translation initiation region, translation termination region, or other defined nucleic acid region. The structurally defined regions for ANGPTL3 can be obtained by accession number from sequence databases such as NCBI and such information is incorporated herein by reference. In certain embodiments, a target region can encompass the sequence from a 5' target site of one target segment within the target region to a 3' target site of another target segment within the target region.

In certain embodiments, a "target segment" is a smaller, sub-portion of a target region within a nucleic acid. For example, a target segment can be the sequence of nucleotides of a target nucleic acid to which one or more antisense compound is targeted. "5' target site" or "5' start stie" refers to the 5'-most nucleotide of a target segment. "3' target site" or "3' stop site" refers to the 3'-most nucleotide of a target segment.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region can contain one or more target segments. Multiple target segments within a target region can be overlapping. Alternatively, they can be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments can be found within a 5' UTR, a coding region, a 3' UTR, an intron, an exon, or an exon/intron junction. Target segments containing a start codon or a stop codon are also suitable target segments. A suitable target segment can specifically exclude a certain structurally defined region such as the start codon or stop codon.

The determination of suitable target segments can include a comparison of the sequence of a target nucleic acid to other sequences throughout the genome. For example, the BLAST algorithm can be used to identify regions of similarity amongst different nucleic acids. This comparison can prevent the selection of antisense compound sequences that can hybridize in a non-specific manner to sequences other than a selected target nucleic acid (i.e., non-target or off-target sequences).

There can be variation in activity (e.g., as defined by percent reduction of target nucleic acid levels) of the antisense compounds within an active target region. In certain embodiments, reductions in ANGPTL3 mRNA levels are indicative of inhibition of ANGPTL3 protein expression. Reductions in levels of an ANGPTL3 protein are also indicative of inhibition of target mRNA expression. Further, phenotypic changes, such as a reduction of the level of cholesterol, LDL, triglyceride, or glucose, can be indicative of inhibition of ANGPTL3 mRNA and/or protein expression.

Hybridization

In some embodiments, hybridization occurs between an antisense compound disclosed herein and an ANGPTL3 nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art (Sambrook and Russell, Molecular Cloning: A Laboratory Manual, 3$^{rd}$ Ed., 2001). In certain embodiments, the antisense compounds provided herein are specifically hybridizable with an ANGPTL3 nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as an ANGPTL3 nucleic acid).

An antisense compound can hybridize over one or more segments of an ANGPTL3 nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 75%, 80%, 85%, 86%, 87%, 88%, 89%, 90%, 91%, 92%, 93%, 94%, 95%, 96%, 97%, 98%, 99%, or 100% complementary to an ANGPTL3 nucleic acid, a target region, target segment, or specified portion thereof. In certain embodiments, the antisense compounds provided herein, or a specified portion thereof, are, or are at least, 70%, 75%, 80%, 85%, 86%, 87%, 88%, 89%, 90%, 91%, 92%, 93%, 94%, 95%, 96%, 97%, 98%, 99%, or 100% complementary to the sequence of one or more of SEQ ID NOs: 1-2. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases can be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e. 100% complementary) to a target nucleic acid, or specified portion thereof. For example, an antisense compound can be fully complementary to an ANGPTL3 nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound can be fully complementary to the target sequence, depending on whether the remaining 10 nucleobases of the antisense compound are also complementary to the target sequence.

The location of a non-complementary nucleobase can be at the 5' end or 3' end of the antisense compound. Alternatively, the non-complementary nucleobase or nucleobases can be at an internal position of the antisense compound. When two or more non-complementary nucleobases are present, they can be either contiguous (i.e. linked) or non-contiguous. In one embodiment, a non-complementary nucleobase is located in the wing segment of a gapmer antisense oligonucleotide.

In certain embodiments, antisense compounds that are, or are up to 10, 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as an ANGPTL3 nucleic acid, or specified portion thereof.

In certain embodiments, antisense compounds that are, or are up to 10, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as an ANGPTL3 nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 10 nucleobase portion of a target segment. In certain embodiments, the antisense compounds are complementary to at least a 15 nucleobase portion of a target segment. Also contemplated are antisense compounds that are complementary to at least an 8, 9, 10, 11, 12, 13, 14, 15, 16, 17, 18, 19, 20, or more nucleobase portion of a target segment, or a range defined by any two of these values.

Identity

The antisense compounds provided herein can also have a defined percent identity to a particular nucleotide sequence, SEQ ID NO, or the sequence of a compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases can be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides can also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to an ANGPTL3 nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds of the invention can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise chemically modified ribofuranose ring moieties. Examples of chemically modified ribofuranose rings include without limitation, addition of substitutent groups (including 5' and 2' substituent groups, bridging of non-geminal ring atoms to form bicyclic nucleic acids (BNA), replacement of the ribosyl ring oxygen atom with S, N(R), or $C(R_1)(R_2)$ (R, $R_1$ and $R_2$ are each independently H, $C_1$-$C_{12}$ alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-OCH$_3$, 2'—OCH$_2$CH$_3$, 2'-OCH$_2$CH$_2$F and 2'-O(CH$_2$)$_2$OCH$_3$ substituent groups. The substituent at the 2' position can also be selected from allyl, amino, azido, thio, O-allyl, O—C$_1$-C$_{10}$ alkyl, OCF$_3$, OCH$_2$F, O(CH$_2$)$_2$SCH$_3$, O(CH$_2$)$_2$—O—N(R$_m$)(R$_n$), O—CH$_2$—C(=O)—N(R$_m$)(R$_n$), and O—CH$_2$—C(=O)—N(R$_l$)—(CH$_2$)$_2$—N(R$_m$)(R$_n$), where each R$_l$, R$_m$ and R$_n$ is, independently, H or substituted or unsubstituted C$_1$-C$_{10}$ alkyl.

As used herein, "bicyclic nucleosides" refer to modified nucleosides comprising a bicyclic sugar moiety. Examples of bicyclic nucleic acids (BNAs) include without limitation nucleosides comprising a bridge between the 4' and the 2' ribosyl ring atoms. In certain embodiments, antisense compounds provided herein include one or more BNA nucleosides wherein the bridge comprises one of the formulas: 4'-(CH$_2$)—O-2' (LNA); 4'-(CH$_2$)—S-2; 4'-(CH$_2$)$_2$—O-2' (ENA); 4'-CH(CH$_3$)—O-2' and 4'-CH(CH$_2$OCH$_3$)—O-2' (and analogs thereof see U.S. Pat. No. 7,399,845, issued on Jul. 15, 2008); 4'-C(CH$_3$)(CH$_3$)—O-2' (and analogs thereof see PCT/US2008/068922 published as WO/2009/006478, published Jan. 8, 2009); 4'-CH$_2$—N(OCH$_3$)-2' (and analogs thereof see PCT/US2008/064591 published as WO/2008/150729, published Dec. 11, 2008); 4'-CH$_2$—O—N(CH$_3$)-2' (see published U.S. Patent Application US2004-0171570, published Sep. 2, 2004); 4'-CH$_2$—N(R)—O-2', wherein R is H, C$_1$-C$_{12}$ alkyl, or a protecting group (see U.S. Pat. No. 7,427,672, issued on Sep. 23, 2008); 4'-CH$_2$—C(H)(CH$_3$)-2' (see Chattopadhyaya et al., *J. Org. Chem.*, 2009, 74, 118-134); and 4'-CH$_2$—C(=CH$_2$)-2' (and analogs thereof see PCT/US2008/066154 published as WO 2008/154401, published on Dec. 8, 2008).

Further bicyclic nucleosides have been reported in published literature (see for example: Srivastava et al., *J. Am. Chem. Soc.*, 2007, 129(26) 8362-8379; Frieden et al., *Nucleic Acids Research*, 2003, 21, 6365-6372; Elayadi et al., *Curr. Opinion Invens. Drugs*, 2001, 2, 558-561; Braasch et al., *Chem. Biol.*, 2001, 8, 1-7; Orum et al., *Curr. Opinion Mol. Ther.*, 2001, 3, 239-243; Wahlestedt et al., *Proc. Natl. Acad. Sci. U S. A.*, 2000, 97, 5633-5638; Singh et al., *Chem. Commun.*, 1998, 4, 455-456; Koshkin et al., *Tetrahedron*, 1998, 54, 3607-3630; Kumar et al., *Bioorg. Med. Chem. Lett.*, 1998, 8, 2219-2222; Singh et al., *J. Org. Chem.*, 1998, 63, 10035-10039; U.S. Pat. Nos. 7,399,845; 7,053,207; 7,034,133; 6,794,499; 6,770,748; 6,670,461; 6,525,191; 6,268,490; U.S. Patent Publication Nos.: US2008-0039618; US2007-0287831; US2004-0171570; U.S. patent application Ser. Nos. 12/129,154; 61/099,844; 61/097,787; 61/086,231; 61/056,564; 61/026,998; 61/026,995; 60/989,574; International applications WO 2007/134181; WO 2005/021570; WO 2004/106356; WO 94/14226; and PCT International Applications Nos.: PCT/US2008/068922; PCT/US-2008/066154; and PCT/US2008/064591). Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

As used herein, "monocylic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "4'-2' bicyclic nucleoside" or "4' to 2' bicyclic nucleoside" refers to a bicyclic nucleoside comprising a furanose ring comprising a bridge connecting two carbon atoms of the furanose ring connects the 2' carbon atom and the 4' carbon atom of the sugar ring.

In certain embodiments, bicyclic sugar moieties of BNA nucleosides include, but are not limited to, compounds having at least one bridge between the 4' and the 2' carbon atoms of the pentofuranosyl sugar moiety including without limitation, bridges comprising 1 or from 1 to 4 linked groups independently selected from —[C(R$_a$)(R$_b$)]$_n$—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—; wherein: x is 0, 1, or 2; n is 1, 2, 3, or 4; each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl or a protecting group.

In certain embodiments, the bridge of a bicyclic sugar moiety is, —[C(R$_a$)(R$_b$)]$_n$—, —[C(R$_a$)(R$_b$)]$_n$—O—, —C(R$_a$R$_b$)—N(R)—O— or —C(R$_a$R$_b$)—O—N(R)—. In certain embodiments, the bridge is 4'-CH$_2$-2', 4'-(CH$_2$)$_2$-2', 4'-(CH$_2$)$_3$-2', 4'-CH$_2$—O-2', 4'-(CH$_2$)$_2$—O-2', 4'-CH$_2$—O—N(R)-2' and 4'-CH$_2$—N(R)—O-2'- wherein each R is, independently, H, a protecting group or C$_1$-C$_{12}$ alkyl.

In certain embodiments, bicyclic nucleosides are further defined by isomeric configuration. For example, a nucleoside comprising a 4'-(CH$_2$)—O-2' bridge, may be in the α-L configuration or in the β-D configuration. Previously, α-L-methyleneoxy (4'-CH$_2$—O-2') BNA's have been incorporated into antisense oligonucleotides that showed antisense activity (Frieden et al., Nucleic Acids Research, 2003, 21, 6365-6372).

In certain embodiments, bicyclic nucleosides include those having a 4' to 2' bridge wherein such bridges include without limitation, α-L-4'-(CH$_2$)—O-2', β-D-4'-CH$_2$—O-2', 4'-(CH$_2$)$_2$—O-2', 4'-CH$_2$—O—N(R)-2', 4'-CH$_2$—N(R)—O-2', 4'-CH(CH$_3$)—O-2', 4'-CH$_2$—S-2', 4'-CH$_2$—N(R)-2', 4'-CH$_2$—CH(CH$_3$)-2', and 4'-(CH$_2$)$_3$-2', wherein R is H, a protecting group or C$_1$-C$_{12}$ alkyl.

In certain embodiment, bicyclic nucleosides have the formula:

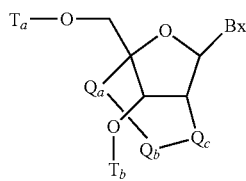

wherein:

Bx is a heterocyclic base moiety;

-$Q_a$-$Q_b$-$Q_c$- is —$CH_2$—N($R_c$)—$CH_2$—, —C(=O)—N($R_c$)—$CH_2$—, —$CH_2$—O—N($R_c$)—, —$CH_2$—N($R_c$)—O— or —N($R_c$)—O—$CH_2$;

$R_c$ is $C_1$-$C_{12}$ alkyl or an amino protecting group; and $T_a$ and $T_b$ are each, independently H, a hydroxyl protecting group, a conjugate group, a reactive phosphorus group, a phosphorus moiety or a covalent attachment to a support medium.

In certain embodiments, bicyclic nucleosides have the formula:

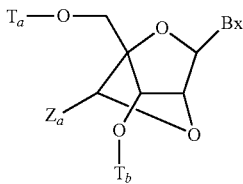

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol or substituted thiol.

In one embodiment, each of the substituted groups, is, independently, mono or poly substituted with substituent groups independently selected from halogen, oxo, hydroxyl, $OJ_c$, $NJ_cJ_d$, $SJ_c$, $N_3$, OC(=X)$J_c$, and $NJ_eC$(=X)$NJ_cJ_d$, wherein each $J_c$, $J_d$ and $J_e$ is, independently, H, $C_1$-$C_6$ alkyl, or substituted $C_1$-$C_6$ alkyl and X is O or $NJ_c$.

In certain embodiments, bicyclic nucleosides have the formula:

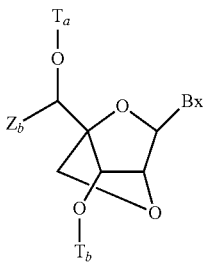

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl (C(=O)—).

In certain embodiments, bicyclic nucleosides have the formula:

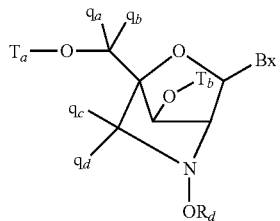

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl; In certain embodiments, bicyclic nucleosides have the formula:

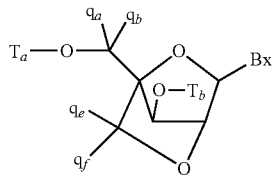

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$;

or $q_e$ and $q_f$ together are =C($q_g$)($q_h$);

$q_g$ and $q_h$ are each, independently, H, halogen, $C_1$-$C_{12}$ alkyl or substituted $C_1$-$C_{12}$ alkyl.

The synthesis and preparation of adenine, cytosine, guanine, 5-methyl-cytosine, thymine and uracil bicyclic nucleosides having a 4'—$CH_2$—O-2' bridge, along with their oligomerization, and nucleic acid recognition properties have been described (Koshkin et al., *Tetrahedron*, 1998, 54, 3607-3630). The synthesis of bicyclic nucleosides has also been described in WO 98/39352 and WO 99/14226.

Analogs of various bicyclic nucleosides that have 4' to 2' bridging groups such as 4'—$CH_2$—O-2' and 4'—$CH_2$—S-2', have also been prepared (Kumar et al., *Bioorg. Med. Chem. Lett.*, 1998, 8, 2219-2222). Preparation of oligodeoxyribonucleotide duplexes comprising bicyclic nucleosides for use as substrates for nucleic acid polymerases has also been described (Wengel et al., WO 99/14226). Furthermore, synthesis of 2′-amino-BNA, a novel conformationally restricted high-affinity oligonucleotide analog has been described in the art (Singh et al., *J. Org. Chem.*, 1998, 63, 10035-10039). In addition, 2′-amino- and 2′-methylamino-BNA's have been prepared and the thermal stability of their duplexes with complementary RNA and DNA strands has been previously reported.

In certain embodiments, bicyclic nucleosides have the formula:

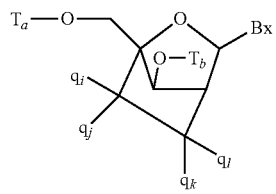

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$; and $q_i$ and $q_j$ or $q_l$ and $q_k$ together are =C($q_g$)($q_h$), wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4′-(CH$_2$)$_3$-2′ bridge and the alkenyl analog bridge 4′—CH=CH—CH$_2$—2′ have been described (Frier et al., *Nucleic Acids Research*, 1997, 25(22), 4429-4443 and Albaek et al., *J. Org. Chem.*, 2006, 71, 7731-7740). The synthesis and preparation of carbocyclic bicyclic nucleosides along with their oligomerization and biochemical studies have also been described (Srivastava et al., *J. Am. Chem. Soc.* 2007, 129(26), 8362-8379).

In certain embodiments, bicyclic nucleosides include, but are not limited to, (A) α-L-methyleneoxy (4′—CH$_2$—O-2′) BNA, (B) β-D-methyleneoxy (4′—CH$_2$—O-2′) BNA, (C) ethyleneoxy (4′-(CH$_2$)$_2$—O-2′) BNA, (D) aminooxy (4′—CH$_2$—O—N(R)-2′) BNA, (E) oxyamino (4′—CH$_2$—N(R)—O-2′) BNA, (F) methyl(methyleneoxy) (4′—CH(CH$_3$)—O-2′) BNA (also referred to as constrained ethyl or cEt), (G) methylene-thio (4′—CH$_2$—S-2′) BNA, (H) methylene-amino (4′—CH$_2$—N(R)-2′) BNA, (I) methyl carbocyclic (4′—CH$_2$—CH(CH$_3$)-2′) BNA, (J) propylene carbocyclic (4′-(CH$_2$)$_3$-2′) BNA, and (K) vinyl BNA as depicted below.

(A)

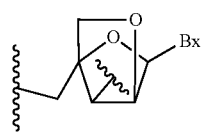

(B)

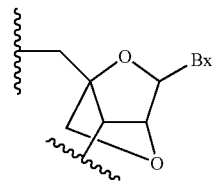

(C)

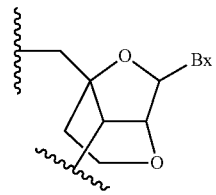

(D)

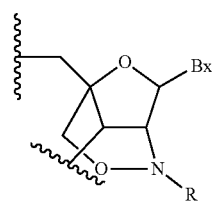

(E)

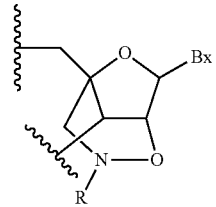

(F)

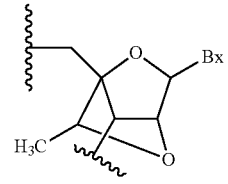

(G)

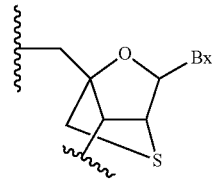

(H)

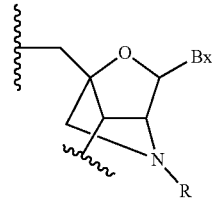

(I)

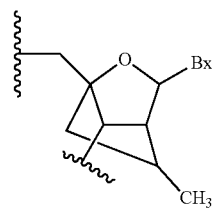

-continued

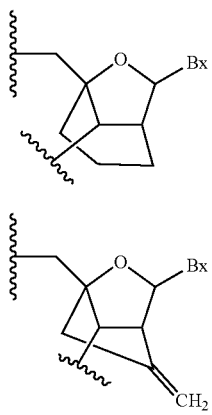

wherein Bx is the base moiety and R is, independently, H, a protecting group, $C_1$-$C_6$ alkyl or $C_1$-$C_6$ alkoxy.

As used herein, the term "modified tetrahydropyran nucleoside" or "modified THP nucleoside" means a nucleoside having a six-membered tetrahydropyran "sugar" substituted for the pentofuranosyl residue in normal nucleosides and can be referred to as a sugar surrogate. Modified THP nucleosides include, but are not limited to, what is referred to in the art as hexitol nucleic acid (HNA), anitol nucleic acid (ANA), manitol nucleic acid (MNA) (see Leumann, *Bioorg. Med. Chem.*, 2002, 10, 841-854) or fluoro HNA (F-HNA) having a tetrahydropyranyl ring system as illustrated below.

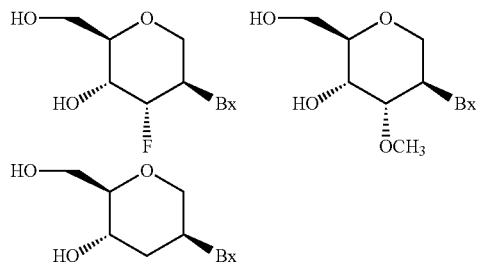

In certain embodiment, sugar surrogates are selected having the formula:

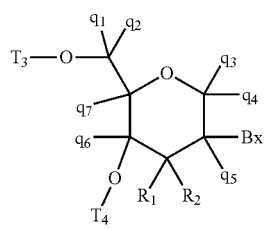

wherein:

Bx is a heterocyclic base moiety;

$T_3$ and $T_4$ are each, independently, an internucleoside linking group linking the tetrahydropyran nucleoside analog to the oligomeric compound or one of $T_3$ and $T_4$ is an internucleoside linking group linking the tetrahydropyran nucleoside analog to an oligomeric compound or oligonucleotide and the other of $T_3$ and $T_4$ is H, a hydroxyl protecting group, a linked conjugate group or a 5' or 3'-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and one of $R_1$ and $R_2$ is hydrogen and the other is selected from halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$ and CN, wherein X is O, S or $NJ_1$ and each $J_1$, $J_2$ and $J_3$ is, independently, H or $C_1$-$C_6$ alkyl.

In certain embodiments, $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides are provided wherein one of $R_1$ and $R_2$ is F. In certain embodiments, $R_1$ is fluoro and $R_2$ is H; $R_1$ is methoxy and $R_2$ is H, and $R_1$ is methoxyethoxy and $R_2$ is H.

In certain embodiments, sugar surrogates comprise rings having more than 5 atoms and more than one heteroatom. For example nucleosides comprising morpholino sugar moieties and their use in oligomeric compounds has been reported (see for example: Braasch et al., *Biochemistry*, 2002, 41, 4503-4510; and U.S. Pat. Nos. 5,698,685; 5,166,315; 5,185,444; and 5,034,506). As used here, the term "morpholino" means a sugar surrogate having the following formula:

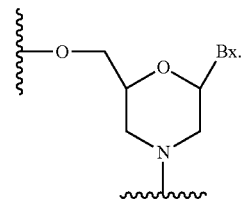

In certain embodiments, morpholinos may be modified, for example by adding or altering various substituent groups from the above morpholino structure. Such sugar surrogates are referred to herein as "modified morpholinos."

Combinations of modifications are also provided without limitation, such as 2'-F-5'-methyl substituted nucleosides (see PCT International Application WO 2008/101157 published on Aug. 21, 2008 for other disclosed 5', 2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'—$CH_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

In certain embodiments, antisense compounds comprise one or more modified cyclohexenyl nucleosides, which is a nucleoside having a six-membered cyclohexenyl in place of the pentofuranosyl residue in naturally occurring nucleosides. Modified cyclohexenyl nucleosides include, but are not limited to those described in the art (see for example commonly owned, published PCT Application WO 2010/036696, published on Apr. 10, 2010, Robeyns et al., *J. Am. Chem. Soc.*, 2008, 130(6), 1979-1984; Horvath et al., *Tetrahedron Letters*, 2007, 48, 3621-3623; Nauwelaerts et al., J. Am. Chem. Soc., 2007, 129(30), 9340-9348; Gu et al., Nucleosides, Nucleotides & Nucleic Acids, 2005, 24(5-7), 993-998; Nauwelaerts et al., Nucleic Acids Research, 2005, 33(8), 2452-2463; Robeyns et al., Acta Crystallographica, Section F: Structural Biology and Crystallization Communications, 2005, F61(6), 585-586; Gu et al., Tetrahedron, 2004, 60(9), 2111-2123; Gu et al., Oligonucleotides, 2003, 13(6), 479-489; Wang et al., J. Org. Chem., 2003, 68, 4499-4505; Verbeure et al., Nucleic Acids Research, 2001, 29(24), 4941-4947; Wang et al., J Org. Chem., 2001, 66, 8478-82; Wang et al., Nucleosides, Nucleotides & Nucleic Acids, 2001, 20(4-7), 785-788; Wang et al., J Am. Chem., 2000, 122, 8595-8602; Published PCT application, WO 06/047842; and Published PCT Application WO 01/049687; the text of each is incorporated by reference herein, in their entirety). Certain modified cyclohexenyl nucleosides have Formula X.

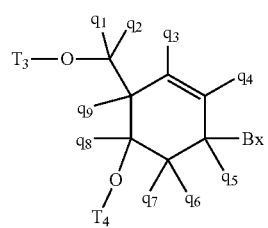

X wherein independently for each of said at least one cyclohexenyl nucleoside analog of Formula X:

Bx is a heterocyclic base moiety;

$T_3$ and $T_4$ are each, independently, an internucleoside linking group linking the cyclohexenyl nucleoside analog to an antisense compound or one of $T_3$ and $T_4$ is an internucleoside linking group linking the tetrahydropyran nucleoside analog to an antisense compound and the other of $T_3$ and $T_4$ is H, a hydroxyl protecting group, a linked conjugate group, or a 5'- or 3'-terminal group; and $q_1$, $q_2$, $q_3$, $q_4$, $q_5$, $q_6$, $q_7$, $q_8$ and $q_9$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or other sugar substituent group.

Many other monocyclic, bicyclic and tricyclic ring systems are known in the art and are suitable as sugar surrogates that can be used to modify nucleosides for incorporation into oligomeric compounds as provided herein (see for example review article: Leumann, Christian J. Bioorg. & Med. Chem., 2002, 10, 841-854). Such ring systems can undergo various additional substitutions to further enhance their activity.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: O[(CH$_2$)$_n$O]$_m$CH$_3$, O(CH$_2$)$_n$NH$_2$, O(CH$_2$)$_n$CH$_3$, O(CH$_2$)$_n$F, O(CH$_2$)$_n$ONH$_2$, OCH$_2$C(=O)N(H)CH$_3$, and O(CH$_2$)$_n$ON[(CH$_2$)$_n$CH$_3$]$_2$, where n and m are from 1 to about 10. Other 2'-substituent groups can also be selected from: $C_1$-$C_{12}$ alkyl, substituted alkyl, alkenyl, alkynyl, alkaryl, aralkyl, O-alkaryl or O-aralkyl, SH, SCH$_3$, OCN, Cl, Br, CN, F, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an antisense compound, and other substituents having similar properties. In certain embodiments, modified nucleosides comprise a 2'-MOE side chain (Baker et al., J Biol. Chem., 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin, Helv. Chim. Acta, 1995, 78, 486-504; Altmann et al., Chimia, 1996, 50, 168-176; Altmann et al., Biochem. Soc. Trans., 1996, 24, 630-637; and Altmann et al., Nucleosides Nucleotides, 1997, 16, 917-926).

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring; and nucleosides with non-bridging 2'substituents, such as allyl, amino, azido, thio, O-allyl, O—$C_1$-$C_{10}$ alkyl, —OCF$_3$, O—(CH$_2$)$_2$—O—CH$_3$, 2'-O(CH$_2$)$_2$SCH$_3$, O—(CH$_2$)$_2$—O—N(R$_m$)(R$_n$), or O—CH$_2$—C(=O)—N(R$_m$)(R$_n$), where each R$_m$ and R$_n$ is, independently, H or substituted or unsubstituted $C_1$-$C_{10}$ alkyl. 2'-modified nucleosides may further comprise other modifications, for example at other positions of the sugar and/or at the nucleobase.

As used herein, "2'-F" refers to a nucleoside comprising a sugar comprising a fluoro group at the 2' position of the sugar ring.

As used herein, "2'-OMe" or "2'-OCH$_3$", "2'-O-methyl" or "2'-methoxy" each refers to a nucleoside comprising a sugar comprising an —OCH$_3$ group at the 2' position of the sugar ring.

As used herein, "MOE" or "2'-MOE" or "2'-OCH$_2$CH$_2$OCH$_3$" or "2'-O-methoxyethyl" each refers to a nucleoside comprising a sugar comprising a —OCH$_2$CH$_2$OCH$_3$ group at the 2' position of the sugar ring.

Methods for the preparations of modified sugars are well known to those skilled in the art. Some representative U.S. patents that teach the preparation of such modified sugars include without limitation, U.S. Pat. Nos. 4,981,957; 5,118, 800; 5,319,080; 5,359,044; 5,393,878; 5,446,137; 5,466, 786; 5,514,785; 5,519,134; 5,567,811; 5,576,427; 5,591, 722; 5,597,909; 5,610,300; 5,627,053; 5,639,873; 5,646, 265; 5,670,633; 5,700,920; 5,792,847 and 6,600,032 and International Application PCT/US2005/019219, filed Jun. 2, 2005 and published as WO 2005/121371 on Dec. 22, 2005, and each of which is herein incorporated by reference in its entirety.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

In nucleotides having modified sugar moieties, the nucleobase moieties (natural, modified or a combination thereof) are maintained for hybridization with an appropriate nucleic acid target.

In certain embodiments, antisense compounds comprise one or more nucleosides having modified sugar moieties. In certain embodiments, the modified sugar moiety is 2'-MOE. In certain embodiments, the 2'-MOE modified nucleosides are arranged in a gapmer motif. In certain embodiments, the modified sugar moiety is a bicyclic nucleoside having a (4'—CH(CH$_3$)—O-2') bridging group. In certain embodiments, the (4'—CH(CH$_3$)—O-2') modified nucleosides are arranged throughout the wings of a gapmer motif.

Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications can impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., Antisense Research and Applications, CRC Press, Boca Raton, 1993, pp. 276-278).

Additional modified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties can also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and O-6 substituted purines, including 2 aminopropyladenine, 5-propynyluracil and 5-propynylcytosine.

In certain embodiments, antisense compounds targeted to an ANGPTL3 nucleic acid comprise one or more modified nucleobases. In certain embodiments, shortened or gap-widened antisense oligonucleotides targeted to an ANGPTL3 nucleic acid comprise one or more modified nucleobases. In certain embodiments, the modified nucleobase is 5-methylcytosine. In certain embodiments, each cytosine is a 5-methylcytosine.

Compositions and Methods for Formulating Pharmaceutical Compositions

Antisense oligonucleotides can be admixed with pharmaceutically acceptable active or inert substance for the preparation of pharmaceutical compositions or formulations. Compositions and methods for the formulation of pharmaceutical compositions are dependent upon a number of criteria, including, but not limited to, route of administration, extent of disease, or dose to be administered.

Antisense compound targeted to an ANGPTL3 nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to an ANGPTL3 nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

Conjugated Antisense Compounds

Antisense compounds can be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acids from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression of ANGPTL3 nucleic acids can be tested in vitro in a variety of cell types. Cell types used for such analyses are available from commercial vendors (e.g. American Type Culture Collection, Manassas, Va.; Zen-Bio, Inc., Research Triangle Park, N.C.; Clonetics Corporation, Walkersville, Md.) and cells are cultured according to the vendor's instructions using commercially available reagents (e.g. Invitrogen Life Technologies, Carlsbad, Calif.). Illustrative cell types include, but are not limited to, HepG2 cells, Hep3B cells, Huh7 (hepatocellular carcinoma) cells, primary hepatocytes, A549 cells, GM04281 fibroblasts and LLC-MK2 cells.

In Vitro Testing of Antisense Oligonucleotides

Described herein are methods for treatment of cells with antisense oligonucleotides, which can be modified appropriately for treatment with other antisense compounds.

In general, cells are treated with antisense oligonucleotides when the cells reach approximately 60-80% confluence in culture.

One reagent commonly used to introduce antisense oligonucleotides into cultured cells includes the cationic lipid transfection reagent LIPOFECTIN® (Invitrogen, Carlsbad, Calif.). Antisense oligonucleotides are mixed with LIPOFECTIN® in OPTI-MEM® 1 (Invitrogen, Carlsbad, Calif.) to achieve the desired final concentration of antisense oligonucleotide and a LIPOFECTIN® concentration that typically ranges 2 to 12 ug/mL per 100 nM antisense oligonucleotide.

Another reagent used to introduce antisense oligonucleotides into cultured cells includes LIPOFECTAMINE 2000® (Invitrogen, Carlsbad, Calif.). Antisense oligonucleotide is mixed with LIPOFECTAMINE 2000® in OPTI-MEM® 1 reduced serum medium (Invitrogen, Carlsbad, Calif.) to achieve the desired concentration of antisense oligonucleotide and a LIPOFECTAMINE® concentration that typically ranges 2 to 12 ug/mL per 100 nM antisense oligonucleotide.

Another reagent used to introduce antisense oligonucleotides into cultured cells includes Cytofectin® (Invitrogen, Carlsbad, Calif.). Antisense oligonucleotide is mixed with Cytofectin® in OPTI-MEM® 1 reduced serum medium (Invitrogen, Carlsbad, Calif.) to achieve the desired concentration of antisense oligonucleotide and a Cytofectin® concentration that typically ranges 2 to 12 ug/mL per 100 nM antisense oligonucleotide.

Another reagent used to introduce antisense oligonucleotides into cultured cells includes Oligofectamine™ (Invitrogen Life Technologies, Carlsbad, Calif.). Antisense oligonucleotide is mixed with Oligofectamine™ in Opti-MEM™-1 reduced serum medium (Invitrogen Life Technologies, Carlsbad, Calif.) to achieve the desired concentration of oligonucleotide with an Oligofectamine™ to oligonucleotide ratio of approximately 0.2 to 0.8 µL per 100 nM.

Another reagent used to introduce antisense oligonucleotides into cultured cells includes FuGENE 6 (Roche Diagnostics Corp., Indianapolis, Ind.). Antisense oligomeric compound was mixed with FuGENE 6 in 1 mL of serum-free RPMI to achieve the desired concentration of oligonucleotide with a FuGENE 6 to oligomeric compound ratio of 1 to 4 µL of FuGENE 6 per 100 nM.

Another technique used to introduce antisense oligonucleotides into cultured cells includes electroporation (Sambrook and Russell, Molecular Cloning: A Laboratory Manual, $3^{rd}$ Ed., 2001).

Cells are treated with antisense oligonucleotides by routine methods. Cells are typically harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE2000®, Lipofectin or Cytofectin. Antisense oligonucleotides are used at higher concentrations ranging from 625 to 20,000 nM when transfected using electroporation.

RNA Isolation

RNA analysis can be performed on total cellular RNA or poly(A)+mRNA. Methods of RNA isolation are well known in the art (Sambrook and Russell, Molecular Cloning: A Laboratory Manual, $3^{rd}$ Ed., 2001). RNA is prepared using methods well known in the art, for example, using the TRIZOL® Reagent (Invitrogen, Carlsbad, Calif.) according to the manufacturer's recommended protocols.

Analysis of Inhibition of Target Levels or Expression

Inhibition of levels or expression of an ANGPTL3 nucleic acid can be assayed in a variety of ways known in the art (Sambrook and Russell, Molecular Cloning: A Laboratory Manual, $3^{rd}$ Ed., 2001). For example, target nucleic acid levels can be quantitated by, e.g., Northern blot analysis, competitive polymerase chain reaction (PCR), or quantitative real-time PCR. RNA analysis can be performed on total cellular RNA or poly(A)+mRNA. Methods of RNA isolation are well known in the art. Northern blot analysis is also routine in the art. Quantitative real-time PCR can be conveniently accomplished using the commercially available ABI PRISM® 7600, 7700, or 7900 Sequence Detection System, available from PE-Applied Biosystems, Foster City, Calif. and used according to manufacturer's instructions.

Quantitative Real-Time PCR Analysis of Target RNA Levels

Quantitation of target RNA levels can be accomplished by quantitative real-time PCR using the ABI PRISM® 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, Calif.). RT and real-time-PCR reactions are carried out by methods well known to those skilled in the art.

Gene (or RNA) target quantities obtained by real time PCR can be normalized using either the expression level of a gene whose expression is constant, such as cyclophilin A or GADPH or by quantifying total RNA using RIBOGREEN® (Life Technologies™, Inc. Carlsbad, Calif.). Cyclophilin A or GADPH expression can be quantified by real time PCR, by being run simultaneously with the target, multiplexing, or separately. Total RNA can be quantified using RIBOGREEN® RNA quantification reagent. Methods of RNA quantification by RIBOGREEN® are taught in Jones, L. J., et al, (Analytical Biochemistry, 1998, 265, 368-374). A CYTOFLUOR® 4000 instrument (PE Applied Biosystems) can be used to measure RIBOGREEN® fluorescence.

Methods for designing real-time PCR probes and primers are well known in the art, and can include the use of software such as PRIMER EXPRESS® Software (Applied Biosystems, Foster City, Calif.). Probes and primers used in real-time PCR were designed to hybridize to ANGPTL3 specific sequences and are disclosed in the Examples below. The target specific PCR probes can have FAM covalently linked to the 5' end and TAMRA or MGB covalently linked to the 3' end, where FAM is the fluorescent dye and TAMRA or MGB is the quencher dye.

Analysis of Protein Levels

Antisense inhibition of ANGPTL3 nucleic acids can be assessed by measuring ANGPTL3 protein levels. Protein levels of ANGPTL3 can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS) (Sambrook and Russell, Molecular Cloning: A Laboratory Manual, $3^{rd}$ Ed., 2001). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art.

In Vivo Testing of Antisense Compounds

Antisense compounds, for example, antisense oligonucleotides, are tested in animals to assess their ability to inhibit expression of ANGPTL3 and produce phenotypic changes. Testing can be performed in normal animals, or in experimental disease models. For administration to animals, antisense oligonucleotides are formulated in a pharmaceutically acceptable diluent, such as phosphate-buffered saline. Administration includes parenteral routes of administration. Following a period of treatment with antisense oligonucleotides, RNA is isolated from tissue and changes in ANGPTL3 nucleic acid expression are measured. Changes in ANGPTL3 protein levels are also measured.

Certain Indications

In certain embodiments, provided herein are methods of treating an individual comprising administering one or more pharmaceutical compositions as described herein. In certain embodiments, the individual has a metabolic disease and/or cardiovascular disease. In certain embodiments, the individual has hypercholesterolemia (e.g., familial homozygous hypercholesterolemia (HoFH), familial heterozygous hypercholesterolemia (HeFH)), dyslipidemia, hypertriglyceridemia (e.g., heterozygous LPL deficiency, homozygous LPL deficiency), coronary artery disease (CAD), familial chylomicronemia syndrome (FCS), hyperlipoproteinemia Type IV), lipodystrophy, hyperlipidemia (e.g., combined hyperlipidemia, familial combined hyperlipidemia (FCHL)), metabolic syndrome, non-alcoholic fatty liver disease (NAFLD), nonalcoholic steatohepatitis (NASH), diabetes (e.g., Type 2 diabetes), vascular wall thickening, high blood pressure (e.g., pulmonary arterial hypertension), sclerosis (e.g., atherosclerosis, systemic sclerosis, progressive skin sclerosis and proliferative obliterative vasculopathy such as digital ulcers and pulmonary vascular involvement).

In certain embodiments, the compounds targeted to ANGPTL3 described herein modulate lipid and/or energy metabolism in an animal. In certain embodiments, the compounds targeted to ANGPTL3 described herein modulate physiological markers or phenotypes of hypercholesterolemia, dyslipidemia, hypertriglyceridemia, metabolic syndrome, NAFLD, NASH and/or diabetes. For example, administration of the compounds to animals can modulate one or more of VLDL, non-esterified fatty acids (NEFA), LDL, cholesterol, triglyceride, glucose, insulin or ANGPTL3 levels. In certain embodiments, the modulation of the physiological markers or phenotypes can be associated with inhibition of ANGPTL3 by the compounds.

In certain embodiments, the compounds targeted to ANGPTL3 described herein reduce and/or prevent one or more of hepatic TG accumulation (i.e. hepatic steatosis), atherosclerosis, vascular wall thickening (e.g., arterial intima-media thickening), hypercholesterolemia (e.g., familial homozygous hypercholesterolemia (HoFH), familial heterozygous hypercholesterolemia (HeFH)), dyslipidemia, hypertriglyceridemia (e.g., heterozygous LPL deficiency, homozygous LPL deficiency, familial chylomicronemia syndrome (FCS), hyperlipoproteinemia Type IV), lipodystrophy, hyperlipidemia (e.g., combined hyperlipidemia, familial combined hyperlipidemia (FCHL)), metabolic syndrome, non-alcoholic fatty liver disease (NAFLD), nonalcoholic steatohepatitis (NASH), diabetes (e.g., Type 2 diabetes), high blood pressure and sclerosis. In certain embodiments, the compounds targeted to ANGPTL3 described herein improve insulin sensitivity.

In certain embodiments, administration of an antisense compound targeted to an ANGPTL3 nucleic acid as described herein results in reduction of ANGPTL3 expression by about at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 99%, or a range defined by any two of these values.

In certain embodiments, administration of an antisense compound targeted to an ANGPTL3 nucleic acid as described herein results in reduction of one or more of triglycerides, LDL-cholesterol, non-HDL cholesterol, VLDL-cholesterol, total cholesterol, ApoB and ApoC-III by about at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 99%, or a range defined by any two of these values.

In certain embodiments, pharmaceutical compositions comprising an antisense compound targeted to ANGPTL3 are used for the preparation of a medicament for treating a patient suffering from, or susceptible to, a metabolic disease or cardiovascular disease. In certain embodiments, pharmaceutical compositions comprising an antisense compound targeted to ANGPTL3 are used in the preparation of a medicament for treating a patient suffering from, or susceptible to, one or more of hypercholesterolemia (e.g., familial homozygous hypercholesterolemia (HoFH), familial heterozygous hypercholesterolemia (HeFH)), dyslipidemia, hypertriglyceridemia (e.g., familial chylomicronemia syndrome (FCS), hyperlipoproteinemia Type IV), lipodystrophy, hyperlipidemia (e.g., combined hyperlipidemia, familial combined hyperlipidemia (FCHL)), metabolic syndrome, non-alcoholic fatty liver disease (NAFLD), nonalcoholic steatohepatitis (NASH), diabetes (e.g., Type 2 diabetes) vascular wall thickening, high blood pressure and sclerosis.

Administration

In certain embodiments, the compounds and compositions as described herein are administered parenterally.

In certain embodiments, parenteral administration is by infusion. Infusion can be chronic or continuous or short or intermittent. In certain embodiments, infused pharmaceutical agents are delivered with a pump.

In certain embodiments, parenteral administration is by injection. The injection can be delivered with a syringe or a pump. In certain embodiments, the injection is a bolus injection. In certain embodiments, the injection is administered directly to a tissue or organ. In certain embodiments, the injection is subcutaneous.

Certain Combination Therapies

In certain embodiments, a first agent comprising the modified oligonucleotide disclosed herein is co-administered with one or more secondary agents. In certain embodiments, such second agents are designed to treat the same disease, disorder or condition as the first agent described herein. In certain embodiments, such second agents are designed to treat a different disease, disorder, or condition as the first agent described herein. In certain embodiments, such second agents are designed to treat an undesired side effect of one or more pharmaceutical compositions as described herein. In certain embodiments, second agents are co-administered with the first agent to treat an undesired effect of the first agent. In certain embodiments, second agents are co-administered with the first agent to produce a combinational effect. In certain embodiments, second agents are co-administered with the first agent to produce a synergistic effect.

In certain embodiments, a first agent and one or more second agents are administered at the same time. In certain embodiments, the first agent and one or more second agents are administered at different times. In certain embodiments, the first agent and one or more second agents are prepared together in a single pharmaceutical formulation. In certain embodiments, the first agent and one or more second agents are prepared separately.

In certain embodiments, second agents include, but are not limited to a glucose-lowering agent or a lipid-lowering agent. The glucose lowering agent can include, but is not limited to, a therapeutic lifestyle change, PPAR agonist, a dipeptidyl peptidase (IV) inhibitor, a GLP-1 analog, insulin or an insulin analog, an insulin secretagogue, a SGLT2 inhibitor, a human amylin analog, a biguanide, an alpha-glucosidase inhibitor, or a combination thereof. The glucose-lowering agent can include, but is not limited to metformin, sulfonylurea, rosiglitazone, meglitinide, thiazolidinedione, alpha-glucosidase inhibitor or a combination thereof. The sulfonylurea can be acetohexamide, chlorpropamide, tolbutamide, tolazamide, glimepiride, a glipizide, a glyburide, or a gliclazide. The meglitinide can be nateglinide or repaglinide. The thiazolidinedione can be pioglitazone or rosiglitazone. The alpha-glucosidase can be acarbose or miglitol. In certain embodiments the lipid lowering therapy can include, but is not limited to, a therapeutic lifestyle change, niacin, HMG-CoA reductase inhibitor, cholesterol absorption inhibitor, MTP inhibitor (e.g., a small molecule, polypeptide, antibody or antisense compound targeted to MTP), fibrate, PCSK9 inhibitor (e.g., PCSK9 antibodies, polypeptides, small molecules nucleic acid compounds targeting PCSK9), CETP inhibitor (e.g., small molecules such as torcetrapib and anacetrapib, polypeptides, antibodies or nucleic acid compounds targeted to CETP), apoC-III inhibitor (e.g., a small molecule, polypeptide, antibody or nucleic acid compounds targeted to apoC-III), apoB inhibitor (e.g., a small molecule, polypeptide, antibody or nucleic acid compounds targeted to apoB), beneficial oils rich in omega-3 fatty acids, omega-3 fatty acids or any combination thereof. The HMG-CoA reductase inhibitor can be atorvastatin, rosuvastatin, fluvastatin, lovastatin, pravastatin, simvastatin and the like. The cholesterol absorption inhibitor can be ezetimibe. The fibrate can be fenofibrate, bezafibrate, ciprofibrate, clofibrate, gemfibrozil and the like. The beneficial oil rich in omega-3 fatty acids can be krill, fish (e.g., Vascepa®), flaxseed oil and the like. The omega-3 fatty acid can be ALA, DHA, EPA and the like.

Certain Compounds

Antisense oligonucleotides targeting human ANGPTL3 were described in an earlier publication (see PCT Patent Publication No. WO 2011/085271 published Jul. 14, 2011, incorporated by reference herein, in its entirety). Several oligonucleotides (233676, 233690, 233710, 233717, 233721, 233722, 337459, 337460, 337474, 337477, 337478, 337479, 337481, 337484, 337487, 337488, 337490, 337491, 337492, 337497, 337498, 337503, 337505, 337506, 337508, 337513, 337514, 337516, 337520, 337521, 337525, 337526 and 337528) described therein, including the top ten most potent antisense compounds in vitro, were used as benchmarks throughout select in vitro screens for new antisense compounds described hereinbelow. Of the most potent compounds described in WO 2011/085271, ISIS 233722 was found to be highly variable in its ability to inhibit ANGPTL3. According, although initially included in some in vitro studies, 233722 was not selected as a benchmark for further studies. Of the previously identified potent in vitro benchmark compounds, five (233710, 233717, 337477, 337478, 337479 and 337487) were selected for testing in vivo, as described hereinbelow, in huANGPTL3 transgenic mice to assess the most potent in reducing human mRNA transcript and protein expression (Example 11). The antisense oligonucleotide with the highest initial in vivo potency in reducing ANGPTL3 levels (233710) was used as a benchmark for in vivo assessment of the new antisense compounds described hereinbelow.

In certain embodiments, the antisense compounds described herein benefit from one or more improved properties relative to the antisense compounds described in WO 2011/085271. These improved properties are demonstrated in the examples herein, and a non-exhaustive summary of the examples is provided below for ease of reference.

In a first screen described herein, about 3000 newly designed 5-10-5 MOE gapmer antisense compounds targeting human ANGPTL3 were tested in Hep3B cells for their effect on human ANGPTL3 mRNA in vitro (Example 1). The mRNA inhibition levels of the new antisense compounds were assessed with some previously designed antisense compounds (233717, 337484, 337487, 337492 and 337516) used as benchmarks in select studies. Of the about 3000 newly designed antisense compounds from this first screen, about 85 antisense compounds were selected for in vitro dose-dependent inhibition studies to determine their half maximal inhibitory concentration ($IC_{50}$) (Examples 2-3). Of the about 85 new antisense compounds tested for their half maximal inhibitory concentration ($IC_{50}$), about 38 antisense compounds that demonstrated potent dose-dependent reduction of ANGPTL3 were selected for in vivo potency and tolerability (ALT and AST) testing in mice (Examples 11-12) with antisense compound 233710 used as a benchmark.

In a second screen described herein, about 2000 newly designed antisense compounds targeting human ANGPTL3 with a MOE gapmer motif or a mixed motif (deoxy, 5-10-5 MOE and cET gapmers) were also tested in Hep3B cells for their effect on human ANGPTL3 mRNA in vitro (Examples 4-6). The inhibition levels of the new antisense compounds were assessed with some previously designed antisense compounds (233717, 337487, 337513, 337514 and 337516) used as benchmarks in select studies. Of the about 2000 newly designed antisense compounds from this second screen, about 147 antisense compounds were selected for in vitro dose-dependent inhibition studies to determine their half maximal inhibitory concentration ($IC_{50}$) (Examples 7-10). Of the about 147 new antisense compounds from tested for their half maximal inhibitory concentration (IC$_{50}$), about 73 antisense compounds that demonstrated potent dose-dependent reduction of ANGPTL3 were selected for in vivo potency and tolerability (e.g., ALT and AST) testing in mice (Examples 11-12) with antisense compound 233710 used as a benchmark.

Of the about 111 antisense compounds from screens one and two that were tested for potency and tolerability in mice, 24 were selected for more extensive tolerability testing in mice by assessing liver metabolic markers, such as alanine transaminase (ALT), aspartate transaminase (AST), albumin and bilirubin, as well as kidney metabolic markers BUN and creatinine and organ weight (Example 12).

In parallel with the in vivo murine studies seventeen antisense compounds were selected for viscosity testing (Example 13). Generally, antisense compounds that were not optimal for viscosity were not taken forward in further studies.

Based on the results of the mice tolerability study, twenty antisense compounds were selected for in vivo tolerability testing in rats (Example 14). In the rats, liver metabolic markers, such as ALT, AST, albumin and bilirubin, body and organ weights, as well as kidney metabolic markers, such as BUN, creatinine and total protein/creatinine ratio, were measured to determine the tolerability of a compound in vivo.

The twenty antisense compounds tested in the rats were also assessed for cross-reactivity to a rhesus monkey ANGPTL3 gene sequence (Example 15). Although the antisense compounds in this study were tested in cynomolgus monkeys, the cynomolgus monkey ANGPTL3 sequence was not available for comparison to the sequences of the full-length compounds, therefore the sequences of the antisense compounds were compared to that of the closely related rhesus monkey. The sequences of eight antisense compounds were found to have 0-2 mismatches with the rhesus ANGPTL3 gene sequence and were further studied in cynomolgus monkeys (Example 15). The eight antisense compounds (ISIS 563580, ISIS 560400, ISIS 567320, ISIS 567321, ISIS 544199, ISIS 567233, ISIS 561011 and ISIS 559277) were tested for inhibition of ANGPTL3 mRNA and protein expression as well as tolerability in the monkeys. In the tolerability studies, body weights, liver metabolic markers (ALT, AST and bilirubin), kidney metabolic markers (BUN and creatinine), hematology parameters (blood cell counts, hemoglobin and hematocrit), and pro-inflammatory markers (CRP and C3) were measured. Additionally, the full-length oligonucleotide concentration present in liver and kidney was measured and the ratio of full-length oligonucleotide in the kidney/liver was calculated.

Accordingly, provided herein are antisense compounds with any one or more improved characteristics e.g., improved relative to the antisense compounds described in WO 2011/085271. In certain embodiments, provided herein are antisense compounds comprising a modified oligonucleotide as described herein targeted to, or specifically hybridizable with, a region of nucleotides of any one of SEQ ID NOs: 1-2.

In certain embodiments, certain antisense compounds as described herein are efficacious by virtue of their potency in inhibiting ANGPTL3 expression. In certain embodiments, the compounds or compositions inhibit ANGPTL3 by at least 40%, at least 45%, at least 50%, at least 55%, at least 60%, at least 65%, at least 70%, at least 75%, at least 80%, at least 85%, at least 90% or at least 95%.

In certain embodiments, certain antisense compounds as described herein are efficacious by virtue of an in vitro IC$_{50}$ of less than 20 µM, less than 10 µM, less than 8 µM, less than 5 µM, less than 2 µM, less than 1 µM, less than 0.9 µM, less than 0.8 µM, less than 0.7 µM, less than 0.6 µM, or less than 0.5 µM when tested in human cells, for example, in the Hep3B cell line (as described in Examples 2-3 and 7-10). In certain embodiments, preferred antisense compounds having an IC$_{50}$<1.0 µM include SEQ ID NOs: 15, 20, 24, 34, 35, 36, 37, 42, 43, 44, 47, 50, 51, 57, 58, 60, 77, 79, 82, 87, 88, 90, 91, 93, 94, 100, 101, 104, 110, 111, 112, 113, 114, 115, 116, 117, 118, 119, 120, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 169, 170, 177, 188, 209, 210, 211, 212, 213, 214, 215, 216, 217, 218, 219, 220, 221, 222, 223, 224, 225, 226, 227, 228, 229, 230, 231, and 232. In certain embodiments, preferred antisense compounds having an IC$_{50}$<0.9 µM include SEQ ID NOs: 15, 20, 35, 36, 42, 43, 44, 50, 57, 60, 77, 79, 87, 88, 90, 91, 93, 94, 101, 104, 110, 111, 112, 113, 114, 115, 116, 117, 118, 119, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 177, 209, 210, 211, 212, 213, 214, 215, 216, 217, 218, 219, 220, 221, 222, 223, 224, 225, 226, 227, 228, 229, 230, 231, and 232. In certain embodiments, preferred antisense compounds having an IC$_{50}$<0.8 µM include SEQ ID NOs: 15, 20, 35, 36, 42, 43, 44, 50, 57, 60, 77, 79, 87, 88, 90, 91, 93, 94, 101, 104, 110, 111, 112, 113, 114, 115, 116, 117, 118, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 177, 209, 210, 211, 212, 213, 214, 215, 217, 218, 219, 220, 221, 222, 223, 224, 225, 228, 229, 230, 231, and 232. In certain embodiments, preferred antisense compounds having an IC$_{50}$<0.7 µM include SEQ ID NOs: 15, 20, 36, 42, 43, 57, 60, 114, 117, 127, 131, 177, 209, 210, 211, 212, 213, 214, 215, 217, 218, 219, 220, 221, 222, 223, 224, 225, 228, 229, 230, 231, and 232. In certain embodiments, preferred antisense compounds having an IC$_{50}$<0.6 µM include SEQ ID NOs: 15, 20, 36, 42, 43, 57, 60, 114, 117, 127, 131, 177, 209, 210, 211, 212, 213, 215, 217, 218, 219, 220, 221, 222, 224, 225, 228, 229, 230, 231, and 232. In certain embodiments, preferred antisense compounds having an IC$_{50}$<0.5 µM include SEQ ID NOs: 43, 114, 117, 127, 131, 177, 209, 210, 211, 212, 215, 217, 218, 219, 220, 221, 222, 229, 230, and 232.

In certain embodiments, certain antisense compounds as described herein are efficacious by virtue of having a viscosity of less than 40 cP, less than 35 cP, less than 30 cP, less than 25 cP, less than 20 cP, less than 15 cP, or less than 10 cP when measured by an assay (as described in Example 13). Oligonucleotides having a viscosity greater than 40 cP would have less than optimal viscosity. In certain embodiments, preferred antisense compounds having a viscosity <20 cP include SEQ ID NOs: 16, 18, 20, 34, 35, 36, 38, 49, 77, 90, 93, and 94. In certain embodiments, preferred antisense compounds having a viscosity <15 cP include SEQ ID NOs: 16, 18, 20, 34, 35, 38, 49, 90, 93, and 94. In certain embodiments, preferred antisense compounds having a viscosity <10 cP include SEQ ID NOs: 18, 34, 35, 49, 90, 93, and 94.

In certain embodiments, certain antisense compounds as described herein are highly tolerable, as demonstrated by the in vivo tolerability measurements described in the examples. In certain embodiments, the certain antisense compounds as described herein are highly tolerable, as demonstrated by having an increase in ALT and/or AST value of no more than 3 fold, 2 fold or 1.5 fold over saline treated animals.

In certain embodiments, certain antisense compounds as described herein are efficacious by virtue of having one or more of an inhibition potency of greater than 50%, an in vitro $IC_{50}$ of less than 1 µM, a viscosity of less than 20 cP, and no more than a 3 fold increase in ALT and/or AST.

In certain embodiments, ISIS 563580 (SEQ ID NO: 77) is preferred. This compound was found to be a potent inhibitor in ANGPTL3 transgenic mice and the most tolerable antisense compound. It had an acceptable viscosity of about 16.83 cP and an $IC_{50}$ value of <0.8 µM in vitro. In mice it had no more than a 3 fold increase in ALT and/or AST levels over saline treated animals. Also, in monkeys, it was among the most tolerable and potent compounds in inhibiting ANGPTL3 and had the best ratio of full-length oligonucleotide concentration.

In certain embodiments, ISIS 544199 (SEQ ID NO: 20) is preferred. This compound was found to be a potent and tolerable antisense compound. It had an acceptable viscosity of 1.7 cP and an $IC_{50}$ value of <0.5 µM in vitro. In mice it had no more than a 3 fold increase in ALT and/or AST levels over saline treated animals. Also, in monkeys, it was among the most potent compounds in inhibiting ANGPTL3 and had a good ratio of full-length oligonucleotide concentration.

In certain embodiments, ISIS 559277 (SEQ ID NO: 110) is preferred. This compound was found to be a potent and tolerable antisense compound. It had an $IC_{50}$ value of <0.8 µM in vitro. In mice it had no more than a 3 fold increase in ALT and/or AST levels over saline treated animals. Also, in monkeys, it was among the most potent compounds in inhibiting ANGPTL3 and had a good ratio of full-length oligonucleotide concentration.

EXAMPLES

Non-Limiting Disclosure and Incorporation by Reference

While certain compounds, compositions, and methods described herein have been described with specificity in accordance with certain embodiments, the following examples serve only to illustrate the compounds described herein and are not intended to limit the same. Each of the references recited in the present application is incorporated herein by reference in its entirety.

Example 1: Antisense Inhibition of Human Angiopoietin-Like 3 in Hep3B Cells by MOE Gapmers Antisense oligonucleotides were designed targeting an Angiopoietin-like 3 (ANGPTL3) nucleic acid and were tested for their effects on ANGPTL3 mRNA in vitro. The antisense oligonucleotides were tested in a series of experiments that had similar culture conditions. The results for each experiment are presented in separate tables shown below. Cultured Hep3B cells at a density of 20,000 cells per well were transfected using electroporation with 4,500 nM antisense oligonucleotide. After a treatment period of approximately 24 hours, RNA was isolated from the cells and ANGPTL3 mRNA levels were measured by quantitative real-time PCR. Human primer probe set RTS3492_MGB (forward sequence CCGTGGAAGAC-CAATATAAACAATT, designated herein as SEQ ID NO: 4; AGTCCTTCTGAGCTGATTTTCTATTTCT; reverse sequence, designated herein as SEQ ID NO: 5; probe sequence AACCAACAGCATAGTCAAATA, designated herein as SEQ ID NO: 6) was used to measure mRNA levels. ANGPTL3 mRNA levels were adjusted according to total RNA content, as measured by RIBOGREEN®. Results are presented as percent inhibition of ANGPTL3, relative to untreated control cells.

The newly designed chimeric antisense oligonucleotides in the Tables below were designed as 5-10-5 MOE gapmers. The 5-10-5 MOE gapmers are 20 nucleosides in length, wherein the central gap segment comprises often 2'-deoxynucleosides and is flanked by wing segments on the 5' direction and the 3' direction comprising five nucleosides each. Each nucleoside in the 5' wing segment and each nucleoside in the 3' wing segment has a 2'-MOE modification. The internucleoside linkages throughout each gapmer are phosphorothioate (P=S) linkages. All cytosine residues throughout each gapmer are 5-methylcytosines. "Start site" indicates the 5'-most nucleoside to which the gapmer is targeted in the human gene sequence. "Stop site" indicates the 3'-most nucleoside to which the gapmer is targeted human gene sequence. Each gapmer listed in the Tables below is targeted to either the human ANGPTL3 mRNA, designated herein as SEQ ID NO: 1 (GENBANK Accession No. NM_014495.2) or the human ANGPTL3 genomic sequence, designated herein as SEQ ID NO: 2 (GENBANK Accession No. NT_032977.9 truncated from nucleotides 33032001 to 33046000). 'n/a' indicates that the antisense oligonucleotide does not target that particular gene sequence with 100% complementarity.

TABLE 1

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 544059 | 23 | 42 | GATTTTCAATTTCAAGCAAC | 40 | 3127 | 3146 | 238 |
| 337459 | 49 | 68 | AGCTTAATTGTGAACATTTT | 47 | 3153 | 3172 | 239 |
| 544060 | 54 | 73 | GAAGGAGCTTAATTGTGAAC | 1 | 3158 | 3177 | 240 |
| 544061 | 63 | 82 | CAATAAAAGAAGGAGCTTA | 37 | 3167 | 3186 | 241 |
| 544062 | 66 | 85 | GAACAATAAAAGAAGGAGC | 38 | 3170 | 3189 | 242 |
| 544063 | 85 | 104 | CTGGAGGAAATAACTAGAGG | 30 | 3189 | 3208 | 243 |

TABLE 1-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 337460 | 88 | 107 | ATTCTGGAGGAAATAACTAG | 39 | 3192 | 3211 | 244 |
| 544064 | 112 | 131 | TCAAATGATGAATTGTCTTG | 36 | 3216 | 3235 | 245 |
| 544065 | 138 | 157 | TTGATTTTGGCTCTGGAGAT | 26 | 3242 | 3261 | 246 |
| 544066 | 145 | 164 | GCAAATCTTGATTTTGGCTC | 56 | 3249 | 3268 | 247 |
| 233676 | 148 | 167 | ATAGCAAATCTTGATTTTGG | 69 | 3252 | 3271 | 248 |
| 544067 | 156 | 175 | CGTCTAACATAGCAAATCTT | 64 | 3260 | 3279 | 249 |
| 544068 | 174 | 193 | TGGCTAAAATTTTTACATCG | 28 | 3278 | 3297 | 250 |
| 544069 | 178 | 197 | CCATTGGCTAAAATTTTTAC | 0 | 3282 | 3301 | 251 |
| 544070 | 184 | 203 | AGGAGGCCATTGGCTAAAAT | 7 | 3288 | 3307 | 252 |
| 544071 | 187 | 206 | TGAAGGAGGCCATTGGCTAA | 32 | 3291 | 3310 | 253 |
| 544072 | 195 | 214 | GTCCCAACTGAAGGAGGCCA | 9 | 3299 | 3318 | 254 |
| 544073 | 199 | 218 | CCATGTCCCAACTGAAGGAG | 6 | 3303 | 3322 | 255 |
| 544074 | 202 | 221 | AGACCATGTCCCAACTGAAG | 18 | 3306 | 3325 | 256 |
| 544075 | 206 | 225 | TTTAAGACCATGTCCCAACT | 0 | 3310 | 3329 | 257 |
| 544076 | 209 | 228 | GTCTTTAAGACCATGTCCCA | 0 | 3313 | 3332 | 258 |
| 544077 | 216 | 235 | GGACAAAGTCTTTAAGACCA | 0 | 3320 | 3339 | 259 |
| 544078 | 222 | 241 | TCTTATGGACAAAGTCTTTA | 0 | 3326 | 3345 | 260 |
| 544079 | 245 | 264 | TATGTCATTAATTTGGCCCT | 0 | 3349 | 3368 | 261 |
| 544080 | 270 | 289 | GATCAAATATGTTGAGTTTT | 27 | 3374 | 3393 | 262 |
| 233690 | 274 | 293 | GACTGATCAAATATGTTGAG | 49 | 3378 | 3397 | 263 |
| 544081 | 316 | 335 | TCTTCTTTGATTTCACTGGT | 62 | 3420 | 3439 | 264 |
| 544082 | 334 | 353 | CTTCTCAGTTCCTTTTCTTC | 35 | 3438 | 3457 | 265 |
| 544083 | 337 | 356 | GTTCTTCTCAGTTCCTTTTC | 60 | 3441 | 3460 | 266 |
| 544084 | 341 | 360 | TGTAGTTCTTCTCAGTTCCT | 51 | 3445 | 3464 | 267 |
| 544431 | 345 | 364 | TATATGTAGTTCTTCTCAGT | 9 | 3449 | 3468 | 268 |
| 544086 | 348 | 367 | GTTTATATGTAGTTCTTCTC | 39 | 3452 | 3471 | 269 |
| 544087 | 352 | 371 | TGTAGTTTATATGTAGTTCT | 30 | 3456 | 3475 | 270 |
| 544088 | 356 | 375 | GACTTGTAGTTTATATGTAG | 12 | 3460 | 3479 | 271 |
| 544089 | 364 | 383 | TCATTTTGACTTGTAGTTT | 31 | 3468 | 3487 | 272 |
| 544090 | 369 | 388 | CCTCTTCATTTTGACTTGT | 61 | 3473 | 3492 | 273 |
| 544091 | 375 | 394 | TCTTTACCTCTTCATTTTG | 48 | 3479 | 3498 | 274 |
| 544092 | 380 | 399 | CATATTCTTTACCTCTTCAT | 35 | 3484 | 3503 | 275 |
| 544093 | 384 | 403 | GTGACATATTCTTTACCTCT | 63 | 3488 | 3507 | 276 |
| 544094 | 392 | 411 | GAGTTCAAGTGACATATTCT | 53 | 3496 | 3515 | 277 |
| 544095 | 398 | 417 | TGAGTTGAGTTCAAGTGACA | 31 | 3502 | 3521 | 278 |

TABLE 1-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 544096 | 403 | 422 | AGTTTTGAGTTGAGTTCAAG | 14 | 3507 | 3526 | 279 |
| 544097 | 406 | 425 | TCAAGTTTTGAGTTGAGTTC | 38 | 3510 | 3529 | 280 |
| 544098 | 414 | 433 | GGAGGCTTTCAAGTTTTGAG | 39 | 3518 | 3537 | 281 |
| 544099 | 423 | 442 | TTTCTTCTAGGAGGCTTTCA | 57 | 3527 | 3546 | 282 |
| 544100 | 427 | 446 | ATTTTTTCTTCTAGGAGGCT | 39 | 3531 | 3550 | 283 |
| 544101 | 432 | 451 | GTAGAATTTTTCTTCTAGG | 28 | 3536 | 3555 | 284 |
| 544102 | 462 | 481 | GCTCTTCTAAATATTTCACT | 60 | 3566 | 3585 | 285 |
| 544103 | 474 | 493 | AGTTAGTTAGTTGCTCTTCT | 40 | 3578 | 3597 | 286 |
| 544104 | 492 | 511 | CAGGTTGATTTTGAATTAAG | 38 | 3596 | 3615 | 287 |
| 544105 | 495 | 514 | TTTCAGGTTGATTTTGAATT | 28 | 3599 | 3618 | 288 |
| 544106 | 499 | 518 | GGAGTTTCAGGTTGATTTTG | 38 | 3603 | 3622 | 289 |
| 544107 | 504 | 523 | GTTCTGGAGTTTCAGGTTGA | 50 | 3608 | 3627 | 290 |
| 544108 | 526 | 545 | TTAAGTGAAGTTACTTCTGG | 20 | 3630 | 3649 | 291 |
| 544109 | 555 | 574 | TGCTATTATCTTGTTTTTCT | 23 | 4293 | 4312 | 292 |
| 544110 | 564 | 583 | GGTCTTTGATGCTATTATCT | 67 | 4302 | 4321 | 293 |
| 544111 | 567 | 586 | GAAGGTCTTTGATGCTATTA | 49 | 4305 | 4324 | 294 |
| 544112 | 572 | 591 | CTGGAGAAGGTCTTTGATGC | 52 | 4310 | 4329 | 295 |
| 544113 | 643 | 662 | CTGAGCTGATTTTCTATTTC | 12 | n/a | n/a | 296 |
| 337477 | 664 | 683 | GGTTCTTGAATACTAGTCCT | 70 | 6677 | 6696 | 234 |
| 544114 | 673 | 692 | ATTTCTGTGGGTTCTTGAAT | 32 | 6686 | 6705 | 297 |
| 337478 | 675 | 694 | AAATTTCTGTGGGTTCTTGA | 51 | 6688 | 6707 | 235 |
| 544115 | 678 | 697 | GAGAAATTTCTGTGGGTTCT | 54 | 6691 | 6710 | 298 |
| 544116 | 682 | 701 | GATAGAGAAATTTCTGTGGG | 25 | 6695 | 6714 | 299 |
| 544117 | 689 | 708 | CTTGGAAGATAGAGAAATTT | 16 | 6702 | 6721 | 300 |
| 337479 | 692 | 711 | TGGCTTGGAAGATAGAGAAA | 34 | 6705 | 6724 | 236 |
| 544118 | 699 | 718 | GTGCTCTTGGCTTGGAAGAT | 64 | 6712 | 6731 | 301 |
| 544119 | 703 | 722 | CTTGGTGCTCTTGGCTTGGA | 70 | 6716 | 6735 | 302 |
| 544120 | 707 | 726 | AGTTCTTGGTGCTCTTGGCT | 82 | 6720 | 6739 | 15 |
| 233710 | 710 | 729 | AGTAGTTCTTGGTGCTCTTG | 63 | 6723 | 6742 | 233 |
| 544121 | 713 | 732 | GGGAGTAGTTCTTGGTGCTC | 64 | 6726 | 6745 | 303 |
| 544122 | 722 | 741 | CTGAAGAAAGGGAGTAGTTC | 24 | 6735 | 6754 | 304 |
| 544123 | 752 | 771 | ATCATGTTTTACATTTCTTA | 0 | 6765 | 6784 | 305 |
| 544124 | 755 | 774 | GCCATCATGTTTTACATTTC | 35 | n/a | n/a | 306 |
| 544125 | 759 | 778 | GAATGCCATCATGTTTTACA | 8 | n/a | n/a | 307 |

TABLE 1-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 544126 | 762 | 781 | CAGGAATGCCATCATGTTTT | 6 | n/a | n/a | 308 |
| 337487 | 804 | 823 | CACTTGTATGTTCACCTCTG | 65 | 7389 | 7408 | 28 |
| 233717 | 889 | 908 | TGAATTAATGTCCATGGACT | 33 | 7876 | 7895 | 14 |

TABLE 2

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 544204 | n/a | n/a | GACTTCTTAACTCTATATAT | 0 | 3076 | 3095 | 309 |
| 544205 | n/a | n/a | CTAGACTTCTTAACTCTATA | 0 | 3079 | 3098 | 310 |
| 544206 | n/a | n/a | GACCTAGACTTCTTAACTCT | 0 | 3082 | 3101 | 311 |
| 544207 | n/a | n/a | GGAAGCAGACCTAGACTTCT | 21 | 3089 | 3108 | 312 |
| 544208 | n/a | n/a | TCTGGAAGCAGACCTAGACT | 23 | 3092 | 3111 | 313 |
| 544209 | n/a | n/a | TCTTCTGGAAGCAGACCTAG | 7 | 3095 | 3114 | 314 |
| 544210 | n/a | n/a | CTAATCTTTAGGGATTTAGG | 24 | 11433 | 11452 | 315 |
| 544211 | n/a | n/a | TGTATCTAATCTTTAGGGAT | 2 | 11438 | 11457 | 316 |
| 544213 | n/a | n/a | TAACTTGGGCACTATATCCT | 44 | 11553 | 11572 | 317 |
| 544214 | n/a | n/a | ATTGACAAAGGTAGGTCACC | 59 | 11576 | 11595 | 318 |
| 544215 | n/a | n/a | ATATGACATGTATATTGGAT | 41 | 11620 | 11639 | 319 |
| 544216 | n/a | n/a | TTTTGTACTTTTCTGGAACA | 34 | 11704 | 11723 | 320 |
| 544217 | n/a | n/a | TAGTCTGTGGTCCTGAAAAT | 32 | 11748 | 11767 | 321 |
| 544218 | n/a | n/a | AGCTTAGTCTGTGGTCCTGA | 20 | 11752 | 11771 | 322 |
| 544219 | n/a | n/a | GACAGCTTAGTCTGTGGTCC | 45 | 11755 | 11774 | 323 |
| 544220 | n/a | n/a | GTATTCTGGCCCTAAAAAAA | 2 | 11789 | 11808 | 324 |
| 544221 | n/a | n/a | ATTTTGGTATTCTGGCCCTA | 39 | 11795 | 11814 | 325 |
| 544223 | n/a | n/a | TTTGCATTTGAAATTGTCCA | 32 | 11837 | 11856 | 326 |
| 544224 | n/a | n/a | GGAAGCAACTCATATATTAA | 39 | 11869 | 11888 | 327 |
| 544225 | n/a | n/a | TATCAGAAAAGATACCTGA | 0 | 9821 | 9840 | 328 |
| 544226 | n/a | n/a | ATAATAGCTAATAATGTGGG | 15 | 9875 | 9894 | 329 |
| 544227 | n/a | n/a | TGCAGATAATAGCTAATAAT | 31 | 9880 | 9899 | 330 |
| 544228 | n/a | n/a | TGTCATTGCAGATAATAGCT | 61 | 9886 | 9905 | 331 |
| 544229 | n/a | n/a | TAAAAGTTGTCATTGCAGAT | 38 | 9893 | 9912 | 332 |
| 544230 | n/a | n/a | CGGATTTTTAAAAGTTGTCA | 45 | 9901 | 9920 | 333 |

TABLE 2-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 544231 | n/a | n/a | GGGATTCGGATTTTTAAAAG | 0 | 9907 | 9926 | 334 |
| 544232 | n/a | n/a | TTTGGGATTCGGATTTTTAA | 24 | 9910 | 9929 | 335 |
| 544233 | n/a | n/a | ACGCTTATTTGGGATTCGGA | 53 | 9917 | 9936 | 336 |
| 544251 | n/a | n/a | TTTAAGAGATTTACAAGTCA | 11 | 2811 | 2830 | 337 |
| 544252 | n/a | n/a | GACTACCTGTTTTTAAAAGC | 6 | 2851 | 2870 | 338 |
| 544253 | n/a | n/a | TATGGTGACTACCTGTTTTT | 12 | 2857 | 2876 | 339 |
| 544254 | n/a | n/a | ACTTTGCTGTATTATAAACT | 12 | 2890 | 2909 | 340 |
| 544255 | n/a | n/a | ATTGTATTTAACTTTGCTGT | 0 | 2900 | 2919 | 341 |
| 544256 | n/a | n/a | GAGCAACTAACTTAATAGGT | 13 | 2928 | 2947 | 342 |
| 544257 | n/a | n/a | GAAATGAGCAACTAACTTAA | 25 | 2933 | 2952 | 343 |
| 544258 | n/a | n/a | AATCAAAGAAATGAGCAACT | 0 | 2940 | 2959 | 344 |
| 544259 | n/a | n/a | ACCTTCTTCCACATTGAGTT | 8 | 2977 | 2996 | 345 |
| 544260 | n/a | n/a | CACGAATGTAACCTTCTTCC | 0 | 2987 | 3006 | 346 |
| 544261 | n/a | n/a | TTAACTTGCACGAATGTAAC | 27 | 2995 | 3014 | 347 |
| 544262 | n/a | n/a | TATATATACCAATATTTGCC | 0 | 3063 | 3082 | 348 |
| 544263 | n/a | n/a | TCTTAACTCTATATATACCA | 0 | 3072 | 3091 | 349 |
| 544264 | n/a | n/a | CTTTAAGTGAAGTTACTTCT | 17 | 3632 | 3651 | 350 |
| 544265 | n/a | n/a | TCTACTTACTTTAAGTGAAG | 9 | 3640 | 3659 | 351 |
| 544266 | n/a | n/a | GAACCCTCTTTATTTTCTAC | 1 | 3655 | 3674 | 352 |
| 544267 | n/a | n/a | ACATAAACATGAACCCTCTT | 6 | 3665 | 3684 | 353 |
| 544268 | n/a | n/a | CCACATTGAAAACATAAACA | 25 | 3676 | 3695 | 354 |
| 544269 | n/a | n/a | GCATGCCTTAGAAATATTTT | 7 | 3707 | 3726 | 355 |
| 544270 | n/a | n/a | CAATGCAACAAAGTATTTCA | 0 | 3731 | 3750 | 356 |
| 544271 | n/a | n/a | CTGGAGATTATTTTCTTGG | 34 | 3768 | 3787 | 357 |
| 544272 | n/a | n/a | TTCATATATAACATTAGGGA | 0 | 3830 | 3849 | 358 |
| 544273 | n/a | n/a | TCAGTGTTTTCATATATAAC | 18 | 3838 | 3857 | 359 |
| 544274 | n/a | n/a | GACATAGTGTTCTAGATTGT | 14 | 3900 | 3919 | 360 |
| 544275 | n/a | n/a | CAATAGTGTAATGACATAGT | 21 | 3912 | 3931 | 361 |
| 544276 | n/a | n/a | TTACTTACCTTCAGTAATTT | 0 | 3933 | 3952 | 362 |
| 544277 | n/a | n/a | ATCTTTTCCATTTACTGTAT | 8 | 4005 | 4024 | 363 |
| 544278 | n/a | n/a | AGAAAAAGCCCAGCATATTT | 11 | 4037 | 4056 | 364 |
| 544279 | n/a | n/a | GTATGCTTCTTTCAAATAGC | 36 | 4130 | 4149 | 365 |
| 544280 | n/a | n/a | CCTTCCCCTTGTATGCTTCT | 41 | 4140 | 4159 | 366 |
| 544281 | n/a | n/a | CCTGTAACACTATCATAATC | 1 | 4207 | 4226 | 367 |
| 544282 | n/a | n/a | TGACTTACCTGATTTTCTAT | 6 | 4384 | 4403 | 368 |
| 544283 | n/a | n/a | GATGGGACATACCATTAAAA | 0 | 4407 | 4426 | 369 |

TABLE 2-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 544284 | n/a | n/a | GTGAAAGATGGGACATACCA | 20 | 4413 | 4432 | 370 |
| 544285 | n/a | n/a | CCTGTGTGAAAGATGGGACA | 6 | 4418 | 4437 | 371 |
| 544286 | n/a | n/a | CATTGGCTGCTATGAATTAA | 41 | 4681 | 4700 | 372 |
| 544287 | n/a | n/a | GATGACATTGGCTGCTATGA | 40 | 4686 | 4705 | 373 |
| 544288 | n/a | n/a | GAGAAACATGATCTAATTTG | 12 | 4717 | 4736 | 374 |
| 544289 | n/a | n/a | ATGGAAAGCTATTGTGTGGT | 0 | 4747 | 4766 | 375 |
| 544290 | n/a | n/a | GTCTAAAGAGCCAATATGAG | 22 | 4771 | 4790 | 376 |
| 544291 | n/a | n/a | AATCTTGGTCTAAAGAGCCA | 46 | 4778 | 4797 | 377 |
| 544433 | n/a | n/a | GAGATTTACAAGTCAAAAAT | 4 | 2806 | 2825 | 378 |
| 544434 | n/a | n/a | ATTTAACTTTGCTGTATTAT | 0 | 2895 | 2914 | 379 |
| 544435 | n/a | n/a | ATCAATGCTAAATGAAATCA | 0 | 2955 | 2974 | 380 |
| 544436 | n/a | n/a | TATTTTCTGGAGATTATTTT | 0 | 3774 | 3793 | 381 |
| 544437 | n/a | n/a | AAAATGAATATTGGCAATTC | 0 | 4159 | 4178 | 382 |
| 233717 | 889 | 908 | TGAATTAATGTCCATGGACT | 36 | 7876 | 7895 | 14 |
| 544202 | 2081 | 2100 | AAAGTCAATGTGACTTAGTA | 42 | 11053 | 11072 | 383 |
| 544203 | 2104 | 2123 | AAGGTATAGTGATACCTCAT | 56 | 11076 | 11095 | 384 |

TABLE 3

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 544127 | 765 | 784 | CAGCAGGAATGCCATCATGT | 4 | N/A | N/A | 385 |
| 544128 | 819 | 838 | TGATGGCATACATGCCACTT | 0 | 7404 | 7423 | 386 |
| 544129 | 828 | 847 | TGCTGGGTCTGATGGCATAC | 44 | 7413 | 7432 | 387 |
| 544130 | 832 | 851 | GAGTTGCTGGGTCTGATGGC | 16 | 7417 | 7436 | 388 |
| 544131 | 841 | 860 | AAAACTTGAGAGTTGCTGGG | 0 | 7426 | 7445 | 389 |
| 544132 | 848 | 867 | GACATGAAAACTTGAGAGT | 0 | 7433 | 7452 | 390 |
| 544133 | 859 | 878 | ACATCACAGTAGACATGAAA | 25 | 7444 | 7463 | 391 |
| 233717 | 889 | 908 | TGAATTAATGTCCATGGACT | 36 | 7876 | 7895 | 14 |
| 544134 | 915 | 934 | AGTTTTGTGATCCATCTATT | 46 | 7902 | 7921 | 392 |
| 544135 | 918 | 937 | TGAAGTTTTGTGATCCATCT | 42 | 7905 | 7924 | 393 |
| 544136 | 926 | 945 | CGTTTCATTGAAGTTTTGTG | 45 | 7913 | 7932 | 394 |
| 544137 | 946 | 965 | CCATATTTGTAGTTCTCCCA | 44 | 7933 | 7952 | 395 |
| 544138 | 949 | 968 | AAACCATATTTGTAGTTCTC | 25 | 7936 | 7955 | 396 |

TABLE 3-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 544139 | 970 | 989 | AATTCTCCATCAAGCCTCCC | 35 | N/A | N/A | 397 |
| 233722 | 991 | 1010 | ATCTTCTCTAGGCCCAACCA | 65 | 9566 | 9585 | 398 |
| 544432 | 997 | 1016 | GAGTATATCTTCTCTAGGCC | 0 | 9572 | 9591 | 399 |
| 544140 | 1002 | 1021 | CTATGGAGTATATCTTCTCT | 6 | 9577 | 9596 | 400 |
| 544141 | 1008 | 1027 | GCTTCACTATGGAGTATATC | 63 | 9583 | 9602 | 401 |
| 544142 | 1013 | 1032 | AGATTGCTTCACTATGGAGT | 52 | 9588 | 9607 | 402 |
| 544143 | 1046 | 1065 | CCAGTCTTCCAACTCAATTC | 35 | 9621 | 9640 | 403 |
| 544144 | 1052 | 1071 | GTCTTTCCAGTCTTCCAACT | 64 | 9627 | 9646 | 404 |
| 544145 | 1055 | 1074 | GTTGTCTTTCCAGTCTTCCA | 80 | 9630 | 9649 | 16 |
| 544146 | 1059 | 1078 | GTTTGTTGTCTTTCCAGTCT | 59 | 9634 | 9653 | 405 |
| 544147 | 1062 | 1081 | AATGTTTGTTGTCTTTCCAG | 12 | 9637 | 9656 | 406 |
| 544148 | 1095 | 1114 | CGTGATTTCCCAAGTAAAAA | 56 | 9670 | 9689 | 407 |
| 544149 | 1160 | 1179 | GTTTTCCGGGATTGCATTGG | 33 | 9735 | 9754 | 408 |
| 544150 | 1165 | 1184 | TCTTTGTTTTCCGGGATTGC | 54 | 9740 | 9759 | 409 |
| 544151 | 1170 | 1189 | CCAAATCTTTGTTTTCCGGG | 64 | 9745 | 9764 | 410 |
| 544152 | 1173 | 1192 | ACACCAAATCTTTGTTTTCC | 37 | 9748 | 9767 | 411 |
| 544153 | 1178 | 1197 | AGAAAACACCAAATCTTTGT | 32 | 9753 | 9772 | 412 |
| 544154 | 1183 | 1202 | CAAGTAGAAAACACCAAATC | 13 | 9758 | 9777 | 413 |
| 544155 | 1188 | 1207 | GATCCCAAGTAGAAAACACC | 0 | 9763 | 9782 | 414 |
| 544156 | 1195 | 1214 | GCTTTGTGATCCCAAGTAGA | 74 | 9770 | 9789 | 17 |
| 544157 | 1198 | 1217 | TTTGCTTTGTGATCCCAAGT | 73 | 9773 | 9792 | 415 |
| 544158 | 1202 | 1221 | TCCTTTTGCTTTGTGATCCC | 62 | 9777 | 9796 | 416 |
| 544159 | 1208 | 1227 | GAAGTGTCCTTTTGCTTTGT | 30 | 9783 | 9802 | 417 |
| 544160 | 1246 | 1265 | TGCCACCACCAGCCTCCTGA | 60 | N/A | N/A | 418 |
| 544161 | 1253 | 1272 | CTCATCATGCCACCACCAGC | 73 | 10225 | 10244 | 419 |
| 544162 | 1269 | 1288 | GGTTGTTTTCTCCACACTCA | 76 | 10241 | 10260 | 18 |
| 544163 | 1276 | 1295 | CCATTTAGGTTGTTTTCTCC | 25 | 10248 | 10267 | 420 |
| 544164 | 1283 | 1302 | ATATTTACCATTTAGGTTGT | 25 | 10255 | 10274 | 421 |
| 544165 | 1294 | 1313 | CTTGGTTTGTTATATTTACC | 63 | 10266 | 10285 | 422 |
| 544166 | 1353 | 1372 | ACCTTCCATTTTGAGACTTC | 75 | 10325 | 10344 | 19 |
| 544167 | 1363 | 1382 | ATAGAGTATAACCTTCCATT | 71 | 10335 | 10354 | 423 |
| 544168 | 1367 | 1386 | TTTTATAGAGTATAACCTTC | 37 | 10339 | 10358 | 424 |
| 544169 | 1374 | 1393 | TGGTTGATTTTATAGAGTAT | 37 | 10346 | 10365 | 425 |
| 544170 | 1378 | 1397 | ATTTGGTTGATTTTATAGA | 3 | 10350 | 10369 | 426 |
| 544171 | 1383 | 1402 | TCAACATTTGGTTGATTTT | 16 | 10355 | 10374 | 427 |
| 544172 | 1390 | 1409 | GGATGGATCAACATTTTGGT | 51 | 10362 | 10381 | 428 |

TABLE 3-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 544173 | 1393 | 1412 | GTTGGATGGATCAACATTTT | 62 | 10365 | 10384 | 429 |
| 544174 | 1396 | 1415 | TCTGTTGGATGGATCAACAT | 5 | 10368 | 10387 | 430 |
| 544175 | 1401 | 1420 | CTGAATCTGTTGGATGGATC | 55 | 10373 | 10392 | 431 |
| 544176 | 1407 | 1426 | AGCTTTCTGAATCTGTTGGA | 65 | 10379 | 10398 | 432 |
| 544177 | 1414 | 1433 | CATTCAAAGCTTTCTGAATC | 21 | 10386 | 10405 | 433 |
| 544178 | 1417 | 1436 | GTTCATTCAAAGCTTTCTGA | 66 | 10389 | 10408 | 434 |
| 544179 | 1420 | 1439 | TCAGTTCATTCAAAGCTTTC | 6 | 10392 | 10411 | 435 |
| 544180 | 1423 | 1442 | GCCTCAGTTCATTCAAAGCT | 68 | 10395 | 10414 | 436 |
| 544181 | 1427 | 1446 | ATTTGCCTCAGTTCATTCAA | 53 | 10399 | 10418 | 437 |
| 544182 | 1431 | 1450 | TTAAATTTGCCTCAGTTCAT | 40 | 10403 | 10422 | 438 |
| 544183 | 1436 | 1455 | GCCTTTTAAATTTGCCTCAG | 70 | 10408 | 10427 | 439 |
| 544184 | 1498 | 1517 | AGGATTTAATACCAGATTAT | 38 | 10470 | 10489 | 440 |
| 544185 | 1502 | 1521 | CTTAAGGATTTAATACCAGA | 56 | 10474 | 10493 | 441 |
| 544186 | 1505 | 1524 | TCTCTTAAGGATTTAATACC | 33 | 10477 | 10496 | 442 |
| 544187 | 1546 | 1565 | GACAGTGACTTTAAGATAAA | 35 | 10518 | 10537 | 443 |
| 544188 | 1572 | 1591 | TGTGATTGTATGTTTAATCT | 48 | 10544 | 10563 | 444 |
| 544189 | 1578 | 1597 | AGGTTATGTGATTGTATGTT | 48 | 10550 | 10569 | 445 |
| 544190 | 1583 | 1602 | CTTTAAGGTTATGTGATTGT | 48 | 10555 | 10574 | 446 |
| 544191 | 1589 | 1608 | GGTATTCTTTAAGGTTATGT | 62 | 10561 | 10580 | 447 |
| 544192 | 1656 | 1675 | ATTGATTCCCACATCACAAA | 47 | 10628 | 10647 | 448 |
| 544193 | 1661 | 1680 | CTAAAATTGATTCCCACATC | 67 | 10633 | 10652 | 449 |
| 544194 | 1665 | 1684 | CCATCTAAAATTGATTCCCA | 63 | 10637 | 10656 | 450 |
| 544195 | 1771 | 1790 | TTGTGATATTAGCTCATATG | 59 | 10743 | 10762 | 451 |
| 544196 | 1794 | 1813 | ACTAGTTTTTAAACTGGGA | 28 | 10766 | 10785 | 452 |
| 544197 | 1820 | 1839 | GTCAAGTTTAGAGTTTTAAC | 44 | 10792 | 10811 | 453 |
| 544198 | 1826 | 1845 | TATTTAGTCAAGTTTAGAGT | 14 | 10798 | 10817 | 454 |
| 544199 | 1907 | 1926 | TACACATACTCTGTGCTGAC | 82 | 10879 | 10898 | 20 |
| 544200 | 1913 | 1932 | GATTTTACACATACTCTGT | 57 | 10885 | 10904 | 455 |
| 544201 | 2008 | 2027 | CTGCTTCATTAGGTTTCATA | 61 | 10980 | 10999 | 456 |

TABLE 4

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 544127 | 765 | 784 | CAGCAGGAATGCCATCATGT | 0 | N/A | N/A | 457 |
| 544128 | 819 | 838 | TGATGGCATACATGCCACTT | 13 | 7404 | 7423 | 458 |
| 544129 | 828 | 847 | TGCTGGGTCTGATGGCATAC | 49 | 7413 | 7432 | 459 |
| 544130 | 832 | 851 | GAGTTGCTGGGTCTGATGGC | 27 | 7417 | 7436 | 460 |
| 544131 | 841 | 860 | AAAACTTGAGAGTTGCTGGG | 0 | 7426 | 7445 | 461 |
| 544132 | 848 | 867 | GACATGAAAACTTGAGAGT | 0 | 7433 | 7452 | 462 |
| 544133 | 859 | 878 | ACATCACAGTAGACATGAAA | 18 | 7444 | 7463 | 463 |
| 233717 | 889 | 908 | TGAATTAATGTCCATGGACT | 55 | 7876 | 7895 | 14 |
| 544134 | 915 | 934 | AGTTTTGTGATCCATCTATT | 68 | 7902 | 7921 | 464 |
| 544135 | 918 | 937 | TGAAGTTTTGTGATCCATCT | 77 | 7905 | 7924 | 465 |
| 544136 | 926 | 945 | CGTTTCATTGAAGTTTTGTG | 60 | 7913 | 7932 | 466 |
| 544137 | 946 | 965 | CCATATTTGTAGTTCTCCCA | 64 | 7933 | 7952 | 467 |
| 544138 | 949 | 968 | AAACCATATTTGTAGTTCTC | 45 | 7936 | 7955 | 468 |
| 544139 | 970 | 989 | AATTCTCCATCAAGCCTCCC | 70 | N/A | N/A | 469 |
| 233722 | 991 | 1010 | ATCTTCTCTAGGCCCAACCA | 96 | 9566 | 9585 | 470 |
| 544432 | 997 | 1016 | GAGTATATCTTCTCTAGGCC | 69 | 9572 | 9591 | 471 |
| 544140 | 1002 | 1021 | CTATGGAGTATATCTTCTCT | 37 | 9577 | 9596 | 472 |
| 544141 | 1008 | 1027 | GCTTCACTATGGAGTATATC | 65 | 9583 | 9602 | 473 |
| 544142 | 1013 | 1032 | AGATTGCTTCACTATGGAGT | 55 | 9588 | 9607 | 474 |
| 544143 | 1046 | 1065 | CCAGTCTTCCAACTCAATTC | 31 | 9621 | 9640 | 475 |
| 544144 | 1052 | 1071 | GTCTTTCCAGTCTTCCAACT | 72 | 9627 | 9646 | 476 |
| 544145 | 1055 | 1074 | GTTGTCTTTCCAGTCTTCCA | 86 | 9630 | 9649 | 16 |
| 544146 | 1059 | 1078 | GTTTGTTGTCTTTCCAGTCT | 66 | 9634 | 9653 | 477 |
| 544147 | 1062 | 1081 | AATGTTTGTTGTCTTTCCAG | 21 | 9637 | 9656 | 478 |
| 544148 | 1095 | 1114 | CGTGATTTCCCAAGTAAAAA | 63 | 9670 | 9689 | 479 |
| 544149 | 1160 | 1179 | GTTTTCCGGGATTGCATTGG | 32 | 9735 | 9754 | 480 |
| 544150 | 1165 | 1184 | TCTTTGTTTTCCGGGATTGC | 48 | 9740 | 9759 | 481 |
| 544151 | 1170 | 1189 | CCAAATCTTTGTTTTCCGGG | 72 | 9745 | 9764 | 482 |
| 544152 | 1173 | 1192 | ACACCAAATCTTTGTTTTCC | 39 | 9748 | 9767 | 483 |
| 544153 | 1178 | 1197 | AGAAACACCAAATCTTTGT | 39 | 9753 | 9772 | 484 |
| 544154 | 1183 | 1202 | CAAGTAGAAAACACCAAATC | 22 | 9758 | 9777 | 485 |
| 544155 | 1188 | 1207 | GATCCCAAGTAGAAAACACC | 5 | 9763 | 9782 | 486 |
| 544156 | 1195 | 1214 | GCTTTGTGATCCCAAGTAGA | 79 | 9770 | 9789 | 17 |
| 544157 | 1198 | 1217 | TTTGCTTTGTGATCCCAAGT | 80 | 9773 | 9792 | 487 |
| 544158 | 1202 | 1221 | TCCTTTTGCTTTGTGATCCC | 73 | 9777 | 9796 | 488 |
| 544159 | 1208 | 1227 | GAAGTGTCCTTTTGCTTTGT | 33 | 9783 | 9802 | 489 |

TABLE 4-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 544160 | 1246 | 1265 | TGCCACCACCAGCCTCCTGA | 67 | N/A | N/A | 490 |
| 544161 | 1253 | 1272 | CTCATCATGCCACCACCAGC | 79 | 10225 | 10244 | 491 |
| 544162 | 1269 | 1288 | GGTTGTTTTCTCCACACTCA | 84 | 10241 | 10260 | 18 |
| 544163 | 1276 | 1295 | CCATTTAGGTTGTTTTCTCC | 34 | 10248 | 10267 | 492 |
| 544164 | 1283 | 1302 | ATATTTACCATTTAGGTTGT | 17 | 10255 | 10274 | 493 |
| 544165 | 1294 | 1313 | CTTGGTTTGTTATATTTACC | 76 | 10266 | 10285 | 494 |
| 544166 | 1353 | 1372 | ACCTTCCATTTTGAGACTTC | 79 | 10325 | 10344 | 19 |
| 544167 | 1363 | 1382 | ATAGAGTATAACCTTCCATT | 73 | 10335 | 10354 | 495 |
| 544168 | 1367 | 1386 | TTTTATAGAGTATAACCTTC | 41 | 10339 | 10358 | 496 |
| 544169 | 1374 | 1393 | TGGTTGATTTTATAGAGTAT | 53 | 10346 | 10365 | 497 |
| 544170 | 1378 | 1397 | ATTTTGGTTGATTTTATAGA | 28 | 10350 | 10369 | 498 |
| 544171 | 1383 | 1402 | TCAACATTTTGGTTGATTTT | 19 | 10355 | 10374 | 499 |
| 544172 | 1390 | 1409 | GGATGGATCAACATTTTGGT | 66 | 10362 | 10381 | 500 |
| 544173 | 1393 | 1412 | GTTGGATGGATCAACATTTT | 71 | 10365 | 10384 | 501 |
| 544174 | 1396 | 1415 | TCTGTTGGATGGATCAACAT | 35 | 10368 | 10387 | 502 |
| 544175 | 1401 | 1420 | CTGAATCTGTTGGATGGATC | 68 | 10373 | 10392 | 503 |
| 544176 | 1407 | 1426 | AGCTTTCTGAATCTGTTGGA | 70 | 10379 | 10398 | 504 |
| 544177 | 1414 | 1433 | CATTCAAAGCTTTCTGAATC | 35 | 10386 | 10405 | 505 |
| 544178 | 1417 | 1436 | GTTCATTCAAAGCTTTCTGA | 76 | 10389 | 10408 | 506 |
| 544179 | 1420 | 1439 | TCAGTTCATTCAAAGCTTTC | 15 | 10392 | 10411 | 507 |
| 544180 | 1423 | 1442 | GCCTCAGTTCATTCAAAGCT | 68 | 10395 | 10414 | 508 |
| 544181 | 1427 | 1446 | ATTTGCCTCAGTTCATTCAA | 67 | 10399 | 10418 | 509 |
| 544182 | 1431 | 1450 | TTAAATTTGCCTCAGTTCAT | 51 | 10403 | 10422 | 510 |
| 544183 | 1436 | 1455 | GCCTTTTAAATTTGCCTCAG | 80 | 10408 | 10427 | 511 |
| 544184 | 1498 | 1517 | AGGATTAATACCAGATTAT | 54 | 10470 | 10489 | 512 |
| 544185 | 1502 | 1521 | CTTAAGGATTAATACCAGA | 69 | 10474 | 10493 | 513 |
| 544186 | 1505 | 1524 | TCTCTTAAGGATTTAATACC | 58 | 10477 | 10496 | 514 |
| 544187 | 1546 | 1565 | GACAGTGACTTTAAGATAAA | 34 | 10518 | 10537 | 515 |
| 544188 | 1572 | 1591 | TGTGATTGTATGTTTAATCT | 47 | 10544 | 10563 | 516 |
| 544189 | 1578 | 1597 | AGGTTATGTGATTGTATGTT | 68 | 10550 | 10569 | 517 |
| 544190 | 1583 | 1602 | CTTTAAGGTTATGTGATTGT | 62 | 10555 | 10574 | 518 |
| 544191 | 1589 | 1608 | GGTATTCTTTAAGGTTATGT | 66 | 10561 | 10580 | 519 |
| 544192 | 1656 | 1675 | ATTGATTCCCACATCACAAA | 50 | 10628 | 10647 | 520 |
| 544193 | 1661 | 1680 | CTAAAATTGATTCCCACATC | 73 | 10633 | 10652 | 521 |
| 544194 | 1665 | 1684 | CCATCTAAAATTGATTCCCA | 73 | 10637 | 10656 | 522 |
| 544195 | 1771 | 1790 | TTGTGATATTAGCTCATATG | 57 | 10743 | 10762 | 523 |

TABLE 4-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 544196 | 1794 | 1813 | ACTAGTTTTTTAAACTGGGA | 21 | 10766 | 10785 | 524 |
| 544197 | 1820 | 1839 | GTCAAGTTTAGAGTTTTAAC | 53 | 10792 | 10811 | 525 |
| 544198 | 1826 | 1845 | TATTTAGTCAAGTTTAGAGT | 11 | 10798 | 10817 | 526 |
| 544199 | 1907 | 1926 | TACACATACTCTGTGCTGAC | 84 | 10879 | 10898 | 20 |
| 544200 | 1913 | 1932 | GATTTTTACACATACTCTGT | 53 | 10885 | 10904 | 527 |
| 544201 | 2008 | 2027 | CTGCTTCATTAGGTTTCATA | 67 | 10980 | 10999 | 528 |

TABLE 5

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 544127 | 765 | 784 | CAGCAGGAATGCCATCATGT | 18 | N/A | N/A | 529 |
| 544128 | 819 | 838 | TGATGGCATACATGCCACTT | 0 | 7404 | 7423 | 530 |
| 544129 | 828 | 847 | TGCTGGGTCTGATGGCATAC | 48 | 7413 | 7432 | 531 |
| 544130 | 832 | 851 | GAGTTGCTGGGTCTGATGGC | 14 | 7417 | 7436 | 532 |
| 544131 | 841 | 860 | AAAACTTGAGAGTTGCTGGG | 5 | 7426 | 7445 | 533 |
| 544132 | 848 | 867 | GACATGAAAAACTTGAGAGT | 0 | 7433 | 7452 | 534 |
| 544133 | 859 | 878 | ACATCACAGTAGACATGAAA | 28 | 7444 | 7463 | 535 |
| 233717 | 889 | 908 | TGAATTAATGTCCATGGACT | 51 | 7876 | 7895 | 14 |
| 544134 | 915 | 934 | AGTTTTGTGATCCATCTATT | 36 | 7902 | 7921 | 536 |
| 544135 | 918 | 937 | TGAAGTTTTGTGATCCATCT | 61 | 7905 | 7924 | 537 |
| 544136 | 926 | 945 | CGTTTCATTGAAGTTTTGTG | 54 | 7913 | 7932 | 538 |
| 544137 | 946 | 965 | CCATATTTGTAGTTCTCCCA | 67 | 7933 | 7952 | 539 |
| 544138 | 949 | 968 | AAACCATATTTGTAGTTCTC | 39 | 7936 | 7955 | 540 |
| 544139 | 970 | 989 | AATTCTCCATCAAGCCTCCC | 77 | N/A | N/A | 541 |
| 233722 | 991 | 1010 | ATCTTCTCTAGGCCCAACCA | 95 | 9566 | 9585 | 542 |
| 544432 | 997 | 1016 | GAGTATATCTTCTCTAGGCC | 86 | 9572 | 9591 | 543 |
| 544140 | 1002 | 1021 | CTATGGAGTATATCTTCTCT | 57 | 9577 | 9596 | 544 |
| 544141 | 1008 | 1027 | GCTTCACTATGGAGTATATC | 52 | 9583 | 9602 | 545 |
| 544142 | 1013 | 1032 | AGATTGCTTCACTATGGAGT | 40 | 9588 | 9607 | 546 |
| 544143 | 1046 | 1065 | CCAGTCTTCCAACTCAATTC | 32 | 9621 | 9640 | 547 |
| 544144 | 1052 | 1071 | GTCTTTCCAGTCTTCCAACT | 53 | 9627 | 9646 | 548 |
| 544145 | 1055 | 1074 | GTTGTCTTTCCAGTCTTCCA | 80 | 9630 | 9649 | 16 |
| 544146 | 1059 | 1078 | GTTTGTTGTCTTTCCAGTCT | 59 | 9634 | 9653 | 549 |
| 544147 | 1062 | 1081 | AATGTTTGTTGTCTTTCCAG | 42 | 9637 | 9656 | 550 |

TABLE 5-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 544148 | 1095 | 1114 | CGTGATTTCCCAAGTAAAAA | 76 | 9670 | 9689 | 551 |
| 544149 | 1160 | 1179 | GTTTTCCGGGATTGCATTGG | 29 | 9735 | 9754 | 552 |
| 544150 | 1165 | 1184 | TCTTTGTTTTCCGGGATTGC | 50 | 9740 | 9759 | 553 |
| 544151 | 1170 | 1189 | CCAAATCTTTGTTTTCCGGG | 56 | 9745 | 9764 | 554 |
| 544152 | 1173 | 1192 | ACACCAAATCTTTGTTTTCC | 26 | 9748 | 9767 | 555 |
| 544153 | 1178 | 1197 | AGAAAACACCAAATCTTTGT | 22 | 9753 | 9772 | 556 |
| 544154 | 1183 | 1202 | CAAGTAGAAAACACCAAATC | 29 | 9758 | 9777 | 557 |
| 544155 | 1188 | 1207 | GATCCCAAGTAGAAAACACC | 16 | 9763 | 9782 | 558 |
| 544156 | 1195 | 1214 | GCTTTGTGATCCCAAGTAGA | 71 | 9770 | 9789 | 17 |
| 544157 | 1198 | 1217 | TTTGCTTTGTGATCCCAAGT | 55 | 9773 | 9792 | 559 |
| 544158 | 1202 | 1221 | TCCTTTTGCTTTGTGATCCC | 51 | 9777 | 9796 | 560 |
| 544159 | 1208 | 1227 | GAAGTGTCCTTTTGCTTTGT | 8 | 9783 | 9802 | 561 |
| 544160 | 1246 | 1265 | TGCCACCACCAGCCTCCTGA | 68 | N/A | N/A | 562 |
| 544161 | 1253 | 1272 | CTCATCATGCCACCACCAGC | 48 | 10225 | 10244 | 563 |
| 544162 | 1269 | 1288 | GGTTGTTTTCTCCACACTCA | 74 | 10241 | 10260 | 18 |
| 544163 | 1276 | 1295 | CCATTTAGGTTGTTTTCTCC | 33 | 10248 | 10267 | 564 |
| 544164 | 1283 | 1302 | ATATTTACCATTTAGGTTGT | 0 | 10255 | 10274 | 565 |
| 544165 | 1294 | 1313 | CTTGGTTTGTTATATTTACC | 52 | 10266 | 10285 | 566 |
| 544166 | 1353 | 1372 | ACCTTCCATTTTGAGACTTC | 69 | 10325 | 10344 | 19 |
| 544167 | 1363 | 1382 | ATAGAGTATAACCTTCCATT | 72 | 10335 | 10354 | 567 |
| 544168 | 1367 | 1386 | TTTTATAGAGTATAACCTTC | 27 | 10339 | 10358 | 568 |
| 544169 | 1374 | 1393 | TGGTTGATTTTATAGAGTAT | 39 | 10346 | 10365 | 569 |
| 544170 | 1378 | 1397 | ATTTTGGTTGATTTTATAGA | 7 | 10350 | 10369 | 570 |
| 544171 | 1383 | 1402 | TCAACATTTTGGTTGATTTT | 0 | 10355 | 10374 | 571 |
| 544172 | 1390 | 1409 | GGATGGATCAACATTTTGGT | 48 | 10362 | 10381 | 572 |
| 544173 | 1393 | 1412 | GTTGGATGGATCAACATTTT | 51 | 10365 | 10384 | 573 |
| 544174 | 1396 | 1415 | TCTGTTGGATGGATCAACAT | 46 | 10368 | 10387 | 574 |
| 544175 | 1401 | 1420 | CTGAATCTGTTGGATGGATC | 58 | 10373 | 10392 | 575 |
| 544176 | 1407 | 1426 | AGCTTTCTGAATCTGTTGGA | 57 | 10379 | 10398 | 576 |
| 544177 | 1414 | 1433 | CATTCAAAGCTTTCTGAATC | 0 | 10386 | 10405 | 577 |
| 544178 | 1417 | 1436 | GTTCATTCAAAGCTTTCTGA | 62 | 10389 | 10408 | 578 |
| 544179 | 1420 | 1439 | TCAGTTCATTCAAAGCTTTC | 21 | 10392 | 10411 | 579 |
| 544180 | 1423 | 1442 | GCCTCAGTTCATTCAAAGCT | 73 | 10395 | 10414 | 580 |
| 544181 | 1427 | 1446 | ATTTGCCTCAGTTCATTCAA | 46 | 10399 | 10418 | 581 |
| 544182 | 1431 | 1450 | TTAAATTTGCCTCAGTTCAT | 52 | 10403 | 10422 | 582 |
| 544183 | 1436 | 1455 | GCCTTTTAAATTTGCCTCAG | 66 | 10408 | 10427 | 583 |

TABLE 5-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 544184 | 1498 | 1517 | AGGATTTAATACCAGATTAT | 31 | 10470 | 10489 | 584 |
| 544185 | 1502 | 1521 | CTTAAGGATTTAATACCAGA | 49 | 10474 | 10493 | 585 |
| 544186 | 1505 | 1524 | TCTCTTAAGGATTTAATACC | 49 | 10477 | 10496 | 586 |
| 544187 | 1546 | 1565 | GACAGTGACTTTAAGATAAA | 27 | 10518 | 10537 | 587 |
| 544188 | 1572 | 1591 | TGTGATTGTATGTTTAATCT | 30 | 10544 | 10563 | 588 |
| 544189 | 1578 | 1597 | AGGTTATGTGATTGTATGTT | 35 | 10550 | 10569 | 589 |
| 544190 | 1583 | 1602 | CTTTAAGGTTATGTGATTGT | 50 | 10555 | 10574 | 590 |
| 544191 | 1589 | 1608 | GGTATTCTTTAAGGTTATGT | 54 | 10561 | 10580 | 591 |
| 544192 | 1656 | 1675 | ATTGATTCCCACATCACAAA | 47 | 10628 | 10647 | 592 |
| 544193 | 1661 | 1680 | CTAAAATTGATTCCCACATC | 69 | 10633 | 10652 | 593 |
| 544194 | 1665 | 1684 | CCATCTAAAATTGATTCCCA | 74 | 10637 | 10656 | 594 |
| 544195 | 1771 | 1790 | TTGTGATATTAGCTCATATG | 54 | 10743 | 10762 | 595 |
| 544196 | 1794 | 1813 | ACTAGTTTTTAAACTGGGA | 27 | 10766 | 10785 | 596 |
| 544197 | 1820 | 1839 | GTCAAGTTTAGAGTTTTAAC | 18 | 10792 | 10811 | 597 |
| 544198 | 1826 | 1845 | TATTTAGTCAAGTTTAGAGT | 12 | 10798 | 10817 | 598 |
| 544199 | 1907 | 1926 | TACACATACTCTGTGCTGAC | 83 | 10879 | 10898 | 20 |
| 544200 | 1913 | 1932 | GATTTTACACATACTCTGT | 58 | 10885 | 10904 | 599 |
| 544201 | 2008 | 2027 | CTGCTTCATTAGGTTTCATA | 62 | 10980 | 10999 | 600 |

TABLE 6

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 337520 | N/A | N/A | CAGTGTTATTCAGATTGTAC | 64 | 6517 | 6536 | 601 |
| 337521 | N/A | N/A | AGTGTCTTACCATCATGTTT | 40 | 6776 | 6795 | 602 |
| 337525 | N/A | N/A | CACCAGCCTCCTAAAGGAGA | 39 | 10212 | 10231 | 603 |
| 544292 | N/A | N/A | GAGGAGGTGAAGTCAGTGAG | 35 | 4815 | 4834 | 604 |
| 544293 | N/A | N/A | TAGAGTAGAGGAGGTGAAGT | 23 | 4822 | 4841 | 605 |
| 544294 | N/A | N/A | TGTTTGATGTGTTTGAATAC | 19 | 4863 | 4882 | 606 |
| 544295 | N/A | N/A | GAAACAACAAGGGCAAAGGC | 23 | 4898 | 4917 | 607 |
| 544296 | N/A | N/A | TGTTTGATAACGACCCTAAG | 43 | 4974 | 4993 | 608 |
| 544297 | N/A | N/A | TTTTTGGTTAAGTGACCTTG | 48 | 5016 | 5035 | 609 |
| 544298 | N/A | N/A | GTAGAAGTTTTCAGGGATGG | 23 | 5052 | 5071 | 610 |
| 544299 | N/A | N/A | AGGAAGTAGAAGTTTTCAGG | 5 | 5057 | 5076 | 611 |

TABLE 6-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 544300 | N/A | N/A | AGGTGAGTGTGCAGGAGAAA | 11 | 5085 | 5104 | 612 |
| 544301 | N/A | N/A | TTAAATAAGGTGAGTGTGC | 14 | 5093 | 5112 | 613 |
| 544302 | N/A | N/A | AGTGCAGGAATAGAAGAGAT | 35 | 5136 | 5155 | 614 |
| 544303 | N/A | N/A | CATTTTAGTGCAGGAATAGA | 21 | 5142 | 5161 | 615 |
| 544306 | N/A | N/A | CTATATTCTGGAGTATATAC | 39 | 5216 | 5235 | 616 |
| 544307 | N/A | N/A | CAGTATTCTATATTCTGGAG | 72 | 5223 | 5242 | 617 |
| 544308 | N/A | N/A | GTGCCATACAGTATTCTATA | 50 | 5231 | 5250 | 618 |
| 544309 | N/A | N/A | CTGTGTGAATATGACATTAC | 52 | 5281 | 5300 | 619 |
| 544310 | N/A | N/A | TGAGGCACACTATTTCTAGT | 47 | 5333 | 5352 | 620 |
| 544311 | N/A | N/A | GACCTTTAATTATGAGGCAC | 67 | 5345 | 5364 | 621 |
| 544312 | N/A | N/A | GAATGTTGACCTTTAATTAT | 23 | 5352 | 5371 | 622 |
| 544313 | N/A | N/A | TTGTTGAATGTTGACCTTTA | 69 | 5357 | 5376 | 623 |
| 544314 | N/A | N/A | TCTACTAAGTAACTATGTGA | 37 | 5915 | 5934 | 624 |
| 544315 | N/A | N/A | CTCTTTTCTACTAAGTAACT | 31 | 5921 | 5940 | 625 |
| 544316 | N/A | N/A | AAGGATCTATTGTAAAGTTT | 24 | 5956 | 5975 | 626 |
| 544317 | N/A | N/A | CTAGGACCTTATTTAAAAGG | 24 | 5972 | 5991 | 627 |
| 544318 | N/A | N/A | ATTTCCTAGGACCTTATTTA | 8 | 5977 | 5996 | 628 |
| 544319 | N/A | N/A | TTGACAGTAAGAAAAGCAGA | 28 | 6051 | 6070 | 629 |
| 544320 | N/A | N/A | TTCTCATTGACAGTAAGAAA | 56 | 6057 | 6076 | 630 |
| 544321 | N/A | N/A | AGTTTTTCTCATTGACAGTA | 50 | 6062 | 6081 | 631 |
| 544322 | N/A | N/A | ATTGAATGATAGTTTTTCTC | 42 | 6072 | 6091 | 632 |
| 544323 | N/A | N/A | TTGGGTTTGCAATTTATTGA | 36 | 6087 | 6106 | 633 |
| 544324 | N/A | N/A | AGTGTGTTGGGTTTGCAATT | 25 | 6093 | 6112 | 634 |
| 544325 | N/A | N/A | TATTTAAGTGTGTTGGGTTT | 27 | 6099 | 6118 | 635 |
| 544326 | N/A | N/A | ATATATTCAGTAGTTTATCG | 25 | 6145 | 6164 | 636 |
| 544327 | N/A | N/A | AGATGTTGGCAGGTTGGCAA | 51 | 6184 | 6203 | 637 |
| 544328 | N/A | N/A | TCTGTAGATGTTGGCAGGTT | 48 | 6189 | 6208 | 638 |
| 544329 | N/A | N/A | TTGATAATTTTTGACCTGTA | 34 | 6215 | 6234 | 639 |
| 544330 | N/A | N/A | GGCTTTCTTGATAATTTGAT | 52 | 6230 | 6249 | 640 |
| 544331 | N/A | N/A | GTCTTACTGATCTTCAGACC | 27 | 6282 | 6301 | 641 |
| 544332 | N/A | N/A | TTTAGGTCTTACTGATCTTC | 14 | 6287 | 6306 | 642 |
| 544333 | N/A | N/A | TCAGTTTTAGGTCTTACTGA | 28 | 6292 | 6311 | 643 |
| 544334 | N/A | N/A | TGATATTCTGTTCAGATTTT | 44 | 6326 | 6345 | 644 |
| 544335 | N/A | N/A | TAGAGACTGCTTTGCTTAGA | 31 | 6388 | 6407 | 645 |
| 544336 | N/A | N/A | AGGCCAAAAGTAGAGACTGC | 29 | 6398 | 6417 | 646 |
| 544337 | N/A | N/A | GGCAAAAAAGCAGACATTGG | 38 | 6433 | 6452 | 647 |

TABLE 6-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 544338 | N/A | N/A | AATCAGGGACATTATTTAAT | 13 | 6473 | 6492 | 648 |
| 544339 | N/A | N/A | TATTTAATCAGGGACATTAT | 28 | 6478 | 6497 | 649 |
| 544340 | N/A | N/A | CTCAAAATATTTAATCAGGG | 27 | 6485 | 6504 | 650 |
| 544341 | N/A | N/A | TACCTGTTCTCAAAATATTT | 18 | 6493 | 6512 | 651 |
| 544342 | N/A | N/A | GTACAGATTACCTGTTCTCA | 68 | 6501 | 6520 | 652 |
| 544343 | N/A | N/A | GGTGTTTGATATTTAGATAA | 25 | 6538 | 6557 | 653 |
| 544344 | N/A | N/A | TTGTCTTTCAGTTCATAATG | 29 | 6565 | 6584 | 654 |
| 544345 | N/A | N/A | ACAGTTTGTCTTTCAGTTCA | 23 | 6570 | 6589 | 655 |
| 544346 | N/A | N/A | TCTGAGCTGATAAAAGAATA | 15 | 6657 | 6676 | 656 |
| 544347 | N/A | N/A | CCCACCAAAGTGTCTTACCA | 49 | 6784 | 6803 | 657 |
| 544348 | N/A | N/A | CTTCAAGAAGGAAACCCACC | 39 | 6798 | 6817 | 658 |
| 544349 | N/A | N/A | AATAGCTTCAAGAAGGAAAC | 12 | 6803 | 6822 | 659 |
| 544350 | N/A | N/A | ACAAGTCCTAAGAATAGGGA | 25 | 6833 | 6852 | 660 |
| 544351 | N/A | N/A | GTCTAGAACAAGTCCTAAGA | 53 | 6840 | 6859 | 661 |
| 544352 | N/A | N/A | TCTAATAATCAAGTCCATAT | 33 | 6972 | 6991 | 662 |
| 544353 | N/A | N/A | ACCTTCTATATTATCTAATA | 19 | 6985 | 7004 | 663 |
| 544354 | N/A | N/A | GCATGTATCTCTTAAACAGG | 50 | 7060 | 7079 | 664 |
| 544355 | N/A | N/A | TTTCAGCATGTATCTCTTAA | 79 | 7065 | 7084 | 21 |
| 544356 | N/A | N/A | GTCCAGTGACCTTTAACTCC | 69 | 7092 | 7111 | 665 |
| 544357 | N/A | N/A | TCTTACCAAACTATTTTCTT | 28 | 7166 | 7185 | 666 |
| 544358 | N/A | N/A | GTAATGTTTATGTTAAAGCA | 17 | 7226 | 7245 | 667 |
| 544359 | N/A | N/A | TTGTGGCAAATGTAGCATTT | 52 | 7251 | 7270 | 668 |
| 544360 | N/A | N/A | GAGATTTCACTTGACATTTT | 30 | 7277 | 7296 | 669 |
| 544361 | N/A | N/A | GGAGCTTGAGATTTCACTTG | 30 | 7284 | 7303 | 670 |
| 544362 | N/A | N/A | CATCAGATTAGTAATAGGA | 0 | 7315 | 7334 | 671 |
| 544363 | N/A | N/A | GTTATTACATCAGATTTAGT | 6 | 7322 | 7341 | 672 |
| 544365 | N/A | N/A | CAGCAGGAATGCCTAGAATC | 32 | 7350 | 7369 | 673 |
| 544366 | N/A | N/A | CTCCTTAGACAGGTTTTACC | 31 | 7471 | 7490 | 674 |
| 544367 | N/A | N/A | GTCTATTCTCCTTAGACAGG | 23 | 7478 | 7497 | 675 |
| 544368 | N/A | N/A | ACCAGGTTAATCTTCCTAAT | 71 | 7526 | 7545 | 22 |
| 544369 | N/A | N/A | ATGAATGATTGAATGTAGTC | 26 | 7977 | 7996 | 676 |
| 544370 | N/A | N/A | ATATGAAGGCTGAGACTGCT | 58 | 8072 | 8091 | 677 |
| 544371 | N/A | N/A | ATAAATTATATGAAGGCTGA | 7 | 8079 | 8098 | 678 |
| 544372 | N/A | N/A | ATATTTAAGAACAGACATGT | 12 | 8175 | 8194 | 679 |
| 544373 | N/A | N/A | AGTTATGATCATTGTAAGCC | 60 | 8217 | 8236 | 23 |
| 544374 | N/A | N/A | ATTTGTAACAGTTACTACTT | 51 | 8276 | 8295 | 680 |

TABLE 6-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 544375 | N/A | N/A | CACAGCTTATTTGTAACAGT | 70 | 8284 | 8303 | 681 |
| 544376 | N/A | N/A | GGAGTGGTTCTTTTCACAGC | 71 | 8298 | 8317 | 24 |
| 544377 | N/A | N/A | GTGACTAATGCTAGGAGTGG | 34 | 8311 | 8330 | 682 |
| 544378 | N/A | N/A | GAATAGAGTGACTAATGCTA | 45 | 8318 | 8337 | 683 |
| 544379 | N/A | N/A | ATGAGAGAATAGAGTGACTA | 58 | 8324 | 8343 | 684 |
| 544380 | N/A | N/A | TGGTCCTTTTAACTTCCAAT | 70 | 8365 | 8384 | 25 |
| 544381 | N/A | N/A | TATACTGTATGTCTGAGTTT | 66 | 8387 | 8406 | 685 |
| 544382 | N/A | N/A | AACTAATTCATTATAAGCCA | 67 | 8450 | 8469 | 686 |
| 544383 | N/A | N/A | GCATTGAGTTAACTAATTCA | 64 | 8460 | 8479 | 26 |
| 544385 | N/A | N/A | TTTGGATTTTAAACATCTGT | 61 | 8528 | 8547 | 687 |
| 544386 | N/A | N/A | TGTATGTGCTTTTTGGATTT | 37 | 8539 | 8558 | 688 |
| 544387 | N/A | N/A | CATGGATTTTTGTATGTGCT | 62 | 8549 | 8568 | 689 |
| 544388 | N/A | N/A | TCATTCATGGATTTTTGTAT | 34 | 8554 | 8573 | 690 |
| 544389 | N/A | N/A | ACTTAGACATCATTCATGGA | 55 | 8563 | 8582 | 691 |
| 544390 | N/A | N/A | GTGAGTACTTAGACATCATT | 66 | 8569 | 8588 | 692 |
| 544391 | N/A | N/A | TTTATAAGTGAGTACTTAGA | 36 | 8576 | 8595 | 693 |
| 544392 | N/A | N/A | GTCTTCTACTTTATAAGTGA | 65 | 8585 | 8604 | 694 |
| 544393 | N/A | N/A | ATGAATGTCTTCTACTTTAT | 34 | 8591 | 8610 | 695 |
| 544394 | N/A | N/A | CAAATAGTACTGAGCATTTA | 30 | 8627 | 8646 | 696 |
| 544395 | N/A | N/A | TTAGAAGATTTGGAGCTACA | 54 | 8718 | 8737 | 697 |
| 544396 | N/A | N/A | TCACTATTAGAAGATTTGGA | 37 | 8724 | 8743 | 698 |
| 544397 | N/A | N/A | GGGTTACACTCACTATTAGA | 36 | 8733 | 8752 | 699 |
| 544398 | N/A | N/A | ACTTACCTGTCAGCCTTTTA | 54 | 8758 | 8777 | 700 |
| 544399 | N/A | N/A | CTTACCAGAATTAAGTGAGT | 26 | 8785 | 8804 | 701 |
| 544400 | N/A | N/A | AATACAAGTACAAATGGGTT | 22 | 8810 | 8829 | 702 |
| 544401 | N/A | N/A | CTGGTAAATACAAGTACAAA | 55 | 8816 | 8835 | 703 |
| 544402 | N/A | N/A | GGATTGCTGGTAAATACAAG | 40 | 8822 | 8841 | 704 |
| 544403 | N/A | N/A | TCATTTTAAGGATTGCTGGT | 62 | 8831 | 8850 | 705 |
| 544404 | N/A | N/A | AGTTAGTAGGAAGCTTCATT | 56 | 8846 | 8865 | 706 |
| 544405 | N/A | N/A | GCTATTGAGTTAGTAGGAAG | 67 | 8853 | 8872 | 707 |
| 544407 | N/A | N/A | AGCATGGTTCTTAATAACTT | 67 | 9012 | 9031 | 708 |
| 544408 | N/A | N/A | CTTTGTAGAAAAAGACAGGA | 27 | 9062 | 9081 | 709 |
| 544409 | N/A | N/A | ACCTGGCCTTTGGTATTTGC | 49 | 9096 | 9115 | 710 |
| 544410 | N/A | N/A | CATCCATATACAGTCAAGAG | 80 | 9174 | 9193 | 27 |
| 544411 | N/A | N/A | AGTCTTTATATGGATAAACT | 15 | 9215 | 9234 | 711 |
| 544412 | N/A | N/A | CGTCATTGGTAGAGGAATAT | 51 | 9240 | 9259 | 712 |

TABLE 6-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 544413 | N/A | N/A | GATTATCCTTTCTATAATGC | 48 | 9321 | 9340 | 713 |
| 544414 | N/A | N/A | GTCTTGAATCCCTTGATCAT | 40 | 9436 | 9455 | 714 |
| 544415 | N/A | N/A | GGTGCAACTAATTGAGTTGT | 27 | 9459 | 9478 | 715 |
| 544416 | N/A | N/A | GTGTTTTTATTGGTGCAAC | 31 | 9471 | 9490 | 716 |
| 544417 | N/A | N/A | ATTCTCCTGAAAAGAAAAGT | 24 | 9544 | 9563 | 717 |
| 544418 | N/A | N/A | ATGCCACCACCAGCCTCCTA | 73 | 10219 | 10238 | 718 |
| 544419 | N/A | N/A | ATATCCTTTAACAAATGGGT | 62 | 11540 | 11559 | 719 |
| 544420 | N/A | N/A | GCACTATATCCTTTAACAAA | 50 | 11545 | 11564 | 720 |
| 544421 | N/A | N/A | ACTTGGGCACTATATCCTTT | 68 | 11551 | 11570 | 721 |
| 544422 | N/A | N/A | GAAACATGTCCTATGAGAGT | 32 | 11918 | 11937 | 722 |
| 544424 | N/A | N/A | TTGAGCACTTTAAGCAAAGT | 7 | 12070 | 12089 | 723 |
| 544425 | N/A | N/A | GGAATTTGAGCACTTTAAGC | 34 | 12075 | 12094 | 724 |
| 544426 | N/A | N/A | TAGATTAGACAACTGTGAGT | 52 | 12101 | 12120 | 725 |
| 544427 | N/A | N/A | AAAATGAAGGTCAAGTTTGA | 17 | 12197 | 12216 | 726 |
| 544428 | N/A | N/A | GTGAAAGCAAAATGAAGGTC | 33 | 12205 | 12224 | 727 |
| 544429 | N/A | N/A | GTATTGTGAAAGCAAAATGA | 39 | 12210 | 12229 | 728 |
| 544430 | N/A | N/A | TGGAGAGTATAGTATTGTGA | 35 | 12221 | 12240 | 729 |
| 544438 | N/A | N/A | AGGAATAGAAGAGATAAATA | 10 | 5131 | 5150 | 730 |
| 544439 | N/A | N/A | TGGAGTATATACAAATAATG | 30 | 5208 | 5227 | 731 |
| 544440 | N/A | N/A | TGTTTACATTGTAGATTAAT | 15 | 5381 | 5400 | 732 |
| 544441 | N/A | N/A | CAGAATATATAATATCTTGC | 57 | 6035 | 6054 | 733 |
| 544442 | N/A | N/A | TGCAATTTATTGAATGATAG | 31 | 6080 | 6099 | 734 |
| 544443 | N/A | N/A | CATAATACATAATTTGAACC | 0 | 6251 | 6270 | 735 |
| 544444 | N/A | N/A | ATAATTTTCAGTTTTAGGTC | 0 | 6299 | 6318 | 736 |
| 544445 | N/A | N/A | TTTCAGTAATGTTTATGTTA | 9 | 7231 | 7250 | 737 |
| 544446 | N/A | N/A | AATGCCTAGAATCAATAAAA | 36 | 7343 | 7362 | 738 |
| 544447 | N/A | N/A | GTAAATATTTGTAGATTAGC | 49 | 8003 | 8022 | 739 |
| 544448 | N/A | N/A | ACAAATGTGTAATTGTTTGA | 25 | 8101 | 8120 | 740 |
| 544449 | N/A | N/A | TACTAACAAATGTGTAATTG | 35 | 8106 | 8125 | 741 |
| 544450 | N/A | N/A | TGATAAGTATATTTAAGAAC | 35 | 8183 | 8202 | 742 |
| 544451 | N/A | N/A | TTAACTTCCAATTAATTGAT | 29 | 8357 | 8376 | 743 |
| 544452 | N/A | N/A | TCTGTTATTTTATCTTGCTT | 67 | 8513 | 8532 | 744 |
| 544453 | N/A | N/A | ATCACAATCCTTTTTATTAA | 18 | 8921 | 8940 | 745 |
| 544454 | N/A | N/A | AGAGACTTGAGTAATAATAA | 25 | 9137 | 9156 | 746 |
| 544455 | N/A | N/A | AACAAAATGAAACATGTCCT | 59 | 11926 | 11945 | 747 |
| 544127 | 765 | 784 | CAGCAGGAATGCCATCATGT | 33 | N/A | N/A | 748 |

TABLE 6-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 544128 | 819 | 838 | TGATGGCATACATGCCACTT | 13 | 7404 | 7423 | 749 |
| 544129 | 828 | 847 | TGCTGGGTCTGATGGCATAC | 53 | 7413 | 7432 | 750 |
| 544130 | 832 | 851 | GAGTTGCTGGGTCTGATGGC | 22 | 7417 | 7436 | 751 |
| 544131 | 841 | 860 | AAAACTTGAGAGTTGCTGGG | 13 | 7426 | 7445 | 752 |
| 544132 | 848 | 867 | GACATGAAAAACTTGAGAGT | 0 | 7433 | 7452 | 753 |
| 544133 | 859 | 878 | ACATCACAGTAGACATGAAA | 27 | 7444 | 7463 | 754 |
| 233717 | 889 | 908 | TGAATTAATGTCCATGGACT | 58 | 7876 | 7895 | 14 |
| 544134 | 915 | 934 | AGTTTTGTGATCCATCTATT | 46 | 7902 | 7921 | 755 |
| 544135 | 918 | 937 | TGAAGTTTTGTGATCCATCT | 54 | 7905 | 7924 | 756 |
| 544136 | 926 | 945 | CGTTTCATTGAAGTTTTGTG | 40 | 7913 | 7932 | 757 |
| 544137 | 946 | 965 | CCATATTTGTAGTTCTCCCA | 45 | 7933 | 7952 | 758 |
| 544138 | 949 | 968 | AAACCATATTTGTAGTTCTC | 41 | 7936 | 7955 | 759 |
| 544139 | 970 | 989 | AATTCTCCATCAAGCCTCCC | 43 | N/A | N/A | 760 |
| 233722 | 991 | 1010 | ATCTTCTCTAGGCCCAACCA | 65 | 9566 | 9585 | 761 |
| 544432 | 997 | 1016 | GAGTATATCTTCTCTAGGCC | 40 | 9572 | 9591 | 762 |
| 544140 | 1002 | 1021 | CTATGGAGTATATCTTCTCT | 28 | 9577 | 9596 | 763 |
| 544141 | 1008 | 1027 | GCTTCACTATGGAGTATATC | 55 | 9583 | 9602 | 764 |
| 544142 | 1013 | 1032 | AGATTGCTTCACTATGGAGT | 47 | 9588 | 9607 | 765 |
| 544143 | 1046 | 1065 | CCAGTCTTCCAACTCAATTC | 33 | 9621 | 9640 | 766 |
| 544144 | 1052 | 1071 | GTCTTTCCAGTCTTCCAACT | 59 | 9627 | 9646 | 767 |
| 544145 | 1055 | 1074 | GTTGTCTTTCCAGTCTTCCA | 77 | 9630 | 9649 | 16 |
| 544146 | 1059 | 1078 | GTTTGTTGTCTTTCCAGTCT | 58 | 9634 | 9653 | 768 |
| 544147 | 1062 | 1081 | AATGTTTGTTGTCTTTCCAG | 43 | 9637 | 9656 | 769 |
| 544148 | 1095 | 1114 | CGTGATTTCCCAAGTAAAAA | 57 | 9670 | 9689 | 770 |
| 544149 | 1160 | 1179 | GTTTTCCGGGATTGCATTGG | 44 | 9735 | 9754 | 771 |
| 544150 | 1165 | 1184 | TCTTTGTTTTCCGGGATTGC | 53 | 9740 | 9759 | 772 |
| 544151 | 1170 | 1189 | CCAAATCTTTGTTTTCCGGG | 57 | 9745 | 9764 | 773 |
| 544152 | 1173 | 1192 | ACACCAAATCTTTGTTTTCC | 44 | 9748 | 9767 | 774 |
| 544153 | 1178 | 1197 | AGAAAACACCAAATCTTTGT | 36 | 9753 | 9772 | 775 |
| 544154 | 1183 | 1202 | CAAGTAGAAAACACCAAATC | 29 | 9758 | 9777 | 776 |
| 544155 | 1188 | 1207 | GATCCCAAGTAGAAAACACC | 29 | 9763 | 9782 | 777 |
| 544156 | 1195 | 1214 | GCTTTGTGATCCCAAGTAGA | 71 | 9770 | 9789 | 17 |
| 544157 | 1198 | 1217 | TTTGCTTTGTGATCCCAAGT | 66 | 9773 | 9792 | 778 |
| 544158 | 1202 | 1221 | TCCTTTTGCTTTGTGATCCC | 53 | 9777 | 9796 | 779 |
| 544159 | 1208 | 1227 | GAAGTGTCCTTTTGCTTTGT | 10 | 9783 | 9802 | 780 |
| 544160 | 1246 | 1265 | TGCCACCACCAGCCTCCTGA | 65 | N/A | N/A | 781 |

TABLE 6-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 544161 | 1253 | 1272 | CTCATCATGCCACCACCAGC | 59 | 10225 | 10244 | 782 |
| 544162 | 1269 | 1288 | GGTTGTTTTCTCCACACTCA | 74 | 10241 | 10260 | 18 |
| 544163 | 1276 | 1295 | CCATTTAGGTTGTTTTCTCC | 38 | 10248 | 10267 | 783 |
| 544164 | 1283 | 1302 | ATATTTACCATTTAGGTTGT | 13 | 10255 | 10274 | 784 |
| 544165 | 1294 | 1313 | CTTGGTTTGTTATATTTACC | 53 | 10266 | 10285 | 785 |
| 544166 | 1353 | 1372 | ACCTTCCATTTTGAGACTTC | 70 | 10325 | 10344 | 19 |
| 544167 | 1363 | 1382 | ATAGAGTATAACCTTCCATT | 69 | 10335 | 10354 | 786 |
| 544168 | 1367 | 1386 | TTTTATAGAGTATAACCTTC | 34 | 10339 | 10358 | 787 |
| 544169 | 1374 | 1393 | TGGTTGATTTTATAGAGTAT | 38 | 10346 | 10365 | 788 |
| 544170 | 1378 | 1397 | ATTTTGGTTGATTTTATAGA | 0 | 10350 | 10369 | 789 |
| 544171 | 1383 | 1402 | TCAACATTTTGGTTGATTTT | 12 | 10355 | 10374 | 790 |
| 544172 | 1390 | 1409 | GGATGGATCAACATTTTGGT | 58 | 10362 | 10381 | 791 |
| 544173 | 1393 | 1412 | GTTGGATGGATCAACATTTT | 66 | 10365 | 10384 | 792 |
| 544174 | 1396 | 1415 | TCTGTTGGATGGATCAACAT | 49 | 10368 | 10387 | 793 |
| 544175 | 1401 | 1420 | CTGAATCTGTTGGATGGATC | 60 | 10373 | 10392 | 794 |
| 544176 | 1407 | 1426 | AGCTTTCTGAATCTGTTGGA | 64 | 10379 | 10398 | 795 |
| 544177 | 1414 | 1433 | CATTCAAAGCTTTCTGAATC | 21 | 10386 | 10405 | 796 |
| 544178 | 1417 | 1436 | GTTCATTCAAAGCTTTCTGA | 60 | 10389 | 10408 | 797 |
| 544179 | 1420 | 1439 | TCAGTTCATTCAAAGCTTTC | 18 | 10392 | 10411 | 798 |
| 544180 | 1423 | 1442 | GCCTCAGTTCATTCAAAGCT | 72 | 10395 | 10414 | 799 |
| 544181 | 1427 | 1446 | ATTTGCCTCAGTTCATTCAA | 51 | 10399 | 10418 | 800 |
| 544182 | 1431 | 1450 | TTAAATTTGCCTCAGTTCAT | 48 | 10403 | 10422 | 801 |
| 544183 | 1436 | 1455 | GCCTTTTAAATTTGCCTCAG | 70 | 10408 | 10427 | 802 |
| 544184 | 1498 | 1517 | AGGATTAATACCAGATTAT | 44 | 10470 | 10489 | 803 |
| 544185 | 1502 | 1521 | CTTAAGGATTTAATACCAGA | 47 | 10474 | 10493 | 804 |
| 544186 | 1505 | 1524 | TCTCTTAAGGATTTAATACC | 44 | 10477 | 10496 | 805 |
| 544187 | 1546 | 1565 | GACAGTGACTTTAAGATAAA | 38 | 10518 | 10537 | 806 |
| 544188 | 1572 | 1591 | TGTGATTGTATGTTTAATCT | 47 | 10544 | 10563 | 807 |
| 544189 | 1578 | 1597 | AGGTTATGTGATTGTATGTT | 43 | 10550 | 10569 | 808 |
| 544190 | 1583 | 1602 | CTTTAAGGTTATGTGATTGT | 42 | 10555 | 10574 | 809 |
| 544191 | 1589 | 1608 | GGTATTCTTTAAGGTTATGT | 60 | 10561 | 10580 | 810 |
| 544192 | 1656 | 1675 | ATTGATTCCCACATCACAAA | 46 | 10628 | 10647 | 811 |
| 544193 | 1661 | 1680 | CTAAAATTGATTCCCACATC | 65 | 10633 | 10652 | 812 |
| 544194 | 1665 | 1684 | CCATCTAAAATTGATTCCCA | 70 | 10637 | 10656 | 813 |
| 544195 | 1771 | 1790 | TTGTGATATTAGCTCATATG | 56 | 10743 | 10762 | 814 |
| 544196 | 1794 | 1813 | ACTAGTTTTTTAAACTGGGA | 33 | 10766 | 10785 | 815 |

TABLE 6-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 544197 | 1820 | 1839 | GTCAAGTTTAGAGTTTTAAC | 39 | 10792 | 10811 | 816 |
| 544198 | 1826 | 1845 | TATTTAGTCAAGTTTAGAGT | 21 | 10798 | 10817 | 817 |
| 544199 | 1907 | 1926 | TACACATACTCTGTGCTGAC | 80 | 10879 | 10898 | 20 |
| 544200 | 1913 | 1932 | GATTTTTACACATACTCTGT | 56 | 10885 | 10904 | 818 |
| 544201 | 2008 | 2027 | CTGCTTCATTAGGTTTCATA | 65 | 10980 | 10999 | 819 |

TABLE 7

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 337525 | N/A | N/A | CACCAGCCTCCTAAAGGAGA | 58 | 10212 | 10231 | 820 |
| 544204 | N/A | N/A | GACTTCTTAACTCTATATAT | 67 | 3076 | 3095 | 821 |
| 544205 | N/A | N/A | CTAGACTTCTTAACTCTATA | 61 | 3079 | 3098 | 822 |
| 544206 | N/A | N/A | GACCTAGACTTCTTAACTCT | 54 | 3082 | 3101 | 823 |
| 544207 | N/A | N/A | GGAAGCAGACCTAGACTTCT | 58 | 3089 | 3108 | 824 |
| 544208 | N/A | N/A | TCTGGAAGCAGACCTAGACT | 48 | 3092 | 3111 | 825 |
| 544209 | N/A | N/A | TCTTCTGGAAGCAGACCTAG | 54 | 3095 | 3114 | 826 |
| 544210 | N/A | N/A | CTAATCTTTAGGGATTTAGG | 57 | 11433 | 11452 | 827 |
| 544211 | N/A | N/A | TGTATCTAATCTTTAGGGAT | 53 | 11438 | 11457 | 828 |
| 544213 | N/A | N/A | TAACTTGGGCACTATATCCT | 74 | 11553 | 11572 | 829 |
| 544214 | N/A | N/A | ATTGACAAAGGTAGGTCACC | 79 | 11576 | 11595 | 830 |
| 544215 | N/A | N/A | ATATGACATGTATATTGGAT | 66 | 11620 | 11639 | 831 |
| 544216 | N/A | N/A | TTTTGTACTTTTCTGGAACA | 61 | 11704 | 11723 | 832 |
| 544217 | N/A | N/A | TAGTCTGTGGTCCTGAAAAT | 56 | 11748 | 11767 | 833 |
| 544218 | N/A | N/A | AGCTTAGTCTGTGGTCCTGA | 72 | 11752 | 11771 | 834 |
| 544219 | N/A | N/A | GACAGCTTAGTCTGTGGTCC | 74 | 11755 | 11774 | 835 |
| 544220 | N/A | N/A | GTATTCTGGCCCTAAAAAAA | 52 | 11789 | 11808 | 836 |
| 544221 | N/A | N/A | ATTTGGTATTCTGGCCCTA | 56 | 11795 | 11814 | 837 |
| 544222 | N/A | N/A | GAAATTGTCCAATTTTTGGG | 56 | N/A | N/A | 838 |
| 544223 | N/A | N/A | TTTGCATTTGAAATTGTCCA | 61 | 11837 | 11856 | 839 |
| 544224 | N/A | N/A | GGAAGCAACTCATATATTAA | 57 | 11869 | 11888 | 840 |
| 544225 | N/A | N/A | TATCAGAAAAGATACCTGA | 56 | 9821 | 9840 | 841 |
| 544226 | N/A | N/A | ATAATAGCTAATAATGTGGG | 59 | 9875 | 9894 | 842 |
| 544227 | N/A | N/A | TGCAGATAATAGCTAATAAT | 60 | 9880 | 9899 | 843 |
| 544228 | N/A | N/A | TGTCATTGCAGATAATAGCT | 79 | 9886 | 9905 | 844 |

TABLE 7-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 544229 | N/A | N/A | TAAAAGTTGTCATTGCAGAT | 59 | 9893 | 9912 | 845 |
| 544230 | N/A | N/A | CGGATTTTTAAAAGTTGTCA | 61 | 9901 | 9920 | 846 |
| 544231 | N/A | N/A | GGGATTCGGATTTTTAAAAG | 28 | 9907 | 9926 | 847 |
| 544232 | N/A | N/A | TTTGGGATTCGGATTTTTAA | 44 | 9910 | 9929 | 848 |
| 544233 | N/A | N/A | ACGCTTATTTGGGATTCGGA | 72 | 9917 | 9936 | 849 |
| 544251 | N/A | N/A | TTTAAGAGATTTACAAGTCA | 52 | 2811 | 2830 | 850 |
| 544252 | N/A | N/A | GACTACCTGTTTTTAAAAGC | 48 | 2851 | 2870 | 851 |
| 544253 | N/A | N/A | TATGGTGACTACCTGTTTTT | 39 | 2857 | 2876 | 852 |
| 544254 | N/A | N/A | ACTTTGCTGTATTATAAACT | 35 | 2890 | 2909 | 853 |
| 544255 | N/A | N/A | ATTGTATTTAACTTTGCTGT | 35 | 2900 | 2919 | 854 |
| 544256 | N/A | N/A | GAGCAACTAACTTAATAGGT | 42 | 2928 | 2947 | 855 |
| 544257 | N/A | N/A | GAAATGAGCAACTAACTTAA | 32 | 2933 | 2952 | 856 |
| 544258 | N/A | N/A | AATCAAAGAAATGAGCAACT | 42 | 2940 | 2959 | 857 |
| 544259 | N/A | N/A | ACCTTCTTCCACATTGAGTT | 44 | 2977 | 2996 | 858 |
| 544260 | N/A | N/A | CACGAATGTAACCTTCTTCC | 52 | 2987 | 3006 | 859 |
| 544261 | N/A | N/A | TTAACTTGCACGAATGTAAC | 45 | 2995 | 3014 | 860 |
| 544262 | N/A | N/A | TATATATACCAATATTTGCC | 43 | 3063 | 3082 | 861 |
| 544263 | N/A | N/A | TCTTAACTCTATATATACCA | 49 | 3072 | 3091 | 862 |
| 544264 | N/A | N/A | CTTTAAGTGAAGTTACTTCT | 53 | 3632 | 3651 | 863 |
| 544265 | N/A | N/A | TCTACTTACTTTAAGTGAAG | 44 | 3640 | 3659 | 864 |
| 544266 | N/A | N/A | GAACCCTCTTTATTTTCTAC | 46 | 3655 | 3674 | 865 |
| 544267 | N/A | N/A | ACATAAACATGAACCCTCTT | 50 | 3665 | 3684 | 866 |
| 544268 | N/A | N/A | CCACATTGAAAACATAAACA | 57 | 3676 | 3695 | 867 |
| 544269 | N/A | N/A | GCATGCCTTAGAAATATTTT | 23 | 3707 | 3726 | 868 |
| 544270 | N/A | N/A | CAATGCAACAAAGTATTTCA | 37 | 3731 | 3750 | 869 |
| 544271 | N/A | N/A | CTGGAGATTATTTTCTTGG | 61 | 3768 | 3787 | 870 |
| 544272 | N/A | N/A | TTCATATATAACATTAGGGA | 14 | 3830 | 3849 | 871 |
| 544273 | N/A | N/A | TCAGTGTTTTCATATATAAC | 32 | 3838 | 3857 | 872 |
| 544274 | N/A | N/A | GACATAGTGTTCTAGATTGT | 47 | 3900 | 3919 | 873 |
| 544275 | N/A | N/A | CAATAGTGTAATGACATAGT | 39 | 3912 | 3931 | 874 |
| 544276 | N/A | N/A | TTACTTACCTTCAGTAATTT | 35 | 3933 | 3952 | 875 |
| 544277 | N/A | N/A | ATCTTTTCCATTTACTGTAT | 39 | 4005 | 4024 | 876 |
| 544278 | N/A | N/A | AGAAAAAGCCCAGCATATTT | 23 | 4037 | 4056 | 877 |
| 544279 | N/A | N/A | GTATGCTTCTTTCAAATAGC | 46 | 4130 | 4149 | 878 |
| 544280 | N/A | N/A | CCTTCCCCTTGTATGCTTCT | 47 | 4140 | 4159 | 879 |
| 544281 | N/A | N/A | CCTGTAACACTATCATAATC | 49 | 4207 | 4226 | 880 |

TABLE 7-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 544282 | N/A | N/A | TGACTTACCTGATTTTCTAT | 24 | 4384 | 4403 | 881 |
| 544283 | N/A | N/A | GATGGGACATACCATTAAAA | 41 | 4407 | 4426 | 882 |
| 544284 | N/A | N/A | GTGAAAGATGGGACATACCA | 54 | 4413 | 4432 | 883 |
| 544285 | N/A | N/A | CCTGTGTGAAAGATGGGACA | 27 | 4418 | 4437 | 884 |
| 544286 | N/A | N/A | CATTGGCTGCTATGAATTAA | 45 | 4681 | 4700 | 885 |
| 544287 | N/A | N/A | GATGACATTGGCTGCTATGA | 49 | 4686 | 4705 | 886 |
| 544288 | N/A | N/A | GAGAAACATGATCTAATTTG | 33 | 4717 | 4736 | 887 |
| 544289 | N/A | N/A | ATGGAAAGCTATTGTGTGGT | 42 | 4747 | 4766 | 888 |
| 544290 | N/A | N/A | GTCTAAAGAGCCAATATGAG | 39 | 4771 | 4790 | 889 |
| 544291 | N/A | N/A | AATCTTGGTCTAAAGAGCCA | 65 | 4778 | 4797 | 890 |
| 544361 | N/A | N/A | GGAGCTTGAGATTTCACTTG | 66 | 7284 | 7303 | 891 |
| 544362 | N/A | N/A | CATCAGATTTAGTAATAGGA | 61 | 7315 | 7334 | 892 |
| 544363 | N/A | N/A | GTTATTACATCAGATTTAGT | 63 | 7322 | 7341 | 893 |
| 544365 | N/A | N/A | CAGCAGGAATGCCTAGAATC | 72 | 7350 | 7369 | 894 |
| 544366 | N/A | N/A | CTCCTTAGACAGGTTTTACC | 67 | 7471 | 7490 | 895 |
| 544367 | N/A | N/A | GTCTATTCTCCTTAGACAGG | 59 | 7478 | 7497 | 896 |
| 544368 | N/A | N/A | ACCAGGTTAATCTTCCTAAT | 79 | 7526 | 7545 | 22 |
| 544369 | N/A | N/A | ATGAATGATTGAATGTAGTC | 56 | 7977 | 7996 | 897 |
| 544370 | N/A | N/A | ATATGAAGGCTGAGACTGCT | 73 | 8072 | 8091 | 898 |
| 544371 | N/A | N/A | ATAAATTATATGAAGGCTGA | 51 | 8079 | 8098 | 899 |
| 544372 | N/A | N/A | ATATTTAAGAACAGACATGT | 54 | 8175 | 8194 | 900 |
| 544373 | N/A | N/A | AGTTATGATCATTGTAAGCC | 77 | 8217 | 8236 | 23 |
| 544374 | N/A | N/A | ATTTGTAACAGTTACTACTT | 69 | 8276 | 8295 | 901 |
| 544375 | N/A | N/A | CACAGCTTATTTGTAACAGT | 72 | 8284 | 8303 | 902 |
| 544376 | N/A | N/A | GGAGTGGTTCTTTTCACAGC | 82 | 8298 | 8317 | 24 |
| 544377 | N/A | N/A | GTGACTAATGCTAGGAGTGG | 54 | 8311 | 8330 | 903 |
| 544378 | N/A | N/A | GAATAGAGTGACTAATGCTA | 55 | 8318 | 8337 | 904 |
| 544379 | N/A | N/A | ATGAGAGAATAGAGTGACTA | 66 | 8324 | 8343 | 905 |
| 544380 | N/A | N/A | TGGTCCTTTTAACTTCCAAT | 79 | 8365 | 8384 | 25 |
| 544381 | N/A | N/A | TATACTGTATGTCTGAGTTT | 72 | 8387 | 8406 | 906 |
| 544382 | N/A | N/A | AACTAATTCATTATAAGCCA | 56 | 8450 | 8469 | 907 |
| 544383 | N/A | N/A | GCATTGAGTTAACTAATTCA | 78 | 8460 | 8479 | 26 |
| 544385 | N/A | N/A | TTTGGATTTAAACATCTGT | 73 | 8528 | 8547 | 908 |
| 544386 | N/A | N/A | TGTATGTGCTTTTTGGATTT | 57 | 8539 | 8558 | 909 |
| 544387 | N/A | N/A | CATGGATTTTTGTATGTGCT | 64 | 8549 | 8568 | 910 |
| 544388 | N/A | N/A | TCATTCATGGATTTTTGTAT | 53 | 8554 | 8573 | 911 |

TABLE 7-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 544389 | N/A | N/A | ACTTAGACATCATTCATGGA | 66 | 8563 | 8582 | 912 |
| 544390 | N/A | N/A | GTGAGTACTTAGACATCATT | 74 | 8569 | 8588 | 913 |
| 544391 | N/A | N/A | TTTATAAGTGAGTACTTAGA | 32 | 8576 | 8595 | 914 |
| 544392 | N/A | N/A | GTCTTCTACTTTATAAGTGA | 63 | 8585 | 8604 | 915 |
| 544393 | N/A | N/A | ATGAATGTCTTCTACTTTAT | 68 | 8591 | 8610 | 916 |
| 544394 | N/A | N/A | CAAATAGTACTGAGCATTTA | 53 | 8627 | 8646 | 917 |
| 544395 | N/A | N/A | TTAGAAGATTTGGAGCTACA | 55 | 8718 | 8737 | 918 |
| 544396 | N/A | N/A | TCACTATTAGAAGATTTGGA | 60 | 8724 | 8743 | 919 |
| 544397 | N/A | N/A | GGGTTACACTCACTATTAGA | 52 | 8733 | 8752 | 920 |
| 544398 | N/A | N/A | ACTTACCTGTCAGCCTTTTA | 61 | 8758 | 8777 | 921 |
| 544399 | N/A | N/A | CTTACCAGAATTAAGTGAGT | 43 | 8785 | 8804 | 922 |
| 544400 | N/A | N/A | AATACAAGTACAAATGGGTT | 29 | 8810 | 8829 | 923 |
| 544401 | N/A | N/A | CTGGTAAATACAAGTACAAA | 76 | 8816 | 8835 | 924 |
| 544402 | N/A | N/A | GGATTGCTGGTAAATACAAG | 59 | 8822 | 8841 | 925 |
| 544403 | N/A | N/A | TCATTTTAAGGATTGCTGGT | 63 | 8831 | 8850 | 926 |
| 544404 | N/A | N/A | AGTTAGTAGGAAGCTTCATT | 54 | 8846 | 8865 | 927 |
| 544405 | N/A | N/A | GCTATTGAGTTAGTAGGAAG | 63 | 8853 | 8872 | 928 |
| 544407 | N/A | N/A | AGCATGGTTCTTAATAACTT | 69 | 9012 | 9031 | 929 |
| 544408 | N/A | N/A | CTTTGTAGAAAAAGACAGGA | 45 | 9062 | 9081 | 930 |
| 544409 | N/A | N/A | ACCTGGCCTTTGGTATTTGC | 66 | 9096 | 9115 | 931 |
| 544410 | N/A | N/A | CATCCATATACAGTCAAGAG | 78 | 9174 | 9193 | 27 |
| 544411 | N/A | N/A | AGTCTTTATATGGATAAACT | 46 | 9215 | 9234 | 932 |
| 544412 | N/A | N/A | CGTCATTGGTAGAGGAATAT | 45 | 9240 | 9259 | 933 |
| 544413 | N/A | N/A | GATTATCCTTTCTATAATGC | 45 | 9321 | 9340 | 934 |
| 544414 | N/A | N/A | GTCTTGAATCCCTTGATCAT | 61 | 9436 | 9455 | 935 |
| 544415 | N/A | N/A | GGTGCAACTAATTGAGTTGT | 49 | 9459 | 9478 | 936 |
| 544416 | N/A | N/A | GTGTTTTTATTGGTGCAAC | 46 | 9471 | 9490 | 937 |
| 544417 | N/A | N/A | ATTCTCCTGAAAAGAAAAGT | 50 | 9544 | 9563 | 938 |
| 544418 | N/A | N/A | ATGCCACCACCAGCCTCCTA | 73 | 10219 | 10238 | 939 |
| 544419 | N/A | N/A | ATATCCTTTAACAAATGGGT | 68 | 11540 | 11559 | 940 |
| 544420 | N/A | N/A | GCACTATATCCTTTAACAAA | 74 | 11545 | 11564 | 941 |
| 544421 | N/A | N/A | ACTTGGGCACTATATCCTTT | 68 | 11551 | 11570 | 942 |
| 544422 | N/A | N/A | GAAACATGTCCTATGAGAGT | 56 | 11918 | 11937 | 943 |
| 544424 | N/A | N/A | TTGAGCACTTTAAGCAAAGT | 15 | 12070 | 12089 | 944 |
| 544425 | N/A | N/A | GGAATTTGAGCACTTTAAGC | 35 | 12075 | 12094 | 945 |
| 544426 | N/A | N/A | TAGATTAGACAACTGTGAGT | 54 | 12101 | 12120 | 946 |

TABLE 7-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 544427 | N/A | N/A | AAAATGAAGGTCAAGTTTGA | 45 | 12197 | 12216 | 947 |
| 544428 | N/A | N/A | GTGAAAGCAAAATGAAGGTC | 55 | 12205 | 12224 | 948 |
| 544429 | N/A | N/A | GTATTGTGAAAGCAAAATGA | 54 | 12210 | 12229 | 949 |
| 544430 | N/A | N/A | TGGAGAGTATAGTATTGTGA | 53 | 12221 | 12240 | 950 |
| 544433 | N/A | N/A | GAGATTTACAAGTCAAAAAT | 41 | 2806 | 2825 | 951 |
| 544434 | N/A | N/A | ATTTAACTTTGCTGTATTAT | 29 | 2895 | 2914 | 952 |
| 544435 | N/A | N/A | ATCAATGCTAAATGAAATCA | 34 | 2955 | 2974 | 953 |
| 544436 | N/A | N/A | TATTTTCTGGAGATTATTTT | 24 | 3774 | 3793 | 954 |
| 544437 | N/A | N/A | AAAATGAATATTGGCAATTC | 34 | 4159 | 4178 | 955 |
| 544446 | N/A | N/A | AATGCCTAGAATCAATAAAA | 50 | 7343 | 7362 | 956 |
| 544447 | N/A | N/A | GTAAATATTTGTAGATTAGC | 38 | 8003 | 8022 | 957 |
| 544448 | N/A | N/A | ACAAATGTGTAATTGTTTGA | 43 | 8101 | 8120 | 958 |
| 544449 | N/A | N/A | TACTAACAAATGTGTAATTG | 59 | 8106 | 8125 | 959 |
| 544450 | N/A | N/A | TGATAAGTATATTTAAGAAC | 45 | 8183 | 8202 | 960 |
| 544451 | N/A | N/A | TTAACTTCCAATTAATTGAT | 55 | 8357 | 8376 | 961 |
| 544452 | N/A | N/A | TCTGTTATTTTATCTTGCTT | 67 | 8513 | 8532 | 962 |
| 544453 | N/A | N/A | ATCACAATCCTTTTTATTAA | 39 | 8921 | 8940 | 963 |
| 544454 | N/A | N/A | AGAGACTTGAGTAATAATAA | 43 | 9137 | 9156 | 964 |
| 544455 | N/A | N/A | AACAAAATGAAACATGTCCT | 47 | 11926 | 11945 | 965 |
| 544059 | 23 | 42 | GATTTTCAATTTCAAGCAAC | 74 | 3127 | 3146 | 966 |
| 337459 | 49 | 68 | AGCTTAATTGTGAACATTTT | 77 | 3153 | 3172 | 967 |
| 544060 | 54 | 73 | GAAGGAGCTTAATTGTGAAC | 59 | 3158 | 3177 | 968 |
| 544061 | 63 | 82 | CAATAAAAGAAGGAGCTTA | 64 | 3167 | 3186 | 969 |
| 544062 | 66 | 85 | GAACAATAAAAGAAGGAGC | 67 | 3170 | 3189 | 970 |
| 544063 | 85 | 104 | CTGGAGGAAATAACTAGAGG | 49 | 3189 | 3208 | 971 |
| 337460 | 88 | 107 | ATTCTGGAGGAAATAACTAG | 65 | 3192 | 3211 | 972 |
| 544064 | 112 | 131 | TCAAATGATGAATTGTCTTG | 58 | 3216 | 3235 | 973 |
| 544065 | 138 | 157 | TTGATTTTGGCTCTGGAGAT | 67 | 3242 | 3261 | 974 |
| 544066 | 145 | 164 | GCAAATCTTGATTTTGGCTC | 82 | 3249 | 3268 | 975 |
| 233676 | 148 | 167 | ATAGCAAATCTTGATTTTGG | 81 | 3252 | 3271 | 976 |
| 544067 | 156 | 175 | CGTCTAACATAGCAAATCTT | 87 | 3260 | 3279 | 977 |
| 544068 | 174 | 193 | TGGCTAAAATTTTACATCG | 66 | 3278 | 3297 | 978 |
| 544069 | 178 | 197 | CCATTGGCTAAAATTTTTAC | 41 | 3282 | 3301 | 979 |
| 544070 | 184 | 203 | AGGAGGCCATTGGCTAAAAT | 36 | 3288 | 3307 | 980 |
| 544071 | 187 | 206 | TGAAGGAGGCCATTGGCTAA | 44 | 3291 | 3310 | 981 |
| 544072 | 195 | 214 | GTCCCAACTGAAGGAGGCCA | 59 | 3299 | 3318 | 982 |

TABLE 7-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 544073 | 199 | 218 | CCATGTCCCAACTGAAGGAG | 54 | 3303 | 3322 | 983 |
| 544074 | 202 | 221 | AGACCATGTCCCAACTGAAG | 68 | 3306 | 3325 | 984 |
| 544075 | 206 | 225 | TTTAAGACCATGTCCCAACT | 51 | 3310 | 3329 | 985 |
| 544076 | 209 | 228 | GTCTTTAAGACCATGTCCCA | 64 | 3313 | 3332 | 986 |
| 544077 | 216 | 235 | GGACAAAGTCTTTAAGACCA | 45 | 3320 | 3339 | 987 |
| 544078 | 222 | 241 | TCTTATGGACAAAGTCTTTA | 40 | 3326 | 3345 | 988 |
| 544079 | 245 | 264 | TATGTCATTAATTTGGCCCT | 30 | 3349 | 3368 | 989 |
| 544080 | 270 | 289 | GATCAAATATGTTGAGTTTT | 65 | 3374 | 3393 | 990 |
| 233690 | 274 | 293 | GACTGATCAAATATGTTGAG | 75 | 3378 | 3397 | 991 |
| 544081 | 316 | 335 | TCTTCTTTGATTTCACTGGT | 86 | 3420 | 3439 | 992 |
| 544082 | 334 | 353 | CTTCTCAGTTCCTTTTCTTC | 69 | 3438 | 3457 | 993 |
| 544083 | 337 | 356 | GTTCTTCTCAGTTCCTTTTC | 77 | 3441 | 3460 | 994 |
| 544084 | 341 | 360 | TGTAGTTCTTCTCAGTTCCT | 75 | 3445 | 3464 | 995 |
| 544431 | 345 | 364 | TATATGTAGTTCTTCTCAGT | 15 | 3449 | 3468 | 996 |
| 544086 | 348 | 367 | GTTTATATGTAGTTCTTCTC | 65 | 3452 | 3471 | 997 |
| 544087 | 352 | 371 | TGTAGTTTATATGTAGTTCT | 49 | 3456 | 3475 | 998 |
| 544088 | 356 | 375 | GACTTGTAGTTTATATGTAG | 21 | 3460 | 3479 | 999 |
| 544089 | 364 | 383 | TCATTTTTGACTTGTAGTTT | 60 | 3468 | 3487 | 1000 |
| 544090 | 369 | 388 | CCTCTTCATTTTTGACTTGT | 83 | 3473 | 3492 | 1001 |
| 544091 | 375 | 394 | TCTTTACCTCTTCATTTTTG | 75 | 3479 | 3498 | 1002 |
| 544092 | 380 | 399 | CATATTCTTTACCTCTTCAT | 77 | 3484 | 3503 | 1003 |
| 544093 | 384 | 403 | GTGACATATTCTTTACCTCT | 76 | 3488 | 3507 | 1004 |
| 544094 | 392 | 411 | GAGTTCAAGTGACATATTCT | 71 | 3496 | 3515 | 1005 |
| 544095 | 398 | 417 | TGAGTTGAGTTCAAGTGACA | 44 | 3502 | 3521 | 1006 |
| 544096 | 403 | 422 | AGTTTTGAGTTGAGTTCAAG | 33 | 3507 | 3526 | 1007 |
| 544097 | 406 | 425 | TCAAGTTTTGAGTTGAGTTC | 69 | 3510 | 3529 | 1008 |
| 544098 | 414 | 433 | GGAGGCTTTCAAGTTTTGAG | 68 | 3518 | 3537 | 1009 |
| 544099 | 423 | 442 | TTTCTTCTAGGAGGCTTTCA | 79 | 3527 | 3546 | 1010 |
| 544100 | 427 | 446 | ATTTTTTCTTCTAGGAGGCT | 63 | 3531 | 3550 | 1011 |
| 544101 | 432 | 451 | GTAGAATTTTTTCTTCTAGG | 56 | 3536 | 3555 | 1012 |
| 544102 | 462 | 481 | GCTCTTCTAAATATTTCACT | 85 | 3566 | 3585 | 1013 |
| 544103 | 474 | 493 | AGTTAGTTAGTTGCTCTTCT | 71 | 3578 | 3597 | 1014 |
| 544104 | 492 | 511 | CAGGTTGATTTTGAATTAAG | 69 | 3596 | 3615 | 1015 |
| 544105 | 495 | 514 | TTTCAGGTTGATTTTGAATT | 53 | 3599 | 3618 | 1016 |
| 544106 | 499 | 518 | GGAGTTTCAGGTTGATTTTG | 64 | 3603 | 3622 | 1017 |
| 544107 | 504 | 523 | GTTCTGGAGTTTCAGGTTGA | 74 | 3608 | 3627 | 1018 |

TABLE 7-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 544108 | 526 | 545 | TTAAGTGAAGTTACTTCTGG | 60 | 3630 | 3649 | 1019 |
| 544109 | 555 | 574 | TGCTATTATCTTGTTTTTCT | 63 | 4293 | 4312 | 1020 |
| 544110 | 564 | 583 | GGTCTTTGATGCTATTATCT | 65 | 4302 | 4321 | 1021 |
| 544111 | 567 | 586 | GAAGGTCTTTGATGCTATTA | 49 | 4305 | 4324 | 1022 |
| 544112 | 572 | 591 | CTGGAGAAGGTCTTTGATGC | 65 | 4310 | 4329 | 1023 |
| 544113 | 643 | 662 | CTGAGCTGATTTTCTATTTC | 64 | N/A | N/A | 1024 |
| 337477 | 664 | 683 | GGTTCTTGAATACTAGTCCT | 82 | 6677 | 6696 | 234 |
| 544114 | 673 | 692 | ATTTCTGTGGGTTCTTGAAT | 57 | 6686 | 6705 | 1025 |
| 337478 | 675 | 694 | AAATTTCTGTGGGTTCTTGA | 29 | 6688 | 6707 | 235 |
| 544115 | 678 | 697 | GAGAAATTTCTGTGGGTTCT | 68 | 6691 | 6710 | 1026 |
| 544116 | 682 | 701 | GATAGAGAAATTTCTGTGGG | 54 | 6695 | 6714 | 1027 |
| 544117 | 689 | 708 | CTTGGAAGATAGAGAAATTT | 36 | 6702 | 6721 | 1028 |
| 337479 | 692 | 711 | TGGCTTGGAAGATAGAGAAA | 54 | 6705 | 6724 | 236 |
| 544118 | 699 | 718 | GTGCTCTTGGCTTGGAAGAT | 64 | 6712 | 6731 | 1029 |
| 544119 | 703 | 722 | CTTGGTGCTCTTGGCTTGGA | 68 | 6716 | 6735 | 1030 |
| 544120 | 707 | 726 | AGTTCTTGGTGCTCTTGGCT | 91 | 6720 | 6739 | 15 |
| 233710 | 710 | 729 | AGTAGTTCTTGGTGCTCTTG | 80 | 6723 | 6742 | 233 |
| 544121 | 713 | 732 | GGGAGTAGTTCTTGGTGCTC | 76 | 6726 | 6745 | 1031 |
| 544122 | 722 | 741 | CTGAAGAAAGGGAGTAGTTC | 55 | 6735 | 6754 | 1032 |
| 544123 | 752 | 771 | ATCATGTTTTACATTTCTTA | 52 | 6765 | 6784 | 1033 |
| 544124 | 755 | 774 | GCCATCATGTTTTACATTTC | 61 | N/A | N/A | 1034 |
| 544125 | 759 | 778 | GAATGCCATCATGTTTTACA | 30 | N/A | N/A | 1035 |
| 544126 | 762 | 781 | CAGGAATGCCATCATGTTTT | 34 | N/A | N/A | 1036 |
| 337487 | 804 | 823 | CACTTGTATGTTCACCTCTG | 83 | 7389 | 7408 | 28 |
| 233717 | 889 | 908 | TGAATTAATGTCCATGGACT | 75 | 7876 | 7895 | 14 |
| 544202 | 2081 | 2100 | AAAGTCAATGTGACTTAGTA | 70 | 11053 | 11072 | 1037 |
| 544203 | 2104 | 2123 | AAGGTATAGTGATACCTCAT | 84 | 11076 | 11095 | 1038 |

TABLE 8

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 560535 | N/A | N/A | ACTGTTTTCTTCTGGAAGCA | 0 | 3102 | 3121 | 1039 |
| 560536 | N/A | N/A | AAATAAGGTATAGTGATACC | 0 | 11080 | 11099 | 1040 |

TABLE 8-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 560537 | N/A | N/A | ACAAATAAGGTATAGTGATA | 1 | 11082 | 11101 | 1041 |
| 560538 | N/A | N/A | TAACAAATAAGGTATAGTGA | 0 | 11084 | 11103 | 1042 |
| 560539 | N/A | N/A | TTTAACAAATAAGGTATAGT | 16 | 11086 | 11105 | 1043 |
| 560540 | N/A | N/A | ATATATTTTAACAAATAAGG | 0 | 11092 | 11111 | 1044 |
| 560541 | N/A | N/A | CAGTATATATTTTAACAAAT | 0 | 11096 | 11115 | 1045 |
| 560542 | N/A | N/A | TACAGTATATATTTTAACAA | 0 | 11098 | 11117 | 1046 |
| 560543 | N/A | N/A | TATACAGTATATATTTTAAC | 0 | 11100 | 11119 | 1047 |
| 560544 | N/A | N/A | ATAGTATTAAGTGTTAAAAT | 0 | 11130 | 11149 | 1048 |
| 560545 | N/A | N/A | TCATAGTATTAAGTGTTAAA | 0 | 11132 | 11151 | 1049 |
| 560546 | N/A | N/A | GTTTTCATAGTATTAAGTGT | 26 | 11136 | 11155 | 1050 |
| 560547 | N/A | N/A | ATTATTTGTTTTCATAGTAT | 0 | 11143 | 11162 | 1051 |
| 560548 | N/A | N/A | CTTTACAATTATTTGTTTTC | 0 | 11150 | 11169 | 1052 |
| 560549 | N/A | N/A | ATTCCTTTACAATTATTTGT | 21 | 11154 | 11173 | 1053 |
| 560550 | N/A | N/A | AGATTCCTTTACAATTATTT | 18 | 11156 | 11175 | 1054 |
| 560551 | N/A | N/A | CAAGATTCCTTTACAATTAT | 21 | 11158 | 11177 | 1055 |
| 560552 | N/A | N/A | GACAAGATTCCTTTACAATT | 55 | 11160 | 11179 | 1056 |
| 560553 | N/A | N/A | CTGACAAGATTCCTTTACAA | 47 | 11162 | 11181 | 1057 |
| 560554 | N/A | N/A | AATCTGACAAGATTCCTTTA | 52 | 11165 | 11184 | 1058 |
| 560555 | N/A | N/A | GTAATCTGACAAGATTCCTT | 56 | 11167 | 11186 | 1059 |
| 560556 | N/A | N/A | CTGTAATCTGACAAGATTCC | 51 | 11169 | 11188 | 1060 |
| 560557 | N/A | N/A | TACTGTAATCTGACAAGATT | 18 | 11171 | 11190 | 1061 |
| 560558 | N/A | N/A | CTTACTGTAATCTGACAAGA | 33 | 11173 | 11192 | 1062 |
| 560559 | N/A | N/A | TTCTTACTGTAATCTGACAA | 47 | 11175 | 11194 | 1063 |
| 560560 | N/A | N/A | CATTCTTACTGTAATCTGAC | 65 | 11177 | 11196 | 1064 |
| 560561 | N/A | N/A | TTCATTCTTACTGTAATCTG | 54 | 11179 | 11198 | 1065 |
| 560562 | N/A | N/A | TGTTCATTCTTACTGTAATC | 44 | 11181 | 11200 | 1066 |
| 560563 | N/A | N/A | TATGTTCATTCTTACTGTAA | 39 | 11183 | 11202 | 1067 |
| 560564 | N/A | N/A | AATATGTTCATTCTTACTGT | 0 | 11185 | 11204 | 1068 |
| 560565 | N/A | N/A | ACAAATATGTTCATTCTTAC | 3 | 11188 | 11207 | 1069 |
| 560566 | N/A | N/A | CCACAAATATGTTCATTCTT | 75 | 11190 | 11209 | 42 |
| 560567 | N/A | N/A | TGCCACAAATATGTTCATTC | 80 | 11192 | 11211 | 43 |
| 560568 | N/A | N/A | CGATGCCACAAATATGTTCA | 64 | 11195 | 11214 | 1070 |
| 560569 | N/A | N/A | CTCGATGCCACAAATATGTT | 65 | 11197 | 11216 | 1071 |
| 560570 | N/A | N/A | AACTCGATGCCACAAATATG | 46 | 11199 | 11218 | 1072 |
| 560571 | N/A | N/A | TTAACTCGATGCCACAAATA | 52 | 11201 | 11220 | 1073 |

TABLE 8-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 560572 | N/A | N/A | CTTTAACTCGATGCCACAAA | 66 | 11203 | 11222 | 1074 |
| 560573 | N/A | N/A | AACTTTAACTCGATGCCACA | 53 | 11205 | 11224 | 1075 |
| 560574 | N/A | N/A | TAAACTTTAACTCGATGCCA | 72 | 11207 | 11226 | 44 |
| 560575 | N/A | N/A | AATATAAACTTTAACTCGAT | 6 | 11211 | 11230 | 1076 |
| 560576 | N/A | N/A | GAAATATAAACTTTAACTCG | 17 | 11213 | 11232 | 1077 |
| 560577 | N/A | N/A | GGGAAATATAAACTTTAACT | 0 | 11215 | 11234 | 1078 |
| 560578 | N/A | N/A | GAATCACAGCATATTTAGGG | 46 | 11233 | 11252 | 1079 |
| 560579 | N/A | N/A | TAGAATCACAGCATATTTAG | 32 | 11235 | 11254 | 1080 |
| 560580 | N/A | N/A | GTATTAGAATCACAGCATAT | 51 | 11239 | 11258 | 1081 |
| 560581 | N/A | N/A | ATGTATTAGAATCACAGCAT | 64 | 11241 | 11260 | 1082 |
| 560582 | N/A | N/A | GAATGTATTAGAATCACAGC | 44 | 11243 | 11262 | 1083 |
| 560583 | N/A | N/A | ACGAATGTATTAGAATCACA | 44 | 11245 | 11264 | 1084 |
| 560584 | N/A | N/A | ACACGAATGTATTAGAATCA | 41 | 11247 | 11266 | 1085 |
| 560585 | N/A | N/A | CTACACGAATGTATTAGAAT | 15 | 11249 | 11268 | 1086 |
| 560586 | N/A | N/A | ACCTACACGAATGTATTAGA | 37 | 11251 | 11270 | 1087 |
| 560587 | N/A | N/A | AAACCTACACGAATGTATTA | 3 | 11253 | 11272 | 1088 |
| 560588 | N/A | N/A | GAAACCTACACGAATGTAT | 27 | 11255 | 11274 | 1089 |
| 560589 | N/A | N/A | TTGAAAACCTACACGAATGT | 19 | 11257 | 11276 | 1090 |
| 560590 | N/A | N/A | ACTTGAAAACCTACACGAAT | 21 | 11259 | 11278 | 1091 |
| 560591 | N/A | N/A | CTACTTGAAAACCTACACGA | 43 | 11261 | 11280 | 1092 |
| 560592 | N/A | N/A | TATTTCTACTTGAAAACCTA | 29 | 11266 | 11285 | 1093 |
| 560593 | N/A | N/A | TTTATTTCTACTTGAAAACC | 2 | 11268 | 11287 | 1094 |
| 560594 | N/A | N/A | GGTTTATTTCTACTTGAAAA | 27 | 11270 | 11289 | 1095 |
| 560595 | N/A | N/A | GAGGTTTATTTCTACTTGAA | 45 | 11272 | 11291 | 1096 |
| 560596 | N/A | N/A | ACGAGGTTTATTTCTACTTG | 75 | 11274 | 11293 | 45 |
| 560597 | N/A | N/A | TTACGAGGTTTATTTCTACT | 49 | 11276 | 11295 | 1097 |
| 560598 | N/A | N/A | TGTTACGAGGTTTATTTCTA | 39 | 11278 | 11297 | 1098 |
| 560599 | N/A | N/A | CTTGTTACGAGGTTTATTTC | 32 | 11280 | 11299 | 1099 |
| 560600 | N/A | N/A | AACTTGTTACGAGGTTTATT | 27 | 11282 | 11301 | 1100 |
| 560601 | N/A | N/A | GTAACTTGTTACGAGGTTTA | 55 | 11284 | 11303 | 1101 |
| 560602 | N/A | N/A | CAGTAACTTGTTACGAGGTT | 51 | 11286 | 11305 | 1102 |
| 560603 | N/A | N/A | TTCAGTAACTTGTTACGAGG | 40 | 11288 | 11307 | 1103 |
| 560604 | N/A | N/A | CGTTCAGTAACTTGTTACGA | 53 | 11290 | 11309 | 1104 |
| 560605 | N/A | N/A | CTTGTCAGGCTGTTTAAACG | 24 | 11308 | 11327 | 1105 |
| 560606 | N/A | N/A | TGCTTGTCAGGCTGTTTAAA | 46 | 11310 | 11329 | 1106 |
| 560607 | N/A | N/A | CATGCTTGTCAGGCTGTTTA | 72 | 11312 | 11331 | 46 |

TABLE 8-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 560608 | N/A | N/A | TACATGCTTGTCAGGCTGTT | 72 | 11314 | 11333 | 47 |
| 560609 | N/A | N/A | TATACATGCTTGTCAGGCTG | 63 | 11316 | 11335 | 1107 |
| 560610 | N/A | N/A | TATATACATGCTTGTCAGGC | 55 | 11318 | 11337 | 1108 |
| 560611 | N/A | N/A | CATATATACATGCTTGTCAG | 47 | 11320 | 11339 | 1109 |
| 560235 | 2 | 21 | TGGAACTGTTTTCTTCTGGA | 43 | 3106 | 3125 | 1110 |
| 337526 | 4 | 23 | CGTGGAACTGTTTTCTTCTG | 54 | 3108 | 3127 | 1111 |
| 560236 | 25 | 44 | TTGATTTTCAATTTCAAGCA | 91 | 3129 | 3148 | 30 |
| 560237 | 27 | 46 | TCTTGATTTTCAATTTCAAG | 33 | 3131 | 3150 | 1112 |
| 560238 | 32 | 51 | TTTTATCTTGATTTTCAATT | 0 | 3136 | 3155 | 1113 |
| 560239 | 35 | 54 | CATTTTTATCTTGATTTTCA | 6 | 3139 | 3158 | 1114 |
| 560240 | 43 | 62 | ATTGTGAACATTTTTATCTT | 0 | 3147 | 3166 | 1115 |
| 560241 | 45 | 64 | TAATTGTGAACATTTTTATC | 20 | 3149 | 3168 | 1116 |
| 560242 | 56 | 75 | AAGAAGGAGCTTAATTGTGA | 39 | 3160 | 3179 | 1117 |
| 560243 | 58 | 77 | AAAAGAAGGAGCTTAATTGT | 17 | 3162 | 3181 | 1118 |
| 560244 | 60 | 79 | TAAAAGAAGGAGCTTAATT | 0 | 3164 | 3183 | 1119 |
| 560245 | 75 | 94 | TAACTAGAGGAACAATAAAA | 37 | 3179 | 3198 | 1120 |
| 560246 | 77 | 96 | AATAACTAGAGGAACAATAA | 3 | 3181 | 3200 | 1121 |
| 560247 | 79 | 98 | GAAATAACTAGAGGAACAAT | 13 | 3183 | 3202 | 1122 |
| 560248 | 81 | 100 | AGGAAATAACTAGAGGAACA | 28 | 3185 | 3204 | 1123 |
| 560249 | 83 | 102 | GGAGGAAATAACTAGAGGAA | 12 | 3187 | 3206 | 1124 |
| 560250 | 90 | 109 | CAATTCTGGAGGAAATAACT | 34 | 3194 | 3213 | 1125 |
| 560251 | 92 | 111 | ATCAATTCTGGAGGAAATAA | 32 | 3196 | 3215 | 1126 |
| 560252 | 96 | 115 | CTTGATCAATTCTGGAGGAA | 15 | 3200 | 3219 | 1127 |
| 560253 | 98 | 117 | GTCTTGATCAATTCTGGAGG | 53 | 3202 | 3221 | 1128 |
| 560254 | 100 | 119 | TTGTCTTGATCAATTCTGGA | 48 | 3204 | 3223 | 1129 |
| 560255 | 102 | 121 | AATTGTCTTGATCAATTCTG | 23 | 3206 | 3225 | 1130 |
| 560256 | 104 | 123 | TGAATTGTCTTGATCAATTC | 14 | 3208 | 3227 | 1131 |
| 560257 | 106 | 125 | GATGAATTGTCTTGATCAAT | 46 | 3210 | 3229 | 1132 |
| 560258 | 108 | 127 | ATGATGAATTGTCTTGATCA | 33 | 3212 | 3231 | 1133 |
| 560259 | 110 | 129 | AAATGATGAATTGTCTTGAT | 24 | 3214 | 3233 | 1134 |
| 560260 | 114 | 133 | AATCAAATGATGAATTGTCT | 25 | 3218 | 3237 | 1135 |
| 560261 | 116 | 135 | AGAATCAAATGATGAATTGT | 16 | 3220 | 3239 | 1136 |
| 560262 | 119 | 138 | TAGAGAATCAAATGATGAAT | 7 | 3223 | 3242 | 1137 |
| 560263 | 126 | 145 | CTGGAGATAGAGAATCAAAT | 40 | 3230 | 3249 | 1138 |
| 560264 | 128 | 147 | CTCTGGAGATAGAGAATCAA | 51 | 3232 | 3251 | 1139 |

TABLE 8-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 560265 | 130 | 149 | GGCTCTGGAGATAGAGAATC | 63 | 3234 | 3253 | 31 |
| 560266 | 132 | 151 | TTGGCTCTGGAGATAGAGAA | 49 | 3236 | 3255 | 1140 |
| 560267 | 135 | 154 | ATTTTGGCTCTGGAGATAGA | 49 | 3239 | 3258 | 1141 |
| 560268 | 140 | 159 | TCTTGATTTTGGCTCTGGAG | 69 | 3244 | 3263 | 32 |
| 560269 | 142 | 161 | AATCTTGATTTTGGCTCTGG | 53 | 3246 | 3265 | 1142 |
| 560270 | 150 | 169 | ACATAGCAAATCTTGATTTT | 25 | 3254 | 3273 | 1143 |
| 560271 | 152 | 171 | TAACATAGCAAATCTTGATT | 0 | 3256 | 3275 | 1144 |
| 560272 | 154 | 173 | TCTAACATAGCAAATCTTGA | 53 | 3258 | 3277 | 1145 |
| 560273 | 176 | 195 | ATTGGCTAAAATTTTTACAT | 12 | 3280 | 3299 | 1146 |
| 560274 | 180 | 199 | GGCCATTGGCTAAAATTTTT | 34 | 3284 | 3303 | 1147 |
| 560275 | 182 | 201 | GAGGCCATTGGCTAAAATTT | 26 | 3286 | 3305 | 1148 |
| 560276 | 189 | 208 | ACTGAAGGAGGCCATTGGCT | 51 | 3293 | 3312 | 1149 |
| 560277 | 191 | 210 | CAACTGAAGGAGGCCATTGG | 28 | 3295 | 3314 | 1150 |
| 560278 | 193 | 212 | CCCAACTGAAGGAGGCCATT | 10 | 3297 | 3316 | 1151 |
| 560279 | 197 | 216 | ATGTCCCAACTGAAGGAGGC | 0 | 3301 | 3320 | 1152 |
| 560280 | 204 | 223 | TAAGACCATGTCCCAACTGA | 13 | 3308 | 3327 | 1153 |
| 560281 | 211 | 230 | AAGTCTTTAAGACCATGTCC | 4 | 3315 | 3334 | 1154 |
| 560282 | 213 | 232 | CAAAGTCTTTAAGACCATGT | 24 | 3317 | 3336 | 1155 |
| 560283 | 219 | 238 | TATGGACAAAGTCTTTAAGA | 8 | 3323 | 3342 | 1156 |
| 560284 | 224 | 243 | CGTCTTATGGACAAAGTCTT | 11 | 3328 | 3347 | 1157 |
| 560285 | 242 | 261 | GTCATTAATTTGGCCCTTCG | 57 | 3346 | 3365 | 33 |
| 560286 | 247 | 266 | AATATGTCATTAATTTGGCC | 0 | 3351 | 3370 | 1158 |
| 560287 | 249 | 268 | GAAATATGTCATTAATTTGG | 0 | 3353 | 3372 | 1159 |
| 560288 | 252 | 271 | TTTGAAATATGTCATTAATT | 4 | 3356 | 3375 | 1160 |
| 560289 | 256 | 275 | AGTTTTTGAAATATGTCATT | 7 | 3360 | 3379 | 1161 |
| 560290 | 258 | 277 | TGAGTTTTTGAAATATGTCA | 41 | 3362 | 3381 | 1162 |
| 560291 | 267 | 286 | CAAATATGTTGAGTTTTTGA | 30 | 3371 | 3390 | 1163 |
| 560292 | 272 | 291 | CTGATCAAATATGTTGAGTT | 32 | 3376 | 3395 | 1164 |
| 560293 | 276 | 295 | AAGACTGATCAAATATGTTG | 37 | 3380 | 3399 | 1165 |
| 560294 | 280 | 299 | TAAAAAGACTGATCAAATAT | 0 | 3384 | 3403 | 1166 |
| 560295 | 282 | 301 | CATAAAAAGACTGATCAAAT | 6 | 3386 | 3405 | 1167 |
| 560296 | 284 | 303 | ATCATAAAAAGACTGATCAA | 10 | 3388 | 3407 | 1168 |
| 560297 | 287 | 306 | TAGATCATAAAAAGACTGAT | 0 | 3391 | 3410 | 1169 |
| 560298 | 289 | 308 | GATAGATCATAAAAAGACTG | 21 | 3393 | 3412 | 1170 |
| 560299 | 291 | 310 | GCGATAGATCATAAAAAGAC | 20 | 3395 | 3414 | 1171 |
| 560300 | 293 | 312 | CAGCGATAGATCATAAAAAG | 16 | 3397 | 3416 | 1172 |

TABLE 8-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 560301 | 295 | 314 | TGCAGCGATAGATCATAAAA | 38 | 3399 | 3418 | 1173 |
| 560302 | 297 | 316 | TTTGCAGCGATAGATCATAA | 32 | 3401 | 3420 | 1174 |
| 560303 | 299 | 318 | GGTTTGCAGCGATAGATCAT | 34 | 3403 | 3422 | 1175 |
| 560304 | 301 | 320 | CTGGTTTGCAGCGATAGATC | 25 | 3405 | 3424 | 1176 |
| 560305 | 303 | 322 | CACTGGTTTGCAGCGATAGA | 28 | 3407 | 3426 | 1177 |
| 560306 | 305 | 324 | TTCACTGGTTTGCAGCGATA | 65 | 3409 | 3428 | 34 |
| 560307 | 307 | 326 | ATTTCACTGGTTTGCAGCGA | 23 | 3411 | 3430 | 1178 |
| 560308 | 310 | 329 | TTGATTTCACTGGTTTGCAG | 5 | 3414 | 3433 | 1179 |
| 560309 | 318 | 337 | CTTCTTCTTTGATTTCACTG | 25 | 3422 | 3441 | 1180 |
| 560310 | 327 | 346 | GTTCCTTTTCTTCTTCTTTG | 19 | 3431 | 3450 | 1181 |
| 544120 | 707 | 726 | AGTTCTTGGTGCTCTTGGCT | 77 | 6720 | 6739 | 15 |
| 560311 | 801 | 820 | TTGTATGTTCACCTCTGTTA | 25 | 7386 | 7405 | 1182 |
| 560312 | 802 | 821 | CTTGTATGTTCACCTCTGTT | 37 | 7387 | 7406 | 1183 |
| 337487 | 804 | 823 | CACTTGTATGTTCACCTCTG | 83 | 7389 | 7408 | 28 |
| 560313 | 806 | 825 | GCCACTTGTATGTTCACCTC | 40 | 7391 | 7410 | 1184 |
| 560314 | 807 | 826 | TGCCACTTGTATGTTCACCT | 56 | 7392 | 7411 | 1185 |
| 560315 | 808 | 827 | ATGCCACTTGTATGTTCACC | 39 | 7393 | 7412 | 1186 |
| 337488 | 809 | 828 | CATGCCACTTGTATGTTCAC | 19 | 7394 | 7413 | 1187 |
| 560316 | 810 | 829 | ACATGCCACTTGTATGTTCA | 26 | 7395 | 7414 | 1188 |
| 560317 | 811 | 830 | TACATGCCACTTGTATGTTC | 20 | 7396 | 7415 | 1189 |
| 560318 | 814 | 833 | GCATACATGCCACTTGTATG | 2 | 7399 | 7418 | 1190 |
| 560319 | 815 | 834 | GGCATACATGCCACTTGTAT | 24 | 7400 | 7419 | 1191 |
| 560320 | 816 | 835 | TGGCATACATGCCACTTGTA | 7 | 7401 | 7420 | 1192 |
| 560321 | 817 | 836 | ATGGCATACATGCCACTTGT | 0 | 7402 | 7421 | 1193 |
| 560322 | 821 | 840 | TCTGATGGCATACATGCCAC | 26 | 7406 | 7425 | 1194 |
| 560323 | 822 | 841 | GTCTGATGGCATACATGCCA | 39 | 7407 | 7426 | 1195 |
| 560324 | 824 | 843 | GGGTCTGATGGCATACATGC | 15 | 7409 | 7428 | 1196 |
| 560325 | 825 | 844 | TGGGTCTGATGGCATACATG | 23 | 7410 | 7429 | 1197 |
| 560326 | 826 | 845 | CTGGGTCTGATGGCATACAT | 9 | 7411 | 7430 | 1198 |
| 560327 | 834 | 853 | GAGAGTTGCTGGGTCTGATG | 0 | 7419 | 7438 | 1199 |
| 560328 | 835 | 854 | TGAGAGTTGCTGGGTCTGAT | 2 | 7420 | 7439 | 1200 |
| 560329 | 836 | 855 | TTGAGAGTTGCTGGGTCTGA | 35 | 7421 | 7440 | 1201 |
| 560330 | 837 | 856 | CTTGAGAGTTGCTGGGTCTG | 17 | 7422 | 7441 | 1202 |
| 560331 | 838 | 857 | ACTTGAGAGTTGCTGGGTCT | 0 | 7423 | 7442 | 1203 |
| 560332 | 839 | 858 | AACTTGAGAGTTGCTGGGTC | 13 | 7424 | 7443 | 1204 |

TABLE 8-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 560333 | 843 | 862 | GAAAAACTTGAGAGTTGCTG | 22 | 7428 | 7447 | 1205 |
| 560334 | 844 | 863 | TGAAAAACTTGAGAGTTGCT | 16 | 7429 | 7448 | 1206 |
| 560335 | 845 | 864 | ATGAAAAACTTGAGAGTTGC | 10 | 7430 | 7449 | 1207 |
| 560336 | 846 | 865 | CATGAAAAACTTGAGAGTTG | 2 | 7431 | 7450 | 1208 |
| 560337 | 851 | 870 | GTAGACATGAAAAACTTGAG | 13 | 7436 | 7455 | 1209 |
| 560338 | 853 | 872 | CAGTAGACATGAAAAACTTG | 3 | 7438 | 7457 | 1210 |
| 560339 | 861 | 880 | TAACATCACAGTAGACATGA | 30 | 7446 | 7465 | 1211 |
| 560340 | 862 | 881 | ATAACATCACAGTAGACATG | 34 | 7447 | 7466 | 1212 |
| 560341 | 863 | 882 | TATAACATCACAGTAGACAT | 0 | 7448 | 7467 | 1213 |
| 560342 | 864 | 883 | ATATAACATCACAGTAGACA | 10 | 7449 | 7468 | 1214 |
| 560343 | 865 | 884 | GATATAACATCACAGTAGAC | 9 | 7450 | 7469 | 1215 |
| 560344 | 866 | 885 | TGATATAACATCACAGTAGA | 20 | 7451 | 7470 | 1216 |
| 337490 | 867 | 886 | CTGATATAACATCACAGTAG | 24 | 7452 | 7471 | 1217 |
| 560345 | 868 | 887 | CCTGATATAACATCACAGTA | 36 | 7453 | 7472 | 1218 |
| 560346 | 869 | 888 | ACCTGATATAACATCACAGT | 35 | 7454 | 7473 | 1219 |
| 560347 | 870 | 889 | TACCTGATATAACATCACAG | 26 | 7455 | 7474 | 1220 |
| 560348 | 871 | 890 | CTACCTGATATAACATCACA | 38 | N/A | N/A | 1221 |
| 560349 | 872 | 891 | ACTACCTGATATAACATCAC | 12 | N/A | N/A | 1222 |
| 560350 | 873 | 892 | GACTACCTGATATAACATCA | 28 | N/A | N/A | 1223 |
| 560351 | 874 | 893 | GGACTACCTGATATAACATC | 15 | N/A | N/A | 1224 |
| 560352 | 875 | 894 | TGGACTACCTGATATAACAT | 0 | N/A | N/A | 1225 |
| 560353 | 876 | 895 | ATGGACTACCTGATATAACA | 11 | N/A | N/A | 1226 |
| 337491 | 877 | 896 | CATGGACTACCTGATATAAC | 3 | N/A | N/A | 1227 |
| 560354 | 878 | 897 | CCATGGACTACCTGATATAA | 0 | N/A | N/A | 1228 |
| 560355 | 879 | 898 | TCCATGGACTACCTGATATA | 13 | N/A | N/A | 1229 |
| 560356 | 880 | 899 | GTCCATGGACTACCTGATAT | 50 | N/A | N/A | 1230 |
| 560357 | 881 | 900 | TGTCCATGGACTACCTGATA | 12 | N/A | N/A | 1231 |
| 560358 | 882 | 901 | ATGTCCATGGACTACCTGAT | 20 | N/A | N/A | 1232 |
| 560359 | 883 | 902 | AATGTCCATGGACTACCTGA | 16 | 7870 | 7889 | 1233 |
| 560360 | 884 | 903 | TAATGTCCATGGACTACCTG | 26 | 7871 | 7890 | 1234 |
| 560361 | 885 | 904 | TTAATGTCCATGGACTACCT | 31 | 7872 | 7891 | 1235 |
| 560362 | 886 | 905 | ATTAATGTCCATGGACTACC | 42 | 7873 | 7892 | 1236 |
| 560363 | 887 | 906 | AATTAATGTCCATGGACTAC | 21 | 7874 | 7893 | 1237 |
| 560364 | 891 | 910 | GTTGAATTAATGTCCATGGA | 18 | 7878 | 7897 | 1238 |
| 560365 | 892 | 911 | TGTTGAATTAATGTCCATGG | 36 | 7879 | 7898 | 1239 |
| 560366 | 893 | 912 | ATGTTGAATTAATGTCCATG | 13 | 7880 | 7899 | 1240 |

TABLE 8-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 560367 | 894 | 913 | GATGTTGAATTAATGTCCAT | 14 | 7881 | 7900 | 1241 |
| 560368 | 895 | 914 | CGATGTTGAATTAATGTCCA | 30 | 7882 | 7901 | 1242 |
| 560369 | 896 | 915 | TCGATGTTGAATTAATGTCC | 29 | 7883 | 7902 | 1243 |
| 560370 | 897 | 916 | TTCGATGTTGAATTAATGTC | 4 | 7884 | 7903 | 1244 |
| 560371 | 898 | 917 | ATTCGATGTTGAATTAATGT | 22 | 7885 | 7904 | 1245 |
| 560372 | 899 | 918 | TATTCGATGTTGAATTAATG | 0 | 7886 | 7905 | 1246 |
| 560373 | 900 | 919 | CTATTCGATGTTGAATTAAT | 0 | 7887 | 7906 | 1247 |
| 337492 | 901 | 920 | TCTATTCGATGTTGAATTAA | 59 | 7888 | 7907 | 29 |
| 560374 | 902 | 921 | ATCTATTCGATGTTGAATTA | 18 | 7889 | 7908 | 1248 |
| 560375 | 903 | 922 | CATCTATTCGATGTTGAATT | 27 | 7890 | 7909 | 1249 |
| 560376 | 904 | 923 | CCATCTATTCGATGTTGAAT | 40 | 7891 | 7910 | 1250 |
| 560377 | 905 | 924 | TCCATCTATTCGATGTTGAA | 23 | 7892 | 7911 | 1251 |
| 560378 | 906 | 925 | ATCCATCTATTCGATGTTGA | 47 | 7893 | 7912 | 1252 |
| 560379 | 907 | 926 | GATCCATCTATTCGATGTTG | 46 | 7894 | 7913 | 1253 |
| 560380 | 908 | 927 | TGATCCATCTATTCGATGTT | 16 | 7895 | 7914 | 1254 |
| 560381 | 909 | 928 | GTGATCCATCTATTCGATGT | 24 | 7896 | 7915 | 1255 |
| 560382 | 910 | 929 | TGTGATCCATCTATTCGATG | 21 | 7897 | 7916 | 1256 |
| 560383 | 911 | 930 | TTGTGATCCATCTATTCGAT | 19 | 7898 | 7917 | 1257 |
| 560384 | 1273 | 1292 | TTTAGGTTGTTTTCTCCACA | 35 | 10245 | 10264 | 1258 |
| 560385 | 1274 | 1293 | ATTTAGGTTGTTTTCTCCAC | 34 | 10246 | 10265 | 1259 |
| 560386 | 1278 | 1297 | TACCATTTAGGTTGTTTTCT | 15 | 10250 | 10269 | 1260 |
| 560387 | 1286 | 1305 | GTTATATTTACCATTTAGGT | 20 | 10258 | 10277 | 1261 |
| 560388 | 1287 | 1306 | TGTTATATTTACCATTTAGG | 17 | 10259 | 10278 | 1262 |
| 560389 | 1288 | 1307 | TTGTTATATTTACCATTTAG | 21 | 10260 | 10279 | 1263 |
| 560390 | 1289 | 1308 | TTTGTTATATTTACCATTTA | 4 | 10261 | 10280 | 1264 |
| 560391 | 1292 | 1311 | TGGTTTGTTATATTTACCAT | 23 | 10264 | 10283 | 1265 |
| 560392 | 1296 | 1315 | CTCTTGGTTTGTTATATTTA | 63 | 10268 | 10287 | 1266 |
| 560393 | 1297 | 1316 | GCTCTTGGTTTGTTATATTT | 61 | 10269 | 10288 | 1267 |
| 560394 | 1298 | 1317 | TGCTCTTGGTTTGTTATATT | 51 | 10270 | 10289 | 1268 |
| 560395 | 1301 | 1320 | TTTTGCTCTTGGTTTGTTAT | 2 | 10273 | 10292 | 1269 |
| 560396 | 1302 | 1321 | ATTTTGCTCTTGGTTTGTTA | 0 | 10274 | 10293 | 1270 |
| 560397 | 1303 | 1322 | GATTTTGCTCTTGGTTTGTT | 0 | 10275 | 10294 | 1271 |
| 560398 | 1304 | 1323 | AGATTTTGCTCTTGGTTTGT | 16 | 10276 | 10295 | 1272 |
| 560399 | 1305 | 1324 | TAGATTTTGCTCTTGGTTTG | 28 | 10277 | 10296 | 1273 |
| 560400 | 1307 | 1326 | CTTAGATTTTGCTCTTGGTT | 69 | 10279 | 10298 | 35 |

TABLE 8-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 560401 | 1308 | 1327 | GCTTAGATTTTGCTCTTGGT | 77 | 10280 | 10299 | 36 |
| 560402 | 1309 | 1328 | GGCTTAGATTTTGCTCTTGG | 72 | 10281 | 10300 | 37 |
| 560403 | 1315 | 1334 | CTCTCTGGCTTAGATTTTGC | 38 | 10287 | 10306 | 1274 |
| 560404 | 1316 | 1335 | CCTCTCTGGCTTAGATTTTG | 49 | 10288 | 10307 | 1275 |
| 560405 | 1317 | 1336 | TCCTCTCTGGCTTAGATTTT | 46 | 10289 | 10308 | 1276 |
| 560406 | 1321 | 1340 | CTTCTCCTCTCTGGCTTAGA | 40 | 10293 | 10312 | 1277 |
| 560407 | 1322 | 1341 | TCTTCTCCTCTCTGGCTTAG | 57 | 10294 | 10313 | 1278 |
| 560408 | 1323 | 1342 | CTCTTCTCCTCTCTGGCTTA | 40 | 10295 | 10314 | 1279 |
| 337505 | 1328 | 1347 | TAATCCTCTTCTCCTCTCTG | 28 | 10300 | 10319 | 1280 |
| 560409 | 1329 | 1348 | ATAATCCTCTTCTCCTCTCT | 30 | 10301 | 10320 | 1281 |
| 560410 | 1330 | 1349 | GATAATCCTCTTCTCCTCTC | 9 | 10302 | 10321 | 1282 |
| 560411 | 1331 | 1350 | AGATAATCCTCTTCTCCTCT | 23 | 10303 | 10322 | 1283 |
| 560412 | 1332 | 1351 | AAGATAATCCTCTTCTCCTC | 12 | 10304 | 10323 | 1284 |
| 560413 | 1333 | 1352 | CAAGATAATCCTCTTCTCCT | 40 | 10305 | 10324 | 1285 |
| 560414 | 1334 | 1353 | CCAAGATAATCCTCTTCTCC | 52 | 10306 | 10325 | 1286 |
| 560415 | 1335 | 1354 | TCCAAGATAATCCTCTTCTC | 56 | 10307 | 10326 | 1287 |
| 560416 | 1336 | 1355 | TTCCAAGATAATCCTCTTCT | 60 | 10308 | 10327 | 1288 |
| 560417 | 1337 | 1356 | CTTCCAAGATAATCCTCTTC | 58 | 10309 | 10328 | 1289 |
| 560418 | 1338 | 1357 | ACTTCCAAGATAATCCTCTT | 31 | 10310 | 10329 | 1290 |
| 560419 | 1339 | 1358 | GACTTCCAAGATAATCCTCT | 52 | 10311 | 10330 | 1291 |
| 560420 | 1340 | 1359 | AGACTTCCAAGATAATCCTC | 49 | 10312 | 10331 | 1292 |
| 560421 | 1341 | 1360 | GAGACTTCCAAGATAATCCT | 56 | 10313 | 10332 | 1293 |
| 337506 | 1342 | 1361 | TGAGACTTCCAAGATAATCC | 49 | 10314 | 10333 | 1294 |
| 560422 | 1343 | 1362 | TTGAGACTTCCAAGATAATC | 34 | 10315 | 10334 | 1295 |
| 560423 | 1344 | 1363 | TTTGAGACTTCCAAGATAAT | 14 | 10316 | 10335 | 1296 |
| 560424 | 1345 | 1364 | TTTTGAGACTTCCAAGATAA | 27 | 10317 | 10336 | 1297 |
| 560425 | 1346 | 1365 | ATTTTGAGACTTCCAAGATA | 23 | 10318 | 10337 | 1298 |
| 560426 | 1348 | 1367 | CCATTTTGAGACTTCCAAGA | 40 | 10320 | 10339 | 1299 |
| 560427 | 1351 | 1370 | CTTCCATTTTGAGACTTCCA | 58 | 10323 | 10342 | 1300 |
| 560428 | 1355 | 1374 | TAACCTTCCATTTTGAGACT | 36 | 10327 | 10346 | 1301 |
| 560429 | 1356 | 1375 | ATAACCTTCCATTTTGAGAC | 51 | 10328 | 10347 | 1302 |
| 560430 | 1357 | 1376 | TATAACCTTCCATTTTGAGA | 33 | 10329 | 10348 | 1303 |
| 560431 | 1358 | 1377 | GTATAACCTTCCATTTTGAG | 53 | 10330 | 10349 | 1304 |
| 337508 | 1360 | 1379 | GAGTATAACCTTCCATTTTG | 28 | 10332 | 10351 | 1305 |
| 560432 | 1361 | 1380 | AGAGTATAACCTTCCATTTT | 50 | 10333 | 10352 | 1306 |
| 560433 | 1365 | 1384 | TTATAGAGTATAACCTTCCA | 63 | 10337 | 10356 | 1307 |

TABLE 8-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 560434 | 1369 | 1388 | GATTTTATAGAGTATAACCT | 31 | 10341 | 10360 | 1308 |
| 560435 | 1370 | 1389 | TGATTTTATAGAGTATAACC | 6 | 10342 | 10361 | 1309 |
| 560436 | 1371 | 1390 | TTGATTTTATAGAGTATAAC | 14 | 10343 | 10362 | 1310 |
| 560437 | 1372 | 1391 | GTTGATTTTATAGAGTATAA | 2 | 10344 | 10363 | 1311 |
| 560438 | 1376 | 1395 | TTTGGTTGATTTTATAGAGT | 20 | 10348 | 10367 | 1312 |
| 560439 | 1386 | 1405 | GGATCAACATTTTGGTTGAT | 42 | 10358 | 10377 | 1313 |
| 560440 | 1387 | 1406 | TGGATCAACATTTTGGTTGA | 10 | 10359 | 10378 | 1314 |
| 560441 | 1388 | 1407 | ATGGATCAACATTTTGGTTG | 34 | 10360 | 10379 | 1315 |
| 560442 | 1398 | 1417 | AATCTGTTGGATGGATCAAC | 52 | 10370 | 10389 | 1316 |
| 560443 | 1399 | 1418 | GAATCTGTTGGATGGATCAA | 47 | 10371 | 10390 | 1317 |
| 560444 | 1403 | 1422 | TTCTGAATCTGTTGGATGGA | 30 | 10375 | 10394 | 1318 |
| 560445 | 1404 | 1423 | TTTCTGAATCTGTTGGATGG | 34 | 10376 | 10395 | 1319 |
| 560446 | 1405 | 1424 | CTTTCTGAATCTGTTGGATG | 50 | 10377 | 10396 | 1320 |
| 560447 | 1409 | 1428 | AAAGCTTTCTGAATCTGTTG | 29 | 10381 | 10400 | 1321 |
| 560448 | 1425 | 1444 | TTGCCTCAGTTCATTCAAAG | 38 | 10397 | 10416 | 1322 |
| 560449 | 1429 | 1448 | AAATTTGCCTCAGTTCATTC | 27 | 10401 | 10420 | 1323 |
| 560450 | 1434 | 1453 | CTTTTAAATTTGCCTCAGTT | 34 | 10406 | 10425 | 1324 |
| 560451 | 1440 | 1459 | TATTGCCTTTTAAATTTGCC | 21 | 10412 | 10431 | 1325 |
| 560452 | 1441 | 1460 | TTATTGCCTTTTAAATTTGC | 23 | 10413 | 10432 | 1326 |
| 560453 | 1446 | 1465 | TTAAATTATTGCCTTTTAAA | 1 | 10418 | 10437 | 1327 |
| 560454 | 1447 | 1466 | TTTAAATTATTGCCTTTTAA | 1 | 10419 | 10438 | 1328 |
| 560455 | 1448 | 1467 | GTTTAAATTATTGCCTTTTA | 48 | 10420 | 10439 | 1329 |
| 560456 | 1449 | 1468 | TGTTTAAATTATTGCCTTTT | 25 | 10421 | 10440 | 1330 |
| 560457 | 1450 | 1469 | ATGTTTAAATTATTGCCTTT | 0 | 10422 | 10441 | 1331 |
| 560458 | 1704 | 1723 | TTTAATAAGTTCACCTATTG | 26 | 10676 | 10695 | 1332 |
| 560459 | 1705 | 1724 | ATTTAATAAGTTCACCTATT | 26 | 10677 | 10696 | 1333 |
| 560460 | 1706 | 1725 | TATTTAATAAGTTCACCTAT | 16 | 10678 | 10697 | 1334 |
| 560461 | 1707 | 1726 | TTATTTAATAAGTTCACCTA | 4 | 10679 | 10698 | 1335 |
| 560462 | 1708 | 1727 | GTTATTTAATAAGTTCACCT | 36 | 10680 | 10699 | 1336 |
| 560463 | 1709 | 1728 | AGTTATTTAATAAGTTCACC | 0 | 10681 | 10700 | 1337 |
| 560464 | 1712 | 1731 | AAAGTTATTTAATAAGTTC | 12 | 10684 | 10703 | 1338 |
| 560465 | 1719 | 1738 | TATTTAGAAAAGTTATTTAA | 0 | 10691 | 10710 | 1339 |
| 560466 | 1738 | 1757 | TAAAAGTCTCTAAATTTTTT | 0 | 10710 | 10729 | 1340 |
| 560467 | 1739 | 1758 | ATAAAAGTCTCTAAATTTTT | 0 | 10711 | 10730 | 1341 |
| 560468 | 1740 | 1759 | AATAAAAGTCTCTAAATTTT | 25 | 10712 | 10731 | 1342 |

TABLE 8-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 560469 | 1760 | 1779 | GCTCATATGATGCCTTTAA | 77 | 10732 | 10751 | 38 |
| 560470 | 1761 | 1780 | AGCTCATATGATGCCTTTA | 73 | 10733 | 10752 | 39 |
| 560471 | 1762 | 1781 | TAGCTCATATGATGCCTTT | 67 | 10734 | 10753 | 40 |
| 560472 | 1763 | 1782 | TTAGCTCATATGATGCCTT | 42 | 10735 | 10754 | 1343 |
| 560473 | 1764 | 1783 | ATTAGCTCATATGATGCCT | 61 | 10736 | 10755 | 1344 |
| 560474 | 1765 | 1784 | TATTAGCTCATATGATGCC | 55 | 10737 | 10756 | 41 |
| 560475 | 1766 | 1785 | ATATTAGCTCATATGATGC | 42 | 10738 | 10757 | 1345 |
| 560476 | 1767 | 1786 | GATATTAGCTCATATGATG | 36 | 10739 | 10758 | 1346 |
| 560477 | 1768 | 1787 | TGATATTAGCTCATATGAT | 21 | 10740 | 10759 | 1347 |
| 560478 | 1769 | 1788 | GTGATATTAGCTCATATGA | 40 | 10741 | 10760 | 1348 |
| 560479 | 1776 | 1795 | GAAAGTTGTGATATTAGCTC | 43 | 10748 | 10767 | 1349 |
| 560480 | 1777 | 1796 | GGAAAGTTGTGATATTAGCT | 19 | 10749 | 10768 | 1350 |
| 560481 | 1778 | 1797 | GGGAAAGTTGTGATATTAGC | 17 | 10750 | 10769 | 1351 |
| 560482 | 1779 | 1798 | TGGGAAAGTTGTGATATTAG | 29 | 10751 | 10770 | 1352 |
| 560483 | 1780 | 1799 | CTGGGAAAGTTGTGATATTA | 35 | 10752 | 10771 | 1353 |
| 560484 | 1781 | 1800 | ACTGGGAAAGTTGTGATATT | 25 | 10753 | 10772 | 1354 |
| 560485 | 1782 | 1801 | AACTGGGAAAGTTGTGATAT | 12 | 10754 | 10773 | 1355 |
| 560486 | 1783 | 1802 | AAACTGGGAAAGTTGTGATA | 21 | 10755 | 10774 | 1356 |
| 560487 | 1784 | 1803 | TAAACTGGGAAAGTTGTGAT | 22 | 10756 | 10775 | 1357 |
| 560488 | 1785 | 1804 | TTAAACTGGGAAAGTTGTGA | 12 | 10757 | 10776 | 1358 |
| 560489 | 1786 | 1805 | TTTAAACTGGGAAAGTTGTG | 22 | 10758 | 10777 | 1359 |
| 560490 | 1787 | 1806 | TTTTAAACTGGGAAAGTTGT | 23 | 10759 | 10778 | 1360 |
| 560491 | 1790 | 1809 | GTTTTTTAAACTGGGAAAGT | 1 | 10762 | 10781 | 1361 |
| 560492 | 1791 | 1810 | AGTTTTTTAAACTGGGAAAG | 0 | 10763 | 10782 | 1362 |
| 560493 | 1792 | 1811 | TAGTTTTTTAAACTGGGAAA | 0 | 10764 | 10783 | 1363 |
| 560494 | 1796 | 1815 | GTACTAGTTTTTTAAACTGG | 23 | 10768 | 10787 | 1364 |
| 560495 | 1799 | 1818 | AGAGTACTAGTTTTTTAAAC | 0 | 10771 | 10790 | 1365 |
| 560496 | 1801 | 1820 | CAAGAGTACTAGTTTTTTAA | 0 | 10773 | 10792 | 1366 |
| 560497 | 1806 | 1825 | TTTAACAAGAGTACTAGTTT | 21 | 10778 | 10797 | 1367 |
| 560498 | 1807 | 1826 | TTTTAACAAGAGTACTAGTT | 19 | 10779 | 10798 | 1368 |
| 560499 | 1808 | 1827 | GTTTTAACAAGAGTACTAGT | 37 | 10780 | 10799 | 1369 |
| 560500 | 1809 | 1828 | AGTTTTAACAAGAGTACTAG | 20 | 10781 | 10800 | 1370 |
| 560501 | 1810 | 1829 | GAGTTTTAACAAGAGTACTA | 21 | 10782 | 10801 | 1371 |
| 560502 | 1811 | 1830 | AGAGTTTTAACAAGAGTACT | 0 | 10783 | 10802 | 1372 |
| 560503 | 1814 | 1833 | TTTAGAGTTTTAACAAGAGT | 0 | 10786 | 10805 | 1373 |
| 560504 | 1815 | 1834 | GTTTAGAGTTTTAACAAGAG | 18 | 10787 | 10806 | 1374 |

TABLE 8-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 560505 | 1817 | 1836 | AAGTTTAGAGTTTTAACAAG | 9 | 10789 | 10808 | 1375 |
| 560506 | 1818 | 1837 | CAAGTTTAGAGTTTTAACAA | 1 | 10790 | 10809 | 1376 |
| 560507 | 1822 | 1841 | TAGTCAAGTTTAGAGTTTTA | 21 | 10794 | 10813 | 1377 |
| 560508 | 1823 | 1842 | TTAGTCAAGTTTAGAGTTTT | 10 | 10795 | 10814 | 1378 |
| 560509 | 1824 | 1843 | TTTAGTCAAGTTTAGAGTTT | 20 | 10796 | 10815 | 1379 |
| 560510 | 1828 | 1847 | TGTATTTAGTCAAGTTTAGA | 8 | 10800 | 10819 | 1380 |
| 560511 | 1829 | 1848 | CTGTATTTAGTCAAGTTTAG | 37 | 10801 | 10820 | 1381 |
| 560512 | 1830 | 1849 | TCTGTATTTAGTCAAGTTTA | 46 | 10802 | 10821 | 1382 |
| 560513 | 1834 | 1853 | GTCCTCTGTATTTAGTCAAG | 38 | 10806 | 10825 | 1383 |
| 560514 | 1835 | 1854 | AGTCCTCTGTATTTAGTCAA | 29 | 10807 | 10826 | 1384 |
| 560515 | 1836 | 1855 | CAGTCCTCTGTATTTAGTCA | 47 | 10808 | 10827 | 1385 |
| 560516 | 1837 | 1856 | CCAGTCCTCTGTATTTAGTC | 31 | 10809 | 10828 | 1386 |
| 560517 | 1838 | 1857 | ACCAGTCCTCTGTATTTAGT | 31 | 10810 | 10829 | 1387 |
| 560518 | 1839 | 1858 | TACCAGTCCTCTGTATTTAG | 35 | 10811 | 10830 | 1388 |
| 560519 | 1840 | 1859 | TTACCAGTCCTCTGTATTTA | 30 | 10812 | 10831 | 1389 |
| 560520 | 1841 | 1860 | ATTACCAGTCCTCTGTATTT | 37 | 10813 | 10832 | 1390 |
| 560521 | 1842 | 1861 | AATTACCAGTCCTCTGTATT | 12 | 10814 | 10833 | 1391 |
| 560522 | 1843 | 1862 | CAATTACCAGTCCTCTGTAT | 38 | 10815 | 10834 | 1392 |
| 560523 | 1844 | 1863 | ACAATTACCAGTCCTCTGTA | 35 | 10816 | 10835 | 1393 |
| 560524 | 1845 | 1864 | TACAATTACCAGTCCTCTGT | 51 | 10817 | 10836 | 1394 |
| 560525 | 1846 | 1865 | GTACAATTACCAGTCCTCTG | 52 | 10818 | 10837 | 1395 |
| 560526 | 1847 | 1866 | TGTACAATTACCAGTCCTCT | 38 | 10819 | 10838 | 1396 |
| 560527 | 1848 | 1867 | CTGTACAATTACCAGTCCTC | 19 | 10820 | 10839 | 1397 |
| 560528 | 1849 | 1868 | ACTGTACAATTACCAGTCCT | 13 | 10821 | 10840 | 1398 |
| 560529 | 1850 | 1869 | AACTGTACAATTACCAGTCC | 27 | 10822 | 10841 | 1399 |
| 560530 | 1851 | 1870 | GAACTGTACAATTACCAGTC | 20 | 10823 | 10842 | 1400 |
| 560531 | 1852 | 1871 | AGAACTGTACAATTACCAGT | 24 | 10824 | 10843 | 1401 |
| 560532 | 1854 | 1873 | TAAGAACTGTACAATTACCA | 22 | 10826 | 10845 | 1402 |
| 560533 | 1855 | 1874 | TTAAGAACTGTACAATTACC | 20 | 10827 | 10846 | 1403 |
| 560534 | 1856 | 1875 | TTTAAGAACTGTACAATTAC | 1 | 10828 | 10847 | 1404 |

TABLE 9

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 544355 | N/A | N/A | TTTCAGCATGTATCTCTTAA | 69 | 7065 | 7084 | 21 |
| 544376 | N/A | N/A | GGAGTGGTTCTTTTCACAGC | 64 | 8298 | 8317 | 24 |
| 544380 | N/A | N/A | TGGTCCTTTTAACTTCCAAT | 50 | 8365 | 8384 | 25 |
| 560612 | N/A | N/A | ACTTGAAATTATAATAGGAA | 0 | 3798 | 3817 | 1405 |
| 560613 | N/A | N/A | AAAAAACTAACTTGAAATTA | 0 | 3807 | 3826 | 1406 |
| 560614 | N/A | N/A | GAAACAAAAACTAACTTGA | 21 | 3812 | 3831 | 1407 |
| 560615 | N/A | N/A | GTGTTTTCATATATAACATT | 19 | 3835 | 3854 | 1408 |
| 560616 | N/A | N/A | AATTTTCAGTGTTTTCATAT | 0 | 3843 | 3862 | 1409 |
| 560617 | N/A | N/A | AAAATGCAAATTTTCAGTGT | 0 | 3851 | 3870 | 1410 |
| 560618 | N/A | N/A | GTAATTTTCATATAAAATGC | 0 | 3864 | 3883 | 1411 |
| 560619 | N/A | N/A | GATTTGTAATTTTCATATAA | 0 | 3869 | 3888 | 1412 |
| 560620 | N/A | N/A | TAACCGATTTGTAATTTTCA | 16 | 3874 | 3893 | 1413 |
| 560621 | N/A | N/A | TAATTTAACCGATTTGTAAT | 5 | 3879 | 3898 | 1414 |
| 560622 | N/A | N/A | TTGTATAATTTAACCGATTT | 13 | 3884 | 3903 | 1415 |
| 560623 | N/A | N/A | CTAGATTGTATAATTTAACC | 8 | 3889 | 3908 | 1416 |
| 560624 | N/A | N/A | GTGTTCTAGATTGTATAATT | 24 | 3894 | 3913 | 1417 |
| 560625 | N/A | N/A | AATGACATAGTGTTCTAGAT | 0 | 3903 | 3922 | 1418 |
| 560626 | N/A | N/A | AGTGTAATGACATAGTGTTC | 10 | 3908 | 3927 | 1419 |
| 560627 | N/A | N/A | TTACAATAGTGTAATGACAT | 0 | 3915 | 3934 | 1420 |
| 560628 | N/A | N/A | TTCAGTAATTTACAATAGTG | 12 | 3924 | 3943 | 1421 |
| 560629 | N/A | N/A | TTACCTTCAGTAATTTACAA | 9 | 3929 | 3948 | 1422 |
| 560630 | N/A | N/A | TTAACTTTTTACTTACCTTC | 7 | 3941 | 3960 | 1423 |
| 560631 | N/A | N/A | GAATAGTTTTAAATTTTTTT | 0 | 3960 | 3979 | 1424 |
| 560632 | N/A | N/A | ACACTGGAGAATAGTTTTAA | 10 | 3968 | 3987 | 1425 |
| 560633 | N/A | N/A | TTTAAACACTGGAGAATAGT | 0 | 3973 | 3992 | 1426 |
| 560634 | N/A | N/A | TCTGTTTTAAACACTGGAGA | 25 | 3978 | 3997 | 1427 |
| 560635 | N/A | N/A | GTATTATTTAATCTGTTTTA | 0 | 3989 | 4008 | 1428 |
| 560636 | N/A | N/A | TTACTGTATTATTTAATCTG | 5 | 3994 | 4013 | 1429 |
| 560637 | N/A | N/A | TAAATCTTTTCCATTTACTG | 18 | 4008 | 4027 | 1430 |
| 560638 | N/A | N/A | ATGAATAAATCTTTTCCATT | 12 | 4013 | 4032 | 1431 |
| 560639 | N/A | N/A | GCATATTTTCATATGAATAA | 9 | 4025 | 4044 | 1432 |
| 560640 | N/A | N/A | GCCCAGCATATTTTCATATG | 20 | 4030 | 4049 | 1433 |
| 560641 | N/A | N/A | AAAAGAAAAGCCCAGCATA | 20 | 4040 | 4059 | 1434 |
| 560642 | N/A | N/A | CTGAACTTCAATTAAAAGAA | 5 | 4053 | 4072 | 1435 |
| 560643 | N/A | N/A | GATTTTCTGAACTTCAATTA | 9 | 4059 | 4078 | 1436 |
| 560644 | N/A | N/A | TCTAAAATTTGATTTTCTGA | 0 | 4069 | 4088 | 1437 |

TABLE 9-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 560645 | N/A | N/A | ACTATCTCTAAAATTGATT | 8 | 4075 | 4094 | 1438 |
| 560646 | N/A | N/A | TTAAATTGTACTATCTCTAA | 5 | 4084 | 4103 | 1439 |
| 560647 | N/A | N/A | ACATTTTATTTAAATTGTAC | 17 | 4093 | 4112 | 1440 |
| 560648 | N/A | N/A | GTCCTTAACATTTTATTTAA | 0 | 4100 | 4119 | 1441 |
| 560649 | N/A | N/A | CATATTTTGTCCTTAACAT | 0 | 4109 | 4128 | 1442 |
| 560650 | N/A | N/A | TAGCACATATTTTGTCCTT | 25 | 4114 | 4133 | 1443 |
| 560651 | N/A | N/A | TCAAATAGCACATATTTTG | 0 | 4119 | 4138 | 1444 |
| 560652 | N/A | N/A | CTTCTTTCAAATAGCACATA | 41 | 4125 | 4144 | 1445 |
| 560653 | N/A | N/A | CTTGTATGCTTCTTTCAAAT | 19 | 4133 | 4152 | 1446 |
| 560654 | N/A | N/A | ATTCCTTCCCCTTGTATGCT | 12 | 4143 | 4162 | 1447 |
| 560655 | N/A | N/A | TTGGCAATTCCTTCCCCTTG | 36 | 4149 | 4168 | 1448 |
| 560656 | N/A | N/A | GAATATTGGCAATTCCTTCC | 38 | 4154 | 4173 | 1449 |
| 560657 | N/A | N/A | TGAAAAATGAATATTGGCAA | 0 | 4162 | 4181 | 1450 |
| 560658 | N/A | N/A | TAATGGATTTGAAAAATGAA | 0 | 4171 | 4190 | 1451 |
| 560659 | N/A | N/A | ACTAATAATGGATTTGAAAA | 1 | 4176 | 4195 | 1452 |
| 560660 | N/A | N/A | CATAATCTAAATTTTTAAAC | 6 | 4194 | 4213 | 1453 |
| 560661 | N/A | N/A | CACTATCATAATCTAAATTT | 4 | 4200 | 4219 | 1454 |
| 560662 | N/A | N/A | AATTTCCTGTAACACTATCA | 2 | 4212 | 4231 | 1455 |
| 560663 | N/A | N/A | CTATTAATTTCCTGTAACAC | 9 | 4217 | 4236 | 1456 |
| 560664 | N/A | N/A | CTTTTCTATTAATTTCCTGT | 5 | 4222 | 4241 | 1457 |
| 560665 | N/A | N/A | CTCTTTCTTTTCTATTAATT | 0 | 4228 | 4247 | 1458 |
| 560666 | N/A | N/A | AGTTGCTTTCCTCTTTCTTT | 0 | 4238 | 4257 | 1459 |
| 560667 | N/A | N/A | TTATAAGTTGCTTTCCTCTT | 10 | 4243 | 4262 | 1460 |
| 560668 | N/A | N/A | GTTGGTTATAAGTTGCTTTC | 6 | 4248 | 4267 | 1461 |
| 560669 | N/A | N/A | AGTAGGTTGGTTATAAGTTG | 4 | 4253 | 4272 | 1462 |
| 560670 | N/A | N/A | TAGAGAGTAGGTTGGTTATA | 0 | 4258 | 4277 | 1463 |
| 560671 | N/A | N/A | GGATATAGAGAGTAGGTTGG | 0 | 4263 | 4282 | 1464 |
| 560672 | N/A | N/A | AGTCTGGATATAGAGAGTAG | 0 | 4268 | 4287 | 1465 |
| 560673 | N/A | N/A | TACAAAGTCTGGATATAGA | 7 | 4274 | 4293 | 1466 |
| 560674 | N/A | N/A | GTTTTTCTACAAAGTCTGG | 12 | 4281 | 4300 | 1467 |
| 560675 | N/A | N/A | TTACCTGATTTTCTATTTCT | 15 | 4380 | 4399 | 1468 |
| 560676 | N/A | N/A | ATACTGACTTACCTGATTTT | 15 | 4388 | 4407 | 1469 |
| 560677 | N/A | N/A | TTAAAATACTGACTTACCTG | 2 | 4393 | 4412 | 1470 |
| 560678 | N/A | N/A | TACCATTAAAATACTGACTT | 0 | 4398 | 4417 | 1471 |
| 560679 | N/A | N/A | GGACATACCATTAAAATACT | 7 | 4403 | 4422 | 1472 |

TABLE 9-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 560680 | N/A | N/A | AAAGATGGGACATACCATTA | 0 | 4410 | 4429 | 1473 |
| 560681 | N/A | N/A | AGACCTGTGTGAAAGATGGG | 19 | 4421 | 4440 | 1474 |
| 560682 | N/A | N/A | TTTACAGACCTGTGTGAAAG | 22 | 4426 | 4445 | 1475 |
| 560683 | N/A | N/A | GTGTTTTACAGACCTGTGT | 47 | 4431 | 4450 | 1476 |
| 560684 | N/A | N/A | ATTCAGTGTTTTTACAGACC | 44 | 4436 | 4455 | 1477 |
| 560685 | N/A | N/A | TTAGGATTCAGTGTTTTTAC | 46 | 4441 | 4460 | 1478 |
| 560686 | N/A | N/A | ATAATTTTAGGATTCAGTGT | 15 | 4447 | 4466 | 1479 |
| 560687 | N/A | N/A | GCTTGTAAATAATTTTAGGA | 0 | 4455 | 4474 | 1480 |
| 560688 | N/A | N/A | GTTAAAGCTTGTAAATAATT | 0 | 4461 | 4480 | 1481 |
| 560689 | N/A | N/A | TGTTTTATATCTCTTGAAAA | 0 | 5571 | 5590 | 1482 |
| 560690 | N/A | N/A | TTGGTAATAATATTTGTTTT | 9 | 5585 | 5604 | 1483 |
| 560691 | N/A | N/A | GGAAATTGGTAATAATATTT | 0 | 5590 | 5609 | 1484 |
| 560692 | N/A | N/A | TTAGTGGAAATTGGTAATAA | 22 | 5595 | 5614 | 1485 |
| 560693 | N/A | N/A | TTTGTTTAGTGGAAATTGGT | 8 | 5600 | 5619 | 1486 |
| 560694 | N/A | N/A | TTATGTTTGTTTAGTGGAAA | 0 | 5605 | 5624 | 1487 |
| 560695 | N/A | N/A | TAACATTATGTTTGTTTAGT | 12 | 5610 | 5629 | 1488 |
| 560696 | N/A | N/A | ACTACTAACATTATGTTTGT | 4 | 5615 | 5634 | 1489 |
| 560697 | N/A | N/A | GCAGCACTACTAACATTATG | 38 | 5620 | 5639 | 1490 |
| 560698 | N/A | N/A | TTTTAGCAGCACTACTAACA | 15 | 5625 | 5644 | 1491 |
| 560699 | N/A | N/A | AAACCTTTTAGCAGCACTAC | 52 | 5630 | 5649 | 1492 |
| 560700 | N/A | N/A | GATAAAAACCTTTTAGCAG | 0 | 5636 | 5655 | 1493 |
| 560701 | N/A | N/A | TAGTTGATAAAAACCTTTT | 0 | 5641 | 5660 | 1494 |
| 560702 | N/A | N/A | CAAAAGTAGTTGATAAAAAA | 0 | 5647 | 5666 | 1495 |
| 560703 | N/A | N/A | ATGGAAACCAAAAGTAGTTG | 13 | 5655 | 5674 | 1496 |
| 560704 | N/A | N/A | AAAGTATGGAAACCAAAAGT | 20 | 5660 | 5679 | 1497 |
| 560705 | N/A | N/A | GAAGGAAAGTATGGAAACCA | 45 | 5665 | 5684 | 1498 |
| 560706 | N/A | N/A | CATAAGAAGGAAAGTATGGA | 10 | 5670 | 5689 | 1499 |
| 560707 | N/A | N/A | TAACATCATAAGAAGGAAAG | 0 | 5676 | 5695 | 1500 |
| 560708 | N/A | N/A | GAATAATAACATCATAAGAA | 0 | 5682 | 5701 | 1501 |
| 560709 | N/A | N/A | GAATTTAGAATAATAACATC | 1 | 5689 | 5708 | 1502 |
| 560710 | N/A | N/A | TATAATTGAAAAGAATTTAG | 8 | 5701 | 5720 | 1503 |
| 560711 | N/A | N/A | TAGTAAAAGATATAATTGAA | 0 | 5711 | 5730 | 1504 |
| 560712 | N/A | N/A | AATCATAGTAAAAGATATAA | 10 | 5716 | 5735 | 1505 |
| 560713 | N/A | N/A | CAGGTTCATTTAATCATAGT | 43 | 5727 | 5746 | 1506 |
| 560714 | N/A | N/A | CTATAGTAACATTTTGCTTT | 24 | 5753 | 5772 | 1507 |
| 560715 | N/A | N/A | GTATATTACTATAGTAACAT | 18 | 5761 | 5780 | 1508 |

TABLE 9-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 560716 | N/A | N/A | ACAATGTATATTACTATAGT | 0 | 5766 | 5785 | 1509 |
| 560717 | N/A | N/A | TAGACACAATGTATATTACT | 46 | 5771 | 5790 | 1510 |
| 560718 | N/A | N/A | TATTTTTAGACACAATGTAT | 29 | 5777 | 5796 | 1511 |
| 560719 | N/A | N/A | ACACATTTTATTTTTAGAC | 15 | 5786 | 5805 | 1512 |
| 560720 | N/A | N/A | TTGGTTTCTTCACACATTTT | 62 | 5797 | 5816 | 1513 |
| 560721 | N/A | N/A | TTCATTGTTTTGGTTTCTTC | 55 | 5806 | 5825 | 1514 |
| 560722 | N/A | N/A | CAGAAATTCATTGTTTTGGT | 55 | 5812 | 5831 | 1515 |
| 560723 | N/A | N/A | TCCAACTCAGAAATTCATTG | 65 | 5819 | 5838 | 48 |
| 560724 | N/A | N/A | CTTCTTCCAACTCAGAAATT | 41 | 5824 | 5843 | 1516 |
| 560725 | N/A | N/A | TGATCTAACTCTTCTTCCAA | 24 | 5834 | 5853 | 1517 |
| 560726 | N/A | N/A | TTAAATGATCTAACTCTTCT | 23 | 5839 | 5858 | 1518 |
| 560727 | N/A | N/A | TGAGAAAGTTAAATGATCTA | 0 | 5847 | 5866 | 1519 |
| 560728 | N/A | N/A | TACTTAAATTTTTAGAGTTT | 10 | 5886 | 5905 | 1520 |
| 560729 | N/A | N/A | AAAGTTACTTAAATTTTTAG | 3 | 5891 | 5910 | 1521 |
| 560730 | N/A | N/A | ATCTTAAAGTTACTTAAATT | 0 | 5896 | 5915 | 1522 |
| 560731 | N/A | N/A | ATGTGATCTTAAAGTTACTT | 24 | 5901 | 5920 | 1523 |
| 560732 | N/A | N/A | TAACTATGTGATCTTAAAGT | 0 | 5906 | 5925 | 1524 |
| 560733 | N/A | N/A | TTACTCTTTTCTACTAAGTA | 39 | 5924 | 5943 | 1525 |
| 560734 | N/A | N/A | GGGTATTACTCTTTTCTACT | 48 | 5929 | 5948 | 1526 |
| 560735 | N/A | N/A | TTGCTGGGTATTACTCTTTT | 75 | 5934 | 5953 | 49 |
| 560736 | N/A | N/A | TTTGCTTGCTGGGTATTACT | 65 | 5939 | 5958 | 50 |
| 560737 | N/A | N/A | TAAAGTTTGCTTGCTGGGTA | 49 | 5944 | 5963 | 1527 |
| 560738 | N/A | N/A | TATTGTAAAGTTTGCTTGCT | 15 | 5949 | 5968 | 1528 |
| 560739 | N/A | N/A | TAAAAGGATCTATTGTAAAG | 0 | 5959 | 5978 | 1529 |
| 560740 | N/A | N/A | TTATTTAAAAGGATCTATTG | 9 | 5964 | 5983 | 1530 |
| 560741 | N/A | N/A | GGACCTTATTTAAAAGGATC | 17 | 5969 | 5988 | 1531 |
| 560742 | N/A | N/A | GATATTTCCTAGGACCTTAT | 27 | 5980 | 5999 | 1532 |
| 560743 | N/A | N/A | TGAATGATATTTCCTAGGAC | 0 | 5985 | 6004 | 1533 |
| 560744 | N/A | N/A | TGGCATGAATGATATTTCCT | 74 | 5990 | 6009 | 51 |
| 560745 | N/A | N/A | GATGCTGGCATGAATGATAT | 40 | 5995 | 6014 | 1534 |
| 560746 | N/A | N/A | TTTTTTGATGCTGGCATGAA | 38 | 6001 | 6020 | 1535 |
| 560747 | N/A | N/A | GTTAGTTTTTGATGCTGGC | 35 | 6006 | 6025 | 1536 |
| 560748 | N/A | N/A | TTAGTGTTAGTTTTTTGATG | 0 | 6011 | 6030 | 1537 |
| 560749 | N/A | N/A | GCATTATTAGTGTTAGTTTT | 50 | 6017 | 6036 | 1538 |
| 560750 | N/A | N/A | ATCTTGCATTATTAGTGTTA | 49 | 6022 | 6041 | 1539 |

TABLE 9-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 560751 | N/A | N/A | ATAATATCTTGCATTATTAG | 17 | 6027 | 6046 | 1540 |
| 560752 | N/A | N/A | CAGTAAGAAAAGCAGAATAT | 15 | 6047 | 6066 | 1541 |
| 560753 | N/A | N/A | TCATTGACAGTAAGAAAAGC | 47 | 6054 | 6073 | 1542 |
| 560754 | N/A | N/A | GATAGTTTTTCTCATTGACA | 40 | 6065 | 6084 | 1543 |
| 560755 | N/A | N/A | GTTTGCAATTTATTGAATGA | 12 | 6083 | 6102 | 1544 |
| 560756 | N/A | N/A | GTGTTGGGTTTGCAATTTAT | 55 | 6090 | 6109 | 1545 |
| 560757 | N/A | N/A | TTAAGTGTGTTGGGTTTGCA | 50 | 6096 | 6115 | 1546 |
| 560758 | N/A | N/A | TTTTATTTAAGTGTGTTGGG | 5 | 6102 | 6121 | 1547 |
| 560759 | N/A | N/A | TTTAGCAGTAACATTTTATT | 19 | 6121 | 6140 | 1548 |
| 560760 | N/A | N/A | GTTAGTTTAGCAGTAACATT | 30 | 6126 | 6145 | 1549 |
| 560761 | N/A | N/A | TCTATATATTCAGTAGTTTA | 17 | 6148 | 6167 | 1550 |
| 560762 | N/A | N/A | TTACTTTCTATATATTCAGT | 14 | 6154 | 6173 | 1551 |
| 560763 | N/A | N/A | GTTTGCTTACTTTCTATATA | 20 | 6160 | 6179 | 1552 |
| 560764 | N/A | N/A | AGTTTGTTTGCTTACTTTCT | 36 | 6165 | 6184 | 1553 |
| 560765 | N/A | N/A | TGGCAAGTTTGTTTGCTTAC | 43 | 6170 | 6189 | 1554 |
| 560766 | N/A | N/A | TTACTGTTACTGTATTTCCC | 39 | 10155 | 10174 | 1555 |
| 560767 | N/A | N/A | ATGTAGTTACTGTTACTGTA | 18 | 10161 | 10180 | 1556 |
| 560768 | N/A | N/A | ATTTAATGGGTACAGACTCG | 47 | 10182 | 10201 | 61 |
| 560769 | N/A | N/A | ATGCAATTTAATGGGTACAG | 32 | 10187 | 10206 | 1557 |
| 560770 | N/A | N/A | TAGATATGCAATTTAATGGG | 4 | 10192 | 10211 | 1558 |
| 560771 | N/A | N/A | AGGAGATAGATATGCAATTT | 5 | 10198 | 10217 | 1559 |
| 560772 | N/A | N/A | CCTAAAGGAGATAGATATGC | 36 | 10203 | 10222 | 1560 |
| 560773 | N/A | N/A | AGCCTCCTAAAGGAGATAGA | 0 | 10208 | 10227 | 1561 |
| 560774 | N/A | N/A | CACCACCAGCCTCCTAAAGG | 35 | 10215 | 10234 | 1562 |
| 560775 | N/A | N/A | ATCTAAGAAAATTAATAAAC | 17 | 7003 | 7022 | 1563 |
| 560776 | N/A | N/A | ATGATCACATCTAAGAAAAT | 8 | 7011 | 7030 | 1564 |
| 560777 | N/A | N/A | ATACCATGATCACATCTAAG | 49 | 7016 | 7035 | 62 |
| 560778 | N/A | N/A | GCAATACCATGATCACATCT | 59 | 7019 | 7038 | 52 |
| 560779 | N/A | N/A | AACTGCAATACCATGATCAC | 35 | 7023 | 7042 | 1565 |
| 560780 | N/A | N/A | TAAAACTGCAATACCATGAT | 43 | 7026 | 7045 | 1566 |
| 560781 | N/A | N/A | CTTTAAAACTGCAATACCAT | 13 | 7029 | 7048 | 1567 |
| 560782 | N/A | N/A | TCTCCTTTAAAACTGCAATA | 18 | 7033 | 7052 | 1568 |
| 560783 | N/A | N/A | TGTTCTCCTTTAAAACTGCA | 13 | 7036 | 7055 | 1569 |
| 560784 | N/A | N/A | GATTGTTCTCCTTTAAAACT | 23 | 7039 | 7058 | 1570 |
| 560785 | N/A | N/A | AGGAGATTGTTCTCCTTTAA | 14 | 7043 | 7062 | 1571 |
| 560786 | N/A | N/A | AACAGGAGATTGTTCTCCTT | 0 | 7046 | 7065 | 1572 |

TABLE 9-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 560787 | N/A | N/A | TTAAACAGGAGATTGTTCTC | 7 | 7049 | 7068 | 1573 |
| 560788 | N/A | N/A | CTCTTAAACAGGAGATTGTT | 10 | 7052 | 7071 | 1574 |
| 560789 | N/A | N/A | ACTCCGTAAATATTTCAGCA | 55 | 7077 | 7096 | 53 |
| 560790 | N/A | N/A | CTTTAACTCCGTAAATATTT | 22 | 7082 | 7101 | 1575 |
| 560791 | N/A | N/A | GACCTTTAACTCCGTAAATA | 54 | 7085 | 7104 | 63 |
| 560792 | N/A | N/A | AGTGACCTTTAACTCCGTAA | 35 | 7088 | 7107 | 1576 |
| 560793 | N/A | N/A | GGAGTCCAGTGACCTTTAAC | 15 | 7095 | 7114 | 1577 |
| 560794 | N/A | N/A | TCTGGAGTCCAGTGACCTTT | 46 | 7098 | 7117 | 64 |
| 560795 | N/A | N/A | ACCAGTCTGGAGTCCAGTGA | 8 | 7103 | 7122 | 1578 |
| 560796 | N/A | N/A | TCATCTTACCAAACTATTTT | 22 | 7169 | 7188 | 1579 |
| 560797 | N/A | N/A | GAATCATCTTACCAAACTAT | 39 | 7172 | 7191 | 1580 |
| 560798 | N/A | N/A | TAAGAATCATCTTACCAAAC | 35 | 7175 | 7194 | 1581 |
| 560799 | N/A | N/A | ATGTAAGAATCATCTTACCA | 52 | 7178 | 7197 | 65 |
| 560800 | N/A | N/A | AAGAATGTAAGAATCATCTT | 22 | 7182 | 7201 | 1582 |
| 560801 | N/A | N/A | GTTATTTAAGAATGTAAGAA | 0 | 7189 | 7208 | 1583 |
| 560802 | N/A | N/A | CGTGTTATTTAAGAATGTAA | 3 | 7192 | 7211 | 1584 |
| 560803 | N/A | N/A | AGCATTTTCTTAGATGGCG | 48 | 7210 | 7229 | 66 |
| 560804 | N/A | N/A | TAAAGCATTTTCTTAGATG | 0 | 7213 | 7232 | 1585 |
| 560805 | N/A | N/A | TGTTAAAGCATTTTCTTAG | 0 | 7216 | 7235 | 1586 |
| 560806 | N/A | N/A | TTTATGTTAAAGCATTTTTC | 20 | 7220 | 7239 | 1587 |
| 560807 | N/A | N/A | ATGTTTATGTTAAAGCATTT | 8 | 7223 | 7242 | 1588 |
| 560808 | N/A | N/A | GCATTTTTCAGTAATGTTT | 40 | 7237 | 7256 | 1589 |
| 560809 | N/A | N/A | TGTAGCATTTTTTCAGTAAT | 24 | 7241 | 7260 | 1590 |
| 560810 | N/A | N/A | CAAATGTAGCATTTTTTCAG | 0 | 7245 | 7264 | 1591 |
| 560811 | N/A | N/A | TGGCAAATGTAGCATTTTTT | 60 | 7248 | 7267 | 54 |
| 560812 | N/A | N/A | AAGTTGTGGCAAATGTAGCA | 26 | 7254 | 7273 | 1592 |
| 560813 | N/A | N/A | ATGAAGTTGTGGCAAATGTA | 11 | 7257 | 7276 | 1593 |
| 560814 | N/A | N/A | TTTATGAAGTTGTGGCAAAT | 36 | 7260 | 7279 | 1594 |
| 560815 | N/A | N/A | CATTTTATGAAGTTGTGGCA | 45 | 7263 | 7282 | 67 |
| 560816 | N/A | N/A | TGACATTTATGAAGTTGTG | 16 | 7266 | 7285 | 1595 |
| 560817 | N/A | N/A | CACTTGACATTTATGAAGT | 47 | 7270 | 7289 | 68 |
| 560818 | N/A | N/A | CTTGAGATTTCACTTGACAT | 18 | 7280 | 7299 | 1596 |
| 560819 | N/A | N/A | TTTGGAGCTTGAGATTTCAC | 0 | 7287 | 7306 | 1597 |
| 560820 | N/A | N/A | ATCTTTGGAGCTTGAGATTT | 0 | 7290 | 7309 | 1598 |
| 560821 | N/A | N/A | AATATCTTTGGAGCTTGAGA | 6 | 7293 | 7312 | 1599 |

TABLE 9-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 560822 | N/A | N/A | AATAATATCTTTGGAGCTTG | 24 | 7296 | 7315 | 1600 |
| 560823 | N/A | N/A | AGGAATAATATCTTTGGAGC | 1 | 7299 | 7318 | 1601 |
| 560824 | N/A | N/A | AATAGGAATAATATCTTTGG | 0 | 7302 | 7321 | 1602 |
| 560825 | N/A | N/A | AGTAATAGGAATAATATCTT | 0 | 7305 | 7324 | 1603 |
| 560826 | N/A | N/A | TTACATCAGATTTAGTAATA | 0 | 7318 | 7337 | 1604 |
| 560827 | N/A | N/A | AAATGTTATTACATCAGATT | 0 | 7326 | 7345 | 1605 |
| 560828 | N/A | N/A | ATAAAATGTTATTACATCAG | 12 | 7329 | 7348 | 1606 |
| 560829 | N/A | N/A | CCTAGAATCAATAAAATGTT | 13 | 7339 | 7358 | 1607 |
| 560830 | N/A | N/A | AGGAATGCCTAGAATCAATA | 9 | 7346 | 7365 | 1608 |
| 560831 | N/A | N/A | ATTCAGCAGGAATGCCTAGA | 26 | 7353 | 7372 | 1609 |
| 560832 | N/A | N/A | TACATTCAGCAGGAATGCCT | 23 | 7356 | 7375 | 1610 |
| 560833 | N/A | N/A | TTACCTGATATAACATCACA | 30 | 7456 | 7475 | 1611 |
| 560834 | N/A | N/A | GTTTTACCTGATATAACATC | 6 | 7459 | 7478 | 1612 |
| 560835 | N/A | N/A | CAGGTTTTACCTGATATAAC | 4 | 7462 | 7481 | 1613 |
| 560836 | N/A | N/A | TTAGACAGGTTTTACCTGAT | 6 | 7467 | 7486 | 1614 |
| 560837 | N/A | N/A | ATTCTCCTTAGACAGGTTTT | 6 | 7474 | 7493 | 1615 |
| 560838 | N/A | N/A | ACTGTCTATTCTCCTTAGAC | 0 | 7481 | 7500 | 1616 |
| 560839 | N/A | N/A | ACTACTGTCTATTCTCCTTA | 17 | 7484 | 7503 | 1617 |
| 560840 | N/A | N/A | ACTAACTACTGTCTATTCTC | 0 | 7488 | 7507 | 1618 |
| 560841 | N/A | N/A | TGAACTAACTACTGTCTATT | 0 | 7491 | 7510 | 1619 |
| 560842 | N/A | N/A | AGTTGAACTAACTACTGTCT | 0 | 7494 | 7513 | 1620 |
| 560844 | N/A | N/A | ATTAATTGATATGTAAAACG | 0 | 8347 | 8366 | 1621 |
| 560845 | N/A | N/A | CCAATTAATTGATATGTAAA | 15 | 8350 | 8369 | 1622 |
| 560846 | N/A | N/A | TCCTTTTAACTTCCAATTAA | 29 | 8362 | 8381 | 1623 |
| 560847 | N/A | N/A | TCCTGGTCCTTTTAACTTCC | 58 | 8368 | 8387 | 69 |
| 560848 | N/A | N/A | GTTTCCTGGTCCTTTTAACT | 0 | 8371 | 8390 | 1624 |
| 560849 | N/A | N/A | TCTGAGTTTCCTGGTCCTTT | 36 | 8376 | 8395 | 1625 |
| 560850 | N/A | N/A | ATGTCTGAGTTTCCTGGTCC | 31 | 8379 | 8398 | 1626 |
| 560851 | N/A | N/A | TGTATGTCTGAGTTTCCTGG | 0 | 8382 | 8401 | 1627 |
| 560852 | N/A | N/A | ATGTATACTGTATGTCTGAG | 19 | 8390 | 8409 | 1628 |
| 560853 | N/A | N/A | AAAATGTATACTGTATGTCT | 12 | 8393 | 8412 | 1629 |
| 560854 | N/A | N/A | TTTTAAAATGTATACTGTAT | 0 | 8397 | 8416 | 1630 |
| 560855 | N/A | N/A | CATACATTCTATATATTATA | 29 | 8432 | 8451 | 1631 |
| 560856 | N/A | N/A | AAGCCATACATTCTATATAT | 38 | 8436 | 8455 | 55 |
| 560857 | N/A | N/A | ATTATAAGCCATACATTCTA | 6 | 8441 | 8460 | 1632 |
| 560858 | N/A | N/A | TTCATTATAAGCCATACATT | 0 | 8444 | 8463 | 1633 |

TABLE 9-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 560859 | N/A | N/A | TAATTCATTATAAGCCATAC | 19 | 8447 | 8466 | 1634 |
| 560860 | N/A | N/A | TGAGTTAACTAATTCATTAT | 0 | 8456 | 8475 | 1635 |
| 560861 | N/A | N/A | TTTGCATTGAGTTAACTAAT | 26 | 8463 | 8482 | 1636 |
| 560862 | N/A | N/A | TAATTTGCATTGAGTTAACT | 0 | 8466 | 8485 | 1637 |
| 560863 | N/A | N/A | GAATAATTTGCATTGAGTTA | 0 | 8469 | 8488 | 1638 |
| 560864 | N/A | N/A | ATAGAATAATTTGCATTGAG | 0 | 8472 | 8491 | 1639 |
| 560865 | N/A | N/A | AAAATAGAATAATTTGCATT | 0 | 8475 | 8494 | 1640 |
| 560866 | N/A | N/A | TTGTAATCAAAATAGAATAA | 0 | 8483 | 8502 | 1641 |
| 560867 | N/A | N/A | TATTTGTAATCAAAATAGAA | 16 | 8486 | 8505 | 1642 |
| 560868 | N/A | N/A | TACTATTTGTAATCAAAATA | 0 | 8489 | 8508 | 1643 |
| 560869 | N/A | N/A | TTTTACTATTTGTAATCAAA | 0 | 8492 | 8511 | 1644 |
| 560870 | N/A | N/A | GCTTATTTTACTATTTGTAA | 0 | 8497 | 8516 | 1645 |
| 560871 | N/A | N/A | CTTGCTTATTTTACTATTTG | 0 | 8500 | 8519 | 1646 |
| 560872 | N/A | N/A | TTATCTTGCTTATTTTACTA | 1 | 8504 | 8523 | 1647 |
| 560873 | N/A | N/A | GTTATTTTATCTTGCTTATT | 0 | 8510 | 8529 | 1648 |
| 560874 | N/A | N/A | AAACATCTGTTATTTTATCT | 0 | 8518 | 8537 | 1649 |
| 560875 | N/A | N/A | GGATTTTAAACATCTGTTAT | 0 | 8525 | 8544 | 1650 |
| 560876 | N/A | N/A | CTTTTTGGATTTTAAACATC | 24 | 8531 | 8550 | 1651 |
| 560877 | N/A | N/A | GTGCTTTTTGGATTTTAAAC | 6 | 8534 | 8553 | 1652 |
| 560878 | N/A | N/A | TTTTGTATGTGCTTTTTGGA | 24 | 8542 | 8561 | 1653 |
| 560879 | N/A | N/A | GACATCATTCATGGATTTTT | 50 | 8558 | 8577 | 70 |
| 560880 | N/A | N/A | AGTACTTAGACATCATTCAT | 43 | 8566 | 8585 | 71 |
| 560881 | N/A | N/A | TAAGTGAGTACTTAGACATC | 17 | 8572 | 8591 | 1654 |
| 560882 | N/A | N/A | TACTTTATAAGTGAGTACTT | 0 | 8579 | 8598 | 1655 |
| 560883 | N/A | N/A | TTCTACTTTATAAGTGAGTA | 32 | 8582 | 8601 | 1656 |
| 560884 | N/A | N/A | AATGTCTTCTACTTTATAAG | 0 | 8588 | 8607 | 1657 |
| 560885 | N/A | N/A | AATAATGAATGTCTTCTACT | 9 | 8595 | 8614 | 1658 |
| 560886 | N/A | N/A | TATAATAATGAATGTCTTCT | 0 | 8598 | 8617 | 1659 |
| 560887 | N/A | N/A | TGATATAATAATGAATGTCT | 29 | 8601 | 8620 | 1660 |
| 560888 | N/A | N/A | AAAATTTGATATAATAATGA | 0 | 8607 | 8626 | 1661 |
| 560889 | N/A | N/A | CATTTAAAAATTTGATATAA | 0 | 8613 | 8632 | 1662 |
| 560890 | N/A | N/A | GTACTGAGCATTTAAAAATT | 8 | 8621 | 8640 | 1663 |
| 560891 | N/A | N/A | GGTCAAATAGTACTGAGCAT | 40 | 8630 | 8649 | 72 |
| 560892 | N/A | N/A | AATGGTCAAATAGTACTGAG | 23 | 8633 | 8652 | 1664 |
| 560893 | N/A | N/A | TTAAATGGTCAAATAGTACT | 17 | 8636 | 8655 | 1665 |

TABLE 9-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 560894 | N/A | N/A | AGTTTGAATACAAAATTTTT | 0 | 8654 | 8673 | 1666 |
| 560895 | N/A | N/A | GGTAGTTTGAATACAAAATT | 38 | 8657 | 8676 | 73 |
| 560896 | N/A | N/A | ACTGGTAGTTTGAATACAAA | 0 | 8660 | 8679 | 1667 |
| 560897 | N/A | N/A | TTCACTGGTAGTTTGAATAC | 0 | 8663 | 8682 | 1668 |
| 560898 | N/A | N/A | GCTTTCACTGGTAGTTTGAA | 25 | 8666 | 8685 | 1669 |
| 560899 | N/A | N/A | AGGGCTTTCACTGGTAGTTT | 30 | 8669 | 8688 | 1670 |
| 560900 | N/A | N/A | GGTAGGGCTTTCACTGGTAG | 9 | 8672 | 8691 | 1671 |
| 560901 | N/A | N/A | CTAGGTAGGGCTTTCACTGG | 37 | 8675 | 8694 | 1672 |
| 560902 | N/A | N/A | CTTCTAGGTAGGGCTTTCAC | 32 | 8678 | 8697 | 1673 |
| 560903 | N/A | N/A | TACCTTCTAGGTAGGGCTTT | 26 | 8681 | 8700 | 1674 |
| 560904 | N/A | N/A | GTATACCTTCTAGGTAGGGC | 0 | 8684 | 8703 | 1675 |
| 560905 | N/A | N/A | TGAGTATACCTTCTAGGTAG | 15 | 8687 | 8706 | 1676 |
| 560906 | N/A | N/A | CACTGAGTATACCTTCTAGG | 36 | 8690 | 8709 | 1677 |
| 560907 | N/A | N/A | TATCACTGAGTATACCTTCT | 0 | 8693 | 8712 | 1678 |
| 560908 | N/A | N/A | ACTTATCACTGAGTATACCT | 28 | 8696 | 8715 | 1679 |
| 560909 | N/A | N/A | ACAAAACTTATCACTGAGTA | 32 | 8701 | 8720 | 1680 |
| 560910 | N/A | N/A | GCTACAAAACTTATCACTGA | 15 | 8704 | 8723 | 1681 |
| 560911 | N/A | N/A | GGAGCTACAAAACTTATCAC | 21 | 8707 | 8726 | 1682 |
| 560912 | N/A | N/A | GATTTGGAGCTACAAAACTT | 0 | 8712 | 8731 | 1683 |
| 560913 | N/A | N/A | GAAGATTTGGAGCTACAAAA | 0 | 8715 | 8734 | 1684 |
| 560914 | N/A | N/A | CTATTAGAAGATTTGGAGCT | 0 | 8721 | 8740 | 1685 |
| 560915 | N/A | N/A | CACTCACTATTAGAAGATTT | 33 | 8727 | 8746 | 1686 |
| 560916 | N/A | N/A | TGTCAGCCTTTTATTTGGG | 0 | 8751 | 8770 | 1687 |
| 560917 | N/A | N/A | ACCTGTCAGCCTTTTATTTT | 11 | 8754 | 8773 | 1688 |
| 560918 | N/A | N/A | TCGACTTACCTGTCAGCCTT | 0 | 8761 | 8780 | 1689 |
| 560919 | N/A | N/A | TTCTCGACTTACCTGTCAGC | 0 | 8764 | 8783 | 1690 |
| 560920 | N/A | N/A | GTATTCTCGACTTACCTGTC | 0 | 8767 | 8786 | 1691 |
| 560921 | N/A | N/A | TAACATCCATATACAGTCAA | 25 | 9177 | 9196 | 1692 |
| 560922 | N/A | N/A | TATTAACATCCATATACAGT | 20 | 9180 | 9199 | 1693 |
| 560923 | N/A | N/A | ATTTATTAACATCCATATAC | 20 | 9183 | 9202 | 1694 |
| 560924 | N/A | N/A | GCTATTTATTAACATCCATA | 47 | 9186 | 9205 | 1695 |
| 560925 | N/A | N/A | TCAGCTATTTATTAACATCC | 58 | 9189 | 9208 | 56 |
| 560926 | N/A | N/A | CTGTCAGCTATTTATTAACA | 30 | 9192 | 9211 | 1696 |
| 560927 | N/A | N/A | TTACTGTCAGCTATTTATTA | 22 | 9195 | 9214 | 1697 |
| 560928 | N/A | N/A | ACTTTACTGTCAGCTATTTA | 27 | 9198 | 9217 | 1698 |
| 560929 | N/A | N/A | TAAACTTTACTGTCAGCTAT | 41 | 9201 | 9220 | 1699 |

TABLE 9-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 560930 | N/A | N/A | GGATAAACTTTACTGTCAGC | 45 | 9204 | 9223 | 1700 |
| 560931 | N/A | N/A | TATGGATAAACTTTACTGTC | 15 | 9207 | 9226 | 1701 |
| 560932 | N/A | N/A | TTATATGGATAAACTTTACT | 0 | 9210 | 9229 | 1702 |
| 560933 | N/A | N/A | TTGCAAGTCTTTATATGGAT | 47 | 9220 | 9239 | 1703 |
| 560934 | N/A | N/A | TATTTGCAAGTCTTTATATG | 26 | 9223 | 9242 | 1704 |
| 560935 | N/A | N/A | GAATATTTGCAAGTCTTTAT | 4 | 9226 | 9245 | 1705 |
| 560936 | N/A | N/A | GAGGAATATTTGCAAGTCTT | 58 | 9229 | 9248 | 57 |
| 560937 | N/A | N/A | GTAGAGGAATATTTGCAAGT | 47 | 9232 | 9251 | 1706 |
| 560938 | N/A | N/A | TTGGTAGAGGAATATTTGCA | 65 | 9235 | 9254 | 58 |
| 560939 | N/A | N/A | GTTACATTATTATAGATATT | 33 | 9269 | 9288 | 1707 |
| 560940 | N/A | N/A | TGTGTTACATTATTATAGAT | 20 | 9272 | 9291 | 1708 |
| 560941 | N/A | N/A | GAAATGTGTTACATTATTAT | 0 | 9276 | 9295 | 1709 |
| 560942 | N/A | N/A | ACCAGTGAAATGTGTTACAT | 56 | 9282 | 9301 | 59 |
| 560943 | N/A | N/A | TTCACCAGTGAAATGTGTTA | 19 | 9285 | 9304 | 1710 |
| 560944 | N/A | N/A | TGTTTCACCAGTGAAATGTG | 41 | 9288 | 9307 | 1711 |
| 560945 | N/A | N/A | ACATGTTTCACCAGTGAAAT | 0 | 9291 | 9310 | 1712 |
| 560946 | N/A | N/A | AAGACATGTTTCACCAGTGA | 48 | 9294 | 9313 | 1713 |
| 560947 | N/A | N/A | GACAAGACATGTTTCACCAG | 28 | 9297 | 9316 | 1714 |
| 560948 | N/A | N/A | TATGACAAGACATGTTTCAC | 13 | 9300 | 9319 | 1715 |
| 560949 | N/A | N/A | GCATATGACAAGACATGTTT | 12 | 9303 | 9322 | 1716 |
| 560950 | N/A | N/A | TAATGCATATGACAAGACAT | 4 | 9307 | 9326 | 1717 |
| 560951 | N/A | N/A | CTATAATGCATATGACAAGA | 22 | 9310 | 9329 | 1718 |
| 560952 | N/A | N/A | TTTCTATAATGCATATGACA | 23 | 9313 | 9332 | 1719 |
| 560953 | N/A | N/A | TCCTTTCTATAATGCATATG | 16 | 9316 | 9335 | 1720 |
| 560954 | N/A | N/A | TCTGATTATCCTTTCTATAA | 32 | 9324 | 9343 | 1721 |
| 560955 | N/A | N/A | AAGTCTGATTATCCTTTCTA | 42 | 9327 | 9346 | 1722 |
| 560956 | N/A | N/A | TGAAAGTCTGATTATCCTTT | 51 | 9330 | 9349 | 60 |
| 560957 | N/A | N/A | AACTGAAAGTCTGATTATCC | 31 | 9333 | 9352 | 1723 |
| 560958 | N/A | N/A | TATAACTGAAAGTCTGATTA | 6 | 9336 | 9355 | 1724 |
| 560959 | N/A | N/A | GTTAAAAATATTAATATAAC | 3 | 9350 | 9369 | 1725 |
| 560960 | N/A | N/A | TGTGCACAAAAATGTTAAAA | 0 | 9363 | 9382 | 1726 |
| 560961 | N/A | N/A | CTATGTGCACAAAAATGTTA | 9 | 9366 | 9385 | 1727 |
| 560962 | N/A | N/A | TAGCTATGTGCACAAAAATG | 29 | 9369 | 9388 | 1728 |
| 560963 | N/A | N/A | AGATAGCTATGTGCACAAAA | 41 | 9372 | 9391 | 1729 |
| 560964 | N/A | N/A | TGAAGATAGCTATGTGCACA | 23 | 9375 | 9394 | 1730 |

TABLE 9-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 560965 | N/A | N/A | TATTGAAGATAGCTATGTGC | 13 | 9378 | 9397 | 1731 |
| 560966 | N/A | N/A | TTTTATTGAAGATAGCTATG | 4 | 9381 | 9400 | 1732 |
| 560967 | N/A | N/A | CAATTTTATTGAAGATAGCT | 17 | 9384 | 9403 | 1733 |
| 560968 | N/A | N/A | AAACAATTTTATTGAAGATA | 27 | 9387 | 9406 | 1734 |
| 560969 | N/A | N/A | GTGTATCTTAAAATAATACC | 7 | 9412 | 9431 | 1735 |
| 560970 | N/A | N/A | TTAGTGTATCTTAAAATAAT | 25 | 9415 | 9434 | 1736 |
| 560971 | N/A | N/A | TGATCATTTTAGTGTATCTT | 34 | 9423 | 9442 | 1737 |
| 560972 | N/A | N/A | CCCTTGATCATTTTAGTGTA | 7 | 9427 | 9446 | 1738 |
| 560973 | N/A | N/A | AATCCCTTGATCATTTTAGT | 0 | 9430 | 9449 | 1739 |
| 560974 | N/A | N/A | TTGAATCCCTTGATCATTTT | 20 | 9433 | 9452 | 1740 |
| 560975 | N/A | N/A | TTAGTCTTGAATCCCTTGAT | 28 | 9439 | 9458 | 1741 |
| 560976 | N/A | N/A | TTGTTTAGTCTTGAATCCCT | 40 | 9443 | 9462 | 1742 |
| 560977 | N/A | N/A | GAGTTGTTTAGTCTTGAATC | 6 | 9446 | 9465 | 1743 |
| 560978 | N/A | N/A | ATTGAGTTGTTTAGTCTTGA | 14 | 9449 | 9468 | 1744 |
| 560979 | N/A | N/A | CTAATTGAGTTGTTTAGTCT | 0 | 9452 | 9471 | 1745 |
| 560980 | N/A | N/A | CAACTAATTGAGTTGTTTAG | 0 | 9455 | 9474 | 1746 |
| 560981 | N/A | N/A | ATTGGTGCAACTAATTGAGT | 0 | 9462 | 9481 | 1747 |
| 560982 | N/A | N/A | TTTATTGGTGCAACTAATTG | 9 | 9465 | 9484 | 1748 |
| 560983 | N/A | N/A | TTTTTTATTGGTGCAACTAA | 8 | 9468 | 9487 | 1749 |
| 560984 | N/A | N/A | TAAGTGTTTTTATTGGTGC | 20 | 9474 | 9493 | 1750 |
| 560985 | N/A | N/A | ACTGACAGTTTTTTAAGTG | 16 | 9488 | 9507 | 1751 |
| 560986 | N/A | N/A | GACACTGACAGTTTTTTAA | 6 | 9491 | 9510 | 1752 |
| 560987 | N/A | N/A | TTGGACACTGACAGTTTTTT | 0 | 9494 | 9513 | 1753 |
| 560988 | N/A | N/A | AGGTTGGACACTGACAGTTT | 6 | 9497 | 9516 | 1754 |
| 560989 | N/A | N/A | TACAGGTTGGACACTGACAG | 0 | 9500 | 9519 | 1755 |
| 544120 | 707 | 726 | AGTTCTTGGTGCTCTTGGCT | 72 | 6720 | 6739 | 15 |
| 337487 | 804 | 823 | CACTTGTATGTTCACCTCTG | 80 | 7389 | 7408 | 28 |
| 544145 | 1055 | 1074 | GTTGTCTTTCCAGTCTTCCA | 69 | 9630 | 9649 | 16 |
| 544156 | 1195 | 1214 | GCTTTGTGATCCCAAGTAGA | 61 | 9770 | 9789 | 17 |
| 544162 | 1269 | 1288 | GGTTGTTTTCTCCACACTCA | 71 | 10241 | 10260 | 18 |
| 544166 | 1353 | 1372 | ACCTTCCATTTGAGACTTC | 65 | 10325 | 10344 | 19 |
| 544199 | 1907 | 1926 | TACACATACTCTGTGCTGAC | 69 | 10879 | 10898 | 20 |

TABLE 10

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 563720 | N/A | N/A | TATATTGGATAATTTGAAAT | 7 | 11610 | 11629 | 1756 |
| 563721 | N/A | N/A | ATGTATATTGGATAATTTGA | 17 | 11613 | 11632 | 1757 |
| 563722 | N/A | N/A | GACATGTATATTGGATAATT | 20 | 11616 | 11635 | 1758 |
| 563723 | N/A | N/A | ATGACATGTATATTGGATAA | 29 | 11618 | 11637 | 1759 |
| 563724 | N/A | N/A | TATATATGACATGTATATTG | 9 | 11623 | 11642 | 1760 |
| 563725 | N/A | N/A | ATGTGACATATAAAAATATA | 4 | 11639 | 11658 | 1761 |
| 563726 | N/A | N/A | ATATGTGACATATAAAAATA | 0 | 11641 | 11660 | 1762 |
| 563727 | N/A | N/A | TTTATATATGTGACATATAA | 0 | 11646 | 11665 | 1763 |
| 563728 | N/A | N/A | CTTTTATATATGTGACATAT | 16 | 11648 | 11667 | 1764 |
| 563729 | N/A | N/A | ATCTTTTATATATGTGACAT | 13 | 11650 | 11669 | 1765 |
| 563730 | N/A | N/A | CATATCTTTTATATATGTGA | 2 | 11653 | 11672 | 1766 |
| 563731 | N/A | N/A | TCATACATATCTTTTATATA | 2 | 11658 | 11677 | 1767 |
| 563732 | N/A | N/A | TAGATCATACATATCTTTTA | 31 | 11662 | 11681 | 1768 |
| 563733 | N/A | N/A | CATAGATCATACATATCTTT | 28 | 11664 | 11683 | 1769 |
| 563734 | N/A | N/A | CACATAGATCATACATATCT | 56 | 11666 | 11685 | 1770 |
| 563735 | N/A | N/A | AGGATTCACATAGATCATAC | 56 | 11672 | 11691 | 1771 |
| 563736 | N/A | N/A | TTAGGATTCACATAGATCAT | 24 | 11674 | 11693 | 1772 |
| 563737 | N/A | N/A | ACTTAGGATTCACATAGATC | 49 | 11676 | 11695 | 1773 |
| 563738 | N/A | N/A | TTACTTAGGATTCACATAGA | 15 | 11678 | 11697 | 1774 |
| 563739 | N/A | N/A | TATTTACTTAGGATTCACAT | 6 | 11681 | 11700 | 1775 |
| 563740 | N/A | N/A | AATATTTACTTAGGATTCAC | 28 | 11683 | 11702 | 1776 |
| 563741 | N/A | N/A | TGTACTTTTCTGGAACAAAA | 63 | 11701 | 11720 | 1777 |
| 563742 | N/A | N/A | GATTATTTTTACCTTTATTA | 21 | 11724 | 11743 | 1778 |
| 563743 | N/A | N/A | TAGATTATTTTTACCTTTAT | 5 | 11726 | 11745 | 1779 |
| 563744 | N/A | N/A | ATTATAGATTATTTTTACCT | 12 | 11730 | 11749 | 1780 |
| 563745 | N/A | N/A | GAAAATTATAGATTATTTTT | 15 | 11734 | 11753 | 1781 |
| 563746 | N/A | N/A | GGTCCTGAAAATTATAGATT | 7 | 11740 | 11759 | 1782 |
| 563747 | N/A | N/A | GTGGTCCTGAAAATTATAGA | 29 | 11742 | 11761 | 1783 |
| 563748 | N/A | N/A | CTGTGGTCCTGAAAATTATA | 37 | 11744 | 11763 | 1784 |
| 563749 | N/A | N/A | GTCTGTGGTCCTGAAAATTA | 47 | 11746 | 11765 | 1785 |
| 563750 | N/A | N/A | TCGACAGCTTAGTCTGTGGT | 66 | 11757 | 11776 | 1786 |
| 563751 | N/A | N/A | TTTCGACAGCTTAGTCTGTG | 41 | 11759 | 11778 | 1787 |
| 563752 | N/A | N/A | AATTTCGACAGCTTAGTCTG | 40 | 11761 | 11780 | 1788 |
| 563753 | N/A | N/A | TTAATTTCGACAGCTTAGTC | 35 | 11763 | 11782 | 1789 |
| 563754 | N/A | N/A | CGTTAATTTCGACAGCTTAG | 50 | 11765 | 11784 | 1790 |
| 563755 | N/A | N/A | TGGCCCTAAAAAAATCAGCG | 7 | 11783 | 11802 | 1791 |

TABLE 10-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 563756 | N/A | N/A | TCTGGCCCTAAAAAATCAG | 0 | 11785 | 11804 | 1792 |
| 563757 | N/A | N/A | TGGTATTCTGGCCCTAAAAA | 37 | 11791 | 11810 | 1793 |
| 563758 | N/A | N/A | TTTGGTATTCTGGCCCTAAA | 29 | 11793 | 11812 | 1794 |
| 563759 | N/A | N/A | CCATTTTGGTATTCTGGCCC | 35 | 11797 | 11816 | 1795 |
| 563760 | N/A | N/A | GAGGAGCCATTTTGGTATTC | 34 | 11803 | 11822 | 1796 |
| 563761 | N/A | N/A | GAGAGGAGCCATTTTGGTAT | 18 | 11805 | 11824 | 1797 |
| 563762 | N/A | N/A | AAGAGAGGAGCCATTTTGGT | 17 | 11807 | 11826 | 1798 |
| 563763 | N/A | N/A | TGAAATTGTCCAATTTTGGG | 28 | 11829 | 11848 | 1799 |
| 563764 | N/A | N/A | TTTGAAATTGTCCAATTTTG | 10 | 11831 | 11850 | 1800 |
| 563765 | N/A | N/A | CATTTGAAATTGTCCAATTT | 22 | 11833 | 11852 | 1801 |
| 563766 | N/A | N/A | TGCATTTGAAATTGTCCAAT | 45 | 11835 | 11854 | 1802 |
| 563767 | N/A | N/A | ATTTTGCATTTGAAATTGTC | 35 | 11839 | 11858 | 1803 |
| 563768 | N/A | N/A | ATAATGAATTATTTTGCATT | 0 | 11849 | 11868 | 1804 |
| 563769 | N/A | N/A | TAAATAATGAATTATTTTGC | 17 | 11852 | 11871 | 1805 |
| 563770 | N/A | N/A | CTCATATATTAAATAATGAA | 0 | 11861 | 11880 | 1806 |
| 563771 | N/A | N/A | AACTCATATATTAAATAATG | 16 | 11863 | 11882 | 1807 |
| 563772 | N/A | N/A | TAGAGGAAGCAACTCATATA | 7 | 11873 | 11892 | 1808 |
| 563773 | N/A | N/A | AATAGAGGAAGCAACTCATA | 20 | 11875 | 11894 | 1809 |
| 563774 | N/A | N/A | CAAATAGAGGAAGCAACTCA | 29 | 11877 | 11896 | 1810 |
| 563775 | N/A | N/A | ACCAAATAGAGGAAGCAACT | 27 | 11879 | 11898 | 1811 |
| 563776 | N/A | N/A | AAACCAAATAGAGGAAGCAA | 22 | 11881 | 11900 | 1812 |
| 563777 | N/A | N/A | GGAAACCAAATAGAGGAAGC | 37 | 11883 | 11902 | 1813 |
| 563778 | N/A | N/A | TAAGGAAACCAAATAGAGGA | 0 | 11886 | 11905 | 1814 |
| 563779 | N/A | N/A | TTTAAGGAAACCAAATAGAG | 0 | 11888 | 11907 | 1815 |
| 563780 | N/A | N/A | TGTTTTCTTCTGGAAGCAGA | 5 | 3100 | 3119 | 1816 |
| 563781 | N/A | N/A | CTTACTTTAAGTGAAGTTAC | 0 | 3636 | 3655 | 1817 |
| 563782 | N/A | N/A | TTTTCTACTTACTTTAAGTG | 3 | 3643 | 3662 | 1818 |
| 563783 | N/A | N/A | ACATGAACCCTCTTTATTTT | 0 | 3659 | 3678 | 1819 |
| 563784 | N/A | N/A | GAAAACATAAACATGAACCC | 0 | 3669 | 3688 | 1820 |
| 563785 | N/A | N/A | AGATCCACATTGAAAACATA | 8 | 3680 | 3699 | 1821 |
| 563786 | N/A | N/A | TTAAAAGATCCACATTGAAA | 8 | 3685 | 3704 | 1822 |
| 563787 | N/A | N/A | GCCTTAGAAATATTTTTTTT | 2 | 3703 | 3722 | 1823 |
| 563788 | N/A | N/A | CAAATGGCATGCCTTAGAAA | 29 | 3713 | 3732 | 1824 |
| 563789 | N/A | N/A | TATTTCAAATGGCATGCCTT | 24 | 3718 | 3737 | 1825 |
| 563790 | N/A | N/A | CAAAGTATTTCAAATGGCAT | 8 | 3723 | 3742 | 1826 |

TABLE 10-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 563791 | N/A | N/A | TGCAACAAAGTATTTCAAAT | 0 | 3728 | 3747 | 1827 |
| 563792 | N/A | N/A | TCAACAATGCAACAAAGTAT | 3 | 3735 | 3754 | 1828 |
| 563793 | N/A | N/A | GAAAAAAAGTATTTCAACA | 4 | 3749 | 3768 | 1829 |
| 563794 | N/A | N/A | GATTATTTTCTTGGAAAAA | 11 | 3763 | 3782 | 1830 |
| 563795 | N/A | N/A | GAAATTTATTTTCTGGAGA | 10 | 3781 | 3800 | 1831 |
| 563796 | N/A | N/A | AAATTATAATAGGAAATTTT | 14 | 3793 | 3812 | 1832 |
| 563797 | N/A | N/A | CTGAATATAATGAATGAAAT | 1 | 7854 | 7873 | 1833 |
| 563798 | N/A | N/A | TACCTGAATATAATGAATGA | 4 | 7857 | 7876 | 1834 |
| 563799 | N/A | N/A | GACTACCTGAATATAATGAA | 25 | 7860 | 7879 | 1835 |
| 563800 | N/A | N/A | ATGGACTACCTGAATATAAT | 15 | 7863 | 7882 | 1836 |
| 563801 | N/A | N/A | TCCATGGACTACCTGAATAT | 39 | 7866 | 7885 | 1837 |
| 563802 | N/A | N/A | ACCATCAAGCCTCCCAAAAC | 23 | 7952 | 7971 | 1838 |
| 563803 | N/A | N/A | CCTTACCATCAAGCCTCCCA | 29 | 7956 | 7975 | 1839 |
| 563804 | N/A | N/A | AGTCCCCTTACCATCAAGCC | 31 | 7961 | 7980 | 1840 |
| 563805 | N/A | N/A | TGTAGTCCCCTTACCATCAA | 18 | 7964 | 7983 | 1841 |
| 563806 | N/A | N/A | GAATGTAGTCCCCTTACCAT | 0 | 7967 | 7986 | 1842 |
| 563807 | N/A | N/A | ATTGAATGTAGTCCCCTTAC | 12 | 7970 | 7989 | 1843 |
| 563808 | N/A | N/A | ATGATTGAATGTAGTCCCCT | 14 | 7973 | 7992 | 1844 |
| 563809 | N/A | N/A | GATTAGCAAGTGAATGAATG | 13 | 7990 | 8009 | 1845 |
| 563810 | N/A | N/A | GTAGATTAGCAAGTGAATGA | 25 | 7993 | 8012 | 1846 |
| 563811 | N/A | N/A | TTTGTAGATTAGCAAGTGAA | 9 | 7996 | 8015 | 1847 |
| 563812 | N/A | N/A | ATATTTGTAGATTAGCAAGT | 0 | 7999 | 8018 | 1848 |
| 563813 | N/A | N/A | CCATAAGAGGTTCTCAGTAA | 44 | 8019 | 8038 | 1849 |
| 563814 | N/A | N/A | GGTCCATAAGAGGTTCTCAG | 37 | 8022 | 8041 | 1850 |
| 563815 | N/A | N/A | CCTGGTCCATAAGAGGTTCT | 25 | 8025 | 8044 | 1851 |
| 563816 | N/A | N/A | TAATACCTGGTCCATAAGAG | 9 | 8030 | 8049 | 1852 |
| 563817 | N/A | N/A | TCCTAATACCTGGTCCATAA | 39 | 8033 | 8052 | 1853 |
| 563818 | N/A | N/A | TTTTCCTAATACCTGGTCCA | 43 | 8036 | 8055 | 1854 |
| 563819 | N/A | N/A | TACTTTTCCTAATACCTGGT | 43 | 8039 | 8058 | 1855 |
| 563820 | N/A | N/A | CGTTACTACTTTTCCTAATA | 47 | 8045 | 8064 | 1856 |
| 563821 | N/A | N/A | AAGGCTGAGACTGCTTCTCG | 46 | 8067 | 8086 | 1857 |
| 563822 | N/A | N/A | GATAATAAATTATATGAAGG | 5 | 8083 | 8102 | 1858 |
| 563823 | N/A | N/A | GTTTGATAATAAATTATATG | 0 | 8087 | 8106 | 1859 |
| 563824 | N/A | N/A | GTGTAATTGTTTGATAATAA | 14 | 8095 | 8114 | 1860 |
| 563825 | N/A | N/A | AATGTGTAATTGTTTGATAA | 0 | 8098 | 8117 | 1861 |
| 563826 | N/A | N/A | GTAATTTACTAACAAATGTG | 18 | 8112 | 8131 | 1862 |

TABLE 10-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 563827 | N/A | N/A | AGTGTAATTTACTAACAAAT | 0 | 8115 | 8134 | 1863 |
| 563828 | N/A | N/A | ATAAGTGTAATTTACTAACA | 0 | 8118 | 8137 | 1864 |
| 563829 | N/A | N/A | GTAATAAGTGTAATTTACTA | 0 | 8121 | 8140 | 1865 |
| 563830 | N/A | N/A | GTTGTAATAAGTGTAATTTA | 20 | 8124 | 8143 | 1866 |
| 563831 | N/A | N/A | ACAGTTGTAATAAGTGTAAT | 1 | 8127 | 8146 | 1867 |
| 563832 | N/A | N/A | ATAACAGTTGTAATAAGTGT | 4 | 8130 | 8149 | 1868 |
| 563833 | N/A | N/A | TTCAAATAATAACAGTTGTA | 0 | 8138 | 8157 | 1869 |
| 563834 | N/A | N/A | ATAATTCAAATAATAACAGT | 16 | 8142 | 8161 | 1870 |
| 563835 | N/A | N/A | AATTGTGATAAATATAATTC | 0 | 8155 | 8174 | 1871 |
| 563836 | N/A | N/A | ATGTAATTGTGATAAATATA | 0 | 8159 | 8178 | 1872 |
| 563837 | N/A | N/A | GACATGTAATTGTGATAAAT | 8 | 8162 | 8181 | 1873 |
| 563838 | N/A | N/A | ACAGACATGTAATTGTGATA | 33 | 8165 | 8184 | 1874 |
| 563839 | N/A | N/A | AGAACAGACATGTAATTGTG | 34 | 8168 | 8187 | 1875 |
| 563840 | N/A | N/A | TTAAGAACAGACATGTAATT | 0 | 8171 | 8190 | 1876 |
| 563841 | N/A | N/A | AAGTATATTTAAGAACAGAC | 0 | 8179 | 8198 | 1877 |
| 563842 | N/A | N/A | TTAAATTGTGATAAGTATAT | 1 | 8191 | 8210 | 1878 |
| 563843 | N/A | N/A | GAATTAAATTGTGATAAGTA | 0 | 8194 | 8213 | 1879 |
| 563844 | N/A | N/A | GTGGAATTAAATTGTGATAA | 0 | 8197 | 8216 | 1880 |
| 563845 | N/A | N/A | GCCGTGGAATTAAATTGTGA | 20 | 8200 | 8219 | 1881 |
| 563846 | N/A | N/A | TAAGCCGTGGAATTAAATTG | 16 | 8203 | 8222 | 1882 |
| 563847 | N/A | N/A | TTGTAAGCCGTGGAATTAAA | 28 | 8206 | 8225 | 1883 |
| 563848 | N/A | N/A | TCATTGTAAGCCGTGGAATT | 25 | 8209 | 8228 | 1884 |
| 563849 | N/A | N/A | TGATCATTGTAAGCCGTGGA | 49 | 8212 | 8231 | 1885 |
| 563850 | N/A | N/A | TATAGTTATGATCATTGTAA | 0 | 8220 | 8239 | 1886 |
| 563851 | N/A | N/A | AATTATAGTTATGATCATTG | 0 | 8223 | 8242 | 1887 |
| 563852 | N/A | N/A | CTTTAATAATTATAGTTATG | 0 | 8230 | 8249 | 1888 |
| 563853 | N/A | N/A | TGTCTTTAATAATTATAGTT | 4 | 8233 | 8252 | 1889 |
| 563854 | N/A | N/A | AATTGTCTTTAATAATTATA | 0 | 8236 | 8255 | 1890 |
| 563855 | N/A | N/A | TCAAAATTGTCTTTAATAAT | 7 | 8240 | 8259 | 1891 |
| 563856 | N/A | N/A | ATTTAATCAAAATTGTCTTT | 0 | 8246 | 8265 | 1892 |
| 563857 | N/A | N/A | TAACATTTAATCAAAATTGT | 0 | 8250 | 8269 | 1893 |
| 563858 | N/A | N/A | ACATAACATTTAATCAAAAT | 0 | 8253 | 8272 | 1894 |
| 563859 | N/A | N/A | ATGACATAACATTTAATCAA | 13 | 8256 | 8275 | 1895 |
| 563860 | N/A | N/A | TACTTATGACATAACATTTA | 0 | 8261 | 8280 | 1896 |
| 563861 | N/A | N/A | TTACTACTTATGACATAACA | 0 | 8265 | 8284 | 1897 |

TABLE 10-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 563862 | N/A | N/A | AACAGTTACTACTTATGACA | 31 | 8270 | 8289 | 1898 |
| 563863 | N/A | N/A | TGTAACAGTTACTACTTATG | 29 | 8273 | 8292 | 1899 |
| 563864 | N/A | N/A | CTTATTTGTAACAGTTACTA | 0 | 8279 | 8298 | 1900 |
| 563865 | N/A | N/A | TTTCACAGCTTATTTGTAAC | 29 | 8287 | 8306 | 1901 |
| 563866 | N/A | N/A | TCTTTTCACAGCTTATTTGT | 22 | 8290 | 8309 | 1902 |
| 563867 | N/A | N/A | GGTTCTTTTCACAGCTTATT | 66 | 8293 | 8312 | 1903 |
| 563868 | N/A | N/A | CTAGGAGTGGTTCTTTTCAC | 37 | 8301 | 8320 | 1904 |
| 563869 | N/A | N/A | ATGCTAGGAGTGGTTCTTTT | 20 | 8304 | 8323 | 1905 |
| 563870 | N/A | N/A | CTAATGCTAGGAGTGGTTCT | 30 | 8307 | 8326 | 1906 |
| 563871 | N/A | N/A | AGAGTGACTAATGCTAGGAG | 41 | 8314 | 8333 | 1907 |
| 563872 | N/A | N/A | AGAGAATAGAGTGACTAATG | 28 | 8321 | 8340 | 1908 |
| 563873 | N/A | N/A | TTAATGAGAGAATAGAGTGA | 4 | 8327 | 8346 | 1909 |
| 563496 | 608 | 627 | CTGTTGGTTTAATTGTTTAT | 33 | 4346 | 4365 | 1910 |
| 563497 | 610 | 629 | TGCTGTTGGTTTAATTGTTT | 29 | 4348 | 4367 | 1911 |
| 563498 | 612 | 631 | TATGCTGTTGGTTTAATTGT | 27 | 4350 | 4369 | 1912 |
| 563499 | 614 | 633 | ACTATGCTGTTGGTTTAATT | 24 | 4352 | 4371 | 1913 |
| 563500 | 616 | 635 | TGACTATGCTGTTGGTTTAA | 68 | 4354 | 4373 | 1914 |
| 563501 | 619 | 638 | ATTTGACTATGCTGTTGGTT | 45 | 4357 | 4376 | 1915 |
| 563502 | 621 | 640 | TTATTTGACTATGCTGTTGG | 39 | 4359 | 4378 | 1916 |
| 563503 | 623 | 642 | TTTTATTTGACTATGCTGTT | 33 | 4361 | 4380 | 1917 |
| 563504 | 625 | 644 | TCTTTTATTTGACTATGCTG | 55 | 4363 | 4382 | 1918 |
| 563505 | 627 | 646 | TTTCTTTTATTTGACTATGC | 29 | 4365 | 4384 | 1919 |
| 563506 | 646 | 665 | CTTCTGAGCTGATTTTCTAT | 40 | N/A | N/A | 1920 |
| 563507 | 648 | 667 | TCCTTCTGAGCTGATTTTCT | 76 | N/A | N/A | 1921 |
| 563508 | 650 | 669 | AGTCCTTCTGAGCTGATTTT | 37 | N/A | N/A | 1922 |
| 563509 | 652 | 671 | CTAGTCCTTCTGAGCTGATT | 52 | N/A | N/A | 1923 |
| 563510 | 654 | 673 | TACTAGTCCTTCTGAGCTGA | 52 | 6667 | 6686 | 1924 |
| 563511 | 656 | 675 | AATACTAGTCCTTCTGAGCT | 41 | 6669 | 6688 | 1925 |
| 563512 | 658 | 677 | TGAATACTAGTCCTTCTGAG | 55 | 6671 | 6690 | 1926 |
| 563513 | 660 | 679 | CTTGAATACTAGTCCTTCTG | 43 | 6673 | 6692 | 1927 |
| 563514 | 662 | 681 | TTCTTGAATACTAGTCCTTC | 34 | 6675 | 6694 | 1928 |
| 563515 | 666 | 685 | TGGGTTCTTGAATACTAGTC | 52 | 6679 | 6698 | 1929 |
| 563516 | 668 | 687 | TGTGGGTTCTTGAATACTAG | 34 | 6681 | 6700 | 1930 |
| 563517 | 670 | 689 | TCTGTGGGTTCTTGAATACT | 43 | 6683 | 6702 | 1931 |
| 563518 | 680 | 699 | TAGAGAAATTTCTGTGGGTT | 0 | 6693 | 6712 | 1932 |
| 563519 | 684 | 703 | AAGATAGAGAAATTTCTGTG | 4 | 6697 | 6716 | 1933 |

TABLE 10-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 563520 | 686 | 705 | GGAAGATAGAGAAATTTCTG | 0 | 6699 | 6718 | 1934 |
| 563521 | 694 | 713 | CTTGGCTTGGAAGATAGAGA | 29 | 6707 | 6726 | 1935 |
| 563522 | 696 | 715 | CTCTTGGCTTGGAAGATAGA | 51 | 6709 | 6728 | 1936 |
| 563523 | 705 | 724 | TTCTTGGTGCTCTTGGCTTG | 63 | 6718 | 6737 | 75 |
| 544120 | 707 | 726 | AGTTCTTGGTGCTCTTGGCT | 86 | 6720 | 6739 | 15 |
| 563524 | 715 | 734 | AAGGGAGTAGTTCTTGGTGC | 44 | 6728 | 6747 | 1937 |
| 563525 | 716 | 735 | AAAGGGAGTAGTTCTTGGTG | 14 | 6729 | 6748 | 1938 |
| 563526 | 717 | 736 | GAAAGGGAGTAGTTCTTGGT | 33 | 6730 | 6749 | 1939 |
| 563527 | 718 | 737 | AGAAAGGGAGTAGTTCTTGG | 0 | 6731 | 6750 | 1940 |
| 563528 | 719 | 738 | AAGAAAGGGAGTAGTTCTTG | 0 | 6732 | 6751 | 1941 |
| 563529 | 720 | 739 | GAAGAAAGGGAGTAGTTCTT | 0 | 6733 | 6752 | 1942 |
| 563530 | 726 | 745 | TCAACTGAAGAAAGGGAGTA | 0 | 6739 | 6758 | 1943 |
| 337481 | 728 | 747 | ATTCAACTGAAGAAAGGGAG | 23 | 6741 | 6760 | 1944 |
| 563531 | 729 | 748 | CATTCAACTGAAGAAAGGGA | 16 | 6742 | 6761 | 1945 |
| 563532 | 730 | 749 | TCATTCAACTGAAGAAAGGG | 23 | 6743 | 6762 | 1946 |
| 563533 | 732 | 751 | TTTCATTCAACTGAAGAAAG | 8 | 6745 | 6764 | 1947 |
| 563534 | 733 | 752 | ATTTCATTCAACTGAAGAAA | 6 | 6746 | 6765 | 1948 |
| 563535 | 734 | 753 | TATTTCATTCAACTGAAGAA | 0 | 6747 | 6766 | 1949 |
| 563536 | 735 | 754 | TTATTTCATTCAACTGAAGA | 0 | 6748 | 6767 | 1950 |
| 563537 | 736 | 755 | CTTATTTCATTCAACTGAAG | 11 | 6749 | 6768 | 1951 |
| 337482 | 737 | 756 | TCTTATTTCATTCAACTGAA | 26 | 6750 | 6769 | 1952 |
| 563538 | 738 | 757 | TTCTTATTTCATTCAACTGA | 17 | 6751 | 6770 | 1953 |
| 563539 | 740 | 759 | ATTTCTTATTTCATTCAACT | 18 | 6753 | 6772 | 1954 |
| 563540 | 743 | 762 | TACATTTCTTATTTCATTCA | 20 | 6756 | 6775 | 1955 |
| 563541 | 767 | 786 | TTCAGCAGGAATGCCATCAT | 34 | N/A | N/A | 1956 |
| 563542 | 768 | 787 | ATTCAGCAGGAATGCCATCA | 2 | N/A | N/A | 1957 |
| 563543 | 769 | 788 | CATTCAGCAGGAATGCCATC | 21 | N/A | N/A | 1958 |
| 563544 | 770 | 789 | ACATTCAGCAGGAATGCCAT | 5 | N/A | N/A | 1959 |
| 563545 | 771 | 790 | TACATTCAGCAGGAATGCCA | 37 | N/A | N/A | 1960 |
| 563546 | 772 | 791 | GTACATTCAGCAGGAATGCC | 50 | 7357 | 7376 | 1961 |
| 563547 | 773 | 792 | GGTACATTCAGCAGGAATGC | 64 | 7358 | 7377 | 76 |
| 563548 | 774 | 793 | TGGTACATTCAGCAGGAATG | 42 | 7359 | 7378 | 1962 |
| 563549 | 775 | 794 | GTGGTACATTCAGCAGGAAT | 51 | 7360 | 7379 | 1963 |
| 563550 | 776 | 795 | GGTGGTACATTCAGCAGGAA | 24 | 7361 | 7380 | 1964 |
| 563551 | 777 | 796 | TGGTGGTACATTCAGCAGGA | 47 | 7362 | 7381 | 1965 |

TABLE 10-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 563552 | 778 | 797 | ATGGTGGTACATTCAGCAGG | 0 | 7363 | 7382 | 1966 |
| 563553 | 779 | 798 | AATGGTGGTACATTCAGCAG | 15 | 7364 | 7383 | 1967 |
| 563554 | 780 | 799 | AAATGGTGGTACATTCAGCA | 32 | 7365 | 7384 | 1968 |
| 563555 | 781 | 800 | TAAATGGTGGTACATTCAGC | 29 | 7366 | 7385 | 1969 |
| 563556 | 783 | 802 | TATAAATGGTGGTACATTCA | 33 | 7368 | 7387 | 1970 |
| 563557 | 784 | 803 | TTATAAATGGTGGTACATTC | 1 | 7369 | 7388 | 1971 |
| 563558 | 785 | 804 | GTTATAAATGGTGGTACATT | 4 | 7370 | 7389 | 1972 |
| 563559 | 786 | 805 | TGTTATAAATGGTGGTACAT | 0 | 7371 | 7390 | 1973 |
| 563560 | 787 | 806 | CTGTTATAAATGGTGGTACA | 4 | 7372 | 7391 | 1974 |
| 563561 | 788 | 807 | TCTGTTATAAATGGTGGTAC | 29 | 7373 | 7392 | 1975 |
| 337484 | 789 | 808 | CTCTGTTATAAATGGTGGTA | 62 | 7374 | 7393 | 74 |
| 563562 | 792 | 811 | CACCTCTGTTATAAATGGTG | 22 | 7377 | 7396 | 1976 |
| 563563 | 793 | 812 | TCACCTCTGTTATAAATGGT | 38 | 7378 | 7397 | 1977 |
| 337485 | 794 | 813 | TTCACCTCTGTTATAAATGG | 18 | 7379 | 7398 | 1978 |
| 563564 | 795 | 814 | GTTCACCTCTGTTATAAATG | 52 | 7380 | 7399 | 1979 |
| 563565 | 797 | 816 | ATGTTCACCTCTGTTATAAA | 24 | 7382 | 7401 | 1980 |
| 563566 | 798 | 817 | TATGTTCACCTCTGTTATAA | 2 | 7383 | 7402 | 1981 |
| 337486 | 799 | 818 | GTATGTTCACCTCTGTTATA | 32 | 7384 | 7403 | 1982 |
| 563567 | 800 | 819 | TGTATGTTCACCTCTGTTAT | 38 | 7385 | 7404 | 1983 |
| 337487 | 804 | 823 | CACTTGTATGTTCACCTCTG | 87 | 7389 | 7408 | 28 |
| 563568 | 1128 | 1147 | TAATCGCAACTAGATGTAGC | 39 | 9703 | 9722 | 1984 |
| 563569 | 1129 | 1148 | GTAATCGCAACTAGATGTAG | 26 | 9704 | 9723 | 1985 |
| 563570 | 1130 | 1149 | AGTAATCGCAACTAGATGTA | 17 | 9705 | 9724 | 1986 |
| 563571 | 1131 | 1150 | CAGTAATCGCAACTAGATGT | 43 | 9706 | 9725 | 1987 |
| 563572 | 1132 | 1151 | CCAGTAATCGCAACTAGATG | 39 | 9707 | 9726 | 1988 |
| 563573 | 1133 | 1152 | GCCAGTAATCGCAACTAGAT | 59 | 9708 | 9727 | 1989 |
| 563574 | 1134 | 1153 | TGCCAGTAATCGCAACTAGA | 57 | 9709 | 9728 | 1990 |
| 563575 | 1135 | 1154 | TTGCCAGTAATCGCAACTAG | 54 | 9710 | 9729 | 1991 |
| 563576 | 1136 | 1155 | ATTGCCAGTAATCGCAACTA | 43 | 9711 | 9730 | 1992 |
| 563577 | 1137 | 1156 | CATTGCCAGTAATCGCAACT | 49 | 9712 | 9731 | 1993 |
| 563578 | 1138 | 1157 | ACATTGCCAGTAATCGCAAC | 59 | 9713 | 9732 | 1994 |
| 563579 | 1139 | 1158 | GACATTGCCAGTAATCGCAA | 64 | 9714 | 9733 | 1995 |
| 563580 | 1140 | 1159 | GGACATTGCCAGTAATCGCA | 79 | 9715 | 9734 | 77 |
| 563581 | 1141 | 1160 | GGGACATTGCCAGTAATCGC | 47 | 9716 | 9735 | 1996 |
| 563582 | 1162 | 1181 | TTGTTTTCCGGGATTGCATT | 20 | 9737 | 9756 | 1997 |
| 563583 | 1163 | 1182 | TTTGTTTTCCGGGATTGCAT | 31 | 9738 | 9757 | 1998 |

TABLE 10-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 563584 | 1167 | 1186 | AATCTTTGTTTTCCGGGATT | 14 | 9742 | 9761 | 1999 |
| 563585 | 1168 | 1187 | AAATCTTTGTTTTCCGGGAT | 54 | 9743 | 9762 | 2000 |
| 563586 | 1175 | 1194 | AAACACCAAATCTTTGTTTT | 32 | 9750 | 9769 | 2001 |
| 563587 | 1176 | 1195 | AAAACACCAAATCTTTGTTT | 7 | 9751 | 9770 | 2002 |
| 563588 | 1180 | 1199 | GTAGAAAACACCAAATCTTT | 18 | 9755 | 9774 | 2003 |
| 563589 | 1181 | 1200 | AGTAGAAAACACCAAATCTT | 0 | 9756 | 9775 | 2004 |
| 563590 | 1185 | 1204 | CCCAAGTAGAAAACACCAAA | 26 | 9760 | 9779 | 2005 |
| 563591 | 1186 | 1205 | TCCCAAGTAGAAAACACCAA | 27 | 9761 | 9780 | 2006 |
| 563592 | 1190 | 1209 | GTGATCCCAAGTAGAAAACA | 26 | 9765 | 9784 | 2007 |
| 563593 | 1191 | 1210 | TGTGATCCCAAGTAGAAAAC | 28 | 9766 | 9785 | 2008 |
| 563594 | 1192 | 1211 | TTGTGATCCCAAGTAGAAAA | 12 | 9767 | 9786 | 2009 |
| 563595 | 1193 | 1212 | TTTGTGATCCCAAGTAGAAA | 14 | 9768 | 9787 | 2010 |
| 563596 | 1200 | 1219 | CTTTTGCTTTGTGATCCCAA | 64 | 9775 | 9794 | 2011 |
| 563597 | 1204 | 1223 | TGTCCTTTTGCTTTGTGATC | 24 | 9779 | 9798 | 2012 |
| 563598 | 1205 | 1224 | GTGTCCTTTTGCTTTGTGAT | 31 | 9780 | 9799 | 2013 |
| 563599 | 1206 | 1225 | AGTGTCCTTTTGCTTTGTGA | 41 | 9781 | 9800 | 2014 |
| 563600 | 1210 | 1229 | TTGAAGTGTCCTTTTGCTTT | 21 | 9785 | 9804 | 2015 |
| 563601 | 1211 | 1230 | GTTGAAGTGTCCTTTTGCTT | 35 | 9786 | 9805 | 2016 |
| 563602 | 1212 | 1231 | AGTTGAAGTGTCCTTTTGCT | 27 | 9787 | 9806 | 2017 |
| 563603 | 1213 | 1232 | CAGTTGAAGTGTCCTTTTGC | 17 | 9788 | 9807 | 2018 |
| 563604 | 1214 | 1233 | ACAGTTGAAGTGTCCTTTTG | 0 | 9789 | 9808 | 2019 |
| 563605 | 1215 | 1234 | GACAGTTGAAGTGTCCTTTT | 19 | 9790 | 9809 | 2020 |
| 563606 | 1216 | 1235 | GGACAGTTGAAGTGTCCTTT | 34 | 9791 | 9810 | 2021 |
| 563607 | 1217 | 1236 | TGGACAGTTGAAGTGTCCTT | 12 | 9792 | 9811 | 2022 |
| 563608 | 1218 | 1237 | CTGGACAGTTGAAGTGTCCT | 39 | 9793 | 9812 | 2023 |
| 563609 | 1219 | 1238 | TCTGGACAGTTGAAGTGTCC | 10 | 9794 | 9813 | 2024 |
| 563610 | 1220 | 1239 | CTCTGGACAGTTGAAGTGTC | 6 | 9795 | 9814 | 2025 |
| 563611 | 1221 | 1240 | CCTCTGGACAGTTGAAGTGT | 24 | 9796 | 9815 | 2026 |
| 563612 | 1222 | 1241 | CCCTCTGGACAGTTGAAGTG | 24 | 9797 | 9816 | 2027 |
| 563613 | 1223 | 1242 | ACCCTCTGGACAGTTGAAGT | 31 | 9798 | 9817 | 2028 |
| 563614 | 1224 | 1243 | AACCCTCTGGACAGTTGAAG | 34 | 9799 | 9818 | 2029 |
| 563615 | 1225 | 1244 | TAACCCTCTGGACAGTTGAA | 34 | 9800 | 9819 | 2030 |
| 563616 | 1226 | 1245 | ATAACCCTCTGGACAGTTGA | 31 | 9801 | 9820 | 2031 |
| 563617 | 1227 | 1246 | AATAACCCTCTGGACAGTTG | 22 | 9802 | 9821 | 2032 |
| 563618 | 1228 | 1247 | GAATAACCCTCTGGACAGTT | 25 | 9803 | 9822 | 2033 |

TABLE 10-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 563619 | 1229 | 1248 | TGAATAACCCTCTGGACAGT | 18 | 9804 | 9823 | 2034 |
| 563620 | 1230 | 1249 | CTGAATAACCCTCTGGACAG | 24 | 9805 | 9824 | 2035 |
| 563621 | 1231 | 1250 | CCTGAATAACCCTCTGGACA | 39 | 9806 | 9825 | 2036 |
| 563622 | 1232 | 1251 | TCCTGAATAACCCTCTGGAC | 31 | N/A | N/A | 2037 |
| 563623 | 1233 | 1252 | CTCCTGAATAACCCTCTGGA | 15 | N/A | N/A | 2038 |
| 563624 | 1234 | 1253 | CCTCCTGAATAACCCTCTGG | 27 | N/A | N/A | 2039 |
| 563625 | 1235 | 1254 | GCCTCCTGAATAACCCTCTG | 25 | N/A | N/A | 2040 |
| 563626 | 1236 | 1255 | AGCCTCCTGAATAACCCTCT | 32 | N/A | N/A | 2041 |
| 563627 | 1237 | 1256 | CAGCCTCCTGAATAACCCTC | 44 | N/A | N/A | 2042 |
| 563628 | 1238 | 1257 | CCAGCCTCCTGAATAACCCT | 26 | N/A | N/A | 2043 |
| 563629 | 1239 | 1258 | ACCAGCCTCCTGAATAACCC | 23 | N/A | N/A | 2044 |
| 337503 | 1240 | 1259 | CACCAGCCTCCTGAATAACC | 25 | N/A | N/A | 2045 |
| 563630 | 1241 | 1260 | CCACCAGCCTCCTGAATAAC | 26 | N/A | N/A | 2046 |
| 563631 | 1242 | 1261 | ACCACCAGCCTCCTGAATAA | 25 | N/A | N/A | 2047 |
| 563632 | 1243 | 1262 | CACCACCAGCCTCCTGAATA | 33 | N/A | N/A | 2048 |
| 563633 | 1244 | 1263 | CCACCACCAGCCTCCTGAAT | 45 | N/A | N/A | 2049 |
| 563634 | 1248 | 1267 | CATGCCACCACCAGCCTCCT | 54 | 10220 | 10239 | 2050 |
| 563635 | 1250 | 1269 | ATCATGCCACCACCAGCCTC | 58 | 10222 | 10241 | 2051 |
| 563636 | 1251 | 1270 | CATCATGCCACCACCAGCCT | 61 | 10223 | 10242 | 2052 |
| 563637 | 1255 | 1274 | CACTCATCATGCCACCACCA | 68 | 10227 | 10246 | 78 |
| 563638 | 1256 | 1275 | ACACTCATCATGCCACCACC | 65 | 10228 | 10247 | 2053 |
| 563639 | 1260 | 1279 | CTCCACACTCATCATGCCAC | 76 | 10232 | 10251 | 79 |
| 563640 | 1262 | 1281 | TTCTCCACACTCATCATGCC | 55 | 10234 | 10253 | 2054 |
| 563641 | 1263 | 1282 | TTTCTCCACACTCATCATGC | 63 | 10235 | 10254 | 80 |
| 563642 | 1264 | 1283 | TTTTCTCCACACTCATCATG | 24 | 10236 | 10255 | 2055 |
| 563643 | 1265 | 1284 | GTTTTCTCCACACTCATCAT | 53 | 10237 | 10256 | 2056 |
| 563644 | 1857 | 1876 | ATTTAAGAACTGTACAATTA | 7 | 10829 | 10848 | 2057 |
| 563645 | 1858 | 1877 | CATTTAAGAACTGTACAATT | 15 | 10830 | 10849 | 2058 |
| 563646 | 1859 | 1878 | ACATTTAAGAACTGTACAAT | 4 | 10831 | 10850 | 2059 |
| 563647 | 1860 | 1879 | AACATTTAAGAACTGTACAA | 4 | 10832 | 10851 | 2060 |
| 563648 | 1861 | 1880 | CAACATTTAAGAACTGTACA | 4 | 10833 | 10852 | 2061 |
| 563649 | 1862 | 1881 | ACAACATTTAAGAACTGTAC | 22 | 10834 | 10853 | 2062 |
| 563650 | 1863 | 1882 | TACAACATTTAAGAACTGTA | 21 | 10835 | 10854 | 2063 |
| 563651 | 1864 | 1883 | CTACAACATTTAAGAACTGT | 44 | 10836 | 10855 | 2064 |
| 563652 | 1865 | 1884 | ACTACAACATTTAAGAACTG | 20 | 10837 | 10856 | 2065 |
| 563653 | 1866 | 1885 | TACTACAACATTTAAGAACT | 15 | 10838 | 10857 | 2066 |

TABLE 10-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 563654 | 1867 | 1886 | ATACTACAACATTTAAGAAC | 17 | 10839 | 10858 | 2067 |
| 563655 | 1868 | 1887 | AATACTACAACATTTAAGAA | 11 | 10840 | 10859 | 2068 |
| 563656 | 1869 | 1888 | TAATACTACAACATTTAAGA | 9 | 10841 | 10860 | 2069 |
| 563657 | 1870 | 1889 | TTAATACTACAACATTTAAG | 3 | 10842 | 10861 | 2070 |
| 563658 | 1874 | 1893 | GAAATTAATACTACAACATT | 0 | 10846 | 10865 | 2071 |
| 563659 | 1878 | 1897 | TTTTGAAATTAATACTACAA | 0 | 10850 | 10869 | 2072 |
| 563660 | 1879 | 1898 | GTTTTGAAATTAATACTACA | 15 | 10851 | 10870 | 2073 |
| 563661 | 1880 | 1899 | AGTTTTGAAATTAATACTAC | 2 | 10852 | 10871 | 2074 |
| 563662 | 1881 | 1900 | TAGTTTTGAAATTAATACTA | 14 | 10853 | 10872 | 2075 |
| 563663 | 1882 | 1901 | TTAGTTTTGAAATTAATACT | 8 | 10854 | 10873 | 2076 |
| 563664 | 1888 | 1907 | CGATTTTTAGTTTTGAAATT | 0 | 10860 | 10879 | 2077 |
| 563665 | 1889 | 1908 | ACGATTTTTAGTTTTGAAAT | 0 | 10861 | 10880 | 2078 |
| 563666 | 1890 | 1909 | GACGATTTTTAGTTTTGAAA | 20 | 10862 | 10881 | 2079 |
| 563667 | 1891 | 1910 | TGACGATTTTTAGTTTTGAA | 17 | 10863 | 10882 | 2080 |
| 563668 | 1892 | 1911 | CTGACGATTTTTAGTTTTGA | 64 | 10864 | 10883 | 2081 |
| 563669 | 1893 | 1912 | GCTGACGATTTTTAGTTTTG | 66 | 10865 | 10884 | 81 |
| 563670 | 1894 | 1913 | TGCTGACGATTTTTAGTTTT | 45 | 10866 | 10885 | 2082 |
| 563671 | 1895 | 1914 | GTGCTGACGATTTTTAGTTT | 42 | 10867 | 10886 | 2083 |
| 563672 | 1896 | 1915 | TGTGCTGACGATTTTTAGTT | 50 | 10868 | 10887 | 2084 |
| 563673 | 1897 | 1916 | CTGTGCTGACGATTTTTAGT | 55 | 10869 | 10888 | 2085 |
| 563674 | 1898 | 1917 | TCTGTGCTGACGATTTTTAG | 53 | 10870 | 10889 | 2086 |
| 563675 | 1899 | 1918 | CTCTGTGCTGACGATTTTTA | 49 | 10871 | 10890 | 2087 |
| 563676 | 1900 | 1919 | ACTCTGTGCTGACGATTTTT | 22 | 10872 | 10891 | 2088 |
| 563677 | 1901 | 1920 | TACTCTGTGCTGACGATTTT | 8 | 10873 | 10892 | 2089 |
| 563678 | 1902 | 1921 | ATACTCTGTGCTGACGATTT | 61 | 10874 | 10893 | 2090 |
| 563679 | 1903 | 1922 | CATACTCTGTGCTGACGATT | 68 | 10875 | 10894 | 2091 |
| 563680 | 1904 | 1923 | ACATACTCTGTGCTGACGAT | 4 | 10876 | 10895 | 2092 |
| 563681 | 1905 | 1924 | CACATACTCTGTGCTGACGA | 73 | 10877 | 10896 | 82 |
| 563682 | 1909 | 1928 | TTTACACATACTCTGTGCTG | 67 | 10881 | 10900 | 83 |
| 563683 | 1911 | 1930 | TTTTTACACATACTCTGTGC | 58 | 10883 | 10902 | 2093 |
| 563684 | 1915 | 1934 | CAGATTTTTACACATACTCT | 54 | 10887 | 10906 | 2094 |
| 563685 | 1916 | 1935 | ACAGATTTTTACACATACTC | 52 | 10888 | 10907 | 2095 |
| 563686 | 1917 | 1936 | TACAGATTTTTACACATACT | 40 | 10889 | 10908 | 2096 |
| 563687 | 1918 | 1937 | TTACAGATTTTTACACATAC | 22 | 10890 | 10909 | 2097 |
| 337528 | 1920 | 1939 | TATTACAGATTTTTACACAT | 4 | 6720 | 6739 | 2098 |

TABLE 10-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 563688 | 1922 | 1941 | TGTATTACAGATTTTTACAC | 0 | 10894 | 10913 | 2099 |
| 563689 | 1935 | 1954 | CAGTTTAAAAATTTGTATTA | 8 | 10907 | 10926 | 2100 |
| 563690 | 1938 | 1957 | CATCAGTTTAAAAATTTGTA | 18 | 10910 | 10929 | 2101 |
| 563691 | 1941 | 1960 | AAGCATCAGTTTAAAAATTT | 16 | 10913 | 10932 | 2102 |
| 563692 | 1942 | 1961 | GAAGCATCAGTTTAAAAATT | 16 | 10914 | 10933 | 2103 |
| 563693 | 1951 | 1970 | TAGCAAAATGAAGCATCAGT | 40 | 10923 | 10942 | 2104 |
| 563694 | 1952 | 1971 | GTAGCAAAATGAAGCATCAG | 42 | 10924 | 10943 | 2105 |
| 563695 | 1953 | 1972 | TGTAGCAAAATGAAGCATCA | 44 | 10925 | 10944 | 2106 |
| 563696 | 1954 | 1973 | TTGTAGCAAAATGAAGCATC | 48 | 10926 | 10945 | 2107 |
| 563697 | 1955 | 1974 | TTTGTAGCAAAATGAAGCAT | 19 | 10927 | 10946 | 2108 |
| 563698 | 1974 | 1993 | AACATTTACTCCAAATTATT | 27 | 10946 | 10965 | 2109 |
| 563699 | 1976 | 1995 | CAAACATTTACTCCAAATTA | 23 | 10948 | 10967 | 2110 |
| 563700 | 1978 | 1997 | ATCAAACATTTACTCCAAAT | 24 | 10950 | 10969 | 2111 |
| 563701 | 1981 | 2000 | CATATCAAACATTTACTCCA | 61 | 10953 | 10972 | 2112 |
| 563702 | 1982 | 2001 | TCATATCAAACATTTACTCC | 50 | 10954 | 10973 | 2113 |
| 563703 | 1983 | 2002 | ATCATATCAAACATTTACTC | 31 | 10955 | 10974 | 2114 |
| 563704 | 1990 | 2009 | TAAATAAATCATATCAAACA | 10 | 10962 | 10981 | 2115 |
| 563705 | 1993 | 2012 | TCATAAATAAATCATATCAA | 20 | 10965 | 10984 | 2116 |
| 563706 | 1994 | 2013 | TTCATAAATAAATCATATCA | 11 | 10966 | 10985 | 2117 |
| 563707 | 1995 | 2014 | TTTCATAAATAAATCATATC | 5 | 10967 | 10986 | 2118 |
| 563708 | 1996 | 2015 | GTTTCATAAATAAATCATAT | 0 | 10968 | 10987 | 2119 |
| 563709 | 1997 | 2016 | GGTTTCATAAATAAATCATA | 8 | 10969 | 10988 | 2120 |
| 563710 | 1998 | 2017 | AGGTTTCATAAATAAATCAT | 15 | 10970 | 10989 | 2121 |
| 563711 | 1999 | 2018 | TAGGTTTCATAAATAAATCA | 19 | 10971 | 10990 | 2122 |
| 563712 | 2001 | 2020 | ATTAGGTTTCATAAATAAAT | 12 | 10973 | 10992 | 2123 |
| 563713 | 2002 | 2021 | CATTAGGTTTCATAAATAAA | 2 | 10974 | 10993 | 2124 |
| 563714 | 2003 | 2022 | TCATTAGGTTTCATAAATAA | 7 | 10975 | 10994 | 2125 |
| 563715 | 2004 | 2023 | TTCATTAGGTTTCATAAATA | 11 | 10976 | 10995 | 2126 |
| 563716 | 2005 | 2024 | CTTCATTAGGTTTCATAAAT | 15 | 10977 | 10996 | 2127 |
| 563717 | 2006 | 2025 | GCTTCATTAGGTTTCATAAA | 49 | 10978 | 10997 | 2128 |
| 563718 | 2010 | 2029 | TTCTGCTTCATTAGGTTTCA | 57 | 10982 | 11001 | 2129 |
| 563719 | 2013 | 2032 | TAATTCTGCTTCATTAGGTT | 43 | 10985 | 11004 | 2130 |

TABLE 11

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 566915 | 343 | 362 | TATGTAGTTCTTCTCAGTTC | 22 | 3447 | 3466 | 2131 |
| 566916 | 350 | 369 | TAGTTTATATGTAGTTCTTC | 21 | 3454 | 3473 | 2132 |
| 566917 | 354 | 373 | CTTGTAGTTTATATGTAGTT | 12 | 3458 | 3477 | 2133 |
| 566918 | 358 | 377 | TTGACTTGTAGTTTATATGT | 12 | 3462 | 3481 | 2134 |
| 566919 | 360 | 379 | TTTTGACTTGTAGTTTATAT | 0 | 3464 | 3483 | 2135 |
| 566920 | 362 | 381 | ATTTTGACTTGTAGTTTAT | 7 | 3466 | 3485 | 2136 |
| 566921 | 367 | 386 | TCTTCATTTTGACTTGTAG | 33 | 3471 | 3490 | 2137 |
| 566922 | 371 | 390 | TACCTCTTCATTTTGACTT | 22 | 3475 | 3494 | 2138 |
| 566923 | 377 | 396 | ATTCTTTACCTCTTCATTTT | 12 | 3481 | 3500 | 2139 |
| 566924 | 387 | 406 | CAAGTGACATATTCTTTACC | 36 | 3491 | 3510 | 2140 |
| 566925 | 389 | 408 | TTCAAGTGACATATTCTTTA | 31 | 3493 | 3512 | 2141 |
| 566926 | 394 | 413 | TTGAGTTCAAGTGACATATT | 18 | 3498 | 3517 | 2142 |
| 566927 | 396 | 415 | AGTTGAGTTCAAGTGACATA | 6 | 3500 | 3519 | 2143 |
| 566928 | 400 | 419 | TTTGAGTTGAGTTCAAGTGA | 11 | 3504 | 3523 | 2144 |
| 566929 | 408 | 427 | TTTCAAGTTTTGAGTTGAGT | 15 | 3512 | 3531 | 2145 |
| 566930 | 410 | 429 | GCTTTCAAGTTTTGAGTTGA | 13 | 3514 | 3533 | 2146 |
| 566931 | 412 | 431 | AGGCTTTCAAGTTTTGAGTT | 22 | 3516 | 3535 | 2147 |
| 566932 | 416 | 435 | TAGGAGGCTTTCAAGTTTTG | 4 | 3520 | 3539 | 2148 |
| 566933 | 419 | 438 | TTCTAGGAGGCTTTCAAGTT | 35 | 3523 | 3542 | 2149 |
| 566934 | 421 | 440 | TCTTCTAGGAGGCTTTCAAG | 26 | 3525 | 3544 | 2150 |
| 566935 | 429 | 448 | GAATTTTTCTTCTAGGAGG | 1 | 3533 | 3552 | 2151 |
| 566936 | 434 | 453 | AAGTAGAATTTTTCTTCTA | 0 | 3538 | 3557 | 2152 |
| 566937 | 436 | 455 | TGAAGTAGAATTTTTCTTC | 11 | 3540 | 3559 | 2153 |
| 566938 | 438 | 457 | GTTGAAGTAGAATTTTTCT | 29 | 3542 | 3561 | 2154 |
| 566939 | 441 | 460 | TTTGTTGAAGTAGAATTTTT | 11 | 3545 | 3564 | 2155 |
| 566940 | 443 | 462 | TTTTTGTTGAAGTAGAATTT | 35 | 3547 | 3566 | 2156 |
| 566941 | 464 | 483 | TTGCTCTTCTAAATATTTCA | 35 | 3568 | 3587 | 2157 |
| 566942 | 466 | 485 | AGTTGCTCTTCTAAATATTT | 53 | 3570 | 3589 | 2158 |
| 566943 | 468 | 487 | TTAGTTGCTCTTCTAAATAT | 18 | 3572 | 3591 | 2159 |
| 566944 | 471 | 490 | TAGTTAGTTGCTCTTCTAAA | 38 | 3575 | 3594 | 2160 |
| 566945 | 476 | 495 | TAAGTTAGTTAGTTGCTCTT | 28 | 3580 | 3599 | 2161 |
| 566946 | 478 | 497 | ATTAAGTTAGTTAGTTGCTC | 28 | 3582 | 3601 | 2162 |
| 566947 | 480 | 499 | GAATTAAGTTAGTTAGTTGC | 27 | 3584 | 3603 | 2163 |
| 566948 | 482 | 501 | TTGAATTAAGTTAGTTAGTT | 21 | 3586 | 3605 | 2164 |
| 566949 | 484 | 503 | TTTTGAATTAAGTTAGTTAG | 2 | 3588 | 3607 | 2165 |
| 566950 | 487 | 506 | TGATTTTGAATTAAGTTAGT | 9 | 3591 | 3610 | 2166 |

TABLE 11-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 566951 | 490 | 509 | GGTTGATTTTGAATTAAGTT | 52 | 3594 | 3613 | 2167 |
| 566952 | 497 | 516 | AGTTTCAGGTTGATTTTGAA | 13 | 3601 | 3620 | 2168 |
| 566953 | 501 | 520 | CTGGAGTTTCAGGTTGATTT | 50 | 3605 | 3624 | 2169 |
| 566954 | 507 | 526 | GGTGTTCTGGAGTTTCAGGT | 35 | 3611 | 3630 | 2170 |
| 566955 | 509 | 528 | TGGGTGTTCTGGAGTTTCAG | 18 | 3613 | 3632 | 2171 |
| 566956 | 511 | 530 | TCTGGGTGTTCTGGAGTTTC | 32 | 3615 | 3634 | 2172 |
| 566957 | 513 | 532 | CTTCTGGGTGTTCTGGAGTT | 28 | 3617 | 3636 | 2173 |
| 566958 | 515 | 534 | TACTTCTGGGTGTTCTGGAG | 23 | 3619 | 3638 | 2174 |
| 566959 | 517 | 536 | GTTACTTCTGGGTGTTCTGG | 12 | 3621 | 3640 | 2175 |
| 566960 | 519 | 538 | AAGTTACTTCTGGGTGTTCT | 1 | 3623 | 3642 | 2176 |
| 566961 | 522 | 541 | GTGAAGTTACTTCTGGGTGT | 0 | 3626 | 3645 | 2177 |
| 566962 | 528 | 547 | TTTTAAGTGAAGTTACTTCT | 6 | N/A | N/A | 2178 |
| 566963 | 530 | 549 | AGTTTTAAGTGAAGTTACTT | 16 | N/A | N/A | 2179 |
| 566964 | 532 | 551 | AAAGTTTTAAGTGAAGTTAC | 12 | N/A | N/A | 2180 |
| 566965 | 535 | 554 | ACAAAAGTTTTAAGTGAAGT | 8 | N/A | N/A | 2181 |
| 337474 | 537 | 556 | CTACAAAAGTTTTAAGTGAA | 10 | N/A | N/A | 2182 |
| 566966 | 539 | 558 | TTCTACAAAAGTTTTAAGTG | 46 | N/A | N/A | 2183 |
| 566967 | 544 | 563 | TGTTTTTCTACAAAAGTTTT | 12 | N/A | N/A | 2184 |
| 566968 | 546 | 565 | CTTGTTTTTCTACAAAAGTT | 0 | N/A | N/A | 2185 |
| 566969 | 552 | 571 | TATTATCTTGTTTTTCTACA | 0 | 4290 | 4309 | 2186 |
| 566970 | 557 | 576 | GATGCTATTATCTTGTTTTT | 18 | 4295 | 4314 | 2187 |
| 566971 | 560 | 579 | TTTGATGCTATTATCTTGTT | 22 | 4298 | 4317 | 2188 |
| 566972 | 562 | 581 | TCTTTGATGCTATTATCTTG | 21 | 4300 | 4319 | 2189 |
| 566973 | 569 | 588 | GAGAAGGTCTTTGATGCTAT | 37 | 4307 | 4326 | 2190 |
| 566974 | 574 | 593 | GTCTGGAGAAGGTCTTTGAT | 26 | 4312 | 4331 | 2191 |
| 566975 | 576 | 595 | CGGTCTGGAGAAGGTCTTTG | 20 | 4314 | 4333 | 2192 |
| 566976 | 578 | 597 | CACGGTCTGGAGAAGGTCTT | 53 | 4316 | 4335 | 2193 |
| 566977 | 580 | 599 | TCCACGGTCTGGAGAAGGTC | 58 | 4318 | 4337 | 2194 |
| 566978 | 582 | 601 | CTTCCACGGTCTGGAGAAGG | 39 | 4320 | 4339 | 2195 |
| 566979 | 584 | 603 | GTCTTCCACGGTCTGGAGAA | 63 | 4322 | 4341 | 2196 |
| 566980 | 586 | 605 | TGGTCTTCCACGGTCTGGAG | 81 | 4324 | 4343 | 2197 |
| 566981 | 588 | 607 | ATTGGTCTTCCACGGTCTGG | 57 | 4326 | 4345 | 2198 |
| 566982 | 590 | 609 | ATATTGGTCTTCCACGGTCT | 60 | 4328 | 4347 | 2199 |
| 566983 | 592 | 611 | TTATATTGGTCTTCCACGGT | 49 | 4330 | 4349 | 2200 |
| 566984 | 594 | 613 | GTTTATATTGGTCTTCCACG | 54 | 4332 | 4351 | 2201 |

TABLE 11-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 566985 | 596 | 615 | TTGTTTATATTGGTCTTCCA | 36 | 4334 | 4353 | 2202 |
| 566986 | 598 | 617 | AATTGTTTATATTGGTCTTC | 23 | 4336 | 4355 | 2203 |
| 566987 | 600 | 619 | TTAATTGTTTATATTGGTCT | 26 | 4338 | 4357 | 2204 |
| 566988 | 602 | 621 | GTTTAATTGTTTATATTGGT | 23 | 4340 | 4359 | 2205 |
| 566989 | 604 | 623 | TGGTTTAATTGTTTATATTG | 8 | 4342 | 4361 | 2206 |
| 566990 | 606 | 625 | GTTGGTTTAATTGTTTATAT | 1 | 4344 | 4363 | 2207 |
| 544120 | 707 | 726 | AGTTCTTGGTGCTCTTGGCT | 78 | 6720 | 6739 | 15 |
| 337487 | 804 | 823 | CACTTGTATGTTCACCTCTG | 82 | 7389 | 7408 | 28 |
| 566991 | 912 | 931 | TTTGTGATCCATCTATTCGA | 25 | 7899 | 7918 | 2208 |
| 566992 | 913 | 932 | TTTTGTGATCCATCTATTCG | 12 | 7900 | 7919 | 2209 |
| 566993 | 920 | 939 | ATTGAAGTTTTGTGATCCAT | 32 | 7907 | 7926 | 2210 |
| 566994 | 921 | 940 | CATTGAAGTTTTGTGATCCA | 26 | 7908 | 7927 | 2211 |
| 566995 | 922 | 941 | TCATTGAAGTTTTGTGATCC | 0 | 7909 | 7928 | 2212 |
| 566996 | 923 | 942 | TTCATTGAAGTTTTGTGATC | 1 | 7910 | 7929 | 2213 |
| 566997 | 924 | 943 | TTTCATTGAAGTTTTGTGAT | 20 | 7911 | 7930 | 2214 |
| 566998 | 944 | 963 | ATATTTGTAGTTCTCCCACG | 35 | 7931 | 7950 | 2215 |
| 566999 | 952 | 971 | CCAAAACCATATTTGTAGTT | 13 | 7939 | 7958 | 2216 |
| 567000 | 953 | 972 | CCCAAAACCATATTTGTAGT | 21 | 7940 | 7959 | 2217 |
| 567001 | 954 | 973 | TCCCAAAACCATATTTGTAG | 0 | 7941 | 7960 | 2218 |
| 567002 | 955 | 974 | CTCCCAAAACCATATTTGTA | 5 | 7942 | 7961 | 2219 |
| 567003 | 958 | 977 | AGCCTCCCAAAACCATATTT | 0 | 7945 | 7964 | 2220 |
| 567004 | 960 | 979 | CAAGCCTCCCAAAACCATAT | 14 | 7947 | 7966 | 2221 |
| 567005 | 961 | 980 | TCAAGCCTCCCAAAACCATA | 0 | 7948 | 7967 | 2222 |
| 567006 | 962 | 981 | ATCAAGCCTCCCAAAACCAT | 17 | 7949 | 7968 | 2223 |
| 567007 | 963 | 982 | CATCAAGCCTCCCAAAACCA | 31 | 7950 | 7969 | 2224 |
| 567008 | 964 | 983 | CCATCAAGCCTCCCAAAACC | 11 | 7951 | 7970 | 2225 |
| 567009 | 965 | 984 | TCCATCAAGCCTCCCAAAAC | 27 | N/A | N/A | 2226 |
| 567010 | 966 | 985 | CTCCATCAAGCCTCCCAAAA | 42 | N/A | N/A | 2227 |
| 567011 | 972 | 991 | AAAATTCTCCATCAAGCCTC | 48 | N/A | N/A | 2228 |
| 567012 | 974 | 993 | CCAAAATTCTCCATCAAGCC | 41 | N/A | N/A | 2229 |
| 567013 | 975 | 994 | ACCAAAATTCTCCATCAAGC | 49 | N/A | N/A | 2230 |
| 567014 | 978 | 997 | CCAACCAAAATTCTCCATCA | 32 | N/A | N/A | 2231 |
| 567015 | 979 | 998 | CCCAACCAAAATTCTCCATC | 47 | N/A | N/A | 2232 |
| 337497 | 980 | 999 | GCCCAACCAAAATTCTCCAT | 46 | N/A | N/A | 2233 |
| 567016 | 981 | 1000 | GGCCCAACCAAAATTCTCCA | 48 | N/A | N/A | 2234 |
| 567017 | 982 | 1001 | AGGCCCAACCAAAATTCTCC | 30 | 9557 | 9576 | 2235 |

TABLE 11-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 567018 | 983 | 1002 | TAGGCCCAACCAAAATTCTC | 0 | 9558 | 9577 | 2236 |
| 567019 | 984 | 1003 | CTAGGCCCAACCAAAATTCT | 31 | 9559 | 9578 | 2237 |
| 567020 | 985 | 1004 | TCTAGGCCCAACCAAAATTC | 39 | 9560 | 9579 | 2238 |
| 233721 | 986 | 1005 | CTCTAGGCCCAACCAAAATT | 15 | 9561 | 9580 | 2239 |
| 567021 | 987 | 1006 | TCTCTAGGCCCAACCAAAAT | 36 | 9562 | 9581 | 2240 |
| 567022 | 988 | 1007 | TTCTCTAGGCCCAACCAAAA | 26 | 9563 | 9582 | 2241 |
| 567023 | 989 | 1008 | CTTCTCTAGGCCCAACCAAA | 44 | 9564 | 9583 | 2242 |
| 567024 | 993 | 1012 | ATATCTTCTCTAGGCCCAAC | 29 | 9568 | 9587 | 2243 |
| 567025 | 994 | 1013 | TATATCTTCTCTAGGCCCAA | 41 | 9569 | 9588 | 2244 |
| 567026 | 995 | 1014 | GTATATCTTCTCTAGGCCCA | 53 | 9570 | 9589 | 2245 |
| 567027 | 1000 | 1019 | ATGGAGTATATCTTCTCTAG | 18 | 9575 | 9594 | 2246 |
| 567028 | 1004 | 1023 | CACTATGGAGTATATCTTCT | 35 | 9579 | 9598 | 2247 |
| 567029 | 1005 | 1024 | TCACTATGGAGTATATCTTC | 9 | 9580 | 9599 | 2248 |
| 567030 | 1006 | 1025 | TTCACTATGGAGTATATCTT | 11 | 9581 | 9600 | 2249 |
| 567031 | 1010 | 1029 | TTGCTTCACTATGGAGTATA | 43 | 9585 | 9604 | 2250 |
| 567032 | 1011 | 1030 | ATTGCTTCACTATGGAGTAT | 4 | 9586 | 9605 | 2251 |
| 567033 | 1015 | 1034 | TTAGATTGCTTCACTATGGA | 17 | 9590 | 9609 | 2252 |
| 567034 | 1016 | 1035 | ATTAGATTGCTTCACTATGG | 35 | 9591 | 9610 | 2253 |
| 567035 | 1017 | 1036 | AATTAGATTGCTTCACTATG | 18 | 9592 | 9611 | 2254 |
| 567036 | 1018 | 1037 | TAATTAGATTGCTTCACTAT | 17 | 9593 | 9612 | 2255 |
| 567037 | 1019 | 1038 | ATAATTAGATTGCTTCACTA | 19 | 9594 | 9613 | 2256 |
| 567038 | 1020 | 1039 | CATAATTAGATTGCTTCACT | 27 | 9595 | 9614 | 2257 |
| 567039 | 1021 | 1040 | ACATAATTAGATTGCTTCAC | 17 | 9596 | 9615 | 2258 |
| 337498 | 1022 | 1041 | AACATAATTAGATTGCTTCA | 9 | 9597 | 9616 | 2259 |
| 567040 | 1023 | 1042 | AAACATAATTAGATTGCTTC | 0 | 9598 | 9617 | 2260 |
| 567041 | 1024 | 1043 | AAAACATAATTAGATTGCTT | 0 | 9599 | 9618 | 2261 |
| 567042 | 1025 | 1044 | TAAAACATAATTAGATTGCT | 23 | 9600 | 9619 | 2262 |
| 567043 | 1026 | 1045 | GTAAAACATAATTAGATTGC | 25 | 9601 | 9620 | 2263 |
| 567044 | 1027 | 1046 | CGTAAAACATAATTAGATTG | 0 | 9602 | 9621 | 2264 |
| 567045 | 1048 | 1067 | TTCCAGTCTTCCAACTCAAT | 9 | 9623 | 9642 | 2265 |
| 337500 | 1050 | 1069 | CTTTCCAGTCTTCCAACTCA | 30 | 9625 | 9644 | 2266 |
| 567046 | 1057 | 1076 | TTGTTGTCTTTCCAGTCTTC | 40 | 9632 | 9651 | 2267 |
| 567047 | 1064 | 1083 | ATAATGTTTGTTGTCTTTCC | 26 | 9639 | 9658 | 2268 |
| 567048 | 1065 | 1084 | TATAATGTTTGTTGTCTTTC | 6 | 9640 | 9659 | 2269 |
| 567049 | 1066 | 1085 | ATATAATGTTTGTTGTCTTT | 9 | 9641 | 9660 | 2270 |

TABLE 11-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 567050 | 1069 | 1088 | TCAATATAATGTTTGTTGTC | 20 | 9644 | 9663 | 2271 |
| 567051 | 1073 | 1092 | ATATTCAATATAATGTTTGT | 15 | 9648 | 9667 | 2272 |
| 567052 | 1074 | 1093 | AATATTCAATATAATGTTTG | 16 | 9649 | 9668 | 2273 |
| 567053 | 1075 | 1094 | GAATATTCAATATAATGTTT | 7 | 9650 | 9669 | 2274 |
| 567054 | 1076 | 1095 | AGAATATTCAATATAATGTT | 3 | 9651 | 9670 | 2275 |
| 567055 | 1077 | 1096 | AAGAATATTCAATATAATGT | 7 | 9652 | 9671 | 2276 |
| 567056 | 1085 | 1104 | CAAGTAAAAGAATATTCAA | 0 | 9660 | 9679 | 2277 |
| 567057 | 1086 | 1105 | CCAAGTAAAAGAATATTCA | 0 | 9661 | 9680 | 2278 |
| 567058 | 1087 | 1106 | CCCAAGTAAAAGAATATTC | 13 | 9662 | 9681 | 2279 |
| 567059 | 1090 | 1109 | TTTCCCAAGTAAAAGAATA | 0 | 9665 | 9684 | 2280 |
| 567060 | 1091 | 1110 | ATTTCCCAAGTAAAAGAAT | 2 | 9666 | 9685 | 2281 |
| 567061 | 1092 | 1111 | GATTTCCCAAGTAAAAGAA | 14 | 9667 | 9686 | 2282 |
| 567062 | 1093 | 1112 | TGATTTCCCAAGTAAAAGA | 14 | 9668 | 9687 | 2283 |
| 567063 | 1127 | 1146 | AATCGCAACTAGATGTAGCG | 15 | 9702 | 9721 | 2284 |
| 563874 | 1586 | 1605 | ATTCTTTAAGGTTATGTGAT | 13 | 10558 | 10577 | 2285 |
| 563875 | 1587 | 1606 | TATTCTTTAAGGTTATGTGA | 25 | 10559 | 10578 | 2286 |
| 563876 | 1591 | 1610 | ACGGTATTCTTTAAGGTTAT | 50 | 10563 | 10582 | 2287 |
| 563877 | 1592 | 1611 | AACGGTATTCTTTAAGGTTA | 48 | 10564 | 10583 | 2288 |
| 563878 | 1593 | 1612 | AAACGGTATTCTTTAAGGTT | 45 | 10565 | 10584 | 2289 |
| 563879 | 1594 | 1613 | TAAACGGTATTCTTTAAGGT | 16 | 10566 | 10585 | 2290 |
| 563880 | 1595 | 1614 | GTAAACGGTATTCTTTAAGG | 14 | 10567 | 10586 | 2291 |
| 563881 | 1596 | 1615 | TGTAAACGGTATTCTTTAAG | 0 | 10568 | 10587 | 2292 |
| 563882 | 1597 | 1616 | ATGTAAACGGTATTCTTTAA | 10 | 10569 | 10588 | 2293 |
| 563883 | 1598 | 1617 | AATGTAAACGGTATTCTTTA | 12 | 10570 | 10589 | 2294 |
| 563884 | 1599 | 1618 | AAATGTAAACGGTATTCTTT | 15 | 10571 | 10590 | 2295 |
| 563885 | 1600 | 1619 | GAAATGTAAACGGTATTCTT | 13 | 10572 | 10591 | 2296 |
| 563886 | 1601 | 1620 | AGAAATGTAAACGGTATTCT | 22 | 10573 | 10592 | 2297 |
| 563887 | 1602 | 1621 | GAGAAATGTAAACGGTATTC | 35 | 10574 | 10593 | 2298 |
| 563888 | 1603 | 1622 | TGAGAAATGTAAACGGTATT | 14 | 10575 | 10594 | 2299 |
| 563889 | 1604 | 1623 | TTGAGAAATGTAAACGGTAT | 0 | 10576 | 10595 | 2300 |
| 563890 | 1605 | 1624 | ATTGAGAAATGTAAACGGTA | 18 | 10577 | 10596 | 2301 |
| 563891 | 1606 | 1625 | GATTGAGAAATGTAAACGGT | 40 | 10578 | 10597 | 2302 |
| 563892 | 1607 | 1626 | TGATTGAGAAATGTAAACGG | 33 | 10579 | 10598 | 2303 |
| 563893 | 1608 | 1627 | TTGATTGAGAAATGTAAACG | 7 | 10580 | 10599 | 2304 |
| 563894 | 1609 | 1628 | TTTGATTGAGAAATGTAAAC | 0 | 10581 | 10600 | 2305 |
| 563895 | 1610 | 1629 | TTTTGATTGAGAAATGTAAA | 0 | 10582 | 10601 | 2306 |

TABLE 11-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 563896 | 1611 | 1630 | ATTTTGATTGAGAAATGTAA | 0 | 10583 | 10602 | 2307 |
| 563897 | 1612 | 1631 | AATTTTGATTGAGAAATGTA | 0 | 10584 | 10603 | 2308 |
| 563898 | 1613 | 1632 | GAATTTTGATTGAGAAATGT | 4 | 10585 | 10604 | 2309 |
| 563899 | 1614 | 1633 | AGAATTTTGATTGAGAAATG | 4 | 10586 | 10605 | 2310 |
| 563900 | 1615 | 1634 | AAGAATTTTGATTGAGAAAT | 26 | 10587 | 10606 | 2311 |
| 563901 | 1617 | 1636 | ATAAGAATTTTGATTGAGAA | 4 | 10589 | 10608 | 2312 |
| 563902 | 1618 | 1637 | TATAAGAATTTTGATTGAGA | 0 | 10590 | 10609 | 2313 |
| 563903 | 1619 | 1638 | TTATAAGAATTTTGATTGAG | 0 | 10591 | 10610 | 2314 |
| 563904 | 1620 | 1639 | ATTATAAGAATTTTGATTGA | 0 | 10592 | 10611 | 2315 |
| 563905 | 1621 | 1640 | TATTATAAGAATTTTGATTG | 3 | 10593 | 10612 | 2316 |
| 563906 | 1622 | 1641 | GTATTATAAGAATTTTGATT | 1 | 10594 | 10613 | 2317 |
| 563907 | 1623 | 1642 | AGTATTATAAGAATTTTGAT | 44 | 10595 | 10614 | 2318 |
| 563908 | 1624 | 1643 | TAGTATTATAAGAATTTTGA | 29 | 10596 | 10615 | 2319 |
| 563909 | 1632 | 1651 | AAAACAAATAGTATTATAAG | 11 | 10604 | 10623 | 2320 |
| 563910 | 1633 | 1652 | TAAAACAAATAGTATTATAA | 16 | 10605 | 10624 | 2321 |
| 563911 | 1652 | 1671 | ATTCCCACATCACAAAATTT | 27 | 10624 | 10643 | 2322 |
| 563912 | 1653 | 1672 | GATTCCCACATCACAAAATT | 21 | 10625 | 10644 | 2323 |
| 563913 | 1654 | 1673 | TGATTCCCACATCACAAAAT | 49 | 10626 | 10645 | 2324 |
| 563914 | 1658 | 1677 | AAATTGATTCCCACATCACA | 47 | 10630 | 10649 | 2325 |
| 563915 | 1659 | 1678 | AAAATTGATTCCCACATCAC | 48 | 10631 | 10650 | 2326 |
| 563916 | 1663 | 1682 | ATCTAAAATTGATTCCCACA | 58 | 10635 | 10654 | 2327 |
| 563917 | 1667 | 1686 | GACCATCTAAAATTGATTCC | 41 | 10639 | 10658 | 2328 |
| 563918 | 1668 | 1687 | TGACCATCTAAAATTGATTC | 25 | 10640 | 10659 | 2329 |
| 563919 | 1669 | 1688 | GTGACCATCTAAAATTGATT | 33 | 10641 | 10660 | 2330 |
| 563920 | 1670 | 1689 | TGTGACCATCTAAAATTGAT | 34 | 10642 | 10661 | 2331 |
| 563921 | 1671 | 1690 | TTGTGACCATCTAAAATTGA | 20 | 10643 | 10662 | 2332 |
| 563922 | 1672 | 1691 | ATTGTGACCATCTAAAATTG | 2 | 10644 | 10663 | 2333 |
| 563923 | 1673 | 1692 | GATTGTGACCATCTAAAATT | 43 | 10645 | 10664 | 2334 |
| 563924 | 1674 | 1693 | AGATTGTGACCATCTAAAAT | 39 | 10646 | 10665 | 2335 |
| 563925 | 1675 | 1694 | TAGATTGTGACCATCTAAAA | 36 | 10647 | 10666 | 2336 |
| 563926 | 1676 | 1695 | CTAGATTGTGACCATCTAAA | 56 | 10648 | 10667 | 2337 |
| 563927 | 1677 | 1696 | TCTAGATTGTGACCATCTAA | 37 | 10649 | 10668 | 2338 |
| 563928 | 1678 | 1697 | ATCTAGATTGTGACCATCTA | 46 | 10650 | 10669 | 2339 |
| 563929 | 1679 | 1698 | AATCTAGATTGTGACCATCT | 56 | 10651 | 10670 | 2340 |
| 563930 | 1680 | 1699 | TAATCTAGATTGTGACCATC | 46 | 10652 | 10671 | 2341 |

TABLE 11-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 563931 | 1681 | 1700 | ATAATCTAGATTGTGACCAT | 35 | 10653 | 10672 | 2342 |
| 563932 | 1682 | 1701 | TATAATCTAGATTGTGACCA | 45 | 10654 | 10673 | 2343 |
| 563933 | 1683 | 1702 | TTATAATCTAGATTGTGACC | 37 | 10655 | 10674 | 2344 |
| 563934 | 1686 | 1705 | TGATTATAATCTAGATTGTG | 28 | 10658 | 10677 | 2345 |
| 563935 | 1687 | 1706 | TTGATTATAATCTAGATTGT | 0 | 10659 | 10678 | 2346 |
| 563936 | 1688 | 1707 | ATTGATTATAATCTAGATTG | 0 | 10660 | 10679 | 2347 |
| 563937 | 1689 | 1708 | TATTGATTATAATCTAGATT | 0 | 10661 | 10680 | 2348 |
| 563938 | 1690 | 1709 | CTATTGATTATAATCTAGAT | 5 | 10662 | 10681 | 2349 |
| 563939 | 1691 | 1710 | CCTATTGATTATAATCTAGA | 0 | 10663 | 10682 | 2350 |
| 563940 | 1692 | 1711 | ACCTATTGATTATAATCTAG | 9 | 10664 | 10683 | 2351 |
| 563941 | 1693 | 1712 | CACCTATTGATTATAATCTA | 5 | 10665 | 10684 | 2352 |
| 563942 | 1694 | 1713 | TCACCTATTGATTATAATCT | 0 | 10666 | 10685 | 2353 |
| 563943 | 1695 | 1714 | TTCACCTATTGATTATAATC | 10 | 10667 | 10686 | 2354 |
| 563944 | 1696 | 1715 | GTTCACCTATTGATTATAAT | 31 | 10668 | 10687 | 2355 |
| 563945 | 1697 | 1716 | AGTTCACCTATTGATTATAA | 15 | 10669 | 10688 | 2356 |
| 563946 | 1698 | 1717 | AAGTTCACCTATTGATTATA | 31 | 10670 | 10689 | 2357 |
| 563947 | 1700 | 1719 | ATAAGTTCACCTATTGATTA | 9 | 10672 | 10691 | 2358 |
| 563948 | 1701 | 1720 | AATAAGTTCACCTATTGATT | 5 | 10673 | 10692 | 2359 |
| 563949 | 1702 | 1721 | TAATAAGTTCACCTATTGAT | 14 | 10674 | 10693 | 2360 |
| 563950 | 1703 | 1722 | TTAATAAGTTCACCTATTGA | 0 | 10675 | 10694 | 2361 |

TABLE 12

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 567064 | N/A | N/A | TGAGTATTCTCGACTTACCT | 26 | 8770 | 8789 | 2362 |
| 567065 | N/A | N/A | AAGTGAGTATTCTCGACTTA | 2 | 8773 | 8792 | 2363 |
| 567066 | N/A | N/A | ATTAAGTGAGTATTCTCGAC | 20 | 8776 | 8795 | 2364 |
| 567067 | N/A | N/A | CCAGAATTAAGTGAGTATTC | 36 | 8781 | 8800 | 2365 |
| 567068 | N/A | N/A | GCTTTCTTACCAGAATTAAG | 75 | 8790 | 8809 | 84 |
| 567069 | N/A | N/A | GTTGCTTTCTTACCAGAATT | 78 | 8793 | 8812 | 85 |
| 567070 | N/A | N/A | TGGGTTGCTTTCTTACCAGA | 26 | 8796 | 8815 | 2366 |
| 567071 | N/A | N/A | AAATGGGTTGCTTTCTTACC | 3 | 8799 | 8818 | 2367 |
| 567072 | N/A | N/A | TACAAATGGGTTGCTTTCTT | 24 | 8802 | 8821 | 2368 |

TABLE 12-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 567073 | N/A | N/A | AAGTACAAATGGGTTGCTTT | 24 | 8805 | 8824 | 2369 |
| 567074 | N/A | N/A | GTAAATACAAGTACAAATGG | 7 | 8813 | 8832 | 2370 |
| 567075 | N/A | N/A | TTGCTGGTAAATACAAGTAC | 24 | 8819 | 8838 | 2371 |
| 567076 | N/A | N/A | TAAGGATTGCTGGTAAATAC | 6 | 8825 | 8844 | 2372 |
| 567077 | N/A | N/A | TTTTAAGGATTGCTGGTAAA | 4 | 8828 | 8847 | 2373 |
| 567078 | N/A | N/A | GCTTCATTTTAAGGATTGCT | 60 | 8834 | 8853 | 87 |
| 567079 | N/A | N/A | GAAGCTTCATTTTAAGGATT | 0 | 8837 | 8856 | 2374 |
| 567080 | N/A | N/A | TAGGAAGCTTCATTTTAAGG | 9 | 8840 | 8859 | 2375 |
| 567081 | N/A | N/A | TAGTAGGAAGCTTCATTTTA | 18 | 8843 | 8862 | 2376 |
| 567082 | N/A | N/A | TTGAGTTAGTAGGAAGCTTC | 30 | 8849 | 8868 | 2377 |
| 567083 | N/A | N/A | ATTGCTATTGAGTTAGTAGG | 21 | 8856 | 8875 | 2378 |
| 567084 | N/A | N/A | CTTATTGCTATTGAGTTAGT | 28 | 8859 | 8878 | 2379 |
| 567085 | N/A | N/A | ATTGTCTTATTGCTATTGAG | 16 | 8864 | 8883 | 2380 |
| 567086 | N/A | N/A | ACTATTGTCTTATTGCTATT | 10 | 8867 | 8886 | 2381 |
| 567087 | N/A | N/A | TTCACTATTGTCTTATTGCT | 35 | 8870 | 8889 | 2382 |
| 567088 | N/A | N/A | ACATTCACTATTGTCTTATT | 30 | 8873 | 8892 | 2383 |
| 567089 | N/A | N/A | TAAACATTCACTATTGTCTT | 58 | 8876 | 8895 | 2384 |
| 567090 | N/A | N/A | CATTAAACATTCACTATTGT | 28 | 8879 | 8898 | 2385 |
| 567091 | N/A | N/A | GTTTTCATTAAACATTCACT | 54 | 8884 | 8903 | 2386 |
| 567092 | N/A | N/A | AAATACTGTTTTCATTAAAC | 34 | 8891 | 8910 | 2387 |
| 567093 | N/A | N/A | AAAGTATTTATAAAATACTG | 0 | 8903 | 8922 | 2388 |
| 567094 | N/A | N/A | CCTTTTTATTAAAGTATTTA | 0 | 8913 | 8932 | 2389 |
| 567095 | N/A | N/A | CAATCCTTTTTATTAAAGTA | 10 | 8917 | 8936 | 2390 |
| 567096 | N/A | N/A | CTTCATCACAATCCTTTTTA | 52 | 8925 | 8944 | 2391 |
| 567097 | N/A | N/A | GTTCTTCATCACAATCCTTT | 57 | 8928 | 8947 | 2392 |
| 567098 | N/A | N/A | ATTGTTCTTCATCACAATCC | 37 | 8931 | 8950 | 2393 |
| 567099 | N/A | N/A | TAGATTGTTCTTCATCACAA | 31 | 8934 | 8953 | 2394 |
| 567100 | N/A | N/A | AAATAGATTGTTCTTCATCA | 11 | 8937 | 8956 | 2395 |
| 567101 | N/A | N/A | AACAAATATAAATAGATTGT | 0 | 8946 | 8965 | 2396 |
| 567102 | N/A | N/A | CAAATAACAAATATAAATAG | 3 | 8951 | 8970 | 2397 |
| 567103 | N/A | N/A | TGGAATTAAAAACAAATAAC | 3 | 8963 | 8982 | 2398 |
| 567104 | N/A | N/A | TTATTGGAATTAAAAACAAA | 12 | 8967 | 8986 | 2399 |
| 567105 | N/A | N/A | TTTTTATTGGAATTAAAAAC | 17 | 8970 | 8989 | 2400 |
| 567106 | N/A | N/A | TAATAACTTTTTTCTGTAAT | 6 | 9001 | 9020 | 2401 |
| 567107 | N/A | N/A | GTTCTTAATAACTTTTTTCT | 21 | 9006 | 9025 | 2402 |

TABLE 12-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 567108 | N/A | N/A | AAAAGCATGGTTCTTAATAA | 0 | 9015 | 9034 | 2403 |
| 567109 | N/A | N/A | AAATTTAAAAGCATGGTTCT | 0 | 9021 | 9040 | 2404 |
| 567110 | N/A | N/A | AGGAATAAATTTAAAAAATC | 0 | 9046 | 9065 | 2405 |
| 567111 | N/A | N/A | AGACAGGAATAAATTTAAAA | 7 | 9050 | 9069 | 2406 |
| 567112 | N/A | N/A | AAAAGACAGGAATAAATTTA | 0 | 9053 | 9072 | 2407 |
| 567113 | N/A | N/A | CTTTCTTTGTAGAAAAAGAC | 29 | 9066 | 9085 | 2408 |
| 567114 | N/A | N/A | ATGCTTTCTTTGTAGAAAAA | 12 | 9069 | 9088 | 2409 |
| 567115 | N/A | N/A | GCTTAATGTATGCTTTCTTT | 67 | 9078 | 9097 | 88 |
| 567116 | N/A | N/A | TTTGCTTAATGTATGCTTTC | 21 | 9081 | 9100 | 2410 |
| 567117 | N/A | N/A | GTATTTGCTTAATGTATGCT | 0 | 9084 | 9103 | 2411 |
| 567118 | N/A | N/A | TTGGTATTTGCTTAATGTAT | 0 | 9087 | 9106 | 2412 |
| 567119 | N/A | N/A | CCTTTGGTATTTGCTTAATG | 35 | 9090 | 9109 | 2413 |
| 567120 | N/A | N/A | TGGCCTTTGGTATTTGCTTA | 0 | 9093 | 9112 | 2414 |
| 567121 | N/A | N/A | TAAACCTGGCCTTTGGTATT | 27 | 9099 | 9118 | 2415 |
| 567122 | N/A | N/A | ATGTAAACCTGGCCTTTGGT | 16 | 9102 | 9121 | 2416 |
| 567123 | N/A | N/A | CAAATGTAAACCTGGCCTTT | 0 | 9105 | 9124 | 2417 |
| 567124 | N/A | N/A | CTTCAAATGTAAACCTGGCC | 25 | 9108 | 9127 | 2418 |
| 567125 | N/A | N/A | TTTCTTCAAATGTAAACCTG | 2 | 9111 | 9130 | 2419 |
| 567126 | N/A | N/A | TGTCACTTTCTTCAAATGTA | 57 | 9117 | 9136 | 2420 |
| 567127 | N/A | N/A | TAATGTCACTTTCTTCAAAT | 6 | 9120 | 9139 | 2421 |
| 567128 | N/A | N/A | AATAATAATGTCACTTTCTT | 3 | 9125 | 9144 | 2422 |
| 567129 | N/A | N/A | GAGTAATAATAATGTCACTT | 18 | 9129 | 9148 | 2423 |
| 567130 | N/A | N/A | GACTTGAGTAATAATAATGT | 1 | 9134 | 9153 | 2424 |
| 567131 | N/A | N/A | CCTAGAGACTTGAGTAATAA | 32 | 9140 | 9159 | 2425 |
| 567132 | N/A | N/A | ATTCCTAGAGACTTGAGTAA | 8 | 9143 | 9162 | 2426 |
| 567133 | N/A | N/A | AAGTATTCCTAGAGACTTGA | 11 | 9147 | 9166 | 2427 |
| 567134 | N/A | N/A | GTTAAGTATTCCTAGAGACT | 61 | 9150 | 9169 | 89 |
| 567135 | N/A | N/A | TGTGTTAAGTATTCCTAGAG | 28 | 9153 | 9172 | 2428 |
| 567136 | N/A | N/A | AGAGATGTGTTAAGTATTCC | 31 | 9158 | 9177 | 2429 |
| 567137 | N/A | N/A | GTCAAGAGATGTGTTAAGTA | 52 | 9162 | 9181 | 2430 |
| 567138 | N/A | N/A | ACAGTCAAGAGATGTGTTAA | 22 | 9165 | 9184 | 2431 |
| 567139 | N/A | N/A | TATACAGTCAAGAGATGTGT | 30 | 9168 | 9187 | 2432 |
| 567140 | N/A | N/A | CCATATACAGTCAAGAGATG | 45 | 9171 | 9190 | 2433 |
| 567141 | N/A | N/A | GTAAGTTGAACTAACTACTG | 9 | 7497 | 7516 | 2434 |
| 567142 | N/A | N/A | TGAGTAAGTTGAACTAACTA | 0 | 7500 | 7519 | 2435 |
| 567143 | N/A | N/A | TAATGAGTAAGTTGAACTAA | 2 | 7503 | 7522 | 2436 |

TABLE 12-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 567144 | N/A | N/A | AGGTTAATCTTCCTAATACG | 18 | 7523 | 7542 | 2437 |
| 567145 | N/A | N/A | ATAACCAGGTTAATCTTCCT | 34 | 7529 | 7548 | 2438 |
| 567146 | N/A | N/A | ATGATAACCAGGTTAATCTT | 13 | 7532 | 7551 | 2439 |
| 567147 | N/A | N/A | AACAATGATAACCAGGTTAA | 7 | 7536 | 7555 | 2440 |
| 567148 | N/A | N/A | TAAAACAATGATAACCAGGT | 45 | 7539 | 7558 | 2441 |
| 567149 | N/A | N/A | GTATAAAACAATGATAACCA | 26 | 7542 | 7561 | 2442 |
| 567150 | N/A | N/A | CGAATACTCATATATATTTC | 25 | 7572 | 7591 | 2443 |
| 567151 | N/A | N/A | ATACGAATACTCATATATAT | 30 | 7575 | 7594 | 2444 |
| 567152 | N/A | N/A | TTTATACGAATACTCATATA | 32 | 7578 | 7597 | 2445 |
| 567153 | N/A | N/A | ATATTTATACGAATACTCAT | 25 | 7581 | 7600 | 2446 |
| 567154 | N/A | N/A | GTATTATATTTATACGAATA | 0 | 7586 | 7605 | 2447 |
| 567155 | N/A | N/A | AAAAGTATTATATTTATACG | 0 | 7590 | 7609 | 2448 |
| 567156 | N/A | N/A | GGTAAAAGTATTATATTTAT | 0 | 7593 | 7612 | 2449 |
| 567157 | N/A | N/A | ACAAGGTAAAAGTATTATAT | 10 | 7597 | 7616 | 2450 |
| 567158 | N/A | N/A | TAAACAAGGTAAAAGTATTA | 11 | 7600 | 7619 | 2451 |
| 567159 | N/A | N/A | ACATAAACAAGGTAAAAGTA | 3 | 7603 | 7622 | 2452 |
| 567160 | N/A | N/A | TTGAGTAAATACATAAACAA | 12 | 7613 | 7632 | 2453 |
| 567161 | N/A | N/A | GAGAATATTGAGTAAATACA | 4 | 7620 | 7639 | 2454 |
| 567162 | N/A | N/A | AAGGAGAATATTGAGTAAAT | 8 | 7623 | 7642 | 2455 |
| 567163 | N/A | N/A | GAAAAGGAGAATATTGAGTA | 3 | 7626 | 7645 | 2456 |
| 567164 | N/A | N/A | GAGGAAAAGGAGAATATTGA | 19 | 7629 | 7648 | 2457 |
| 567165 | N/A | N/A | TTAGAGGAAAAGGAGAATAT | 41 | 7632 | 7651 | 2458 |
| 567166 | N/A | N/A | ATTATTTAGAGGAAAAGGA | 30 | 7638 | 7657 | 2459 |
| 567167 | N/A | N/A | CAGATTATTTTAGAGGAAAA | 9 | 7641 | 7660 | 2460 |
| 567168 | N/A | N/A | CTTCAGATTATTTTAGAGGA | 24 | 7644 | 7663 | 2461 |
| 567169 | N/A | N/A | TAGTCACTTCAGATTATTTT | 38 | 7650 | 7669 | 2462 |
| 567170 | N/A | N/A | TAATAGTCACTTCAGATTAT | 13 | 7653 | 7672 | 2463 |
| 567171 | N/A | N/A | TGATAATAGTCACTTCAGAT | 39 | 7656 | 7675 | 2464 |
| 567172 | N/A | N/A | TATTGATAATAGTCACTTCA | 41 | 7659 | 7678 | 2465 |
| 567173 | N/A | N/A | ACTTATTGATAATAGTCACT | 29 | 7662 | 7681 | 2466 |
| 567174 | N/A | N/A | TAAACTTATTGATAATAGTC | 14 | 7665 | 7684 | 2467 |
| 567175 | N/A | N/A | TAGTAAACTTATTGATAATA | 31 | 7668 | 7687 | 2468 |
| 567176 | N/A | N/A | GCATAGTAAACTTATTGATA | 23 | 7671 | 7690 | 2469 |
| 567177 | N/A | N/A | TTGGCATAGTAAACTTATTG | 21 | 7674 | 7693 | 2470 |
| 567178 | N/A | N/A | ATTTGGCATAGTAAACTTA | 8 | 7677 | 7696 | 2471 |

TABLE 12-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 567179 | N/A | N/A | TGAATTTTGGCATAGTAAAC | 5 | 7680 | 7699 | 2472 |
| 567180 | N/A | N/A | TTAATGAATTTTGGCATAGT | 0 | 7684 | 7703 | 2473 |
| 567181 | N/A | N/A | CAATTAATGAATTTTGGCAT | 39 | 7687 | 7706 | 2474 |
| 567182 | N/A | N/A | AAAGGCAATTAATGAATTTT | 12 | 7692 | 7711 | 2475 |
| 567183 | N/A | N/A | GTGAAAGGCAATTAATGAAT | 28 | 7695 | 7714 | 2476 |
| 567184 | N/A | N/A | TTAAGTGAAAGGCAATTAAT | 7 | 7699 | 7718 | 2477 |
| 567185 | N/A | N/A | AAGTTAAGTGAAAGGCAATT | 25 | 7702 | 7721 | 2478 |
| 567186 | N/A | N/A | CCAAAAGTTAAGTGAAAGGC | 50 | 7706 | 7725 | 2479 |
| 567187 | N/A | N/A | GTCCCAAAAGTTAAGTGAAA | 30 | 7709 | 7728 | 2480 |
| 567188 | N/A | N/A | ATGGTCCCAAAAGTTAAGTG | 39 | 7712 | 7731 | 2481 |
| 567189 | N/A | N/A | ATTATGGTCCCAAAAGTTAA | 19 | 7715 | 7734 | 2482 |
| 567190 | N/A | N/A | TTTATTATGGTCCCAAAAGT | 33 | 7718 | 7737 | 2483 |
| 567191 | N/A | N/A | TTATTATTTATTATGGTCCC | 50 | 7724 | 7743 | 2484 |
| 567192 | N/A | N/A | ATGGCAATACATTTTATTAT | 13 | 7737 | 7756 | 2485 |
| 567193 | N/A | N/A | GTTATGGCAATACATTTTAT | 39 | 7740 | 7759 | 2486 |
| 567194 | N/A | N/A | TAATGTTATGGCAATACATT | 0 | 7744 | 7763 | 2487 |
| 567195 | N/A | N/A | TATTAATGTTATGGCAATAC | 22 | 7747 | 7766 | 2488 |
| 567196 | N/A | N/A | GTTTATTAATGTTATGGCAA | 28 | 7750 | 7769 | 2489 |
| 567197 | N/A | N/A | GTAGTTTATTAATGTTATGG | 20 | 7753 | 7772 | 2490 |
| 567198 | N/A | N/A | AAGGTAGTTTATTAATGTTA | 27 | 7756 | 7775 | 2491 |
| 567199 | N/A | N/A | TGTAAGGTAGTTTATTAATG | 0 | 7759 | 7778 | 2492 |
| 567200 | N/A | N/A | TTTTGTAAGGTAGTTTATTA | 0 | 7762 | 7781 | 2493 |
| 567201 | N/A | N/A | TGGTTTTGTAAGGTAGTTTA | 18 | 7765 | 7784 | 2494 |
| 567202 | N/A | N/A | TGGTGGTTTTGTAAGGTAGT | 0 | 7768 | 7787 | 2495 |
| 567203 | N/A | N/A | AATTGGTGGTTTTGTAAGGT | 11 | 7771 | 7790 | 2496 |
| 567204 | N/A | N/A | TTTAATTGGTGGTTTTGTAA | 0 | 7774 | 7793 | 2497 |
| 567205 | N/A | N/A | TTGATTTAATTGGTGGTTT | 19 | 7779 | 7798 | 2498 |
| 567206 | N/A | N/A | TGTTTGATTTAATTGGTGG | 26 | 7782 | 7801 | 2499 |
| 567207 | N/A | N/A | ATGTAAATAACACTTTTTG | 1 | 7804 | 7823 | 2500 |
| 567208 | N/A | N/A | CAGATGTAAATAACACTTTT | 1 | 7807 | 7826 | 2501 |
| 567209 | N/A | N/A | TGACAGATGTAAATAACACT | 21 | 7810 | 7829 | 2502 |
| 567210 | N/A | N/A | ATGTTGACAGATGTAAATAA | 0 | 7814 | 7833 | 2503 |
| 567211 | N/A | N/A | TTTATGTTGACAGATGTAAA | 0 | 7817 | 7836 | 2504 |
| 567212 | N/A | N/A | AGATTTATGTTGACAGATGT | 0 | 7820 | 7839 | 2505 |
| 567213 | N/A | N/A | AGTAGATTTATGTTGACAGA | 19 | 7823 | 7842 | 2506 |
| 567214 | N/A | N/A | TTTAGTAGATTTATGTTGAC | 4 | 7826 | 7845 | 2507 |

TABLE 12-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 567215 | N/A | N/A | ATTTTTAGTAGATTTATGTT | 0 | 7829 | 7848 | 2508 |
| 567216 | N/A | N/A | CATGTATTTTAGTAGATTT | 5 | 7834 | 7853 | 2509 |
| 567217 | N/A | N/A | GAAATCATGTATTTTAGTA | 0 | 7839 | 7858 | 2510 |
| 567218 | N/A | N/A | ATTGTATTTGATGGATATCT | 43 | 6875 | 6894 | 2511 |
| 567219 | N/A | N/A | GATACATTGTATTTGATGGA | 20 | 6880 | 6899 | 2512 |
| 567220 | N/A | N/A | TAGGTTGATACATTGTATTT | 18 | 6886 | 6905 | 2513 |
| 567221 | N/A | N/A | CAGTTTAGGTTGATACATTG | 18 | 6891 | 6910 | 2514 |
| 567222 | N/A | N/A | GCATCCAGTTTAGGTTGATA | 31 | 6896 | 6915 | 2515 |
| 567223 | N/A | N/A | CCCCAGCATCCAGTTTAGGT | 14 | 6901 | 6920 | 2516 |
| 567224 | N/A | N/A | AAGAACCCCAGCATCCAGTT | 41 | 6906 | 6925 | 2517 |
| 567225 | N/A | N/A | GTGTAAAAGAACCCCAGCA | 0 | 6913 | 6932 | 2518 |
| 567226 | N/A | N/A | ATAGGGTGTAAAAGAACCC | 13 | 6918 | 6937 | 2519 |
| 567227 | N/A | N/A | CTTTTATAGGGTGTAAAAAG | 0 | 6923 | 6942 | 2520 |
| 567228 | N/A | N/A | TATGTCTTTTATAGGGTGTA | 26 | 6928 | 6947 | 2521 |
| 567229 | N/A | N/A | TTAGGTATGTCTTTTATAGG | 0 | 6933 | 6952 | 2522 |
| 567230 | N/A | N/A | TTGTCTTAGGTATGTCTTTT | 30 | 6938 | 6957 | 2523 |
| 567231 | N/A | N/A | CTCTGATTGTCTTAGGTATG | 27 | 6944 | 6963 | 2524 |
| 567232 | N/A | N/A | TATTTCTCTGATTGTCTTAG | 21 | 6949 | 6968 | 2525 |
| 567233 | N/A | N/A | TCCATATTTGTATTTCTCTG | 61 | 6959 | 6978 | 90 |
| 567234 | N/A | N/A | TCAAGTCCATATTTGTATTT | 20 | 6964 | 6983 | 2526 |
| 567235 | N/A | N/A | AATAATCAAGTCCATATTTG | 0 | 6969 | 6988 | 2527 |
| 567236 | N/A | N/A | TTATCTAATAATCAAGTCCA | 0 | 6975 | 6994 | 2528 |
| 567237 | N/A | N/A | CTATATTATCTAATAATCAA | 12 | 6980 | 6999 | 2529 |
| 567238 | N/A | N/A | TAAACCTTCTATATTATCTA | 12 | 6988 | 7007 | 2530 |
| 567239 | N/A | N/A | AATTAATAAACCTTCTATAT | 0 | 6994 | 7013 | 2531 |
| 567240 | N/A | N/A | TAAGTACAGGTTGGACACTG | 0 | 9504 | 9523 | 2532 |
| 567241 | N/A | N/A | GTTATTAAGTACAGGTTGGA | 2 | 9509 | 9528 | 2533 |
| 567242 | N/A | N/A | TGTGAGTTATTAAGTACAGG | 0 | 9514 | 9533 | 2534 |
| 567243 | N/A | N/A | AAATCTGTGAGTTATTAAGT | 0 | 9519 | 9538 | 2535 |
| 567244 | N/A | N/A | GTTTTAAAAATCTGTGAGTT | 19 | 9526 | 9545 | 2536 |
| 567245 | N/A | N/A | CAAAATTCTCCTGAAAAGAA | 20 | 9548 | 9567 | 2537 |
| 567246 | N/A | N/A | CCCAACCAAAATTCTCCTGA | 48 | 9554 | 9573 | 2538 |
| 567247 | N/A | N/A | ACCTGAATAACCCTCTGGAC | 21 | 9807 | 9826 | 2539 |
| 567248 | N/A | N/A | AAGATACCTGAATAACCCTC | 30 | 9812 | 9831 | 2540 |
| 567249 | N/A | N/A | AGAAAAGATACCTGAATAA | 0 | 9817 | 9836 | 2541 |

TABLE 12-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 567250 | N/A | N/A | TGGTATCAGAAAAAGATACC | 0 | 9824 | 9843 | 2542 |
| 567251 | N/A | N/A | AGTATTGGTATCAGAAAAAG | 0 | 9829 | 9848 | 2543 |
| 567252 | N/A | N/A | AATAAAGTATTGGTATCAGA | 10 | 9834 | 9853 | 2544 |
| 567253 | N/A | N/A | ATGAAAATAAAGTATTGGTA | 3 | 9839 | 9858 | 2545 |
| 567254 | N/A | N/A | AGATACTTTGAAGATATGAA | 0 | 9854 | 9873 | 2546 |
| 567255 | N/A | N/A | TGGGAAGATACTTTGAAGAT | 0 | 9859 | 9878 | 2547 |
| 567256 | N/A | N/A | CTAATAATGTGGGAAGATAC | 0 | 9868 | 9887 | 2548 |
| 567257 | N/A | N/A | CATTGCAGATAATAGCTAAT | 0 | 9883 | 9902 | 2549 |
| 567258 | N/A | N/A | AAGTTGTCATTGCAGATAAT | 0 | 9890 | 9909 | 2550 |
| 567259 | N/A | N/A | TTTTAAAGTTGTCATTGCA | 7 | 9896 | 9915 | 2551 |
| 567260 | N/A | N/A | ATTCGGATTTTAAAAGTTG | 5 | 9904 | 9923 | 2552 |
| 567261 | N/A | N/A | TTATTTGGGATTCGGATTTT | 15 | 9913 | 9932 | 2553 |
| 567262 | N/A | N/A | TTATAGTTAAGAGGTTTTCG | 27 | 9949 | 9968 | 2554 |
| 567263 | N/A | N/A | TTTCATTATAGTTAAGAGGT | 12 | 9954 | 9973 | 2555 |
| 567264 | N/A | N/A | GAACACTTTCATTATAGTTA | 13 | 9960 | 9979 | 2556 |
| 567265 | N/A | N/A | GAACTAGAATGAACACTTTC | 28 | 9970 | 9989 | 2557 |
| 567266 | N/A | N/A | TGATTGAACTAGAATGAACA | 23 | 9975 | 9994 | 2558 |
| 567267 | N/A | N/A | ATACCTGATTGAACTAGAAT | 9 | 9980 | 9999 | 2559 |
| 567268 | N/A | N/A | GTAAAATACCTGATTGAACT | 6 | 9985 | 10004 | 2560 |
| 567269 | N/A | N/A | TAGAGGTAAAATACCTGATT | 16 | 9990 | 10009 | 2561 |
| 567270 | N/A | N/A | AAGATTAGAGGTAAAATACC | 0 | 9995 | 10014 | 2562 |
| 567271 | N/A | N/A | TGAGGAAGATTAGAGGTAAA | 6 | 10000 | 10019 | 2563 |
| 567272 | N/A | N/A | GAAAATCTGAGGAAGATTAG | 0 | 10007 | 10026 | 2564 |
| 567273 | N/A | N/A | AAATAGAAAATCTGAGGAAG | 0 | 10012 | 10031 | 2565 |
| 567274 | N/A | N/A | ATCTATACACTACCAAAAAA | 0 | 10029 | 10048 | 2566 |
| 567275 | N/A | N/A | AAATAATCTATACACTACCA | 19 | 10034 | 10053 | 2567 |
| 567276 | N/A | N/A | AAATAATCTGTATAAATAAT | 3 | 10047 | 10066 | 2568 |
| 567277 | N/A | N/A | CCCAATTTTAAATAATCTGT | 24 | 10056 | 10075 | 2569 |
| 567278 | N/A | N/A | TAAGTCCCAATTTTAAATAA | 0 | 10061 | 10080 | 2570 |
| 567279 | N/A | N/A | TCTGTATAAGTCCCAATTTT | 15 | 10067 | 10086 | 2571 |
| 567280 | N/A | N/A | AATAATCTGTATAAGTCCCA | 47 | 10072 | 10091 | 2572 |
| 567281 | N/A | N/A | AGTTTTAAATAATCTGTATA | 0 | 10079 | 10098 | 2573 |
| 567282 | N/A | N/A | ATCCCAGTTTTAAATAATCT | 6 | 10084 | 10103 | 2574 |
| 567283 | N/A | N/A | CATGTATCCCAGTTTTAAAT | 6 | 10089 | 10108 | 2575 |
| 567284 | N/A | N/A | TAGATGCATGTATCCCAGTT | 41 | 10095 | 10114 | 2576 |
| 567285 | N/A | N/A | TGTTTTAGATGCATGTATCC | 4 | 10100 | 10119 | 2577 |

TABLE 12-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 567286 | N/A | N/A | TACAGTGTTTTAGATGCATG | 25 | 10105 | 10124 | 2578 |
| 567287 | N/A | N/A | AATATTACAGTGTTTTAGAT | 0 | 10110 | 10129 | 2579 |
| 567288 | N/A | N/A | CTTATAAATATTACAGTGTT | 2 | 10116 | 10135 | 2580 |
| 567289 | N/A | N/A | CTTCCTTTCTTATAAATATT | 12 | 10124 | 10143 | 2581 |
| 567290 | N/A | N/A | TTTATCTTCCTTTCTTATAA | 0 | 10129 | 10148 | 2582 |
| 567291 | N/A | N/A | CGTAAGTTTATCTTCCTTTC | 61 | 10135 | 10154 | 91 |
| 567292 | N/A | N/A | TTCCCCGTAAGTTTATCTTC | 22 | 10140 | 10159 | 2583 |
| 567293 | N/A | N/A | TGTATTTCCCCGTAAGTTTA | 0 | 10145 | 10164 | 2584 |
| 567294 | N/A | N/A | GTTACTGTATTTCCCCGTAA | 43 | 10150 | 10169 | 2585 |
| 544120 | 707 | 726 | AGTTCTTGGTGCTCTTGGCT | 80 | 6720 | 6739 | 15 |
| 337487 | 804 | 823 | CACTTGTATGTTCACCTCTG | 80 | 7389 | 7408 | 28 |

TABLE 13

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 563780 | N/A | N/A | TGTTTTCTTCTGGAAGCAGA | 10 | 3100 | 3119 | 2586 |
| 568085 | N/A | N/A | CAGACCTAGACTTCTTAACT | 8 | 3084 | 3103 | 2587 |
| 568086 | N/A | N/A | AGCAGACCTAGACTTCTTAA | 6 | 3086 | 3105 | 2588 |
| 568087 | N/A | N/A | TTTTCTTCTGGAAGCAGACC | 0 | 3098 | 3117 | 2589 |
| 568088 | N/A | N/A | AAACATATATACATGCTTGT | 52 | 11323 | 11342 | 2590 |
| 568089 | N/A | N/A | TTAAACATATATACATGCTT | 39 | 11325 | 11344 | 2591 |
| 568090 | N/A | N/A | GTTTATTGAATTTTAAACAT | 0 | 11337 | 11356 | 2592 |
| 568091 | N/A | N/A | TTGTTTATTGAATTTTAAAC | 9 | 11339 | 11358 | 2593 |
| 568092 | N/A | N/A | CTTTGTTTATTGAATTTTAA | 0 | 11341 | 11360 | 2594 |
| 568093 | N/A | N/A | GTCTTTGTTTATTGAATTTT | 28 | 11343 | 11362 | 2595 |
| 568094 | N/A | N/A | GGGTCTTTGTTTATTGAATT | 0 | 11345 | 11364 | 2596 |
| 568095 | N/A | N/A | CTGGGTCTTTGTTTATTGAA | 11 | 11347 | 11366 | 2597 |
| 568096 | N/A | N/A | GACTGGGTCTTTGTTTATTG | 35 | 11349 | 11368 | 2598 |
| 568097 | N/A | N/A | TTTCTATAATTTAGGGACTG | 12 | 11364 | 11383 | 2599 |
| 568098 | N/A | N/A | AATTTCTATAATTTAGGGAC | 0 | 11366 | 11385 | 2600 |
| 568099 | N/A | N/A | TAAATTTCTATAATTTAGGG | 5 | 11368 | 11387 | 2601 |
| 568100 | N/A | N/A | CAAGAATAATTTAAATTTCT | 38 | 11379 | 11398 | 2602 |

TABLE 13-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 568101 | N/A | N/A | GATAAACATGCAAGAATAAT | 1 | 11389 | 11408 | 2603 |
| 568102 | N/A | N/A | TCGATAAACATGCAAGAATA | 51 | 11391 | 11410 | 2604 |
| 568103 | N/A | N/A | TGTCGATAAACATGCAAGAA | 37 | 11393 | 11412 | 2605 |
| 568104 | N/A | N/A | GATGTCGATAAACATGCAAG | 57 | 11395 | 11414 | 2606 |
| 568105 | N/A | N/A | GTGATGTCGATAAACATGCA | 61 | 11397 | 11416 | 2607 |
| 568106 | N/A | N/A | TTGTGATGTCGATAAACATG | 57 | 11399 | 11418 | 2608 |
| 568107 | N/A | N/A | TGTTGTGATGTCGATAAACA | 47 | 11401 | 11420 | 2609 |
| 568108 | N/A | N/A | TCTGTTGTGATGTCGATAAA | 53 | 11403 | 11422 | 2610 |
| 568109 | N/A | N/A | GATCTGTTGTGATGTCGATA | 36 | 11405 | 11424 | 2611 |
| 568110 | N/A | N/A | GGGATCTGTTGTGATGTCGA | 41 | 11407 | 11426 | 2612 |
| 568111 | N/A | N/A | TAGGGATCTGTTGTGATGTC | 43 | 11409 | 11428 | 2613 |
| 568112 | N/A | N/A | TTTAGGGATCTGTTGTGATG | 18 | 11411 | 11430 | 2614 |
| 568113 | N/A | N/A | GATTTAGGGATCTGTTGTGA | 41 | 11413 | 11432 | 2615 |
| 568114 | N/A | N/A | ATCTAATCTTTAGGGATTTA | 37 | 11435 | 11454 | 2616 |
| 568115 | N/A | N/A | TTTGTATCTAATCTTTAGGG | 28 | 11440 | 11459 | 2617 |
| 568116 | N/A | N/A | AATTTGTATCTAATCTTTAG | 0 | 11442 | 11461 | 2618 |
| 568117 | N/A | N/A | GTGGTAAAAATTTGTATCT | 13 | 11451 | 11470 | 2619 |
| 568118 | N/A | N/A | CTGTGGTAAAAATTTGTAT | 5 | 11453 | 11472 | 2620 |
| 568119 | N/A | N/A | TACTGTGGTAAAAATTTGT | 10 | 11455 | 11474 | 2621 |
| 568120 | N/A | N/A | GATACTGTGGTAAAAATTT | 17 | 11457 | 11476 | 2622 |
| 568121 | N/A | N/A | AGTGATACTGTGGTAAAAA | 38 | 11460 | 11479 | 2623 |
| 568122 | N/A | N/A | CAAGTGATACTGTGGTAAAA | 58 | 11462 | 11481 | 2624 |
| 568123 | N/A | N/A | GACAAGTGATACTGTGGTAA | 52 | 11464 | 11483 | 2625 |
| 568124 | N/A | N/A | CTGACAAGTGATACTGTGGT | 62 | 11466 | 11485 | 2626 |
| 568125 | N/A | N/A | TTCTGACAAGTGATACTGTG | 27 | 11468 | 11487 | 2627 |
| 568126 | N/A | N/A | AATTCTGACAAGTGATACTG | 33 | 11470 | 11489 | 2628 |
| 568127 | N/A | N/A | ATAAATTCTGACAAGTGATA | 38 | 11473 | 11492 | 2629 |
| 568128 | N/A | N/A | CTGGCAGTTTTAAAAAATCA | 28 | 11502 | 11521 | 2630 |
| 568129 | N/A | N/A | TTCTTACTGGCAGTTTTAAA | 56 | 11508 | 11527 | 2631 |
| 568130 | N/A | N/A | ATTTCTTACTGGCAGTTTTA | 47 | 11510 | 11529 | 2632 |
| 568131 | N/A | N/A | AAATTTCTTACTGGCAGTTT | 53 | 11512 | 11531 | 2633 |
| 568132 | N/A | N/A | TTTAAAATTTCTTACTGGCA | 46 | 11516 | 11535 | 2634 |
| 568133 | N/A | N/A | TTAATTTAAAATTTCTTACT | 9 | 11520 | 11539 | 2635 |
| 568134 | N/A | N/A | CAAATGGGTTTAATTTAAAA | 1 | 11529 | 11548 | 2636 |
| 568135 | N/A | N/A | AACAAATGGGTTTAATTTAA | 11 | 11531 | 11550 | 2637 |
| 568136 | N/A | N/A | TTAACAAATGGGTTTAATTT | 12 | 11533 | 11552 | 2638 |

TABLE 13-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 568137 | N/A | N/A | CTTTAACAAATGGGTTTAAT | 27 | 11535 | 11554 | 2639 |
| 568138 | N/A | N/A | TCCTTTAACAAATGGGTTTA | 52 | 11537 | 11556 | 2640 |
| 568139 | N/A | N/A | CTATATCCTTTAACAAATGG | 24 | 11542 | 11561 | 2641 |
| 568140 | N/A | N/A | GGGCACTATATCCTTTAACA | 45 | 11547 | 11566 | 2642 |
| 568141 | N/A | N/A | TTGGGCACTATATCCTTTAA | 20 | 11549 | 11568 | 2643 |
| 568142 | N/A | N/A | TATAACTTGGGCACTATATC | 27 | 11555 | 11574 | 2644 |
| 568143 | N/A | N/A | CATATAACTTGGGCACTATA | 40 | 11557 | 11576 | 2645 |
| 568144 | N/A | N/A | ACCATATAACTTGGGCACTA | 69 | 11559 | 11578 | 103 |
| 568145 | N/A | N/A | TCACCATATAACTTGGGCAC | 60 | 11561 | 11580 | 2646 |
| 568146 | N/A | N/A | GGTCACCATATAACTTGGGC | 73 | 11563 | 11582 | 104 |
| 568147 | N/A | N/A | TAGGTCACCATATAACTTGG | 51 | 11565 | 11584 | 2647 |
| 568148 | N/A | N/A | GGTAGGTCACCATATAACTT | 57 | 11567 | 11586 | 2648 |
| 568149 | N/A | N/A | AAGGTAGGTCACCATATAAC | 52 | 11569 | 11588 | 2649 |
| 568150 | N/A | N/A | CAAAGGTAGGTCACCATATA | 28 | 11571 | 11590 | 2650 |
| 568151 | N/A | N/A | GACAAAGGTAGGTCACCATA | 67 | 11573 | 11592 | 105 |
| 568152 | N/A | N/A | GTATTGACAAAGGTAGGTCA | 55 | 11578 | 11597 | 2651 |
| 568153 | N/A | N/A | AAGTATTGACAAAGGTAGGT | 36 | 11580 | 11599 | 2652 |
| 568154 | N/A | N/A | CTAAGTATTGACAAAGGTAG | 24 | 11582 | 11601 | 2653 |
| 568155 | N/A | N/A | TGCTAAGTATTGACAAAGGT | 49 | 11584 | 11603 | 2654 |
| 568156 | N/A | N/A | AATGCTAAGTATTGACAAAG | 10 | 11586 | 11605 | 2655 |
| 568157 | N/A | N/A | CATAATGCTAAGTATTGACA | 19 | 11589 | 11608 | 2656 |
| 568158 | N/A | N/A | TACATAATGCTAAGTATTGA | 4 | 11591 | 11610 | 2657 |
| 568159 | N/A | N/A | AATACATAATGCTAAGTATT | 1 | 11593 | 11612 | 2658 |
| 568160 | N/A | N/A | GAAATACATAATGCTAAGTA | 23 | 11595 | 11614 | 2659 |
| 568161 | N/A | N/A | TTTGAAATACATAATGCTAA | 8 | 11598 | 11617 | 2660 |
| 568162 | N/A | N/A | GGATAATTTGAAATACATAA | 16 | 11604 | 11623 | 2661 |
| 568163 | N/A | N/A | TTGGATAATTTGAAATACAT | 0 | 11606 | 11625 | 2662 |
| 568164 | N/A | N/A | TATTGGATAATTTGAAATAC | 0 | 11608 | 11627 | 2663 |
| 568165 | N/A | N/A | ATCCAGTTAAAGCTTGTAAA | 46 | 4466 | 4485 | 2664 |
| 568166 | N/A | N/A | TCATGATCCAGTTAAAGCTT | 32 | 4471 | 4490 | 2665 |
| 568167 | N/A | N/A | TTTACTCATGATCCAGTTAA | 24 | 4476 | 4495 | 2666 |
| 568168 | N/A | N/A | GATAATTTTACTCATGATCC | 53 | 4482 | 4501 | 2667 |
| 568169 | N/A | N/A | GATGTGATAATTTTACTCAT | 27 | 4487 | 4506 | 2668 |
| 568170 | N/A | N/A | ATGCTGATGTGATAATTTTA | 42 | 4492 | 4511 | 2669 |
| 568171 | N/A | N/A | CAGTTATGCTGATGTGATAA | 0 | 4497 | 4516 | 2670 |

TABLE 13-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 568172 | N/A | N/A | TTTAACAGTTATGCTGATGT | 17 | 4502 | 4521 | 2671 |
| 568173 | N/A | N/A | GCAATTTTAACAGTTATGCT | 11 | 4507 | 4526 | 2672 |
| 568174 | N/A | N/A | AGAGCCTGCAATTTTAACAG | 25 | 4514 | 4533 | 2673 |
| 568175 | N/A | N/A | GCTTCAGAGCCTGCAATTTT | 47 | 4519 | 4538 | 2674 |
| 568176 | N/A | N/A | TATTAGCTTCAGAGCCTGCA | 48 | 4524 | 4543 | 2675 |
| 568177 | N/A | N/A | TAGTTTATTAGCTTCAGAGC | 20 | 4529 | 4548 | 2676 |
| 568178 | N/A | N/A | GCAGGTAGTTTATTAGCTTC | 39 | 4534 | 4553 | 2677 |
| 568179 | N/A | N/A | TAAATGCAGGTAGTTTATTA | 0 | 4539 | 4558 | 2678 |
| 568180 | N/A | N/A | ATGGTTTAAATGCAGGTAGT | 20 | 4545 | 4564 | 2679 |
| 568181 | N/A | N/A | GAGCCATGGTTTAAATGCAG | 33 | 4550 | 4569 | 2680 |
| 568182 | N/A | N/A | TTTTAGAGCCATGGTTTAAA | 40 | 4555 | 4574 | 2681 |
| 568183 | N/A | N/A | CAAAGTTTTAGAGCCATGGT | 54 | 4560 | 4579 | 2682 |
| 568184 | N/A | N/A | TCACACAAAGTTTTAGAGCC | 61 | 4565 | 4584 | 2683 |
| 568185 | N/A | N/A | CAAGGTCACACAAAGTTTTA | 17 | 4570 | 4589 | 2684 |
| 568186 | N/A | N/A | GGGTGAAGTAATTTATTCAA | 0 | 4587 | 4606 | 2685 |
| 568187 | N/A | N/A | GTGAGGAAACTGAGAGATAA | 12 | 4609 | 4628 | 2686 |
| 568188 | N/A | N/A | TGTAGTATATGTGAGGAAAC | 38 | 4619 | 4638 | 2687 |
| 568189 | N/A | N/A | ATCTTTGTAGTATATGTGAG | 30 | 4624 | 4643 | 2688 |
| 568190 | N/A | N/A | TTATTATCTTTGTAGTATAT | 19 | 4629 | 4648 | 2689 |
| 568191 | N/A | N/A | TTCTGTTATTATCTTTGTAG | 48 | 4634 | 4653 | 2690 |
| 568192 | N/A | N/A | ATAAGTTCTGTTATTATCTT | 16 | 4639 | 4658 | 2691 |
| 568193 | N/A | N/A | ATCCTATAAGTTCTGTTATT | 22 | 4644 | 4663 | 2692 |
| 568194 | N/A | N/A | CAATAATCCTATAAGTTCTG | 0 | 4649 | 4668 | 2693 |
| 568195 | N/A | N/A | TAAGATGACATTGGCTGCTA | 49 | 4689 | 4708 | 2694 |
| 568196 | N/A | N/A | TTTAGTAAGATGACATTGGC | 32 | 4694 | 4713 | 2695 |
| 568197 | N/A | N/A | TTGAATTTAGTAAGATGAC | 19 | 4700 | 4719 | 2696 |
| 568198 | N/A | N/A | CTAATTTGAATTTTAGTAAG | 34 | 4705 | 4724 | 2697 |
| 568199 | N/A | N/A | CATGATCTAATTTGAATTTT | 29 | 4711 | 4730 | 2698 |
| 568200 | N/A | N/A | CAAAGAGAAACATGATCTAA | 27 | 4721 | 4740 | 2699 |
| 568201 | N/A | N/A | GTTTTGAGCAAAGAGAAACA | 36 | 4729 | 4748 | 2700 |
| 568202 | N/A | N/A | GTGTGGTTTTGAGCAAAGAG | 3 | 4734 | 4753 | 2701 |
| 568203 | N/A | N/A | AGCTATTGTGTGGTTTTGAG | 13 | 4741 | 4760 | 2702 |
| 568204 | N/A | N/A | TGAAATGGAAAGCTATTGTG | 15 | 4751 | 4770 | 2703 |
| 568205 | N/A | N/A | TATGAGTGAAATGGAAAGCT | 27 | 4757 | 4776 | 2704 |
| 568206 | N/A | N/A | GCCAATATGAGTGAAATGGA | 62 | 4762 | 4781 | 106 |
| 568207 | N/A | N/A | AAAGAGCCAATATGAGTGAA | 25 | 4767 | 4786 | 2705 |

TABLE 13-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 568208 | N/A | N/A | TTGGTCTAAAGAGCCAATAT | 42 | 4774 | 4793 | 2706 |
| 568209 | N/A | N/A | GGTAATCTTGGTCTAAAGAG | 29 | 4781 | 4800 | 2707 |
| 568210 | N/A | N/A | GTGAGATGACGAAGGGTTGG | 0 | 4800 | 4819 | 2708 |
| 568211 | N/A | N/A | AGTCAGTGAGATGACGAAGG | 5 | 4805 | 4824 | 2709 |
| 568212 | N/A | N/A | GGTGAAGTCAGTGAGATGAC | 12 | 4810 | 4829 | 2710 |
| 568213 | N/A | N/A | GTAGAGGAGGTGAAGTCAGT | 13 | 4818 | 4837 | 2711 |
| 568214 | N/A | N/A | AACTAGAGTAGAGGAGGTGA | 20 | 4825 | 4844 | 2712 |
| 568215 | N/A | N/A | AGAATAACTAGAGTAGAGGA | 33 | 4830 | 4849 | 2713 |
| 568216 | N/A | N/A | CGGTCAGAATAACTAGAGTA | 39 | 4835 | 4854 | 2714 |
| 568217 | N/A | N/A | TAAAGCGGTCAGAATAACTA | 29 | 4840 | 4859 | 2715 |
| 568218 | N/A | N/A | ACTGGTAAAGCGGTCAGAAT | 17 | 4845 | 4864 | 2716 |
| 568219 | N/A | N/A | TGAATACTGGTAAAGCGGTC | 37 | 4850 | 4869 | 2717 |
| 568220 | N/A | N/A | TGTGTTTGAATACTGGTAAA | 21 | 4856 | 4875 | 2718 |
| 568221 | N/A | N/A | AGTATGTTTGATGTGTTTGA | 25 | 4867 | 4886 | 2719 |
| 568222 | N/A | N/A | GTGGCAGTATGTTTGATGTG | 15 | 4872 | 4891 | 2720 |
| 568223 | N/A | N/A | TTGAGGTGGCAGTATGTTTG | 14 | 4877 | 4896 | 2721 |
| 568224 | N/A | N/A | AGGCTTTGAGGTGGCAGTAT | 33 | 4882 | 4901 | 2722 |
| 568225 | N/A | N/A | GGCAAAGGCTTTGAGGTGGC | 27 | 4887 | 4906 | 2723 |
| 568226 | N/A | N/A | AACAAGGGCAAAGGCTTTGA | 24 | 4893 | 4912 | 2724 |
| 568227 | N/A | N/A | TAGAGGAAACAACAAGGGCA | 24 | 4903 | 4922 | 2725 |
| 568228 | N/A | N/A | CCAGTTAGAGGAAACAACAA | 4 | 4908 | 4927 | 2726 |
| 568229 | N/A | N/A | GATACCAGGGCAGAAGAGCG | 24 | 4930 | 4949 | 2727 |
| 568230 | N/A | N/A | AAATCAGAGAGTGGGCCACG | 24 | 4952 | 4971 | 2728 |
| 568231 | N/A | N/A | CCTAAGGGAAATCAGAGAGT | 19 | 4960 | 4979 | 2729 |
| 568232 | N/A | N/A | ACGACCCTAAGGGAAATCAG | 30 | 4965 | 4984 | 2730 |
| 568233 | N/A | N/A | TGATAACGACCCTAAGGGAA | 0 | 4970 | 4989 | 2731 |
| 568234 | N/A | N/A | TTTTGTTTGATAACGACCCT | 22 | 4977 | 4996 | 2732 |
| 568235 | N/A | N/A | GTCTTCATTGGGAATTTTTT | 37 | 4993 | 5012 | 2733 |
| 568236 | N/A | N/A | TGTAAGTCTTCATTGGGAAT | 23 | 4998 | 5017 | 2734 |
| 568237 | N/A | N/A | GACCTTGTAAGTCTTCATTG | 52 | 5003 | 5022 | 2735 |
| 568238 | N/A | N/A | TAAGTGACCTTGTAAGTCTT | 36 | 5008 | 5027 | 2736 |
| 568239 | N/A | N/A | TTGGTTAAGTGACCTTGTAA | 11 | 5013 | 5032 | 2737 |
| 568240 | N/A | N/A | TGATTTTGGTTAAGTGACC | 12 | 5019 | 5038 | 2738 |
| 568241 | N/A | N/A | GGTTGTGATTTTGGTTAAG | 11 | 5024 | 5043 | 2739 |
| 568242 | N/A | N/A | CAGGCGGTTGTGATTTTGG | 41 | 5029 | 5048 | 2740 |

TABLE 13-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 568243 | N/A | N/A | GGGACCAGGCGGTTGTGATT | 22 | 5034 | 5053 | 2741 |
| 568244 | N/A | N/A | CTAAGGAAGTAGAAGTTTTC | 42 | 5060 | 5079 | 2742 |
| 568245 | N/A | N/A | AGTAGCTAAGGAAGTAGAAG | 11 | 5065 | 5084 | 2743 |
| 568246 | N/A | N/A | CAGGAGAAAAGTAGCTAAGG | 36 | 5074 | 5093 | 2744 |
| 568247 | N/A | N/A | GTGTGCAGGAGAAAAGTAGC | 14 | 5079 | 5098 | 2745 |
| 568248 | N/A | N/A | TAAAGGTGAGTGTGCAGGAG | 7 | 5088 | 5107 | 2746 |
| 568249 | N/A | N/A | ATGTTAAATAAAGGTGAGTG | 8 | 5096 | 5115 | 2747 |
| 568250 | N/A | N/A | ATGTTATGTTAAATAAAGGT | 27 | 5101 | 5120 | 2748 |
| 568251 | N/A | N/A | AATTTATGTTATGTTAAATA | 27 | 5106 | 5125 | 2749 |
| 568252 | N/A | N/A | TAACTAAAATTTATGTTATG | 28 | 5113 | 5132 | 2750 |
| 568253 | N/A | N/A | GATAAATAACTAAAATTTAT | 32 | 5119 | 5138 | 2751 |
| 568254 | N/A | N/A | TTTAGTGCAGGAATAGAAGA | 33 | 5139 | 5158 | 2752 |
| 568255 | N/A | N/A | AATCCCTGTATTCACAGAGC | 68 | 5165 | 5184 | 2753 |
| 568256 | N/A | N/A | GAAAAAATCCCTGTATTCAC | 0 | 5170 | 5189 | 2754 |
| 568257 | N/A | N/A | TAATGGAAAAAATCCCTGTA | 8 | 5175 | 5194 | 2755 |
| 568258 | N/A | N/A | AAATATGAAGATAATGGAAA | 26 | 5186 | 5205 | 2756 |
| 568259 | N/A | N/A | ATAATGGAAAATATGAAGAT | 18 | 5194 | 5213 | 2757 |
| 568260 | N/A | N/A | TATACAAATAATGGAAAATA | 30 | 5201 | 5220 | 2758 |
| 568261 | N/A | N/A | TTCTGGAGTATATACAAATA | 45 | 5211 | 5230 | 2759 |
| 568262 | N/A | N/A | ATTCTATATTCTGGAGTATA | 40 | 5219 | 5238 | 2760 |
| 568263 | N/A | N/A | CCATACAGTATTCTATATTC | 57 | 5228 | 5247 | 2761 |
| 568264 | N/A | N/A | CTGTGTGCCATACAGTATTC | 28 | 5235 | 5254 | 2762 |
| 568265 | N/A | N/A | GCCTACTGTGTGCCATACAG | 60 | 5240 | 5259 | 2763 |
| 568266 | N/A | N/A | AGAAATGCCTACTGTGTGCC | 42 | 5246 | 5265 | 2764 |
| 568267 | N/A | N/A | TCAACAGAAATGCCTACTGT | 52 | 5251 | 5270 | 2765 |
| 568268 | N/A | N/A | ATTAATTCAACAGAAATGCC | 46 | 5257 | 5276 | 2766 |
| 568269 | N/A | N/A | GACATTACATTTATTAATTC | 32 | 5269 | 5288 | 2767 |
| 568270 | N/A | N/A | GTGAATATGACATTACATTT | 32 | 5277 | 5296 | 2768 |
| 568271 | N/A | N/A | CTTCTGTGTGAATATGACAT | 50 | 5284 | 5303 | 2769 |
| 568272 | N/A | N/A | ACACGCTTCTGTGTGAATAT | 43 | 5289 | 5308 | 2770 |
| 568273 | N/A | N/A | ATAGCACACGCTTCTGTGTG | 31 | 5294 | 5313 | 2771 |
| 568274 | N/A | N/A | TAATCATAGCACACGCTTCT | 40 | 5299 | 5318 | 2772 |
| 568275 | N/A | N/A | AATAATAATCATAGCACACG | 20 | 5304 | 5323 | 2773 |
| 568276 | N/A | N/A | CCAAGTAATAATAATCATAG | 35 | 5310 | 5329 | 2774 |
| 568277 | N/A | N/A | CTAGTAATCCAAGTAATAAT | 38 | 5318 | 5337 | 2775 |
| 568278 | N/A | N/A | TATTTCTAGTAATCCAAGTA | 39 | 5323 | 5342 | 2776 |

TABLE 13-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 568279 | N/A | N/A | CACACTATTTCTAGTAATCC | 51 | 5328 | 5347 | 2777 |
| 568280 | N/A | N/A | TTATGAGGCACACTATTTCT | 25 | 5336 | 5355 | 2778 |
| 568281 | N/A | N/A | TTTAATTATGAGGCACACTA | 35 | 5341 | 5360 | 2779 |
| 568282 | N/A | N/A | GTTGACCTTTAATTATGAGG | 63 | 5348 | 5367 | 2780 |
| 568283 | N/A | N/A | TTACATTGTTGAATGTTGAC | 45 | 5362 | 5381 | 2781 |
| 568284 | N/A | N/A | ATTAATTACATTGTTGAATG | 31 | 5367 | 5386 | 2782 |
| 568285 | N/A | N/A | TGTAGATTAATTACATTGTT | 49 | 5372 | 5391 | 2783 |
| 568286 | N/A | N/A | TACATTGTAGATTAATTACA | 43 | 5377 | 5396 | 2784 |
| 568287 | N/A | N/A | AGATGTTTACATTGTAGATT | 28 | 5384 | 5403 | 2785 |
| 568288 | N/A | N/A | TTCACCAGATGTTTACATTG | 36 | 5390 | 5409 | 2786 |
| 568289 | N/A | N/A | GTCACTTCACCAGATGTTTA | 65 | 5395 | 5414 | 2787 |
| 568290 | N/A | N/A | CCTCTGTCACTTCACCAGAT | 67 | 5400 | 5419 | 2788 |
| 568291 | N/A | N/A | GCTTCCCTCTGTCACTTCAC | 70 | 5405 | 5424 | 2789 |
| 568292 | N/A | N/A | CAAGTGCTTCCCTCTGTCAC | 33 | 5410 | 5429 | 2790 |
| 568293 | N/A | N/A | TTTCTAAACAAGTGCTTCCC | 70 | 5418 | 5437 | 107 |
| 568294 | N/A | N/A | GCTTTTTTCTAAACAAGTGC | 45 | 5423 | 5442 | 2791 |
| 568295 | N/A | N/A | ACATAGCTTTTTTCTAAACA | 9 | 5428 | 5447 | 2792 |
| 568296 | N/A | N/A | TTCTGACATAGCTTTTTTCT | 23 | 5433 | 5452 | 2793 |
| 568297 | N/A | N/A | ATGGATTCTGACATAGCTTT | 46 | 5438 | 5457 | 2794 |
| 568298 | N/A | N/A | AATACATGGATTCTGACATA | 37 | 5443 | 5462 | 2795 |
| 568299 | N/A | N/A | ATTAGAATACATGGATTCTG | 57 | 5448 | 5467 | 2796 |
| 568300 | N/A | N/A | CTGCATATTAGAATACATGG | 75 | 5454 | 5473 | 108 |
| 568301 | N/A | N/A | TTGTACTGCATATTAGAATA | 53 | 5459 | 5478 | 2797 |
| 568302 | N/A | N/A | AACTATTGTACTGCATATTA | 25 | 5464 | 5483 | 2798 |
| 568303 | N/A | N/A | TTTTAAACTATTGTACTGCA | 25 | 5469 | 5488 | 2799 |
| 568304 | N/A | N/A | TGAGAGTATTATTAATATTT | 8 | 5487 | 5506 | 2800 |
| 568305 | N/A | N/A | GCTGTTTGAGAGTATTATTA | 50 | 5493 | 5512 | 2801 |
| 568306 | N/A | N/A | GAATAGCTGTTTGAGAGTAT | 38 | 5498 | 5517 | 2802 |
| 568307 | N/A | N/A | CCTCTTGAATAGCTGTTTGA | 55 | 5504 | 5523 | 2803 |
| 568308 | N/A | N/A | TGAATCCTCTTGAATAGCTG | 55 | 5509 | 5528 | 2804 |
| 568309 | N/A | N/A | TTTTTTGAATCCTCTTGAAT | 46 | 5514 | 5533 | 2805 |
| 568310 | N/A | N/A | TTATGTTTTTTGAATCCTCT | 36 | 5519 | 5538 | 2806 |
| 568311 | N/A | N/A | GTTTATATTATGTTTTTTGA | 6 | 5526 | 5545 | 2807 |
| 568312 | N/A | N/A | TCTGAGTTTATATTATGTTT | 29 | 5531 | 5550 | 2808 |
| 568313 | N/A | N/A | CAGTTTCTCTGAGTTTATAT | 28 | 5538 | 5557 | 2809 |

TABLE 13-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 568314 | N/A | N/A | GTTTACCAGTTTCTCTGAGT | 44 | 5544 | 5563 | 2810 |
| 568315 | N/A | N/A | ATTTTGTTTACCAGTTTCTC | 58 | 5549 | 5568 | 2811 |
| 568316 | N/A | N/A | AAATGATTTTGTTTACCAGT | 29 | 5554 | 5573 | 2812 |
| 568317 | N/A | N/A | CTCTTGAAAATGATTTTGTT | 22 | 5561 | 5580 | 2813 |
| 568318 | N/A | N/A | TATATCTCTTGAAAATGATT | 5 | 5566 | 5585 | 2814 |
| 568319 | N/A | N/A | CAGGTTGGCAAGTTTGTTTG | 27 | 6175 | 6194 | 2815 |
| 568320 | N/A | N/A | GTTGGCAGGTTGGCAAGTTT | 44 | 6180 | 6199 | 2816 |
| 568321 | N/A | N/A | ATATCTGTAGATGTTGGCAG | 59 | 6192 | 6211 | 2817 |
| 568322 | N/A | N/A | TAAACATATCTGTAGATGTT | 18 | 6197 | 6216 | 2818 |
| 568323 | N/A | N/A | ACCTGTAAACATATCTGTAG | 57 | 6202 | 6221 | 2819 |
| 568324 | N/A | N/A | TTTTGACCTGTAAACATATC | 23 | 6207 | 6226 | 2820 |
| 568325 | N/A | N/A | ATAATTTTGACCTGTAAAC | 7 | 6212 | 6231 | 2821 |
| 568326 | N/A | N/A | TAATTTGATAATTTTTGACC | 7 | 6219 | 6238 | 2822 |
| 568327 | N/A | N/A | TTCTTGATAATTTGATAATT | 8 | 6226 | 6245 | 2823 |
| 568328 | N/A | N/A | ACCAGGCTTTCTTGATAATT | 55 | 6234 | 6253 | 2824 |
| 568329 | N/A | N/A | TTTGAACCAGGCTTTCTTGA | 49 | 6239 | 6258 | 2825 |
| 568330 | N/A | N/A | CATAATTTGAACCAGGCTTT | 68 | 6244 | 6263 | 109 |
| 568331 | N/A | N/A | AGACATAATACATAATTTGA | 8 | 6254 | 6273 | 2826 |
| 568332 | N/A | N/A | CTGTGATAAAGACATAATAC | 40 | 6263 | 6282 | 2827 |
| 568333 | N/A | N/A | CAGACCTGTGATAAAGACAT | 16 | 6268 | 6287 | 2828 |
| 568334 | N/A | N/A | ATCTTCAGACCTGTGATAAA | 7 | 6273 | 6292 | 2829 |
| 568335 | N/A | N/A | TACTGATCTTCAGACCTGTG | 47 | 6278 | 6297 | 2830 |
| 568336 | N/A | N/A | TTAATAATTTTCAGTTTTAG | 35 | 6302 | 6321 | 2831 |
| 568337 | N/A | N/A | TAAGTTTAATAATTTTCAGT | 23 | 6307 | 6326 | 2832 |
| 568338 | N/A | N/A | TTCAGATTTAAGTTTAATA | 10 | 6316 | 6335 | 2833 |
| 568339 | N/A | N/A | TATATTTGATATTCTGTTCA | 42 | 6332 | 6351 | 2834 |
| 568340 | N/A | N/A | ATATTGTAATGTATTCTTTT | 0 | 6368 | 6387 | 2835 |
| 568341 | N/A | N/A | TTAGAATATTGTAATGTATT | 19 | 6373 | 6392 | 2836 |
| 568342 | N/A | N/A | TTTGCTTAGAATATTGTAAT | 9 | 6378 | 6397 | 2837 |
| 568343 | N/A | N/A | ACTGCTTTGCTTAGAATATT | 36 | 6383 | 6402 | 2838 |
| 568344 | N/A | N/A | AAGTAGAGACTGCTTTGCTT | 60 | 6391 | 6410 | 2839 |
| 568345 | N/A | N/A | GCAAGGCCAAAAGTAGAGAC | 59 | 6401 | 6420 | 2840 |
| 568346 | N/A | N/A | ACAGAGCAAGGCCAAAAGTA | 45 | 6406 | 6425 | 2841 |
| 568347 | N/A | N/A | GGAAAACAGAGCAAGGCCAA | 49 | 6411 | 6430 | 2842 |
| 568348 | N/A | N/A | TGGTCGGAAAACAGAGCAAG | 38 | 6416 | 6435 | 2843 |
| 568349 | N/A | N/A | GACATTGGTCGGAAAACAGA | 26 | 6421 | 6440 | 2844 |

TABLE 13-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 568350 | N/A | N/A | AAGCAGACATTGGTCGGAAA | 50 | 6426 | 6445 | 2845 |
| 568351 | N/A | N/A | CAAGGCAAAAAGCAGACAT | 39 | 6436 | 6455 | 2846 |
| 568352 | N/A | N/A | ATAAAGCAAGGCAAAAAGC | 20 | 6442 | 6461 | 2847 |
| 568353 | N/A | N/A | CATTATTTAATAAGATAAAA | 29 | 6464 | 6483 | 2848 |
| 568354 | N/A | N/A | AAATATTTAATCAGGGACAT | 35 | 6481 | 6500 | 2849 |
| 568355 | N/A | N/A | TGTTCTCAAAATATTTAATC | 32 | 6489 | 6508 | 2850 |
| 568356 | N/A | N/A | GATTACCTGTTCTCAAAATA | 40 | 6496 | 6515 | 2851 |
| 568357 | N/A | N/A | GATTGTACAGATTACCTGTT | 12 | 6505 | 6524 | 2852 |
| 568358 | N/A | N/A | ATTCAGATTGTACAGATTAC | 34 | 6510 | 6529 | 2853 |
| 568359 | N/A | N/A | AAACAGTGTTATTCAGATTG | 32 | 6520 | 6539 | 2854 |
| 568360 | N/A | N/A | TAGATAAACAGTGTTATTCA | 25 | 6525 | 6544 | 2855 |
| 568361 | N/A | N/A | ATATTTAGATAAACAGTGTT | 14 | 6530 | 6549 | 2856 |
| 568362 | N/A | N/A | GTTTGATATTTAGATAAACA | 27 | 6535 | 6554 | 2857 |
| 568363 | N/A | N/A | AACGGTGTTTGATATTTAGA | 33 | 6541 | 6560 | 2858 |
| 568364 | N/A | N/A | GTTATAACGGTGTTTGATAT | 29 | 6546 | 6565 | 2859 |
| 568365 | N/A | N/A | ATAATGTTATAACGGTGTTT | 21 | 6551 | 6570 | 2860 |
| 568366 | N/A | N/A | AGTTCATAATGTTATAACGG | 37 | 6556 | 6575 | 2861 |
| 568367 | N/A | N/A | CTTTCAGTTCATAATGTTAT | 46 | 6561 | 6580 | 2862 |
| 568368 | N/A | N/A | AGTACAGTTTGTCTTTCAGT | 48 | 6573 | 6592 | 2863 |
| 568369 | N/A | N/A | TCAGAAGTACAGTTTGTCTT | 47 | 6578 | 6597 | 2864 |
| 568370 | N/A | N/A | GGATGTCAGAAGTACAGTTT | 46 | 6583 | 6602 | 2865 |
| 568371 | N/A | N/A | GAGTAAGGATGTCAGAAGTA | 45 | 6589 | 6608 | 2866 |
| 568372 | N/A | N/A | GAAATCTGAGTAAGGATGTC | 31 | 6596 | 6615 | 2867 |
| 568373 | N/A | N/A | TACTGAATATACAATTAGGG | 5 | 6616 | 6635 | 2868 |
| 568374 | N/A | N/A | AATGATACTGAATATACAAT | 21 | 6621 | 6640 | 2869 |
| 568375 | N/A | N/A | GAATATAAATCTGTTTTTA | 19 | 6642 | 6661 | 2870 |
| 568376 | N/A | N/A | TAAAAGAATATAAATCTGTT | 32 | 6647 | 6666 | 2871 |
| 568377 | N/A | N/A | GCTGATAAAGAATATAAAT | 50 | 6652 | 6671 | 2872 |
| 568378 | N/A | N/A | CCTTCTGAGCTGATAAAGA | 37 | 6660 | 6679 | 2873 |
| 568379 | N/A | N/A | CTAGTCCTTCTGAGCTGATA | 45 | 6665 | 6684 | 2874 |
| 568380 | N/A | N/A | TTACCATCATGTTTTACATT | 30 | 6770 | 6789 | 2875 |
| 568381 | N/A | N/A | CAAAGTGTCTTACCATCATG | 24 | 6779 | 6798 | 2876 |
| 568382 | N/A | N/A | AAACCCACCAAAGTGTCTTA | 15 | 6787 | 6806 | 2877 |
| 568383 | N/A | N/A | AGAAGGAAACCCACCAAAGT | 22 | 6793 | 6812 | 2878 |
| 568384 | N/A | N/A | AATAATAGCTTCAAGAAGGA | 25 | 6806 | 6825 | 2879 |

TABLE 13-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 568385 | N/A | N/A | AATTTGATAATAATAGCTTC | 24 | 6814 | 6833 | 2880 |
| 568386 | N/A | N/A | TAGGGAATTTGATAATAATA | 20 | 6819 | 6838 | 2881 |
| 568387 | N/A | N/A | AAGAATAGGGAATTTGATAA | 0 | 6824 | 6843 | 2882 |
| 568388 | N/A | N/A | GTCCTAAGAATAGGGAATTT | 45 | 6829 | 6848 | 2883 |
| 568389 | N/A | N/A | TAGAACAAGTCCTAAGAATA | 21 | 6837 | 6856 | 2884 |
| 568390 | N/A | N/A | TTAGTCTAGAACAAGTCCTA | 28 | 6843 | 6862 | 2885 |
| 568391 | N/A | N/A | ATCTTTTAGTCTAGAACAAG | 21 | 6848 | 6867 | 2886 |
| 568392 | N/A | N/A | TAACTATCTTTTAGTCTAGA | 13 | 6853 | 6872 | 2887 |
| 568393 | N/A | N/A | ATCTCTTAACTATCTTTTAG | 28 | 6859 | 6878 | 2888 |
| 568394 | N/A | N/A | TGGATATCTCTTAACTATCT | 48 | 6864 | 6883 | 2889 |
| 568395 | N/A | N/A | TTTGATGGATATCTCTTAAC | 35 | 6869 | 6888 | 2890 |
| 544120 | 707 | 726 | AGTTCTTGGTGCTCTTGGCT | 80 | 6720 | 6739 | 15 |
| 337487 | 804 | 823 | CACTTGTATGTTCACCTCTG | 76 | 7389 | 7408 | 28 |
| 568006 | 2014 | 2033 | TTAATTCTGCTTCATTAGGT | 53 | 10986 | 11005 | 2891 |
| 568007 | 2015 | 2034 | TTTAATTCTGCTTCATTAGG | 38 | 10987 | 11006 | 2892 |
| 568008 | 2020 | 2039 | CAGTATTTAATTCTGCTTCA | 56 | 10992 | 11011 | 2893 |
| 568009 | 2021 | 2040 | ACAGTATTTAATTCTGCTTC | 63 | 10993 | 11012 | 2894 |
| 568010 | 2022 | 2041 | TACAGTATTTAATTCTGCTT | 56 | 10994 | 11013 | 2895 |
| 568011 | 2023 | 2042 | ATACAGTATTTAATTCTGCT | 39 | 10995 | 11014 | 2896 |
| 568012 | 2024 | 2043 | AATACAGTATTTAATTCTGC | 21 | 10996 | 11015 | 2897 |
| 568013 | 2025 | 2044 | TAATACAGTATTTAATTCTG | 12 | 10997 | 11016 | 2898 |
| 568014 | 2027 | 2046 | TTTAATACAGTATTTAATTC | 0 | 10999 | 11018 | 2899 |
| 568015 | 2028 | 2047 | TTTTAATACAGTATTTAATT | 15 | 11000 | 11019 | 2900 |
| 568016 | 2031 | 2050 | TTATTTTAATACAGTATTTA | 0 | 11003 | 11022 | 2901 |
| 568017 | 2034 | 2053 | AACTTATTTTAATACAGTAT | 24 | 11006 | 11025 | 2902 |
| 568018 | 2035 | 2054 | GAACTTATTTTAATACAGTA | 21 | 11007 | 11026 | 2903 |
| 568019 | 2036 | 2055 | CGAACTTATTTTAATACAGT | 2 | 11008 | 11027 | 2904 |
| 568020 | 2037 | 2056 | GCGAACTTATTTTAATACAG | 54 | 11009 | 11028 | 2905 |
| 568021 | 2038 | 2057 | AGCGAACTTATTTTAATACA | 35 | 11010 | 11029 | 2906 |
| 568022 | 2039 | 2058 | CAGCGAACTTATTTTAATAC | 50 | 11011 | 11030 | 2907 |
| 568023 | 2040 | 2059 | ACAGCGAACTTATTTTAATA | 34 | 11012 | 11031 | 2908 |
| 568024 | 2041 | 2060 | GACAGCGAACTTATTTTAAT | 52 | 11013 | 11032 | 2909 |
| 568025 | 2042 | 2061 | AGACAGCGAACTTATTTTAA | 58 | 11014 | 11033 | 2910 |
| 568026 | 2044 | 2063 | AAAGACAGCGAACTTATTTT | 32 | 11016 | 11035 | 2911 |
| 568027 | 2045 | 2064 | TAAAGACAGCGAACTTATTT | 26 | 11017 | 11036 | 2912 |
| 568028 | 2048 | 2067 | GTTTAAAGACAGCGAACTTA | 62 | 11020 | 11039 | 2913 |

TABLE 13-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 568029 | 2049 | 2068 | TGTTTAAAGACAGCGAACTT | 58 | 11021 | 11040 | 2914 |
| 568030 | 2050 | 2069 | TTGTTTAAAGACAGCGAACT | 52 | 11022 | 11041 | 2915 |
| 568031 | 2051 | 2070 | TTTGTTTAAAGACAGCGAAC | 61 | 11023 | 11042 | 2916 |
| 568032 | 2052 | 2071 | ATTTGTTTAAAGACAGCGAA | 41 | 11024 | 11043 | 2917 |
| 568033 | 2053 | 2072 | CATTTGTTTAAAGACAGCGA | 60 | 11025 | 11044 | 2918 |
| 568034 | 2054 | 2073 | CCATTTGTTTAAAGACAGCG | 88 | 11026 | 11045 | 98 |
| 568035 | 2055 | 2074 | TCCATTTGTTTAAAGACAGC | 57 | 11027 | 11046 | 2919 |
| 568036 | 2056 | 2075 | CTCCATTTGTTTAAAGACAG | 58 | 11028 | 11047 | 2920 |
| 568037 | 2058 | 2077 | ATCTCCATTTGTTTAAAGAC | 56 | 11030 | 11049 | 2921 |
| 568038 | 2059 | 2078 | CATCTCCATTTGTTTAAAGA | 54 | 11031 | 11050 | 2922 |
| 568039 | 2060 | 2079 | TCATCTCCATTTGTTTAAAG | 62 | 11032 | 11051 | 2923 |
| 568040 | 2061 | 2080 | GTCATCTCCATTTGTTTAAA | 53 | 11033 | 11052 | 2924 |
| 568041 | 2063 | 2082 | TAGTCATCTCCATTTGTTTA | 48 | 11035 | 11054 | 2925 |
| 568042 | 2064 | 2083 | GTAGTCATCTCCATTTGTTT | 44 | 11036 | 11055 | 2926 |
| 568043 | 2065 | 2084 | AGTAGTCATCTCCATTTGTT | 48 | 11037 | 11056 | 2927 |
| 568044 | 2066 | 2085 | TAGTAGTCATCTCCATTTGT | 45 | 11038 | 11057 | 2928 |
| 568045 | 2067 | 2086 | TTAGTAGTCATCTCCATTTG | 66 | 11039 | 11058 | 2929 |
| 568046 | 2068 | 2087 | CTTAGTAGTCATCTCCATTT | 66 | 11040 | 11059 | 2930 |
| 568047 | 2069 | 2088 | ACTTAGTAGTCATCTCCATT | 68 | 11041 | 11060 | 99 |
| 568048 | 2070 | 2089 | GACTTAGTAGTCATCTCCAT | 77 | 11042 | 11061 | 100 |
| 568049 | 2071 | 2090 | TGACTTAGTAGTCATCTCCA | 70 | 11043 | 11062 | 101 |
| 568050 | 2072 | 2091 | GTGACTTAGTAGTCATCTCC | 65 | 11044 | 11063 | 2931 |
| 568051 | 2073 | 2092 | TGTGACTTAGTAGTCATCTC | 49 | 11045 | 11064 | 2932 |
| 568052 | 2074 | 2093 | ATGTGACTTAGTAGTCATCT | 47 | 11046 | 11065 | 2933 |
| 568053 | 2075 | 2094 | AATGTGACTTAGTAGTCATC | 48 | 11047 | 11066 | 2934 |
| 568054 | 2076 | 2095 | CAATGTGACTTAGTAGTCAT | 60 | 11048 | 11067 | 2935 |
| 568055 | 2077 | 2096 | TCAATGTGACTTAGTAGTCA | 54 | 11049 | 11068 | 2936 |
| 568056 | 2078 | 2097 | GTCAATGTGACTTAGTAGTC | 72 | 11050 | 11069 | 102 |
| 568057 | 2079 | 2098 | AGTCAATGTGACTTAGTAGT | 62 | 11051 | 11070 | 2937 |
| 568058 | 2083 | 2102 | TTAAAGTCAATGTGACTTAG | 15 | 11055 | 11074 | 2938 |
| 568059 | 2084 | 2103 | GTTAAAGTCAATGTGACTTA | 28 | 11056 | 11075 | 2939 |
| 568060 | 2085 | 2104 | TGTTAAAGTCAATGTGACTT | 35 | 11057 | 11076 | 2940 |
| 568061 | 2086 | 2105 | ATGTTAAAGTCAATGTGACT | 17 | 11058 | 11077 | 2941 |
| 568062 | 2087 | 2106 | CATGTTAAAGTCAATGTGAC | 27 | 11059 | 11078 | 2942 |
| 568063 | 2089 | 2108 | CTCATGTTAAAGTCAATGTG | 28 | 11061 | 11080 | 2943 |

TABLE 13-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 568064 | 2090 | 2109 | CCTCATGTTAAAGTCAATGT | 50 | 11062 | 11081 | 2944 |
| 568066 | 2091 | 2110 | ACCTCATGTTAAAGTCAATG | 48 | 11063 | 11082 | 2945 |
| 568068 | 2092 | 2111 | TACCTCATGTTAAAGTCAAT | 13 | 11064 | 11083 | 2946 |
| 568069 | 2093 | 2112 | ATACCTCATGTTAAAGTCAA | 43 | 11065 | 11084 | 2947 |
| 568072 | 2094 | 2113 | GATACCTCATGTTAAAGTCA | 40 | 11066 | 11085 | 2948 |
| 568073 | 2095 | 2114 | TGATACCTCATGTTAAAGTC | 40 | 11067 | 11086 | 2949 |
| 568075 | 2096 | 2115 | GTGATACCTCATGTTAAAGT | 37 | 11068 | 11087 | 2950 |
| 568077 | 2097 | 2116 | AGTGATACCTCATGTTAAAG | 6 | 11069 | 11088 | 2951 |
| 568078 | 2098 | 2117 | TAGTGATACCTCATGTTAAA | 12 | 11070 | 11089 | 2952 |
| 568079 | 2099 | 2118 | ATAGTGATACCTCATGTTAA | 8 | 11071 | 11090 | 2953 |
| 568080 | 2100 | 2119 | TATAGTGATACCTCATGTTA | 13 | 11072 | 11091 | 2954 |
| 568081 | 2101 | 2120 | GTATAGTGATACCTCATGTT | 41 | 11073 | 11092 | 2955 |
| 568082 | 2102 | 2121 | GGTATAGTGATACCTCATGT | 53 | 11074 | 11093 | 2956 |
| 568083 | 2106 | 2125 | ATAAGGTATAGTGATACCTC | 54 | 11078 | 11097 | 2957 |
| 568084 | 2107 | 2126 | AATAAGGTATAGTGATACCT | 38 | 11079 | 11098 | 2958 |

TABLE 14

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 544120 | 707 | 726 | AGTTCTTGGTGCTCTTGGCT | 83 | 6720 | 6739 | 15 |
| 337487 | 804 | 823 | CACTTGTATGTTCACCTCTG | 81 | 7389 | 7408 | 28 |
| 567295 | 1452 | 1471 | TAATGTTTAAATTATTGCCT | 43 | 10424 | 10443 | 2959 |
| 567296 | 1455 | 1474 | GGTTAATGTTTAAATTATTG | 22 | 10427 | 10446 | 2960 |
| 567297 | 1456 | 1475 | AGGTTAATGTTTAAATTATT | 0 | 10428 | 10447 | 2961 |
| 567298 | 1457 | 1476 | GAGGTTAATGTTTAAATTAT | 0 | 10429 | 10448 | 2962 |
| 567299 | 1458 | 1477 | TGAGGTTAATGTTTAAATTA | 6 | 10430 | 10449 | 2963 |
| 567300 | 1460 | 1479 | AATGAGGTTAATGTTTAAAT | 14 | 10432 | 10451 | 2964 |
| 567301 | 1461 | 1480 | GAATGAGGTTAATGTTTAAA | 5 | 10433 | 10452 | 2965 |
| 567302 | 1462 | 1481 | GGAATGAGGTTAATGTTTAA | 27 | 10434 | 10453 | 2966 |
| 567303 | 1463 | 1482 | TGGAATGAGGTTAATGTTTA | 32 | 10435 | 10454 | 2967 |
| 567304 | 1464 | 1483 | TTGGAATGAGGTTAATGTTT | 37 | 10436 | 10455 | 2968 |
| 567305 | 1465 | 1484 | CTTGGAATGAGGTTAATGTT | 25 | 10437 | 10456 | 2969 |
| 567306 | 1468 | 1487 | TAACTTGGAATGAGGTTAAT | 29 | 10440 | 10459 | 2970 |

TABLE 14-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 567307 | 1469 | 1488 | TTAACTTGGAATGAGGTTAA | 44 | 10441 | 10460 | 2971 |
| 337513 | 1470 | 1489 | ATTAACTTGGAATGAGGTTA | 52 | 10442 | 10461 | 2972 |
| 567308 | 1471 | 1490 | CATTAACTTGGAATGAGGTT | 62 | 10443 | 10462 | 2973 |
| 567309 | 1472 | 1491 | ACATTAACTTGGAATGAGGT | 58 | 10444 | 10463 | 2974 |
| 567310 | 1473 | 1492 | CACATTAACTTGGAATGAGG | 78 | 10445 | 10464 | 92 |
| 567311 | 1475 | 1494 | ACCACATTAACTTGGAATGA | 59 | 10447 | 10466 | 2975 |
| 567312 | 1476 | 1495 | GACCACATTAACTTGGAATG | 57 | 10448 | 10467 | 2976 |
| 337514 | 1477 | 1496 | AGACCACATTAACTTGGAAT | 71 | 10449 | 10468 | 2977 |
| 567313 | 1478 | 1497 | TAGACCACATTAACTTGGAA | 43 | 10450 | 10469 | 2978 |
| 567314 | 1479 | 1498 | TTAGACCACATTAACTTGGA | 59 | 10451 | 10470 | 2979 |
| 567315 | 1480 | 1499 | ATTAGACCACATTAACTTGG | 70 | 10452 | 10471 | 2980 |
| 567316 | 1481 | 1500 | TATTAGACCACATTAACTTG | 53 | 10453 | 10472 | 2981 |
| 567317 | 1482 | 1501 | TTATTAGACCACATTAACTT | 49 | 10454 | 10473 | 2982 |
| 567318 | 1483 | 1502 | ATTATTAGACCACATTAACT | 41 | 10455 | 10474 | 2983 |
| 567319 | 1484 | 1503 | GATTATTAGACCACATTAAC | 47 | 10456 | 10475 | 2984 |
| 567320 | 1487 | 1506 | CCAGATTATTAGACCACATT | 86 | 10459 | 10478 | 93 |
| 567321 | 1489 | 1508 | TACCAGATTATTAGACCACA | 85 | 10461 | 10480 | 94 |
| 337516 | 1490 | 1509 | ATACCAGATTATTAGACCAC | 77 | 10462 | 10481 | 86 |
| 567322 | 1491 | 1510 | AATACCAGATTATTAGACCA | 50 | 10463 | 10482 | 2985 |
| 567323 | 1492 | 1511 | TAATACCAGATTATTAGACC | 56 | 10464 | 10483 | 2986 |
| 567324 | 1494 | 1513 | TTTAATACCAGATTATTAGA | 9 | 10466 | 10485 | 2987 |
| 567325 | 1495 | 1514 | ATTTAATACCAGATTATTAG | 24 | 10467 | 10486 | 2988 |
| 567326 | 1496 | 1515 | GATTTAATACCAGATTATTA | 37 | 10468 | 10487 | 2989 |
| 567327 | 1500 | 1519 | TAAGGATTTAATACCAGATT | 60 | 10472 | 10491 | 2990 |
| 567328 | 1507 | 1526 | TTTCTCTTAAGGATTTAATA | 34 | 10479 | 10498 | 2991 |
| 567329 | 1508 | 1527 | CTTTCTCTTAAGGATTTAAT | 46 | 10480 | 10499 | 2992 |
| 567330 | 1509 | 1528 | GCTTTCTCTTAAGGATTTAA | 75 | 10481 | 10500 | 95 |
| 567331 | 1510 | 1529 | AGCTTTCTCTTAAGGATTTA | 59 | 10482 | 10501 | 2993 |
| 567332 | 1511 | 1530 | AAGCTTTCTCTTAAGGATTT | 30 | 10483 | 10502 | 2994 |
| 567333 | 1513 | 1532 | TCAAGCTTTCTCTTAAGGAT | 65 | 10485 | 10504 | 2995 |
| 567334 | 1514 | 1533 | CTCAAGCTTTCTCTTAAGGA | 77 | 10486 | 10505 | 96 |
| 567335 | 1515 | 1534 | TCTCAAGCTTTCTCTTAAGG | 75 | 10487 | 10506 | 97 |
| 567336 | 1516 | 1535 | TTCTCAAGCTTTCTCTTAAG | 59 | 10488 | 10507 | 2996 |
| 567337 | 1517 | 1536 | TTTCTCAAGCTTTCTCTTAA | 52 | 10489 | 10508 | 2997 |
| 567338 | 1521 | 1540 | TCTATTTCTCAAGCTTTCTC | 68 | 10493 | 10512 | 2998 |

TABLE 14-continued

Inhibition of ANGPTL3 mRNA by 5-10-5 MOE gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 567339 | 1522 | 1541 | ATCTATTTCTCAAGCTTTCT | 71 | 10494 | 10513 | 2999 |
| 567340 | 1523 | 1542 | AATCTATTTCTCAAGCTTTC | 74 | 10495 | 10514 | 3000 |
| 567341 | 1524 | 1543 | AAATCTATTTCTCAAGCTTT | 63 | 10496 | 10515 | 3001 |
| 567342 | 1525 | 1544 | AAAATCTATTTCTCAAGCTT | 54 | 10497 | 10516 | 3002 |
| 567343 | 1532 | 1551 | GATAAAAAAATCTATTTCT | 30 | 10504 | 10523 | 3003 |
| 567344 | 1548 | 1567 | TAGACAGTGACTTTAAGATA | 37 | 10520 | 10539 | 3004 |
| 567345 | 1549 | 1568 | ATAGACAGTGACTTTAAGAT | 29 | 10521 | 10540 | 3005 |
| 567346 | 1550 | 1569 | AATAGACAGTGACTTTAAGA | 48 | 10522 | 10541 | 3006 |
| 567347 | 1551 | 1570 | AAATAGACAGTGACTTTAAG | 26 | 10523 | 10542 | 3007 |
| 567348 | 1552 | 1571 | TAAATAGACAGTGACTTTAA | 26 | 10524 | 10543 | 3008 |
| 567349 | 1553 | 1572 | TTAAATAGACAGTGACTTTA | 50 | 10525 | 10544 | 3009 |
| 567350 | 1554 | 1573 | CTTAAATAGACAGTGACTTT | 63 | 10526 | 10545 | 3010 |
| 567351 | 1555 | 1574 | TCTTAAATAGACAGTGACTT | 57 | 10527 | 10546 | 3011 |
| 567352 | 1556 | 1575 | ATCTTAAATAGACAGTGACT | 69 | 10528 | 10547 | 3012 |
| 567353 | 1557 | 1576 | AATCTTAAATAGACAGTGAC | 40 | 10529 | 10548 | 3013 |
| 567354 | 1558 | 1577 | TAATCTTAAATAGACAGTGA | 30 | 10530 | 10549 | 3014 |
| 567355 | 1559 | 1578 | TTAATCTTAAATAGACAGTG | 25 | 10531 | 10550 | 3015 |
| 567356 | 1560 | 1579 | TTTAATCTTAAATAGACAGT | 0 | 10532 | 10551 | 3016 |
| 567357 | 1561 | 1580 | GTTTAATCTTAAATAGACAG | 34 | 10533 | 10552 | 3017 |
| 567358 | 1562 | 1581 | TGTTTAATCTTAAATAGACA | 5 | 10534 | 10553 | 3018 |
| 567359 | 1563 | 1582 | ATGTTTAATCTTAAATAGAC | 0 | 10535 | 10554 | 3019 |
| 567360 | 1567 | 1586 | TTGTATGTTTAATCTTAAAT | 0 | 10539 | 10558 | 3020 |
| 567361 | 1568 | 1587 | ATTGTATGTTTAATCTTAAA | 8 | 10540 | 10559 | 3021 |
| 567362 | 1569 | 1588 | GATTGTATGTTTAATCTTAA | 20 | 10541 | 10560 | 3022 |
| 567363 | 1570 | 1589 | TGATTGTATGTTTAATCTTA | 29 | 10542 | 10561 | 3023 |
| 567364 | 1574 | 1593 | TATGTGATTGTATGTTTAAT | 7 | 10546 | 10565 | 3024 |
| 567365 | 1576 | 1595 | GTTATGTGATTGTATGTTTA | 43 | 10548 | 10567 | 3025 |
| 567366 | 1580 | 1599 | TAAGGTTATGTGATTGTATG | 28 | 10552 | 10571 | 3026 |
| 567367 | 1581 | 1600 | TTAAGGTTATGTGATTGTAT | 31 | 10553 | 10572 | 3027 |
| 567368 | 1585 | 1604 | TTCTTTAAGGTTATGTGATT | 12 | 10557 | 10576 | 3028 |

Example 2: Dose-Dependent Antisense Inhibition of Human ANGPTL3 in Hep3B Cells by MOE Gapmers 5-10-5 MOE gapmers from the studies described above exhibiting significant in vitro inhibition of ANGPTL3 mRNA were selected and tested at various doses in Hep3B cells. Cells were plated at a density of 20,000 cells per well and transfected using electroporation with 0.75 µM, 1.50 µM, 3.00 µM, 6.00 µM and 12.00 µM concentrations of antisense oligonucleotide, as specified in the Table below. After a treatment period of approximately 16 hours, RNA was isolated from the cells and ANGPTL3 mRNA levels were measured by quantitative real-time PCR. Human primer probe set RTS3492_MGB was used to measure mRNA levels. ANGPTL3 mRNA levels were adjusted according to total RNA content, as measured by RIBOGREEN®. Results are presented as percent inhibition of ANGPTL3, relative to untreated control cells.

The half maximal inhibitory concentration (IC$_{50}$) of each oligonucleotide is also presented. ANGPTL3 mRNA levels were significantly reduced in a dose-dependent manner in antisense oligonucleotide treated cells.

TABLE 15

| ISIS No | 0.75 µM | 1.50 µM | 3.00 µM | 6.00 µM | 12.00 µM | IC$_{50}$ (µM) | SEQ ID NO |
|---|---|---|---|---|---|---|---|
| 233717 | 23 | 45 | 13 | 33 | 40 | >12 | 14 |
| 544120 | 45 | 65 | 76 | 88 | 91 | 0.7 | 15 |
| 544145 | 38 | 42 | 61 | 82 | 84 | 1.6 | 16 |
| 544156 | 31 | 42 | 63 | 78 | 84 | 1.8 | 17 |
| 544162 | 35 | 43 | 71 | 76 | 82 | 1.6 | 18 |
| 544166 | 30 | 47 | 60 | 76 | 84 | 1.8 | 19 |
| 544199 | 54 | 61 | 73 | 83 | 84 | 0.5 | 20 |
| 544355 | 45 | 46 | 69 | 77 | 83 | 1.2 | 21 |
| 544368 | 12 | 37 | 63 | 74 | 81 | 2.6 | 22 |
| 544373 | 1 | 27 | 40 | 29 | 28 | >12 | 23 |
| 544376 | 26 | 53 | 61 | 63 | 59 | 2.4 | 24 |
| 544380 | 16 | 33 | 41 | 64 | 39 | 8.4 | 25 |
| 544383 | 14 | 33 | 46 | 61 | 63 | 4.4 | 26 |
| 544410 | 10 | 41 | 48 | 62 | 69 | 3.6 | 27 |

Example 3: Dose-Dependent Antisense Inhibition of Human ANGPTL3 in Hep3B Cells by MOE Gapmers 5-10-5 MOE gapmers from the studies described above exhibiting significant in vitro inhibition of ANGPTL3 mRNA were selected and tested at various doses in Hep3B cells. Cells were plated at a density of 20,000 cells per well and transfected using electroporation with 0.813 µM, 1.625 µM, 3.25 µM, 6.50 µM and 13.00 µM concentrations of antisense oligonucleotide, as specified in the Table below. After a treatment period of approximately 16 hours, RNA was isolated from the cells and ANGPTL3 mRNA levels were measured by quantitative real-time PCR. Human primer probe set RTS3492_MGB was used to measure mRNA levels. ANGPTL3 mRNA levels were adjusted according to total RNA content, as measured by RIBOGREEN®. Results are presented as percent inhibition of ANGPTL3, relative to untreated control cells.

The half maximal inhibitory concentration (IC$_{50}$) of each oligonucleotide is also presented. ANGPTL3 mRNA levels were significantly reduced in a dose-dependent manner in antisense oligonucleotide treated cells.

TABLE 16

| ISIS No | 0.813 µM | 1.625 µM | 3.25 µM | 6.50 µM | 13.00 µM | IC$_{50}$ (µM) | SEQ ID NO |
|---|---|---|---|---|---|---|---|
| 337487 | 17 | 37 | 58 | 72 | 92 | 2.7 | 28 |
| 337492 | 0 | 0 | 0 | 5 | 58 | >13 | 29 |
| 544120 | 23 | 40 | 65 | 81 | 91 | 2.2 | 15 |
| 560236 | 39 | 22 | 46 | 9 | 60 | >13 | 30 |
| 560265 | 38 | 48 | 58 | 64 | 73 | 2.0 | 31 |
| 560268 | 37 | 57 | 60 | 71 | 83 | 1.5 | 32 |
| 560285 | 5 | 29 | 48 | 68 | 78 | 3.8 | 33 |
| 560306 | 45 | 64 | 67 | 81 | 86 | 0.9 | 34 |
| 560400 | 48 | 63 | 75 | 87 | 88 | 0.7 | 35 |
| 560401 | 49 | 75 | 79 | 89 | 88 | 0.5 | 36 |
| 560402 | 42 | 67 | 70 | 85 | 90 | 0.9 | 37 |
| 560469 | 43 | 55 | 70 | 74 | 83 | 1.2 | 38 |
| 560470 | 31 | 54 | 64 | 73 | 81 | 1.8 | 39 |

TABLE 16-continued

| ISIS No | 0.813 µM | 1.625 µM | 3.25 µM | 6.50 µM | 13.00 µM | IC$_{50}$ (µM) | SEQ ID NO |
|---|---|---|---|---|---|---|---|
| 560471 | 26 | 43 | 59 | 62 | 77 | 2.7 | 40 |
| 560474 | 42 | 50 | 60 | 54 | 72 | 1.8 | 41 |

TABLE 17

| ISIS No | 0.813 µM | 1.625 µM | 3.25 µM | 6.50 µM | 13.00 µM | IC$_{50}$ (µM) | SEQ ID NO |
|---|---|---|---|---|---|---|---|
| 337487 | 20 | 35 | 51 | 78 | 89 | 1.8 | 28 |
| 544120 | 31 | 46 | 62 | 84 | 90 | 0.5 | 15 |
| 544145 | 4 | 36 | 60 | 58 | 89 | 3.8 | 16 |
| 544156 | 22 | 35 | 46 | 66 | 73 | 1.8 | 17 |
| 544162 | 2 | 21 | 54 | 69 | 87 | >13 | 18 |
| 544166 | 15 | 0 | 25 | 59 | 89 | >13 | 19 |
| 544199 | 61 | 37 | 57 | 53 | 81 | 0.9 | 20 |
| 544355 | 0 | 47 | 50 | 73 | 84 | >13 | 21 |
| 544376 | 4 | 14 | 38 | 66 | 88 | 0.9 | 24 |
| 560566 | 53 | 68 | 70 | 76 | 85 | >13 | 42 |
| 560567 | 55 | 70 | 75 | 78 | 89 | 2.7 | 43 |
| 560574 | 49 | 63 | 68 | 74 | 84 | 2.0 | 44 |
| 560596 | 28 | 40 | 41 | 52 | 75 | 1.5 | 45 |
| 560607 | 35 | 53 | 65 | 70 | 85 | 3.8 | 46 |
| 560608 | 40 | 50 | 62 | 68 | 83 | 0.9 | 47 |
| 560723 | 36 | 51 | 59 | 65 | 75 | 2.2 | 48 |
| 560735 | 36 | 44 | 59 | 72 | 85 | >13 | 49 |
| 560736 | 26 | 34 | 50 | 64 | 80 | 0.7 | 50 |
| 560744 | 28 | 49 | 59 | 75 | 83 | 0.9 | 51 |
| 560778 | 24 | 46 | 60 | 67 | 85 | 1.8 | 52 |
| 560789 | 14 | 23 | 36 | 49 | 71 | 2.7 | 53 |
| 560811 | 32 | 50 | 65 | 73 | 87 | 1.2 | 54 |
| 560856 | 0 | 20 | 17 | 32 | 69 | 3.8 | 55 |
| 560925 | 2 | 16 | 38 | 52 | 82 | 2.7 | 56 |
| 560936 | 0 | 0 | 24 | 41 | 65 | 0.5 | 57 |
| 560938 | 0 | 26 | 30 | 43 | 50 | 0.9 | 58 |
| 560942 | 0 | 0 | 12 | 36 | 74 | 1.8 | 59 |
| 560956 | 0 | 16 | 16 | 68 | 81 | 0.5 | 60 |

TABLE 18

| ISIS No | 0.813 µM | 1.625 µM | 3.25 µM | 6.50 µM | 13.00 µM | IC$_{50}$ (µM) | SEQ ID NO |
|---|---|---|---|---|---|---|---|
| 337487 | 20 | 35 | 51 | 78 | 89 | 2.7 | 28 |
| 544120 | 31 | 46 | 62 | 84 | 90 | 1.9 | 15 |
| 560566 | 53 | 68 | 70 | 76 | 85 | 0.5 | 42 |
| 560567 | 55 | 70 | 75 | 78 | 89 | 0.4 | 43 |
| 560574 | 49 | 63 | 68 | 74 | 84 | 0.7 | 44 |
| 560596 | 28 | 40 | 41 | 52 | 75 | 3.9 | 45 |
| 560607 | 35 | 53 | 65 | 70 | 85 | 1.6 | 46 |
| 560608 | 40 | 50 | 62 | 68 | 83 | 1.6 | 47 |
| 560723 | 36 | 51 | 59 | 65 | 75 | 1.9 | 48 |
| 560735 | 36 | 44 | 59 | 72 | 85 | 2.0 | 49 |
| 560736 | 26 | 34 | 50 | 64 | 80 | 3.2 | 50 |
| 560744 | 28 | 49 | 59 | 75 | 83 | 2.1 | 51 |
| 560778 | 24 | 46 | 60 | 67 | 85 | 2.4 | 52 |
| 560789 | 14 | 23 | 36 | 49 | 71 | 5.7 | 53 |
| 560811 | 32 | 50 | 65 | 73 | 87 | 1.8 | 54 |

TABLE 19

| ISIS No | 0.813 µM | 1.625 µM | 3.25 µM | 6.50 µM | 13.00 µM | IC$_{50}$ (µM) | SEQ ID NO |
|---|---|---|---|---|---|---|---|
| 337487 | 10 | 21 | 49 | 73 | 90 | 3.4 | 28 |
| 544120 | 19 | 38 | 62 | 77 | 88 | 2.5 | 15 |
| 560768 | 1 | 14 | 14 | 28 | 51 | >13 | 61 |
| 560777 | 13 | 35 | 37 | 56 | 80 | 4.2 | 62 |
| 560791 | 13 | 28 | 28 | 24 | 11 | >13 | 63 |
| 560794 | 8 | 31 | 42 | 57 | 76 | 4.4 | 64 |
| 560799 | 0 | 14 | 21 | 43 | 72 | 7.2 | 65 |

TABLE 19-continued

| ISIS No | 0.813 µM | 1.625 µM | 3.25 µM | 6.50 µM | 13.00 µM | IC$_{50}$ (µM) | SEQ ID NO |
|---|---|---|---|---|---|---|---|
| 560803 | 26 | 44 | 52 | 55 | 69 | 3.4 | 66 |
| 560815 | 16 | 26 | 26 | 52 | 60 | 7.6 | 67 |
| 560817 | 0 | 0 | 11 | 18 | 37 | >13 | 68 |
| 560847 | 37 | 52 | 56 | 68 | 87 | 1.8 | 69 |
| 560879 | 15 | 18 | 38 | 53 | 72 | 5.4 | 70 |
| 560880 | 0 | 8 | 21 | 38 | 71 | 8.0 | 71 |
| 560891 | 7 | 25 | 32 | 35 | 62 | 8.9 | 72 |
| 560895 | 11 | 10 | 0 | 5 | 48 | >13 | 73 |

TABLE 20

| ISIS No | 0.813 µM | 1.625 µM | 3.25 µM | 6.50 µM | 13.00 µM | IC$_{50}$ (µM) | SEQ ID NO |
|---|---|---|---|---|---|---|---|
| 337487 | 20 | 14 | 38 | 65 | 88 | 3.9 | 28 |
| 544120 | 22 | 34 | 51 | 71 | 86 | 2.9 | 15 |
| 544145 | 21 | 39 | 62 | 63 | 90 | 2.6 | 16 |
| 544156 | 31 | 41 | 55 | 72 | 78 | 2.4 | 17 |
| 544162 | 0 | 37 | 59 | 75 | 87 | 2.7 | 18 |
| 544166 | 8 | 43 | 45 | 55 | 75 | 4.0 | 19 |
| 544199 | 53 | 46 | 64 | 62 | 81 | 1.1 | 20 |
| 544355 | 0 | 0 | 52 | 72 | 84 | 2.9 | 21 |
| 544376 | 2 | 22 | 39 | 51 | 76 | 5.2 | 24 |
| 560856 | 10 | 29 | 36 | 41 | 69 | 6.4 | 55 |
| 560925 | 0 | 35 | 46 | 59 | 81 | 3.5 | 56 |
| 560936 | 18 | 9 | 35 | 55 | 69 | 5.9 | 57 |
| 560938 | 14 | 34 | 42 | 49 | 58 | 6.5 | 58 |
| 560942 | 8 | 13 | 27 | 47 | 77 | 6.1 | 59 |
| 560956 | 16 | 31 | 0 | 69 | 81 | 3.9 | 60 |

TABLE 21

| ISIS No | 0.813 µM | 1.625 µM | 3.25 µM | 6.50 µM | 13.00 µM | IC$_{50}$ (µM) | SEQ ID NO |
|---|---|---|---|---|---|---|---|
| 233717 | 11 | 0 | 33 | 58 | 75 | 5.0 | 14 |
| 337484 | 39 | 54 | 55 | 66 | 79 | 1.7 | 74 |
| 337487 | 35 | 42 | 67 | 82 | 92 | 1.8 | 28 |
| 544120 | 53 | 47 | 78 | 84 | 92 | <0.8 | 15 |
| 563523 | 12 | 44 | 59 | 63 | 79 | 3.0 | 75 |
| 563547 | 33 | 51 | 55 | 43 | 58 | 4.6 | 76 |
| 563580 | 61 | 73 | 71 | 82 | 91 | <0.8 | 77 |
| 563637 | 36 | 55 | 69 | 77 | 88 | 1.4 | 78 |
| 563639 | 56 | 71 | 79 | 88 | 93 | <0.8 | 79 |
| 563641 | 30 | 42 | 56 | 77 | 84 | 2.2 | 80 |
| 563669 | 28 | 61 | 66 | 79 | 85 | 1.6 | 81 |
| 563681 | 35 | 67 | 74 | 75 | 70 | 0.9 | 82 |
| 563682 | 41 | 45 | 68 | 76 | 85 | 1.5 | 83 |
| 567068 | 32 | 37 | 50 | 66 | 81 | 2.8 | 84 |
| 567069 | 23 | 28 | 48 | 56 | 62 | 5.0 | 85 |

TABLE 22

| ISIS No | 0.813 µM | 1.625 µM | 3.25 µM | 6.50 µM | 13.00 µM | IC$_{50}$ (µM) | SEQ ID NO |
|---|---|---|---|---|---|---|---|
| 233717 | 9 | 0 | 25 | 62 | 74 | 5.5 | 14 |
| 337487 | 22 | 40 | 71 | 84 | 92 | 2.1 | 28 |
| 337516 | 36 | 54 | 78 | 81 | 92 | 1.3 | 86 |
| 544120 | 25 | 50 | 72 | 86 | 92 | 1.8 | 15 |
| 567078 | 54 | 64 | 70 | 78 | 78 | <0.8 | 87 |
| 567115 | 55 | 65 | 72 | 80 | 81 | <0.8 | 88 |
| 567134 | 33 | 58 | 53 | 57 | 69 | 2.2 | 89 |
| 567233 | 54 | 74 | 83 | 87 | 91 | <0.8 | 90 |
| 567291 | 54 | 67 | 71 | 80 | 89 | <0.8 | 91 |
| 567310 | 36 | 61 | 73 | 80 | 89 | 1.2 | 92 |
| 567320 | 63 | 77 | 88 | 88 | 92 | <0.8 | 93 |
| 567321 | 55 | 75 | 89 | 89 | 93 | <0.8 | 94 |

TABLE 22-continued

| ISIS No | 0.813 µM | 1.625 µM | 3.25 µM | 6.50 µM | 13.00 µM | IC$_{50}$ (µM) | SEQ ID NO |
|---|---|---|---|---|---|---|---|
| 567330 | 31 | 68 | 76 | 85 | 93 | 1.2 | 95 |
| 567334 | 36 | 54 | 76 | 82 | 87 | 1.3 | 96 |
| 567335 | 31 | 49 | 72 | 80 | 92 | 1.7 | 97 |

TABLE 23

| ISIS No | 0.813 µM | 1.625 µM | 3.25 µM | 6.50 µM | 13.00 µM | IC$_{50}$ (µM) | SEQ ID NO |
|---|---|---|---|---|---|---|---|
| 233717 | 0 | 0 | 23 | 66 | 64 | 6.6 | 14 |
| 337487 | 13 | 44 | 60 | 74 | 85 | 2.6 | 28 |
| 544120 | 24 | 47 | 53 | 78 | 83 | 2.3 | 15 |
| 568034 | 35 | 54 | 51 | 59 | 46 | 4.2 | 98 |
| 568047 | 36 | 55 | 70 | 69 | 72 | 1.4 | 99 |
| 568048 | 41 | 64 | 63 | 66 | 66 | 0.9 | 100 |
| 568049 | 50 | 70 | 70 | 74 | 73 | <0.8 | 101 |
| 568056 | 33 | 56 | 68 | 63 | 64 | 1.7 | 102 |
| 568144 | 27 | 57 | 63 | 63 | 76 | 2.0 | 103 |
| 568146 | 50 | 61 | 61 | 63 | 77 | <0.8 | 104 |
| 568151 | 23 | 46 | 59 | 68 | 66 | 2.8 | 105 |
| 568206 | 24 | 40 | 56 | 61 | 75 | 3.0 | 106 |
| 568293 | 0 | 39 | 46 | 59 | 78 | 4.1 | 107 |
| 568300 | 22 | 36 | 61 | 68 | 73 | 3.0 | 108 |
| 568330 | 16 | 48 | 54 | 73 | 82 | 2.7 | 109 |

Example 4: Antisense Inhibition of Human ANGPTL3 in Hep3B Cells by Deoxy, MOE and (S)-cEt Gapmers Additional antisense oligonucleotides were designed targeting an ANGPTL3 nucleic acid and were tested for their effects on ANGPTL3 mRNA in vitro. Cultured Hep3B cells at a density of 20,000 cells per well were transfected using electroporation with 4,500 nM of antisense oligonucleotide. After a treatment period of approximately 24 hours, RNA was isolated from the cells and ANGPTL3 mRNA levels were measured by quantitative real-time PCR. Human primer probe set RTS3492_MGB was used to measure mRNA levels. ANGPTL3 mRNA levels were adjusted according to total RNA content, as measured by RIBOGREEN®. Results are presented as percent inhibition of ANGPTL3, relative to untreated control cells.

The newly designed chimeric antisense oligonucleotides in the Tables below were designed as deoxy, MOE, and (S)-cEt oligonucleotides. The deoxy, MOE and (S)-cEt oligonucleotides are 16 nucleosides in length wherein the nucleoside have either a MOE sugar modification, a (S)-cEt sugar modification, or a deoxy sugar residue. The sugar modifications of each antisense oligonucleotide is described as 'eek-d10-kke', where 'k' indicates a (S)-cEt sugar modification; 'd' indicates deoxyribose; the number indicates the number of deoxyribose sugars residues; and 'e' indicates a MOE sugar modification. The internucleoside linkages throughout each oligonucleotide are phosphorothioate (P=S) linkages. All cytosine residues throughout each oligonucleotide are 5-methylcytosines. "Start site" indicates the 5'-most nucleoside to which the oligonucleotide is targeted in the human gene sequence. "Stop site" indicates the 3'-most nucleoside to which the oligonucleotide is targeted human gene sequence. Each oligonucleotide listed in the Tables below is targeted to either the human ANGPTL3 mRNA, designated herein as SEQ ID NO: 1 (GENBANK Accession No. NM_014495.2) or the human ANGPTL3 genomic sequence, designated herein as SEQ ID NO: 2 (GENBANK Accession No. NT_032977.9 truncated from nucleotides 33032001 to 33046000). 'n/a' indicates that the antisense oligonucleotide does not target that particular gene sequence with 100% complementarity.

TABLE 24

Inhibition of ANGPTL3 mRNA by deoxy, MOE and cEt oligonucleotides targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 561681 | N/A | N/A | TCTGGAAGCAGACCTA | 37 | 3096 | 3111 | 3029 |
| 561682 | N/A | N/A | CTTCTGGAAGCAGACC | 27 | 3098 | 3113 | 3030 |
| 561683 | N/A | N/A | AAATAAGGTATAGTGA | 2 | 11084 | 11099 | 3031 |
| 561684 | N/A | N/A | TAGTATTAAGTGTTAA | 14 | 11133 | 11148 | 3032 |
| 561685 | N/A | N/A | TCATAGTATTAAGTGT | 0 | 11136 | 11151 | 3033 |
| 561686 | N/A | N/A | AGATTCCTTTACAATT | 21 | 11160 | 11175 | 3034 |
| 561687 | N/A | N/A | ACAAGATTCCTTTACA | 21 | 11163 | 11178 | 3035 |
| 561688 | N/A | N/A | CTGACAAGATTCCTTT | 70 | 11166 | 11181 | 3036 |
| 561689 | N/A | N/A | AATCTGACAAGATTCC | 83 | 11169 | 11184 | 180 |
| 561690 | N/A | N/A | TGTAATCTGACAAGAT | 46 | 11172 | 11187 | 3037 |
| 561691 | N/A | N/A | TACTGTAATCTGACAA | 47 | 11175 | 11190 | 3038 |
| 561692 | N/A | N/A | TCTTACTGTAATCTGA | 50 | 11178 | 11193 | 3039 |
| 561693 | N/A | N/A | CATTCTTACTGTAATC | 40 | 11181 | 11196 | 3040 |
| 561694 | N/A | N/A | GTTCATTCTTACTGTA | 71 | 11184 | 11199 | 3041 |
| 561695 | N/A | N/A | ATATGTTCATTCTTAC | 2 | 11188 | 11203 | 3042 |
| 561696 | N/A | N/A | GCCACAAATATGTTCA | 80 | 11195 | 11210 | 3043 |
| 561697 | N/A | N/A | GATGCCACAAATATGT | 70 | 11198 | 11213 | 3044 |
| 561698 | N/A | N/A | CTCGATGCCACAAATA | 80 | 11201 | 11216 | 181 |
| 561699 | N/A | N/A | TAACTCGATGCCACAA | 86 | 11204 | 11219 | 182 |
| 561700 | N/A | N/A | CTTTAACTCGATGCCA | 77 | 11207 | 11222 | 3045 |
| 561701 | N/A | N/A | AAACTTTAACTCGATG | 39 | 11210 | 11225 | 3046 |
| 561702 | N/A | N/A | TATAAACTTTAACTCG | 13 | 11213 | 11228 | 3047 |
| 561703 | N/A | N/A | CACAGCATATTTAGGG | 71 | 11233 | 11248 | 3048 |
| 561704 | N/A | N/A | TAGAATCACAGCATAT | 68 | 11239 | 11254 | 3049 |
| 561705 | N/A | N/A | TATTAGAATCACAGCA | 73 | 11242 | 11257 | 3050 |
| 561706 | N/A | N/A | AATGTATTAGAATCAC | 40 | 11246 | 11261 | 3051 |
| 561707 | N/A | N/A | ACGAATGTATTAGAAT | 22 | 11249 | 11264 | 3052 |
| 561708 | N/A | N/A | TACACGAATGTATTAG | 33 | 11252 | 11267 | 3053 |
| 561709 | N/A | N/A | ACCTACACGAATGTAT | 42 | 11255 | 11270 | 3054 |
| 561710 | N/A | N/A | AAACCTACACGAATG | 24 | 11258 | 11273 | 3055 |
| 561711 | N/A | N/A | TTGAAAACCTACACGA | 34 | 11261 | 11276 | 3056 |
| 561712 | N/A | N/A | TACTTGAAAACCTACA | 33 | 11264 | 11279 | 3057 |
| 561713 | N/A | N/A | GTTTATTTCTACTTGA | 53 | 11273 | 11288 | 3058 |
| 561714 | N/A | N/A | GAGGTTTATTTCTACT | 69 | 11276 | 11291 | 3059 |
| 561715 | N/A | N/A | TACGAGGTTTATTTCT | 21 | 11279 | 11294 | 3060 |
| 561716 | N/A | N/A | TGTTACGAGGTTTATT | 47 | 11282 | 11297 | 3061 |

TABLE 24-continued

Inhibition of ANGPTL3 mRNA by deoxy, MOE and cEt oligonucleotides targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 561717 | N/A | N/A | ACTTGTTACGAGGTTT | 70 | 11285 | 11300 | 3062 |
| 561718 | N/A | N/A | CAGTAACTTGTTACGA | 60 | 11290 | 11305 | 3063 |
| 561719 | N/A | N/A | GTTCAGTAACTTGTTA | 40 | 11293 | 11308 | 3064 |
| 561720 | N/A | N/A | TCAGGCTGTTTAAACG | 59 | 11308 | 11323 | 3065 |
| 561721 | N/A | N/A | TTGTCAGGCTGTTTAA | 74 | 11311 | 11326 | 3066 |
| 561722 | N/A | N/A | TGCTTGTCAGGCTGTT | 82 | 11314 | 11329 | 183 |
| 561723 | N/A | N/A | ACATGCTTGTCAGGCT | 84 | 11317 | 11332 | 184 |
| 561724 | N/A | N/A | TATACATGCTTGTCAG | 75 | 11320 | 11335 | 3067 |
| 561725 | N/A | N/A | GTCTTTGTTTATTGAA | 49 | 11347 | 11362 | 3068 |
| 561726 | N/A | N/A | TGGGTCTTTGTTTATT | 27 | 11350 | 11365 | 3069 |
| 561727 | N/A | N/A | GACTGGGTCTTTGTTT | 20 | 11353 | 11368 | 3070 |
| 561728 | N/A | N/A | ATAATTTAGGGACTGG | 20 | 11363 | 11378 | 3071 |
| 561729 | N/A | N/A | TCTATAATTTAGGGAC | 39 | 11366 | 11381 | 3072 |
| 561730 | N/A | N/A | CGATAAACATGCAAGA | 68 | 11394 | 11409 | 3073 |
| 561731 | N/A | N/A | TGTCGATAAACATGCA | 80 | 11397 | 11412 | 3074 |
| 561732 | N/A | N/A | TGATGTCGATAAACAT | 68 | 11400 | 11415 | 3075 |
| 561733 | N/A | N/A | TTGTGATGTCGATAAA | 28 | 11403 | 11418 | 3076 |
| 561734 | N/A | N/A | CTGTTGTGATGTCGAT | 74 | 11406 | 11421 | 3077 |
| 561735 | N/A | N/A | GATCTGTTGTGATGTC | 59 | 11409 | 11424 | 3078 |
| 561736 | N/A | N/A | AGGGATCTGTTGTGAT | 24 | 11412 | 11427 | 3079 |
| 561737 | N/A | N/A | TTTAGGGATCTGTTGT | 19 | 11415 | 11430 | 3080 |
| 561738 | N/A | N/A | GGATTTAGGGATCTGT | 27 | 11418 | 11433 | 3081 |
| 561739 | N/A | N/A | GATTTAGGGATTTAGG | 44 | 11425 | 11440 | 3082 |
| 561740 | N/A | N/A | TCTTTAGGGATTTAGG | 38 | 11433 | 11448 | 3083 |
| 561741 | N/A | N/A | TAATCTTTAGGGATTT | 0 | 11436 | 11451 | 3084 |
| 561742 | N/A | N/A | ATCTAATCTTTAGGGA | 0 | 11439 | 11454 | 3085 |
| 561743 | N/A | N/A | TGTATCTAATCTTTAG | 15 | 11442 | 11457 | 3086 |
| 561744 | N/A | N/A | AAATTTGTATCTAATC | 21 | 11447 | 11462 | 3087 |
| 561745 | N/A | N/A | GTAAAAATTTGTATC | 23 | 11452 | 11467 | 3088 |
| 561746 | N/A | N/A | GTGGTAAAAATTTGT | 32 | 11455 | 11470 | 3089 |
| 561747 | N/A | N/A | GATACTGTGGTAAAAA | 45 | 11461 | 11476 | 3090 |
| 561748 | N/A | N/A | AGTGATACTGTGGTAA | 60 | 11464 | 11479 | 3091 |
| 561749 | N/A | N/A | ACAAGTGATACTGTGG | 75 | 11467 | 11482 | 3092 |
| 561750 | N/A | N/A | CTGACAAGTGATACTG | 59 | 11470 | 11485 | 3093 |
| 561751 | N/A | N/A | ATTCTGACAAGTGATA | 48 | 11473 | 11488 | 3094 |

TABLE 24-continued

Inhibition of ANGPTL3 mRNA by deoxy, MOE and cEt oligonucleotides targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 561752 | N/A | N/A | TAAATTCTGACAAGTG | 59 | 11476 | 11491 | 3095 |
| 561753 | N/A | N/A | TACTGGCAGTTTTAAA | 42 | 11508 | 11523 | 3096 |
| 561754 | N/A | N/A | TCTTACTGGCAGTTTT | 51 | 11511 | 11526 | 3097 |
| 561755 | N/A | N/A | ATTTCTTACTGGCAGT | 69 | 11514 | 11529 | 3098 |
| 561756 | N/A | N/A | AAAATTCTTACTGGC | 57 | 11517 | 11532 | 3099 |
| 561757 | N/A | N/A | AACAAATGGGTTTAAT | 0 | 11535 | 11550 | 3100 |
| 562374 | N/A | N/A | GAATATTTGCAAGTCT | 68 | 9230 | 9245 | 3101 |
| 562375 | N/A | N/A | GTAGAGGAATATTTGC | 83 | 9236 | 9251 | 151 |
| 562376 | N/A | N/A | TCATTGGTAGAGGAAT | 23 | 9242 | 9257 | 3102 |
| 562377 | N/A | N/A | ATATTTTAAAGTCTCG | 17 | 9258 | 9273 | 3103 |
| 562378 | N/A | N/A | GTTACATTATTATAGA | 29 | 9273 | 9288 | 3104 |
| 562379 | N/A | N/A | GTGAAATGTGTTACAT | 54 | 9282 | 9297 | 3105 |
| 562380 | N/A | N/A | TCACCAGTGAAATGTG | 64 | 9288 | 9303 | 3106 |
| 562381 | N/A | N/A | CATGTTTCACCAGTGA | 78 | 9294 | 9309 | 3107 |
| 562382 | N/A | N/A | ACAAGACATGTTTCAC | 36 | 9300 | 9315 | 3108 |
| 562383 | N/A | N/A | CATATGACAAGACATG | 42 | 9306 | 9321 | 3109 |
| 562384 | N/A | N/A | CTATAATGCATATGAC | 5 | 9314 | 9329 | 3110 |
| 562385 | N/A | N/A | TCCTTTCTATAATGCA | 65 | 9320 | 9335 | 3111 |
| 562386 | N/A | N/A | TGATTATCCTTTCTAT | 27 | 9326 | 9341 | 3112 |
| 562387 | N/A | N/A | AAAGTCTGATTATCCT | 90 | 9332 | 9347 | 152 |
| 562388 | N/A | N/A | TAACTGAAAGTCTGAT | 59 | 9338 | 9353 | 3113 |
| 562389 | N/A | N/A | GTGCACAAAAATGTTA | 42 | 9366 | 9381 | 3114 |
| 562390 | N/A | N/A | AGCTATGTGCACAAAA | 77 | 9372 | 9387 | 3115 |
| 562391 | N/A | N/A | GAAGATAGCTATGTGC | 64 | 9378 | 9393 | 3116 |
| 562392 | N/A | N/A | TTTATTGAAGATAGCT | 33 | 9384 | 9399 | 3117 |
| 562393 | N/A | N/A | TCATTTTAGTGTATCT | 40 | 9424 | 9439 | 3118 |
| 562394 | N/A | N/A | CCTTGATCATTTTAGT | 15 | 9430 | 9445 | 3119 |
| 562395 | N/A | N/A | TGAATCCCTTGATCAT | 59 | 9436 | 9451 | 3120 |
| 562396 | N/A | N/A | TAGTCTTGAATCCCTT | 83 | 9442 | 9457 | 153 |
| 562397 | N/A | N/A | GTTGTTAGTCTTGAA | 65 | 9448 | 9463 | 3121 |
| 562398 | N/A | N/A | AATTGAGTTGTTTAGT | 21 | 9454 | 9469 | 3122 |
| 562399 | N/A | N/A | GCAACTAATTGAGTTG | 15 | 9460 | 9475 | 3123 |
| 562400 | N/A | N/A | ATTGGTGCAACTAATT | 25 | 9466 | 9481 | 3124 |
| 562401 | N/A | N/A | GTTTTTTATTGGTGCA | 53 | 9473 | 9488 | 3125 |
| 562402 | N/A | N/A | GGACACTGACAGTTTT | 43 | 9496 | 9511 | 3126 |
| 562403 | N/A | N/A | CAGGTTGGACACTGAC | 23 | 9502 | 9517 | 3127 |

TABLE 24-continued

Inhibition of ANGPTL3 mRNA by deoxy, MOE and cEt oligonucleotides targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 562404 | N/A | N/A | TAAGTACAGGTTGGAC | 33 | 9508 | 9523 | 3128 |
| 562405 | N/A | N/A | AGTTATTAAGTACAGG | 34 | 9514 | 9529 | 3129 |
| 562406 | N/A | N/A | TCTGTGAGTTATTAAG | 10 | 9520 | 9535 | 3130 |
| 562407 | N/A | N/A | ACCAAAATTCTCCTGA | 1 | 9554 | 9569 | 3131 |
| 562408 | N/A | N/A | ACCTGAATAACCCTCT | 73 | 9811 | 9826 | 3132 |
| 562409 | N/A | N/A | GGTATCAGAAAAGAT | 14 | 9827 | 9842 | 3133 |
| 562410 | N/A | N/A | AGTATTGGTATCAGAA | 13 | 9833 | 9848 | 3134 |
| 562411 | N/A | N/A | GGAAGATACTTTGAAG | 25 | 9861 | 9876 | 3135 |
| 562412 | N/A | N/A | AATGTGGGAAGATACT | 23 | 9867 | 9882 | 3136 |
| 562413 | N/A | N/A | CAGATAATAGCTAATA | 29 | 9882 | 9897 | 3137 |
| 562414 | N/A | N/A | TCATTGCAGATAATAG | 45 | 9888 | 9903 | 3138 |
| 562415 | N/A | N/A | AAGTTGTCATTGCAGA | 86 | 9894 | 9909 | 154 |
| 562416 | N/A | N/A | GATTCGGATTTTTAAA | 19 | 9909 | 9924 | 3139 |
| 562417 | N/A | N/A | ATTTGGGATTCGGATT | 34 | 9915 | 9930 | 3140 |
| 562418 | N/A | N/A | ACGCTTATTTGGGATT | 64 | 9921 | 9936 | 3141 |
| 562419 | N/A | N/A | TCTAGAGAGAAAACGC | 64 | 9933 | 9948 | 3142 |
| 562420 | N/A | N/A | AGTTAAGAGGTTTTCG | 34 | 9949 | 9964 | 3143 |
| 562421 | N/A | N/A | CATTATAGTTAAGAGG | 24 | 9955 | 9970 | 3144 |
| 562422 | N/A | N/A | CACTTTCATTATAGTT | 13 | 9961 | 9976 | 3145 |
| 562423 | N/A | N/A | TAGAATGAACACTTTC | 63 | 9970 | 9985 | 3146 |
| 562424 | N/A | N/A | TTGAACTAGAATGAAC | 16 | 9976 | 9991 | 3147 |
| 562425 | N/A | N/A | ACCTGATTGAACTAGA | 51 | 9982 | 9997 | 3148 |
| 562426 | N/A | N/A | TAAAATACCTGATTGA | 19 | 9988 | 10003 | 3149 |
| 562427 | N/A | N/A | TAGAGGTAAAATACCT | 12 | 9994 | 10009 | 3150 |
| 562428 | N/A | N/A | GAAGATTAGAGGTAAA | 1 | 10000 | 10015 | 3151 |
| 562429 | N/A | N/A | TCTGAGGAAGATTAGA | 31 | 10006 | 10021 | 3152 |
| 562430 | N/A | N/A | TATACACTACCAAAAA | 0 | 10030 | 10045 | 3153 |
| 562431 | N/A | N/A | ATAATCTATACACTAC | 0 | 10036 | 10051 | 3154 |
| 562432 | N/A | N/A | TAAGTCCCAATTTTAA | 33 | 10065 | 10080 | 3155 |
| 562433 | N/A | N/A | TCTGTATAAGTCCCAA | 89 | 10071 | 10086 | 155 |
| 562434 | N/A | N/A | CCAGTTTTAAATAATC | 20 | 10085 | 10100 | 3156 |
| 562435 | N/A | N/A | TGTATCCCAGTTTTAA | 44 | 10091 | 10106 | 3157 |
| 562436 | N/A | N/A | GATGCATGTATCCCAG | 91 | 10097 | 10112 | 156 |
| 562437 | N/A | N/A | GTTTTAGATGCATGTA | 69 | 10103 | 10118 | 3158 |
| 562438 | N/A | N/A | TACAGTGTTTTAGATG | 28 | 10109 | 10124 | 3159 |

TABLE 24-continued

Inhibition of ANGPTL3 mRNA by deoxy, MOE and cEt oligonucleotides targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 562439 | N/A | N/A | GTAAGTTTATCTTCCT | 78 | 10138 | 10153 | 157 |
| 562440 | N/A | N/A | TTCCCCGTAAGTTTAT | 33 | 10144 | 10159 | 3160 |
| 562441 | N/A | N/A | CTGTATTTCCCCGTAA | 55 | 10150 | 10165 | 3161 |
| 562442 | N/A | N/A | CTGTTACTGTATTTCC | 79 | 10156 | 10171 | 158 |
| 562443 | N/A | N/A | TAGTTACTGTTACTGT | 70 | 10162 | 10177 | 3162 |
| 562444 | N/A | N/A | CGTATGTAGTTACTGT | 66 | 10168 | 10183 | 3163 |
| 562445 | N/A | N/A | AATGGGTACAGACTCG | 72 | 10182 | 10197 | 3164 |
| 562446 | N/A | N/A | GCAATTTAATGGGTAC | 59 | 10189 | 10204 | 3165 |
| 562447 | N/A | N/A | GATAGATATGCAATTT | 20 | 10198 | 10213 | 3166 |
| 562448 | N/A | N/A | AAAGGAGATAGATATG | 22 | 10204 | 10219 | 3167 |
| 562449 | N/A | N/A | CCTCCTAAAGGAGATA | 42 | 10210 | 10225 | 3168 |
| 562450 | N/A | N/A | CACCAGCCTCCTAAAG | 37 | 10216 | 10231 | 3169 |
| 560990 | 709 | 724 | TTCTTGGTGCTCTTGG | 89 | 6722 | 6737 | 111 |
| 561373 | 1197 | 1212 | TTTGTGATCCCAAGTA | 40 | 9772 | 9787 | 3170 |
| 561374 | 1199 | 1214 | GCTTTGTGATCCCAAG | 76 | 9774 | 9789 | 3171 |
| 561375 | 1201 | 1216 | TTGCTTTGTGATCCCA | 82 | 9776 | 9791 | 3172 |
| 561376 | 1203 | 1218 | TTTTGCTTTGTGATCC | 40 | 9778 | 9793 | 3173 |
| 561377 | 1205 | 1220 | CCTTTTGCTTTGTGAT | 38 | 9780 | 9795 | 3174 |
| 561378 | 1207 | 1222 | GTCCTTTTGCTTTGTG | 75 | 9782 | 9797 | 3175 |
| 561379 | 1209 | 1224 | GTGTCCTTTTGCTTTG | 40 | 9784 | 9799 | 3176 |
| 561527 | 1604 | 1619 | GAAATGTAAACGGTAT | 47 | 10576 | 10591 | 3177 |
| 561528 | 1606 | 1621 | GAGAAATGTAAACGGT | 89 | 10578 | 10593 | 174 |
| 561529 | 1608 | 1623 | TTGAGAAATGTAAACG | 55 | 10580 | 10595 | 3178 |
| 561530 | 1611 | 1626 | TGATTGAGAAATGTAA | 18 | 10583 | 10598 | 3179 |
| 561531 | 1613 | 1628 | TTTGATTGAGAAATGT | 30 | 10585 | 10600 | 3180 |
| 561532 | 1619 | 1634 | AAGAATTTTGATTGAG | 53 | 10591 | 10606 | 3181 |
| 561533 | 1621 | 1636 | ATAAGAATTTTGATTG | 29 | 10593 | 10608 | 3182 |
| 561534 | 1632 | 1647 | CAAATAGTATTATAAG | 6 | 10604 | 10619 | 3183 |
| 561535 | 1653 | 1668 | CCCACATCACAAAATT | 70 | 10625 | 10640 | 3184 |
| 561536 | 1657 | 1672 | GATTCCCACATCACAA | 77 | 10629 | 10644 | 3185 |
| 561537 | 1659 | 1674 | TTGATTCCCACATCAC | 78 | 10631 | 10646 | 3186 |
| 561538 | 1661 | 1676 | AATTGATTCCCACATC | 68 | 10633 | 10648 | 3187 |
| 561539 | 1663 | 1678 | AAAATTGATTCCCACA | 72 | 10635 | 10650 | 3188 |
| 561540 | 1665 | 1680 | CTAAAATTGATTCCCA | 54 | 10637 | 10652 | 3189 |
| 561541 | 1668 | 1683 | CATCTAAAATTGATTC | 0 | 10640 | 10655 | 3190 |
| 561542 | 1670 | 1685 | ACCATCTAAAATTGAT | 35 | 10642 | 10657 | 3191 |

TABLE 24-continued

Inhibition of ANGPTL3 mRNA by deoxy, MOE and cEt oligonucleotides targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 561543 | 1672 | 1687 | TGACCATCTAAAATTG | 55 | 10644 | 10659 | 3192 |
| 561544 | 1674 | 1689 | TGTGACCATCTAAAAT | 56 | 10646 | 10661 | 3193 |
| 561545 | 1676 | 1691 | ATTGTGACCATCTAAA | 73 | 10648 | 10663 | 3194 |
| 561546 | 1678 | 1693 | AGATTGTGACCATCTA | 67 | 10650 | 10665 | 3195 |
| 561547 | 1680 | 1695 | CTAGATTGTGACCATC | 50 | 10652 | 10667 | 3196 |
| 561548 | 1682 | 1697 | ATCTAGATTGTGACCA | 77 | 10654 | 10669 | 3197 |
| 561549 | 1684 | 1699 | TAATCTAGATTGTGAC | 55 | 10656 | 10671 | 3198 |
| 561550 | 1686 | 1701 | TATAATCTAGATTGTG | 28 | 10658 | 10673 | 3199 |
| 561551 | 1688 | 1703 | ATTATAATCTAGATTG | 52 | 10660 | 10675 | 3200 |
| 561552 | 1690 | 1705 | TGATTATAATCTAGAT | 43 | 10662 | 10677 | 3201 |
| 561553 | 1692 | 1707 | ATTGATTATAATCTAG | 53 | 10664 | 10679 | 3202 |
| 561554 | 1694 | 1709 | CTATTGATTATAATCT | 54 | 10666 | 10681 | 3203 |
| 561555 | 1696 | 1711 | ACCTATTGATTATAAT | 44 | 10668 | 10683 | 3204 |
| 561556 | 1698 | 1713 | TCACCTATTGATTATA | 52 | 10670 | 10685 | 3205 |
| 561557 | 1700 | 1715 | GTTCACCTATTGATTA | 50 | 10672 | 10687 | 3206 |
| 561558 | 1702 | 1717 | AAGTTCACCTATTGAT | 58 | 10674 | 10689 | 3207 |
| 561559 | 1704 | 1719 | ATAAGTTCACCTATTG | 66 | 10676 | 10691 | 3208 |
| 561560 | 1706 | 1721 | TAATAAGTTCACCTAT | 38 | 10678 | 10693 | 3209 |
| 561561 | 1708 | 1723 | TTTAATAAGTTCACCT | 50 | 10680 | 10695 | 3210 |
| 561562 | 1710 | 1725 | TATTTAATAAGTTCAC | 32 | 10682 | 10697 | 3211 |
| 561563 | 1712 | 1727 | GTTATTTAATAAGTTC | 47 | 10684 | 10699 | 3212 |
| 561564 | 1761 | 1776 | CATATGATGCCTTTTA | 63 | 10733 | 10748 | 3213 |
| 561565 | 1763 | 1778 | CTCATATGATGCCTTT | 81 | 10735 | 10750 | 175 |
| 561566 | 1765 | 1780 | AGCTCATATGATGCCT | 81 | 10737 | 10752 | 176 |
| 561567 | 1767 | 1782 | TTAGCTCATATGATGC | 84 | 10739 | 10754 | 177 |
| 561568 | 1769 | 1784 | TATTAGCTCATATGAT | 46 | 10741 | 10756 | 3214 |
| 561569 | 1771 | 1786 | GATATTAGCTCATATG | 49 | 10743 | 10758 | 3215 |
| 561570 | 1773 | 1788 | GTGATATTAGCTCATA | 81 | 10745 | 10760 | 3216 |
| 561571 | 1775 | 1790 | TTGTGATATTAGCTCA | 85 | 10747 | 10762 | 178 |
| 561572 | 1777 | 1792 | AGTTGTGATATTAGCT | 68 | 10749 | 10764 | 3217 |
| 561573 | 1779 | 1794 | AAAGTTGTGATATTAG | 45 | 10751 | 10766 | 3218 |
| 561574 | 1781 | 1796 | GGAAAGTTGTGATATT | 27 | 10753 | 10768 | 3219 |
| 561575 | 1783 | 1798 | TGGGAAAGTTGTGATA | 36 | 10755 | 10770 | 3220 |
| 561576 | 1785 | 1800 | ACTGGGAAAGTTGTGA | 83 | 10757 | 10772 | 179 |
| 561577 | 1787 | 1802 | AAACTGGGAAAGTTGT | 56 | 10759 | 10774 | 3221 |

TABLE 24-continued

Inhibition of ANGPTL3 mRNA by deoxy, MOE and cEt oligonucleotides targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 561578 | 1789 | 1804 | TTAAACTGGGAAAGTT | 44 | 10761 | 10776 | 3222 |
| 561579 | 1794 | 1809 | GTTTTTTAAACTGGGA | 58 | 10766 | 10781 | 3223 |
| 561580 | 1796 | 1811 | TAGTTTTTTAAACTGG | 0 | 10768 | 10783 | 3224 |
| 561581 | 1802 | 1817 | GAGTACTAGTTTTTA | 18 | 10774 | 10789 | 3225 |
| 561582 | 1804 | 1819 | AAGAGTACTAGTTTTT | 55 | 10776 | 10791 | 3226 |
| 561583 | 1806 | 1821 | ACAAGAGTACTAGTTT | 51 | 10778 | 10793 | 3227 |
| 561584 | 1808 | 1823 | TAACAAGAGTACTAGT | 53 | 10780 | 10795 | 3228 |
| 561585 | 1810 | 1825 | TTTAACAAGAGTACTA | 48 | 10782 | 10797 | 3229 |
| 561586 | 1812 | 1827 | GTTTTAACAAGAGTAC | 49 | 10784 | 10799 | 3230 |
| 561587 | 1814 | 1829 | GAGTTTTAACAAGAGT | 54 | 10786 | 10801 | 3231 |
| 561588 | 1816 | 1831 | TAGAGTTTTAACAAGA | 9 | 10788 | 10803 | 3232 |
| 561589 | 1819 | 1834 | GTTTAGAGTTTTAACA | 24 | 10791 | 10806 | 3233 |
| 561590 | 1822 | 1837 | CAAGTTTAGAGTTTTA | 30 | 10794 | 10809 | 3234 |
| 561591 | 1824 | 1839 | GTCAAGTTTAGAGTTT | 60 | 10796 | 10811 | 3235 |
| 561592 | 1826 | 1841 | TAGTCAAGTTTAGAGT | 56 | 10798 | 10813 | 3236 |
| 561593 | 1828 | 1843 | TTTAGTCAAGTTTAGA | 41 | 10800 | 10815 | 3237 |
| 561594 | 1830 | 1845 | TATTTAGTCAAGTTTA | 14 | 10802 | 10817 | 3238 |
| 561595 | 1832 | 1847 | TGTATTTAGTCAAGTT | 39 | 10804 | 10819 | 3239 |
| 561596 | 1834 | 1849 | TCTGTATTTAGTCAAG | 51 | 10806 | 10821 | 3240 |
| 561597 | 1836 | 1851 | CCTCTGTATTTAGTCA | 72 | 10808 | 10823 | 3241 |
| 561598 | 1838 | 1853 | GTCCTCTGTATTTAGT | 55 | 10810 | 10825 | 3242 |
| 561599 | 1840 | 1855 | CAGTCCTCTGTATTTA | 63 | 10812 | 10827 | 3243 |
| 561600 | 1842 | 1857 | ACCAGTCCTCTGTATT | 66 | 10814 | 10829 | 3244 |
| 561601 | 1844 | 1859 | TTACCAGTCCTCTGTA | 57 | 10816 | 10831 | 3245 |
| 561602 | 1846 | 1861 | AATTACCAGTCCTCTG | 43 | 10818 | 10833 | 3246 |
| 561603 | 1848 | 1863 | ACAATTACCAGTCCTC | 67 | 10820 | 10835 | 3247 |

TABLE 25

Inhibition of ANGPTL3 mRNA by deoxy, MOE and (S)-cEt gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 561770 | N/A | N/A | ACAAAGGTAGGTCACC | 77 | 11576 | 11591 | 143 |
| 586719 | N/A | N/A | TCTGACAAGATTCCTT | 76 | 11167 | 11182 | 3248 |
| 586720 | N/A | N/A | ATCTGACAAGATTCCT | 79 | 11168 | 11183 | 3249 |

TABLE 25-continued

Inhibition of ANGPTL3 mRNA by deoxy, MOE and (S)-cEt gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 586721 | N/A | N/A | TAATCTGACAAGATTC | 50 | 11170 | 11185 | 3250 |
| 586722 | N/A | N/A | GTAATCTGACAAGATT | 41 | 11171 | 11186 | 3251 |
| 586723 | N/A | N/A | CTTGTCAGGCTGTTTA | 50 | 11312 | 11327 | 3252 |
| 586724 | N/A | N/A | GCTTGTCAGGCTGTTT | 81 | 11313 | 11328 | 3253 |
| 586725 | N/A | N/A | ATGCTTGTCAGGCTGT | 78 | 11315 | 11330 | 3254 |
| 586726 | N/A | N/A | TACATGCTTGTCAGGC | 78 | 11318 | 11333 | 3255 |
| 586727 | N/A | N/A | ATACATGCTTGTCAGG | 76 | 11319 | 11334 | 3256 |
| 586728 | N/A | N/A | AAAGGTAGGTCACCAT | 72 | 11574 | 11589 | 3257 |
| 586729 | N/A | N/A | CAAAGGTAGGTCACCA | 69 | 11575 | 11590 | 3258 |
| 586730 | N/A | N/A | GACAAAGGTAGGTCAC | 55 | 11577 | 11592 | 3259 |
| 586731 | N/A | N/A | TGACAAAGGTAGGTCA | 32 | 11578 | 11593 | 3260 |
| 586732 | N/A | N/A | TCTGACATAGCTTTTT | 63 | 5436 | 5451 | 3261 |
| 586733 | N/A | N/A | ATTCTGACATAGCTTT | 76 | 5438 | 5453 | 3262 |
| 586734 | N/A | N/A | GATTCTGACATAGCTT | 73 | 5439 | 5454 | 3263 |
| 586735 | N/A | N/A | GGATTCTGACATAGCT | 81 | 5440 | 5455 | 3264 |
| 586736 | N/A | N/A | ATGGATTCTGACATAG | 74 | 5442 | 5457 | 3265 |
| 586737 | N/A | N/A | CATGGATTCTGACATA | 72 | 5443 | 5458 | 3266 |
| 586738 | N/A | N/A | ACATGGATTCTGACAT | 59 | 5444 | 5459 | 3267 |
| 586739 | N/A | N/A | TACATGGATTCTGACA | 71 | 5445 | 5460 | 3268 |
| 586740 | N/A | N/A | ATACATGGATTCTGAC | 60 | 5446 | 5461 | 3269 |
| 586741 | N/A | N/A | TTTAGCAGCACTACTA | 65 | 5628 | 5643 | 3270 |
| 586742 | N/A | N/A | TTTTAGCAGCACTACT | 51 | 5629 | 5644 | 3271 |
| 586743 | N/A | N/A | CTTTTAGCAGCACTAC | 74 | 5630 | 5645 | 3272 |
| 586744 | N/A | N/A | CCTTTTAGCAGCACTA | 83 | 5631 | 5646 | 223 |
| 586745 | N/A | N/A | ACCTTTTAGCAGCACT | 84 | 5632 | 5647 | 224 |
| 586746 | N/A | N/A | AAACCTTTTAGCAGCA | 87 | 5634 | 5649 | 225 |
| 586747 | N/A | N/A | AAAACCTTTTAGCAGC | 80 | 5635 | 5650 | 3273 |
| 586748 | N/A | N/A | GATAAAAACCTTTTA | 16 | 5640 | 5655 | 3274 |
| 586749 | N/A | N/A | TGATAAAAACCTTTT | 25 | 5641 | 5656 | 3275 |
| 586750 | N/A | N/A | AGATGTTGGCAGGTTG | 72 | 6188 | 6203 | 3276 |
| 586751 | N/A | N/A | TAGATGTTGGCAGGTT | 76 | 6189 | 6204 | 3277 |
| 586752 | N/A | N/A | GTAGATGTTGGCAGGT | 73 | 6190 | 6205 | 3278 |
| 586753 | N/A | N/A | TGTAGATGTTGGCAGG | 65 | 6191 | 6206 | 3279 |
| 586754 | N/A | N/A | CTGTAGATGTTGGCAG | 61 | 6192 | 6207 | 3280 |
| 586755 | N/A | N/A | ATCTGTAGATGTTGGC | 84 | 6194 | 6209 | 226 |

TABLE 25-continued

Inhibition of ANGPTL3 mRNA by deoxy, MOE and (S)-cEt gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 586756 | N/A | N/A | TATCTGTAGATGTTGG | 71 | 6195 | 6210 | 3281 |
| 586757 | N/A | N/A | ATATCTGTAGATGTTG | 61 | 6196 | 6211 | 3282 |
| 586758 | N/A | N/A | CATATCTGTAGATGTT | 63 | 6197 | 6212 | 3283 |
| 586759 | N/A | N/A | TTTGAACCAGGCTTTC | 47 | 6243 | 6258 | 3284 |
| 586760 | N/A | N/A | AATTTGAACCAGGCTT | 78 | 6245 | 6260 | 3285 |
| 586761 | N/A | N/A | TAATTTGAACCAGGCT | 83 | 6246 | 6261 | 227 |
| 586762 | N/A | N/A | CATAATTTGAACCAGG | 81 | 6248 | 6263 | 3286 |
| 586763 | N/A | N/A | ACATAATTTGAACCAG | 36 | 6249 | 6264 | 3287 |
| 586764 | N/A | N/A | TACATAATTTGAACCA | 38 | 6250 | 6265 | 3288 |
| 586765 | N/A | N/A | ATACATAATTTGAACC | 15 | 6251 | 6266 | 3289 |
| 586766 | N/A | N/A | ACATTGGTCGGAAAAC | 43 | 6424 | 6439 | 3290 |
| 586767 | N/A | N/A | GACATTGGTCGGAAAA | 49 | 6425 | 6440 | 3291 |
| 586768 | N/A | N/A | AGACATTGGTCGGAAA | 59 | 6426 | 6441 | 3292 |
| 586769 | N/A | N/A | CAGACATTGGTCGGAA | 66 | 6427 | 6442 | 3293 |
| 586770 | N/A | N/A | GCAGACATTGGTCGGA | 80 | 6428 | 6443 | 3294 |
| 586771 | N/A | N/A | AAGCAGACATTGGTCG | 65 | 6430 | 6445 | 3295 |
| 586772 | N/A | N/A | TGTACAGATTACCTGT | 51 | 6506 | 6521 | 3296 |
| 586773 | N/A | N/A | TTGTACAGATTACCTG | 34 | 6507 | 6522 | 3297 |
| 586774 | N/A | N/A | ATTGTACAGATTACCT | 62 | 6508 | 6523 | 3298 |
| 586775 | N/A | N/A | GATTGTACAGATTACC | 59 | 6509 | 6524 | 3299 |
| 586776 | N/A | N/A | AGATTGTACAGATTAC | 46 | 6510 | 6525 | 3300 |
| 586777 | N/A | N/A | TCAGATTGTACAGATT | 63 | 6512 | 6527 | 3301 |
| 586778 | N/A | N/A | TTCAGATTGTACAGAT | 63 | 6513 | 6528 | 3302 |
| 586779 | N/A | N/A | ATTCAGATTGTACAGA | 71 | 6514 | 6529 | 3303 |
| 586780 | N/A | N/A | TATTCAGATTGTACAG | 55 | 6515 | 6530 | 3304 |
| 586781 | N/A | N/A | TTATTCAGATTGTACA | 52 | 6516 | 6531 | 3305 |
| 586782 | N/A | N/A | TAGGTATGTCTTTTAT | 52 | 6936 | 6951 | 3306 |
| 586783 | N/A | N/A | TGTCTTAGGTATGTCT | 76 | 6941 | 6956 | 3307 |
| 586784 | N/A | N/A | ATTGTCTTAGGTATGT | 73 | 6943 | 6958 | 3308 |
| 586785 | N/A | N/A | GATTGTCTTAGGTATG | 60 | 6944 | 6959 | 3309 |
| 586786 | N/A | N/A | TTCTTAGATGGCGTGT | 74 | 7207 | 7222 | 3310 |
| 586787 | N/A | N/A | TTTTCTTAGATGGCGT | 86 | 7209 | 7224 | 228 |
| 586788 | N/A | N/A | ATTTTTCTTAGATGGC | 75 | 7211 | 7226 | 3311 |
| 586789 | N/A | N/A | CATTTTTCTTAGATGG | 49 | 7212 | 7227 | 3312 |
| 586790 | N/A | N/A | GCATTTTTCTTAGATG | 47 | 7213 | 7228 | 3313 |
| 586791 | N/A | N/A | ATAAGTCCCAATTTTA | 27 | 10066 | 10081 | 3314 |

TABLE 25-continued

Inhibition of ANGPTL3 mRNA by deoxy, MOE and (S)-cEt gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 586792 | N/A | N/A | TATAAGTCCCAATTTT | 27 | 10067 | 10082 | 3315 |
| 586793 | N/A | N/A | GTATAAGTCCCAATTT | 28 | 10068 | 10083 | 3316 |
| 586794 | N/A | N/A | TGTATAAGTCCCAATT | 38 | 10069 | 10084 | 3317 |
| 586795 | N/A | N/A | CTGTATAAGTCCCAAT | 69 | 10070 | 10085 | 3318 |
| 586796 | N/A | N/A | ATCTGTATAAGTCCCA | 88 | 10072 | 10087 | 229 |
| 586797 | N/A | N/A | AATCTGTATAAGTCCC | 84 | 10073 | 10088 | 230 |
| 586798 | N/A | N/A | TAATCTGTATAAGTCC | 58 | 10074 | 10089 | 3319 |
| 586799 | N/A | N/A | ATAATCTGTATAAGTC | 21 | 10075 | 10090 | 3320 |
| 586800 | N/A | N/A | AATAATCTGTATAAGT | 12 | 10076 | 10091 | 3321 |
| 586801 | N/A | N/A | TGCATGTATCCCAGTT | 80 | 10095 | 10110 | 3322 |
| 586802 | N/A | N/A | ATGCATGTATCCCAGT | 83 | 10096 | 10111 | 231 |
| 586803 | N/A | N/A | AGATGCATGTATCCCA | 79 | 10098 | 10113 | 232 |
| 586804 | N/A | N/A | TAGATGCATGTATCCC | 87 | 10099 | 10114 | 3323 |
| 586805 | N/A | N/A | TTAGATGCATGTATCC | 78 | 10100 | 10115 | 3324 |
| 586806 | N/A | N/A | TTTAGATGCATGTATC | 50 | 10101 | 10116 | 3325 |
| 586653 | 7 | 22 | GTGGAACTGTTTTCTT | 63 | 3111 | 3126 | 3326 |
| 586656 | 9 | 24 | ACGTGGAACTGTTTTC | 72 | 3113 | 3128 | 3327 |
| 586658 | 99 | 114 | TTGATCAATTCTGGAG | 74 | 3203 | 3218 | 3328 |
| 586660 | 101 | 116 | TCTTGATCAATTCTGG | 71 | 3205 | 3220 | 3329 |
| 561011 | 102 | 117 | GTCTTGATCAATTCTG | 91 | 3206 | 3221 | 114 |
| 586661 | 103 | 118 | TGTCTTGATCAATTCT | 85 | 3207 | 3222 | 209 |
| 586663 | 134 | 149 | GGCTCTGGAGATAGAG | 63 | 3238 | 3253 | 3330 |
| 586665 | 136 | 151 | TTGGCTCTGGAGATAG | 63 | 3240 | 3255 | 3331 |
| 586668 | 140 | 155 | GATTTTGGCTCTGGAG | 64 | 3244 | 3259 | 3332 |
| 586669 | 142 | 157 | TTGATTTTGGCTCTGG | 89 | 3246 | 3261 | 210 |
| 561026 | 143 | 158 | CTTGATTTTGGCTCTG | 84 | 3247 | 3262 | 117 |
| 586670 | 144 | 159 | TCTTGATTTTGGCTCT | 71 | 3248 | 3263 | 3333 |
| 586671 | 146 | 161 | AATCTTGATTTTGGCT | 70 | 3250 | 3265 | 3334 |
| 586672 | 148 | 163 | CAAATCTTGATTTTGG | 81 | 3252 | 3267 | 3335 |
| 586673 | 298 | 313 | GCAGCGATAGATCATA | 76 | 3402 | 3417 | 3336 |
| 586674 | 300 | 315 | TTGCAGCGATAGATCA | 76 | 3404 | 3419 | 3337 |
| 586675 | 304 | 319 | TGGTTTGCAGCGATAG | 82 | 3408 | 3423 | 3338 |
| 586676 | 306 | 321 | ACTGGTTTGCAGCGAT | 89 | 3410 | 3425 | 211 |
| 586677 | 315 | 330 | TTTGATTTCACTGGTT | 62 | 3419 | 3434 | 3339 |
| 586678 | 317 | 332 | TCTTTGATTTCACTGG | 66 | 3421 | 3436 | 3340 |

TABLE 25-continued

Inhibition of ANGPTL3 mRNA by deoxy, MOE and (S)-cEt gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 586679 | 342 | 357 | AGTTCTTCTCAGTTCC | 77 | 3446 | 3461 | 3341 |
| 586680 | 476 | 491 | TTAGTTAGTTGCTCTT | 65 | 3580 | 3595 | 3342 |
| 586681 | 478 | 493 | AGTTAGTTAGTTGCTC | 69 | 3582 | 3597 | 3343 |
| 586682 | 703 | 718 | GTGCTCTTGGCTTGGA | 78 | 6716 | 6731 | 3344 |
| 586683 | 705 | 720 | TGGTGCTCTTGGCTTG | 77 | 6718 | 6733 | 3345 |
| 586684 | 802 | 817 | TATGTTCACCTCTGTT | 55 | 7387 | 7402 | 3346 |
| 586685 | 804 | 819 | TGTATGTTCACCTCTG | 79 | 7389 | 7404 | 3347 |
| 586686 | 1260 | 1275 | ACACTCATCATGCCAC | 72 | 10232 | 10247 | 3348 |
| 586687 | 1262 | 1277 | CCACACTCATCATGCC | 82 | 10234 | 10249 | 3349 |
| 586688 | 1308 | 1323 | AGATTTGCTCTTGGT | 87 | 10280 | 10295 | 212 |
| 586689 | 1310 | 1325 | TTAGATTTTGCTCTTG | 78 | 10282 | 10297 | 3350 |
| 586690 | 1351 | 1366 | CATTTTGAGACTTCCA | 91 | 10323 | 10338 | 213 |
| 586691 | 1353 | 1368 | TCCATTTTGAGACTTC | 86 | 10325 | 10340 | 214 |
| 586692 | 1365 | 1380 | AGAGTATAACCTTCCA | 88 | 10337 | 10352 | 220 |
| 586693 | 1367 | 1382 | ATAGAGTATAACCTTC | 69 | 10339 | 10354 | 3351 |
| 586694 | 1402 | 1417 | AATCTGTTGGATGGAT | 59 | 10374 | 10389 | 3352 |
| 586695 | 1404 | 1419 | TGAATCTGTTGGATGG | 79 | 10376 | 10391 | 3353 |
| 586696 | 1420 | 1435 | TTCATTCAAAGCTTTC | 82 | 10392 | 10407 | 3354 |
| 586697 | 1422 | 1437 | AGTTCATTCAAAGCTT | 73 | 10394 | 10409 | 3355 |
| 561463 | 1423 | 1438 | CAGTTCATTCAAAGCT | 88 | 10395 | 10410 | 127 |
| 586698 | 1424 | 1439 | TCAGTTCATTCAAAGC | 69 | 10396 | 10411 | 3356 |
| 586699 | 1488 | 1503 | GATTATTAGACCACAT | 63 | 10460 | 10475 | 3357 |
| 586700 | 1490 | 1505 | CAGATTATTAGACCAC | 90 | 10462 | 10477 | 221 |
| 561487 | 1491 | 1506 | CCAGATTATTAGACCA | 95 | 10463 | 10478 | 131 |
| 586701 | 1492 | 1507 | ACCAGATTATTAGACC | 85 | 10464 | 10479 | 215 |
| 586702 | 1552 | 1567 | TAGACAGTGACTTTAA | 83 | 10524 | 10539 | 216 |
| 586703 | 1554 | 1569 | AATAGACAGTGACTTT | 70 | 10526 | 10541 | 3358 |
| 586704 | 1605 | 1620 | AGAAATGTAAACGGTA | 76 | 10577 | 10592 | 3359 |
| 586705 | 1607 | 1622 | TGAGAAATGTAAACGG | 83 | 10579 | 10594 | 217 |
| 586706 | 1762 | 1777 | TCATATGATGCCTTTT | 69 | 10734 | 10749 | 3360 |
| 586707 | 1764 | 1779 | GCTCATATGATGCCTT | 84 | 10736 | 10751 | 218 |
| 586708 | 1766 | 1781 | TAGCTCATATGATGCC | 83 | 10738 | 10753 | 222 |
| 561567 | 1767 | 1782 | TTAGCTCATATGATGC | 81 | 10739 | 10754 | 177 |
| 586709 | 1768 | 1783 | ATTAGCTCATATGATG | 40 | 10740 | 10755 | 3361 |
| 586710 | 1774 | 1789 | TGTGATATTAGCTCAT | 73 | 10746 | 10761 | 3362 |
| 586711 | 1776 | 1791 | GTTGTGATATTAGCTC | 80 | 10748 | 10763 | 3363 |

TABLE 25-continued

Inhibition of ANGPTL3 mRNA by deoxy, MOE and (S)-cEt gapmers targeting SEQ ID NO: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 586712 | 1905 | 1920 | TACTCTGTGCTGACGA | 81 | 10877 | 10892 | 3364 |
| 586713 | 1907 | 1922 | CATACTCTGTGCTGAC | 81 | 10879 | 10894 | 3365 |
| 586714 | 2052 | 2067 | GTTTAAAGACAGCGAA | 72 | 11024 | 11039 | 3366 |
| 586715 | 2054 | 2069 | TTGTTTAAAGACAGCG | 81 | 11026 | 11041 | 3367 |
| 586716 | 2068 | 2083 | GTAGTCATCTCCATTT | 63 | 11040 | 11055 | 3368 |
| 586717 | 2070 | 2085 | TAGTAGTCATCTCCAT | 74 | 11042 | 11057 | 3369 |
| 561650 | 2071 | 2086 | TTAGTAGTCATCTCCA | 79 | 11043 | 11058 | 142 |
| 586718 | 2072 | 2087 | CTTAGTAGTCATCTCC | 84 | 11044 | 11059 | 219 |

Example 5: Antisense Inhibition of Human ANGPTL3 in Hep3B Cells by Deoxy, MOE and (S)-cEt Gapmers Additional antisense oligonucleotides were designed targeting an ANGPTL3 nucleic acid and were tested for their effects on ANGPTL3 mRNA in vitro. ISIS 337487 and ISIS 233717, which are 5-10-5 MOE gapmers, were also included in the assay as benchmark oligonucleotides. Cultured Hep3B cells at a density of 20,000 cells per well were transfected using electroporation with 4,500 nM antisense oligonucleotide. After a treatment period of approximately 24 hours, RNA was isolated from the cells and ANGPTL3 mRNA levels were measured by quantitative real-time PCR. Human primer probe set RTS3492_MGB was used to measure mRNA levels. ANGPTL3 mRNA levels were adjusted according to total RNA content, as measured by RIBOGREEN®. Results are presented as percent inhibition of ANGPTL3, relative to untreated control cells.

The newly designed chimeric antisense oligonucleotides in the Tables below were designed as deoxy, MOE, and (S)-cEt oligonucleotides or 5-10-5 MOE gapmers. The deoxy, MOE and (S)-cEt oligonucleotides are 16 nucleosides in length wherein the nucleoside have either a MOE sugar modification, an (S)-cEt sugar modification, or a deoxy sugar residue. The sugar modifications of each antisense oligonucleotide is described as 'eek-d10-kke', where 'k' indicates an (S)-cEt sugar modification; 'd' indicates deoxyribose; the number indicates the number of deoxyribose sugars residues; and 'e' indicates a MOE modification. The 5-10-5 MOE gapmers are 20 nucleosides in length, wherein the central gap segment comprises often 2'-deoxynucleosides and is flanked by wing segments on the 5' direction and the 3' direction comprising five nucleosides each. The internucleoside linkages throughout each oligonucleotide are phosphorothioate (P=S) linkages. All cytosine residues throughout each oligonucleotide are 5-methylcytosines. "Start site" indicates the 5'-most nucleoside to which the oligonucleotide is targeted in the human gene sequence. "Stop site" indicates the 3'-most nucleoside to which the oligonucleotide is targeted human gene sequence. Each oligonucleotide listed in the Tables below is targeted to either the human ANGPTL3 mRNA, designated herein as SEQ ID NO: 1 (GENBANK Accession No. NM_014495.2) or the human ANGPTL3 genomic sequence, designated herein as SEQ ID NO: 2 (GENBANK Accession No. NT_032977.9 truncated from nucleotides 33032001 to 33046000). 'n/a' indicates that the antisense oligonucleotide does not target that particular gene sequence with 100% complementarity.

TABLE 26

Inhibition of ANGPTL3 mRNA by oligonucleotides targeting SEQ ID NO: 1 and 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 561671 | N/A | N/A | TCTTAACTCTATATAT | Deoxy, MOE, and cEt | 12 | 3076 | 3091 | 3370 |
| 561672 | N/A | N/A | CTTCTTAACTCTATAT | Deoxy, MOE, and cEt | 12 | 3078 | 3093 | 3371 |
| 561673 | N/A | N/A | GACTTCTTAACTCTAT | Deoxy, MOE, and cEt | 18 | 3080 | 3095 | 3372 |
| 561674 | N/A | N/A | TAGACTTCTTAACTCT | Deoxy, MOE, and cEt | 20 | 3082 | 3097 | 3373 |
| 561675 | N/A | N/A | CCTAGACTTCTTAACT | Deoxy, MOE, and cEt | 9 | 3084 | 3099 | 3374 |

TABLE 26-continued

Inhibition of ANGPTL3 mRNA by oligonucleotides targeting SEQ ID NO: 1 and 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 561676 | N/A | N/A | GACCTAGACTTCTTAA | Deoxy, MOE, and cEt | 0 | 3086 | 3101 | 3375 |
| 561677 | N/A | N/A | CAGACCTAGACTTCTT | Deoxy, MOE, and cEt | 18 | 3088 | 3103 | 3376 |
| 561678 | N/A | N/A | AGCAGACCTAGACTTC | Deoxy, MOE, and cEt | 26 | 3090 | 3105 | 3377 |
| 561679 | N/A | N/A | GAAGCAGACCTAGACT | Deoxy, MOE, and cEt | 24 | 3092 | 3107 | 3378 |
| 561680 | N/A | N/A | TGGAAGCAGACCTAGA | Deoxy, MOE, and cEt | 30 | 3094 | 3109 | 3379 |
| 561758 | N/A | N/A | CTTTAACAAATGGGTT | Deoxy, MOE, and cEt | 25 | 11539 | 11554 | 3380 |
| 561759 | N/A | N/A | ATCCTTTAACAAATGG | Deoxy, MOE, and cEt | 31 | 11542 | 11557 | 3381 |
| 561760 | N/A | N/A | CTATATCCTTTAACAA | Deoxy, MOE, and cEt | 28 | 11546 | 11561 | 3382 |
| 561761 | N/A | N/A | GCACTATATCCTTTAA | Deoxy, MOE, and cEt | 59 | 11549 | 11564 | 3383 |
| 561762 | N/A | N/A | TGGGCACTATATCCTT | Deoxy, MOE, and cEt | 34 | 11552 | 11567 | 3384 |
| 561763 | N/A | N/A | ACTTGGGCACTATATC | Deoxy, MOE, and cEt | 30 | 11555 | 11570 | 3385 |
| 561764 | N/A | N/A | ATAACTTGGGCACTAT | Deoxy, MOE, and cEt | 51 | 11558 | 11573 | 3386 |
| 561765 | N/A | N/A | CATATAACTTGGGCAC | Deoxy, MOE, and cEt | 47 | 11561 | 11576 | 3387 |
| 561766 | N/A | N/A | CACCATATAACTTGGG | Deoxy, MOE, and cEt | 47 | 11564 | 11579 | 3388 |
| 561767 | N/A | N/A | GGTCACCATATAACTT | Deoxy, MOE, and cEt | 58 | 11567 | 11582 | 3389 |
| 561768 | N/A | N/A | GTAGGTCACCATATAA | Deoxy, MOE, and cEt | 62 | 11570 | 11585 | 3390 |
| 561769 | N/A | N/A | AAGGTAGGTCACCATA | Deoxy, MOE, and cEt | 65 | 11573 | 11588 | 3391 |
| 561770 | N/A | N/A | ACAAAGGTAGGTCACC | Deoxy, MOE, and cEt | 73 | 11576 | 11591 | 143 |
| 561771 | N/A | N/A | TTGACAAAGGTAGGTC | Deoxy, MOE, and cEt | 70 | 11579 | 11594 | 3392 |
| 561772 | N/A | N/A | GTATTGACAAAGGTAG | Deoxy, MOE, and cEt | 58 | 11582 | 11597 | 3393 |
| 561773 | N/A | N/A | TAAGTATTGACAAAGG | Deoxy, MOE, and cEt | 42 | 11585 | 11600 | 3394 |
| 561774 | N/A | N/A | TGCTAAGTATTGACAA | Deoxy, MOE, and cEt | 51 | 11588 | 11603 | 3395 |
| 561775 | N/A | N/A | TAATGCTAAGTATTGA | Deoxy, MOE, and cEt | 42 | 11591 | 11606 | 3396 |
| 561776 | N/A | N/A | TACATAATGCTAAGTA | Deoxy, MOE, and cEt | 36 | 11595 | 11610 | 3397 |
| 561777 | N/A | N/A | GGATAATTTGAAATAC | Deoxy, MOE, and cEt | 24 | 11608 | 11623 | 3398 |
| 561778 | N/A | N/A | TATTGGATAATTTGAA | Deoxy, MOE, and cEt | 35 | 11612 | 11627 | 3399 |
| 561779 | N/A | N/A | GTATATTGGATAATTT | Deoxy, MOE, and cEt | 0 | 11615 | 11630 | 3400 |
| 561780 | N/A | N/A | CATGTATATTGGATAA | Deoxy, MOE, and cEt | 20 | 11618 | 11633 | 3401 |
| 561781 | N/A | N/A | TGACATGTATATTGGA | Deoxy, MOE, and cEt | 73 | 11621 | 11636 | 144 |
| 561782 | N/A | N/A | CTTTTATATATGTGAC | Deoxy, MOE, and cEt | 37 | 11652 | 11667 | 3402 |
| 561783 | N/A | N/A | GATCATACATATCTTT | Deoxy, MOE, and cEt | 51 | 11664 | 11679 | 3403 |
| 561784 | N/A | N/A | ATAGATCATACATATC | Deoxy, MOE, and cEt | 46 | 11667 | 11682 | 3404 |
| 561785 | N/A | N/A | CACATAGATCATACAT | Deoxy, MOE, and cEt | 65 | 11670 | 11685 | 3405 |
| 561786 | N/A | N/A | ATTCACATAGATCATA | Deoxy, MOE, and cEt | 48 | 11673 | 11688 | 3406 |
| 561787 | N/A | N/A | AGGATTCACATAGATC | Deoxy, MOE, and cEt | 48 | 11676 | 11691 | 3407 |
| 561788 | N/A | N/A | CTTAGGATTCACATAG | Deoxy, MOE, and cEt | 42 | 11679 | 11694 | 3408 |

TABLE 26-continued

Inhibition of ANGPTL3 mRNA by oligonucleotides targeting SEQ ID NO: 1 and 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 561789 | N/A | N/A | TTACTTAGGATTCACA | Deoxy, MOE, and cEt | 58 | 11682 | 11697 | 3409 |
| 561790 | N/A | N/A | TATTTACTTAGGATTC | Deoxy, MOE, and cEt | 45 | 11685 | 11700 | 3410 |
| 561791 | N/A | N/A | GTACTTTTCTGGAACA | Deoxy, MOE, and cEt | 77 | 11704 | 11719 | 145 |
| 561792 | N/A | N/A | CCTGAAAATTATAGAT | Deoxy, MOE, and cEt | 35 | 11741 | 11756 | 3411 |
| 561793 | N/A | N/A | GGTCCTGAAAATTATA | Deoxy, MOE, and cEt | 32 | 11744 | 11759 | 3412 |
| 561794 | N/A | N/A | TGTGGTCCTGAAAATT | Deoxy, MOE, and cEt | 45 | 11747 | 11762 | 3413 |
| 561795 | N/A | N/A | GTCTGTGGTCCTGAAA | Deoxy, MOE, and cEt | 47 | 11750 | 11765 | 3414 |
| 561796 | N/A | N/A | TTAGTCTGTGGTCCTG | Deoxy, MOE, and cEt | 67 | 11753 | 11768 | 3415 |
| 561797 | N/A | N/A | AGCTTAGTCTGTGGTC | Deoxy, MOE, and cEt | 55 | 11756 | 11771 | 3416 |
| 561798 | N/A | N/A | GACAGCTTAGTCTGTG | Deoxy, MOE, and cEt | 47 | 11759 | 11774 | 3417 |
| 561799 | N/A | N/A | TTCGACAGCTTAGTCT | Deoxy, MOE, and cEt | 68 | 11762 | 11777 | 3418 |
| 561800 | N/A | N/A | AATTTCGACAGCTTAG | Deoxy, MOE, and cEt | 61 | 11765 | 11780 | 3419 |
| 561801 | N/A | N/A | GTTAATTTCGACAGCT | Deoxy, MOE, and cEt | 70 | 11768 | 11783 | 3420 |
| 561802 | N/A | N/A | CCTAAAAAAATCAGCG | Deoxy, MOE, and cEt | 19 | 11783 | 11798 | 3421 |
| 561803 | N/A | N/A | GGCCCTAAAAAAATCA | Deoxy, MOE, and cEt | 0 | 11786 | 11801 | 3422 |
| 561804 | N/A | N/A | TTCTGGCCCTAAAAAA | Deoxy, MOE, and cEt | 10 | 11790 | 11805 | 3423 |
| 561805 | N/A | N/A | GTATTCTGGCCCTAAA | Deoxy, MOE, and cEt | 44 | 11793 | 11808 | 3424 |
| 561806 | N/A | N/A | TTGGTATTCTGGCCCT | Deoxy, MOE, and cEt | 45 | 11796 | 11811 | 3425 |
| 561807 | N/A | N/A | ATTTTGGTATTCTGGC | Deoxy, MOE, and cEt | 59 | 11799 | 11814 | 3426 |
| 561808 | N/A | N/A | GCCATTTTGGTATTCT | Deoxy, MOE, and cEt | 58 | 11802 | 11817 | 3427 |
| 561809 | N/A | N/A | GGAGCCATTTTGGTAT | Deoxy, MOE, and cEt | 33 | 11805 | 11820 | 3428 |
| 561810 | N/A | N/A | AGAGGAGCCATTTTGG | Deoxy, MOE, and cEt | 36 | 11808 | 11823 | 3429 |
| 561811 | N/A | N/A | AAGAGAGGAGCCATTT | Deoxy, MOE, and cEt | 14 | 11811 | 11826 | 3430 |
| 561812 | N/A | N/A | ATTGTCCAATTTTGGG | Deoxy, MOE, and cEt | 25 | 11829 | 11844 | 3431 |
| 561813 | N/A | N/A | GAAATTGTCCAATTTT | Deoxy, MOE, and cEt | 38 | 11832 | 11847 | 3432 |
| 561814 | N/A | N/A | TTTGAAATTGTCCAAT | Deoxy, MOE, and cEt | 36 | 11835 | 11850 | 3433 |
| 561815 | N/A | N/A | GCATTTGAAATTGTCC | Deoxy, MOE, and cEt | 67 | 11838 | 11853 | 3434 |
| 561816 | N/A | N/A | GCAACTCATATATTAA | Deoxy, MOE, and cEt | 57 | 11869 | 11884 | 3435 |
| 561817 | N/A | N/A | GAAGCAACTCATATAT | Deoxy, MOE, and cEt | 46 | 11872 | 11887 | 3436 |
| 561818 | N/A | N/A | GAGGAAGCAACTCATA | Deoxy, MOE, and cEt | 14 | 11875 | 11890 | 3437 |
| 561819 | N/A | N/A | ATAGAGGAAGCAACTC | Deoxy, MOE, and cEt | 60 | 11878 | 11893 | 3438 |
| 561820 | N/A | N/A | CAAATAGAGGAAGCAA | Deoxy, MOE, and cEt | 36 | 11881 | 11896 | 3439 |
| 561821 | N/A | N/A | AACCAAATAGAGGAAG | Deoxy, MOE, and cEt | 38 | 11884 | 11899 | 3440 |
| 561822 | N/A | N/A | GGAAACCAAATAGAGG | Deoxy, MOE, and cEt | 51 | 11887 | 11902 | 3441 |
| 561823 | N/A | N/A | CTTTAAGTGAAGTTAC | Deoxy, MOE, and cEt | 30 | 3636 | 3651 | 3442 |
| 561824 | N/A | N/A | TACTTACTTTAAGTGA | Deoxy, MOE, and cEt | 27 | 3642 | 3657 | 3443 |

TABLE 26-continued

Inhibition of ANGPTL3 mRNA by oligonucleotides targeting SEQ ID NO: 1 and 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 561825 | N/A | N/A | GAACCCTCTTTATTTT | Deoxy, MOE, and cEt | 25 | 3659 | 3674 | 3444 |
| 561826 | N/A | N/A | AAACATGAACCCTCTT | Deoxy, MOE, and cEt | 14 | 3665 | 3680 | 3445 |
| 561827 | N/A | N/A | GATCCACATTGAAAAC | Deoxy, MOE, and cEt | 0 | 3683 | 3698 | 3446 |
| 561828 | N/A | N/A | CATGCCTTAGAAATAT | Deoxy, MOE, and cEt | 33 | 3710 | 3725 | 3447 |
| 561829 | N/A | N/A | AAATGGCATGCCTTAG | Deoxy, MOE, and cEt | 46 | 3716 | 3731 | 3448 |
| 561830 | N/A | N/A | GTATTTCAAATGGCAT | Deoxy, MOE, and cEt | 54 | 3723 | 3738 | 3449 |
| 561831 | N/A | N/A | GCAACAAAGTATTTCA | Deoxy, MOE, and cEt | 60 | 3731 | 3746 | 3450 |
| 561832 | N/A | N/A | GTATTTCAACAATGCA | Deoxy, MOE, and cEt | 28 | 3744 | 3759 | 3451 |
| 561833 | N/A | N/A | ATAACATTAGGGAAAC | Deoxy, MOE, and cEt | 18 | 3827 | 3842 | 3452 |
| 561834 | N/A | N/A | TCATATATAACATTAG | Deoxy, MOE, and cEt | 18 | 3833 | 3848 | 3453 |
| 561912 | N/A | N/A | GTGGTTTTGAGCAAAG | Deoxy, MOE, and cEt | 5 | 4736 | 4751 | 3454 |
| 561913 | N/A | N/A | CTATTGTGTGGTTTTG | Deoxy, MOE, and cEt | 36 | 4743 | 4758 | 3455 |
| 561914 | N/A | N/A | GGAAAGCTATTGTGTG | Deoxy, MOE, and cEt | 18 | 4749 | 4764 | 3456 |
| 561915 | N/A | N/A | TATGAGTGAAATGGAA | Deoxy, MOE, and cEt | 13 | 4761 | 4776 | 3457 |
| 561916 | N/A | N/A | AGCCAATATGAGTGAA | Deoxy, MOE, and cEt | 57 | 4767 | 4782 | 3458 |
| 561917 | N/A | N/A | CTAAAGAGCCAATATG | Deoxy, MOE, and cEt | 33 | 4773 | 4788 | 3459 |
| 561918 | N/A | N/A | CTTGGTCTAAAGAGCC | Deoxy, MOE, and cEt | 70 | 4779 | 4794 | 146 |
| 561919 | N/A | N/A | GGTAATCTTGGTCTAA | Deoxy, MOE, and cEt | 46 | 4785 | 4800 | 3460 |
| 561920 | N/A | N/A | GATGACGAAGGGTTGG | Deoxy, MOE, and cEt | 28 | 4800 | 4815 | 3461 |
| 561921 | N/A | N/A | CAGTGAGATGACGAAG | Deoxy, MOE, and cEt | 39 | 4806 | 4821 | 3462 |
| 561922 | N/A | N/A | TGAAGTCAGTGAGATG | Deoxy, MOE, and cEt | 49 | 4812 | 4827 | 3463 |
| 561923 | N/A | N/A | AGGAGGTGAAGTCAGT | Deoxy, MOE, and cEt | 35 | 4818 | 4833 | 3464 |
| 561924 | N/A | N/A | GAGTAGAGGAGGTGAA | Deoxy, MOE, and cEt | 33 | 4824 | 4839 | 3465 |
| 561925 | N/A | N/A | TAACTAGAGTAGAGGA | Deoxy, MOE, and cEt | 35 | 4830 | 4845 | 3466 |
| 561926 | N/A | N/A | TCAGAATAACTAGAGT | Deoxy, MOE, and cEt | 24 | 4836 | 4851 | 3467 |
| 561927 | N/A | N/A | AAGCGGTCAGAATAAC | Deoxy, MOE, and cEt | 39 | 4842 | 4857 | 3468 |
| 561928 | N/A | N/A | CTGGTAAAGCGGTCAG | Deoxy, MOE, and cEt | 51 | 4848 | 4863 | 3469 |
| 561929 | N/A | N/A | TGAATACTGGTAAAGC | Deoxy, MOE, and cEt | 63 | 4854 | 4869 | 3470 |
| 561930 | N/A | N/A | TGTGTTTGAATACTGG | Deoxy, MOE, and cEt | 65 | 4860 | 4875 | 3471 |
| 561931 | N/A | N/A | GTTTGATGTGTTTGAA | Deoxy, MOE, and cEt | 49 | 4866 | 4881 | 3472 |
| 561932 | N/A | N/A | CAGTATGTTTGATGTG | Deoxy, MOE, and cEt | 48 | 4872 | 4887 | 3473 |
| 561933 | N/A | N/A | AGGTGGCAGTATGTTT | Deoxy, MOE, and cEt | 0 | 4878 | 4893 | 3474 |
| 561934 | N/A | N/A | GCTTTGAGGTGGCAGT | Deoxy, MOE, and cEt | 48 | 4884 | 4899 | 3475 |
| 561935 | N/A | N/A | GGGCAAAGGCTTTGAG | Deoxy, MOE, and cEt | 28 | 4892 | 4907 | 3476 |
| 561936 | N/A | N/A | CAACAGGGCAAAGGC | Deoxy, MOE, and cEt | 65 | 4898 | 4913 | 3477 |
| 561937 | N/A | N/A | GAGGAAACAACAAGGG | Deoxy, MOE, and cEt | 42 | 4905 | 4920 | 3478 |

TABLE 26-continued

Inhibition of ANGPTL3 mRNA by oligonucleotides targeting SEQ ID NO: 1 and 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 561938 | N/A | N/A | CCAGTTAGAGGAAACA | Deoxy, MOE, and cEt | 52 | 4912 | 4927 | 3479 |
| 561939 | N/A | N/A | CCAGGGCAGAAGAGCG | Deoxy, MOE, and cEt | 61 | 4930 | 4945 | 3480 |
| 561940 | N/A | N/A | TAGATACCAGGGCAGA | Deoxy, MOE, and cEt | 68 | 4936 | 4951 | 3481 |
| 561941 | N/A | N/A | CAGAGAGTGGGCCACG | Deoxy, MOE, and cEt | 46 | 4952 | 4967 | 3482 |
| 561942 | N/A | N/A | GGAAATCAGAGAGTGG | Deoxy, MOE, and cEt | 42 | 4958 | 4973 | 3483 |
| 561943 | N/A | N/A | CCTAAGGGAAATCAGA | Deoxy, MOE, and cEt | 26 | 4964 | 4979 | 3484 |
| 561944 | N/A | N/A | AACGACCCTAAGGGAA | Deoxy, MOE, and cEt | 45 | 4970 | 4985 | 3485 |
| 561945 | N/A | N/A | TTTGATAACGACCCTA | Deoxy, MOE, and cEt | 57 | 4976 | 4991 | 3486 |
| 561946 | N/A | N/A | TTTTTGTTTGATAACG | Deoxy, MOE, and cEt | 21 | 4982 | 4997 | 3487 |
| 561947 | N/A | N/A | CATTGGGAATTTTTTG | Deoxy, MOE, and cEt | 35 | 4992 | 5007 | 3488 |
| 561948 | N/A | N/A | AGTCTTCATTGGGAAT | Deoxy, MOE, and cEt | 69 | 4998 | 5013 | 3489 |
| 561949 | N/A | N/A | CTTGTAAGTCTTCATT | Deoxy, MOE, and cEt | 35 | 5004 | 5019 | 3490 |
| 561950 | N/A | N/A | AGTGACCTTGTAAGTC | Deoxy, MOE, and cEt | 56 | 5010 | 5025 | 3491 |
| 561951 | N/A | N/A | TGGTTAAGTGACCTTG | Deoxy, MOE, and cEt | 67 | 5016 | 5031 | 3492 |
| 561952 | N/A | N/A | GATTTTGGTTAAGTG | Deoxy, MOE, and cEt | 43 | 5022 | 5037 | 3493 |
| 561953 | N/A | N/A | GGTTGTGATTTTTGGT | Deoxy, MOE, and cEt | 58 | 5028 | 5043 | 3494 |
| 561954 | N/A | N/A | CCAGGCGGTTGTGATT | Deoxy, MOE, and cEt | 49 | 5034 | 5049 | 3495 |
| 561955 | N/A | N/A | ATGGGACCAGGCGGTT | Deoxy, MOE, and cEt | 52 | 5040 | 5055 | 3496 |
| 561956 | N/A | N/A | AAGTTTTCAGGGATGG | Deoxy, MOE, and cEt | 49 | 5052 | 5067 | 3497 |
| 561957 | N/A | N/A | AAGTAGAAGTTTTCAG | Deoxy, MOE, and cEt | 16 | 5058 | 5073 | 3498 |
| 561958 | N/A | N/A | CTAAGGAAGTAGAAGT | Deoxy, MOE, and cEt | 33 | 5064 | 5079 | 3499 |
| 561959 | N/A | N/A | AAGTAGCTAAGGAAGT | Deoxy, MOE, and cEt | 35 | 5070 | 5085 | 3500 |
| 561960 | N/A | N/A | GGAGAAAAGTAGCTAA | Deoxy, MOE, and cEt | 36 | 5076 | 5091 | 3501 |
| 561961 | N/A | N/A | TGTGCAGGAGAAAAGT | Deoxy, MOE, and cEt | 53 | 5082 | 5097 | 3502 |
| 561962 | N/A | N/A | GGTGAGTGTGCAGGAG | Deoxy, MOE, and cEt | 44 | 5088 | 5103 | 3503 |
| 561963 | N/A | N/A | AATAAGGTGAGTGTG | Deoxy, MOE, and cEt | 38 | 5094 | 5109 | 3504 |
| 561964 | N/A | N/A | TGCAGGAATAGAAGAG | Deoxy, MOE, and cEt | 58 | 5138 | 5153 | 3505 |
| 561965 | N/A | N/A | TTTTAGTGCAGGAATA | Deoxy, MOE, and cEt | 20 | 5144 | 5159 | 3506 |
| 561966 | N/A | N/A | TATTCACAGAGCTTAC | Deoxy, MOE, and cEt | 63 | 5161 | 5176 | 3507 |
| 561967 | N/A | N/A | TCCCTGTATTCACAGA | Deoxy, MOE, and cEt | 61 | 5167 | 5182 | 3508 |
| 561968 | N/A | N/A | GAAAAAATCCCTGTAT | Deoxy, MOE, and cEt | 22 | 5174 | 5189 | 3509 |
| 561969 | N/A | N/A | TATGAAGATAATGGAA | Deoxy, MOE, and cEt | 34 | 5187 | 5202 | 3510 |
| 561970 | N/A | N/A | GGAGTATATACAAATA | Deoxy, MOE, and cEt | 46 | 5211 | 5226 | 3511 |
| 561971 | N/A | N/A | TATTCTGGAGTATATA | Deoxy, MOE, and cEt | 29 | 5217 | 5232 | 3512 |
| 561972 | N/A | N/A | ATTCTATATTCTGGAG | Deoxy, MOE, and cEt | 58 | 5223 | 5238 | 3513 |
| 561973 | N/A | N/A | CATACAGTATTCTATA | Deoxy, MOE, and cEt | 39 | 5231 | 5246 | 3514 |

TABLE 26-continued

Inhibition of ANGPTL3 mRNA by oligonucleotides targeting SEQ ID NO: 1 and 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 561974 | N/A | N/A | GTGTGCCATACAGTAT | Deoxy, MOE, and cEt | 48 | 5237 | 5252 | 3515 |
| 561975 | N/A | N/A | AGAAATGCCTACTGTG | Deoxy, MOE, and cEt | 34 | 5250 | 5265 | 3516 |
| 561976 | N/A | N/A | ATTCAACAGAAATGCC | Deoxy, MOE, and cEt | 52 | 5257 | 5272 | 3517 |
| 561977 | N/A | N/A | GAATATGACATTACAT | Deoxy, MOE, and cEt | 33 | 5279 | 5294 | 3518 |
| 561978 | N/A | N/A | CTGTGTGAATATGACA | Deoxy, MOE, and cEt | 63 | 5285 | 5300 | 3519 |
| 561979 | N/A | N/A | ACGCTTCTGTGTGAAT | Deoxy, MOE, and cEt | 59 | 5291 | 5306 | 3520 |
| 561980 | N/A | N/A | TAGCACACGCTTCTGT | Deoxy, MOE, and cEt | 29 | 5297 | 5312 | 3521 |
| 561981 | N/A | N/A | TAATCATAGCACACGC | Deoxy, MOE, and cEt | 64 | 5303 | 5318 | 3522 |
| 561982 | N/A | N/A | CCAAGTAATAATAATC | Deoxy, MOE, and cEt | 26 | 5314 | 5329 | 3523 |
| 561983 | N/A | N/A | AGTAATCCAAGTAATA | Deoxy, MOE, and cEt | 33 | 5320 | 5335 | 3524 |
| 561984 | N/A | N/A | ATTTCTAGTAATCCAA | Deoxy, MOE, and cEt | 42 | 5326 | 5341 | 3525 |
| 561985 | N/A | N/A | CACACTATTTCTAGTA | Deoxy, MOE, and cEt | 40 | 5332 | 5347 | 3526 |
| 561986 | N/A | N/A | ATGAGGCACACTATTT | Deoxy, MOE, and cEt | 47 | 5338 | 5353 | 3527 |
| 561987 | N/A | N/A | TTAATTATGAGGCACA | Deoxy, MOE, and cEt | 58 | 5344 | 5359 | 3528 |
| 561988 | N/A | N/A | TGACCTTTAATTATGA | Deoxy, MOE, and cEt | 38 | 5350 | 5365 | 3529 |
| 562066 | N/A | N/A | GCAATTTATTGAATGA | Deoxy, MOE, and cEt | 27 | 6083 | 6098 | 3530 |
| 562067 | N/A | N/A | GGGTTTGCAATTTATT | Deoxy, MOE, and cEt | 38 | 6089 | 6104 | 3531 |
| 562068 | N/A | N/A | TGTGTTGGGTTTGCAA | Deoxy, MOE, and cEt | 43 | 6095 | 6110 | 3532 |
| 562069 | N/A | N/A | TTTAAGTGTGTTGGGT | Deoxy, MOE, and cEt | 71 | 6101 | 6116 | 3533 |
| 562070 | N/A | N/A | GTTTAGCAGTAACATT | Deoxy, MOE, and cEt | 38 | 6126 | 6141 | 3534 |
| 562071 | N/A | N/A | ATTCAGTAGTTTATCG | Deoxy, MOE, and cEt | 17 | 6145 | 6160 | 3535 |
| 562072 | N/A | N/A | CTATATATTCAGTAGT | Deoxy, MOE, and cEt | 0 | 6151 | 6166 | 3536 |
| 562073 | N/A | N/A | GCTTACTTTCTATATA | Deoxy, MOE, and cEt | 21 | 6160 | 6175 | 3537 |
| 562074 | N/A | N/A | AGTTTGTTTGCTTACT | Deoxy, MOE, and cEt | 63 | 6169 | 6184 | 3538 |
| 562075 | N/A | N/A | TTGGCAAGTTTGTTTG | Deoxy, MOE, and cEt | 55 | 6175 | 6190 | 3539 |
| 562076 | N/A | N/A | GGCAGGTTGGCAAGTT | Deoxy, MOE, and cEt | 68 | 6181 | 6196 | 3540 |
| 562077 | N/A | N/A | GATGTTGGCAGGTTGG | Deoxy, MOE, and cEt | 54 | 6187 | 6202 | 3541 |
| 562078 | N/A | N/A | TCTGTAGATGTTGGCA | Deoxy, MOE, and cEt | 81 | 6193 | 6208 | 147 |
| 562079 | N/A | N/A | AACATATCTGTAGATG | Deoxy, MOE, and cEt | 32 | 6199 | 6214 | 3542 |
| 562080 | N/A | N/A | CCTGTAAACATATCTG | Deoxy, MOE, and cEt | 51 | 6205 | 6220 | 3543 |
| 562081 | N/A | N/A | TTTTGACCTGTAAACA | Deoxy, MOE, and cEt | 14 | 6211 | 6226 | 3544 |
| 562082 | N/A | N/A | GATAATTTTTGACCTG | Deoxy, MOE, and cEt | 49 | 6217 | 6232 | 3545 |
| 562083 | N/A | N/A | TCTTGATAATTTGATA | Deoxy, MOE, and cEt | 13 | 6229 | 6244 | 3546 |
| 562084 | N/A | N/A | AGGCTTTCTTGATAAT | Deoxy, MOE, and cEt | 55 | 6235 | 6250 | 3547 |
| 562085 | N/A | N/A | TGAACCAGGCTTTCTT | Deoxy, MOE, and cEt | 74 | 6241 | 6256 | 3548 |
| 562086 | N/A | N/A | ATAATTTGAACCAGGC | Deoxy, MOE, and cEt | 82 | 6247 | 6262 | 148 |

TABLE 26-continued

Inhibition of ANGPTL3 mRNA by oligonucleotides targeting SEQ ID NO: 1 and 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 562087 | N/A | N/A | GATAAAGACATAATAC | Deoxy, MOE, and cEt | 21 | 6263 | 6278 | 3549 |
| 562088 | N/A | N/A | ACCTGTGATAAAGACA | Deoxy, MOE, and cEt | 27 | 6269 | 6284 | 3550 |
| 562089 | N/A | N/A | CTTCAGACCTGTGATA | Deoxy, MOE, and cEt | 23 | 6275 | 6290 | 3551 |
| 562090 | N/A | N/A | ACTGATCTTCAGACCT | Deoxy, MOE, and cEt | 48 | 6281 | 6296 | 3552 |
| 562091 | N/A | N/A | GGTCTTACTGATCTTC | Deoxy, MOE, and cEt | 59 | 6287 | 6302 | 3553 |
| 562092 | N/A | N/A | GTTTTAGGTCTTACTG | Deoxy, MOE, and cEt | 21 | 6293 | 6308 | 3554 |
| 562093 | N/A | N/A | GTTCAGATTTTAAGTT | Deoxy, MOE, and cEt | 31 | 6321 | 6336 | 3555 |
| 562094 | N/A | N/A | ATATTCTGTTCAGATT | Deoxy, MOE, and cEt | 36 | 6328 | 6343 | 3556 |
| 562095 | N/A | N/A | ATATTGTAATGTATTC | Deoxy, MOE, and cEt | 52 | 6372 | 6387 | 3557 |
| 562096 | N/A | N/A | CTTAGAATATTGTAAT | Deoxy, MOE, and cEt | 13 | 6378 | 6393 | 3558 |
| 562097 | N/A | N/A | GCTTTGCTTAGAATAT | Deoxy, MOE, and cEt | 47 | 6384 | 6399 | 3559 |
| 562098 | N/A | N/A | GAGACTGCTTTGCTTA | Deoxy, MOE, and cEt | 48 | 6390 | 6405 | 3560 |
| 562099 | N/A | N/A | AAAGTAGAGACTGCTT | Deoxy, MOE, and cEt | 44 | 6396 | 6411 | 3561 |
| 562100 | N/A | N/A | AGGCCAAAAGTAGAGA | Deoxy, MOE, and cEt | 59 | 6402 | 6417 | 3562 |
| 562101 | N/A | N/A | TCGGAAAACAGAGCAA | Deoxy, MOE, and cEt | 63 | 6417 | 6432 | 3563 |
| 562102 | N/A | N/A | CATTGGTCGGAAAACA | Deoxy, MOE, and cEt | 53 | 6423 | 6438 | 3564 |
| 562103 | N/A | N/A | AGCAGACATTGGTCGG | Deoxy, MOE, and cEt | 83 | 6429 | 6444 | 149 |
| 562104 | N/A | N/A | AGCAAGGCAAAAAAGC | Deoxy, MOE, and cEt | 22 | 6442 | 6457 | 3565 |
| 562105 | N/A | N/A | GACATTATTTAATAAG | Deoxy, MOE, and cEt | 21 | 6470 | 6485 | 3566 |
| 562106 | N/A | N/A | ATCAGGGACATTATTT | Deoxy, MOE, and cEt | 34 | 6476 | 6491 | 3567 |
| 562107 | N/A | N/A | TATTTAATCAGGGACA | Deoxy, MOE, and cEt | 47 | 6482 | 6497 | 3568 |
| 562108 | N/A | N/A | ATTACCTGTTCTCAAA | Deoxy, MOE, and cEt | 30 | 6499 | 6514 | 3569 |
| 562109 | N/A | N/A | GTACAGATTACCTGTT | Deoxy, MOE, and cEt | 38 | 6505 | 6520 | 3570 |
| 562110 | N/A | N/A | CAGATTGTACAGATTA | Deoxy, MOE, and cEt | 76 | 6511 | 6526 | 150 |
| 562111 | N/A | N/A | GTTATTCAGATTGTAC | Deoxy, MOE, and cEt | 32 | 6517 | 6532 | 3571 |
| 562112 | N/A | N/A | AACAGTGTTATTCAGA | Deoxy, MOE, and cEt | 58 | 6523 | 6538 | 3572 |
| 562113 | N/A | N/A | TAGATAAACAGTGTTA | Deoxy, MOE, and cEt | 33 | 6529 | 6544 | 3573 |
| 562114 | N/A | N/A | TGATATTTAGATAAAC | Deoxy, MOE, and cEt | 26 | 6536 | 6551 | 3574 |
| 562115 | N/A | N/A | GGTGTTTGATATTTAG | Deoxy, MOE, and cEt | 60 | 6542 | 6557 | 3575 |
| 562116 | N/A | N/A | TATAACGGTGTTTGAT | Deoxy, MOE, and cEt | 42 | 6548 | 6563 | 3576 |
| 562117 | N/A | N/A | TAATGTTATAACGGTG | Deoxy, MOE, and cEt | 62 | 6554 | 6569 | 3577 |
| 562118 | N/A | N/A | AGTTCATAATGTTATA | Deoxy, MOE, and cEt | 21 | 6560 | 6575 | 3578 |
| 562119 | N/A | N/A | GTCTTTCAGTTCATAA | Deoxy, MOE, and cEt | 57 | 6567 | 6582 | 3579 |
| 562120 | N/A | N/A | ACAGTTTGTCTTTCAG | Deoxy, MOE, and cEt | 59 | 6574 | 6589 | 3580 |
| 562121 | N/A | N/A | AGAAGTACAGTTTGTC | Deoxy, MOE, and cEt | 3 | 6580 | 6595 | 3581 |
| 562122 | N/A | N/A | GATGTCAGAAGTACAG | Deoxy, MOE, and cEt | 45 | 6586 | 6601 | 3582 |

TABLE 26-continued

Inhibition of ANGPTL3 mRNA by oligonucleotides targeting SEQ ID NO: 1 and 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 562123 | N/A | N/A | AGTAAGGATGTCAGAA | Deoxy, MOE, and cEt | 44 | 6592 | 6607 | 3583 |
| 562124 | N/A | N/A | AATCTGAGTAAGGATG | Deoxy, MOE, and cEt | 45 | 6598 | 6613 | 3584 |
| 562125 | N/A | N/A | GAATATACAATTAGGG | Deoxy, MOE, and cEt | 13 | 6616 | 6631 | 3585 |
| 562126 | N/A | N/A | TGATACTGAATATACA | Deoxy, MOE, and cEt | 13 | 6623 | 6638 | 3586 |
| 562127 | N/A | N/A | CTGAGCTGATAAAAGA | Deoxy, MOE, and cEt | 1 | 6660 | 6675 | 3587 |
| 562128 | N/A | N/A | ACCATCATGTTTTACA | Deoxy, MOE, and cEt | 44 | 6772 | 6787 | 3588 |
| 562129 | N/A | N/A | TGTCTTACCATCATGT | Deoxy, MOE, and cEt | 29 | 6778 | 6793 | 3589 |
| 562130 | N/A | N/A | CCAAAGTGTCTTACCA | Deoxy, MOE, and cEt | 42 | 6784 | 6799 | 3590 |
| 562131 | N/A | N/A | AACCCACCAAAGTGTC | Deoxy, MOE, and cEt | 33 | 6790 | 6805 | 3591 |
| 562132 | N/A | N/A | GAAGGAAACCCACCAA | Deoxy, MOE, and cEt | 24 | 6796 | 6811 | 3592 |
| 562133 | N/A | N/A | CTTCAAGAAGGAAACC | Deoxy, MOE, and cEt | 28 | 6802 | 6817 | 3593 |
| 562134 | N/A | N/A | TAATAGCTTCAAGAAG | Deoxy, MOE, and cEt | 1 | 6808 | 6823 | 3594 |
| 562135 | N/A | N/A | GGGAATTTGATAATAA | Deoxy, MOE, and cEt | 0 | 6821 | 6836 | 3595 |
| 562136 | N/A | N/A | AGAATAGGGAATTTGA | Deoxy, MOE, and cEt | 18 | 6827 | 6842 | 3596 |
| 562137 | N/A | N/A | GTCCTAAGAATAGGGA | Deoxy, MOE, and cEt | 9 | 6833 | 6848 | 3597 |
| 562138 | N/A | N/A | GAACAAGTCCTAAGAA | Deoxy, MOE, and cEt | 7 | 6839 | 6854 | 3598 |
| 562139 | N/A | N/A | AGTCTAGAACAAGTCC | Deoxy, MOE, and cEt | 70 | 6845 | 6860 | 3599 |
| 562140 | N/A | N/A | TCTTTTAGTCTAGAAC | Deoxy, MOE, and cEt | 22 | 6851 | 6866 | 3600 |
| 562141 | N/A | N/A | TAACTATCTTTTAGTC | Deoxy, MOE, and cEt | 15 | 6857 | 6872 | 3601 |
| 562142 | N/A | N/A | ATCTCTTAACTATCTT | Deoxy, MOE, and cEt | 35 | 6863 | 6878 | 3602 |
| 560991 | 3 | 18 | AACTGTTTTCTTCTGG | Deoxy, MOE, and cEt | 37 | 3107 | 3122 | 3603 |
| 560992 | 8 | 23 | CGTGGAACTGTTTTCT | Deoxy, MOE, and cEt | 74 | 3112 | 3127 | 112 |
| 560993 | 22 | 37 | TCAATTTCAAGCAACG | Deoxy, MOE, and cEt | 68 | 3126 | 3141 | 3604 |
| 560994 | 51 | 66 | CTTAATTGTGAACATT | Deoxy, MOE, and cEt | 21 | 3155 | 3170 | 3605 |
| 560995 | 53 | 68 | AGCTTAATTGTGAACA | Deoxy, MOE, and cEt | 59 | 3157 | 3172 | 3606 |
| 560996 | 55 | 70 | GGAGCTTAATTGTGAA | Deoxy, MOE, and cEt | 0 | 3159 | 3174 | 3607 |
| 560997 | 57 | 72 | AAGGAGCTTAATTGTG | Deoxy, MOE, and cEt | 36 | 3161 | 3176 | 3608 |
| 560998 | 59 | 74 | AGAAGGAGCTTAATTG | Deoxy, MOE, and cEt | 47 | 3163 | 3178 | 3609 |
| 560999 | 61 | 76 | AAAGAAGGAGCTTAAT | Deoxy, MOE, and cEt | 20 | 3165 | 3180 | 3610 |
| 561000 | 76 | 91 | CTAGAGGAACAATAAA | Deoxy, MOE, and cEt | 23 | 3180 | 3195 | 3611 |
| 561001 | 79 | 94 | TAACTAGAGGAACAAT | Deoxy, MOE, and cEt | 19 | 3183 | 3198 | 3612 |
| 561002 | 81 | 96 | AATAACTAGAGGAACA | Deoxy, MOE, and cEt | 38 | 3185 | 3200 | 3613 |
| 561003 | 84 | 99 | GGAAATAACTAGAGGA | Deoxy, MOE, and cEt | 48 | 3188 | 3203 | 3614 |
| 561004 | 86 | 101 | GAGGAAATAACTAGAG | Deoxy, MOE, and cEt | 37 | 3190 | 3205 | 3615 |
| 561005 | 88 | 103 | TGGAGGAAATAACTAG | Deoxy, MOE, and cEt | 68 | 3192 | 3207 | 3616 |
| 561006 | 90 | 105 | TCTGGAGGAAATAACT | Deoxy, MOE, and cEt | 49 | 3194 | 3209 | 3617 |

TABLE 26-continued

Inhibition of ANGPTL3 mRNA by oligonucleotides targeting SEQ ID NO: 1 and 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 561007 | 94 | 109 | CAATTCTGGAGGAAAT | Deoxy, MOE, and cEt | 43 | 3198 | 3213 | 3618 |
| 561008 | 96 | 111 | ATCAATTCTGGAGGAA | Deoxy, MOE, and cEt | 73 | 3200 | 3215 | 3619 |
| 561009 | 98 | 113 | TGATCAATTCTGGAGG | Deoxy, MOE, and cEt | 72 | 3202 | 3217 | 3620 |
| 561010 | 100 | 115 | CTTGATCAATTCTGGA | Deoxy, MOE, and cEt | 82 | 3204 | 3219 | 113 |
| 561011 | 102 | 117 | GTCTTGATCAATTCTG | Deoxy, MOE, and cEt | 85 | 3206 | 3221 | 114 |
| 561012 | 104 | 119 | TTGTCTTGATCAATTC | Deoxy, MOE, and cEt | 64 | 3208 | 3223 | 3621 |
| 561013 | 106 | 121 | AATTGTCTTGATCAAT | Deoxy, MOE, and cEt | 21 | 3210 | 3225 | 3622 |
| 561014 | 108 | 123 | TGAATTGTCTTGATCA | Deoxy, MOE, and cEt | 66 | 3212 | 3227 | 3623 |
| 561015 | 110 | 125 | GATGAATTGTCTTGAT | Deoxy, MOE, and cEt | 51 | 3214 | 3229 | 3624 |
| 561016 | 112 | 127 | ATGATGAATTGTCTTG | Deoxy, MOE, and cEt | 71 | 3216 | 3231 | 3625 |
| 561017 | 115 | 130 | CAAATGATGAATTGTC | Deoxy, MOE, and cEt | 36 | 3219 | 3234 | 3626 |
| 561018 | 117 | 132 | ATCAAATGATGAATTG | Deoxy, MOE, and cEt | 27 | 3221 | 3236 | 3627 |
| 561019 | 125 | 140 | GATAGAGAATCAAATG | Deoxy, MOE, and cEt | 11 | 3229 | 3244 | 3628 |
| 561020 | 129 | 144 | TGGAGATAGAGAATCA | Deoxy, MOE, and cEt | 73 | 3233 | 3248 | 3629 |
| 561021 | 131 | 146 | TCTGGAGATAGAGAAT | Deoxy, MOE, and cEt | 51 | 3235 | 3250 | 3630 |
| 561022 | 135 | 150 | TGGCTCTGGAGATAGA | Deoxy, MOE, and cEt | 76 | 3239 | 3254 | 115 |
| 561023 | 137 | 152 | TTTGGCTCTGGAGATA | Deoxy, MOE, and cEt | 73 | 3241 | 3256 | 3631 |
| 561024 | 139 | 154 | ATTTTGGCTCTGGAGA | Deoxy, MOE, and cEt | 61 | 3243 | 3258 | 3632 |
| 561025 | 141 | 156 | TGATTTTGGCTCTGGA | Deoxy, MOE, and cEt | 83 | 3245 | 3260 | 116 |
| 561026 | 143 | 158 | CTTGATTTTGGCTCTG | Deoxy, MOE, and cEt | 83 | 3247 | 3262 | 117 |
| 561027 | 145 | 160 | ATCTTGATTTTGGCTC | Deoxy, MOE, and cEt | 67 | 3249 | 3264 | 3633 |
| 559277 | 147 | 162 | AAATCTTGATTTTGGC | Deoxy, MOE, and cEt | 75 | 3251 | 3266 | 110 |
| 561028 | 149 | 164 | GCAAATCTTGATTTTG | Deoxy, MOE, and cEt | 53 | 3253 | 3268 | 3634 |
| 561029 | 151 | 166 | TAGCAAATCTTGATTT | Deoxy, MOE, and cEt | 27 | 3255 | 3270 | 3635 |
| 561030 | 153 | 168 | CATAGCAAATCTTGAT | Deoxy, MOE, and cEt | 63 | 3257 | 3272 | 3636 |
| 561031 | 155 | 170 | AACATAGCAAATCTTG | Deoxy, MOE, and cEt | 56 | 3259 | 3274 | 3637 |
| 561032 | 157 | 172 | CTAACATAGCAAATCT | Deoxy, MOE, and cEt | 67 | 3261 | 3276 | 3638 |
| 561033 | 159 | 174 | GTCTAACATAGCAAAT | Deoxy, MOE, and cEt | 51 | 3263 | 3278 | 3639 |
| 561034 | 174 | 189 | TAAAATTTTTACATCG | Deoxy, MOE, and cEt | 4 | 3278 | 3293 | 3640 |
| 561035 | 177 | 192 | GGCTAAAATTTTTACA | Deoxy, MOE, and cEt | 0 | 3281 | 3296 | 3641 |
| 561036 | 182 | 197 | CCATTGGCTAAAATTT | Deoxy, MOE, and cEt | 3 | 3286 | 3301 | 3642 |
| 561037 | 184 | 199 | GGCCATTGGCTAAAAT | Deoxy, MOE, and cEt | 16 | 3288 | 3303 | 3643 |
| 561038 | 186 | 201 | GAGGCCATTGGCTAAA | Deoxy, MOE, and cEt | 42 | 3290 | 3305 | 3644 |
| 561039 | 188 | 203 | AGGAGGCCATTGGCTA | Deoxy, MOE, and cEt | 61 | 3292 | 3307 | 3645 |
| 561040 | 190 | 205 | GAAGGAGGCCATTGGC | Deoxy, MOE, and cEt | 35 | 3294 | 3309 | 3646 |
| 561041 | 192 | 207 | CTGAAGGAGGCCATTG | Deoxy, MOE, and cEt | 37 | 3296 | 3311 | 3647 |

TABLE 26-continued

Inhibition of ANGPTL3 mRNA by oligonucleotides targeting SEQ ID NO: 1 and 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 561042 | 194 | 209 | AACTGAAGGAGGCCAT | Deoxy, MOE, and cEt | 22 | 3298 | 3313 | 3648 |
| 561043 | 196 | 211 | CCAACTGAAGGAGGCC | Deoxy, MOE, and cEt | 33 | 3300 | 3315 | 3649 |
| 561044 | 198 | 213 | TCCCAACTGAAGGAGG | Deoxy, MOE, and cEt | 19 | 3302 | 3317 | 3650 |
| 561045 | 200 | 215 | TGTCCCAACTGAAGGA | Deoxy, MOE, and cEt | 33 | 3304 | 3319 | 3651 |
| 561046 | 202 | 217 | CATGTCCCAACTGAAG | Deoxy, MOE, and cEt | 19 | 3306 | 3321 | 3652 |
| 561047 | 204 | 219 | ACCATGTCCCAACTGA | Deoxy, MOE, and cEt | 19 | 3308 | 3323 | 3653 |
| 561048 | 206 | 221 | AGACCATGTCCCAACT | Deoxy, MOE, and cEt | 19 | 3310 | 3325 | 3654 |
| 561049 | 208 | 223 | TAAGACCATGTCCCAA | Deoxy, MOE, and cEt | 0 | 3312 | 3327 | 3655 |
| 561050 | 210 | 225 | TTTAAGACCATGTCCC | Deoxy, MOE, and cEt | 5 | 3314 | 3329 | 3656 |
| 561051 | 212 | 227 | TCTTTAAGACCATGTC | Deoxy, MOE, and cEt | 10 | 3316 | 3331 | 3657 |
| 561052 | 214 | 229 | AGTCTTTAAGACCATG | Deoxy, MOE, and cEt | 10 | 3318 | 3333 | 3658 |
| 561053 | 216 | 231 | AAAGTCTTTAAGACCA | Deoxy, MOE, and cEt | 29 | 3320 | 3335 | 3659 |
| 561054 | 218 | 233 | ACAAAGTCTTTAAGAC | Deoxy, MOE, and cEt | 19 | 3322 | 3337 | 3660 |
| 561055 | 220 | 235 | GGACAAAGTCTTTAAG | Deoxy, MOE, and cEt | 21 | 3324 | 3339 | 3661 |
| 561056 | 222 | 237 | ATGGACAAAGTCTTTA | Deoxy, MOE, and cEt | 12 | 3326 | 3341 | 3662 |
| 561057 | 224 | 239 | TTATGGACAAAGTCTT | Deoxy, MOE, and cEt | 10 | 3328 | 3343 | 3663 |
| 561058 | 226 | 241 | TCTTATGGACAAAGTC | Deoxy, MOE, and cEt | 9 | 3330 | 3345 | 3664 |
| 561059 | 228 | 243 | CGTCTTATGGACAAAG | Deoxy, MOE, and cEt | 0 | 3332 | 3347 | 3665 |
| 561060 | 242 | 257 | TTAATTTGGCCCTTCG | Deoxy, MOE, and cEt | 28 | 3346 | 3361 | 3666 |
| 561061 | 244 | 259 | CATTAATTTGGCCCTT | Deoxy, MOE, and cEt | 13 | 3348 | 3363 | 3667 |
| 561062 | 246 | 261 | GTCATTAATTTGGCCC | Deoxy, MOE, and cEt | 63 | 3350 | 3365 | 3668 |
| 561063 | 248 | 263 | ATGTCATTAATTTGGC | Deoxy, MOE, and cEt | 37 | 3352 | 3367 | 3669 |
| 561064 | 267 | 282 | TATGTTGAGTTTTTGA | Deoxy, MOE, and cEt | 16 | 3371 | 3386 | 3670 |
| 561065 | 272 | 287 | TCAAATATGTTGAGTT | Deoxy, MOE, and cEt | 21 | 3376 | 3391 | 3671 |
| 561066 | 274 | 289 | GATCAAATATGTTGAG | Deoxy, MOE, and cEt | 36 | 3378 | 3393 | 3672 |
| 560990 | 709 | 724 | TTCTTGGTGCTCTTGG | Deoxy, MOE, and cEt | 73 | 6722 | 6737 | 111 |
| 337487 | 804 | 823 | CACTTGTATGTTCACCTCTG | 5-10-5 MOE | 76 | 7389 | 7408 | 28 |
| 561604 | 1850 | 1865 | GTACAATTACCAGTCC | Deoxy, MOE, and cEt | 59 | 10822 | 10837 | 3673 |
| 561605 | 1852 | 1867 | CTGTACAATTACCAGT | Deoxy, MOE, and cEt | 54 | 10824 | 10839 | 3674 |
| 561606 | 1854 | 1869 | AACTGTACAATTACCA | Deoxy, MOE, and cEt | 57 | 10826 | 10841 | 3675 |
| 561607 | 1856 | 1871 | AGAACTGTACAATTAC | Deoxy, MOE, and cEt | 36 | 10828 | 10843 | 3676 |
| 561608 | 1858 | 1873 | TAAGAACTGTACAATT | Deoxy, MOE, and cEt | 29 | 10830 | 10845 | 3677 |
| 561609 | 1862 | 1877 | CATTTAAGAACTGTAC | Deoxy, MOE, and cEt | 24 | 10834 | 10849 | 3678 |
| 561610 | 1870 | 1885 | TACTACAACATTTAAG | Deoxy, MOE, and cEt | 1 | 10842 | 10857 | 3679 |
| 561611 | 1874 | 1889 | TTAATACTACAACATT | Deoxy, MOE, and cEt | 0 | 10846 | 10861 | 3680 |
| 561612 | 1880 | 1895 | TTGAAATTAATACTAC | Deoxy, MOE, and cEt | 6 | 10852 | 10867 | 3681 |

TABLE 26-continued

Inhibition of ANGPTL3 mRNA by oligonucleotides targeting SEQ ID NO: 1 and 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 561613 | 1883 | 1898 | GTTTTGAAATTAATAC | Deoxy, MOE, and cEt | 34 | 10855 | 10870 | 3682 |
| 561614 | 1892 | 1907 | CGATTTTTAGTTTTGA | Deoxy, MOE, and cEt | 22 | 10864 | 10879 | 3683 |
| 561615 | 1894 | 1909 | GACGATTTTTAGTTTT | Deoxy, MOE, and cEt | 29 | 10866 | 10881 | 3684 |
| 561616 | 1896 | 1911 | CTGACGATTTTTAGTT | Deoxy, MOE, and cEt | 50 | 10868 | 10883 | 3685 |
| 561617 | 1898 | 1913 | TGCTGACGATTTTTAG | Deoxy, MOE, and cEt | 54 | 10870 | 10885 | 3686 |
| 561618 | 1900 | 1915 | TGTGCTGACGATTTTT | Deoxy, MOE, and cEt | 70 | 10872 | 10887 | 3687 |
| 561619 | 1902 | 1917 | TCTGTGCTGACGATTT | Deoxy, MOE, and cEt | 69 | 10874 | 10889 | 3688 |
| 561620 | 1904 | 1919 | ACTCTGTGCTGACGAT | Deoxy, MOE, and cEt | 78 | 10876 | 10891 | 135 |
| 561621 | 1906 | 1921 | ATACTCTGTGCTGACG | Deoxy, MOE, and cEt | 87 | 10878 | 10893 | 134 |
| 561622 | 1908 | 1923 | ACATACTCTGTGCTGA | Deoxy, MOE, and cEt | 80 | 10880 | 10895 | 136 |
| 561623 | 1911 | 1926 | TACACATACTCTGTGC | Deoxy, MOE, and cEt | 61 | 10883 | 10898 | 3689 |
| 561624 | 1913 | 1928 | TTTACACATACTCTGT | Deoxy, MOE, and cEt | 68 | 10885 | 10900 | 3690 |
| 561625 | 1917 | 1932 | GATTTTTACACATACT | Deoxy, MOE, and cEt | 17 | 10889 | 10904 | 3691 |
| 561626 | 1946 | 1961 | GAAGCATCAGTTTAAA | Deoxy, MOE, and cEt | 27 | 10918 | 10933 | 3692 |
| 561627 | 1948 | 1963 | ATGAAGCATCAGTTTA | Deoxy, MOE, and cEt | 5 | 10920 | 10935 | 3693 |
| 561628 | 1956 | 1971 | GTAGCAAAATGAAGCA | Deoxy, MOE, and cEt | 73 | 10928 | 10943 | 137 |
| 561629 | 1958 | 1973 | TTGTAGCAAAATGAAG | Deoxy, MOE, and cEt | 42 | 10930 | 10945 | 3694 |
| 561630 | 1976 | 1991 | CATTTACTCCAAATTA | Deoxy, MOE, and cEt | 43 | 10948 | 10963 | 3695 |
| 561631 | 1981 | 1996 | TCAAACATTTACTCCA | Deoxy, MOE, and cEt | 82 | 10953 | 10968 | 138 |
| 561632 | 2006 | 2021 | CATTAGGTTTCATAAA | Deoxy, MOE, and cEt | 19 | 10978 | 10993 | 3696 |
| 561633 | 2008 | 2023 | TTCATTAGGTTTCATA | Deoxy, MOE, and cEt | 15 | 10980 | 10995 | 3697 |
| 561634 | 2010 | 2025 | GCTTCATTAGGTTTCA | Deoxy, MOE, and cEt | 57 | 10982 | 10997 | 3698 |
| 561635 | 2012 | 2027 | CTGCTTCATTAGGTTT | Deoxy, MOE, and cEt | 0 | 10984 | 10999 | 3699 |
| 561636 | 2014 | 2029 | TTCTGCTTCATTAGGT | Deoxy, MOE, and cEt | 65 | 10986 | 11001 | 3700 |
| 561637 | 2016 | 2031 | AATTCTGCTTCATTAG | Deoxy, MOE, and cEt | 48 | 10988 | 11003 | 3701 |
| 561638 | 2024 | 2039 | CAGTATTTAATTCTGC | Deoxy, MOE, and cEt | 38 | 10996 | 11011 | 3702 |
| 561639 | 2039 | 2054 | GAACTTATTTAATAC | Deoxy, MOE, and cEt | 29 | 11011 | 11026 | 3703 |
| 561640 | 2041 | 2056 | GCGAACTTATTTTAAT | Deoxy, MOE, and cEt | 38 | 11013 | 11028 | 3704 |
| 561641 | 2043 | 2058 | CAGCGAACTTATTTTA | Deoxy, MOE, and cEt | 46 | 11015 | 11030 | 3705 |
| 561642 | 2045 | 2060 | GACAGCGAACTTATTT | Deoxy, MOE, and cEt | 64 | 11017 | 11032 | 3706 |
| 561643 | 2047 | 2062 | AAGACAGCGAACTTAT | Deoxy, MOE, and cEt | 19 | 11019 | 11034 | 3707 |
| 561644 | 2049 | 2064 | TAAAGACAGCGAACTT | Deoxy, MOE, and cEt | 76 | 11021 | 11036 | 139 |
| 561645 | 2051 | 2066 | TTTAAAGACAGCGAAC | Deoxy, MOE, and cEt | 49 | 11023 | 11038 | 3708 |
| 561646 | 2053 | 2068 | TGTTTAAAGACAGCGA | Deoxy, MOE, and cEt | 81 | 11025 | 11040 | 140 |
| 561647 | 2065 | 2080 | GTCATCTCCATTTGTT | Deoxy, MOE, and cEt | 60 | 11037 | 11052 | 3709 |
| 561648 | 2067 | 2082 | TAGTCATCTCCATTTG | Deoxy, MOE, and cEt | 69 | 11039 | 11054 | 3710 |

TABLE 26-continued

Inhibition of ANGPTL3 mRNA by oligonucleotides targeting SEQ ID NO: 1 and 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 561649 | 2069 | 2084 | AGTAGTCATCTCCATT | Deoxy, MOE, and cEt | 82 | 11041 | 11056 | 141 |
| 561650 | 2071 | 2086 | TTAGTAGTCATCTCCA | Deoxy, MOE, and cEt | 79 | 11043 | 11058 | 142 |
| 561651 | 2073 | 2088 | ACTTAGTAGTCATCTC | Deoxy, MOE, and cEt | 66 | 11045 | 11060 | 3711 |
| 561652 | 2075 | 2090 | TGACTTAGTAGTCATC | Deoxy, MOE, and cEt | 62 | 11047 | 11062 | 3712 |
| 561653 | 2077 | 2092 | TGTGACTTAGTAGTCA | Deoxy, MOE, and cEt | 52 | 11049 | 11064 | 3713 |
| 561654 | 2079 | 2094 | AATGTGACTTAGTAGT | Deoxy, MOE, and cEt | 44 | 11051 | 11066 | 3714 |
| 561655 | 2081 | 2096 | TCAATGTGACTTAGTA | Deoxy, MOE, and cEt | 65 | 11053 | 11068 | 3715 |
| 561656 | 2083 | 2098 | AGTCAATGTGACTTAG | Deoxy, MOE, and cEt | 70 | 11055 | 11070 | 3716 |
| 561657 | 2085 | 2100 | AAAGTCAATGTGACTT | Deoxy, MOE, and cEt | 2 | 11057 | 11072 | 3717 |
| 561658 | 2087 | 2102 | TTAAAGTCAATGTGAC | Deoxy, MOE, and cEt | 15 | 11059 | 11074 | 3718 |
| 561659 | 2089 | 2104 | TGTTAAAGTCAATGTG | Deoxy, MOE, and cEt | 27 | 11061 | 11076 | 3719 |
| 561660 | 2091 | 2106 | CATGTTAAAGTCAATG | Deoxy, MOE, and cEt | 51 | 11063 | 11078 | 3720 |
| 561661 | 2093 | 2108 | CTCATGTTAAAGTCAA | Deoxy, MOE, and cEt | 53 | 11065 | 11080 | 3721 |
| 561662 | 2095 | 2110 | ACCTCATGTTAAAGTC | Deoxy, MOE, and cEt | 55 | 11067 | 11082 | 3722 |
| 561663 | 2097 | 2112 | ATACCTCATGTTAAAG | Deoxy, MOE, and cEt | 25 | 11069 | 11084 | 3723 |
| 561664 | 2099 | 2114 | TGATACCTCATGTTAA | Deoxy, MOE, and cEt | 0 | 11071 | 11086 | 3724 |
| 561665 | 2101 | 2116 | AGTGATACCTCATGTT | Deoxy, MOE, and cEt | 38 | 11073 | 11088 | 3725 |
| 561666 | 2103 | 2118 | ATAGTGATACCTCATG | Deoxy, MOE, and cEt | 61 | 11075 | 11090 | 3726 |
| 561667 | 2105 | 2120 | GTATAGTGATACCTCA | Deoxy, MOE, and cEt | 63 | 11077 | 11092 | 3727 |
| 561668 | 2107 | 2122 | AGGTATAGTGATACCT | Deoxy, MOE, and cEt | 27 | 11079 | 11094 | 3728 |
| 561669 | 2109 | 2124 | TAAGGTATAGTGATAC | Deoxy, MOE, and cEt | 34 | 11081 | 11096 | 3729 |
| 561670 | 2111 | 2126 | AATAAGGTATAGTGAT | Deoxy, MOE, and cEt | 22 | 11083 | 11098 | 3730 |

TABLE 27

Inhibition of ANGPTL3 mRNA by oligonucleotides targeting SEQ ID NO: 1 and 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 562220 | N/A | N/A | GTAAACTTATTGATAA | Deoxy, MOE, and cEt | 0 | 7670 | 7685 | 3731 |
| 562221 | N/A | N/A | GGCATAGTAAACTTAT | Deoxy, MOE, and cEt | 22 | 7676 | 7691 | 3732 |
| 562222 | N/A | N/A | AATTTTGGCATAGTAA | Deoxy, MOE, and cEt | 0 | 7682 | 7697 | 3733 |
| 562223 | N/A | N/A | GGCAATTAATGAATTT | Deoxy, MOE, and cEt | 15 | 7693 | 7708 | 3734 |
| 562224 | N/A | N/A | GTGAAAGGCAATTAAT | Deoxy, MOE, and cEt | 7 | 7699 | 7714 | 3735 |
| 562225 | N/A | N/A | AGTTAAGTGAAAGGCA | Deoxy, MOE, and cEt | 0 | 7705 | 7720 | 3736 |
| 562226 | N/A | N/A | CCCAAAAGTTAAGTGA | Deoxy, MOE, and cEt | 27 | 7711 | 7726 | 3737 |
| 562227 | N/A | N/A | TATGGTCCCAAAAGTT | Deoxy, MOE, and cEt | 35 | 7717 | 7732 | 3738 |

TABLE 27-continued

Inhibition of ANGPTL3 mRNA by oligonucleotides targeting SEQ ID NO: 1 and 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 562228 | N/A | N/A | ATTTATTATGGTCCCA | Deoxy, MOE, and cEt | 67 | 7723 | 7738 | 3739 |
| 562229 | N/A | N/A | GTTATGGCAATACATT | Deoxy, MOE, and cEt | 37 | 7744 | 7759 | 3740 |
| 562230 | N/A | N/A | ATTAATGTTATGGCAA | Deoxy, MOE, and cEt | 33 | 7750 | 7765 | 3741 |
| 562231 | N/A | N/A | GTAGTTTATTAATGTT | Deoxy, MOE, and cEt | 15 | 7757 | 7772 | 3742 |
| 562232 | N/A | N/A | TGTAAGGTAGTTTATT | Deoxy, MOE, and cEt | 23 | 7763 | 7778 | 3743 |
| 562233 | N/A | N/A | TGGTTTTGTAAGGTAG | Deoxy, MOE, and cEt | 43 | 7769 | 7784 | 3744 |
| 562234 | N/A | N/A | AATTGGTGGTTTTGTA | Deoxy, MOE, and cEt | 18 | 7775 | 7790 | 3745 |
| 562235 | N/A | N/A | GATTTTAATTGGTGGT | Deoxy, MOE, and cEt | 21 | 7781 | 7796 | 3746 |
| 562236 | N/A | N/A | GATGTAAATAACACTT | Deoxy, MOE, and cEt | 9 | 7809 | 7824 | 3747 |
| 562237 | N/A | N/A | TTGACAGATGTAAATA | Deoxy, MOE, and cEt | 11 | 7815 | 7830 | 3748 |
| 562238 | N/A | N/A | TTTATGTTGACAGATG | Deoxy, MOE, and cEt | 20 | 7821 | 7836 | 3749 |
| 562239 | N/A | N/A | AGTAGATTTATGTTGA | Deoxy, MOE, and cEt | 9 | 7827 | 7842 | 3750 |
| 562240 | N/A | N/A | CCTGAATATAATGAAT | Deoxy, MOE, and cEt | 29 | 7859 | 7874 | 3751 |
| 562241 | N/A | N/A | GGACTACCTGAATATA | Deoxy, MOE, and cEt | 17 | 7865 | 7880 | 3752 |
| 562242 | N/A | N/A | ACCATCAAGCCTCCCA | Deoxy, MOE, and cEt | 45 | 7956 | 7971 | 3753 |
| 562243 | N/A | N/A | CCCCTTACCATCAAGC | Deoxy, MOE, and cEt | 31 | 7962 | 7977 | 3754 |
| 562244 | N/A | N/A | TGTAGTCCCCTTACCA | Deoxy, MOE, and cEt | 16 | 7968 | 7983 | 3755 |
| 562245 | N/A | N/A | ATTGAATGTAGTCCCC | Deoxy, MOE, and cEt | 19 | 7974 | 7989 | 3756 |
| 562246 | N/A | N/A | GATTAGCAAGTGAATG | Deoxy, MOE, and cEt | 6 | 7994 | 8009 | 3757 |
| 562247 | N/A | N/A | TTTGTAGATTAGCAAG | Deoxy, MOE, and cEt | 24 | 8000 | 8015 | 3758 |
| 562248 | N/A | N/A | AAGAGGTTCTCAGTAA | Deoxy, MOE, and cEt | 28 | 8019 | 8034 | 3759 |
| 562249 | N/A | N/A | GTCCATAAGAGGTTCT | Deoxy, MOE, and cEt | 34 | 8025 | 8040 | 3760 |
| 562250 | N/A | N/A | TACCTGGTCCATAAGA | Deoxy, MOE, and cEt | 10 | 8031 | 8046 | 3761 |
| 562251 | N/A | N/A | TCCTAATACCTGGTCC | Deoxy, MOE, and cEt | 32 | 8037 | 8052 | 3762 |
| 562252 | N/A | N/A | TACTTTTCCTAATACC | Deoxy, MOE, and cEt | 20 | 8043 | 8058 | 3763 |
| 562253 | N/A | N/A | CGTTACTACTTTTCCT | Deoxy, MOE, and cEt | 29 | 8049 | 8064 | 3764 |
| 562254 | N/A | N/A | CTGAGACTGCTTCTCG | Deoxy, MOE, and cEt | 36 | 8067 | 8082 | 3765 |
| 562255 | N/A | N/A | TGAAGGCTGAGACTGC | Deoxy, MOE, and cEt | 40 | 8073 | 8088 | 3766 |
| 562256 | N/A | N/A | TAAATTATATGAAGGC | Deoxy, MOE, and cEt | 9 | 8082 | 8097 | 3767 |
| 562257 | N/A | N/A | GTAATTGTTTGATAAT | Deoxy, MOE, and cEt | 0 | 8097 | 8112 | 3768 |
| 562258 | N/A | N/A | TACTAACAAATGTGTA | Deoxy, MOE, and cEt | 0 | 8110 | 8125 | 3769 |
| 562259 | N/A | N/A | GTAATTTACTAACAAA | Deoxy, MOE, and cEt | 0 | 8116 | 8131 | 3770 |
| 562260 | N/A | N/A | ATAAGTGTAATTTACT | Deoxy, MOE, and cEt | 0 | 8122 | 8137 | 3771 |
| 562261 | N/A | N/A | GTTGTAATAAGTGTAA | Deoxy, MOE, and cEt | 0 | 8128 | 8143 | 3772 |
| 562262 | N/A | N/A | GTGATAAATATAATTC | Deoxy, MOE, and cEt | 0 | 8155 | 8170 | 3773 |
| 562263 | N/A | N/A | CATGTAATTGTGATAA | Deoxy, MOE, and cEt | 20 | 8164 | 8179 | 3774 |

TABLE 27-continued

Inhibition of ANGPTL3 mRNA by oligonucleotides targeting SEQ ID NO: 1 and 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 562264 | N/A | N/A | GTATATTTAAGAACAG | Deoxy, MOE, and cEt | 13 | 8181 | 8196 | 3775 |
| 562265 | N/A | N/A | TTGTGATAAGTATATT | Deoxy, MOE, and cEt | 3 | 8190 | 8205 | 3776 |
| 562266 | N/A | N/A | TGGAATTAAATTGTGA | Deoxy, MOE, and cEt | 0 | 8200 | 8215 | 3777 |
| 562267 | N/A | N/A | AAGCCGTGGAATTAAA | Deoxy, MOE, and cEt | 10 | 8206 | 8221 | 3778 |
| 562268 | N/A | N/A | CATTGTAAGCCGTGGA | Deoxy, MOE, and cEt | 54 | 8212 | 8227 | 3779 |
| 562269 | N/A | N/A | TATGATCATTGTAAGC | Deoxy, MOE, and cEt | 0 | 8218 | 8233 | 3780 |
| 562270 | N/A | N/A | TATAGTTATGATCATT | Deoxy, MOE, and cEt | 0 | 8224 | 8239 | 3781 |
| 562271 | N/A | N/A | GACATAACATTTAATC | Deoxy, MOE, and cEt | 21 | 8258 | 8273 | 3782 |
| 562272 | N/A | N/A | ACTTATGACATAACAT | Deoxy, MOE, and cEt | 14 | 8264 | 8279 | 3783 |
| 562273 | N/A | N/A | GTTACTACTTATGACA | Deoxy, MOE, and cEt | 30 | 8270 | 8285 | 3784 |
| 562274 | N/A | N/A | GTAACAGTTACTACTT | Deoxy, MOE, and cEt | 24 | 8276 | 8291 | 3785 |
| 562275 | N/A | N/A | GCTTATTTGTAACAGT | Deoxy, MOE, and cEt | 17 | 8284 | 8299 | 3786 |
| 562276 | N/A | N/A | TTCACAGCTTATTTGT | Deoxy, MOE, and cEt | 20 | 8290 | 8305 | 3787 |
| 562277 | N/A | N/A | GTTCTTTTCACAGCTT | Deoxy, MOE, and cEt | 46 | 8296 | 8311 | 3788 |
| 562278 | N/A | N/A | GGAGTGGTTCTTTTCA | Deoxy, MOE, and cEt | 35 | 8302 | 8317 | 3789 |
| 562279 | N/A | N/A | ATGCTAGGAGTGGTTC | Deoxy, MOE, and cEt | 29 | 8308 | 8323 | 3790 |
| 562280 | N/A | N/A | TGACTAATGCTAGGAG | Deoxy, MOE, and cEt | 4 | 8314 | 8329 | 3791 |
| 562281 | N/A | N/A | ATAGAGTGACTAATGC | Deoxy, MOE, and cEt | 23 | 8320 | 8335 | 3792 |
| 562282 | N/A | N/A | GAGAGAATAGAGTGAC | Deoxy, MOE, and cEt | 15 | 8326 | 8341 | 3793 |
| 562284 | N/A | N/A | ATTGATATGTAAAACG | Deoxy, MOE, and cEt | 7 | 8347 | 8362 | 3794 |
| 562285 | N/A | N/A | CAATTAATTGATATGT | Deoxy, MOE, and cEt | 14 | 8353 | 8368 | 3795 |
| 562286 | N/A | N/A | CCTTTTAACTTCCAAT | Deoxy, MOE, and cEt | 40 | 8365 | 8380 | 3796 |
| 562287 | N/A | N/A | CCTGGTCCTTTTAACT | Deoxy, MOE, and cEt | 29 | 8371 | 8386 | 3797 |
| 562288 | N/A | N/A | GAGTTTCCTGGTCCTT | Deoxy, MOE, and cEt | 49 | 8377 | 8392 | 3798 |
| 562289 | N/A | N/A | ATGTCTGAGTTTCCTG | Deoxy, MOE, and cEt | 16 | 8383 | 8398 | 3799 |
| 562290 | N/A | N/A | TACTGTATGTCTGAGT | Deoxy, MOE, and cEt | 33 | 8389 | 8404 | 3800 |
| 562291 | N/A | N/A | CCATACATTCTATATA | Deoxy, MOE, and cEt | 10 | 8437 | 8452 | 3801 |
| 562292 | N/A | N/A | TATAAGCCATACATTC | Deoxy, MOE, and cEt | 24 | 8443 | 8458 | 3802 |
| 562293 | N/A | N/A | ATTCATTATAAGCCAT | Deoxy, MOE, and cEt | 38 | 8449 | 8464 | 3803 |
| 562295 | N/A | N/A | CATTGAGTTAACTAAT | Deoxy, MOE, and cEt | 7 | 8463 | 8478 | 3804 |
| 562296 | N/A | N/A | AATTTGCATTGAGTTA | Deoxy, MOE, and cEt | 18 | 8469 | 8484 | 3805 |
| 561144 | 525 | 540 | TGAAGTTACTTCTGGG | Deoxy, MOE, and cEt | 39 | 3629 | 3644 | 3806 |
| 561145 | 527 | 542 | AGTGAAGTTACTTCTG | Deoxy, MOE, and cEt | 51 | 3631 | 3646 | 3807 |
| 561146 | 529 | 544 | TAAGTGAAGTTACTTC | Deoxy, MOE, and cEt | 40 | 3633 | 3648 | 3808 |
| 561147 | 533 | 548 | GTTTAAGTGAAGTTA | Deoxy, MOE, and cEt | 29 | N/A | N/A | 3809 |
| 561148 | 535 | 550 | AAGTTTTAAGTGAAGT | Deoxy, MOE, and cEt | 19 | N/A | N/A | 3810 |

TABLE 27-continued

Inhibition of ANGPTL3 mRNA by oligonucleotides targeting SEQ ID NO: 1 and 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 561149 | 547 | 562 | GTTTTTCTACAAAAGT | Deoxy, MOE, and cEt | 38 | 4285 | 4300 | 3811 |
| 561150 | 560 | 575 | ATGCTATTATCTTGTT | Deoxy, MOE, and cEt | 30 | 4298 | 4313 | 3812 |
| 561151 | 562 | 577 | TGATGCTATTATCTTG | Deoxy, MOE, and cEt | 36 | 4300 | 4315 | 3813 |
| 561152 | 564 | 579 | TTTGATGCTATTATCT | Deoxy, MOE, and cEt | 23 | 4302 | 4317 | 3814 |
| 561153 | 567 | 582 | GTCTTTGATGCTATTA | Deoxy, MOE, and cEt | 51 | 4305 | 4320 | 3815 |
| 561154 | 569 | 584 | AGGTCTTTGATGCTAT | Deoxy, MOE, and cEt | 60 | 4307 | 4322 | 3816 |
| 561155 | 571 | 586 | GAAGGTCTTTGATGCT | Deoxy, MOE, and cEt | 61 | 4309 | 4324 | 3817 |
| 561156 | 573 | 588 | GAGAAGGTCTTTGATG | Deoxy, MOE, and cEt | 30 | 4311 | 4326 | 3818 |
| 561157 | 575 | 590 | TGGAGAAGGTCTTTGA | Deoxy, MOE, and cEt | 40 | 4313 | 4328 | 3819 |
| 561158 | 577 | 592 | TCTGGAGAAGGTCTTT | Deoxy, MOE, and cEt | 46 | 4315 | 4330 | 3820 |
| 561159 | 579 | 594 | GGTCTGGAGAAGGTCT | Deoxy, MOE, and cEt | 57 | 4317 | 4332 | 3821 |
| 561160 | 581 | 596 | ACGGTCTGGAGAAGGT | Deoxy, MOE, and cEt | 57 | 4319 | 4334 | 3822 |
| 561161 | 583 | 598 | CCACGGTCTGGAGAAG | Deoxy, MOE, and cEt | 56 | 4321 | 4336 | 3823 |
| 561162 | 585 | 600 | TTCCACGGTCTGGAGA | Deoxy, MOE, and cEt | 50 | 4323 | 4338 | 3824 |
| 561163 | 587 | 602 | TCTTCCACGGTCTGGA | Deoxy, MOE, and cEt | 77 | 4325 | 4340 | 3825 |
| 561164 | 589 | 604 | GGTCTTCCACGGTCTG | Deoxy, MOE, and cEt | 89 | 4327 | 4342 | 3826 |
| 561165 | 591 | 606 | TTGGTCTTCCACGGTC | Deoxy, MOE, and cEt | 79 | 4329 | 4344 | 3827 |
| 561166 | 593 | 608 | TATTGGTCTTCCACGG | Deoxy, MOE, and cEt | 39 | 4331 | 4346 | 3828 |
| 561167 | 595 | 610 | TATATTGGTCTTCCAC | Deoxy, MOE, and cEt | 22 | 4333 | 4348 | 3829 |
| 561168 | 597 | 612 | TTTATATTGGTCTTCC | Deoxy, MOE, and cEt | 43 | 4335 | 4350 | 3830 |
| 561169 | 599 | 614 | TGTTTATATTGGTCTT | Deoxy, MOE, and cEt | 50 | 4337 | 4352 | 3831 |
| 561170 | 601 | 616 | ATTGTTTATATTGGTC | Deoxy, MOE, and cEt | 27 | 4339 | 4354 | 3832 |
| 561171 | 603 | 618 | TAATTGTTTATATTGG | Deoxy, MOE, and cEt | 21 | 4341 | 4356 | 3833 |
| 561172 | 607 | 622 | GGTTAATTGTTTATA | Deoxy, MOE, and cEt | 22 | 4345 | 4360 | 3834 |
| 561173 | 610 | 625 | GTTGGTTTAATTGTTT | Deoxy, MOE, and cEt | 33 | 4348 | 4363 | 3835 |
| 561174 | 612 | 627 | CTGTTGGTTTAATTGT | Deoxy, MOE, and cEt | 13 | 4350 | 4365 | 3836 |
| 561175 | 614 | 629 | TGCTGTTGGTTTAATT | Deoxy, MOE, and cEt | 26 | 4352 | 4367 | 3837 |
| 561176 | 616 | 631 | TATGCTGTTGGTTTAA | Deoxy, MOE, and cEt | 40 | 4354 | 4369 | 3838 |
| 561177 | 618 | 633 | ACTATGCTGTTGGTTT | Deoxy, MOE, and cEt | 68 | 4356 | 4371 | 3839 |
| 561178 | 620 | 635 | TGACTATGCTGTTGGT | Deoxy, MOE, and cEt | 64 | 4358 | 4373 | 3840 |
| 561179 | 622 | 637 | TTTGACTATGCTGTTG | Deoxy, MOE, and cEt | 42 | 4360 | 4375 | 3841 |
| 561180 | 624 | 639 | TATTTGACTATGCTGT | Deoxy, MOE, and cEt | 16 | 4362 | 4377 | 3842 |
| 561181 | 626 | 641 | TTTATTTGACTATGCT | Deoxy, MOE, and cEt | 17 | 4364 | 4379 | 3843 |
| 561182 | 628 | 643 | CTTTTATTTGACTATG | Deoxy, MOE, and cEt | 7 | 4366 | 4381 | 3844 |
| 561183 | 645 | 660 | GAGCTGATTTTCTATT | Deoxy, MOE, and cEt | 18 | N/A | N/A | 3845 |
| 561184 | 647 | 662 | CTGAGCTGATTTTCTA | Deoxy, MOE, and cEt | 42 | N/A | N/A | 3846 |

TABLE 27-continued

Inhibition of ANGPTL3 mRNA by oligonucleotides targeting SEQ ID NO: 1 and 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 561185 | 649 | 664 | TTCTGAGCTGATTTTC | Deoxy, MOE, and cEt | 32 | N/A | N/A | 3847 |
| 561186 | 651 | 666 | CCTTCTGAGCTGATTT | Deoxy, MOE, and cEt | 14 | N/A | N/A | 3848 |
| 561187 | 653 | 668 | GTCCTTCTGAGCTGAT | Deoxy, MOE, and cEt | 39 | 6666 | 6681 | 3849 |
| 561188 | 655 | 670 | TAGTCCTTCTGAGCTG | Deoxy, MOE, and cEt | 7 | 6668 | 6683 | 3850 |
| 561189 | 657 | 672 | ACTAGTCCTTCTGAGC | Deoxy, MOE, and cEt | 32 | 6670 | 6685 | 3851 |
| 561190 | 659 | 674 | ATACTAGTCCTTCTGA | Deoxy, MOE, and cEt | 19 | 6672 | 6687 | 3852 |
| 561191 | 661 | 676 | GAATACTAGTCCTTCT | Deoxy, MOE, and cEt | 37 | 6674 | 6689 | 3853 |
| 561192 | 663 | 678 | TTGAATACTAGTCCTT | Deoxy, MOE, and cEt | 50 | 6676 | 6691 | 3854 |
| 561193 | 665 | 680 | TCTTGAATACTAGTCC | Deoxy, MOE, and cEt | 28 | 6678 | 6693 | 3855 |
| 561194 | 667 | 682 | GTTCTTGAATACTAGT | Deoxy, MOE, and cEt | 34 | 6680 | 6695 | 3856 |
| 561195 | 669 | 684 | GGGTTCTTGAATACTA | Deoxy, MOE, and cEt | 61 | 6682 | 6697 | 3857 |
| 561196 | 671 | 686 | GTGGGTTCTTGAATAC | Deoxy, MOE, and cEt | 21 | 6684 | 6699 | 3858 |
| 561197 | 673 | 688 | CTGTGGGTTCTTGAAT | Deoxy, MOE, and cEt | 45 | 6686 | 6701 | 3859 |
| 561198 | 675 | 690 | TTCTGTGGGTTCTTGA | Deoxy, MOE, and cEt | 0 | 6688 | 6703 | 3860 |
| 561199 | 679 | 694 | AAATTTCTGTGGGTTC | Deoxy, MOE, and cEt | 31 | 6692 | 6707 | 3861 |
| 561200 | 681 | 696 | AGAAATTTCTGTGGGT | Deoxy, MOE, and cEt | 60 | 6694 | 6709 | 3862 |
| 561201 | 684 | 699 | TAGAGAAATTTCTGTG | Deoxy, MOE, and cEt | 35 | 6697 | 6712 | 3863 |
| 561202 | 686 | 701 | GATAGAGAAATTTCTG | Deoxy, MOE, and cEt | 36 | 6699 | 6714 | 3864 |
| 561203 | 694 | 709 | GCTTGGAAGATAGAGA | Deoxy, MOE, and cEt | 39 | 6707 | 6722 | 3865 |
| 561204 | 696 | 711 | TGGCTTGGAAGATAGA | Deoxy, MOE, and cEt | 32 | 6709 | 6724 | 3866 |
| 561205 | 698 | 713 | CTTGGCTTGGAAGATA | Deoxy, MOE, and cEt | 23 | 6711 | 6726 | 3867 |
| 561206 | 700 | 715 | CTCTTGGCTTGGAAGA | Deoxy, MOE, and cEt | 21 | 6713 | 6728 | 3868 |
| 561207 | 702 | 717 | TGCTCTTGGCTTGGAA | Deoxy, MOE, and cEt | 34 | 6715 | 6730 | 3869 |
| 561208 | 704 | 719 | GGTGCTCTTGGCTTGG | Deoxy, MOE, and cEt | 71 | 6717 | 6732 | 118 |
| 561209 | 706 | 721 | TTGGTGCTCTTGGCTT | Deoxy, MOE, and cEt | 59 | 6719 | 6734 | 3870 |
| 561210 | 708 | 723 | TCTTGGTGCTCTTGGC | Deoxy, MOE, and cEt | 65 | 6721 | 6736 | 3871 |
| 560990 | 709 | 724 | TTCTTGGTGCTCTTGG | Deoxy, MOE, and cEt | 54 | 6722 | 6737 | 111 |
| 561211 | 710 | 725 | GTTCTTGGTGCTCTTG | Deoxy, MOE, and cEt | 60 | 6723 | 6738 | 3872 |
| 561212 | 712 | 727 | TAGTTCTTGGTGCTCT | Deoxy, MOE, and cEt | 53 | 6725 | 6740 | 3873 |
| 561213 | 714 | 729 | AGTAGTTCTTGGTGCT | Deoxy, MOE, and cEt | 50 | 6727 | 6742 | 3874 |
| 561214 | 716 | 731 | GGAGTAGTTCTTGGTG | Deoxy, MOE, and cEt | 31 | 6729 | 6744 | 3875 |
| 561215 | 718 | 733 | AGGGAGTAGTTCTTGG | Deoxy, MOE, and cEt | 0 | 6731 | 6746 | 3876 |
| 561216 | 720 | 735 | AAAGGGAGTAGTTCTT | Deoxy, MOE, and cEt | 25 | 6733 | 6748 | 3877 |
| 561217 | 722 | 737 | AGAAAGGGAGTAGTTC | Deoxy, MOE, and cEt | 28 | 6735 | 6750 | 3878 |
| 561218 | 724 | 739 | GAAGAAAGGGAGTAGT | Deoxy, MOE, and cEt | 10 | 6737 | 6752 | 3879 |
| 561219 | 726 | 741 | CTGAAGAAAGGGAGTA | Deoxy, MOE, and cEt | 47 | 6739 | 6754 | 3880 |

TABLE 27-continued

Inhibition of ANGPTL3 mRNA by oligonucleotides targeting SEQ ID NO: 1 and 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 561220 | 730 | 745 | TCAACTGAAGAAAGGG | Deoxy, MOE, and cEt | 50 | 6743 | 6758 | 3881 |
| 337487 | 804 | 823 | CACTTGTATGTTCACCTCTG | 5-10-5 MOE | 52 | 7389 | 7408 | 28 |
| 561297 | 926 | 941 | TCATTGAAGTTTTGTG | Deoxy, MOE, and cEt | 28 | 7913 | 7928 | 3882 |
| 561298 | 930 | 945 | CGTTTCATTGAAGTTT | Deoxy, MOE, and cEt | 35 | 7917 | 7932 | 3883 |
| 561299 | 944 | 959 | TTGTAGTTCTCCCACG | Deoxy, MOE, and cEt | 30 | 7931 | 7946 | 3884 |
| 561300 | 946 | 961 | ATTTGTAGTTCTCCCA | Deoxy, MOE, and cEt | 32 | 7933 | 7948 | 3885 |
| 561301 | 948 | 963 | ATATTTGTAGTTCTCC | Deoxy, MOE, and cEt | 24 | 7935 | 7950 | 3886 |
| 561302 | 950 | 965 | CCATATTTGTAGTTCT | Deoxy, MOE, and cEt | 5 | 7937 | 7952 | 3887 |
| 561303 | 952 | 967 | AACCATATTTGTAGTT | Deoxy, MOE, and cEt | 3 | 7939 | 7954 | 3888 |
| 561304 | 956 | 971 | CCAAAACCATATTTGT | Deoxy, MOE, and cEt | 19 | 7943 | 7958 | 3889 |
| 561305 | 959 | 974 | CTCCCAAAACCATATT | Deoxy, MOE, and cEt | 23 | 7946 | 7961 | 3890 |
| 561306 | 961 | 976 | GCCTCCCAAAACCATA | Deoxy, MOE, and cEt | 25 | 7948 | 7963 | 3891 |
| 561307 | 963 | 978 | AAGCCTCCCAAAACCA | Deoxy, MOE, and cEt | 30 | 7950 | 7965 | 3892 |
| 561308 | 965 | 980 | TCAAGCCTCCCAAAAC | Deoxy, MOE, and cEt | 16 | 7952 | 7967 | 3893 |
| 561309 | 969 | 984 | TCCATCAAGCCTCCCA | Deoxy, MOE, and cEt | 46 | N/A | N/A | 3894 |
| 561310 | 971 | 986 | TCTCCATCAAGCCTCC | Deoxy, MOE, and cEt | 13 | N/A | N/A | 3895 |
| 561311 | 973 | 988 | ATTCTCCATCAAGCCT | Deoxy, MOE, and cEt | 16 | N/A | N/A | 3896 |
| 561312 | 975 | 990 | AAATTCTCCATCAAGC | Deoxy, MOE, and cEt | 20 | N/A | N/A | 3897 |
| 561313 | 979 | 994 | ACCAAAATTCTCCATC | Deoxy, MOE, and cEt | 18 | N/A | N/A | 3898 |
| 561314 | 981 | 996 | CAACCAAAATTCTCCA | Deoxy, MOE, and cEt | 26 | N/A | N/A | 3899 |
| 561315 | 983 | 998 | CCCAACCAAAATTCTC | Deoxy, MOE, and cEt | 38 | 9558 | 9573 | 3900 |
| 559316 | 985 | 1000 | GGCCCAACCAAAATTC | Deoxy, MOE, and cEt | 14 | 9560 | 9575 | 3901 |
| 561316 | 987 | 1002 | TAGGCCCAACCAAAAT | Deoxy, MOE, and cEt | 38 | 9562 | 9577 | 3902 |
| 561317 | 989 | 1004 | TCTAGGCCCAACCAAA | Deoxy, MOE, and cEt | 51 | 9564 | 9579 | 3903 |
| 561318 | 991 | 1006 | TCTCTAGGCCCAACCA | Deoxy, MOE, and cEt | 35 | 9566 | 9581 | 3904 |
| 561319 | 993 | 1008 | CTTCTCTAGGCCCAAC | Deoxy, MOE, and cEt | 31 | 9568 | 9583 | 3905 |
| 561320 | 995 | 1010 | ATCTTCTCTAGGCCCA | Deoxy, MOE, and cEt | 68 | 9570 | 9585 | 119 |
| 561321 | 997 | 1012 | ATATCTTCTCTAGGCC | Deoxy, MOE, and cEt | 30 | 9572 | 9587 | 3906 |
| 561322 | 999 | 1014 | GTATATCTTCTCTAGG | Deoxy, MOE, and cEt | 25 | 9574 | 9589 | 3907 |
| 561323 | 1001 | 1016 | GAGTATATCTTCTCTA | Deoxy, MOE, and cEt | 26 | 9576 | 9591 | 3908 |
| 561324 | 1003 | 1018 | TGGAGTATATCTTCTC | Deoxy, MOE, and cEt | 46 | 9578 | 9593 | 3909 |
| 561325 | 1005 | 1020 | TATGGAGTATATCTTC | Deoxy, MOE, and cEt | 20 | 9580 | 9595 | 3910 |
| 561326 | 1007 | 1022 | ACTATGGAGTATATCT | Deoxy, MOE, and cEt | 20 | 9582 | 9597 | 3911 |
| 561327 | 1009 | 1024 | TCACTATGGAGTATAT | Deoxy, MOE, and cEt | 22 | 9584 | 9599 | 3912 |
| 561328 | 1011 | 1026 | CTTCACTATGGAGTAT | Deoxy, MOE, and cEt | 33 | 9586 | 9601 | 3913 |
| 561329 | 1013 | 1028 | TGCTTCACTATGGAGT | Deoxy, MOE, and cEt | 50 | 9588 | 9603 | 3914 |

TABLE 27-continued

Inhibition of ANGPTL3 mRNA by oligonucleotides targeting SEQ ID NO: 1 and 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 561330 | 1015 | 1030 | ATTGCTTCACTATGGA | Deoxy, MOE, and cEt | 43 | 9590 | 9605 | 3915 |
| 561331 | 1017 | 1032 | AGATTGCTTCACTATG | Deoxy, MOE, and cEt | 31 | 9592 | 9607 | 3916 |
| 561332 | 1019 | 1034 | TTAGATTGCTTCACTA | Deoxy, MOE, and cEt | 36 | 9594 | 9609 | 3917 |
| 561333 | 1021 | 1036 | AATTAGATTGCTTCAC | Deoxy, MOE, and cEt | 17 | 9596 | 9611 | 3918 |
| 561334 | 1023 | 1038 | ATAATTAGATTGCTTC | Deoxy, MOE, and cEt | 23 | 9598 | 9613 | 3919 |
| 561335 | 1025 | 1040 | ACATAATTAGATTGCT | Deoxy, MOE, and cEt | 13 | 9600 | 9615 | 3920 |
| 561336 | 1031 | 1046 | CGTAAAACATAATTAG | Deoxy, MOE, and cEt | 25 | 9606 | 9621 | 3921 |
| 561337 | 1045 | 1060 | CTTCCAACTCAATTCG | Deoxy, MOE, and cEt | 0 | 9620 | 9635 | 3922 |
| 561338 | 1047 | 1062 | GTCTTCCAACTCAATT | Deoxy, MOE, and cEt | 0 | 9622 | 9637 | 3923 |
| 561339 | 1049 | 1064 | CAGTCTTCCAACTCAA | Deoxy, MOE, and cEt | 15 | 9624 | 9639 | 3924 |
| 561340 | 1051 | 1066 | TCCAGTCTTCCAACTC | Deoxy, MOE, and cEt | 22 | 9626 | 9641 | 3925 |
| 561341 | 1053 | 1068 | TTTCCAGTCTTCCAAC | Deoxy, MOE, and cEt | 2 | 9628 | 9643 | 3926 |
| 561342 | 1056 | 1071 | GTCTTTCCAGTCTTCC | Deoxy, MOE, and cEt | 45 | 9631 | 9646 | 3927 |
| 561343 | 1059 | 1074 | GTTGTCTTTCCAGTCT | Deoxy, MOE, and cEt | 67 | 9634 | 9649 | 120 |
| 561344 | 1061 | 1076 | TTGTTGTCTTTCCAGT | Deoxy, MOE, and cEt | 43 | 9636 | 9651 | 3928 |
| 561345 | 1063 | 1078 | GTTTGTTGTCTTTCCA | Deoxy, MOE, and cEt | 57 | 9638 | 9653 | 121 |
| 561346 | 1068 | 1083 | ATAATGTTTGTTGTCT | Deoxy, MOE, and cEt | 6 | 9643 | 9658 | 3929 |
| 561347 | 1098 | 1113 | GTGATTTCCCAAGTAA | Deoxy, MOE, and cEt | 66 | 9673 | 9688 | 122 |
| 561348 | 1113 | 1128 | CGTATAGTTGGTTTCG | Deoxy, MOE, and cEt | 54 | 9688 | 9703 | 3930 |
| 561349 | 1127 | 1142 | GCAACTAGATGTAGCG | Deoxy, MOE, and cEt | 50 | 9702 | 9717 | 3931 |
| 561350 | 1129 | 1144 | TCGCAACTAGATGTAG | Deoxy, MOE, and cEt | 9 | 9704 | 9719 | 3932 |
| 561351 | 1131 | 1146 | AATCGCAACTAGATGT | Deoxy, MOE, and cEt | 9 | 9706 | 9721 | 3933 |
| 561352 | 1133 | 1148 | GTAATCGCAACTAGAT | Deoxy, MOE, and cEt | 15 | 9708 | 9723 | 3934 |
| 561353 | 1135 | 1150 | CAGTAATCGCAACTAG | Deoxy, MOE, and cEt | 41 | 9710 | 9725 | 3935 |
| 561354 | 1137 | 1152 | GCCAGTAATCGCAACT | Deoxy, MOE, and cEt | 38 | 9712 | 9727 | 3936 |
| 561355 | 1139 | 1154 | TTGCCAGTAATCGCAA | Deoxy, MOE, and cEt | 32 | 9714 | 9729 | 3937 |
| 561356 | 1141 | 1156 | CATTGCCAGTAATCGC | Deoxy, MOE, and cEt | 54 | 9716 | 9731 | 3938 |
| 561357 | 1143 | 1158 | GACATTGCCAGTAATC | Deoxy, MOE, and cEt | 20 | 9718 | 9733 | 3939 |
| 561358 | 1145 | 1160 | GGGACATTGCCAGTAA | Deoxy, MOE, and cEt | 0 | 9720 | 9735 | 3940 |
| 561359 | 1160 | 1175 | TCCGGGATTGCATTGG | Deoxy, MOE, and cEt | 43 | 9735 | 9750 | 3941 |
| 561360 | 1162 | 1177 | TTTCCGGGATTGCATT | Deoxy, MOE, and cEt | 31 | 9737 | 9752 | 3942 |
| 561361 | 1164 | 1179 | GTTTTCCGGGATTGCA | Deoxy, MOE, and cEt | 31 | 9739 | 9754 | 3943 |
| 561362 | 1166 | 1181 | TTGTTTTCCGGGATTG | Deoxy, MOE, and cEt | 36 | 9741 | 9756 | 3944 |
| 561363 | 1168 | 1183 | CTTTGTTTTCCGGGAT | Deoxy, MOE, and cEt | 22 | 9743 | 9758 | 3945 |
| 561364 | 1170 | 1185 | ATCTTTGTTTTCCGGG | Deoxy, MOE, and cEt | 13 | 9745 | 9760 | 3946 |
| 561365 | 1172 | 1187 | AAATCTTTGTTTTCCG | Deoxy, MOE, and cEt | 7 | 9747 | 9762 | 3947 |

TABLE 27-continued

Inhibition of ANGPTL3 mRNA by oligonucleotides targeting SEQ ID NO: 1 and 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 561366 | 1177 | 1192 | ACACCAAATCTTTGTT | Deoxy, MOE, and cEt | 8 | 9752 | 9767 | 3948 |
| 561367 | 1179 | 1194 | AAACACCAAATCTTTG | Deoxy, MOE, and cEt | 11 | 9754 | 9769 | 3949 |
| 561368 | 1187 | 1202 | CAAGTAGAAAACACCA | Deoxy, MOE, and cEt | 16 | 9762 | 9777 | 3950 |
| 561369 | 1189 | 1204 | CCCAAGTAGAAAACAC | Deoxy, MOE, and cEt | 23 | 9764 | 9779 | 3951 |
| 561370 | 1191 | 1206 | ATCCCAAGTAGAAAAC | Deoxy, MOE, and cEt | 27 | 9766 | 9781 | 3952 |
| 561371 | 1193 | 1208 | TGATCCCAAGTAGAAA | Deoxy, MOE, and cEt | 25 | 9768 | 9783 | 3953 |
| 561372 | 1195 | 1210 | TGTGATCCCAAGTAGA | Deoxy, MOE, and cEt | 45 | 9770 | 9785 | 3954 |

TABLE 28

Inhibition of ANGPTL3 mRNA by oligonucleotides targeting SEQ ID NO: 1 and 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 561067 | 276 | 291 | CTGATCAAATATGTTG | Deoxy, MOE, and cEt | 54 | 3380 | 3395 | 3955 |
| 561068 | 278 | 293 | GACTGATCAAATATGT | Deoxy, MOE, and cEt | 19 | 3382 | 3397 | 3956 |
| 561069 | 280 | 295 | AAGACTGATCAAATAT | Deoxy, MOE, and cEt | 17 | 3384 | 3399 | 3957 |
| 561070 | 286 | 301 | CATAAAAGACTGATC | Deoxy, MOE, and cEt | 18 | 3390 | 3405 | 3958 |
| 561071 | 289 | 304 | GATCATAAAAGACTG | Deoxy, MOE, and cEt | 11 | 3393 | 3408 | 3959 |
| 561072 | 291 | 306 | TAGATCATAAAAGAC | Deoxy, MOE, and cEt | 0 | 3395 | 3410 | 3960 |
| 561073 | 293 | 308 | GATAGATCATAAAAG | Deoxy, MOE, and cEt | 15 | 3397 | 3412 | 3961 |
| 561074 | 295 | 310 | GCGATAGATCATAAAA | Deoxy, MOE, and cEt | 39 | 3399 | 3414 | 3962 |
| 561075 | 297 | 312 | CAGCGATAGATCATAA | Deoxy, MOE, and cEt | 53 | 3401 | 3416 | 3963 |
| 561076 | 299 | 314 | TGCAGCGATAGATCAT | Deoxy, MOE, and cEt | 70 | 3403 | 3418 | 159 |
| 561077 | 301 | 316 | TTTGCAGCGATAGATC | Deoxy, MOE, and cEt | 60 | 3405 | 3420 | 3964 |
| 561078 | 303 | 318 | GGTTTGCAGCGATAGA | Deoxy, MOE, and cEt | 63 | 3407 | 3422 | 3965 |
| 561079 | 305 | 320 | CTGGTTTGCAGCGATA | Deoxy, MOE, and cEt | 76 | 3409 | 3424 | 160 |
| 561080 | 307 | 322 | CACTGGTTTGCAGCGA | Deoxy, MOE, and cEt | 65 | 3411 | 3426 | 3966 |
| 561081 | 309 | 324 | TTCACTGGTTTGCAGC | Deoxy, MOE, and cEt | 45 | 3413 | 3428 | 3967 |
| 561082 | 311 | 326 | ATTTCACTGGTTTGCA | Deoxy, MOE, and cEt | 56 | 3415 | 3430 | 3968 |
| 561083 | 313 | 328 | TGATTTCACTGGTTTG | Deoxy, MOE, and cEt | 65 | 3417 | 3432 | 3969 |
| 561084 | 316 | 331 | CTTTGATTTCACTGGT | Deoxy, MOE, and cEt | 73 | 3420 | 3435 | 161 |
| 561085 | 341 | 356 | GTTCTTCTCAGTTCCT | Deoxy, MOE, and cEt | 79 | 3445 | 3460 | 162 |
| 561086 | 343 | 358 | TAGTTCTTCTCAGTTC | Deoxy, MOE, and cEt | 50 | 3447 | 3462 | 3970 |
| 561087 | 345 | 360 | TGTAGTTCTTCTCAGT | Deoxy, MOE, and cEt | 42 | 3449 | 3464 | 3971 |
| 561088 | 347 | 362 | TATGTAGTTCTTCTCA | Deoxy, MOE, and cEt | 27 | 3451 | 3466 | 3972 |

TABLE 28-continued

Inhibition of ANGPTL3 mRNA by oligonucleotides targeting SEQ ID NO: 1 and 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 561089 | 349 | 364 | TATATGTAGTTCTTCT | Deoxy, MOE, and cEt | 37 | 3453 | 3468 | 3973 |
| 561090 | 352 | 367 | GTTTATATGTAGTTCT | Deoxy, MOE, and cEt | 39 | 3456 | 3471 | 3974 |
| 561091 | 355 | 370 | GTAGTTTATATGTAGT | Deoxy, MOE, and cEt | 55 | 3459 | 3474 | 3975 |
| 561092 | 358 | 373 | CTTGTAGTTTATATGT | Deoxy, MOE, and cEt | 48 | 3462 | 3477 | 3976 |
| 561093 | 360 | 375 | GACTTGTAGTTTATAT | Deoxy, MOE, and cEt | 43 | 3464 | 3479 | 3977 |
| 561094 | 362 | 377 | TTGACTTGTAGTTTAT | Deoxy, MOE, and cEt | 35 | 3466 | 3481 | 3978 |
| 561095 | 365 | 380 | TTTTTGACTTGTAGTT | Deoxy, MOE, and cEt | 37 | 3469 | 3484 | 3979 |
| 561096 | 367 | 382 | CATTTTTGACTTGTAG | Deoxy, MOE, and cEt | 34 | 3471 | 3486 | 3980 |
| 561097 | 373 | 388 | CCTCTTCATTTTTGAC | Deoxy, MOE, and cEt | 48 | 3477 | 3492 | 3981 |
| 561098 | 386 | 401 | GACATATTCTTTACCT | Deoxy, MOE, and cEt | 40 | 3490 | 3505 | 3982 |
| 561099 | 388 | 403 | GTGACATATTCTTTAC | Deoxy, MOE, and cEt | 43 | 3492 | 3507 | 3983 |
| 561100 | 393 | 408 | TTCAAGTGACATATTC | Deoxy, MOE, and cEt | 51 | 3497 | 3512 | 3984 |
| 561101 | 395 | 410 | AGTTCAAGTGACATAT | Deoxy, MOE, and cEt | 27 | 3499 | 3514 | 3985 |
| 561102 | 397 | 412 | TGAGTTCAAGTGACAT | Deoxy, MOE, and cEt | 63 | 3501 | 3516 | 3986 |
| 561103 | 399 | 414 | GTTGAGTTCAAGTGAC | Deoxy, MOE, and cEt | 48 | 3503 | 3518 | 3987 |
| 561104 | 401 | 416 | GAGTTGAGTTCAAGTG | Deoxy, MOE, and cEt | 57 | 3505 | 3520 | 3988 |
| 561105 | 403 | 418 | TTGAGTTGAGTTCAAG | Deoxy, MOE, and cEt | 32 | 3507 | 3522 | 3989 |
| 561106 | 405 | 420 | TTTTGAGTTGAGTTCA | Deoxy, MOE, and cEt | 47 | 3509 | 3524 | 3990 |
| 561107 | 407 | 422 | AGTTTTGAGTTGAGTT | Deoxy, MOE, and cEt | 46 | 3511 | 3526 | 3991 |
| 561108 | 409 | 424 | CAAGTTTTGAGTTGAG | Deoxy, MOE, and cEt | 48 | 3513 | 3528 | 3992 |
| 561109 | 411 | 426 | TTCAAGTTTTGAGTTG | Deoxy, MOE, and cEt | 17 | 3515 | 3530 | 3993 |
| 561110 | 413 | 428 | CTTTCAAGTTTTGAGT | Deoxy, MOE, and cEt | 48 | 3517 | 3532 | 3994 |
| 561111 | 415 | 430 | GGCTTTCAAGTTTTGA | Deoxy, MOE, and cEt | 56 | 3519 | 3534 | 3995 |
| 561112 | 417 | 432 | GAGGCTTTCAAGTTTT | Deoxy, MOE, and cEt | 39 | 3521 | 3536 | 3996 |
| 561113 | 419 | 434 | AGGAGGCTTTCAAGTT | Deoxy, MOE, and cEt | 49 | 3523 | 3538 | 3997 |
| 561114 | 421 | 436 | CTAGGAGGCTTTCAAG | Deoxy, MOE, and cEt | 49 | 3525 | 3540 | 3998 |
| 561115 | 423 | 438 | TTCTAGGAGGCTTTCA | Deoxy, MOE, and cEt | 40 | 3527 | 3542 | 3999 |
| 561116 | 425 | 440 | TCTTCTAGGAGGCTTT | Deoxy, MOE, and cEt | 66 | 3529 | 3544 | 4000 |
| 561117 | 427 | 442 | TTTCTTCTAGGAGGCT | Deoxy, MOE, and cEt | 74 | 3531 | 3546 | 4001 |
| 561118 | 442 | 457 | GTTGAAGTAGAATTTT | Deoxy, MOE, and cEt | 40 | 3546 | 3561 | 4002 |
| 561119 | 469 | 484 | GTTGCTCTTCTAAATA | Deoxy, MOE, and cEt | 44 | 3573 | 3588 | 4003 |
| 561120 | 471 | 486 | TAGTTGCTCTTCTAAA | Deoxy, MOE, and cEt | 19 | 3575 | 3590 | 4004 |
| 561121 | 473 | 488 | GTTAGTTGCTCTTCTA | Deoxy, MOE, and cEt | 67 | 3577 | 3592 | 4005 |
| 561122 | 475 | 490 | TAGTTAGTTGCTCTTC | Deoxy, MOE, and cEt | 51 | 3579 | 3594 | 4006 |
| 561123 | 477 | 492 | GTTAGTTAGTTGCTCT | Deoxy, MOE, and cEt | 73 | 3581 | 3596 | 163 |
| 561124 | 479 | 494 | AAGTTAGTTAGTTGCT | Deoxy, MOE, and cEt | 51 | 3583 | 3598 | 4007 |

TABLE 28-continued

Inhibition of ANGPTL3 mRNA by oligonucleotides targeting SEQ ID NO: 1 and 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
| --- | --- | --- | --- | --- | --- | --- | --- | --- |
| 561125 | 481 | 496 | TTAAGTTAGTTAGTTG | Deoxy, MOE, and cEt | 33 | 3585 | 3600 | 4008 |
| 561126 | 483 | 498 | AATTAAGTTAGTTAGT | Deoxy, MOE, and cEt | 0 | 3587 | 3602 | 4009 |
| 561127 | 485 | 500 | TGAATTAAGTTAGTTA | Deoxy, MOE, and cEt | 5 | 3589 | 3604 | 4010 |
| 561128 | 487 | 502 | TTTGAATTAAGTTAGT | Deoxy, MOE, and cEt | 18 | 3591 | 3606 | 4011 |
| 561129 | 494 | 509 | GGTTGATTTTGAATTA | Deoxy, MOE, and cEt | 20 | 3598 | 3613 | 4012 |
| 561130 | 496 | 511 | CAGGTTGATTTTGAAT | Deoxy, MOE, and cEt | 27 | 3600 | 3615 | 4013 |
| 561131 | 498 | 513 | TTCAGGTTGATTTTGA | Deoxy, MOE, and cEt | 33 | 3602 | 3617 | 4014 |
| 561132 | 500 | 515 | GTTTCAGGTTGATTTT | Deoxy, MOE, and cEt | 38 | 3604 | 3619 | 4015 |
| 561133 | 502 | 517 | GAGTTTCAGGTTGATT | Deoxy, MOE, and cEt | 33 | 3606 | 3621 | 4016 |
| 561134 | 504 | 519 | TGGAGTTTCAGGTTGA | Deoxy, MOE, and cEt | 67 | 3608 | 3623 | 4017 |
| 561135 | 507 | 522 | TTCTGGAGTTTCAGGT | Deoxy, MOE, and cEt | 32 | 3611 | 3626 | 4018 |
| 561136 | 509 | 524 | TGTTCTGGAGTTTCAG | Deoxy, MOE, and cEt | 14 | 3613 | 3628 | 4019 |
| 561137 | 511 | 526 | GGTGTTCTGGAGTTTC | Deoxy, MOE, and cEt | 23 | 3615 | 3630 | 4020 |
| 561138 | 513 | 528 | TGGGTGTTCTGGAGTT | Deoxy, MOE, and cEt | 30 | 3617 | 3632 | 4021 |
| 561139 | 515 | 530 | TCTGGGTGTTCTGGAG | Deoxy, MOE, and cEt | 24 | 3619 | 3634 | 4022 |
| 561140 | 517 | 532 | CTTCTGGGTGTTCTGG | Deoxy, MOE, and cEt | 17 | 3621 | 3636 | 4023 |
| 561141 | 519 | 534 | TACTTCTGGGTGTTCT | Deoxy, MOE, and cEt | 10 | 3623 | 3638 | 4024 |
| 561142 | 521 | 536 | GTTACTTCTGGGTGTT | Deoxy, MOE, and cEt | 11 | 3625 | 3640 | 4025 |
| 561143 | 523 | 538 | AAGTTACTTCTGGGTG | Deoxy, MOE, and cEt | 15 | 3627 | 3642 | 4026 |
| 560990 | 709 | 724 | TTCTTGGTGCTCTTGG | Deoxy, MOE, and cEt | 79 | 6722 | 6737 | 111 |
| 561221 | 758 | 773 | CCATCATGTTTTACAT | Deoxy, MOE, and cEt | 17 | 6771 | 6786 | 4027 |
| 561222 | 760 | 775 | TGCCATCATGTTTTAC | Deoxy, MOE, and cEt | 22 | N/A | N/A | 4028 |
| 561223 | 763 | 778 | GAATGCCATCATGTTT | Deoxy, MOE, and cEt | 12 | N/A | N/A | 4029 |
| 561224 | 765 | 780 | AGGAATGCCATCATGT | Deoxy, MOE, and cEt | 26 | N/A | N/A | 4030 |
| 561225 | 767 | 782 | GCAGGAATGCCATCAT | Deoxy, MOE, and cEt | 32 | N/A | N/A | 4031 |
| 561226 | 769 | 784 | CAGCAGGAATGCCATC | Deoxy, MOE, and cEt | 29 | N/A | N/A | 4032 |
| 561227 | 771 | 786 | TTCAGCAGGAATGCCA | Deoxy, MOE, and cEt | 22 | N/A | N/A | 4033 |
| 561228 | 773 | 788 | CATTCAGCAGGAATGC | Deoxy, MOE, and cEt | 23 | 7358 | 7373 | 4034 |
| 561229 | 775 | 790 | TACATTCAGCAGGAAT | Deoxy, MOE, and cEt | 28 | 7360 | 7375 | 4035 |
| 561230 | 777 | 792 | GGTACATTCAGCAGGA | Deoxy, MOE, and cEt | 61 | 7362 | 7377 | 4036 |
| 561231 | 779 | 794 | GTGGTACATTCAGCAG | Deoxy, MOE, and cEt | 57 | 7364 | 7379 | 4037 |
| 561232 | 781 | 796 | TGGTGGTACATTCAGC | Deoxy, MOE, and cEt | 59 | 7366 | 7381 | 4038 |
| 561233 | 787 | 802 | TATAAATGGTGGTACA | Deoxy, MOE, and cEt | 51 | 7372 | 7387 | 4039 |
| 561234 | 789 | 804 | GTTATAAATGGTGGTA | Deoxy, MOE, and cEt | 50 | 7374 | 7389 | 4040 |
| 561235 | 791 | 806 | CTGTTATAAATGGTGG | Deoxy, MOE, and cEt | 49 | 7376 | 7391 | 4041 |
| 561236 | 793 | 808 | CTCTGTTATAAATGGT | Deoxy, MOE, and cEt | 39 | 7378 | 7393 | 4042 |

TABLE 28-continued

Inhibition of ANGPTL3 mRNA by oligonucleotides targeting SEQ ID NO: 1 and 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 561237 | 795 | 810 | ACCTCTGTTATAAATG | Deoxy, MOE, and cEt | 47 | 7380 | 7395 | 4043 |
| 561238 | 797 | 812 | TCACCTCTGTTATAAA | Deoxy, MOE, and cEt | 44 | 7382 | 7397 | 4044 |
| 561239 | 799 | 814 | GTTCACCTCTGTTATA | Deoxy, MOE, and cEt | 43 | 7384 | 7399 | 4045 |
| 561240 | 801 | 816 | ATGTTCACCTCTGTTA | Deoxy, MOE, and cEt | 59 | 7386 | 7401 | 4046 |
| 561241 | 803 | 818 | GTATGTTCACCTCTGT | Deoxy, MOE, and cEt | 69 | 7388 | 7403 | 164 |
| 337487 | 804 | 823 | CACTTGTATGTTCACCTCTG | 5-10-5 MOE | 74 | 7389 | 7408 | 28 |
| 561242 | 805 | 820 | TTGTATGTTCACCTCT | Deoxy, MOE, and cEt | 63 | 7390 | 7405 | 4047 |
| 561243 | 807 | 822 | ACTTGTATGTTCACCT | Deoxy, MOE, and cEt | 63 | 7392 | 7407 | 4048 |
| 561244 | 809 | 824 | CCACTTGTATGTTCAC | Deoxy, MOE, and cEt | 57 | 7394 | 7409 | 4049 |
| 561245 | 811 | 826 | TGCCACTTGTATGTTC | Deoxy, MOE, and cEt | 36 | 7396 | 7411 | 4050 |
| 561246 | 813 | 828 | CATGCCACTTGTATGT | Deoxy, MOE, and cEt | 33 | 7398 | 7413 | 4051 |
| 561247 | 815 | 830 | TACATGCCACTTGTAT | Deoxy, MOE, and cEt | 37 | 7400 | 7415 | 4052 |
| 561248 | 817 | 832 | CATACATGCCACTTGT | Deoxy, MOE, and cEt | 36 | 7402 | 7417 | 4053 |
| 561249 | 819 | 834 | GGCATACATGCCACTT | Deoxy, MOE, and cEt | 20 | 7404 | 7419 | 4054 |
| 561250 | 821 | 836 | ATGGCATACATGCCAC | Deoxy, MOE, and cEt | 0 | 7406 | 7421 | 4055 |
| 561251 | 823 | 838 | TGATGGCATACATGCC | Deoxy, MOE, and cEt | 22 | 7408 | 7423 | 4056 |
| 561252 | 825 | 840 | TCTGATGGCATACATG | Deoxy, MOE, and cEt | 34 | 7410 | 7425 | 4057 |
| 561253 | 827 | 842 | GGTCTGATGGCATACA | Deoxy, MOE, and cEt | 46 | 7412 | 7427 | 4058 |
| 561254 | 829 | 844 | TGGGTCTGATGGCATA | Deoxy, MOE, and cEt | 51 | 7414 | 7429 | 4059 |
| 561255 | 834 | 849 | GTTGCTGGGTCTGATG | Deoxy, MOE, and cEt | 45 | 7419 | 7434 | 4060 |
| 561256 | 836 | 851 | GAGTTGCTGGGTCTGA | Deoxy, MOE, and cEt | 70 | 7421 | 7436 | 165 |
| 561257 | 838 | 853 | GAGAGTTGCTGGGTCT | Deoxy, MOE, and cEt | 57 | 7423 | 7438 | 4061 |
| 561258 | 840 | 855 | TTGAGAGTTGCTGGGT | Deoxy, MOE, and cEt | 47 | 7425 | 7440 | 4062 |
| 561259 | 842 | 857 | ACTTGAGAGTTGCTGG | Deoxy, MOE, and cEt | 53 | 7427 | 7442 | 4063 |
| 561260 | 844 | 859 | AAACTTGAGAGTTGCT | Deoxy, MOE, and cEt | 71 | 7429 | 7444 | 166 |
| 561261 | 846 | 861 | AAAAACTTGAGAGTTG | Deoxy, MOE, and cEt | 23 | 7431 | 7446 | 4064 |
| 561262 | 848 | 863 | TGAAAACTTGAGAGT | Deoxy, MOE, and cEt | 11 | 7433 | 7448 | 4065 |
| 561263 | 850 | 865 | CATGAAAACTTGAGA | Deoxy, MOE, and cEt | 34 | 7435 | 7450 | 4066 |
| 561264 | 852 | 867 | GACATGAAAACTTGA | Deoxy, MOE, and cEt | 25 | 7437 | 7452 | 4067 |
| 561265 | 860 | 875 | TCACAGTAGACATGAA | Deoxy, MOE, and cEt | 16 | 7445 | 7460 | 4068 |
| 561266 | 862 | 877 | CATCACAGTAGACATG | Deoxy, MOE, and cEt | 37 | 7447 | 7462 | 4069 |
| 561267 | 864 | 879 | AACATCACAGTAGACA | Deoxy, MOE, and cEt | 57 | 7449 | 7464 | 4070 |
| 561268 | 866 | 881 | ATAACATCACAGTAGA | Deoxy, MOE, and cEt | 40 | 7451 | 7466 | 4071 |
| 561269 | 868 | 883 | ATATAACATCACAGTA | Deoxy, MOE, and cEt | 26 | 7453 | 7468 | 4072 |
| 561270 | 870 | 885 | TGATATAACATCACAG | Deoxy, MOE, and cEt | 35 | 7455 | 7470 | 4073 |
| 561271 | 872 | 887 | CCTGATATAACATCAC | Deoxy, MOE, and cEt | 60 | 7457 | 7472 | 4074 |

TABLE 28-continued

Inhibition of ANGPTL3 mRNA by oligonucleotides targeting SEQ ID NO: 1 and 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 561272 | 874 | 889 | TACCTGATATAACATC | Deoxy, MOE, and cEt | 37 | 7459 | 7474 | 4075 |
| 561273 | 876 | 891 | ACTACCTGATATAACA | Deoxy, MOE, and cEt | 24 | N/A | N/A | 4076 |
| 561274 | 878 | 893 | GGACTACCTGATATAA | Deoxy, MOE, and cEt | 7 | N/A | N/A | 4077 |
| 561275 | 880 | 895 | ATGGACTACCTGATAT | Deoxy, MOE, and cEt | 33 | N/A | N/A | 4078 |
| 561276 | 882 | 897 | CCATGGACTACCTGAT | Deoxy, MOE, and cEt | 52 | N/A | N/A | 4079 |
| 561277 | 884 | 899 | GTCCATGGACTACCTG | Deoxy, MOE, and cEt | 71 | 7871 | 7886 | 167 |
| 561278 | 886 | 901 | ATGTCCATGGACTACC | Deoxy, MOE, and cEt | 67 | 7873 | 7888 | 4080 |
| 561279 | 888 | 903 | TAATGTCCATGGACTA | Deoxy, MOE, and cEt | 44 | 7875 | 7890 | 4081 |
| 559390 | 890 | 905 | ATTAATGTCCATGGAC | Deoxy, MOE, and cEt | 28 | 7877 | 7892 | 4082 |
| 561280 | 892 | 907 | GAATTAATGTCCATGG | Deoxy, MOE, and cEt | 51 | 7879 | 7894 | 4083 |
| 561281 | 894 | 909 | TTGAATTAATGTCCAT | Deoxy, MOE, and cEt | 30 | 7881 | 7896 | 4084 |
| 561282 | 896 | 911 | TGTTGAATTAATGTCC | Deoxy, MOE, and cEt | 38 | 7883 | 7898 | 4085 |
| 561283 | 898 | 913 | GATGTTGAATTAATGT | Deoxy, MOE, and cEt | 11 | 7885 | 7900 | 4086 |
| 561284 | 900 | 915 | TCGATGTTGAATTAAT | Deoxy, MOE, and cEt | 20 | 7887 | 7902 | 4087 |
| 561285 | 902 | 917 | ATTCGATGTTGAATTA | Deoxy, MOE, and cEt | 12 | 7889 | 7904 | 4088 |
| 561286 | 904 | 919 | CTATTCGATGTTGAAT | Deoxy, MOE, and cEt | 17 | 7891 | 7906 | 4089 |
| 561287 | 906 | 921 | ATCTATTCGATGTTGA | Deoxy, MOE, and cEt | 32 | 7893 | 7908 | 4090 |
| 561288 | 908 | 923 | CCATCTATTCGATGTT | Deoxy, MOE, and cEt | 69 | 7895 | 7910 | 168 |
| 561289 | 910 | 925 | ATCCATCTATTCGATG | Deoxy, MOE, and cEt | 32 | 7897 | 7912 | 4091 |
| 561290 | 912 | 927 | TGATCCATCTATTCGA | Deoxy, MOE, and cEt | 41 | 7899 | 7914 | 4092 |
| 561291 | 914 | 929 | TGTGATCCATCTATTC | Deoxy, MOE, and cEt | 50 | 7901 | 7916 | 4093 |
| 561292 | 916 | 931 | TTTGTGATCCATCTAT | Deoxy, MOE, and cEt | 50 | 7903 | 7918 | 4094 |
| 561293 | 918 | 933 | GTTTTGTGATCCATCT | Deoxy, MOE, and cEt | 41 | 7905 | 7920 | 4095 |
| 561294 | 920 | 935 | AAGTTTTGTGATCCAT | Deoxy, MOE, and cEt | 56 | 7907 | 7922 | 4096 |
| 561295 | 922 | 937 | TGAAGTTTTGTGATCC | Deoxy, MOE, and cEt | 57 | 7909 | 7924 | 4097 |
| 561296 | 924 | 939 | ATTGAAGTTTTGTGAT | Deoxy, MOE, and cEt | 0 | 7911 | 7926 | 4098 |
| 561450 | 1386 | 1401 | CAACATTTTGGTTGAT | Deoxy, MOE, and cEt | 45 | 10358 | 10373 | 4099 |
| 561451 | 1389 | 1404 | GATCAACATTTTGGTT | Deoxy, MOE, and cEt | 33 | 10361 | 10376 | 4100 |
| 561452 | 1391 | 1406 | TGGATCAACATTTTGG | Deoxy, MOE, and cEt | 81 | 10363 | 10378 | 123 |
| 561453 | 1393 | 1408 | GATGGATCAACATTTT | Deoxy, MOE, and cEt | 59 | 10365 | 10380 | 4101 |
| 561455 | 1397 | 1412 | GTTGGATGGATCAACA | Deoxy, MOE, and cEt | 53 | 10369 | 10384 | 4102 |
| 561456 | 1399 | 1414 | CTGTTGGATGGATCAA | Deoxy, MOE, and cEt | 71 | 10371 | 10386 | 4103 |
| 561457 | 1401 | 1416 | ATCTGTTGGATGGATC | Deoxy, MOE, and cEt | 71 | 10373 | 10388 | 4104 |
| 561458 | 1403 | 1418 | GAATCTGTTGGATGGA | Deoxy, MOE, and cEt | 84 | 10375 | 10390 | 124 |
| 561459 | 1405 | 1420 | CTGAATCTGTTGGATG | Deoxy, MOE, and cEt | 72 | 10377 | 10392 | 4105 |
| 561460 | 1407 | 1422 | TTCTGAATCTGTTGGA | Deoxy, MOE, and cEt | 78 | 10379 | 10394 | 125 |

TABLE 28-continued

Inhibition of ANGPTL3 mRNA by oligonucleotides targeting SEQ ID NO: 1 and 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 561461 | 1414 | 1429 | CAAAGCTTTCTGAATC | Deoxy, MOE, and cEt | 45 | 10386 | 10401 | 4106 |
| 561462 | 1421 | 1436 | GTTCATTCAAAGCTTT | Deoxy, MOE, and cEt | 87 | 10393 | 10408 | 126 |
| 561463 | 1423 | 1438 | CAGTTCATTCAAAGCT | Deoxy, MOE, and cEt | 85 | 10395 | 10410 | 127 |
| 561464 | 1425 | 1440 | CTCAGTTCATTCAAAG | Deoxy, MOE, and cEt | 47 | 10397 | 10412 | 4107 |
| 561465 | 1427 | 1442 | GCCTCAGTTCATTCAA | Deoxy, MOE, and cEt | 60 | 10399 | 10414 | 4108 |
| 561466 | 1429 | 1444 | TTGCCTCAGTTCATTC | Deoxy, MOE, and cEt | 68 | 10401 | 10416 | 4109 |
| 561467 | 1431 | 1446 | ATTTGCCTCAGTTCAT | Deoxy, MOE, and cEt | 61 | 10403 | 10418 | 4110 |
| 561468 | 1433 | 1448 | AAATTTGCCTCAGTTC | Deoxy, MOE, and cEt | 48 | 10405 | 10420 | 4111 |
| 561469 | 1436 | 1451 | TTTAAATTTGCCTCAG | Deoxy, MOE, and cEt | 59 | 10408 | 10423 | 4112 |
| 561470 | 1438 | 1453 | CTTTTAAATTTGCCTC | Deoxy, MOE, and cEt | 50 | 10410 | 10425 | 4113 |
| 561471 | 1440 | 1455 | GCCTTTTAAATTTGCC | Deoxy, MOE, and cEt | 73 | 10412 | 10427 | 4114 |
| 561472 | 1452 | 1467 | GTTTAAATTATTGCCT | Deoxy, MOE, and cEt | 48 | 10424 | 10439 | 4115 |
| 561473 | 1463 | 1478 | ATGAGGTTAATGTTTA | Deoxy, MOE, and cEt | 33 | 10435 | 10450 | 4116 |
| 561474 | 1465 | 1480 | GAATGAGGTTAATGTT | Deoxy, MOE, and cEt | 29 | 10437 | 10452 | 4117 |
| 561475 | 1467 | 1482 | TGGAATGAGGTTAATG | Deoxy, MOE, and cEt | 66 | 10439 | 10454 | 4118 |
| 561476 | 1469 | 1484 | CTTGGAATGAGGTTAA | Deoxy, MOE, and cEt | 72 | 10441 | 10456 | 4119 |
| 561477 | 1471 | 1486 | AACTTGGAATGAGGTT | Deoxy, MOE, and cEt | 69 | 10443 | 10458 | 4120 |
| 561478 | 1473 | 1488 | TTAACTTGGAATGAGG | Deoxy, MOE, and cEt | 74 | 10445 | 10460 | 128 |
| 561479 | 1475 | 1490 | CATTAACTTGGAATGA | Deoxy, MOE, and cEt | 5 | 10447 | 10462 | 4121 |
| 561480 | 1477 | 1492 | CACATTAACTTGGAAT | Deoxy, MOE, and cEt | 26 | 10449 | 10464 | 4122 |
| 561481 | 1479 | 1494 | ACCACATTAACTTGGA | Deoxy, MOE, and cEt | 59 | 10451 | 10466 | 4123 |
| 561482 | 1481 | 1496 | AGACCACATTAACTTG | Deoxy, MOE, and cEt | 76 | 10453 | 10468 | 129 |
| 561483 | 1483 | 1498 | TTAGACCACATTAACT | Deoxy, MOE, and cEt | 47 | 10455 | 10470 | 4124 |
| 561484 | 1485 | 1500 | TATTAGACCACATTAA | Deoxy, MOE, and cEt | 38 | 10457 | 10472 | 4125 |
| 561485 | 1487 | 1502 | ATTATTAGACCACATT | Deoxy, MOE, and cEt | 59 | 10459 | 10474 | 4126 |
| 561486 | 1489 | 1504 | AGATTATTAGACCACA | Deoxy, MOE, and cEt | 84 | 10461 | 10476 | 130 |
| 561487 | 1491 | 1506 | CCAGATTATTAGACCA | Deoxy, MOE, and cEt | 93 | 10463 | 10478 | 131 |
| 561488 | 1493 | 1508 | TACCAGATTATTAGAC | Deoxy, MOE, and cEt | 22 | 10465 | 10480 | 4127 |
| 561489 | 1495 | 1510 | AATACCAGATTATTAG | Deoxy, MOE, and cEt | 48 | 10467 | 10482 | 4128 |
| 561490 | 1497 | 1512 | TTAATACCAGATTATT | Deoxy, MOE, and cEt | 22 | 10469 | 10484 | 4129 |
| 561491 | 1499 | 1514 | ATTTAATACCAGATTA | Deoxy, MOE, and cEt | 14 | 10471 | 10486 | 4130 |
| 561492 | 1501 | 1516 | GGATTTAATACCAGAT | Deoxy, MOE, and cEt | 74 | 10473 | 10488 | 4131 |
| 561493 | 1503 | 1518 | AAGGATTTAATACCAG | Deoxy, MOE, and cEt | 70 | 10475 | 10490 | 4132 |
| 561494 | 1505 | 1520 | TTAAGGATTTAATACC | Deoxy, MOE, and cEt | 14 | 10477 | 10492 | 4133 |
| 561495 | 1508 | 1523 | CTCTTAAGGATTTAAT | Deoxy, MOE, and cEt | 12 | 10480 | 10495 | 4134 |
| 561496 | 1510 | 1525 | TTCTCTTAAGGATTTA | Deoxy, MOE, and cEt | 47 | 10482 | 10497 | 4135 |

TABLE 28-continued

Inhibition of ANGPTL3 mRNA by oligonucleotides targeting SEQ ID NO: 1 and 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 561497 | 1513 | 1528 | GCTTTCTCTTAAGGAT | Deoxy, MOE, and cEt | 73 | 10485 | 10500 | 4136 |
| 561498 | 1515 | 1530 | AAGCTTTCTCTTAAGG | Deoxy, MOE, and cEt | 59 | 10487 | 10502 | 4137 |
| 561499 | 1517 | 1532 | TCAAGCTTTCTCTTAA | Deoxy, MOE, and cEt | 62 | 10489 | 10504 | 4138 |
| 561500 | 1526 | 1541 | ATCTATTTCTCAAGCT | Deoxy, MOE, and cEt | 76 | 10498 | 10513 | 132 |
| 561501 | 1547 | 1562 | AGTGACTTTAAGATAA | Deoxy, MOE, and cEt | 23 | 10519 | 10534 | 4139 |
| 561502 | 1549 | 1564 | ACAGTGACTTTAAGAT | Deoxy, MOE, and cEt | 62 | 10521 | 10536 | 4140 |
| 561503 | 1551 | 1566 | AGACAGTGACTTTAAG | Deoxy, MOE, and cEt | 55 | 10523 | 10538 | 4141 |
| 561504 | 1553 | 1568 | ATAGACAGTGACTTTA | Deoxy, MOE, and cEt | 74 | 10525 | 10540 | 133 |
| 561505 | 1555 | 1570 | AAATAGACAGTGACTT | Deoxy, MOE, and cEt | 59 | 10527 | 10542 | 4142 |
| 561506 | 1557 | 1572 | TTAAATAGACAGTGAC | Deoxy, MOE, and cEt | 38 | 10529 | 10544 | 4143 |
| 561507 | 1559 | 1574 | TCTTAAATAGACAGTG | Deoxy, MOE, and cEt | 54 | 10531 | 10546 | 4144 |
| 561508 | 1561 | 1576 | AATCTTAAATAGACAG | Deoxy, MOE, and cEt | 22 | 10533 | 10548 | 4145 |
| 561509 | 1563 | 1578 | TTAATCTTAAATAGAC | Deoxy, MOE, and cEt | 0 | 10535 | 10550 | 4146 |
| 561510 | 1565 | 1580 | GTTTAATCTTAAATAG | Deoxy, MOE, and cEt | 0 | 10537 | 10552 | 4147 |
| 561511 | 1569 | 1584 | GTATGTTTAATCTTAA | Deoxy, MOE, and cEt | 13 | 10541 | 10556 | 4148 |
| 561512 | 1572 | 1587 | ATTGTATGTTTAATCT | Deoxy, MOE, and cEt | 40 | 10544 | 10559 | 4149 |
| 561513 | 1575 | 1590 | GTGATTGTATGTTTAA | Deoxy, MOE, and cEt | 71 | 10547 | 10562 | 4150 |
| 561514 | 1578 | 1593 | TATGTGATTGTATGTT | Deoxy, MOE, and cEt | 58 | 10550 | 10565 | 4151 |
| 561515 | 1580 | 1595 | GTTATGTGATTGTATG | Deoxy, MOE, and cEt | 68 | 10552 | 10567 | 4152 |
| 561516 | 1582 | 1597 | AGGTTATGTGATTGTA | Deoxy, MOE, and cEt | 73 | 10554 | 10569 | 4153 |
| 561517 | 1584 | 1599 | TAAGGTTATGTGATTG | Deoxy, MOE, and cEt | 64 | 10556 | 10571 | 4154 |
| 561518 | 1586 | 1601 | TTTAAGGTTATGTGAT | Deoxy, MOE, and cEt | 0 | 10558 | 10573 | 4155 |
| 561519 | 1588 | 1603 | TCTTTAAGGTTATGTG | Deoxy, MOE, and cEt | 53 | 10560 | 10575 | 4156 |
| 561520 | 1590 | 1605 | ATTCTTTAAGGTTATG | Deoxy, MOE, and cEt | 29 | 10562 | 10577 | 4157 |
| 561521 | 1592 | 1607 | GTATTCTTTAAGGTTA | Deoxy, MOE, and cEt | 24 | 10564 | 10579 | 4158 |
| 561522 | 1594 | 1609 | CGGTATTCTTTAAGGT | Deoxy, MOE, and cEt | 70 | 10566 | 10581 | 4159 |
| 561523 | 1596 | 1611 | AACGGTATTCTTTAAG | Deoxy, MOE, and cEt | 42 | 10568 | 10583 | 4160 |
| 561524 | 1598 | 1613 | TAAACGGTATTCTTTA | Deoxy, MOE, and cEt | 26 | 10570 | 10585 | 4161 |
| 561525 | 1600 | 1615 | TGTAAACGGTATTCTT | Deoxy, MOE, and cEt | 59 | 10572 | 10587 | 4162 |
| 561526 | 1602 | 1617 | AATGTAAACGGTATTC | Deoxy, MOE, and cEt | 57 | 10574 | 10589 | 4142 |

TABLE 29

Inhibition of ANGPTL3 mRNA by oligonucleotides targeting SEQ ID NO: 1 and 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 561681 | N/A | N/A | TCTGGAAGCAGACCTA | Deoxy, MOE, and cEt | 37 | 3096 | 3111 | 4164 |
| 561682 | N/A | N/A | CTTCTGGAAGCAGACC | Deoxy, MOE, and cEt | 27 | 3098 | 3113 | 4165 |
| 561683 | N/A | N/A | AAATAAGGTATAGTGA | Deoxy, MOE, and cEt | 2 | 11084 | 11099 | 4166 |
| 561684 | N/A | N/A | TAGTATTAAGTGTTAA | Deoxy, MOE, and cEt | 14 | 11133 | 11148 | 4167 |
| 561685 | N/A | N/A | TCATAGTATTAAGTGT | Deoxy, MOE, and cEt | 0 | 11136 | 11151 | 4168 |
| 561686 | N/A | N/A | AGATTCCTTTACAATT | Deoxy, MOE, and cEt | 21 | 11160 | 11175 | 4169 |
| 561687 | N/A | N/A | ACAAGATTCCTTTACA | Deoxy, MOE, and cEt | 21 | 11163 | 11178 | 4170 |
| 561688 | N/A | N/A | CTGACAAGATTCCTTT | Deoxy, MOE, and cEt | 70 | 11166 | 11181 | 4171 |
| 561689 | N/A | N/A | AATCTGACAAGATTCC | Deoxy, MOE, and cEt | 83 | 11169 | 11184 | 180 |
| 561690 | N/A | N/A | TGTAATCTGACAAGAT | Deoxy, MOE, and cEt | 46 | 11172 | 11187 | 4172 |
| 561691 | N/A | N/A | TACTGTAATCTGACAA | Deoxy, MOE, and cEt | 47 | 11175 | 11190 | 4173 |
| 561692 | N/A | N/A | TCTTACTGTAATCTGA | Deoxy, MOE, and cEt | 50 | 11178 | 11193 | 4174 |
| 561693 | N/A | N/A | CATTCTTACTGTAATC | Deoxy, MOE, and cEt | 40 | 11181 | 11196 | 4175 |
| 561694 | N/A | N/A | GTTCATTCTTACTGTA | Deoxy, MOE, and cEt | 71 | 11184 | 11199 | 4176 |
| 561695 | N/A | N/A | ATATGTTCATTCTTAC | Deoxy, MOE, and cEt | 2 | 11188 | 11203 | 4177 |
| 561696 | N/A | N/A | GCCACAAATATGTTCA | Deoxy, MOE, and cEt | 80 | 11195 | 11210 | 4178 |
| 561697 | N/A | N/A | GATGCCACAAATATGT | Deoxy, MOE, and cEt | 70 | 11198 | 11213 | 4179 |
| 561698 | N/A | N/A | CTCGATGCCACAAATA | Deoxy, MOE, and cEt | 80 | 11201 | 11216 | 181 |
| 561699 | N/A | N/A | TAACTCGATGCCACAA | Deoxy, MOE, and cEt | 86 | 11204 | 11219 | 182 |
| 561700 | N/A | N/A | CTTTAACTCGATGCCA | Deoxy, MOE, and cEt | 77 | 11207 | 11222 | 4180 |
| 561701 | N/A | N/A | AAACTTTAACTCGATG | Deoxy, MOE, and cEt | 39 | 11210 | 11225 | 4181 |
| 561702 | N/A | N/A | TATAAACTTTAACTCG | Deoxy, MOE, and cEt | 13 | 11213 | 11228 | 4182 |
| 561703 | N/A | N/A | CACAGCATATTTAGGG | Deoxy, MOE, and cEt | 71 | 11233 | 11248 | 4183 |
| 561704 | N/A | N/A | TAGAATCACAGCATAT | Deoxy, MOE, and cEt | 68 | 11239 | 11254 | 4184 |
| 561705 | N/A | N/A | TATTAGAATCACAGCA | Deoxy, MOE, and cEt | 73 | 11242 | 11257 | 4185 |
| 561706 | N/A | N/A | AATGTATTAGAATCAC | Deoxy, MOE, and cEt | 40 | 11246 | 11261 | 4186 |
| 561707 | N/A | N/A | ACGAATGTATTAGAAT | Deoxy, MOE, and cEt | 22 | 11249 | 11264 | 4187 |
| 561708 | N/A | N/A | TACACGAATGTATTAG | Deoxy, MOE, and cEt | 33 | 11252 | 11267 | 4188 |
| 561709 | N/A | N/A | ACCTACACGAATGTAT | Deoxy, MOE, and cEt | 42 | 11255 | 11270 | 4189 |
| 561710 | N/A | N/A | AAACCTACACGAATG | Deoxy, MOE, and cEt | 24 | 11258 | 11273 | 4190 |
| 561711 | N/A | N/A | TTGAAAACCTACACGA | Deoxy, MOE, and cEt | 34 | 11261 | 11276 | 4191 |
| 561712 | N/A | N/A | TACTTGAAAACCTACA | Deoxy, MOE, and cEt | 33 | 11264 | 11279 | 4192 |
| 561713 | N/A | N/A | GTTTATTTCTACTTGA | Deoxy, MOE, and cEt | 53 | 11273 | 11288 | 4193 |
| 561714 | N/A | N/A | GAGGTTTATTTCTACT | Deoxy, MOE, and cEt | 69 | 11276 | 11291 | 4194 |
| 561715 | N/A | N/A | TACGAGGTTTATTTCT | Deoxy, MOE, and cEt | 21 | 11279 | 11294 | 4195 |
| 561716 | N/A | N/A | TGTTACGAGGTTTATT | Deoxy, MOE, and cEt | 47 | 11282 | 11297 | 4196 |

TABLE 29-continued

Inhibition of ANGPTL3 mRNA by oligonucleotides targeting SEQ ID NO: 1 and 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 561717 | N/A | N/A | ACTTGTTACGAGGTTT | Deoxy, MOE, and cEt | 70 | 11285 | 11300 | 4197 |
| 561718 | N/A | N/A | CAGTAACTTGTTACGA | Deoxy, MOE, and cEt | 60 | 11290 | 11305 | 4198 |
| 561719 | N/A | N/A | GTTCAGTAACTTGTTA | Deoxy, MOE, and cEt | 40 | 11293 | 11308 | 4199 |
| 561720 | N/A | N/A | TCAGGCTGTTTAAACG | Deoxy, MOE, and cEt | 59 | 11308 | 11323 | 4200 |
| 561721 | N/A | N/A | TTGTCAGGCTGTTTAA | Deoxy, MOE, and cEt | 74 | 11311 | 11326 | 4201 |
| 561722 | N/A | N/A | TGCTTGTCAGGCTGTT | Deoxy, MOE, and cEt | 82 | 11314 | 11329 | 183 |
| 561723 | N/A | N/A | ACATGCTTGTCAGGCT | Deoxy, MOE, and cEt | 84 | 11317 | 11332 | 184 |
| 561724 | N/A | N/A | TATACATGCTTGTCAG | Deoxy, MOE, and cEt | 75 | 11320 | 11335 | 4202 |
| 561725 | N/A | N/A | GTCTTTGTTTATTGAA | Deoxy, MOE, and cEt | 49 | 11347 | 11362 | 4203 |
| 561726 | N/A | N/A | TGGGTCTTTGTTTATT | Deoxy, MOE, and cEt | 27 | 11350 | 11365 | 4204 |
| 561727 | N/A | N/A | GACTGGGTCTTTGTTT | Deoxy, MOE, and cEt | 20 | 11353 | 11368 | 4205 |
| 561728 | N/A | N/A | ATAATTTAGGGACTGG | Deoxy, MOE, and cEt | 20 | 11363 | 11378 | 4206 |
| 561729 | N/A | N/A | TCTATAATTTAGGGAC | Deoxy, MOE, and cEt | 39 | 11366 | 11381 | 4207 |
| 561730 | N/A | N/A | CGATAAACATGCAAGA | Deoxy, MOE, and cEt | 68 | 11394 | 11409 | 4208 |
| 561731 | N/A | N/A | TGTCGATAAACATGCA | Deoxy, MOE, and cEt | 80 | 11397 | 11412 | 4209 |
| 561732 | N/A | N/A | TGATGTCGATAAACAT | Deoxy, MOE, and cEt | 68 | 11400 | 11415 | 4210 |
| 561733 | N/A | N/A | TTGTGATGTCGATAAA | Deoxy, MOE, and cEt | 28 | 11403 | 11418 | 4211 |
| 561734 | N/A | N/A | CTGTTGTGATGTCGAT | Deoxy, MOE, and cEt | 74 | 11406 | 11421 | 4212 |
| 561735 | N/A | N/A | GATCTGTTGTGATGTC | Deoxy, MOE, and cEt | 59 | 11409 | 11424 | 4213 |
| 561736 | N/A | N/A | AGGGATCTGTTGTGAT | Deoxy, MOE, and cEt | 24 | 11412 | 11427 | 4214 |
| 561737 | N/A | N/A | TTTAGGGATCTGTTGT | Deoxy, MOE, and cEt | 19 | 11415 | 11430 | 4215 |
| 561738 | N/A | N/A | GGATTTAGGGATCTGT | Deoxy, MOE, and cEt | 27 | 11418 | 11433 | 4216 |
| 561739 | N/A | N/A | GATTTAGGGATTTAGG | Deoxy, MOE, and cEt | 44 | 11425 | 11440 | 4217 |
| 561740 | N/A | N/A | TCTTTAGGGATTTAGG | Deoxy, MOE, and cEt | 38 | 11433 | 11448 | 4218 |
| 561741 | N/A | N/A | TAATCTTTAGGGATTT | Deoxy, MOE, and cEt | 0 | 11436 | 11451 | 4219 |
| 561742 | N/A | N/A | ATCTAATCTTTAGGGA | Deoxy, MOE, and cEt | 0 | 11439 | 11454 | 4220 |
| 561743 | N/A | N/A | TGTATCTAATCTTTAG | Deoxy, MOE, and cEt | 15 | 11442 | 11457 | 4221 |
| 561744 | N/A | N/A | AAATTTGTATCTAATC | Deoxy, MOE, and cEt | 21 | 11447 | 11462 | 4222 |
| 561745 | N/A | N/A | GTAAAAATTTGTATC | Deoxy, MOE, and cEt | 23 | 11452 | 11467 | 4223 |
| 561746 | N/A | N/A | GTGGTAAAAATTTGT | Deoxy, MOE, and cEt | 32 | 11455 | 11470 | 4224 |
| 561747 | N/A | N/A | GATACTGTGGTAAAAA | Deoxy, MOE, and cEt | 45 | 11461 | 11476 | 4225 |
| 561748 | N/A | N/A | AGTGATACTGTGGTAA | Deoxy, MOE, and cEt | 60 | 11464 | 11479 | 4226 |
| 561749 | N/A | N/A | ACAAGTGATACTGTGG | Deoxy, MOE, and cEt | 75 | 11467 | 11482 | 4227 |
| 561750 | N/A | N/A | CTGACAAGTGATACTG | Deoxy, MOE, and cEt | 59 | 11470 | 11485 | 4228 |
| 561751 | N/A | N/A | ATTCTGACAAGTGATA | Deoxy, MOE, and cEt | 48 | 11473 | 11488 | 4229 |
| 561752 | N/A | N/A | TAAATTCTGACAAGTG | Deoxy, MOE, and cEt | 59 | 11476 | 11491 | 4230 |

TABLE 29-continued

Inhibition of ANGPTL3 mRNA by oligonucleotides targeting SEQ ID NO: 1 and 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
| --- | --- | --- | --- | --- | --- | --- | --- | --- |
| 561753 | N/A | N/A | TACTGGCAGTTTTAAA | Deoxy, MOE, and cEt | 42 | 11508 | 11523 | 4231 |
| 561754 | N/A | N/A | TCTTACTGGCAGTTTT | Deoxy, MOE, and cEt | 51 | 11511 | 11526 | 4232 |
| 561755 | N/A | N/A | ATTTCTTACTGGCAGT | Deoxy, MOE, and cEt | 69 | 11514 | 11529 | 4233 |
| 561756 | N/A | N/A | AAAATTTCTTACTGGC | Deoxy, MOE, and cEt | 57 | 11517 | 11532 | 4234 |
| 561757 | N/A | N/A | AACAAATGGGTTTAAT | Deoxy, MOE, and cEt | 0 | 11535 | 11550 | 4235 |
| 562374 | N/A | N/A | GAATATTTGCAAGTCT | Deoxy, MOE, and cEt | 68 | 9230 | 9245 | 4236 |
| 562375 | N/A | N/A | GTAGAGGAATATTTGC | Deoxy, MOE, and cEt | 83 | 9236 | 9251 | 151 |
| 562376 | N/A | N/A | TCATTGGTAGAGGAAT | Deoxy, MOE, and cEt | 23 | 9242 | 9257 | 4237 |
| 562377 | N/A | N/A | ATATTTTAAAGTCTCG | Deoxy, MOE, and cEt | 17 | 9258 | 9273 | 4238 |
| 562378 | N/A | N/A | GTTACATTATTATAGA | Deoxy, MOE, and cEt | 29 | 9273 | 9288 | 4239 |
| 562379 | N/A | N/A | GTGAAATGTGTTACAT | Deoxy, MOE, and cEt | 54 | 9282 | 9297 | 4240 |
| 562380 | N/A | N/A | TCACCAGTGAAATGTG | Deoxy, MOE, and cEt | 64 | 9288 | 9303 | 4241 |
| 562381 | N/A | N/A | CATGTTTCACCAGTGA | Deoxy, MOE, and cEt | 78 | 9294 | 9309 | 4242 |
| 562382 | N/A | N/A | ACAAGACATGTTTCAC | Deoxy, MOE, and cEt | 36 | 9300 | 9315 | 4243 |
| 562383 | N/A | N/A | CATATGACAAGACATG | Deoxy, MOE, and cEt | 42 | 9306 | 9321 | 4244 |
| 562384 | N/A | N/A | CTATAATGCATATGAC | Deoxy, MOE, and cEt | 5 | 9314 | 9329 | 4245 |
| 562385 | N/A | N/A | TCCTTTCTATAATGCA | Deoxy, MOE, and cEt | 65 | 9320 | 9335 | 4246 |
| 562386 | N/A | N/A | TGATTATCCTTTCTAT | Deoxy, MOE, and cEt | 27 | 9326 | 9341 | 4247 |
| 562387 | N/A | N/A | AAAGTCTGATTATCCT | Deoxy, MOE, and cEt | 90 | 9332 | 9347 | 152 |
| 562388 | N/A | N/A | TAACTGAAAGTCTGAT | Deoxy, MOE, and cEt | 59 | 9338 | 9353 | 4248 |
| 562389 | N/A | N/A | GTGCACAAAAATGTTA | Deoxy, MOE, and cEt | 42 | 9366 | 9381 | 4249 |
| 562390 | N/A | N/A | AGCTATGTGCACAAAA | Deoxy, MOE, and cEt | 77 | 9372 | 9387 | 4250 |
| 562391 | N/A | N/A | GAAGATAGCTATGTGC | Deoxy, MOE, and cEt | 64 | 9378 | 9393 | 4251 |
| 562392 | N/A | N/A | TTTATTGAAGATAGCT | Deoxy, MOE, and cEt | 33 | 9384 | 9399 | 4252 |
| 562393 | N/A | N/A | TCATTTAGTGTATCT | Deoxy, MOE, and cEt | 40 | 9424 | 9439 | 4253 |
| 562394 | N/A | N/A | CCTTGATCATTTTAGT | Deoxy, MOE, and cEt | 15 | 9430 | 9445 | 4254 |
| 562395 | N/A | N/A | TGAATCCCTTGATCAT | Deoxy, MOE, and cEt | 59 | 9436 | 9451 | 4255 |
| 562396 | N/A | N/A | TAGTCTTGAATCCCTT | Deoxy, MOE, and cEt | 83 | 9442 | 9457 | 153 |
| 562397 | N/A | N/A | GTTGTTAGTCTTGAA | Deoxy, MOE, and cEt | 65 | 9448 | 9463 | 4256 |
| 562398 | N/A | N/A | AATTGAGTTGTTTAGT | Deoxy, MOE, and cEt | 21 | 9454 | 9469 | 4257 |
| 562399 | N/A | N/A | GCAACTAATTGAGTTG | Deoxy, MOE, and cEt | 15 | 9460 | 9475 | 4258 |
| 562400 | N/A | N/A | ATTGGTGCAACTAATT | Deoxy, MOE, and cEt | 25 | 9466 | 9481 | 4259 |
| 562401 | N/A | N/A | GTTTTTTATTGGTGCA | Deoxy, MOE, and cEt | 53 | 9473 | 9488 | 4260 |
| 562402 | N/A | N/A | GGACACTGACAGTTTT | Deoxy, MOE, and cEt | 43 | 9496 | 9511 | 4261 |
| 562403 | N/A | N/A | CAGGTTGGACACTGAC | Deoxy, MOE, and cEt | 23 | 9502 | 9517 | 4262 |
| 562404 | N/A | N/A | TAAGTACAGGTTGGAC | Deoxy, MOE, and cEt | 33 | 9508 | 9523 | 4263 |

TABLE 29-continued

Inhibition of ANGPTL3 mRNA by oligonucleotides targeting SEQ ID NO: 1 and 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 562405 | N/A | N/A | AGTTATTAAGTACAGG | Deoxy, MOE, and cEt | 34 | 9514 | 9529 | 4264 |
| 562406 | N/A | N/A | TCTGTGAGTTATTAAG | Deoxy, MOE, and cEt | 10 | 9520 | 9535 | 4265 |
| 562407 | N/A | N/A | ACCAAAATTCTCCTGA | Deoxy, MOE, and cEt | 1 | 9554 | 9569 | 4266 |
| 562408 | N/A | N/A | ACCTGAATAACCCTCT | Deoxy, MOE, and cEt | 73 | 9811 | 9826 | 4267 |
| 562409 | N/A | N/A | GGTATCAGAAAAAGAT | Deoxy, MOE, and cEt | 14 | 9827 | 9842 | 4268 |
| 562410 | N/A | N/A | AGTATTGGTATCAGAA | Deoxy, MOE, and cEt | 13 | 9833 | 9848 | 4269 |
| 562411 | N/A | N/A | GGAAGATACTTTGAAG | Deoxy, MOE, and cEt | 25 | 9861 | 9876 | 4270 |
| 562412 | N/A | N/A | AATGTGGGAAGATACT | Deoxy, MOE, and cEt | 23 | 9867 | 9882 | 4271 |
| 562413 | N/A | N/A | CAGATAATAGCTAATA | Deoxy, MOE, and cEt | 29 | 9882 | 9897 | 4272 |
| 562414 | N/A | N/A | TCATTGCAGATAATAG | Deoxy, MOE, and cEt | 45 | 9888 | 9903 | 4273 |
| 562415 | N/A | N/A | AAGTTGTCATTGCAGA | Deoxy, MOE, and cEt | 86 | 9894 | 9909 | 154 |
| 562416 | N/A | N/A | GATTCGGATTTTTAAA | Deoxy, MOE, and cEt | 19 | 9909 | 9924 | 4274 |
| 562417 | N/A | N/A | ATTTGGGATTCGGATT | Deoxy, MOE, and cEt | 34 | 9915 | 9930 | 4275 |
| 562418 | N/A | N/A | ACGCTTATTTGGGATT | Deoxy, MOE, and cEt | 64 | 9921 | 9936 | 4276 |
| 562419 | N/A | N/A | TCTAGAGAGAAAACGC | Deoxy, MOE, and cEt | 64 | 9933 | 9948 | 4277 |
| 562420 | N/A | N/A | AGTTAAGAGGTTTTCG | Deoxy, MOE, and cEt | 34 | 9949 | 9964 | 4278 |
| 562421 | N/A | N/A | CATTATAGTTAAGAGG | Deoxy, MOE, and cEt | 24 | 9955 | 9970 | 4279 |
| 562422 | N/A | N/A | CACTTTCATTATAGTT | Deoxy, MOE, and cEt | 13 | 9961 | 9976 | 4280 |
| 562423 | N/A | N/A | TAGAATGAACACTTTC | Deoxy, MOE, and cEt | 63 | 9970 | 9985 | 4281 |
| 562424 | N/A | N/A | TTGAACTAGAATGAAC | Deoxy, MOE, and cEt | 16 | 9976 | 9991 | 4282 |
| 562425 | N/A | N/A | ACCTGATTGAACTAGA | Deoxy, MOE, and cEt | 51 | 9982 | 9997 | 4283 |
| 562426 | N/A | N/A | TAAAATACCTGATTGA | Deoxy, MOE, and cEt | 19 | 9988 | 10003 | 4284 |
| 562427 | N/A | N/A | TAGAGGTAAAATACCT | Deoxy, MOE, and cEt | 12 | 9994 | 10009 | 4285 |
| 562428 | N/A | N/A | GAAGATTAGAGGTAAA | Deoxy, MOE, and cEt | 1 | 10000 | 10015 | 4286 |
| 562429 | N/A | N/A | TCTGAGGAAGATTAGA | Deoxy, MOE, and cEt | 31 | 10006 | 10021 | 4287 |
| 562430 | N/A | N/A | TATACACTACCAAAAA | Deoxy, MOE, and cEt | 0 | 10030 | 10045 | 4288 |
| 562431 | N/A | N/A | ATAATCTATACACTAC | Deoxy, MOE, and cEt | 0 | 10036 | 10051 | 4289 |
| 562432 | N/A | N/A | TAAGTCCCAATTTTAA | Deoxy, MOE, and cEt | 33 | 10065 | 10080 | 4290 |
| 562433 | N/A | N/A | TCTGTATAAGTCCCAA | Deoxy, MOE, and cEt | 89 | 10071 | 10086 | 155 |
| 562434 | N/A | N/A | CCAGTTTTAAATAATC | Deoxy, MOE, and cEt | 20 | 10085 | 10100 | 4291 |
| 562435 | N/A | N/A | TGTATCCCAGTTTTAA | Deoxy, MOE, and cEt | 44 | 10091 | 10106 | 4292 |
| 562436 | N/A | N/A | GATGCATGTATCCCAG | Deoxy, MOE, and cEt | 91 | 10097 | 10112 | 156 |
| 562437 | N/A | N/A | GTTTTAGATGCATGTA | Deoxy, MOE, and cEt | 69 | 10103 | 10118 | 4293 |
| 562438 | N/A | N/A | TACAGTGTTTTAGATG | Deoxy, MOE, and cEt | 28 | 10109 | 10124 | 4294 |
| 562439 | N/A | N/A | GTAAGTTATCTTCCT | Deoxy, MOE, and cEt | 78 | 10138 | 10153 | 157 |
| 562440 | N/A | N/A | TTCCCCGTAAGTTTAT | Deoxy, MOE, and cEt | 33 | 10144 | 10159 | 4295 |

TABLE 29-continued

Inhibition of ANGPTL3 mRNA by oligonucleotides targeting SEQ ID NO: 1 and 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 562441 | N/A | N/A | CTGTATTTCCCCGTAA | Deoxy, MOE, and cEt | 55 | 10150 | 10165 | 4296 |
| 562442 | N/A | N/A | CTGTTACTGTATTTCC | Deoxy, MOE, and cEt | 79 | 10156 | 10171 | 158 |
| 562443 | N/A | N/A | TAGTTACTGTTACTGT | Deoxy, MOE, and cEt | 70 | 10162 | 10177 | 4297 |
| 562444 | N/A | N/A | CGTATGTAGTTACTGT | Deoxy, MOE, and cEt | 66 | 10168 | 10183 | 4298 |
| 562445 | N/A | N/A | AATGGGTACAGACTCG | Deoxy, MOE, and cEt | 72 | 10182 | 10197 | 4299 |
| 562446 | N/A | N/A | GCAATTTAATGGGTAC | Deoxy, MOE, and cEt | 59 | 10189 | 10204 | 4300 |
| 562447 | N/A | N/A | GATAGATATGCAATTT | Deoxy, MOE, and cEt | 20 | 10198 | 10213 | 4301 |
| 562448 | N/A | N/A | AAAGGAGATAGATATG | Deoxy, MOE, and cEt | 22 | 10204 | 10219 | 4302 |
| 562449 | N/A | N/A | CCTCCTAAAGGAGATA | Deoxy, MOE, and cEt | 42 | 10210 | 10225 | 4303 |
| 562450 | N/A | N/A | CACCAGCCTCCTAAAG | Deoxy, MOE, and cEt | 37 | 10216 | 10231 | 4304 |
| 544120 | 707 | 726 | AGTTCTTGGTGCTCTTGGCT | 5-10-5 MOE | 83 | 6720 | 6739 | 15 |
| 560990 | 709 | 724 | TTCTTGGTGCTCTTGG | Deoxy, MOE, and cEt | 89 | 6722 | 6737 | 111 |
| 337487 | 804 | 823 | CACTTGTATGTTCACCTCTG | 5-10-5 MOE | 81 | 7389 | 7408 | 28 |
| 561373 | 1197 | 1212 | TTTGTGATCCCAAGTA | Deoxy, MOE, and cEt | 40 | 9772 | 9787 | 4305 |
| 561374 | 1199 | 1214 | GCTTTGTGATCCCAAG | Deoxy, MOE, and cEt | 76 | 9774 | 9789 | 4306 |
| 561375 | 1201 | 1216 | TTGCTTTGTGATCCCA | Deoxy, MOE, and cEt | 82 | 9776 | 9791 | 4307 |
| 561376 | 1203 | 1218 | TTTTGCTTTGTGATCC | Deoxy, MOE, and cEt | 40 | 9778 | 9793 | 4308 |
| 561377 | 1205 | 1220 | CCTTTTGCTTTGTGAT | Deoxy, MOE, and cEt | 38 | 9780 | 9795 | 4309 |
| 561378 | 1207 | 1222 | GTCCTTTTGCTTTGTG | Deoxy, MOE, and cEt | 75 | 9782 | 9797 | 4310 |
| 561379 | 1209 | 1224 | GTGTCCTTTTGCTTTG | Deoxy, MOE, and cEt | 40 | 9784 | 9799 | 4311 |
| 561380 | 1212 | 1227 | GAAGTGTCCTTTTGCT | Deoxy, MOE, and cEt | 23 | 9787 | 9802 | 4312 |
| 561381 | 1214 | 1229 | TTGAAGTGTCCTTTTG | Deoxy, MOE, and cEt | 26 | 9789 | 9804 | 4313 |
| 561382 | 1216 | 1231 | AGTTGAAGTGTCCTTT | Deoxy, MOE, and cEt | 34 | 9791 | 9806 | 4314 |
| 561383 | 1218 | 1233 | ACAGTTGAAGTGTCCT | Deoxy, MOE, and cEt | 27 | 9793 | 9808 | 4315 |
| 561384 | 1220 | 1235 | GGACAGTTGAAGTGTC | Deoxy, MOE, and cEt | 19 | 9795 | 9810 | 4316 |
| 561385 | 1222 | 1237 | CTGGACAGTTGAAGTG | Deoxy, MOE, and cEt | 34 | 9797 | 9812 | 4317 |
| 561386 | 1224 | 1239 | CTCTGGACAGTTGAAG | Deoxy, MOE, and cEt | 19 | 9799 | 9814 | 4318 |
| 561387 | 1226 | 1241 | CCCTCTGGACAGTTGA | Deoxy, MOE, and cEt | 54 | 9801 | 9816 | 4319 |
| 561388 | 1228 | 1243 | AACCCTCTGGACAGTT | Deoxy, MOE, and cEt | 50 | 9803 | 9818 | 4320 |
| 561389 | 1230 | 1245 | ATAACCCTCTGGACAG | Deoxy, MOE, and cEt | 35 | 9805 | 9820 | 4321 |
| 561390 | 1232 | 1247 | GAATAACCCTCTGGAC | Deoxy, MOE, and cEt | 34 | 9807 | 9822 | 4322 |
| 561391 | 1234 | 1249 | CTGAATAACCCTCTGG | Deoxy, MOE, and cEt | 62 | 9809 | 9824 | 4323 |
| 561392 | 1236 | 1251 | TCCTGAATAACCCTCT | Deoxy, MOE, and cEt | 57 | N/A | N/A | 4324 |
| 561393 | 1238 | 1253 | CCTCCTGAATAACCCT | Deoxy, MOE, and cEt | 30 | N/A | N/A | 4325 |
| 561394 | 1246 | 1261 | ACCACCAGCCTCCTGA | Deoxy, MOE, and cEt | 70 | N/A | N/A | 4326 |
| 561395 | 1251 | 1266 | ATGCCACCACCAGCCT | Deoxy, MOE, and cEt | 68 | 10223 | 10238 | 4327 |

TABLE 29-continued

Inhibition of ANGPTL3 mRNA by oligonucleotides targeting SEQ ID NO: 1 and 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 561396 | 1253 | 1268 | TCATGCCACCACCAGC | Deoxy, MOE, and cEt | 72 | 10225 | 10240 | 4328 |
| 561397 | 1255 | 1270 | CATCATGCCACCACCA | Deoxy, MOE, and cEt | 67 | 10227 | 10242 | 4329 |
| 561398 | 1257 | 1272 | CTCATCATGCCACCAC | Deoxy, MOE, and cEt | 77 | 10229 | 10244 | 172 |
| 561399 | 1259 | 1274 | CACTCATCATGCCACC | Deoxy, MOE, and cEt | 74 | 10231 | 10246 | 2330 |
| 561400 | 1261 | 1276 | CACACTCATCATGCCA | Deoxy, MOE, and cEt | 80 | 10233 | 10248 | 173 |
| 561401 | 1263 | 1278 | TCCACACTCATCATGC | Deoxy, MOE, and cEt | 64 | 10235 | 10250 | 4331 |
| 561402 | 1265 | 1280 | TCTCCACACTCATCAT | Deoxy, MOE, and cEt | 42 | 10237 | 10252 | 4332 |
| 561403 | 1267 | 1282 | TTTCTCCACACTCATC | Deoxy, MOE, and cEt | 47 | 10239 | 10254 | 4333 |
| 561404 | 1269 | 1284 | GTTTTCTCCACACTCA | Deoxy, MOE, and cEt | 77 | 10241 | 10256 | 4334 |
| 561405 | 1272 | 1287 | GTTGTTTTCTCCACAC | Deoxy, MOE, and cEt | 53 | 10244 | 10259 | 4335 |
| 561406 | 1274 | 1289 | AGGTTGTTTTCTCCAC | Deoxy, MOE, and cEt | 67 | 10246 | 10261 | 4336 |
| 561407 | 1276 | 1291 | TTAGGTTGTTTTCTCC | Deoxy, MOE, and cEt | 73 | 10248 | 10263 | 4337 |
| 561408 | 1282 | 1297 | TACCATTTAGGTTGTT | Deoxy, MOE, and cEt | 30 | 10254 | 10269 | 4338 |
| 561409 | 1284 | 1299 | TTTACCATTTAGGTTG | Deoxy, MOE, and cEt | 22 | 10256 | 10271 | 4339 |
| 561410 | 1286 | 1301 | TATTTACCATTTAGGT | Deoxy, MOE, and cEt | 24 | 10258 | 10273 | 4340 |
| 561411 | 1292 | 1307 | TTGTTATATTTACCAT | Deoxy, MOE, and cEt | 41 | 10264 | 10279 | 4341 |
| 561412 | 1294 | 1309 | GTTTGTTATATTTACC | Deoxy, MOE, and cEt | 37 | 10266 | 10281 | 4342 |
| 561413 | 1298 | 1313 | CTTGGTTTGTTATATT | Deoxy, MOE, and cEt | 45 | 10270 | 10285 | 4343 |
| 561414 | 1300 | 1315 | CTCTTGGTTTGTTATA | Deoxy, MOE, and cEt | 73 | 10272 | 10287 | 4344 |
| 561415 | 1302 | 1317 | TGCTCTTGGTTTGTTA | Deoxy, MOE, and cEt | 45 | 10274 | 10289 | 4345 |
| 561416 | 1304 | 1319 | TTTGCTCTTGGTTTGT | Deoxy, MOE, and cEt | 67 | 10276 | 10291 | 4346 |
| 561417 | 1307 | 1322 | GATTTTGCTCTTGGTT | Deoxy, MOE, and cEt | 75 | 10279 | 10294 | 4347 |
| 561418 | 1309 | 1324 | TAGATTTTGCTCTTGG | Deoxy, MOE, and cEt | 87 | 10281 | 10296 | 169 |
| 561419 | 1311 | 1326 | CTTAGATTTTGCTCTT | Deoxy, MOE, and cEt | 64 | 10283 | 10298 | 4348 |
| 561420 | 1313 | 1328 | GGCTTAGATTTTGCTC | Deoxy, MOE, and cEt | 58 | 10285 | 10300 | 4349 |
| 561421 | 1315 | 1330 | CTGGCTTAGATTTTGC | Deoxy, MOE, and cEt | 70 | 10287 | 10302 | 4350 |
| 561422 | 1317 | 1332 | CTCTGGCTTAGATTTT | Deoxy, MOE, and cEt | 38 | 10289 | 10304 | 4351 |
| 561423 | 1319 | 1334 | CTCTCTGGCTTAGATT | Deoxy, MOE, and cEt | 63 | 10291 | 10306 | 4352 |
| 561424 | 1321 | 1336 | TCCTCTCTGGCTTAGA | Deoxy, MOE, and cEt | 76 | 10293 | 10308 | 4353 |
| 561425 | 1323 | 1338 | TCTCCTCTCTGGCTTA | Deoxy, MOE, and cEt | 67 | 10295 | 10310 | 4354 |
| 561426 | 1332 | 1347 | TAATCCTCTTCTCCTC | Deoxy, MOE, and cEt | 50 | 10304 | 10319 | 4355 |
| 561427 | 1334 | 1349 | GATAATCCTCTTCTCC | Deoxy, MOE, and cEt | 36 | 10306 | 10321 | 4356 |
| 561428 | 1336 | 1351 | AAGATAATCCTCTTCT | Deoxy, MOE, and cEt | 43 | 10308 | 10323 | 4357 |
| 561429 | 1338 | 1353 | CCAAGATAATCCTCTT | Deoxy, MOE, and cEt | 59 | 10310 | 10325 | 4358 |
| 561430 | 1340 | 1355 | TTCCAAGATAATCCTC | Deoxy, MOE, and cEt | 65 | 10312 | 10327 | 4359 |
| 561431 | 1342 | 1357 | ACTTCCAAGATAATCC | Deoxy, MOE, and cEt | 74 | 10314 | 10329 | 4360 |

TABLE 29-continued

Inhibition of ANGPTL3 mRNA by oligonucleotides targeting SEQ ID NO: 1 and 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 561432 | 1344 | 1359 | AGACTTCCAAGATAAT | Deoxy, MOE, and cEt | 52 | 10316 | 10331 | 4361 |
| 561433 | 1346 | 1361 | TGAGACTTCCAAGATA | Deoxy, MOE, and cEt | 49 | 10318 | 10333 | 4362 |
| 561434 | 1348 | 1363 | TTTGAGACTTCCAAGA | Deoxy, MOE, and cEt | 47 | 10320 | 10335 | 4363 |
| 561435 | 1350 | 1365 | ATTTGAGACTTCCAA | Deoxy, MOE, and cEt | 64 | 10322 | 10337 | 4364 |
| 561436 | 1352 | 1367 | CCATTTGAGACTTCC | Deoxy, MOE, and cEt | 84 | 10324 | 10339 | 170 |
| 561437 | 1354 | 1369 | TTCCATTTGAGACTT | Deoxy, MOE, and cEt | 67 | 10326 | 10341 | 4365 |
| 561438 | 1356 | 1371 | CCTTCCATTTGAGAC | Deoxy, MOE, and cEt | 53 | 10328 | 10343 | 4366 |
| 561439 | 1358 | 1373 | AACCTTCCATTTGAG | Deoxy, MOE, and cEt | 37 | 10330 | 10345 | 4367 |
| 561440 | 1360 | 1375 | ATAACCTTCCATTTG | Deoxy, MOE, and cEt | 50 | 10332 | 10347 | 4368 |
| 561441 | 1362 | 1377 | GTATAACCTTCCATTT | Deoxy, MOE, and cEt | 27 | 10334 | 10349 | 4369 |
| 561442 | 1364 | 1379 | GAGTATAACCTTCCAT | Deoxy, MOE, and cEt | 65 | 10336 | 10351 | 4370 |
| 561443 | 1366 | 1381 | TAGAGTATAACCTTCC | Deoxy, MOE, and cEt | 84 | 10338 | 10353 | 171 |
| 561444 | 1368 | 1383 | TATAGAGTATAACCTT | Deoxy, MOE, and cEt | 17 | 10340 | 10355 | 4371 |
| 561445 | 1370 | 1385 | TTTATAGAGTATAACC | Deoxy, MOE, and cEt | 37 | 10342 | 10357 | 4372 |
| 561446 | 1373 | 1388 | GATTTTATAGAGTATA | Deoxy, MOE, and cEt | 28 | 10345 | 10360 | 4373 |
| 561447 | 1375 | 1390 | TTGATTTTATAGAGTA | Deoxy, MOE, and cEt | 21 | 10347 | 10362 | 4374 |
| 561448 | 1377 | 1392 | GGTTGATTTTATAGAG | Deoxy, MOE, and cEt | 28 | 10349 | 10364 | 4375 |
| 561449 | 1379 | 1394 | TTGGTTGATTTTATAG | Deoxy, MOE, and cEt | 22 | 10351 | 10366 | 4376 |
| 567295 | 1452 | 1471 | TAATGTTTAAATTATTGCCT | 5-10-5 MOE | 43 | 10424 | 10443 | 4377 |
| 567296 | 1455 | 1474 | GGTTAATGTTTAAATTATTG | 5-10-5 MOE | 22 | 10427 | 10446 | 4378 |
| 567297 | 1456 | 1475 | AGGTTAATGTTTAAATTATT | 5-10-5 MOE | 0 | 10428 | 10447 | 4379 |
| 567298 | 1457 | 1476 | GAGGTTAATGTTTAAATTAT | 5-10-5 MOE | 0 | 10429 | 10448 | 4380 |
| 567299 | 1458 | 1477 | TGAGGTTAATGTTTAAATTA | 5-10-5 MOE | 6 | 10430 | 10449 | 4381 |
| 567300 | 1460 | 1479 | AATGAGGTTAATGTTTAAAT | 5-10-5 MOE | 14 | 10432 | 10451 | 4382 |
| 567301 | 1461 | 1480 | GAATGAGGTTAATGTTTAAA | 5-10-5 MOE | 5 | 10433 | 10452 | 4383 |
| 567302 | 1462 | 1481 | GGAATGAGGTTAATGTTTAA | 5-10-5 MOE | 27 | 10434 | 10453 | 4384 |
| 567303 | 1463 | 1482 | TGGAATGAGGTTAATGTTTA | 5-10-5 MOE | 32 | 10435 | 10454 | 4385 |
| 567304 | 1464 | 1483 | TTGGAATGAGGTTAATGTTT | 5-10-5 MOE | 37 | 10436 | 10455 | 4386 |
| 567305 | 1465 | 1484 | CTTGGAATGAGGTTAATGTT | 5-10-5 MOE | 25 | 10437 | 10456 | 4387 |
| 567306 | 1468 | 1487 | TAACTTGGAATGAGGTTAAT | 5-10-5 MOE | 29 | 10440 | 10459 | 4388 |
| 567307 | 1469 | 1488 | TTAACTTGGAATGAGGTTAA | 5-10-5 MOE | 44 | 10441 | 10460 | 4389 |
| 337513 | 1470 | 1489 | ATTAACTTGGAATGAGGTTA | 5-10-5 MOE | 52 | 10442 | 10461 | 4390 |
| 567308 | 1471 | 1490 | CATTAACTTGGAATGAGGTT | 5-10-5 MOE | 62 | 10443 | 10462 | 4391 |
| 567309 | 1472 | 1491 | ACATTAACTTGGAATGAGGT | 5-10-5 MOE | 58 | 10444 | 10463 | 4392 |
| 567310 | 1473 | 1492 | CACATTAACTTGGAATGAGG | 5-10-5 MOE | 78 | 10445 | 10464 | 92 |
| 567311 | 1475 | 1494 | ACCACATTAACTTGGAATGA | 5-10-5 MOE | 59 | 10447 | 10466 | 4393 |

TABLE 29-continued

Inhibition of ANGPTL3 mRNA by oligonucleotides targeting SEQ ID NO: 1 and 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 567312 | 1476 | 1495 | GACCACATTAACTTGGAATG | 5-10-5 MOE | 57 | 10448 | 10467 | 4394 |
| 337514 | 1477 | 1496 | AGACCACATTAACTTGGAAT | 5-10-5 MOE | 71 | 10449 | 10468 | 4395 |
| 567313 | 1478 | 1497 | TAGACCACATTAACTTGGAA | 5-10-5 MOE | 43 | 10450 | 10469 | 4396 |
| 567314 | 1479 | 1498 | TTAGACCACATTAACTTGGA | 5-10-5 MOE | 59 | 10451 | 10470 | 4397 |
| 567315 | 1480 | 1499 | ATTAGACCACATTAACTTGG | 5-10-5 MOE | 70 | 10452 | 10471 | 4398 |
| 567316 | 1481 | 1500 | TATTAGACCACATTAACTTG | 5-10-5 MOE | 53 | 10453 | 10472 | 4399 |
| 567317 | 1482 | 1501 | TTATTAGACCACATTAACTT | 5-10-5 MOE | 49 | 10454 | 10473 | 4400 |
| 567318 | 1483 | 1502 | ATTATTAGACCACATTAACT | 5-10-5 MOE | 41 | 10455 | 10474 | 4401 |
| 567319 | 1484 | 1503 | GATTATTAGACCACATTAAC | 5-10-5 MOE | 47 | 10456 | 10475 | 4402 |
| 567320 | 1487 | 1506 | CCAGATTATTAGACCACATT | 5-10-5 MOE | 86 | 10459 | 10478 | 93 |
| 567321 | 1489 | 1508 | TACCAGATTATTAGACCACA | 5-10-5 MOE | 85 | 10461 | 10480 | 94 |
| 337516 | 1490 | 1509 | ATACCAGATTATTAGACCAC | 5-10-5 MOE | 77 | 10462 | 10481 | 86 |
| 567322 | 1491 | 1510 | AATACCAGATTATTAGACCA | 5-10-5 MOE | 50 | 10463 | 10482 | 4403 |
| 567323 | 1492 | 1511 | TAATACCAGATTATTAGACC | 5-10-5 MOE | 56 | 10464 | 10483 | 4404 |
| 567324 | 1494 | 1513 | TTTAATACCAGATTATTAGA | 5-10-5 MOE | 9 | 10466 | 10485 | 4405 |
| 567325 | 1495 | 1514 | ATTTAATACCAGATTATTAG | 5-10-5 MOE | 24 | 10467 | 10486 | 4406 |
| 567326 | 1496 | 1515 | GATTTAATACCAGATTATTA | 5-10-5 MOE | 37 | 10468 | 10487 | 4407 |
| 567327 | 1500 | 1519 | TAAGGATTTAATACCAGATT | 5-10-5 MOE | 60 | 10472 | 10491 | 4408 |
| 567328 | 1507 | 1526 | TTTCTCTTAAGGATTTAATA | 5-10-5 MOE | 34 | 10479 | 10498 | 4409 |
| 567329 | 1508 | 1527 | CTTTCTCTTAAGGATTTAAT | 5-10-5 MOE | 46 | 10480 | 10499 | 4410 |
| 567330 | 1509 | 1528 | GCTTTCTCTTAAGGATTTAA | 5-10-5 MOE | 75 | 10481 | 10500 | 95 |
| 567331 | 1510 | 1529 | AGCTTTCTCTTAAGGATTTA | 5-10-5 MOE | 59 | 10482 | 10501 | 4411 |
| 567332 | 1511 | 1530 | AAGCTTTCTCTTAAGGATTT | 5-10-5 MOE | 30 | 10483 | 10502 | 4412 |
| 567333 | 1513 | 1532 | TCAAGCTTTCTCTTAAGGAT | 5-10-5 MOE | 65 | 10485 | 10504 | 4413 |
| 567334 | 1514 | 1533 | CTCAAGCTTTCTCTTAAGGA | 5-10-5 MOE | 77 | 10486 | 10505 | 96 |
| 567335 | 1515 | 1534 | TCTCAAGCTTTCTCTTAAGG | 5-10-5 MOE | 75 | 10487 | 10506 | 97 |
| 567336 | 1516 | 1535 | TTCTCAAGCTTTCTCTTAAG | 5-10-5 MOE | 59 | 10488 | 10507 | 4414 |
| 567337 | 1517 | 1536 | TTTCTCAAGCTTTCTCTTAA | 5-10-5 MOE | 52 | 10489 | 10508 | 4415 |
| 567338 | 1521 | 1540 | TCTATTTCTCAAGCTTTCTC | 5-10-5 MOE | 68 | 10493 | 10512 | 4416 |
| 567339 | 1522 | 1541 | ATCTATTTCTCAAGCTTTCT | 5-10-5 MOE | 71 | 10494 | 10513 | 4417 |
| 567340 | 1523 | 1542 | AATCTATTTCTCAAGCTTTC | 5-10-5 MOE | 74 | 10495 | 10514 | 4418 |
| 567341 | 1524 | 1543 | AAATCTATTTCTCAAGCTTT | 5-10-5 MOE | 63 | 10496 | 10515 | 4419 |
| 567342 | 1525 | 1544 | AAAATCTATTTCTCAAGCTT | 5-10-5 MOE | 54 | 10497 | 10516 | 4420 |
| 567343 | 1532 | 1551 | GATAAAAAAATCTATTTCT | 5-10-5 MOE | 30 | 10504 | 10523 | 4421 |
| 567344 | 1548 | 1567 | TAGACAGTGACTTTAAGATA | 5-10-5 MOE | 37 | 10520 | 10539 | 4422 |
| 567345 | 1549 | 1568 | ATAGACAGTGACTTTAAGAT | 5-10-5 MOE | 29 | 10521 | 10540 | 4423 |

TABLE 29-continued

Inhibition of ANGPTL3 mRNA by oligonucleotides targeting SEQ ID NO: 1 and 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 567346 | 1550 | 1569 | AATAGACAGTGACTTTAAGA | 5-10-5 MOE | 48 | 10522 | 10541 | 4424 |
| 567347 | 1551 | 1570 | AAATAGACAGTGACTTTAAG | 5-10-5 MOE | 26 | 10523 | 10542 | 4425 |
| 567348 | 1552 | 1571 | TAAATAGACAGTGACTTTAA | 5-10-5 MOE | 26 | 10524 | 10543 | 4426 |
| 567349 | 1553 | 1572 | TTAAATAGACAGTGACTTTA | 5-10-5 MOE | 50 | 10525 | 10544 | 4427 |
| 567350 | 1554 | 1573 | CTTAAATAGACAGTGACTTT | 5-10-5 MOE | 63 | 10526 | 10545 | 4428 |
| 567351 | 1555 | 1574 | TCTTAAATAGACAGTGACTT | 5-10-5 MOE | 57 | 10527 | 10546 | 4429 |
| 567352 | 1556 | 1575 | ATCTTAAATAGACAGTGACT | 5-10-5 MOE | 69 | 10528 | 10547 | 4430 |
| 567353 | 1557 | 1576 | AATCTTAAATAGACAGTGAC | 5-10-5 MOE | 40 | 10529 | 10548 | 4431 |
| 567354 | 1558 | 1577 | TAATCTTAAATAGACAGTGA | 5-10-5 MOE | 30 | 10530 | 10549 | 4432 |
| 567355 | 1559 | 1578 | TTAATCTTAAATAGACAGTG | 5-10-5 MOE | 25 | 10531 | 10550 | 4433 |
| 567356 | 1560 | 1579 | TTTAATCTTAAATAGACAGT | 5-10-5 MOE | 0 | 10532 | 10551 | 4434 |
| 567357 | 1561 | 1580 | GTTTAATCTTAAATAGACAG | 5-10-5 MOE | 34 | 10533 | 10552 | 4435 |
| 567358 | 1562 | 1581 | TGTTTAATCTTAAATAGACA | 5-10-5 MOE | 5 | 10534 | 10553 | 4436 |
| 567359 | 1563 | 1582 | ATGTTTAATCTTAAATAGAC | 5-10-5 MOE | 0 | 10535 | 10554 | 4437 |
| 567360 | 1567 | 1586 | TTGTATGTTTAATCTTAAAT | 5-10-5 MOE | 0 | 10539 | 10558 | 4438 |
| 567361 | 1568 | 1587 | ATTGTATGTTTAATCTTAAA | 5-10-5 MOE | 8 | 10540 | 10559 | 4439 |
| 567362 | 1569 | 1588 | GATTGTATGTTTAATCTTAA | 5-10-5 MOE | 20 | 10541 | 10560 | 4440 |
| 567363 | 1570 | 1589 | TGATTGTATGTTTAATCTTA | 5-10-5 MOE | 29 | 10542 | 10561 | 4441 |
| 567364 | 1574 | 1593 | TATGTGATTGTATGTTTAAT | 5-10-5 MOE | 7 | 10546 | 10565 | 4442 |
| 567365 | 1576 | 1595 | GTTATGTGATTGTATGTTTA | 5-10-5 MOE | 43 | 10548 | 10567 | 4443 |
| 567366 | 1580 | 1599 | TAAGGTTATGTGATTGTATG | 5-10-5 MOE | 28 | 10552 | 10571 | 4444 |
| 567367 | 1581 | 1600 | TTAAGGTTATGTGATTGTAT | 5-10-5 MOE | 31 | 10553 | 10572 | 4445 |
| 567368 | 1585 | 1604 | TTCTTTAAGGTTATGTGATT | 5-10-5 MOE | 12 | 10557 | 10576 | 4446 |
| 561527 | 1604 | 1619 | GAAATGTAAACGGTAT | Deoxy, MOE, and cEt | 47 | 10576 | 10591 | 4447 |
| 561528 | 1606 | 1621 | GAGAAATGTAAACGGT | Deoxy, MOE, and cEt | 89 | 10578 | 10593 | 174 |
| 561529 | 1608 | 1623 | TTGAGAAATGTAAACG | Deoxy, MOE, and cEt | 55 | 10580 | 10595 | 4448 |
| 561530 | 1611 | 1626 | TGATTGAGAAATGTAA | Deoxy, MOE, and cEt | 18 | 10583 | 10598 | 4449 |
| 561531 | 1613 | 1628 | TTTGATTGAGAAATGT | Deoxy, MOE, and cEt | 30 | 10585 | 10600 | 4450 |
| 561532 | 1619 | 1634 | AAGAATTTTGATTGAG | Deoxy, MOE, and cEt | 53 | 10591 | 10606 | 4451 |
| 561533 | 1621 | 1636 | ATAAGAATTTTGATTG | Deoxy, MOE, and cEt | 29 | 10593 | 10608 | 4452 |
| 561534 | 1632 | 1647 | CAAATAGTATTATAAG | Deoxy, MOE, and cEt | 6 | 10604 | 10619 | 4453 |
| 561535 | 1653 | 1668 | CCCACATCACAAAATT | Deoxy, MOE, and cEt | 70 | 10625 | 10640 | 4454 |
| 561536 | 1657 | 1672 | GATTCCCACATCACAA | Deoxy, MOE, and cEt | 77 | 10629 | 10644 | 4455 |
| 561537 | 1659 | 1674 | TTGATTCCCACATCAC | Deoxy, MOE, and cEt | 78 | 10631 | 10646 | 4456 |
| 561538 | 1661 | 1676 | AATTGATTCCCACATC | Deoxy, MOE, and cEt | 68 | 10633 | 10648 | 4457 |
| 561539 | 1663 | 1678 | AAAATTGATTCCCACA | Deoxy, MOE, and cEt | 72 | 10635 | 10650 | 4458 |

TABLE 29-continued

Inhibition of ANGPTL3 mRNA by oligonucleotides targeting SEQ ID NO: 1 and 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 561540 | 1665 | 1680 | CTAAAATTGATTCCCA | Deoxy, MOE, and cEt | 54 | 10637 | 10652 | 4459 |
| 561541 | 1668 | 1683 | CATCTAAAATTGATTC | Deoxy, MOE, and cEt | 0 | 10640 | 10655 | 4460 |
| 561542 | 1670 | 1685 | ACCATCTAAAATTGAT | Deoxy, MOE, and cEt | 35 | 10642 | 10657 | 4461 |
| 561543 | 1672 | 1687 | TGACCATCTAAAATTG | Deoxy, MOE, and cEt | 55 | 10644 | 10659 | 4462 |
| 561544 | 1674 | 1689 | TGTGACCATCTAAAAT | Deoxy, MOE, and cEt | 56 | 10646 | 10661 | 4463 |
| 561545 | 1676 | 1691 | ATTGTGACCATCTAAA | Deoxy, MOE, and cEt | 73 | 10648 | 10663 | 4464 |
| 561546 | 1678 | 1693 | AGATTGTGACCATCTA | Deoxy, MOE, and cEt | 67 | 10650 | 10665 | 4465 |
| 561547 | 1680 | 1695 | CTAGATTGTGACCATC | Deoxy, MOE, and cEt | 50 | 10652 | 10667 | 4466 |
| 561548 | 1682 | 1697 | ATCTAGATTGTGACCA | Deoxy, MOE, and cEt | 77 | 10654 | 10669 | 4467 |
| 561549 | 1684 | 1699 | TAATCTAGATTGTGAC | Deoxy, MOE, and cEt | 55 | 10656 | 10671 | 4468 |
| 561550 | 1686 | 1701 | TATAATCTAGATTGTG | Deoxy, MOE, and cEt | 28 | 10658 | 10673 | 4469 |
| 561551 | 1688 | 1703 | ATTATAATCTAGATTG | Deoxy, MOE, and cEt | 52 | 10660 | 10675 | 4470 |
| 561552 | 1690 | 1705 | TGATTATAATCTAGAT | Deoxy, MOE, and cEt | 43 | 10662 | 10677 | 4471 |
| 561553 | 1692 | 1707 | ATTGATTATAATCTAG | Deoxy, MOE, and cEt | 53 | 10664 | 10679 | 4472 |
| 561554 | 1694 | 1709 | CTATTGATTATAATCT | Deoxy, MOE, and cEt | 54 | 10666 | 10681 | 4473 |
| 561555 | 1696 | 1711 | ACCTATTGATTATAAT | Deoxy, MOE, and cEt | 44 | 10668 | 10683 | 4474 |
| 561556 | 1698 | 1713 | TCACCTATTGATTATA | Deoxy, MOE, and cEt | 52 | 10670 | 10685 | 4475 |
| 561557 | 1700 | 1715 | GTTCACCTATTGATTA | Deoxy, MOE, and cEt | 50 | 10672 | 10687 | 4476 |
| 561558 | 1702 | 1717 | AAGTTCACCTATTGAT | Deoxy, MOE, and cEt | 58 | 10674 | 10689 | 4477 |
| 561559 | 1704 | 1719 | ATAAGTTCACCTATTG | Deoxy, MOE, and cEt | 66 | 10676 | 10691 | 4478 |
| 561560 | 1706 | 1721 | TAATAAGTTCACCTAT | Deoxy, MOE, and cEt | 38 | 10678 | 10693 | 4479 |
| 561561 | 1708 | 1723 | TTTAATAAGTTCACCT | Deoxy, MOE, and cEt | 50 | 10680 | 10695 | 4480 |
| 561562 | 1710 | 1725 | TATTTAATAAGTTCAC | Deoxy, MOE, and cEt | 32 | 10682 | 10697 | 4481 |
| 561563 | 1712 | 1727 | GTTATTTAATAAGTTC | Deoxy, MOE, and cEt | 47 | 10684 | 10699 | 4482 |
| 561564 | 1761 | 1776 | CATATGATGCCTTTA | Deoxy, MOE, and cEt | 63 | 10733 | 10748 | 4483 |
| 561565 | 1763 | 1778 | CTCATATGATGCCTTT | Deoxy, MOE, and cEt | 81 | 10735 | 10750 | 175 |
| 561566 | 1765 | 1780 | AGCTCATATGATGCCT | Deoxy, MOE, and cEt | 81 | 10737 | 10752 | 176 |
| 561567 | 1767 | 1782 | TTAGCTCATATGATGC | Deoxy, MOE, and cEt | 84 | 10739 | 10754 | 177 |
| 561568 | 1769 | 1784 | TATTAGCTCATATGAT | Deoxy, MOE, and cEt | 46 | 10741 | 10756 | 4484 |
| 561569 | 1771 | 1786 | GATATTAGCTCATATG | Deoxy, MOE, and cEt | 49 | 10743 | 10758 | 4485 |
| 561570 | 1773 | 1788 | GTGATATTAGCTCATA | Deoxy, MOE, and cEt | 81 | 10745 | 10760 | 4486 |
| 561571 | 1775 | 1790 | TTGTGATATTAGCTCA | Deoxy, MOE, and cEt | 85 | 10747 | 10762 | 178 |
| 561572 | 1777 | 1792 | AGTTGTGATATTAGCT | Deoxy, MOE, and cEt | 68 | 10749 | 10764 | 4487 |
| 561573 | 1779 | 1794 | AAAGTTGTGATATTAG | Deoxy, MOE, and cEt | 45 | 10751 | 10766 | 4488 |
| 561574 | 1781 | 1796 | GGAAAGTTGTGATATT | Deoxy, MOE, and cEt | 27 | 10753 | 10768 | 4489 |
| 561575 | 1783 | 1798 | TGGGAAAGTTGTGATA | Deoxy, MOE, and cEt | 36 | 10755 | 10770 | 4490 |

TABLE 29-continued

Inhibition of ANGPTL3 mRNA by oligonucleotides targeting SEQ ID NO: 1 and 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 561576 | 1785 | 1800 | ACTGGGAAAGTTGTGA | Deoxy, MOE, and cEt | 83 | 10757 | 10772 | 179 |
| 561577 | 1787 | 1802 | AAACTGGGAAAGTTGT | Deoxy, MOE, and cEt | 56 | 10759 | 10774 | 4491 |
| 561578 | 1789 | 1804 | TTAAACTGGGAAAGTT | Deoxy, MOE, and cEt | 44 | 10761 | 10776 | 4492 |
| 561579 | 1794 | 1809 | GTTTTTAAACTGGGA | Deoxy, MOE, and cEt | 58 | 10766 | 10781 | 4493 |
| 561580 | 1796 | 1811 | TAGTTTTTAAACTGG | Deoxy, MOE, and cEt | 0 | 10768 | 10783 | 4494 |
| 561581 | 1802 | 1817 | GAGTACTAGTTTTTA | Deoxy, MOE, and cEt | 18 | 10774 | 10789 | 4495 |
| 561582 | 1804 | 1819 | AAGAGTACTAGTTTTT | Deoxy, MOE, and cEt | 55 | 10776 | 10791 | 4496 |
| 561583 | 1806 | 1821 | ACAAGAGTACTAGTTT | Deoxy, MOE, and cEt | 51 | 10778 | 10793 | 4497 |
| 561584 | 1808 | 1823 | TAACAAGAGTACTAGT | Deoxy, MOE, and cEt | 53 | 10780 | 10795 | 4498 |
| 561585 | 1810 | 1825 | TTTAACAAGAGTACTA | Deoxy, MOE, and cEt | 48 | 10782 | 10797 | 4499 |
| 561586 | 1812 | 1827 | GTTTTAACAAGAGTAC | Deoxy, MOE, and cEt | 49 | 10784 | 10799 | 4500 |
| 561587 | 1814 | 1829 | GAGTTTTAACAAGAGT | Deoxy, MOE, and cEt | 54 | 10786 | 10801 | 4501 |
| 561588 | 1816 | 1831 | TAGAGTTTTAACAAGA | Deoxy, MOE, and cEt | 9 | 10788 | 10803 | 4502 |
| 561589 | 1819 | 1834 | GTTTAGAGTTTAACA | Deoxy, MOE, and cEt | 24 | 10791 | 10806 | 4503 |
| 561590 | 1822 | 1837 | CAAGTTTAGAGTTTTA | Deoxy, MOE, and cEt | 30 | 10794 | 10809 | 4504 |
| 561591 | 1824 | 1839 | GTCAAGTTTAGAGTTT | Deoxy, MOE, and cEt | 60 | 10796 | 10811 | 4505 |
| 561592 | 1826 | 1841 | TAGTCAAGTTTAGAGT | Deoxy, MOE, and cEt | 56 | 10798 | 10813 | 4506 |
| 561593 | 1828 | 1843 | TTTAGTCAAGTTTAGA | Deoxy, MOE, and cEt | 41 | 10800 | 10815 | 4507 |
| 561594 | 1830 | 1845 | TATTTAGTCAAGTTTA | Deoxy, MOE, and cEt | 14 | 10802 | 10817 | 4508 |
| 561595 | 1832 | 1847 | TGTATTTAGTCAAGTT | Deoxy, MOE, and cEt | 39 | 10804 | 10819 | 4509 |
| 561596 | 1834 | 1849 | TCTGTATTTAGTCAAG | Deoxy, MOE, and cEt | 51 | 10806 | 10821 | 4510 |
| 561597 | 1836 | 1851 | CCTCTGTATTTAGTCA | Deoxy, MOE, and cEt | 72 | 10808 | 10823 | 4511 |
| 561598 | 1838 | 1853 | GTCCTCTGTATTTAGT | Deoxy, MOE, and cEt | 55 | 10810 | 10825 | 4512 |
| 561599 | 1840 | 1855 | CAGTCCTCTGTATTTA | Deoxy, MOE, and cEt | 63 | 10812 | 10827 | 4513 |
| 561600 | 1842 | 1857 | ACCAGTCCTCTGTATT | Deoxy, MOE, and cEt | 66 | 10814 | 10829 | 4514 |
| 561601 | 1844 | 1859 | TTACCAGTCCTCTGTA | Deoxy, MOE, and cEt | 57 | 10816 | 10831 | 4515 |
| 561602 | 1846 | 1861 | AATTACCAGTCCTCTG | Deoxy, MOE, and cEt | 43 | 10818 | 10833 | 4516 |
| 561603 | 1848 | 1863 | ACAATTACCAGTCCTC | Deoxy, MOE, and cEt | 67 | 10820 | 10835 | 4517 |

TABLE 30

Inhibition of ANGPTL3 mRNA by oligonucleotides targeting SEQ ID NO: 1 and 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 561835 | N/A | N/A | GCAAATTTTCAGTGTT | Deoxy, MOE, and cEt | 49 | 3850 | 3865 | 4518 |
| 561836 | N/A | N/A | CGATTTGTAATTTTCA | Deoxy, MOE, and cEt | 20 | 3874 | 3889 | 4519 |

TABLE 30-continued

Inhibition of ANGPTL3 mRNA by oligonucleotides targeting SEQ ID NO: 1 and 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 561837 | N/A | N/A | TTTAACCGATTTGTAA | Deoxy, MOE, and cEt | 42 | 3880 | 3895 | 4520 |
| 561838 | N/A | N/A | GTATAATTTAACCGAT | Deoxy, MOE, and cEt | 15 | 3886 | 3901 | 4521 |
| 561839 | N/A | N/A | CTAGATTGTATAATTT | Deoxy, MOE, and cEt | 15 | 3893 | 3908 | 4522 |
| 561840 | N/A | N/A | AGTGTTCTAGATTGTA | Deoxy, MOE, and cEt | 45 | 3899 | 3914 | 4523 |
| 561841 | N/A | N/A | TGACATAGTGTTCTAG | Deoxy, MOE, and cEt | 51 | 3905 | 3920 | 4524 |
| 561842 | N/A | N/A | GTGTAATGACATAGTG | Deoxy, MOE, and cEt | 58 | 3911 | 3926 | 4525 |
| 561843 | N/A | N/A | ACAATAGTGTAATGAC | Deoxy, MOE, and cEt | 12 | 3917 | 3932 | 4526 |
| 561844 | N/A | N/A | GTAATTTACAATAGTG | Deoxy, MOE, and cEt | 18 | 3924 | 3939 | 4527 |
| 561845 | N/A | N/A | CCTTCAGTAATTTACA | Deoxy, MOE, and cEt | 0 | 3930 | 3945 | 4528 |
| 561846 | N/A | N/A | TACTTACCTTCAGTAA | Deoxy, MOE, and cEt | 2 | 3936 | 3951 | 4529 |
| 561847 | N/A | N/A | CTGGAGAATAGTTTTA | Deoxy, MOE, and cEt | 19 | 3969 | 3984 | 4530 |
| 561848 | N/A | N/A | TTAAACACTGGAGAAT | Deoxy, MOE, and cEt | 14 | 3976 | 3991 | 4531 |
| 561849 | N/A | N/A | GCCCAGCATATTTTCA | Deoxy, MOE, and cEt | 22 | 4034 | 4049 | 4532 |
| 561850 | N/A | N/A | GAAAAGCCCAGCATA | Deoxy, MOE, and cEt | 15 | 4040 | 4055 | 4533 |
| 561851 | N/A | N/A | GATTTTCTGAACTTCA | Deoxy, MOE, and cEt | 52 | 4063 | 4078 | 4534 |
| 561852 | N/A | N/A | GTACTATCTCTAAAAT | Deoxy, MOE, and cEt | 6 | 4081 | 4096 | 4535 |
| 561853 | N/A | N/A | TAAATTGTACTATCTC | Deoxy, MOE, and cEt | 13 | 4087 | 4102 | 4536 |
| 561854 | N/A | N/A | CACATATTTTGTCCT | Deoxy, MOE, and cEt | 47 | 4115 | 4130 | 4537 |
| 561855 | N/A | N/A | CTTTCAAATAGCACAT | Deoxy, MOE, and cEt | 31 | 4126 | 4141 | 4538 |
| 561856 | N/A | N/A | GTATGCTTCTTTCAAA | Deoxy, MOE, and cEt | 22 | 4134 | 4149 | 4539 |
| 561857 | N/A | N/A | CCCCTTGTATGCTTCT | Deoxy, MOE, and cEt | 55 | 4140 | 4155 | 4540 |
| 561858 | N/A | N/A | TTCCTTCCCCTTGTAT | Deoxy, MOE, and cEt | 32 | 4146 | 4161 | 4541 |
| 561859 | N/A | N/A | TGGCAATTCCTTCCCC | Deoxy, MOE, and cEt | 43 | 4152 | 4167 | 4542 |
| 561860 | N/A | N/A | GAATATTGGCAATTCC | Deoxy, MOE, and cEt | 52 | 4158 | 4173 | 4543 |
| 561861 | N/A | N/A | CTAATAATGGATTTGA | Deoxy, MOE, and cEt | 0 | 4179 | 4194 | 4544 |
| 561862 | N/A | N/A | CTATCATAATCTAAAT | Deoxy, MOE, and cEt | 0 | 4202 | 4217 | 4545 |
| 561863 | N/A | N/A | GTAACACTATCATAAT | Deoxy, MOE, and cEt | 7 | 4208 | 4223 | 4546 |
| 561864 | N/A | N/A | AATTTCCTGTAACACT | Deoxy, MOE, and cEt | 17 | 4216 | 4231 | 4547 |
| 561865 | N/A | N/A | AAGTTGCTTTCCTCTT | Deoxy, MOE, and cEt | 12 | 4243 | 4258 | 4548 |
| 561866 | N/A | N/A | GGTTATAAGTTGCTTT | Deoxy, MOE, and cEt | 6 | 4249 | 4264 | 4549 |
| 561867 | N/A | N/A | TAGGTTGGTTATAAGT | Deoxy, MOE, and cEt | 10 | 4255 | 4270 | 4550 |
| 561868 | N/A | N/A | AGAGAGTAGGTTGGTT | Deoxy, MOE, and cEt | 10 | 4261 | 4276 | 4551 |
| 561869 | N/A | N/A | GGATATAGAGAGTAGG | Deoxy, MOE, and cEt | 23 | 4267 | 4282 | 4552 |
| 561870 | N/A | N/A | AAGTCTGGATATAGAG | Deoxy, MOE, and cEt | 13 | 4273 | 4288 | 4553 |
| 561871 | N/A | N/A | CTACAAAAGTCTGGAT | Deoxy, MOE, and cEt | 1 | 4279 | 4294 | 4554 |
| 561872 | N/A | N/A | CTTACCTGATTTTCTA | Deoxy, MOE, and cEt | 0 | 4385 | 4400 | 4555 |

TABLE 30-continued

Inhibition of ANGPTL3 mRNA by oligonucleotides targeting SEQ ID NO: 1 and 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 561873 | N/A | N/A | TACTGACTTACCTGAT | Deoxy, MOE, and cEt | 2 | 4391 | 4406 | 4556 |
| 561874 | N/A | N/A | CCATTAAAATACTGAC | Deoxy, MOE, and cEt | 1 | 4400 | 4415 | 4557 |
| 561875 | N/A | N/A | GGACATACCATTAAAA | Deoxy, MOE, and cEt | 11 | 4407 | 4422 | 4558 |
| 561876 | N/A | N/A | AAGATGGGACATACCA | Deoxy, MOE, and cEt | 38 | 4413 | 4428 | 4559 |
| 561877 | N/A | N/A | GTGTGAAAGATGGGAC | Deoxy, MOE, and cEt | 25 | 4419 | 4434 | 4560 |
| 561878 | N/A | N/A | AGACCTGTGTGAAAGA | Deoxy, MOE, and cEt | 33 | 4425 | 4440 | 4561 |
| 561879 | N/A | N/A | TTTTACAGACCTGTGT | Deoxy, MOE, and cEt | 29 | 4431 | 4446 | 4562 |
| 561880 | N/A | N/A | CAGTGTTTTACAGAC | Deoxy, MOE, and cEt | 40 | 4437 | 4452 | 4563 |
| 561881 | N/A | N/A | TAGGATTCAGTGTTTT | Deoxy, MOE, and cEt | 62 | 4444 | 4459 | 4564 |
| 561882 | N/A | N/A | GTTAAAGCTTGTAAAT | Deoxy, MOE, and cEt | 16 | 4465 | 4480 | 4565 |
| 561883 | N/A | N/A | GATCCAGTTAAAGCTT | Deoxy, MOE, and cEt | 39 | 4471 | 4486 | 4566 |
| 561884 | N/A | N/A | ACTCATGATCCAGTTA | Deoxy, MOE, and cEt | 60 | 4477 | 4492 | 4567 |
| 561885 | N/A | N/A | AATTTTACTCATGATC | Deoxy, MOE, and cEt | 36 | 4483 | 4498 | 4568 |
| 561886 | N/A | N/A | TGTGATAATTTTACTC | Deoxy, MOE, and cEt | 30 | 4489 | 4504 | 4569 |
| 561887 | N/A | N/A | TGCTGATGTGATAATT | Deoxy, MOE, and cEt | 41 | 4495 | 4510 | 4570 |
| 561888 | N/A | N/A | CAGTTATGCTGATGTG | Deoxy, MOE, and cEt | 86 | 4501 | 4516 | 185 |
| 561889 | N/A | N/A | GCAATTTTAACAGTTA | Deoxy, MOE, and cEt | 13 | 4511 | 4526 | 4571 |
| 561890 | N/A | N/A | GAGCCTGCAATTTTAA | Deoxy, MOE, and cEt | 14 | 4517 | 4532 | 4572 |
| 561891 | N/A | N/A | TAGCTTCAGAGCCTGC | Deoxy, MOE, and cEt | 61 | 4525 | 4540 | 4573 |
| 561892 | N/A | N/A | GTTTATTAGCTTCAGA | Deoxy, MOE, and cEt | 45 | 4531 | 4546 | 4574 |
| 561893 | N/A | N/A | CAGGTAGTTTATTAGC | Deoxy, MOE, and cEt | 37 | 4537 | 4552 | 4575 |
| 561894 | N/A | N/A | TAAATGCAGGTAGTTT | Deoxy, MOE, and cEt | 11 | 4543 | 4558 | 4576 |
| 561895 | N/A | N/A | ATGGTTTAAATGCAGG | Deoxy, MOE, and cEt | 53 | 4549 | 4564 | 4577 |
| 561896 | N/A | N/A | TAGAGCCATGGTTTAA | Deoxy, MOE, and cEt | 58 | 4556 | 4571 | 4578 |
| 561897 | N/A | N/A | AAGTTTTAGAGCCATG | Deoxy, MOE, and cEt | 81 | 4562 | 4577 | 186 |
| 561898 | N/A | N/A | TCACACAAAGTTTTAG | Deoxy, MOE, and cEt | 17 | 4569 | 4584 | 4579 |
| 561899 | N/A | N/A | GTGAAGTAATTTATTC | Deoxy, MOE, and cEt | 8 | 4589 | 4604 | 4580 |
| 561900 | N/A | N/A | ACTGAGAGATAAAGGG | Deoxy, MOE, and cEt | 34 | 4605 | 4620 | 4581 |
| 561901 | N/A | N/A | GTATATGTGAGGAAAC | Deoxy, MOE, and cEt | 18 | 4619 | 4634 | 4582 |
| 561902 | N/A | N/A | TTTGTAGTATATGTGA | Deoxy, MOE, and cEt | 3 | 4625 | 4640 | 4583 |
| 561903 | N/A | N/A | ATTATCTTTGTAGTAT | Deoxy, MOE, and cEt | 8 | 4631 | 4646 | 4584 |
| 561904 | N/A | N/A | ATAAGTTCTGTTATTA | Deoxy, MOE, and cEt | 18 | 4643 | 4658 | 4585 |
| 561905 | N/A | N/A | AATCCTATAAGTTCTG | Deoxy, MOE, and cEt | 55 | 4649 | 4664 | 4586 |
| 561906 | N/A | N/A | CTGCTATGAATTAATT | Deoxy, MOE, and cEt | 16 | 4679 | 4694 | 4587 |
| 561907 | N/A | N/A | CATTGGCTGCTATGAA | Deoxy, MOE, and cEt | 48 | 4685 | 4700 | 4588 |
| 561908 | N/A | N/A | AGATGACATTGGCTGC | Deoxy, MOE, and cEt | 71 | 4691 | 4706 | 4589 |

TABLE 30-continued

Inhibition of ANGPTL3 mRNA by oligonucleotides targeting SEQ ID NO: 1 and 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 561909 | N/A | N/A | TTAGTAAGATGACATT | Deoxy, MOE, and cEt | 0 | 4697 | 4712 | 4590 |
| 561910 | N/A | N/A | GATCTAATTTGAATTT | Deoxy, MOE, and cEt | 7 | 4712 | 4727 | 4591 |
| 561911 | N/A | N/A | TTGAGCAAAGAGAAAC | Deoxy, MOE, and cEt | 6 | 4730 | 4745 | 4592 |
| 561989 | N/A | N/A | GAATGTTGACCTTTAA | Deoxy, MOE, and cEt | 49 | 5356 | 5371 | 4593 |
| 561990 | N/A | N/A | ATTGTTGAATGTTGAC | Deoxy, MOE, and cEt | 57 | 5362 | 5377 | 4594 |
| 561991 | N/A | N/A | TTAATTACATTGTTGA | Deoxy, MOE, and cEt | 0 | 5370 | 5385 | 4595 |
| 561992 | N/A | N/A | TTGTAGATTAATTACA | Deoxy, MOE, and cEt | 18 | 5377 | 5392 | 4596 |
| 561993 | N/A | N/A | TTTACATTGTAGATTA | Deoxy, MOE, and cEt | 3 | 5383 | 5398 | 4597 |
| 561994 | N/A | N/A | CAGATGTTTACATTGT | Deoxy, MOE, and cEt | 71 | 5389 | 5404 | 4598 |
| 561995 | N/A | N/A | CTTCACCAGATGTTTA | Deoxy, MOE, and cEt | 19 | 5395 | 5410 | 4599 |
| 561996 | N/A | N/A | CTGTCACTTCACCAGA | Deoxy, MOE, and cEt | 77 | 5401 | 5416 | 187 |
| 561997 | N/A | N/A | AGTGCTTCCCTCTGTC | Deoxy, MOE, and cEt | 66 | 5412 | 5427 | 4600 |
| 561998 | N/A | N/A | TAAACAAGTGCTTCCC | Deoxy, MOE, and cEt | 62 | 5418 | 5433 | 4601 |
| 561999 | N/A | N/A | TAGCTTTTTTCTAAAC | Deoxy, MOE, and cEt | 0 | 5429 | 5444 | 4602 |
| 562000 | N/A | N/A | CTGACATAGCTTTTTT | Deoxy, MOE, and cEt | 66 | 5435 | 5450 | 4603 |
| 562001 | N/A | N/A | TGGATTCTGACATAGC | Deoxy, MOE, and cEt | 85 | 5441 | 5456 | 188 |
| 562002 | N/A | N/A | AATACATGGATTCTGA | Deoxy, MOE, and cEt | 35 | 5447 | 5462 | 4604 |
| 562003 | N/A | N/A | TATTAGAATACATGGA | Deoxy, MOE, and cEt | 7 | 5453 | 5468 | 4605 |
| 562004 | N/A | N/A | GTACTGCATATTAGAA | Deoxy, MOE, and cEt | 48 | 5461 | 5476 | 4606 |
| 562005 | N/A | N/A | ACTATTGTACTGCATA | Deoxy, MOE, and cEt | 53 | 5467 | 5482 | 4607 |
| 562006 | N/A | N/A | TTTTAAACTATTGTAC | Deoxy, MOE, and cEt | 0 | 5473 | 5488 | 4608 |
| 562007 | N/A | N/A | GAGAGTATTATTAATA | Deoxy, MOE, and cEt | 8 | 5490 | 5505 | 4609 |
| 562008 | N/A | N/A | CTGTTTGAGAGTATTA | Deoxy, MOE, and cEt | 0 | 5496 | 5511 | 4610 |
| 562009 | N/A | N/A | GAATAGCTGTTTGAGA | Deoxy, MOE, and cEt | 34 | 5502 | 5517 | 4611 |
| 562010 | N/A | N/A | AATCCTCTTGAATAGC | Deoxy, MOE, and cEt | 62 | 5511 | 5526 | 4612 |
| 562011 | N/A | N/A | TTTTTGAATCCTCTTG | Deoxy, MOE, and cEt | 50 | 5517 | 5532 | 4613 |
| 562012 | N/A | N/A | GAGTTTATATTATGTT | Deoxy, MOE, and cEt | 5 | 5532 | 5547 | 4614 |
| 562013 | N/A | N/A | GTTTCTCTGAGTTTAT | Deoxy, MOE, and cEt | 58 | 5540 | 5555 | 4615 |
| 562014 | N/A | N/A | TTACCAGTTTCTCTGA | Deoxy, MOE, and cEt | 64 | 5546 | 5561 | 4616 |
| 562015 | N/A | N/A | GATTTTGTTTACCAGT | Deoxy, MOE, and cEt | 68 | 5554 | 5569 | 4617 |
| 562016 | N/A | N/A | GTTTTATATCTCTTGA | Deoxy, MOE, and cEt | 33 | 5574 | 5589 | 4618 |
| 562017 | N/A | N/A | TTGGTAATAATATTTG | Deoxy, MOE, and cEt | 13 | 5589 | 5604 | 4619 |
| 562018 | N/A | N/A | TGGAAATTGGTAATAA | Deoxy, MOE, and cEt | 1 | 5595 | 5610 | 4620 |
| 562019 | N/A | N/A | GTTTAGTGGAAATTGG | Deoxy, MOE, and cEt | 44 | 5601 | 5616 | 4621 |
| 562020 | N/A | N/A | ATGTTTGTTAGTGGA | Deoxy, MOE, and cEt | 47 | 5607 | 5622 | 4622 |
| 562021 | N/A | N/A | CTAACATTATGTTTGT | Deoxy, MOE, and cEt | 0 | 5615 | 5630 | 4623 |

TABLE 30-continued

Inhibition of ANGPTL3 mRNA by oligonucleotides targeting SEQ ID NO: 1 and 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 562022 | N/A | N/A | GCACTACTAACATTAT | Deoxy, MOE, and cEt | 42 | 5621 | 5636 | 4624 |
| 562023 | N/A | N/A | TTAGCAGCACTACTAA | Deoxy, MOE, and cEt | 35 | 5627 | 5642 | 4625 |
| 562024 | N/A | N/A | AACCTTTTAGCAGCAC | Deoxy, MOE, and cEt | 76 | 5633 | 5648 | 189 |
| 562025 | N/A | N/A | TTGATAAAAACCTTT | Deoxy, MOE, and cEt | 0 | 5642 | 5657 | 4626 |
| 562026 | N/A | N/A | CAAAAGTAGTTGATAA | Deoxy, MOE, and cEt | 0 | 5651 | 5666 | 4627 |
| 562027 | N/A | N/A | GGAAACCAAAAGTAGT | Deoxy, MOE, and cEt | 28 | 5657 | 5672 | 4628 |
| 562028 | N/A | N/A | GAAAGTATGGAAACCA | Deoxy, MOE, and cEt | 52 | 5665 | 5680 | 4629 |
| 562029 | N/A | N/A | ACATCATAAGAAGGAA | Deoxy, MOE, and cEt | 8 | 5678 | 5693 | 4630 |
| 562030 | N/A | N/A | TCATAGTAAAAGATAT | Deoxy, MOE, and cEt | 0 | 5718 | 5733 | 4631 |
| 562031 | N/A | N/A | TCATTTAATCATAGTA | Deoxy, MOE, and cEt | 7 | 5726 | 5741 | 4632 |
| 562032 | N/A | N/A | GCAGGTTCATTTAATC | Deoxy, MOE, and cEt | 56 | 5732 | 5747 | 4633 |
| 562033 | N/A | N/A | GTAACATTTGCTTTG | Deoxy, MOE, and cEt | 44 | 5752 | 5767 | 4634 |
| 562034 | N/A | N/A | ATATTACTATAGTAAC | Deoxy, MOE, and cEt | 4 | 5763 | 5778 | 4635 |
| 562035 | N/A | N/A | CAATGTATATTACTAT | Deoxy, MOE, and cEt | 19 | 5769 | 5784 | 4636 |
| 562036 | N/A | N/A | TAGACACAATGTATAT | Deoxy, MOE, and cEt | 17 | 5775 | 5790 | 4637 |
| 562037 | N/A | N/A | GGTTTCTTCACACATT | Deoxy, MOE, and cEt | 63 | 5799 | 5814 | 4638 |
| 562038 | N/A | N/A | CTCAGAAATTCATTGT | Deoxy, MOE, and cEt | 36 | 5818 | 5833 | 4639 |
| 562039 | N/A | N/A | CTTCTTCCAACTCAGA | Deoxy, MOE, and cEt | 56 | 5828 | 5843 | 4640 |
| 562040 | N/A | N/A | CTAACTCTTCTTCCAA | Deoxy, MOE, and cEt | 39 | 5834 | 5849 | 4641 |
| 562041 | N/A | N/A | AATGATCTAACTCTTC | Deoxy, MOE, and cEt | 33 | 5840 | 5855 | 4642 |
| 562042 | N/A | N/A | GAAAGTTAAATGATCT | Deoxy, MOE, and cEt | 3 | 5848 | 5863 | 4643 |
| 562043 | N/A | N/A | ATCTTAAAGTTACTTA | Deoxy, MOE, and cEt | 56 | 5900 | 5915 | 4644 |
| 562044 | N/A | N/A | TATGTGATCTTAAAGT | Deoxy, MOE, and cEt | 5 | 5906 | 5921 | 4645 |
| 562045 | N/A | N/A | AGTAACTATGTGATCT | Deoxy, MOE, and cEt | 60 | 5912 | 5927 | 4646 |
| 562046 | N/A | N/A | CTACTAAGTAACTATG | Deoxy, MOE, and cEt | 0 | 5918 | 5933 | 4647 |
| 562047 | N/A | N/A | TCTTTTCTACTAAGTA | Deoxy, MOE, and cEt | 18 | 5924 | 5939 | 4648 |
| 562048 | N/A | N/A | TATTACTCTTTTCTAC | Deoxy, MOE, and cEt | 3 | 5930 | 5945 | 4649 |
| 562049 | N/A | N/A | GCTGGGTATTACTCTT | Deoxy, MOE, and cEt | 76 | 5936 | 5951 | 4650 |
| 562050 | N/A | N/A | TTGCTTGCTGGGTATT | Deoxy, MOE, and cEt | 77 | 5942 | 5957 | 190 |
| 562051 | N/A | N/A | TAAAGTTTGCTTGCTG | Deoxy, MOE, and cEt | 58 | 5948 | 5963 | 4651 |
| 562052 | N/A | N/A | CTATTGTAAAGTTTGC | Deoxy, MOE, and cEt | 16 | 5954 | 5969 | 4652 |
| 562053 | N/A | N/A | AAGGATCTATTGTAAA | Deoxy, MOE, and cEt | 5 | 5960 | 5975 | 4653 |
| 562054 | N/A | N/A | CTTATTTAAAAGGATC | Deoxy, MOE, and cEt | 0 | 5969 | 5984 | 4654 |
| 562055 | N/A | N/A | TAGGACCTTATTTAAA | Deoxy, MOE, and cEt | 0 | 5975 | 5990 | 4655 |
| 562056 | N/A | N/A | ATTTCCTAGGACCTTA | Deoxy, MOE, and cEt | 10 | 5981 | 5996 | 4656 |
| 562057 | N/A | N/A | CATGAATGATATTTCC | Deoxy, MOE, and cEt | 39 | 5991 | 6006 | 4657 |

TABLE 30-continued

Inhibition of ANGPTL3 mRNA by oligonucleotides targeting SEQ ID NO: 1 and 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 562058 | N/A | N/A | TGCTGGCATGAATGAT | Deoxy, MOE, and cEt | 62 | 5997 | 6012 | 4658 |
| 562059 | N/A | N/A | TTTTGATGCTGGCATG | Deoxy, MOE, and cEt | 74 | 6003 | 6018 | 4659 |
| 562060 | N/A | N/A | TTAGTTTTTGATGCT | Deoxy, MOE, and cEt | 25 | 6009 | 6024 | 4660 |
| 562061 | N/A | N/A | GCATTATTAGTGTTAG | Deoxy, MOE, and cEt | 44 | 6021 | 6036 | 4661 |
| 562062 | N/A | N/A | TATCTTGCATTATTAG | Deoxy, MOE, and cEt | 35 | 6027 | 6042 | 4662 |
| 562063 | N/A | N/A | ATATAATATCTTGCAT | Deoxy, MOE, and cEt | 0 | 6033 | 6048 | 4663 |
| 562064 | N/A | N/A | CATTGACAGTAAGAAA | Deoxy, MOE, and cEt | 0 | 6057 | 6072 | 4664 |
| 562065 | N/A | N/A | AGTTTTTCTCATTGAC | Deoxy, MOE, and cEt | 62 | 6066 | 6081 | 4665 |
| 562143 | N/A | N/A | ATGGATATCTCTTAAC | Deoxy, MOE, and cEt | 18 | 6869 | 6884 | 4666 |
| 562144 | N/A | N/A | TATTTGATGGATATCT | Deoxy, MOE, and cEt | 35 | 6875 | 6890 | 4667 |
| 562145 | N/A | N/A | ACATTGTATTTGATGG | Deoxy, MOE, and cEt | 41 | 6881 | 6896 | 4668 |
| 562146 | N/A | N/A | GTTGATACATTGTATT | Deoxy, MOE, and cEt | 8 | 6887 | 6902 | 4669 |
| 562147 | N/A | N/A | GTTTAGGTTGATACAT | Deoxy, MOE, and cEt | 35 | 6893 | 6908 | 4670 |
| 562148 | N/A | N/A | CATCCAGTTTAGGTTG | Deoxy, MOE, and cEt | 59 | 6899 | 6914 | 4671 |
| 562149 | N/A | N/A | CCCCAGCATCCAGTTT | Deoxy, MOE, and cEt | 37 | 6905 | 6920 | 4672 |
| 562150 | N/A | N/A | AAAGAACCCCAGCATC | Deoxy, MOE, and cEt | 35 | 6911 | 6926 | 4673 |
| 562151 | N/A | N/A | GTGTAAAAAGAACCCC | Deoxy, MOE, and cEt | 33 | 6917 | 6932 | 4674 |
| 562152 | N/A | N/A | TATAGGGTGTAAAAAG | Deoxy, MOE, and cEt | 0 | 6923 | 6938 | 4675 |
| 562153 | N/A | N/A | GTCTTTTATAGGGTGT | Deoxy, MOE, and cEt | 75 | 6929 | 6944 | 191 |
| 562154 | N/A | N/A | AGGTATGTCTTTTATA | Deoxy, MOE, and cEt | 21 | 6935 | 6950 | 4676 |
| 562155 | N/A | N/A | TTGTCTTAGGTATGTC | Deoxy, MOE, and cEt | 84 | 6942 | 6957 | 192 |
| 562156 | N/A | N/A | CTCTGATTGTCTTAGG | Deoxy, MOE, and cEt | 77 | 6948 | 6963 | 193 |
| 562157 | N/A | N/A | GTATTCTCTGATTGT | Deoxy, MOE, and cEt | 77 | 6954 | 6969 | 194 |
| 562158 | N/A | N/A | AGTCCATATTTGTATT | Deoxy, MOE, and cEt | 49 | 6965 | 6980 | 4677 |
| 562159 | N/A | N/A | TAATCAAGTCCATATT | Deoxy, MOE, and cEt | 19 | 6971 | 6986 | 4678 |
| 562160 | N/A | N/A | ATCTAATAATCAAGTC | Deoxy, MOE, and cEt | 5 | 6977 | 6992 | 4679 |
| 562161 | N/A | N/A | CCTTCTATATTATCTA | Deoxy, MOE, and cEt | 38 | 6988 | 7003 | 4680 |
| 562162 | N/A | N/A | TAATAAACCTTCTATA | Deoxy, MOE, and cEt | 8 | 6995 | 7010 | 4681 |
| 562163 | N/A | N/A | GATCACATCTAAGAAA | Deoxy, MOE, and cEt | 25 | 7013 | 7028 | 4682 |
| 562164 | N/A | N/A | TACCATGATCACATCT | Deoxy, MOE, and cEt | 66 | 7019 | 7034 | 4683 |
| 562165 | N/A | N/A | CTGCAATACCATGATC | Deoxy, MOE, and cEt | 54 | 7025 | 7040 | 4684 |
| 562166 | N/A | N/A | GTTCTCCTTTAAAACT | Deoxy, MOE, and cEt | 0 | 7039 | 7054 | 4685 |
| 562167 | N/A | N/A | GAGATTGTTCTCCTTT | Deoxy, MOE, and cEt | 7 | 7045 | 7060 | 4686 |
| 562168 | N/A | N/A | AAACAGGAGATTGTTC | Deoxy, MOE, and cEt | 6 | 7051 | 7066 | 4687 |
| 562169 | N/A | N/A | TCTCTTAAACAGGAGA | Deoxy, MOE, and cEt | 1 | 7057 | 7072 | 4688 |
| 562170 | N/A | N/A | CATGTATCTCTTAAAC | Deoxy, MOE, and cEt | 40 | 7063 | 7078 | 4689 |

TABLE 30-continued

Inhibition of ANGPTL3 mRNA by oligonucleotides targeting SEQ ID NO: 1 and 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 562171 | N/A | N/A | CGTAAATATTTCAGCA | Deoxy, MOE, and cEt | 30 | 7077 | 7092 | 4690 |
| 562172 | N/A | N/A | TAACTCCGTAAATATT | Deoxy, MOE, and cEt | 0 | 7083 | 7098 | 4691 |
| 562173 | N/A | N/A | GACCTTTAACTCCGTA | Deoxy, MOE, and cEt | 68 | 7089 | 7104 | 4692 |
| 562174 | N/A | N/A | TCCAGTGACCTTTAAC | Deoxy, MOE, and cEt | 6 | 7095 | 7110 | 4693 |
| 562175 | N/A | N/A | CACCAGTCTGGAGTCC | Deoxy, MOE, and cEt | 52 | 7108 | 7123 | 4694 |
| 562176 | N/A | N/A | TTCTATCACCAGTCTG | Deoxy, MOE, and cEt | 67 | 7114 | 7129 | 4695 |
| 562177 | N/A | N/A | ATCTTACCAAACTATT | Deoxy, MOE, and cEt | 23 | 7171 | 7186 | 4696 |
| 562178 | N/A | N/A | AGAATCATCTTACCAA | Deoxy, MOE, and cEt | 55 | 7177 | 7192 | 4697 |
| 562179 | N/A | N/A | GAATGTAAGAATCATC | Deoxy, MOE, and cEt | 0 | 7184 | 7199 | 4698 |
| 562180 | N/A | N/A | GTGTTATTTAAGAATG | Deoxy, MOE, and cEt | 0 | 7195 | 7210 | 4699 |
| 562181 | N/A | N/A | TTTTTCTTAGATGGCG | Deoxy, MOE, and cEt | 82 | 7210 | 7225 | 195 |
| 562182 | N/A | N/A | GTTTATGTTAAAGCAT | Deoxy, MOE, and cEt | 8 | 7225 | 7240 | 4700 |
| 562183 | N/A | N/A | AGTAATGTTTATGTTA | Deoxy, MOE, and cEt | 4 | 7231 | 7246 | 4701 |
| 562184 | N/A | N/A | GTAGCATTTTTCAGT | Deoxy, MOE, and cEt | 58 | 7244 | 7259 | 4702 |
| 562185 | N/A | N/A | GCAAATGTAGCATTTT | Deoxy, MOE, and cEt | 61 | 7250 | 7265 | 4703 |
| 562186 | N/A | N/A | GTTGTGGCAAATGTAG | Deoxy, MOE, and cEt | 32 | 7256 | 7271 | 4704 |
| 562187 | N/A | N/A | TATGAAGTTGTGGCAA | Deoxy, MOE, and cEt | 54 | 7262 | 7277 | 4705 |
| 562188 | N/A | N/A | GATTTCACTTGACATT | Deoxy, MOE, and cEt | 19 | 7279 | 7294 | 4706 |
| 562189 | N/A | N/A | GCTTGAGATTTCACTT | Deoxy, MOE, and cEt | 42 | 7285 | 7300 | 4707 |
| 562190 | N/A | N/A | TTTGGAGCTTGAGATT | Deoxy, MOE, and cEt | 22 | 7291 | 7306 | 4708 |
| 562191 | N/A | N/A | AATATCTTTGGAGCTT | Deoxy, MOE, and cEt | 36 | 7297 | 7312 | 4709 |
| 562192 | N/A | N/A | AGGAATAATATCTTTG | Deoxy, MOE, and cEt | 5 | 7303 | 7318 | 4710 |
| 562193 | N/A | N/A | ATTTAGTAATAGGAAT | Deoxy, MOE, and cEt | 5 | 7313 | 7328 | 4711 |
| 562194 | N/A | N/A | CATCAGATTTAGTAAT | Deoxy, MOE, and cEt | 0 | 7319 | 7334 | 4712 |
| 562195 | N/A | N/A | GTTATTACATCAGATT | Deoxy, MOE, and cEt | 23 | 7326 | 7341 | 4713 |
| 562196 | N/A | N/A | GCCTAGAATCAATAAA | Deoxy, MOE, and cEt | 8 | 7344 | 7359 | 4714 |
| 562197 | N/A | N/A | AGGAATGCCTAGAATC | Deoxy, MOE, and cEt | 2 | 7350 | 7365 | 4715 |
| 562198 | N/A | N/A | TTCAGCAGGAATGCCT | Deoxy, MOE, and cEt | 46 | 7356 | 7371 | 4716 |
| 562199 | N/A | N/A | TTACCTGATATAACAT | Deoxy, MOE, and cEt | 41 | 7460 | 7475 | 4717 |
| 562200 | N/A | N/A | CAGGTTTTACCTGATA | Deoxy, MOE, and cEt | 31 | 7466 | 7481 | 4718 |
| 562201 | N/A | N/A | CTTAGACAGGTTTTAC | Deoxy, MOE, and cEt | 41 | 7472 | 7487 | 4719 |
| 562202 | N/A | N/A | ATTCTCCTTAGACAGG | Deoxy, MOE, and cEt | 37 | 7478 | 7493 | 4720 |
| 562203 | N/A | N/A | CTGTCTATTCTCCTTA | Deoxy, MOE, and cEt | 53 | 7484 | 7499 | 4721 |
| 562204 | N/A | N/A | TAACTACTGTCTATTC | Deoxy, MOE, and cEt | 5 | 7490 | 7505 | 4722 |
| 562205 | N/A | N/A | TTGAACTAACTACTGT | Deoxy, MOE, and cEt | 3 | 7496 | 7511 | 4723 |
| 562206 | N/A | N/A | AGTAAGTTGAACTAAC | Deoxy, MOE, and cEt | 11 | 7502 | 7517 | 4724 |

TABLE 30-continued

Inhibition of ANGPTL3 mRNA by oligonucleotides targeting SEQ ID NO: 1 and 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 562207 | N/A | N/A | GTAATGAGTAAGTTGA | Deoxy, MOE, and cEt | 37 | 7508 | 7523 | 4725 |
| 562208 | N/A | N/A | TAATCTTCCTAATACG | Deoxy, MOE, and cEt | 5 | 7523 | 7538 | 4726 |
| 562209 | N/A | N/A | ACCAGGTTAATCTTCC | Deoxy, MOE, and cEt | 71 | 7530 | 7545 | 4727 |
| 562210 | N/A | N/A | ATGATAACCAGGTTAA | Deoxy, MOE, and cEt | 42 | 7536 | 7551 | 4728 |
| 562211 | N/A | N/A | CGAATACTCATATATA | Deoxy, MOE, and cEt | 20 | 7576 | 7591 | 4729 |
| 562212 | N/A | N/A | TTTATACGAATACTCA | Deoxy, MOE, and cEt | 17 | 7582 | 7597 | 4730 |
| 562213 | N/A | N/A | ATTATATTTATACGAA | Deoxy, MOE, and cEt | 0 | 7588 | 7603 | 4731 |
| 562214 | N/A | N/A | GGTAAAAGTATTATAT | Deoxy, MOE, and cEt | 0 | 7597 | 7612 | 4732 |
| 562215 | N/A | N/A | GAGAATATTGAGTAAA | Deoxy, MOE, and cEt | 9 | 7624 | 7639 | 4733 |
| 562216 | N/A | N/A | CAGATTATTTTAGAGG | Deoxy, MOE, and cEt | 16 | 7645 | 7660 | 4734 |
| 562217 | N/A | N/A | TCACTTCAGATTATTT | Deoxy, MOE, and cEt | 34 | 7651 | 7666 | 4735 |
| 562218 | N/A | N/A | TAATAGTCACTTCAGA | Deoxy, MOE, and cEt | 33 | 7657 | 7672 | 4736 |
| 562219 | N/A | N/A | TATTGATAATAGTCAC | Deoxy, MOE, and cEt | 1 | 7663 | 7678 | 4737 |
| 562297 | N/A | N/A | TACTATTTGTAATCAA | Deoxy, MOE, and cEt | 0 | 8493 | 8508 | 4738 |
| 562298 | N/A | N/A | CTTGCTTATTTTACTA | Deoxy, MOE, and cEt | 24 | 8504 | 8519 | 4739 |
| 562299 | N/A | N/A | CATCTGTTATTTTATC | Deoxy, MOE, and cEt | 0 | 8519 | 8534 | 4740 |
| 562300 | N/A | N/A | ATGTGCTTTTTGGATT | Deoxy, MOE, and cEt | 20 | 8540 | 8555 | 4741 |
| 562301 | N/A | N/A | GGATTTTGTATGTGC | Deoxy, MOE, and cEt | 64 | 8550 | 8565 | 4742 |
| 562302 | N/A | N/A | CATCATTCATGGATTT | Deoxy, MOE, and cEt | 55 | 8560 | 8575 | 4743 |
| 562303 | N/A | N/A | CTTAGACATCATTCAT | Deoxy, MOE, and cEt | 32 | 8566 | 8581 | 4744 |
| 562304 | N/A | N/A | TGAGTACTTAGACATC | Deoxy, MOE, and cEt | 58 | 8572 | 8587 | 4745 |
| 562305 | N/A | N/A | TATAAGTGAGTACTTA | Deoxy, MOE, and cEt | 3 | 8578 | 8593 | 4746 |
| 562306 | N/A | N/A | CTACTTTATAAGTGAG | Deoxy, MOE, and cEt | 0 | 8584 | 8599 | 4747 |
| 562307 | N/A | N/A | TGAATGTCTTCTACTT | Deoxy, MOE, and cEt | 42 | 8594 | 8609 | 4748 |
| 562308 | N/A | N/A | TATAATAATGAATGTC | Deoxy, MOE, and cEt | 2 | 8602 | 8617 | 4749 |
| 562309 | N/A | N/A | GTACTGAGCATTTAAA | Deoxy, MOE, and cEt | 24 | 8625 | 8640 | 4750 |
| 562310 | N/A | N/A | CAAATAGTACTGAGCA | Deoxy, MOE, and cEt | 48 | 8631 | 8646 | 4751 |
| 562311 | N/A | N/A | AATGGTCAAATAGTAC | Deoxy, MOE, and cEt | 0 | 8637 | 8652 | 4752 |
| 562312 | N/A | N/A | GTAGTTTGAATACAAA | Deoxy, MOE, and cEt | 9 | 8660 | 8675 | 4753 |
| 562313 | N/A | N/A | TCACTGGTAGTTTGAA | Deoxy, MOE, and cEt | 56 | 8666 | 8681 | 4754 |
| 562314 | N/A | N/A | GGGCTTTCACTGGTAG | Deoxy, MOE, and cEt | 70 | 8672 | 8687 | 196 |
| 562315 | N/A | N/A | TAGGTAGGGCTTTCAC | Deoxy, MOE, and cEt | 50 | 8678 | 8693 | 4755 |
| 562316 | N/A | N/A | ACCTTCTAGGTAGGGC | Deoxy, MOE, and cEt | 47 | 8684 | 8699 | 4756 |
| 562317 | N/A | N/A | GAGTATACCTTCTAGG | Deoxy, MOE, and cEt | 38 | 8690 | 8705 | 4757 |
| 562318 | N/A | N/A | ATCACTGAGTATACCT | Deoxy, MOE, and cEt | 61 | 8696 | 8711 | 4758 |
| 562319 | N/A | N/A | AAACTTATCACTGAGT | Deoxy, MOE, and cEt | 0 | 8702 | 8717 | 4759 |

TABLE 30-continued

Inhibition of ANGPTL3 mRNA by oligonucleotides targeting SEQ ID NO: 1 and 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 562320 | N/A | N/A | GCTACAAAACTTATCA | Deoxy, MOE, and cEt | 8 | 8708 | 8723 | 4760 |
| 562321 | N/A | N/A | TTTGGAGCTACAAAAC | Deoxy, MOE, and cEt | 0 | 8714 | 8729 | 4761 |
| 562322 | N/A | N/A | AGAAGATTTGGAGCTA | Deoxy, MOE, and cEt | 24 | 8720 | 8735 | 4762 |
| 562323 | N/A | N/A | ACTATTAGAAGATTTG | Deoxy, MOE, and cEt | 0 | 8726 | 8741 | 4763 |
| 562324 | N/A | N/A | ACACTCACTATTAGAA | Deoxy, MOE, and cEt | 0 | 8732 | 8747 | 4764 |
| 562325 | N/A | N/A | AGCCTTTTATTTTGGG | Deoxy, MOE, and cEt | 37 | 8751 | 8766 | 4765 |
| 562326 | N/A | N/A | CCTGTCAGCCTTTTAT | Deoxy, MOE, and cEt | 0 | 8757 | 8772 | 4766 |
| 562327 | N/A | N/A | GACTTACCTGTCAGCC | Deoxy, MOE, and cEt | 47 | 8763 | 8778 | 4767 |
| 562328 | N/A | N/A | ATTCTCGACTTACCTG | Deoxy, MOE, and cEt | 12 | 8769 | 8784 | 4768 |
| 562329 | N/A | N/A | GTGAGTATTCTCGACT | Deoxy, MOE, and cEt | 25 | 8775 | 8790 | 4769 |
| 562330 | N/A | N/A | AATTAAGTGAGTATTC | Deoxy, MOE, and cEt | 0 | 8781 | 8796 | 4770 |
| 562331 | N/A | N/A | TACCAGAATTAAGTGA | Deoxy, MOE, and cEt | 0 | 8787 | 8802 | 4771 |
| 562332 | N/A | N/A | GCTTTCTTACCAGAAT | Deoxy, MOE, and cEt | 23 | 8794 | 8809 | 4772 |
| 562333 | N/A | N/A | TGGGTTGCTTTCTTAC | Deoxy, MOE, and cEt | 0 | 8800 | 8815 | 4773 |
| 562334 | N/A | N/A | TACAAGTACAAATGGG | Deoxy, MOE, and cEt | 36 | 8812 | 8827 | 4774 |
| 562335 | N/A | N/A | GGTAAATACAAGTACA | Deoxy, MOE, and cEt | 19 | 8818 | 8833 | 4775 |
| 562336 | N/A | N/A | ATTGCTGGTAAATACA | Deoxy, MOE, and cEt | 13 | 8824 | 8839 | 4776 |
| 562337 | N/A | N/A | TTAAGGATTGCTGGTA | Deoxy, MOE, and cEt | 43 | 8830 | 8845 | 4777 |
| 562338 | N/A | N/A | GCTTCATTTTAAGGAT | Deoxy, MOE, and cEt | 12 | 8838 | 8853 | 4778 |
| 562339 | N/A | N/A | GTAGGAAGCTTCATTT | Deoxy, MOE, and cEt | 23 | 8845 | 8860 | 4779 |
| 562340 | N/A | N/A | GAGTTAGTAGGAAGCT | Deoxy, MOE, and cEt | 58 | 8851 | 8866 | 4780 |
| 562341 | N/A | N/A | GCTATTGAGTTAGTAG | Deoxy, MOE, and cEt | 21 | 8857 | 8872 | 4781 |
| 562342 | N/A | N/A | CTTATTGCTATTGAGT | Deoxy, MOE, and cEt | 34 | 8863 | 8878 | 4782 |
| 562343 | N/A | N/A | TATTGTCTTATTGCTA | Deoxy, MOE, and cEt | 17 | 8869 | 8884 | 4783 |
| 562344 | N/A | N/A | ATTCACTATTGTCTTA | Deoxy, MOE, and cEt | 22 | 8875 | 8890 | 4784 |
| 562345 | N/A | N/A | ATCACAATCCTTTTTA | Deoxy, MOE, and cEt | 18 | 8925 | 8940 | 4785 |
| 562346 | N/A | N/A | TTCTTCATCACAATCC | Deoxy, MOE, and cEt | 43 | 8931 | 8946 | 4786 |
| 562347 | N/A | N/A | AGATTGTTCTTCATCA | Deoxy, MOE, and cEt | 35 | 8937 | 8952 | 4787 |
| 562348 | N/A | N/A | TATAAATAGATTGTTC | Deoxy, MOE, and cEt | 10 | 8944 | 8959 | 4788 |
| 562349 | N/A | N/A | GGTTCTTAATAACTTT | Deoxy, MOE, and cEt | 31 | 9011 | 9026 | 4789 |
| 562350 | N/A | N/A | AAGCATGGTTCTTAAT | Deoxy, MOE, and cEt | 12 | 9017 | 9032 | 4790 |
| 562351 | N/A | N/A | CTTTGTAGAAAAGAC | Deoxy, MOE, and cEt | 0 | 9066 | 9081 | 4791 |
| 562352 | N/A | N/A | TATGCTTTCTTTGTAG | Deoxy, MOE, and cEt | 26 | 9074 | 9089 | 4792 |
| 562353 | N/A | N/A | CTTAATGTATGCTTTC | Deoxy, MOE, and cEt | 55 | 9081 | 9096 | 4793 |
| 562354 | N/A | N/A | GTATTTGCTTAATGTA | Deoxy, MOE, and cEt | 0 | 9088 | 9103 | 4794 |
| 562355 | N/A | N/A | CCTTTGGTATTTGCTT | Deoxy, MOE, and cEt | 54 | 9094 | 9109 | 4795 |

TABLE 30-continued

Inhibition of ANGPTL3 mRNA by oligonucleotides targeting SEQ ID NO: 1 and 2

| ISIS NO | SEQ ID NO: 1 Start Site | SEQ ID NO: 1 Stop Site | Sequence | Chemistry | % inhibition | SEQ ID NO: 2 Start Site | SEQ ID NO: 2 Stop Site | SEQ ID NO |
|---|---|---|---|---|---|---|---|---|
| 562356 | N/A | N/A | ACCTGGCCTTTGGTAT | Deoxy, MOE, and cEt | 0 | 9100 | 9115 | 4796 |
| 562357 | N/A | N/A | ATGTAAACCTGGCCTT | Deoxy, MOE, and cEt | 1 | 9106 | 9121 | 4797 |
| 562358 | N/A | N/A | CTTCAAATGTAAACCT | Deoxy, MOE, and cEt | 0 | 9112 | 9127 | 4798 |
| 562359 | N/A | N/A | GTAATAATAATGTCAC | Deoxy, MOE, and cEt | 0 | 9131 | 9146 | 4799 |
| 562360 | N/A | N/A | AGACTTGAGTAATAAT | Deoxy, MOE, and cEt | 0 | 9139 | 9154 | 4800 |
| 562361 | N/A | N/A | TCCTAGAGACTTGAGT | Deoxy, MOE, and cEt | 25 | 9145 | 9160 | 4801 |
| 562362 | N/A | N/A | AAGTATTCCTAGAGAC | Deoxy, MOE, and cEt | 28 | 9151 | 9166 | 4802 |
| 562363 | N/A | N/A | TGTGTTAAGTATTCCT | Deoxy, MOE, and cEt | 50 | 9157 | 9172 | 4803 |
| 562364 | N/A | N/A | AAGAGATGTGTTAAGT | Deoxy, MOE, and cEt | 21 | 9163 | 9178 | 4804 |
| 562365 | N/A | N/A | ACAGTCAAGAGATGTG | Deoxy, MOE, and cEt | 74 | 9169 | 9184 | 197 |
| 562366 | N/A | N/A | CCATATACAGTCAAGA | Deoxy, MOE, and cEt | 49 | 9175 | 9190 | 4805 |
| 562367 | N/A | N/A | TAACATCCATATACAG | Deoxy, MOE, and cEt | 16 | 9181 | 9196 | 4806 |
| 562368 | N/A | N/A | CTATTTATTAACATCC | Deoxy, MOE, and cEt | 2 | 9189 | 9204 | 4807 |
| 562369 | N/A | N/A | TGTCAGCTATTTATTA | Deoxy, MOE, and cEt | 22 | 9195 | 9210 | 4808 |
| 562370 | N/A | N/A | CTTTACTGTCAGCTAT | Deoxy, MOE, and cEt | 56 | 9201 | 9216 | 4809 |
| 562371 | N/A | N/A | GATAAACTTTACTGTC | Deoxy, MOE, and cEt | 37 | 9207 | 9222 | 4810 |
| 562372 | N/A | N/A | CTTTATATGGATAAAC | Deoxy, MOE, and cEt | 31 | 9216 | 9231 | 4811 |
| 562373 | N/A | N/A | GCAAGTCTTTATATGG | Deoxy, MOE, and cEt | 62 | 9222 | 9237 | 4812 |
| 560990 | 709 | 724 | TTCTTGGTGCTCTTGG | Deoxy, MOE, and cEt | 74 | 6722 | 6737 | 111 |
| 337487 | 804 | 823 | CACTTGTATGTTCACCTCTG | 5-10-5 MOE | 30 | 7389 | 7408 | 28 |
| 233717 | 889 | 908 | TGAATTAATGTCCATGGACT | 5-10-5 MOE | 38 | 7876 | 7895 | 14 |

Example 6: Antisense Inhibition of Human ANGPTL3 in Hep3B Cells by MOE Gapmers

Additional antisense oligonucleotides were designed targeting an ANGPTL3 nucleic acid and were tested for their effects on ANGPTL3 mRNA in vitro. Cultured Hep3B cells at a density of 20,000 cells per well were transfected using electroporation with 4,500 nM antisense oligonucleotide. After a treatment period of approximately 24 hours, RNA was isolated from the cells and ANGPTL3mRNA levels were measured by quantitative real-time PCR. Human primer probe set RTS3492_MGB was used to measure mRNA levels. ANGPTL3 mRNA levels were adjusted according to total RNA content, as measured by RIBOGREEN®. Results are presented as percent inhibition of ANGPTL3, relative to untreated control cells.

The newly designed chimeric antisense oligonucleotides in the Tables below were designed as 5-10-5 MOE or 3-10-4 MOE gapmers. The 5-10-5 MOE gapmers are 20 nucleosides in length, wherein the central gap segment comprises often 2'-deoxynucleosides and is flanked by wing segments on the 5' direction and the 3' direction comprising five nucleosides each. The 3-10-4 MOE gapmers are 17 nucleosides in length, wherein the central gap segment comprises often 2'-deoxynucleosides and is flanked by wing segments on the 5' direction and the 3' direction comprising three and four nucleosides respectively. Each nucleoside in the 5' wing segment and each nucleoside in the 3' wing segment has a 2'-MOE modification. Each nucleoside in the 5' wing segment and each nucleoside in the 3' wing segment has a 2'-MOE modification. The internucleoside linkages throughout each gapmer are phosphorothioate (P=S) linkages. All cytosine residues throughout each gapmer are 5-methylcytosines. "Start site" indicates the 5'-most nucleoside to which the gapmer is targeted in the human gene sequence. "Stop site" indicates the 3'-most nucleoside to which the gapmer is targeted human gene sequence. Each gapmer listed in the Tables below is targeted to either the human ANGPTL3 mRNA, designated herein as SEQ ID NO: 1 (GENBANK Accession No. NM_014495.2) or the human ANGPTL3 genomic sequence, designated herein as SEQ ID NO: 2 (GENBANK Accession No. NT_032977.9 truncated from nucleotides 33032001 to 33046000). 'n/a' indicates that the antisense oligonucleotide does not target that particular gene sequence with 100% complementarity.

TABLE 31

Inhibition of ANGPTL3 mRNA by MOE gapmers targeting SEQ ID NO: 1 and 2

| ISIS NO | SEQ ID NO: 1 Start Site | SEQ ID NO: 1 Stop Site | Sequence | Motif | % inhibition | SEQ ID NO: 2 Start Site | SEQ ID NO: 2 Stop Site | SEQ ID NO |
|---|---|---|---|---|---|---|---|---|
| 582715 | N/A | N/A | CTGGGTATTACTCTTTTCTA | 5-10-5 | 60 | 5931 | 5950 | 4813 |
| 582716 | N/A | N/A | CTTGCTGGGTATTACTCTTT | 5-10-5 | 59 | 5935 | 5954 | 4814 |
| 582717 | N/A | N/A | TGCTTGCTGGGTATTACTCT | 5-10-5 | 59 | 5937 | 5956 | 4815 |
| 582718 | N/A | N/A | CATGAATGATATTTCCTAGG | 5-10-5 | 39 | 5987 | 6006 | 4816 |
| 582719 | N/A | N/A | GGCATGAATGATATTTCCTA | 5-10-5 | 60 | 5989 | 6008 | 4817 |
| 582720 | N/A | N/A | CTGGCATGAATGATATTTCC | 5-10-5 | 46 | 5991 | 6010 | 4818 |
| 582721 | N/A | N/A | TGCTGGCATGAATGATATTT | 5-10-5 | 32 | 5993 | 6012 | 4819 |
| 582722 | N/A | N/A | AAGTCCATATTTGTATTTCT | 5-10-5 | 50 | 6962 | 6981 | 4820 |
| 582723 | N/A | N/A | GCAAATGTAGCATTTTTTCA | 5-10-5 | 32 | 7246 | 7265 | 4821 |
| 582724 | N/A | N/A | GGCAAATGTAGCATTTTTTC | 5-10-5 | 55 | 7247 | 7266 | 4822 |
| 582725 | N/A | N/A | GTGGCAAATGTAGCATTTTT | 5-10-5 | 62 | 7249 | 7268 | 203 |
| 582726 | N/A | N/A | CTGGTCCTTTTAACTTCCAA | 5-10-5 | 40 | 8366 | 8385 | 4823 |
| 582727 | N/A | N/A | CCTGGTCCTTTTAACTTCCA | 5-10-5 | 58 | 8367 | 8386 | 4824 |
| 582728 | N/A | N/A | TTCCTGGTCCTTTTAACTTC | 5-10-5 | 32 | 8369 | 8388 | 4825 |
| 582729 | N/A | N/A | TGCTTAATGTATGCTTTCTT | 5-10-5 | 51 | 9079 | 9098 | 4826 |
| 582730 | N/A | N/A | CCGTAAGTTTATCTTCCTTT | 5-10-5 | 58 | 10136 | 10155 | 4827 |
| 582731 | N/A | N/A | CCCCGTAAGTTTATCTTCCT | 5-10-5 | 51 | 10138 | 10157 | 4828 |
| 582732 | N/A | N/A | CACAAATATGTTCATTCTTA | 5-10-5 | 22 | 11189 | 11208 | 4829 |
| 582733 | N/A | N/A | GCCACAAATATGTTCATTCT | 5-10-5 | 71 | 11191 | 11210 | 204 |
| 582734 | N/A | N/A | AAACTTTAACTCGATGCCAC | 5-10-5 | 51 | 11206 | 11225 | 4830 |
| 582735 | N/A | N/A | ATAAACTTTAACTCGATGCC | 5-10-5 | 57 | 11208 | 11227 | 4831 |
| 582736 | N/A | N/A | ATGCTTGTCAGGCTGTTTAA | 5-10-5 | 56 | 11311 | 11330 | 4832 |
| 582737 | N/A | N/A | GTCACCATATAACTTGGGCA | 5-10-5 | 48 | 11562 | 11581 | 4833 |
| 582738 | N/A | N/A | AGGTCACCATATAACTTGGG | 5-10-5 | 44 | 11564 | 11583 | 4834 |
| 582766 | N/A | N/A | GCTGGGTATTACTCTTT | 3-10-4 | 55 | 5935 | 5951 | 4835 |
| 582767 | N/A | N/A | GCATGAATGATATTTCC | 3-10-4 | 4 | 5991 | 6007 | 4836 |
| 582768 | N/A | N/A | GGCAAATGTAGCATTTT | 3-10-4 | 33 | 7250 | 7266 | 4837 |
| 582769 | N/A | N/A | CTGGTCCTTTTAACTTC | 3-10-4 | 29 | 8369 | 8385 | 4838 |
| 582770 | N/A | N/A | GTAAGTTTATCTTCCTT | 3-10-4 | 26 | 10137 | 10153 | 4839 |
| 582771 | N/A | N/A | ACTTTAACTCGATGCCA | 3-10-4 | 42 | 11207 | 11223 | 4840 |
| 582772 | N/A | N/A | AACTTTAACTCGATGCC | 3-10-4 | 55 | 11208 | 11224 | 4841 |
| 582773 | N/A | N/A | AAACTTTAACTCGATGC | 3-10-4 | 1 | 11209 | 11225 | 4842 |
| 582774 | N/A | N/A | GCTTGTCAGGCTGTTTA | 3-10-4 | 65 | 11312 | 11328 | 208 |
| 582775 | N/A | N/A | CACCATATAACTTGGGC | 3-10-4 | 38 | 11563 | 11579 | 4843 |
| 582776 | N/A | N/A | TCACCATATAACTTGGG | 3-10-4 | 37 | 11564 | 11580 | 4844 |
| 582777 | N/A | N/A | GTCACCATATAACTTGG | 3-10-4 | 31 | 11565 | 11581 | 4845 |

TABLE 31-continued

Inhibition of ANGPTL3 mRNA by MOE gapmers targeting SEQ ID NO: 1 and 2

| ISIS NO | SEQ ID NO: 1 Start Site | SEQ ID NO: 1 Stop Site | Sequence | Motif | % inhibition | SEQ ID NO: 2 Start Site | SEQ ID NO: 2 Stop Site | SEQ ID NO |
|---|---|---|---|---|---|---|---|---|
| 582702 | 139 | 158 | CTTGATTTTGGCTCTGGAGA | 5-10-5 | 53 | 3243 | 3262 | 4846 |
| 582739 | 140 | 156 | TGATTTTGGCTCTGGAG | 3-10-4 | 41 | 3244 | 3260 | 4847 |
| 582703 | 141 | 160 | ATCTTGATTTTGGCTCTGGA | 5-10-5 | 64 | 3245 | 3264 | 198 |
| 582740 | 305 | 321 | ACTGGTTTGCAGCGATA | 3-10-4 | 58 | 3409 | 3425 | 4848 |
| 582704 | 306 | 325 | TTTCACTGGTTTGCAGCGAT | 5-10-5 | 60 | 3410 | 3429 | 4849 |
| 582741 | 306 | 322 | CACTGGTTTGCAGCGAT | 3-10-4 | 57 | 3410 | 3426 | 4850 |
| 582742 | 307 | 323 | TCACTGGTTTGCAGCGA | 3-10-4 | 60 | 3411 | 3427 | 4851 |
| 582705 | 706 | 725 | GTTCTTGGTGCTCTTGGCTT | 5-10-5 | 78 | 6719 | 6738 | 199 |
| 544120 | 707 | 726 | AGTTCTTGGTGCTCTTGGCT | 5-10-5 | 75 | 6720 | 6739 | 15 |
| 582743 | 707 | 723 | TCTTGGTGCTCTTGGCT | 3-10-4 | 63 | 6720 | 6736 | 205 |
| 582706 | 708 | 727 | TAGTTCTTGGTGCTCTTGGC | 5-10-5 | 69 | 6721 | 6740 | 200 |
| 582744 | 708 | 724 | TTCTTGGTGCTCTTGGC | 3-10-4 | 51 | 6721 | 6737 | 4852 |
| 582745 | 709 | 725 | GTTCTTGGTGCTCTTGG | 3-10-4 | 50 | 6722 | 6738 | 4853 |
| 337487 | 804 | 823 | CACTTGTATGTTCACCTCTG | 5-10-5 | 25 | 7389 | 7408 | 28 |
| 233717 | 889 | 908 | TGAATTAATGTCCATGGACT | 5-10-5 | 22 | 7876 | 7895 | 14 |
| 582707 | 1054 | 1073 | TTGTCTTTCCAGTCTTCCAA | 5-10-5 | 42 | 9629 | 9648 | 4854 |
| 582708 | 1056 | 1075 | TGTTGTCTTTCCAGTCTTCC | 5-10-5 | 52 | 9631 | 9650 | 4855 |
| 582746 | 1140 | 1156 | CATTGCCAGTAATCGCA | 3-10-4 | 53 | 9715 | 9731 | 4856 |
| 582747 | 1141 | 1157 | ACATTGCCAGTAATCGC | 3-10-4 | 61 | 9716 | 9732 | 4857 |
| 582748 | 1142 | 1158 | GACATTGCCAGTAATCG | 3-10-4 | 34 | 9717 | 9733 | 4858 |
| 582709 | 1194 | 1213 | CTTTGTGATCCCAAGTAGAA | 5-10-5 | 28 | 9769 | 9788 | 4859 |
| 582749 | 1195 | 1211 | TTGTGATCCCAAGTAGA | 3-10-4 | 16 | 9770 | 9786 | 4860 |
| 582710 | 1196 | 1215 | TGCTTTGTGATCCCAAGTAG | 5-10-5 | 54 | 9771 | 9790 | 4861 |
| 582750 | 1196 | 1212 | TTTGTGATCCCAAGTAG | 3-10-4 | 19 | 9771 | 9787 | 4862 |
| 582751 | 1197 | 1213 | CTTTGTGATCCCAAGTA | 3-10-4 | 32 | 9772 | 9788 | 4863 |
| 582752 | 1260 | 1276 | CACACTCATCATGCCAC | 3-10-4 | 42 | 10232 | 10248 | 4864 |
| 582711 | 1268 | 1287 | GTTGTTTTCTCCACACTCAT | 5-10-5 | 51 | 10240 | 10259 | 4865 |
| 582712 | 1270 | 1289 | AGGTTGTTTTCTCCACACTC | 5-10-5 | 63 | 10242 | 10261 | 201 |
| 582753 | 1307 | 1323 | AGATTTTGCTCTTGGTT | 3-10-4 | 54 | 10279 | 10295 | 4866 |
| 582754 | 1308 | 1324 | TAGATTTTGCTCTTGGT | 3-10-4 | 52 | 10280 | 10296 | 4867 |
| 582755 | 1309 | 1325 | TTAGATTTTGCTCTTGG | 3-10-4 | 44 | 10281 | 10297 | 4868 |
| 582756 | 1310 | 1326 | CTTAGATTTTGCTCTTG | 3-10-4 | 34 | 10282 | 10298 | 4869 |
| 567320 | 1487 | 1506 | CCAGATTATTAGACCACATT | 5-10-5 | 77 | 10459 | 10478 | 93 |
| 582757 | 1488 | 1504 | AGATTATTAGACCACAT | 3-10-4 | 0 | 10460 | 10476 | 4870 |
| 582758 | 1489 | 1505 | CAGATTATTAGACCACA | 3-10-4 | 39 | 10461 | 10477 | 4871 |
| 582759 | 1490 | 1506 | CCAGATTATTAGACCAC | 3-10-4 | 63 | 10462 | 10478 | 206 |

TABLE 31-continued

Inhibition of ANGPTL3 mRNA by MOE gapmers targeting SEQ ID NO: 1 and 2

| ISIS NO | SEQ ID NO: 1 Start Site | SEQ ID NO: 1 Stop Site | Sequence | Motif | % inhibition | SEQ ID NO: 2 Start Site | SEQ ID NO: 2 Stop Site | SEQ ID NO |
|---|---|---|---|---|---|---|---|---|
| 582760 | 1491 | 1507 | ACCAGATTATTAGACCA | 3-10-4 | 31 | 10463 | 10479 | 4872 |
| 582761 | 1763 | 1779 | GCTCATATGATGCCTTT | 3-10-4 | 71 | 10735 | 10751 | 207 |
| 582713 | 1906 | 1925 | ACACATACTCTGTGCTGACG | 5-10-5 | 68 | 10878 | 10897 | 202 |
| 582762 | 1907 | 1923 | ACATACTCTGTGCTGAC | 3-10-4 | 57 | 10879 | 10895 | 4873 |
| 582714 | 1908 | 1927 | TTACACATACTCTGTGCTGA | 5-10-5 | 49 | 10880 | 10899 | 4874 |
| 582763 | 2071 | 2087 | CTTAGTAGTCATCTCCA | 3-10-4 | 49 | 11043 | 11059 | 4875 |
| 582764 | 2072 | 2088 | ACTTAGTAGTCATCTCC | 3-10-4 | 53 | 11044 | 11060 | 4876 |
| 582765 | 2073 | 2089 | GACTTAGTAGTCATCTC | 3-10-4 | 36 | 11045 | 11061 | 4877 |

Example 7: Dose-Dependent Antisense Inhibition of Human ANGPTL3 in Hep3B Cells Deoxy, MOE, and cEt oligonucleotides from the studies described above exhibiting significant in vitro inhibition of ANGPTL3 mRNA were selected and tested at various doses in Hep3B cells. ISIS 233717 and ISIS 337847, both 5-10-5 MOE gapmers, were also included in the studies. The antisense oligonucleotides were tested in a series of experiments that had similar culture conditions. The results of each experiment are presented in separate tables below.

Cells were plated at a density of 20,000 cells per well and transfected using electroporation with 0.813 µM, 1.625 µM, 3.25 µM, 6.500 µM and 13.00 µM concentrations of antisense oligonucleotide, as specified in the Table below. After a treatment period of approximately 16 hours, RNA was isolated from the cells and ANGPTL3 mRNA levels were measured by quantitative real-time PCR. Human primer probe set RTS3492_MGB was used to measure mRNA levels. ANGPTL3 mRNA levels were adjusted according to total RNA content, as measured by RIBOGREEN®. Results are presented as percent inhibition of ANGPTL3, relative to untreated control cells.

The half maximal inhibitory concentration (IC$_{50}$) of each oligonucleotide is also presented. ANGPTL3 mRNA levels were significantly reduced in a dose-dependent manner in antisense oligonucleotide treated cells.

TABLE 32

| ISIS No | 0.813 µM | 1.625 µM | 3.25 µM | 6.50 µM | 13.00 µM | IC$_{50}$ (µM) | SEQ ID NO |
|---|---|---|---|---|---|---|---|
| 233717 | 0 | 27 | 43 | 66 | 79 | 4.4 | 14 |
| 337487 | 26 | 49 | 63 | 85 | 94 | 2.0 | 28 |
| 559277 | 54 | 68 | 70 | 82 | 91 | <0.8 | 110 |
| 560990 | 36 | 61 | 74 | 90 | 96 | 1.2 | 111 |
| 560992 | 60 | 67 | 76 | 81 | 93 | <0.8 | 112 |
| 561010 | 71 | 77 | 82 | 86 | 94 | <0.8 | 113 |
| 561011 | 80 | 87 | 91 | 95 | 97 | <0.8 | 114 |
| 561022 | 75 | 79 | 84 | 89 | 93 | <0.8 | 115 |
| 561025 | 68 | 82 | 81 | 91 | 96 | <0.8 | 116 |
| 561026 | 72 | 85 | 85 | 89 | 90 | <0.8 | 117 |
| 561208 | 63 | 80 | 87 | 92 | 93 | <0.8 | 118 |
| 561320 | 47 | 60 | 86 | 92 | 96 | 0.8 | 119 |
| 561343 | 45 | 59 | 79 | 86 | 93 | 0.9 | 120 |

TABLE 32-continued

| ISIS No | 0.813 µM | 1.625 µM | 3.25 µM | 6.50 µM | 13.00 µM | IC$_{50}$ (µM) | SEQ ID NO |
|---|---|---|---|---|---|---|---|
| 561345 | 38 | 59 | 80 | 88 | 95 | 1.1 | 121 |
| 561347 | 53 | 63 | 84 | 88 | 97 | <0.8 | 122 |

TABLE 33

| ISIS No | 0.813 µM | 1.625 µM | 3.25 µM | 6.50 µM | 13.00 µM | IC$_{50}$ (µM) | SEQ ID NO |
|---|---|---|---|---|---|---|---|
| 233717 | 7 | 19 | 55 | 60 | 77 | 4.2 | 14 |
| 337487 | 33 | 44 | 69 | 83 | 88 | 2.0 | 28 |
| 560990 | 36 | 64 | 81 | 87 | 95 | 1.1 | 111 |
| 561452 | 58 | 69 | 75 | 85 | 88 | <0.8 | 123 |
| 561458 | 69 | 77 | 84 | 91 | 94 | <0.8 | 124 |
| 561460 | 54 | 50 | 72 | 79 | 85 | <0.8 | 125 |
| 561462 | 49 | 72 | 80 | 90 | 92 | <0.8 | 126 |
| 561463 | 63 | 79 | 84 | 92 | 93 | <0.8 | 127 |
| 561478 | 56 | 53 | 80 | 86 | 91 | <0.8 | 128 |
| 561482 | 46 | 69 | 80 | 86 | 91 | <0.8 | 129 |
| 561486 | 56 | 73 | 80 | 91 | 92 | <0.8 | 130 |
| 561487 | 82 | 87 | 88 | 90 | 93 | <0.8 | 131 |
| 561500 | 52 | 60 | 71 | 80 | 91 | <0.8 | 132 |
| 561504 | 49 | 72 | 85 | 91 | 93 | <0.8 | 133 |
| 561621 | 68 | 76 | 85 | 91 | 94 | <0.8 | 134 |

TABLE 34

| ISIS No | 0.813 µM | 1.625 µM | 3.25 µM | 6.50 µM | 13.00 µM | IC$_{50}$ (µM) | SEQ ID NO |
|---|---|---|---|---|---|---|---|
| 233717 | 28 | 35 | 48 | 56 | 60 | 4.7 | 14 |
| 337487 | 43 | 58 | 72 | 82 | 89 | 1.0 | 28 |
| 560990 | 57 | 73 | 82 | 86 | 96 | <0.8 | 111 |
| 561620 | 51 | 74 | 80 | 85 | 88 | <0.8 | 135 |
| 561622 | 63 | 73 | 85 | 88 | 87 | <0.8 | 136 |
| 561628 | 48 | 69 | 77 | 79 | 80 | <0.8 | 137 |
| 561631 | 60 | 75 | 84 | 86 | 90 | <0.8 | 138 |
| 561644 | 59 | 69 | 77 | 85 | 83 | <0.8 | 139 |
| 561646 | 67 | 81 | 84 | 91 | 92 | <0.8 | 140 |
| 561649 | 70 | 76 | 85 | 89 | 89 | <0.8 | 141 |
| 561650 | 78 | 85 | 88 | 90 | 91 | <0.8 | 142 |
| 561770 | 66 | 81 | 79 | 88 | 91 | <0.8 | 143 |
| 561781 | 65 | 67 | 80 | 81 | 91 | <0.8 | 144 |
| 561791 | 68 | 73 | 83 | 82 | 85 | <0.8 | 145 |
| 561918 | 63 | 71 | 81 | 86 | 92 | <0.8 | 146 |

TABLE 35

| ISIS No | 0.813 µM | 1.625 µM | 3.25 µM | 6.50 µM | 13.00 µM | IC$_{50}$ (µM) | SEQ ID NO |
|---|---|---|---|---|---|---|---|
| 233717 | 21 | 26 | 47 | 62 | 69 | 4.2 | 14 |
| 337487 | 35 | 54 | 73 | 82 | 92 | 1.0 | 28 |
| 560990 | 42 | 76 | 81 | 88 | 96 | <0.8 | 111 |
| 562078 | 55 | 85 | 86 | 91 | 93 | <0.8 | 147 |
| 562086 | 64 | 83 | 87 | 92 | 93 | <0.8 | 148 |
| 562103 | 72 | 83 | 90 | 90 | 94 | <0.8 | 149 |
| 562110 | 66 | 80 | 83 | 89 | 92 | <0.8 | 150 |
| 562375 | 56 | 61 | 63 | 84 | 90 | <0.8 | 151 |
| 562387 | 67 | 75 | 81 | 90 | 88 | <0.8 | 152 |
| 562396 | 60 | 71 | 80 | 80 | 85 | <0.8 | 153 |
| 562415 | 66 | 73 | 77 | 77 | 81 | <0.8 | 154 |
| 562433 | 68 | 84 | 86 | 90 | 91 | <0.8 | 155 |
| 562436 | 78 | 87 | 87 | 91 | 94 | <0.8 | 156 |
| 562439 | 55 | 66 | 78 | 82 | 93 | <0.8 | 157 |
| 562442 | 55 | 57 | 60 | 76 | 86 | <0.8 | 158 |

Example 8: Dose-Dependent Antisense Inhibition of Human ANGPTL3 in Hep3B Cells Deoxy, MOE, and cEt oligonucleotides from the studies described above exhibiting significant in vitro inhibition of ANGPTL3 mRNA were selected and tested at various doses in Hep3B cells. ISIS 337847, a 5-10-5 MOE gapmer, was also included in the studies. The antisense oligonucleotides were tested in a series of experiments that had similar culture conditions. The results of each experiment are presented in separate tables below.

Cells were plated at a density of 20,000 cells per well and transfected using electroporation with 0.160 µM, 0.481 µM, 1.444 µM, 4.333 µM and 13.00 µM concentrations of antisense oligonucleotide, as specified in the Table below. After a treatment period of approximately 16 hours, RNA was isolated from the cells and ANGPTL3 mRNA levels were measured by quantitative real-time PCR. Human primer probe set RTS3492_MGB was used to measure mRNA levels. ANGPTL3 mRNA levels were adjusted according to total RNA content, as measured by RIBOGREEN. Results are presented as percent inhibition of ANGPTL3, relative to untreated control cells.

The half maximal inhibitory concentration (IC$_{50}$) of each oligonucleotide is also presented. ANGPTL3 mRNA levels were significantly reduced in a dose-dependent manner in antisense oligonucleotide treated cells.

TABLE 36

| ISIS No | 0.160 µM | 0.481 µM | 1.444 µM | 4.333 µM | 13.00 µM | IC$_{50}$ (µM) | SEQ ID NO |
|---|---|---|---|---|---|---|---|
| 337487 | 0 | 18 | 24 | 49 | 73 | 4.1 | 28 |
| 560990 | 2 | 27 | 39 | 59 | 80 | 2.0 | 111 |
| 561076 | 20 | 33 | 59 | 73 | 89 | 1.1 | 159 |
| 561079 | 24 | 39 | 51 | 72 | 84 | 1.0 | 160 |
| 561084 | 7 | 17 | 46 | 66 | 87 | 1.9 | 161 |
| 561085 | 21 | 35 | 55 | 69 | 86 | 1.2 | 162 |
| 561123 | 20 | 39 | 52 | 72 | 87 | 1.1 | 163 |
| 561241 | 13 | 22 | 41 | 68 | 86 | 2.0 | 164 |
| 561256 | 12 | 22 | 35 | 54 | 82 | 2.6 | 165 |
| 561260 | 22 | 16 | 34 | 54 | 82 | 2.6 | 166 |
| 561277 | 21 | 21 | 37 | 59 | 69 | 2.9 | 167 |
| 561288 | 6 | 8 | 23 | 36 | 68 | 6.9 | 168 |
| 561418 | 25 | 36 | 61 | 79 | 86 | 0.9 | 169 |
| 561436 | 21 | 40 | 61 | 77 | 88 | 0.9 | 170 |
| 561443 | 18 | 32 | 52 | 82 | 88 | 1.1 | 171 |

TABLE 37

| ISIS No | 0.160 µM | 0.481 µM | 1.444 µM | 4.333 µM | 13.00 µM | IC$_{50}$ (µM) | SEQ ID NO |
|---|---|---|---|---|---|---|---|
| 337487 | 0 | 8 | 21 | 52 | 81 | 3.7 | 28 |
| 560990 | 6 | 14 | 40 | 61 | 74 | 3.0 | 111 |
| 561398 | 3 | 9 | 22 | 64 | 79 | 3.0 | 172 |
| 561400 | 11 | 28 | 50 | 65 | 83 | 1.7 | 173 |
| 561528 | 2 | 39 | 59 | 74 | 84 | 1.3 | 174 |
| 561565 | 18 | 43 | 58 | 75 | 83 | 1.0 | 175 |
| 561566 | 21 | 29 | 54 | 71 | 79 | 1.4 | 176 |
| 561567 | 16 | 35 | 56 | 67 | 78 | 1.4 | 177 |
| 561571 | 18 | 32 | 60 | 80 | 86 | 1.1 | 178 |
| 561576 | 11 | 12 | 42 | 65 | 77 | 2.4 | 179 |
| 561689 | 16 | 27 | 52 | 76 | 80 | 1.4 | 180 |
| 561698 | 1 | 24 | 31 | 61 | 74 | 2.9 | 181 |
| 561699 | 2 | 19 | 48 | 65 | 81 | 2.0 | 182 |
| 561722 | 14 | 34 | 59 | 72 | 85 | 1.2 | 183 |
| 561723 | 7 | 31 | 69 | 71 | 75 | 1.4 | 184 |

TABLE 38

| ISIS No | 0.160 µM | 0.481 µM | 1.444 µM | 4.333 µM | 13.00 µM | IC$_{50}$ (µM) | SEQ ID NO |
|---|---|---|---|---|---|---|---|
| 337487 | 14 | 9 | 9 | 47 | 72 | 5.9 | 28 |
| 560990 | 13 | 26 | 39 | 58 | 81 | 2.0 | 111 |
| 561888 | 16 | 19 | 46 | 72 | 84 | 1.7 | 185 |
| 561897 | 6 | 31 | 50 | 67 | 82 | 2.0 | 186 |
| 561996 | 19 | 31 | 49 | 59 | 83 | 1.6 | 187 |
| 562001 | 22 | 46 | 57 | 67 | 89 | 0.9 | 188 |
| 562024 | 17 | 29 | 59 | 71 | 83 | 1.3 | 189 |
| 562050 | 21 | 38 | 46 | 62 | 74 | 1.6 | 190 |
| 562153 | 22 | 35 | 42 | 61 | 71 | 2.0 | 191 |
| 562155 | 29 | 29 | 50 | 72 | 84 | 1.2 | 192 |
| 562156 | 15 | 17 | 39 | 60 | 82 | 2.3 | 193 |
| 562157 | 14 | 15 | 43 | 54 | 75 | 3.0 | 194 |
| 562181 | 24 | 34 | 58 | 73 | 80 | 1.1 | 195 |
| 562314 | 22 | 30 | 42 | 54 | 64 | 3.1 | 196 |
| 562365 | 25 | 27 | 46 | 64 | 77 | 1.7 | 197 |

Example 9: Dose-Dependent Antisense Inhibition of Human ANGPTL3 in Hep3B Cells by MOE Gapmers MOE gapmers from the Examples above exhibiting significant in vitro inhibition of ANGPTL3 mRNA were selected and tested at various doses in Hep3B cells. Cells were plated at a density of 20,000 cells per well and transfected using electroporation with 0.160 µM, 0.481 µM, 1.444 µM, 4.333 µM and 13.00 µM concentrations of antisense oligonucleotide, as specified in the Table below. After a treatment period of approximately 16 hours, RNA was isolated from the cells and ANGPTL3 mRNA levels were measured by quantitative real-time PCR. Human primer probe set RTS3492_MGB was used to measure mRNA levels. ANGPTL3 mRNA levels were adjusted according to total RNA content, as measured by RIBOGREEN®. Results are presented as percent inhibition of ANGPTL3, relative to untreated control cells.

The half maximal inhibitory concentration (IC$_{50}$) of each oligonucleotide is also presented. ANGPTL3 mRNA levels were significantly reduced in a dose-dependent manner in antisense oligonucleotide treated cells.

TABLE 39

| ISIS No | Motif | 0.16 (μM) | 0.48 (μM) | 1.44 (μM) | 4.33 (μM) | 13.00 (μM) | IC$_{50}$ (μM) | SEQ ID NO |
|---|---|---|---|---|---|---|---|---|
| 233717 | 5-10-5 | 0 | 3 | 12 | 38 | 64 | 8.0 | 14 |
| 337487 | 5-10-5 | 0 | 0 | 15 | 30 | 66 | 8.0 | 28 |
| 544120 | 5-10-5 | 10 | 37 | 62 | 81 | 94 | 1.0 | 15 |
| 567320 | 5-10-5 | 0 | 30 | 67 | 84 | 95 | 1.1 | 93 |
| 582703 | 5-10-5 | 0 | 18 | 47 | 71 | 83 | 2.0 | 198 |
| 582705 | 5-10-5 | 22 | 18 | 46 | 82 | 93 | 1.0 | 199 |
| 582706 | 5-10-5 | 2 | 0 | 32 | 67 | 85 | 2.6 | 200 |
| 582712 | 5-10-5 | 0 | 0 | 54 | 71 | 89 | 2.2 | 201 |
| 582713 | 5-10-5 | 25 | 25 | 52 | 75 | 85 | 1.2 | 202 |
| 582725 | 5-10-5 | 0 | 3 | 43 | 62 | 84 | 2.7 | 203 |
| 582733 | 5-10-5 | 0 | 30 | 66 | 77 | 87 | 1.3 | 204 |
| 582743 | 3-10-4 | 0 | 6 | 37 | 51 | 87 | 2.9 | 205 |
| 582759 | 3-10-4 | 0 | 2 | 51 | 76 | 93 | 2.0 | 206 |
| 582761 | 3-10-4 | 4 | 38 | 58 | 72 | 87 | 1.3 | 207 |
| 582774 | 3-10-4 | 5 | 29 | 46 | 72 | 86 | 1.6 | 208 |

Example 10: Dose-Dependent Antisense Inhibition of Human ANGPTL3 in Hep3B Cells by Deoxy, MOE and cEt Oligonucleotides Deoxy, MOE, and cEt oligonucleotides from the studies described above exhibiting significant in vitro inhibition of ANGPTL3 mRNA were selected and tested at various doses in Hep3B cells. Cells were plated at a density of 20,000 cells per well and transfected using electroporation with 0.111 μM, 0.333 μM, 1.00 μM, 3.00 μM and 9.00 μM concentrations of antisense oligonucleotide, as specified in the Table below. After a treatment period of approximately 16 hours, RNA was isolated from the cells and ANGPTL3 mRNA levels were measured by quantitative real-time PCR. Human primer probe set RTS3492_MGB was used to measure mRNA levels. ANGPTL3 mRNA levels were adjusted according to total RNA content, as measured by RIBOGREEN®. Results are presented as percent inhibition of ANGPTL3, relative to untreated control cells.

The half maximal inhibitory concentration (IC$_{50}$) of each oligonucleotide is also presented. ANGPTL3 mRNA levels were significantly reduced in a dose-dependent manner in antisense oligonucleotide treated cells.

TABLE 40

| ISIS No | 0.111 (μM) | 0.333 (μM) | 1.00 (μM) | 3.00 (μM) | 9.00 (μM) | IC$_{50}$ (μM) | SEQ ID NO |
|---|---|---|---|---|---|---|---|
| 561011 | 20 | 39 | 65 | 81 | 94 | 0.5 | 114 |
| 561026 | 23 | 43 | 65 | 84 | 94 | 0.5 | 117 |
| 561463 | 26 | 25 | 59 | 76 | 91 | 0.7 | 127 |
| 561487 | 42 | 61 | 81 | 89 | 95 | 0.1 | 131 |
| 586661 | 24 | 36 | 46 | 76 | 92 | 0.7 | 209 |
| 586669 | 31 | 50 | 68 | 85 | 95 | 0.3 | 210 |
| 586676 | 26 | 50 | 73 | 83 | 95 | 0.3 | 211 |
| 586688 | 4 | 24 | 51 | 82 | 91 | 0.9 | 212 |
| 586690 | 19 | 39 | 64 | 84 | 95 | 0.5 | 213 |
| 586691 | 6 | 37 | 60 | 81 | 93 | 0.7 | 214 |
| 586701 | 10 | 32 | 55 | 76 | 90 | 0.8 | 215 |
| 586702 | 16 | 25 | 55 | 69 | 86 | 0.9 | 216 |
| 586705 | 10 | 30 | 54 | 80 | 89 | 0.8 | 217 |
| 586707 | 33 | 42 | 71 | 83 | 89 | 0.3 | 218 |
| 586718 | 38 | 54 | 72 | 78 | 85 | 0.2 | 219 |

TABLE 41

| ISIS No | 0.111 (μM) | 0.333 (μM) | 1.00 (μM) | 3.00 (μM) | 9.00 (μM) | IC$_{50}$ (μM) | SEQ ID NO |
|---|---|---|---|---|---|---|---|
| 561011 | 13 | 29 | 41 | 76 | 89 | 1.0 | 114 |
| 561567 | 20 | 46 | 57 | 75 | 78 | 0.7 | 177 |
| 586692 | 32 | 30 | 71 | 85 | 95 | 0.4 | 220 |
| 586700 | 3 | 46 | 70 | 82 | 95 | 1.0 | 221 |
| 586708 | 36 | 46 | 62 | 77 | 86 | 0.4 | 222 |
| 586744 | 0 | 19 | 54 | 81 | 92 | 1.0 | 223 |
| 586745 | 35 | 22 | 66 | 78 | 92 | 0.5 | 224 |
| 586746 | 14 | 30 | 59 | 82 | 92 | 0.7 | 225 |
| 586755 | 18 | 22 | 53 | 74 | 90 | 0.9 | 226 |
| 586761 | 26 | 26 | 54 | 73 | 90 | 0.8 | 227 |
| 586787 | 0 | 38 | 64 | 79 | 90 | 0.8 | 228 |
| 586796 | 12 | 13 | 56 | 83 | 93 | 0.9 | 229 |
| 586797 | 4 | 26 | 58 | 82 | 90 | 0.9 | 230 |
| 586802 | 12 | 28 | 56 | 76 | 81 | 0.9 | 231 |
| 586804 | 17 | 40 | 65 | 86 | 93 | 0.5 | 232 |

TABLE 42

| ISIS No | 0.111 (μM) | 0.333 (μM) | 1.00 (μM) | 3.00 (μM) | 9.00 (μM) | IC$_{50}$ (μM) | SEQ ID NO |
|---|---|---|---|---|---|---|---|
| 561011 | 20 | 48 | 75 | 84 | 94 | 0.4 | 114 |
| 561026 | 31 | 48 | 70 | 88 | 95 | 0.3 | 117 |
| 561463 | 27 | 40 | 67 | 85 | 94 | 0.4 | 127 |
| 561487 | 41 | 66 | 84 | 91 | 95 | 0.1 | 131 |
| 586661 | 36 | 45 | 64 | 82 | 91 | 0.3 | 209 |
| 586669 | 21 | 55 | 73 | 90 | 96 | 0.3 | 210 |
| 586676 | 23 | 59 | 77 | 87 | 94 | 0.3 | 211 |
| 586688 | 25 | 41 | 70 | 82 | 93 | 0.4 | 212 |
| 586690 | 16 | 45 | 74 | 86 | 92 | 0.5 | 213 |
| 586691 | 13 | 40 | 65 | 86 | 92 | 0.6 | 214 |
| 586701 | 22 | 49 | 70 | 82 | 93 | 0.4 | 215 |
| 586702 | 11 | 31 | 58 | 76 | 92 | 0.8 | 216 |
| 586705 | 26 | 45 | 66 | 82 | 89 | 0.4 | 217 |
| 586707 | 28 | 58 | 75 | 85 | 88 | 0.3 | 218 |
| 586718 | 33 | 59 | 73 | 80 | 88 | 0.2 | 219 |

TABLE 43

| ISIS No | 0.111 (μM) | 0.333 (μM) | 1.00 (μM) | 3.00 (μM) | 9.00 (μM) | IC$_{50}$ (μM) | SEQ ID NO |
|---|---|---|---|---|---|---|---|
| 561011 | 23 | 41 | 63 | 82 | 92 | 0.5 | 114 |
| 561567 | 31 | 44 | 65 | 75 | 83 | 0.4 | 177 |
| 586692 | 16 | 58 | 74 | 89 | 93 | 0.4 | 220 |
| 586700 | 25 | 62 | 75 | 91 | 94 | 0.3 | 221 |
| 586708 | 36 | 53 | 72 | 81 | 90 | 0.3 | 222 |
| 586744 | 30 | 29 | 64 | 75 | 94 | 0.6 | 223 |
| 586745 | 21 | 44 | 59 | 81 | 89 | 0.5 | 224 |
| 586746 | 19 | 48 | 57 | 85 | 87 | 0.5 | 225 |
| 586755 | 6 | 30 | 59 | 78 | 89 | 0.8 | 226 |
| 586761 | 12 | 29 | 59 | 72 | 87 | 0.9 | 227 |
| 586787 | 27 | 35 | 64 | 84 | 97 | 0.5 | 228 |
| 586796 | 31 | 40 | 72 | 91 | 95 | 0.3 | 229 |
| 586797 | 36 | 47 | 67 | 82 | 88 | 0.3 | 230 |
| 586802 | 35 | 32 | 61 | 76 | 90 | 0.5 | 231 |
| 586804 | 35 | 50 | 75 | 91 | 91 | 0.2 | 232 |

Example 11: Antisense Inhibition of Human ANGPTL3 in huANGPTL3 Transgenic Mice Antisense oligonucleotides described in the studies above were further evaluated for their ability to reduce human ANGPTL3 mRNA transcript in C57Bl/6 mice with the human ANGPTL3 transgene (Tg mice).

Study 1

Female Tg mice were maintained on a 12-hour light/dark cycle. Animals were acclimated for at least 7 days in the research facility before initiation of the experiment. Antisense oligonucleotides (ASOs) were prepared in buffered saline (PBS) and sterilized by filtering through a 0.2 micron filter. Oligonucleotides were dissolved in 0.9% PBS for injection.

Groups of mice received intraperitoneal injections of 5-10-5 MOE gapmers at a dose of 50 mg/kg once per week for 2 weeks. One group of mice received subcutaneous injections of PBS once weekly for 2 weeks. The PBS-injected group served as the control group to which the corresponding oligonucleotide-treated groups were compared.

RNA Analysis

At the end of the treatment period, RNA was extracted from liver for real-time PCR analysis of measurement of mRNA expression of ANGPTL3 with RTS3492_MGB. mRNA levels were also measured with human primer probe set RTS1984 (forward sequence CTTCAATGAAACGTGGGAGAACT, designated herein as SEQ ID NO: 7; reverse sequence TCTCTAGGCCCAACCAAAATTC, designated herein as SEQ ID NO: 8; probe sequence AAATATGGTTTTGGGAGGCTTGAT, designated herein as SEQ ID NO: 9). Results are presented as percent change of mRNA, relative to PBS control, normalized with RIBOGREEN®. As shown in the Table below, treatment with ISIS antisense oligonucleotides resulted in significant reduction of ANGPTL3 mRNA in comparison to the PBS control.

TABLE 44

Percent inhibition of ANGPTL3 mRNA in transgenic mouse liver relative to the PBS control

| ISIS No | RTS3492_MGB | RTS1984 | SEQ ID NO |
|---|---|---|---|
| 233710 | 91 | 94 | 233 |
| 233717 | 49 | 58 | 14 |
| 337477 | 76 | 82 | 234 |
| 337478 | 52 | 65 | 235 |
| 337479 | 53 | 76 | 236 |
| 337487 | 80 | 92 | 28 |

Protein Analysis

Human ANGPTL3 protein levels were quantified using a commercially available ELISA kit (Catalog #DANL30 by R&D Systems, Minneapolis, Minn.) with transgenic plasma samples diluted 1:20,000 using the manufacturer described protocol. The results are presented in the Table below. The results indicate that treatment with ISIS oligonucleotides resulted in reduced ANGPTL3 protein levels.

TABLE 45

Percent inhibition of plasma protein levels in the transgenic mouse

| ISIS No | % | SEQ ID NO |
|---|---|---|
| 233710 | 92 | 233 |
| 233717 | 47 | 14 |
| 337477 | 68 | 234 |
| 337478 | 36 | 235 |
| 337479 | 48 | 236 |
| 337487 | 78 | 28 |

Plasma Chemistry Markers

To evaluate the effect of ISIS oligonucleotides on day 10, plasma levels of transaminases (ALT and AST) were measured using an automated clinical chemistry analyzer (Hitachi Olympus AU400e, Melville, N.Y.). The results are presented in the Table below. ISIS oligonucleotides that caused changes in the levels of any of these liver function markers outside the expected range for antisense oligonucleotides were excluded in further studies.

TABLE 46

Plasma transaminase levels (IU/L) in transgenic mice on day 10

|  | ALT | AST | SEQ ID NO |
|---|---|---|---|
| PBS | 27 | 36 |  |
| ISIS 233710 | 19 | 37 | 233 |
| ISIS 233717 | 16 | 32 | 14 |
| ISIS 337477 | 22 | 35 | 234 |
| ISIS 337478 | 23 | 49 | 235 |
| ISIS 337479 | 21 | 29 | 236 |
| ISIS 337487 | 19 | 35 | 28 |

Study 2

Male Tg mice were maintained on a 12-hour light/dark cycle. Animals were acclimated for at least 7 days in the research facility before initiation of the experiment. Antisense oligonucleotides (ASOs) were prepared in buffered saline (PBS) and sterilized by filtering through a 0.2 micron filter. Oligonucleotides were dissolved in 0.9% PBS for injection.

Groups of mice received intraperitoneal injections of 5-10-5 MOE gapmers at a dose of 50 mg/kg once per week for 2 weeks. One group of mice received subcutaneous injections of PBS once weekly for 2 weeks. The PBS-injected groups served as the control groups to which the corresponding oligonucleotide-treated groups were compared.

RNA Analysis

At the end of the treatment period, RNA was extracted from liver for real-time PCR analysis of measurement of mRNA expression of ANGPTL3 with RTS1984. Results are presented as percent change of mRNA, relative to PBS control, normalized with RIBOGREEN. As shown in the Table below, treatment with ISIS antisense oligonucleotides resulted in significant reduction of ANGPTL3 mRNA in comparison to the PBS control.

TABLE 47

Percent inhibition of ANGPTL3 mRNA in transgenic mouse liver relative to the PBS control

| ISIS No | % | SEQ ID NO |
|---|---|---|
| 233710 | 81 | 233 |
| 337487 | 92 | 28 |
| 544145 | 98 | 16 |
| 544162 | 75 | 18 |
| 544199 | 97 | 20 |
| 560306 | 90 | 34 |
| 560400 | 97 | 35 |
| 560401 | 95 | 36 |
| 560402 | 98 | 37 |
| 560469 | 98 | 38 |
| 560735 | 87 | 49 |
| 567320 | 95 | 93 |
| 567321 | 93 | 94 |

Protein Analysis

Human ANGPTL3 protein levels were quantified using a commercially available ELISA kit (Catalog #DANL30 by R&D Systems, Minneapolis, Minn.) with transgenic plasma samples diluted 1:20,000 using the manufacturer described protocol. The results are presented in the Table below. The results indicate that treatment with ISIS oligonucleotides resulted in reduced ANGPTL3 protein levels.

TABLE 48

Percent inhibition of plasma protein levels in the transgenic mouse

| ISIS No | % | SEQ ID NO |
|---|---|---|
| 233710 | 96 | 233 |
| 337487 | 78 | 28 |
| 544145 | 96 | 16 |
| 544162 | 97 | 18 |
| 544199 | 98 | 20 |
| 560306 | 97 | 34 |
| 560400 | 98 | 35 |
| 560401 | 97 | 36 |
| 560402 | 94 | 37 |
| 560469 | 96 | 38 |
| 560735 | 91 | 49 |
| 567320 | 98 | 93 |
| 567321 | 96 | 94 |

Plasma Chemistry Markers

To evaluate the effect of ISIS oligonucleotides on day 8, plasma levels of transaminases (ALT and AST) were measured using an automated clinical chemistry analyzer (Hitachi Olympus AU400e, Melville, N.Y.). The results are presented in the Table below. ISIS oligonucleotides that caused changes in the levels of any of these liver function markers outside the expected range for antisense oligonucleotides were excluded in further studies.

TABLE 49

Plasma transaminase levels (IU/L) in transgenic mice on day 8

| | ALT | AST | SEQ ID NO |
|---|---|---|---|
| PBS | 29 | 44 | |
| ISIS 233710 | 29 | 47 | 233 |
| ISIS 337487 | 22 | 36 | 28 |
| ISIS 544145 | 29 | 45 | 16 |
| ISIS 544162 | 31 | 62 | 18 |
| ISIS 544199 | 29 | 51 | 20 |
| ISIS 560306 | 23 | 42 | 34 |
| ISIS 560400 | 24 | 52 | 35 |
| ISIS 560401 | 20 | 38 | 36 |
| ISIS 560402 | 29 | 49 | 37 |
| ISIS 560469 | 22 | 50 | 38 |
| ISIS 560735 | 20 | 38 | 49 |
| ISIS 567320 | 49 | 71 | 93 |
| ISIS 567321 | 20 | 44 | 94 |

Study 3

Male and female Tg mice were maintained on a 12-hour light/dark cycle. Animals were acclimated for at least 7 days in the research facility before initiation of the experiment. Antisense oligonucleotides (ASOs) were prepared in buffered saline (PBS) and sterilized by filtering through a 0.2 micron filter. Oligonucleotides were dissolved in 0.9% PBS for injection.

Groups of mice received intraperitoneal injections of 5-10-5 MOE gapmers at a dose of 2.5 mg/kg, 12.5 mg/kg, or 25 mg/kg once per week for 3 weeks. One group of mice received subcutaneous injections of PBS once weekly for 2 weeks. The PBS-injected groups served as the control groups to which the corresponding oligonucleotide-treated groups were compared.

RNA Analysis

At the end of the treatment period, RNA was extracted from liver for real-time PCR analysis of measurement of mRNA expression of ANGPTL3 with hANGPTL3_LTS01022 (forward sequence AAATTT-TAGCCAATGGCCTCC, designated herein as SEQ ID NO: 10; reverse sequence TGTCATTAATTTGGCCCTTCG, designated herein as SEQ ID NO: 11; probe sequence TCAGTTGGGACATGGTCTTAAAGACTTTGTCC, designated herein as SEQ ID NO: 12). Results are presented as percent change of mRNA, relative to PBS control, normalized with RIBOGREEN®. As shown in the Table below, treatment with ISIS antisense oligonucleotides resulted in significant reduction of ANGPTL3 mRNA in comparison to the PBS control. The $ED_{50}$ of each gapmer is also presented in the Table below. 'n.d.' indicates that the $ED_{50}$ could not be determined.

TABLE 50

Percent inhibition of ANGPTL3 mRNA in transgenic mouse liver relative to the PBS control

| ISIS No | Dose (mg/kg) | % | $ED_{50}$ | SEQ ID NO |
|---|---|---|---|---|
| 233710 | 25 | 88 | 8 | 233 |
| | 12.5 | 79 | | |
| | 2.5 | 0 | | |
| 544145 | 25 | 90 | 4 | 16 |
| | 12.5 | 74 | | |
| | 2.5 | 39 | | |
| 544162 | 25 | 53 | 9 | 18 |
| | 12.5 | 63 | | |
| | 2.5 | 39 | | |
| 544199 | 25 | 81 | 7 | 20 |
| | 12.5 | 82 | | |
| | 2.5 | 7 | | |
| 560306 | 25 | 0 | n.d. | 34 |
| | 12.5 | 0 | | |
| | 2.5 | 0 | | |
| 560400 | 25 | 87 | 5 | 35 |
| | 12.5 | 76 | | |
| | 2.5 | 24 | | |
| 560401 | 25 | 89 | 8 | 36 |
| | 12.5 | 62 | | |
| | 2.5 | 5 | | |
| 560469 | 25 | 73 | 3 | 38 |
| | 12.5 | 78 | | |
| | 2.5 | 50 | | |
| 560735 | 25 | 26 | 31 | 49 |
| | 12.5 | 37 | | |
| | 2.5 | 51 | | |
| 567320 | 25 | 74 | 12 | 93 |
| | 12.5 | 37 | | |
| | 2.5 | 32 | | |
| 567321 | 25 | 75 | 11 | 94 |
| | 12.5 | 61 | | |
| | 2.5 | 0 | | |

Protein Analysis

Human ANGPTL3 protein levels were quantified using a commercially available ELISA kit (Catalog #DANL30 by R&D Systems, Minneapolis, Minn.) with transgenic plasma samples diluted 1:20,000 using the manufacturer described protocol. The results are presented in the Table below. The results indicate that treatment with ISIS oligonucleotides resulted in reduced ANGPTL3 protein levels. 'n.d.' indicates that the $ED_{50}$ could not be determined.

TABLE 51

Percent inhibition of plasma protein levels in the transgenic mouse

| ISIS No | Dose (mg/kg) | % | ED50 | SEQ ID NO |
|---|---|---|---|---|
| 233710 | 25 | 80 | 11 | 233 |
|  | 12.5 | 56 |  |  |
|  | 2.5 | 0 |  |  |
| 544145 | 25 | 88 | 9 | 16 |
|  | 12.5 | 64 |  |  |
|  | 2.5 | 0 |  |  |
| 544162 | 25 | 56 | 15 | 18 |
|  | 12.5 | 46 |  |  |
|  | 2.5 | 24 |  |  |
| 544199 | 25 | 73 | 6 | 20 |
|  | 12.5 | 73 |  |  |
|  | 2.5 | 31 |  |  |
| 560306 | 25 | 63 | n.d. | 34 |
|  | 12.5 | 55 |  |  |
|  | 2.5 | 53 |  |  |
| 560400 | 25 | 88 | 6 | 35 |
|  | 12.5 | 73 |  |  |
|  | 2.5 | 20 |  |  |
| 560401 | 25 | 88 | 10 | 36 |
|  | 12.5 | 61 |  |  |
|  | 2.5 | 0 |  |  |
| 560469 | 25 | 75 | 4 | 38 |
|  | 12.5 | 70 |  |  |
|  | 2.5 | 52 |  |  |
| 560735 | 25 | 27 | 34 | 49 |
|  | 12.5 | 37 |  |  |
|  | 2.5 | 34 |  |  |
| 567320 | 25 | 69 | 10 | 93 |
|  | 12.5 | 44 |  |  |
|  | 2.5 | 39 |  |  |
| 567321 | 25 | 68 | 12 | 94 |
|  | 12.5 | 62 |  |  |
|  | 2.5 | 1 |  |  |

Plasma Chemistry Markers

To evaluate the effect of ISIS oligonucleotides on day 17, plasma levels of transaminases (ALT and AST) were measured using an automated clinical chemistry analyzer (Hitachi Olympus AU400e, Melville, N.Y.). The results are presented in the Table below. ISIS oligonucleotides that caused changes in the levels of any of these liver function markers outside the expected range for antisense oligonucleotides were excluded in further studies.

TABLE 52

Plasma transaminase levels (IU/L) in transgenic mice on day 17

| | Dose (mg/kg) | ALT | AST | SEQ ID NO |
|---|---|---|---|---|
| PBS | — | 25 | 38 |  |
| ISIS 233710 | 25 | 27 | 40 | 233 |
|  | 12.5 | 24 | 45 |  |
|  | 2.5 | 23 | 36 |  |
| ISIS 544145 | 25 | 30 | 56 | 16 |
|  | 12.5 | 25 | 52 |  |
|  | 2.5 | 28 | 43 |  |
| ISIS 544162 | 25 | 28 | 52 | 18 |
|  | 12.5 | 36 | 53 |  |
|  | 2.5 | 28 | 50 |  |
| ISIS 544199 | 25 | 24 | 47 | 20 |
|  | 12.5 | 23 | 60 |  |
|  | 2.5 | 24 | 44 |  |
| ISIS 560306 | 25 | 21 | 45 | 34 |
|  | 12.5 | 24 | 49 |  |
|  | 2.5 | 24 | 47 |  |
| ISIS 560400 | 25 | 22 | 38 | 35 |
|  | 12.5 | 21 | 53 |  |
|  | 2.5 | 23 | 52 |  |
| ISIS 560401 | 25 | 36 | 80 | 36 |
|  | 12.5 | 27 | 75 |  |
|  | 2.5 | 22 | 49 |  |
| ISIS 560469 | 25 | 24 | 121 | 38 |
|  | 12.5 | 23 | 53 |  |
|  | 2.5 | 21 | 88 |  |
| ISIS 560735 | 25 | 20 | 48 | 49 |
|  | 12.5 | 22 | 138 |  |
|  | 2.5 | 24 | 78 |  |
| ISIS 567320 | 25 | 21 | 65 | 93 |
|  | 12.5 | 20 | 58 |  |
|  | 2.5 | 23 | 46 |  |
| ISIS 567321 | 25 | 23 | 62 | 94 |
|  | 12.5 | 21 | 49 |  |
|  | 2.5 | 24 | 67 |  |

Study 4

Male and female Tg mice were maintained on a 12-hour light/dark cycle. Animals were acclimated for at least 7 days in the research facility before initiation of the experiment. Antisense oligonucleotides (ASOs) were prepared in buffered saline (PBS) and sterilized by filtering through a 0.2 micron filter. Oligonucleotides were dissolved in 0.9% PBS for injection.

Groups of mice received intraperitoneal injections of 5-10-5 MOE gapmers at a dose of 25 mg/kg once per week for 2 weeks. One group of mice received subcutaneous injections of PBS once weekly for 2 weeks. The PBS-injected group served as the control group to which the corresponding oligonucleotide-treated groups were compared.

RNA Analysis

At the end of the treatment period, RNA was extracted from liver for real-time PCR analysis of measurement of mRNA expression of ANGPTL3 with hANGPTL3_LTS01022. Results are presented as percent change of mRNA, relative to PBS control, normalized with RIBOGREEN. As shown in the Table below, treatment with ISIS antisense oligonucleotides resulted in significant reduction of ANGPTL3 mRNA in comparison to the PBS control.

TABLE 53

Percent inhibition of ANGPTL3 mRNA in transgenic mouse liver relative to the PBS control

| ISIS No | % | SEQ ID NO |
|---|---|---|
| 233710 | 68 | 233 |
| 544120 | 63 | 15 |
| 544199 | 82 | 20 |
| 544355 | 0 | 21 |
| 560268 | 36 | 32 |
| 560470 | 47 | 39 |
| 560471 | 67 | 40 |
| 560474 | 57 | 41 |
| 560566 | 45 | 42 |
| 560567 | 68 | 43 |
| 560607 | 37 | 46 |
| 560608 | 15 | 47 |
| 560744 | 25 | 51 |
| 560778 | 32 | 52 |
| 560811 | 27 | 54 |
| 560925 | 0 | 56 |
| 563639 | 5 | 79 |
| 567291 | 8 | 91 |

TABLE 53-continued

Percent inhibition of ANGPTL3 mRNA in transgenic mouse liver relative to the PBS control

| ISIS No | % | SEQ ID NO |
|---|---|---|
| 567330 | 30 | 95 |
| 568049 | 48 | 101 |
| 568146 | 26 | 104 |

Plasma Chemistry Markers

To evaluate the effect of ISIS oligonucleotides on day 10, plasma levels of transaminases (ALT and AST) were measured using an automated clinical chemistry analyzer (Hitachi Olympus AU400e, Melville, N.Y.). The results are presented in the Table below. ISIS oligonucleotides that caused changes in the levels of any of these liver function markers outside the expected range for antisense oligonucleotides were excluded in further studies.

TABLE 54

Plasma transaminase levels (IU/L) in transgenic mice on day 10

|  | ALT | AST | SEQ ID NO |
|---|---|---|---|
| PBS | 29 | 41 |  |
| ISIS 233710 | 29 | 48 | 233 |
| ISIS 544120 | 24 | 35 | 15 |
| ISIS 544199 | 27 | 57 | 20 |
| ISIS 544355 | 23 | 44 | 21 |
| ISIS 560268 | 23 | 42 | 32 |
| ISIS 560470 | 26 | 42 | 39 |
| ISIS 560471 | 21 | 50 | 40 |
| ISIS 560474 | 20 | 33 | 41 |
| ISIS 560566 | 27 | 102 | 42 |
| ISIS 560567 | 20 | 37 | 43 |
| ISIS 560607 | 25 | 47 | 46 |
| ISIS 560608 | 20 | 49 | 47 |
| ISIS 560744 | 26 | 66 | 51 |
| ISIS 560778 | 24 | 87 | 52 |
| ISIS 560811 | 21 | 63 | 54 |
| ISIS 560925 | 25 | 115 | 56 |
| ISIS 563639 | 20 | 43 | 79 |
| ISIS 567291 | 20 | 67 | 91 |
| ISIS 567330 | 29 | 78 | 95 |
| ISIS 568049 | 25 | 63 | 101 |
| ISIS 568146 | 28 | 140 | 104 |

Study 5

Male and female Tg mice were maintained on a 12-hour light/dark cycle. Animals were acclimated for at least 7 days in the research facility before initiation of the experiment. Antisense oligonucleotides (ASOs) were prepared in buffered saline (PBS) and sterilized by filtering through a 0.2 micron filter. Oligonucleotides were dissolved in 0.9% PBS for injection.

Groups of mice received intraperitoneal injections of 5-10-5 MOE gapmers or deoxy, MOE, and cEt gapmers at a dose of 25 mg/kg once per week for 2 weeks. One group of mice received subcutaneous injections of PBS once weekly for 2 weeks. The PBS-injected group served as the control group to which the corresponding oligonucleotide-treated groups were compared.

RNA Analysis

At the end of the treatment period, RNA was extracted from liver for real-time PCR analysis of measurement of mRNA expression of ANGPTL3 with RTS1984. Results are presented as percent change of mRNA, relative to PBS control, normalized with RIBOGREEN. As shown in the Table below, treatment with ISIS antisense oligonucleotides resulted in significant reduction of ANGPTL3 mRNA in comparison to the PBS control.

TABLE 55

Percent inhibition of ANGPTL3 mRNA in transgenic mouse liver relative to the PBS control

| ISIS No | Chemistry | % | SEQ ID NO |
|---|---|---|---|
| 233710 | 5-10-5 MOE | 79 | 233 |
| 544156 | 5-10-5 MOE | 92 | 17 |
| 559277 | Deoxy, MOE and cEt | 75 | 110 |
| 560265 | 5-10-5 MOE | 52 | 31 |
| 560285 | 5-10-5 MOE | 42 | 33 |
| 560574 | 5-10-5 MOE | 93 | 44 |
| 560847 | 5-10-5 MOE | 61 | 69 |
| 560992 | Deoxy, MOE and cEt | 80 | 112 |
| 561010 | Deoxy, MOE and cEt | 66 | 113 |
| 561011 | Deoxy, MOE and cEt | 96 | 114 |
| 561022 | Deoxy, MOE and cEt | 79 | 115 |
| 561025 | Deoxy, MOE and cEt | 57 | 116 |
| 563580 | 5-10-5 MOE | 80 | 77 |
| 567115 | 5-10-5 MOE | 78 | 88 |
| 567233 | 5-10-5 MOE | 91 | 90 |

Plasma Chemistry Markers

To evaluate the effect of ISIS oligonucleotides on day 9, plasma levels of transaminases (ALT and AST) were measured using an automated clinical chemistry analyzer (Hitachi Olympus AU400e, Melville, N.Y.). The results are presented in the Table below. ISIS oligonucleotides that caused changes in the levels of any of these liver function markers outside the expected range for antisense oligonucleotides were excluded in further studies.

TABLE 56

Plasma transaminase levels (IU/L) in transgenic mice on day 9

|  | Chemistry | ALT | AST | SEQ ID NO |
|---|---|---|---|---|
| PBS | — | 48 | 65 |  |
| ISIS 233710 | 5-10-5 MOE | 24 | 43 | 233 |
| ISIS 544156 | 5-10-5 MOE | 29 | 44 | 17 |
| ISIS 559277 | Deoxy, MOE and cEt | 22 | 38 | 110 |
| ISIS 560265 | 5-10-5 MOE | 28 | 83 | 31 |
| ISIS 560285 | 5-10-5 MOE | 29 | 44 | 33 |
| ISIS 560574 | 5-10-5 MOE | 24 | 54 | 44 |
| ISIS 560847 | 5-10-5 MOE | 25 | 45 | 69 |
| ISIS 560992 | Deoxy, MOE and cEt | 32 | 128 | 112 |
| ISIS 561010 | Deoxy, MOE and cEt | 22 | 51 | 113 |
| ISIS 561011 | Deoxy, MOE and cEt | 28 | 43 | 114 |
| ISIS 561022 | Deoxy, MOE and cEt | 51 | 85 | 115 |
| ISIS 561025 | Deoxy, MOE and cEt | 22 | 48 | 116 |
| ISIS 563580 | 5-10-5 MOE | 28 | 109 | 77 |
| ISIS 567115 | 5-10-5 MOE | 21 | 42 | 88 |
| ISIS 567233 | 5-10-5 MOE | 22 | 73 | 90 |

Study 6

Male and female Tg mice were maintained on a 12-hour light/dark cycle. Animals were acclimated for at least 7 days in the research facility before initiation of the experiment. Antisense oligonucleotides (ASOs) were prepared in buffered saline (PBS) and sterilized by filtering through a 0.2 micron filter. Oligonucleotides were dissolved in 0.9% PBS for injection.

Groups of mice received intraperitoneal injections of deoxy, MOE, and cEt oligonucleotides at a dose of 25 mg/kg once per week for 2 weeks. ISIS 233710, a 5-10-5 MOE gapmer, was also included as a benchmark. One group of mice received subcutaneous injections of PBS once weekly for 2 weeks. The PBS-injected group served as the control group to which the corresponding oligonucleotide-treated groups were compared.

RNA Analysis

At the end of the treatment period, RNA was extracted from liver for real-time PCR analysis of measurement of mRNA expression of ANGPTL3 with hANGPTL3_LTS01022. Results are presented as percent change of mRNA, relative to PBS control, normalized with RIBOGREEN. As shown in the Table below, treatment with several of the ISIS antisense oligonucleotides resulted in significant reduction of ANGPTL3 mRNA in comparison to the PBS control.

TABLE 57

Percent inhibition of ANGPTL3 mRNA in transgenic mouse liver relative to the PBS control

| ISIS No | Chemistry | % | SEQ ID NO |
|---|---|---|---|
| 233710 | 5-10-5 MOE | 68 | 233 |
| 561026 | Deoxy, MOE and cEt | 94 | 117 |
| 561079 | Deoxy, MOE and cEt | 51 | 160 |
| 561084 | Deoxy, MOE and cEt | 56 | 161 |
| 561123 | Deoxy, MOE and cEt | 47 | 163 |
| 561208 | Deoxy, MOE and cEt | 42 | 118 |
| 561241 | Deoxy, MOE and cEt | 13 | 164 |
| 561400 | Deoxy, MOE and cEt | 31 | 173 |
| 561418 | Deoxy, MOE and cEt | 32 | 169 |
| 561436 | Deoxy, MOE and cEt | 67 | 170 |
| 561443 | Deoxy, MOE and cEt | 12 | 171 |
| 561458 | Deoxy, MOE and cEt | 57 | 124 |

Protein Analysis

Human ANGPTL3 protein levels were quantified using a commercially available ELISA kit (Catalog #DANL30 by R&D Systems, Minneapolis, Minn.) with transgenic plasma samples diluted 1:20,000 using the manufacturer described protocol. The results are presented in the Table below. The results indicate that treatment with several of the ISIS oligonucleotides resulted in reduced ANGPTL3 protein levels.

TABLE 58

Percent inhibition of plasma protein levels in the transgenic mouse

| ISIS No | Chemistry | % | SEQ ID NO |
|---|---|---|---|
| 233710 | 5-10-5 MOE | 82 | 233 |
| 561026 | Deoxy, MOE and cEt | 92 | 117 |
| 561079 | Deoxy, MOE and cEt | 80 | 160 |
| 561084 | Deoxy, MOE and cEt | 89 | 161 |
| 561123 | Deoxy, MOE and cEt | 62 | 163 |
| 561208 | Deoxy, MOE and cEt | 0 | 118 |
| 561241 | Deoxy, MOE and cEt | 36 | 164 |
| 561400 | Deoxy, MOE and cEt | 60 | 173 |
| 561418 | Deoxy, MOE and cEt | 42 | 169 |
| 561436 | Deoxy, MOE and cEt | 46 | 170 |
| 561443 | Deoxy, MOE and cEt | 27 | 171 |
| 561458 | Deoxy, MOE and cEt | 71 | 124 |

Plasma Chemistry Markers

To evaluate the effect of ISIS oligonucleotides on day 10, plasma levels of transaminases (ALT and AST) were measured using an automated clinical chemistry analyzer (Hitachi Olympus AU400e, Melville, N.Y.). The results are presented in the Table below. ISIS oligonucleotides that caused changes in the levels of any of these liver function markers outside the expected range for antisense oligonucleotides were excluded in further studies.

TABLE 59

Plasma transaminase levels (IU/L) in transgenic mice on day 10

| | Chemistry | ALT | AST | SAE ID NO |
|---|---|---|---|---|
| PBS | — | 41 | 64 | |
| ISIS 233710 | 5-10-5 MOE | 25 | 74 | 233 |
| ISIS 561026 | Deoxy, MOE and cEt | 30 | 67 | 117 |
| ISIS 561079 | Deoxy, MOE and cEt | 42 | 62 | 160 |
| ISIS 561084 | Deoxy, MOE and cEt | 70 | 101 | 161 |
| ISIS 561123 | Deoxy, MOE and cEt | 24 | 41 | 163 |
| ISIS 561208 | Deoxy, MOE and cEt | 203 | 168 | 118 |
| ISIS 561241 | Deoxy, MOE and cEt | 26 | 47 | 164 |
| ISIS 561400 | Deoxy, MOE and cEt | 27 | 83 | 173 |
| ISIS 561418 | Deoxy, MOE and cEt | 58 | 164 | 169 |
| ISIS 561436 | Deoxy, MOE and cEt | 24 | 42 | 170 |
| ISIS 561443 | Deoxy, MOE and cEt | 27 | 91 | 171 |
| ISIS 561458 | Deoxy, MOE and cEt | 30 | 144 | 124 |

Study 7

Male and female Tg mice were maintained on a 12-hour light/dark cycle. Animals were acclimated for at least 7 days in the research facility before initiation of the experiment. Antisense oligonucleotides (ASOs) were prepared in buffered saline (PBS) and sterilized by filtering through a 0.2 micron filter. Oligonucleotides were dissolved in 0.9% PBS for injection.

Groups of mice received intraperitoneal injections of deoxy, MOE, and cEt oligonucleotides at a dose of 25 mg/kg once per week for 2 weeks. ISIS 233710, a 5-10-5 MOE gapmer, was also included as a benchmark. One group of mice received subcutaneous injections of PBS once weekly for 2 weeks. The PBS-injected group served as the control group to which the corresponding oligonucleotide-treated groups were compared.

RNA Analysis

At the end of the treatment period, RNA was extracted from liver for real-time PCR analysis of measurement of mRNA expression of ANGPTL3 with hANGPTL3_LTS01022. Results are presented as percent change of mRNA, relative to PBS control, normalized with RIBOGREEN. As shown in the Table below, treatment with ISIS antisense oligonucleotides resulted in significant reduction of ANGPTL3 mRNA in comparison to the PBS control.

TABLE 60

Percent inhibition of ANGPTL3 mRNA in transgenic mouse liver relative to the PBS control

| ISIS No | Chemistry | % | SEQ ID NO |
|---|---|---|---|
| 233710 | 5-10-5 MOE | 80 | 233 |
| 561462 | Deoxy, MOE and cEt | 84 | 126 |
| 561463 | Deoxy, MOE and cEt | 84 | 127 |
| 561486 | Deoxy, MOE and cEt | 74 | 130 |
| 561487 | Deoxy, MOE and cEt | 82 | 131 |
| 561504 | Deoxy, MOE and cEt | 51 | 133 |
| 561528 | Deoxy, MOE and cEt | 87 | 174 |
| 561565 | Deoxy, MOE and cEt | 94 | 175 |
| 561566 | Deoxy, MOE and cEt | 76 | 176 |
| 561571 | Deoxy, MOE and cEt | 51 | 178 |
| 561621 | Deoxy, MOE and cEt | 93 | 134 |
| 561646 | Deoxy, MOE and cEt | 39 | 140 |
| 561649 | Deoxy, MOE and cEt | 93 | 141 |
| 561650 | Deoxy, MOE and cEt | 82 | 142 |
| 561689 | Deoxy, MOE and cEt | 51 | 180 |
| 561722 | Deoxy, MOE and cEt | 88 | 183 |

TABLE 60-continued

Percent inhibition of ANGPTL3 mRNA in transgenic mouse liver relative to the PBS control

| ISIS No | Chemistry | % | SEQ ID NO |
|---|---|---|---|
| 561723 | Deoxy, MOE and cEt | 85 | 184 |
| 561770 | Deoxy, MOE and cEt | 70 | 143 |
| 562024 | Deoxy, MOE and cEt | 82 | 189 |

Protein Analysis

Human ANGPTL3 protein levels were quantified using a commercially available ELISA kit (Catalog #DANL30 by R&D Systems, Minneapolis, Minn.) with transgenic plasma samples diluted 1:20,000 using the manufacturer described protocol. The results are presented in the Table below. The results indicate that treatment with some of the ISIS oligonucleotides resulted in reduced ANGPTL3 levels. In this case, '0' value implies that treatment with the ISIS oligonucleotide did not inhibit expression; in some instances, increased levels of expression may have been recorded.

TABLE 61

Percent inhibition of plasma protein levels in the transgenic mouse

| ISIS No | Chemistry | % | SEQ ID NO |
|---|---|---|---|
| 233710 | 5-10-5 MOE | 60 | 233 |
| 561462 | Deoxy, MOE and cEt | 62 | 126 |
| 561463 | Deoxy, MOE and cEt | 59 | 127 |
| 561486 | Deoxy, MOE and cEt | 0 | 130 |
| 561487 | Deoxy, MOE and cEt | 0 | 131 |
| 561504 | Deoxy, MOE and cEt | 0 | 133 |
| 561528 | Deoxy, MOE and cEt | 0 | 174 |
| 561565 | Deoxy, MOE and cEt | 71 | 175 |
| 561566 | Deoxy, MOE and cEt | 0 | 176 |
| 561571 | Deoxy, MOE and cEt | 0 | 178 |
| 561621 | Deoxy, MOE and cEt | 72 | 134 |
| 561646 | Deoxy, MOE and cEt | 0 | 140 |
| 561649 | Deoxy, MOE and cEt | 63 | 141 |
| 561650 | Deoxy, MOE and cEt | 0 | 142 |
| 561689 | Deoxy, MOE and cEt | 0 | 180 |
| 561722 | Deoxy, MOE and cEt | 0 | 183 |
| 561723 | Deoxy, MOE and cEt | 0 | 184 |
| 561770 | Deoxy, MOE and cEt | 0 | 143 |
| 562024 | Deoxy, MOE and cEt | 0 | 189 |

Plasma Chemistry Markers

To evaluate the effect of ISIS oligonucleotides on day 9, plasma levels of transaminases (ALT and AST) were measured using an automated clinical chemistry analyzer (Hitachi Olympus AU400e, Melville, N.Y.). The results are presented in the Table below. ISIS oligonucleotides that caused changes in the levels of any of these liver function markers outside the expected range for antisense oligonucleotides were excluded in further studies.

TABLE 62

Plasma transaminase levels (IU/L) in transgenic mice on day 9

|  | Chemistry | ALT | AST | SEQ ID NO |
|---|---|---|---|---|
| PBS | — | 35 | 72 |  |
| ISIS 233710 | 5-10-5 MOE | 23 | 39 | 233 |
| ISIS 561462 | Deoxy, MOE and cEt | 26 | 56 | 126 |
| ISIS 561463 | Deoxy, MOE and cEt | 34 | 61 | 127 |
| ISIS 561486 | Deoxy, MOE and cEt | 23 | 61 | 130 |
| ISIS 561487 | Deoxy, MOE and cEt | 21 | 64 | 131 |

TABLE 62-continued

Plasma transaminase levels (IU/L) in transgenic mice on day 9

|  | Chemistry | ALT | AST | SEQ ID NO |
|---|---|---|---|---|
| ISIS 561504 | Deoxy, MOE and cEt | 26 | 66 | 133 |
| ISIS 561528 | Deoxy, MOE and cEt | 26 | 86 | 174 |
| ISIS 561565 | Deoxy, MOE and cEt | 24 | 43 | 175 |
| ISIS 561566 | Deoxy, MOE and cEt | 23 | 62 | 176 |
| ISIS 561571 | Deoxy, MOE and cEt | 26 | 68 | 178 |
| ISIS 561621 | Deoxy, MOE and cEt | 26 | 96 | 134 |
| ISIS 561646 | Deoxy, MOE and cEt | 24 | 77 | 140 |
| ISIS 561649 | Deoxy, MOE and cEt | 22 | 94 | 141 |
| ISIS 561650 | Deoxy, MOE and cEt | 34 | 121 | 142 |
| ISIS 561689 | Deoxy, MOE and cEt | 24 | 73 | 180 |
| ISIS 561722 | Deoxy, MOE and cEt | 34 | 89 | 183 |
| ISIS 561723 | Deoxy, MOE and cEt | 24 | 65 | 184 |
| ISIS 561770 | Deoxy, MOE and cEt | 22 | 69 | 143 |
| ISIS 562024 | Deoxy, MOE and cEt | 32 | 162 | 189 |

Study 8

Male and female Tg mice were maintained on a 12-hour light/dark cycle. Animals were acclimated for at least 7 days in the research facility before initiation of the experiment. Antisense oligonucleotides (ASOs) were prepared in buffered saline (PBS) and sterilized by filtering through a 0.2 micron filter. Oligonucleotides were dissolved in 0.9% PBS for injection.

Groups of mice received intraperitoneal injections of deoxy, MOE, and cEt oligonucleotides at a dose of 25 mg/kg once per week for 2 weeks. ISIS 233710, a 5-10-5 MOE gapmer, was also included as a benchmark. One group of mice received subcutaneous injections of PBS once weekly for 2 weeks. The PBS-injected group served as the control group to which the corresponding oligonucleotide-treated groups were compared.

RNA Analysis

At the end of the treatment period, RNA was extracted from liver for real-time PCR analysis of measurement of mRNA expression of ANGPTL3 with hANGPTL3_LTS01022. Results are presented as percent change of mRNA, relative to PBS control, normalized with RIBOGREEN. As shown in the Table below, treatment with ISIS antisense oligonucleotides resulted in significant reduction of ANGPTL3 mRNA in comparison to the PBS control.

TABLE 63

Percent inhibition of ANGPTL3 mRNA in transgenic mouse liver relative to the PBS control

| ISIS No | Chemistry | % | SEQ ID NO |
|---|---|---|---|
| 233710 | 5-10-5 MOE | 99 | 233 |
| 562078 | Deoxy, MOE and cEt | 73 | 147 |
| 562086 | Deoxy, MOE and cEt | 85 | 148 |
| 562103 | Deoxy, MOE and cEt | 58 | 149 |
| 562110 | Deoxy, MOE and cEt | 94 | 150 |
| 562155 | Deoxy, MOE and cEt | 85 | 192 |
| 562181 | Deoxy, MOE and cEt | 79 | 195 |
| 562433 | Deoxy, MOE and cEt | 59 | 155 |
| 562436 | Deoxy, MOE and cEt | 99 | 156 |
| 586669 | Deoxy, MOE and cEt | 95 | 210 |
| 586676 | Deoxy, MOE and cEt | 80 | 211 |

Protein Analysis

Human ANGPTL3 protein levels were quantified using a commercially available ELISA kit (Catalog #DANL30 by R&D Systems, Minneapolis, Minn.) with transgenic plasma samples diluted 1:20,000 using the manufacturer described protocol. The results are presented in the Table below. The results indicate that treatment with the ISIS oligonucleotides resulted in reduced ANGPTL3 levels.

TABLE 64

Percent inhibition of plasma protein levels in the transgenic mouse

| ISIS No | Chemistry | % | SEQ ID NO |
|---|---|---|---|
| 233710 | 5-10-5 MOE | 69 | 233 |
| 562078 | Deoxy, MOE and cEt | 44 | 147 |
| 562086 | Deoxy, MOE and cEt | 91 | 148 |
| 562103 | Deoxy, MOE and cEt | 26 | 149 |
| 562110 | Deoxy, MOE and cEt | 68 | 150 |
| 562155 | Deoxy, MOE and cEt | 75 | 192 |
| 562181 | Deoxy, MOE and cEt | 86 | 195 |
| 562433 | Deoxy, MOE and cEt | 80 | 155 |
| 562436 | Deoxy, MOE and cEt | 98 | 156 |
| 586669 | Deoxy, MOE and cEt | 98 | 210 |
| 586676 | Deoxy, MOE and cEt | 95 | 211 |

Plasma Chemistry Markers

To evaluate the effect of ISIS oligonucleotides on day 8, plasma levels of transaminases (ALT and AST) were measured using an automated clinical chemistry analyzer (Hitachi Olympus AU400e, Melville, N.Y.). The results are presented in the Table below. ISIS oligonucleotides that caused changes in the levels of any of these liver function markers outside the expected range for antisense oligonucleotides were excluded in further studies.

TABLE 65

Plasma transaminase levels (IU/L) in transgenic mice on day 8

| | Chemistry | ALT | AST | SEQ ID NO |
|---|---|---|---|---|
| PBS | — | 44 | 248 | |
| ISIS 233710 | 5-10-5 MOE | 27 | 52 | 233 |
| ISIS 562078 | Deoxy, MOE and cEt | 41 | 130 | 147 |
| ISIS 562086 | Deoxy, MOE and cEt | 30 | 62 | 148 |
| ISIS 562103 | Deoxy, MOE and cEt | 35 | 99 | 149 |
| ISIS 562110 | Deoxy, MOE and cEt | 30 | 161 | 150 |
| ISIS 562155 | Deoxy, MOE and cEt | 68 | 622 | 192 |
| ISIS 562181 | Deoxy, MOE and cEt | 37 | 168 | 195 |
| ISIS 562433 | Deoxy, MOE and cEt | 33 | 209 | 155 |
| ISIS 562436 | Deoxy, MOE and cEt | 30 | 93 | 156 |
| ISIS 586669 | Deoxy, MOE and cEt | 27 | 141 | 210 |
| ISIS 586676 | Deoxy, MOE and cEt | 22 | 60 | 211 |

Study 9

Male and female Tg mice were maintained on a 12-hour light/dark cycle. Animals were acclimated for at least 7 days in the research facility before initiation of the experiment. Antisense oligonucleotides (ASOs) were prepared in buffered saline (PBS) and sterilized by filtering through a 0.2 micron filter. Oligonucleotides were dissolved in 0.9% PBS for injection.

Groups of mice received intraperitoneal injections of deoxy, MOE, and cEt oligonucleotides at a dose of 25 mg/kg once per week for 2 weeks. ISIS 233710, a 5-10-5 MOE gapmer, was also included as a benchmark. One group of mice received subcutaneous injections of PBS once weekly for 2 weeks. The PBS-injected group served as the control group to which the corresponding oligonucleotide-treated groups were compared.

RNA Analysis

At the end of the treatment period, RNA was extracted from liver for real-time PCR analysis of measurement of mRNA expression of ANGPTL3 with hANGPTL3_LTS01022. Results are presented as percent change of mRNA, relative to PBS control, normalized with RIBOGREEN. As shown in the Table below, treatment with some of the ISIS antisense oligonucleotides resulted in significant reduction of ANGPTL3 mRNA in comparison to the PBS control. In this case, '0' value implies that treatment with the ISIS oligonucleotide did not inhibit expression; in some instances, increased levels of expression may have been recorded.

TABLE 66

Percent inhibition of ANGPTL3 mRNA in transgenic mouse liver relative to the PBS control

| ISIS No | Chemistry | % | SEQ ID NO |
|---|---|---|---|
| 233710 | 5-10-5 MOE | 84 | 233 |
| 586690 | Deoxy, MOE and cEt | 45 | 213 |
| 586692 | Deoxy, MOE and cEt | 45 | 220 |
| 586700 | Deoxy, MOE and cEt | 46 | 221 |
| 586707 | Deoxy, MOE and cEt | 88 | 218 |
| 586708 | Deoxy, MOE and cEt | 73 | 222 |
| 586718 | Deoxy, MOE and cEt | 20 | 219 |
| 586744 | Deoxy, MOE and cEt | 0 | 223 |
| 586745 | Deoxy, MOE and cEt | 0 | 224 |
| 586755 | Deoxy, MOE and cEt | 75 | 226 |
| 586761 | Deoxy, MOE and cEt | 66 | 227 |
| 586787 | Deoxy, MOE and cEt | 47 | 228 |
| 586796 | Deoxy, MOE and cEt | 88 | 229 |
| 586797 | Deoxy, MOE and cEt | 81 | 230 |
| 586802 | Deoxy, MOE and cEt | 33 | 231 |
| 586804 | Deoxy, MOE and cEt | 60 | 232 |

Protein Analysis

Human ANGPTL3 protein levels were quantified using a commercially available ELISA kit (Catalog #DANL30 by R&D Systems, Minneapolis, Minn.) with transgenic plasma samples diluted 1:20,000 using the manufacturer described protocol. The results are presented in the Table below. The results indicate that treatment with some of the ISIS oligonucleotides resulted in reduced ANGPTL3 levels. In this case, '0' value implies that treatment with the ISIS oligonucleotide did not inhibit expression; in some instances, increased levels of expression may have been recorded.

TABLE 67

Percent inhibition of plasma protein levels in the transgenic mouse

| ISIS No | Chemistry | % | SEQ ID NO |
|---|---|---|---|
| 233710 | 5-10-5 MOE | 80 | 233 |
| 586690 | Deoxy, MOE and cEt | 21 | 213 |
| 586692 | Deoxy, MOE and cEt | 46 | 220 |
| 586700 | Deoxy, MOE and cEt | 0 | 221 |
| 586707 | Deoxy, MOE and cEt | 84 | 218 |
| 586708 | Deoxy, MOE and cEt | 32 | 222 |
| 586718 | Deoxy, MOE and cEt | 0 | 219 |
| 586744 | Deoxy, MOE and cEt | 0 | 223 |
| 586745 | Deoxy, MOE and cEt | 0 | 224 |
| 586755 | Deoxy, MOE and cEt | 0 | 226 |
| 586761 | Deoxy, MOE and cEt | 0 | 227 |
| 586787 | Deoxy, MOE and cEt | 0 | 228 |
| 586796 | Deoxy, MOE and cEt | 40 | 229 |
| 586797 | Deoxy, MOE and cEt | 50 | 230 |
| 586802 | Deoxy, MOE and cEt | 0 | 231 |
| 586804 | Deoxy, MOE and cEt | 0 | 232 |

Plasma Chemistry Markers

To evaluate the effect of ISIS oligonucleotides on day 9, plasma levels of transaminases (ALT and AST) were measured using an automated clinical chemistry analyzer (Hitachi Olympus AU400e, Melville, N.Y.). The results are presented in the Table below. ISIS oligonucleotides that caused changes in the levels of any of these liver function markers outside the expected range for antisense oligonucleotides were excluded in further studies.

TABLE 68

Plasma transaminase levels (IU/L) in transgenic mice on day 9

|  | Chemistry | ALT | AST | SEQ ID NO |
|---|---|---|---|---|
| PBS | — | 28 | 73 |  |
| ISIS 233710 | 5-10-5 MOE | 22 | 86 | 233 |
| ISIS 586690 | Deoxy, MOE and cEt | 42 | 120 | 213 |
| ISIS 586692 | Deoxy, MOE and cEt | 22 | 45 | 220 |
| ISIS 586700 | Deoxy, MOE and cEt | 24 | 84 | 221 |
| ISIS 586707 | Deoxy, MOE and cEt | 26 | 44 | 218 |
| ISIS 586708 | Deoxy, MOE and cEt | 22 | 48 | 222 |
| ISIS 586718 | Deoxy, MOE and cEt | 22 | 39 | 219 |
| ISIS 586744 | Deoxy, MOE and cEt | 26 | 83 | 223 |
| ISIS 586745 | Deoxy, MOE and cEt | 25 | 56 | 224 |
| ISIS 586746 | Deoxy, MOE and cEt | 77 | 77 | 225 |
| ISIS 586755 | Deoxy, MOE and cEt | 28 | 148 | 226 |
| ISIS 586761 | Deoxy, MOE and cEt | 36 | 126 | 227 |
| ISIS 586787 | Deoxy, MOE and cEt | 23 | 88 | 228 |
| ISIS 586796 | Deoxy, MOE and cEt | 32 | 148 | 229 |
| ISIS 586797 | Deoxy, MOE and cEt | 29 | 151 | 230 |
| ISIS 586802 | Deoxy, MOE and cEt | 35 | 200 | 231 |
| ISIS 586804 | Deoxy, MOE and cEt | 24 | 87 | 232 |

Study 10

Male and female Tg mice were maintained on a 12-hour light/dark cycle. Animals were acclimated for at least 7 days in the research facility before initiation of the experiment. Antisense oligonucleotides (ASOs) were prepared in buffered saline (PBS) and sterilized by filtering through a 0.2 micron filter. Oligonucleotides were dissolved in 0.9% PBS for injection.

Groups of mice received intraperitoneal injections of 5-10-5 MOE gapmers or deoxy, MOE and cEt oligonucleotides at a dose of 5 mg/kg, 12.5 mg/kg, or 25 mg/kg once per week for 2 weeks. One group of mice received subcutaneous injections of PBS once weekly for 2 weeks. The PBS-injected group served as the control group to which the corresponding oligonucleotide-treated groups were compared.

RNA Analysis

At the end of the treatment period, RNA was extracted from liver for real-time PCR analysis of measurement of mRNA expression of ANGPTL3 with hANGPTL3_LTS01022, and also with RTS3492_MGB. Results are presented as percent change of mRNA, relative to PBS control, normalized with RIBOGREEN®. As shown in the Table below, treatment with some of the ISIS antisense oligonucleotides resulted in reduction of ANGPTL3 mRNA in comparison to the PBS control.

TABLE 69

Percent inhibition of ANGPTL3 mRNA in transgenic mouse liver relative to the PBS control

| ISIS No | Chemistry | Dose (mg/kg) | RTS3492_MGB | hANGPTL3_LTS01022 | SEQ ID NO |
|---|---|---|---|---|---|
| 233710 | 5-10-5 MOE | 25 | 0 | 8 | 233 |
|  |  | 12.5 | 24 | 22 |  |
|  |  | 5 | 12 | 22 |  |
| 544199 | 5-10-5 MOE | 25 | 63 | 59 | 20 |
|  |  | 12.5 | 43 | 43 |  |
|  |  | 5 | 17 | 24 |  |
| 559277 | Deoxy, MOE and cEt | 25 | 37 | 46 | 110 |
|  |  | 12.5 | 0 | 0 |  |
|  |  | 5 | 0 | 0 |  |
| 560400 | 5-10-5 MOE | 25 | 45 | 48 | 35 |
|  |  | 12.5 | 36 | 50 |  |
|  |  | 5 | 0 | 0 |  |
| 561010 | Deoxy, MOE and cEt | 25 | 5 | 37 | 113 |
|  |  | 12.5 | 0 | 6 |  |
|  |  | 5 | 0 | 0 |  |
| 563580 | 5-10-5 MOE | 25 | 56 | 59 | 77 |
|  |  | 12.5 | 43 | 44 |  |
|  |  | 5 | 5 | 9 |  |
| 567320 | 5-10-5 MOE | 25 | 47 | 50 | 93 |
|  |  | 12.5 | 0 | 0 |  |
|  |  | 5 | 0 | 0 |  |
| 567321 | 5-10-5 MOE | 25 | 46 | 32 | 94 |
|  |  | 12.5 | 0 | 0 |  |
|  |  | 5 | 0 | 0 |  |

Plasma Chemistry Markers

To evaluate the effect of ISIS oligonucleotides on day 8, plasma levels of transaminases (ALT and AST) were measured using an automated clinical chemistry analyzer (Hitachi Olympus AU400e, Melville, N.Y.). The results are presented in the Table below. ISIS oligonucleotides that caused changes in the levels of any of these liver function markers outside the expected range for antisense oligonucleotides were excluded in further studies.

TABLE 70

Plasma transaminase levels (IU/L) in transgenic mice on day 8

|  | Chemistry | Dose (mg/kg) | ALT | AST | SEQ ID NO |
|---|---|---|---|---|---|
| PBS | — | — | 22 | 82 |  |
| ISIS 233710 | 5-10-5 MOE | 25 | 21 | 41 | 233 |
|  |  | 12.5 | 23 | 66 |  |
|  |  | 5 | 22 | 118 |  |
| ISIS 544199 | 5-10-5 MOE | 25 | 25 | 47 | 20 |
|  |  | 12.5 | 20 | 40 |  |
|  |  | 5 | 27 | 43 |  |
| ISIS 559277 | Deoxy, MOE and cEt | 25 | 21 | 34 | 110 |
|  |  | 12.5 | 21 | 37 |  |
|  |  | 5 | 22 | 39 |  |
| ISIS 560400 | 5-10-5 MOE | 25 | 21 | 37 | 35 |
|  |  | 12.5 | 20 | 44 |  |
|  |  | 5 | 24 | 35 |  |
| ISIS 561010 | Deoxy, MOE and cEt | 25 | 22 | 48 | 113 |
|  |  | 12.5 | 33 | 64 |  |
|  |  | 5 | 24 | 41 |  |
| ISIS 563580 | 5-10-5 MOE | 25 | 21 | 36 | 77 |
|  |  | 12.5 | 29 | 81 |  |
|  |  | 5 | 21 | 59 |  |
| ISIS 567320 | 5-10-5 MOE | 25 | 22 | 47 | 93 |
|  |  | 12.5 | 29 | 58 |  |
|  |  | 5 | 21 | 70 |  |
| ISIS 567321 | 5-10-5 MOE | 25 | 20 | 50 | 94 |
|  |  | 12.5 | 24 | 102 |  |
|  |  | 5 | 19 | 53 |  |

Example 12: Tolerability of Antisense Oligonucleotides Targeting Human ANGPTL3 in CD1 Mice CD1® mice (Charles River, Mass.) are a multipurpose mice model, frequently utilized for safety and efficacy testing. The mice were treated with ISIS antisense oligonucleotides selected from studies described above and evaluated for changes in the levels of various plasma chemistry markers.

Study 1

Male CD1 mice (one animal per treatment group) were injected intraperitoneally with a single dose of 200 mg/kg of deoxy, MOE, and cEt oligonucleotide. One male CD1 mouse was injected subcutaneously with a single dose of PBS. Mice were euthanized 48 hours after the last dose, and organs and plasma were harvested for further analysis.

Plasma Chemistry Markers

To evaluate the effect of ISIS oligonucleotides on day 4 plasma levels of transaminases (ALT and AST) were measured using an automated clinical chemistry analyzer (Hitachi Olympus AU400e, Melville, N.Y.). The results are presented in the Table below. ISIS oligonucleotides that caused changes in the levels of any of these liver function markers outside the expected range for antisense oligonucleotides were excluded in further studies.

TABLE 71

Plasma transaminase levels in CD1 mice plasma on day 4

|  | ALT (IU/L) | AST (IU/L) | SEQ ID NO |
|---|---|---|---|
| ISIS 559277 | 29 | 43 | 110 |
| ISIS 560990 | 19 | 43 | 111 |
| ISIS 560992 | 21 | 36 | 112 |
| ISIS 561010 | 31 | 40 | 113 |
| ISIS 561011 | 27 | 32 | 114 |
| ISIS 561022 | 35 | 48 | 115 |
| ISIS 561025 | 17 | 28 | 116 |
| ISIS 561026 | 31 | 43 | 117 |
| ISIS 561208 | 32 | 47 | 118 |
| ISIS 561320 | 25 | 37 | 119 |
| ISIS 561343 | 41 | 90 | 120 |
| ISIS 561345 | 30 | 45 | 121 |
| ISIS 561347 | 31 | 41 | 122 |
| ISIS 561458 | 18 | 38 | 124 |
| ISIS 561460 | 42 | 59 | 125 |
| ISIS 561463 | 21 | 33 | 127 |
| ISIS 561486 | 17 | 39 | 130 |
| ISIS 561487 | 18 | 39 | 131 |
| ISIS 561504 | 24 | 41 | 133 |
| ISIS 561621 | 31 | 56 | 134 |

Body Weights

Body weights were measured one day after the single dose of ISIS oligonucleotide, and are presented in the Table below. ISIS oligonucleotides that caused any changes in organ weights outside the expected range for antisense oligonucleotides were excluded from further studies.

TABLE 72

Body weights (g) of CD1 mice after antisense oligonucleotide treatment

|  | Body weight | SEQ ID NO |
|---|---|---|
| ISIS 559277 | 27 | 110 |
| ISIS 560990 | 28 | 111 |
| ISIS 560992 | 29 | 112 |
| ISIS 561010 | 30 | 113 |
| ISIS 561011 | 27 | 114 |
| ISIS 561022 | 24 | 115 |
| ISIS 561025 | 28 | 116 |
| ISIS 561026 | 27 | 117 |
| ISIS 561208 | 29 | 118 |
| ISIS 561320 | 27 | 119 |
| ISIS 561343 | 24 | 120 |
| ISIS 561345 | 25 | 121 |
| ISIS 561347 | 28 | 122 |
| ISIS 561458 | 25 | 124 |
| ISIS 561460 | 26 | 125 |
| ISIS 561463 | 26 | 127 |
| ISIS 561486 | 26 | 130 |
| ISIS 561487 | 27 | 131 |
| ISIS 561504 | 26 | 133 |
| ISIS 561621 | 27 | 134 |

Study 2

Male CD1 mice (one animal per treatment group) were injected intraperitoneally with a single dose of 200 mg/kg of deoxy, MOE and cEt oligonucleotides. One male CD1 mouse was injected subcutaneously with a single dose of PBS. Mice were euthanized 48 hours after the last dose, and organs and plasma were harvested for further analysis.

Plasma Chemistry Markers

To evaluate the effect of ISIS oligonucleotides on day 5 plasma levels of transaminases (ALT and AST) were measured using an automated clinical chemistry analyzer (Hitachi Olympus AU400e, Melville, N.Y.). The results are presented in the Table below. ISIS oligonucleotides that caused changes in the levels of any of these liver function markers outside the expected range for antisense oligonucleotides were excluded in further studies.

TABLE 73

Plasma transaminase levels in CD1 mice plasma on day 5

|  | ALT (IU/L) | AST (IU/L) | SEQ ID NO |
|---|---|---|---|
| ISIS 561622 | 29 | 64 | 136 |
| ISIS 561628 | 17 | 24 | 137 |
| ISIS 561646 | 16 | 34 | 140 |
| ISIS 561650 | 32 | 51 | 142 |
| ISIS 561079 | 19 | 32 | 160 |
| ISIS 561084 | 24 | 56 | 161 |
| ISIS 561241 | 60 | 70 | 164 |
| ISIS 561462 | 22 | 54 | 126 |
| ISIS 561649 | 56 | 53 | 141 |
| ISIS 561770 | 23 | 39 | 143 |
| ISIS 561781 | 20 | 41 | 144 |
| ISIS 561918 | 31 | 112 | 146 |
| ISIS 562078 | 15 | 33 | 147 |
| ISIS 562086 | 19 | 32 | 148 |
| ISIS 562110 | 20 | 41 | 150 |
| ISIS 562415 | 13 | 30 | 154 |
| ISIS 562433 | 19 | 35 | 155 |
| ISIS 562436 | 21 | 37 | 156 |
| ISIS 562442 | 19 | 34 | 158 |

Body Weights

Body weights were measured on day 5 after the single dose of ISIS oligonucleotide, and are presented in the Table below. ISIS oligonucleotides that caused any changes in organ weights outside the expected range for antisense oligonucleotides were excluded from further studies.

TABLE 74

Body weights (g) of CD1 mice after antisense oligonucleotide treatment

|  | Body weights | SEQ ID NO |
|---|---|---|
| ISIS 561622 | 27 | 136 |
| ISIS 561628 | 28 | 137 |
| ISIS 561646 | 29 | 140 |
| ISIS 561650 | 30 | 142 |
| ISIS 561079 | 27 | 160 |
| ISIS 561084 | 24 | 161 |
| ISIS 561241 | 28 | 164 |
| ISIS 561462 | 27 | 126 |
| ISIS 561649 | 29 | 141 |
| ISIS 561770 | 27 | 143 |
| ISIS 561781 | 24 | 144 |
| ISIS 561918 | 25 | 146 |
| ISIS 562078 | 28 | 147 |
| ISIS 562086 | 25 | 148 |
| ISIS 562110 | 26 | 150 |
| ISIS 562415 | 26 | 154 |
| ISIS 562433 | 26 | 155 |
| ISIS 562436 | 27 | 156 |
| ISIS 562442 | 26 | 158 |

Study 3

Male CD1 mice (four animals per treatment group) were injected intraperitoneally with 100 mg/kg of 5-10-5 MOE gapmers given once a week for 6 weeks. One group of 4 male CD1 mice was injected intraperitoneally with PBS given once a week for 6 weeks. Mice were euthanized 48 hours after the last dose, and organs and plasma were harvested for further analysis.

Plasma Chemistry Markers

To evaluate the effect of ISIS oligonucleotides, plasma levels of various liver and kidney function markers were measured on day 45 using an automated clinical chemistry analyzer (Hitachi Olympus AU400e, Melville, N.Y.). The results are presented in the Table below. ISIS oligonucleotides that caused changes in the levels of any of these markers outside the expected range for antisense oligonucleotides were excluded in further studies.

TABLE 75

Plasma chemistry marker levels in CD1 mice plasma on day 45

|  | ALT (IU/L) | AST (IU/L) | Albumin (g/dL) | BUN (mg/dL) | Creatinine (mg/dL) | Bilurubin (mg/dL) | SEQ ID NO |
|---|---|---|---|---|---|---|---|
| PBS | 30 | 55 | 2.7 | 26 | 0.15 | 0.17 |  |
| ISIS 544145 | 1146 | 1081 | 2.5 | 29 | 0.14 | 0.24 | 16 |
| ISIS 544199 | 244 | 213 | 2.6 | 25 | 0.13 | 0.15 | 20 |
| ISIS 560400 | 211 | 244 | 2.5 | 28 | 0.14 | 0.14 | 35 |
| ISIS 560401 | 212 | 269 | 2.4 | 31 | 0.14 | 0.12 | 36 |
| ISIS 560469 | 165 | 160 | 2.4 | 24 | 0.11 | 0.14 | 38 |
| ISIS 567320 | 141 | 146 | 2.7 | 25 | 0.14 | 0.15 | 93 |
| ISIS 567321 | 106 | 122 | 2.5 | 24 | 0.11 | 0.13 | 94 |

Body Weights

Body weights were measured on day 43, and are presented in the Table below. Kidney, liver and spleen weights were measured at the end of the study on day 45. ISIS oligonucleotides that caused any changes in organ weights outside the expected range for antisense oligonucleotides were excluded from further studies.

TABLE 76

Weights (g) of CD1 mice after antisense oligonucleotide treatment

|  | Body | Kidney | Liver | Spleen | SEQ ID NO |
|---|---|---|---|---|---|
| PBS | 39 | 0.6 | 2.1 | 0.1 |  |
| ISIS 544145 | 30 | 0.5 | 1.9 | 0.1 | 16 |
| ISIS 544199 | 42 | 0.6 | 2.9 | 0.3 | 20 |
| ISIS 560400 | 40 | 0.6 | 2.8 | 0.3 | 35 |
| ISIS 560401 | 38 | 0.6 | 2.7 | 0.2 | 36 |
| ISIS 560469 | 40 | 0.6 | 2.7 | 0.2 | 38 |
| ISIS 567320 | 39 | 0.6 | 2.3 | 0.3 | 93 |
| ISIS 567321 | 42 | 0.6 | 2.6 | 0.3 | 94 |

Study 4

Male CD1 mice (four animals per treatment group) were injected intraperitoneally with 50 mg/kg or 100 mg/kg of 5-10-5 MOE gapmers or deoxy, MOE and cEt oligonucleotides given once a week for 6 weeks. One group of 4 male CD1 mice was injected intraperitoneally with PBS given once a week for 6 weeks. Mice were euthanized 48 hours after the last dose, and organs and plasma were harvested for further analysis.

Plasma Chemistry Markers

To evaluate the effect of ISIS oligonucleotides, plasma levels of various liver and kidney function markers were measured on day 46 using an automated clinical chemistry analyzer (Hitachi Olympus AU400e, Melville, N.Y.). The results are presented in the Table below. ISIS oligonucleotides that caused changes in the levels of any of these markers outside the expected range for antisense oligonucleotides were excluded in further studies.

TABLE 77

Plasma chemistry marker levels in CD1 mice plasma on day 45

|  | Chemistry | Dose (mg/kg) | ALT (IU/L) | AST (IU/L) | Albumin (g/dL) | BUN (mg/dL) | Creatinine (mg/dL) | Bilirubin (mg/dL) | SEQ ID NO |
|---|---|---|---|---|---|---|---|---|---|
| PBS |  | — | 28 | 46 | 2.7 | 28 | 0.13 | 0.13 |  |
| ISIS 544156 | 5-10-5 MOE | 100 | 80 | 145 | 2.2 | 26 | 0.12 | 0.10 | 17 |
| ISIS 560574 | 5-10-5 MOE | 100 | 182 | 184 | 2.5 | 25 | 0.14 | 0.15 | 44 |
| ISIS 561010 | Deoxy, MOE and cEt | 50 | 32 | 53 | 2.4 | 31 | 0.15 | 0.12 | 113 |
| ISIS 561011 | Deoxy, MOE and cEt | 50 | 93 | 152 | 1.8 | 27 | 0.15 | 0.08 | 114 |
| ISIS 560580 | 5-10-5 MOE | 100 | 50 | 76 | 2.5 | 25 | 0.12 | 0.13 | 237 |
| ISIS 567115 | 5-10-5 MOE | 100 | 202 | 304 | 2.5 | 19 | 0.14 | 0.12 | 88 |
| ISIS 567233 | 5-10-5 MOE | 100 | 123 | 145 | 2.5 | 24 | 0.12 | 0.12 | 90 |

Body Weights

Body weights were measured on day 44, and are presented in the Table below. Kidney, liver and spleen weights were measured at the end of the study on day 46. ISIS oligonucleotides that caused any changes in organ weights outside the expected range for antisense oligonucleotides were excluded from further studies.

TABLE 78

Weights (g) of CD1 mice after antisense oligonucleotide treatment

|  | Chemistry | Dose (mg/kg) | Body | Kidney | Liver | Spleen | SEQ ID NO |
|---|---|---|---|---|---|---|---|
| PBS |  | — | 38 | 0.6 | 2.1 | 0.2 |  |
| ISIS 544156 | 5-10-5 MOE | 100 | 36 | 0.5 | 2.2 | 0.2 | 17 |
| ISIS 560574 | 5-10-5 MOE | 100 | 40 | 0.6 | 2.6 | 0.4 | 44 |
| ISIS 561010 | Deoxy, MOE and cEt | 50 | 39 | 0.5 | 2.2 | 0.2 | 113 |
| ISIS 561011 | Deoxy, MOE and cEt | 50 | 39 | 0.6 | 2.9 | 0.3 | 114 |
| ISIS 560580 | 5-10-5 MOE | 100 | 39 | 0.5 | 2.4 | 0.2 | 237 |
| ISIS 567115 | 5-10-5 MOE | 100 | 36 | 0.5 | 2.2 | 0.2 | 88 |
| ISIS 567233 | 5-10-5 MOE | 100 | 39 | 0.6 | 2.2 | 0.3 | 90 |

Study 5

Male CD1 mice (four animals per treatment group) were injected intraperitoneally with 50 mg/kg of deoxy, MOE and cEt oligonucleotides given once a week for 6 weeks. One group of 4 male CD1 mice was injected intraperitoneally with PBS given once a week for 6 weeks. Mice were euthanized 48 hours after the last dose, and organs and plasma were harvested for further analysis.

Plasma Chemistry Markers

To evaluate the effect of ISIS oligonucleotides, plasma levels of various liver and kidney function markers were measured on day 43 using an automated clinical chemistry analyzer (Hitachi Olympus AU400e, Melville, N.Y.). The results are presented in the Table below. ISIS oligonucleotides that caused changes in the levels of any of these markers outside the expected range for antisense oligonucleotides were excluded in further studies.

TABLE 79

Plasma chemistry marker levels in CD1 mice plasma on day 43

|  | ALT (IU/L) | AST (IU/L) | Albumin (g/dL) | BUN (mg/dL) | Creatinine (mg/dL) | Bilirubin (mg/dL) | SEQ ID NO |
|---|---|---|---|---|---|---|---|
| PBS | 35 | 166 | 2.6 | 29 | 0.12 | 0.32 |  |
| ISIS 559277 | 45 | 77 | 2.5 | 29 | 0.13 | 0.16 | 110 |
| ISIS 561022 | 826 | 802 | 2.9 | 29 | 0.13 | 0.99 | 115 |
| ISIS 561025 | 146 | 183 | 2.3 | 28 | 0.14 | 0.13 | 116 |
| ISIS 561026 | 93 | 154 | 2.6 | 26 | 0.11 | 0.16 | 117 |
| ISIS 561079 | 1943 | 1511 | 2.9 | 28 | 0.15 | 0.94 | 160 |
| ISIS 561084 | 153 | 227 | 2.6 | 27 | 0.12 | 0.16 | 161 |
| ISIS 561123 | 49 | 90 | 2.5 | 31 | 0.13 | 0.13 | 163 |
| ISIS 561436 | 29 | 57 | 2.6 | 25 | 0.12 | 0.12 | 170 |

Body Weights

Body weights were measured on day 41, and are presented in the Table below. Kidney, liver and spleen weights were measured at the end of the study on day 43. ISIS oligonucleotides that caused any changes in organ weights outside the expected range for antisense oligonucleotides were excluded from further studies.

TABLE 80

Weights (g) of CD1 mice after antisense oligonucleotide treatment

|  | Body | Kidney | Liver | Spleen | SEQ ID NO |
|---|---|---|---|---|---|
| PBS | 37 | 0.5 | 2.0 | 0.1 |  |
| ISIS 559277 | 38 | 0.6 | 2.5 | 0.3 | 110 |
| ISIS 561022 | 31 | 0.4 | 3.2 | 0.1 | 115 |
| ISIS 561025 | 37 | 0.5 | 2.6 | 0.2 | 116 |
| ISIS 561026 | 39 | 0.6 | 2.1 | 0.2 | 117 |
| ISIS 561079 | 42 | 0.6 | 4.0 | 0.2 | 160 |
| ISIS 561084 | 37 | 0.6 | 2.4 | 0.2 | 161 |
| ISIS 561123 | 36 | 0.6 | 2.2 | 0.2 | 163 |
| ISIS 561436 | 41 | 0.6 | 2.4 | 0.2 | 170 |

Example 13: Measurement of Viscosity of ISIS Antisense Oligonucleotides Targeting Human ANGPTL3

The viscosity of select antisense oligonucleotides from the studies described above was measured with the aim of screening out antisense oligonucleotides which have a viscosity of more than 40 centipoise (cP). Oligonucleotides having a viscosity greater than 40 cP would have less than optimal viscosity.

ISIS oligonucleotides (32-35 mg) were weighed into a glass vial, 120 μL of water was added and the antisense oligonucleotide was dissolved into solution by heating the vial at 50° C. Part (75 μL) of the pre-heated sample was pipetted to a micro-viscometer (Cambridge). The temperature of the micro-viscometer was set to 25° C. and the viscosity of the sample was measured. Another part (20 μL) of the pre-heated sample was pipetted into 10 mL of water for UV reading at 260 nM at 85° C. (Cary UV instrument). The results are presented in the Table below, where the concentration of each antisense oligonucleotide was 350 mg/ml, and indicate that most of the antisense oligonucleotides solutions are optimal in their viscosity under the criterion stated above.

TABLE 81

Viscosity of ISIS antisense oligonucleotides targeting human ANGPTL3

| ISIS No. | Viscosity (cP) | SEQ ID NO |
|---|---|---|
| 233710 | 14.65 | 233 |
| 337478 | 13.34 | 235 |
| 544145 | 11.97 | 16 |
| 544162 | 8.50 | 18 |
| 544199 | 11.70 | 20 |
| 560306 | 5.67 | 34 |
| 560400 | 9.26 | 35 |
| 560401 | 18.11 | 36 |
| 560402 | 90.67 | 37 |
| 560469 | 12.04 | 38 |
| 560735 | 7.49 | 49 |
| 567320 | 9.05 | 93 |
| 567321 | 9.62 | 94 |
| 567233 | 6.72 | 90 |
| 563580 | 16.83 | 77 |
| 561010 | 26.32 | 113 |
| 561011 | 43.15 | 114 |

Example 14: Tolerability of Antisense Oligonucleotides Targeting Human ANGPTL3 in Sprague-Dawley Rats Sprague-Dawley rats are a multipurpose model used for safety and efficacy evaluations. The rats were treated with ISIS antisense oligonucleotides from the studies described in the Examples above and evaluated for changes in the levels of various plasma chemistry markers.

Study 1

Male Sprague-Dawley rats were maintained on a 12-hour light/dark cycle and fed ad libitum with Purina normal rat chow, diet 5001. Groups of 4 Sprague-Dawley rats each were injected subcutaneously once a week for 6 weeks with PBS or with 100 mg/kg of 5-10-5 MOE gapmers. Forty eight hours after the last dose, rats were euthanized and organs and plasma were harvested for further analysis.

Liver Function

To evaluate the effect of ISIS oligonucleotides on hepatic function, plasma levels of transaminases were measured using an automated clinical chemistry analyzer (Hitachi Olympus AU400e, Melville, N.Y.). Plasma levels of ALT (alanine transaminase) and AST (aspartate transaminase) were measured on day 45 and the results are presented in the Table below expressed in IU/L. Plasma levels of bilirubin were also measured using the same clinical chemistry analyzer and the results are also presented in the Table below expressed in mg/dL. ISIS oligonucleotides that caused changes in the levels of any markers of liver function outside the expected range for antisense oligonucleotides were excluded in further studies.

TABLE 82

Liver function markers in Sprague-Dawley rats

|  | ALT (IU/L) | AST (IU/L) | Bilirubin (mg/dL) | SEQ ID NO |
|---|---|---|---|---|
| PBS | 25 | 65 | 0.11 |  |
| ISIS 544145 | 225 | 407 | 0.30 | 16 |
| ISIS 544199 | 56 | 102 | 0.11 | 20 |
| ISIS 560400 | 55 | 175 | 0.12 | 35 |
| ISIS 560401 | 89 | 206 | 0.13 | 36 |
| ISIS 560469 | 227 | 290 | 0.15 | 38 |
| ISIS 567320 | 55 | 172 | 0.11 | 93 |
| ISIS 567321 | 39 | 109 | 0.10 | 94 |

Kidney Function

To evaluate the effect of ISIS oligonucleotides on kidney function, plasma levels of blood urea nitrogen (BUN) and creatinine were measured using an automated clinical chemistry analyzer (Hitachi Olympus AU400e, Melville, N.Y.). Results are presented in the Table below, expressed in mg/dL. ISIS oligonucleotides that caused changes in the levels of any of the kidney function markers outside the expected range for antisense oligonucleotides were excluded in further studies. Total urine protein and urine creatinine levels were measured, and the ratio of total urine protein to creatinine was evaluated. The results are presented in the Table below.

TABLE 83

Kidney function plasma markers (mg/dL) in Sprague-Dawley rats

|  | BUN | Creatinine | SEQ ID NO |
|---|---|---|---|
| PBS | 16 | 0.27 |  |
| ISIS 544145 | 53 | 0.26 | 16 |
| ISIS 544199 | 24 | 0.34 | 20 |
| ISIS 560400 | 28 | 0.31 | 35 |
| ISIS 560401 | 29 | 0.28 | 36 |
| ISIS 560469 | 23 | 0.32 | 38 |
| ISIS 567320 | 26 | 0.35 | 93 |
| ISIS 567321 | 24 | 0.37 | 94 |

TABLE 84

Kidney function urine markers in Sprague-Dawley rats

|  | Creatinine (mg/dL) | Total protein (mg/dL) | Protein:Creatinine ratio | SEQ ID NO |
|---|---|---|---|---|
| PBS | 59 | 90 | 1.5 |  |
| ISIS 544145 | 27 | 2131 | 84.8 | 16 |
| ISIS 544199 | 24 | 199 | 8.6 | 20 |
| ISIS 560400 | 32 | 176 | 5.4 | 35 |
| ISIS 560401 | 29 | 521 | 17.3 | 36 |
| ISIS 560469 | 43 | 351 | 8.2 | 38 |
| ISIS 567320 | 34 | 177 | 5.2 | 93 |
| ISIS 567321 | 54 | 269 | 5.3 | 94 |

Organ Weights

Body weights were measured on day 42 and presented in the Table below. Liver, spleen and kidney weights were measured at the end of the study on day 45, and are presented in the Table below. ISIS oligonucleotides that caused any changes in organ weights outside the expected range for antisense oligonucleotides were excluded from further studies.

TABLE 85

Body and organ weights (g) of Sprague Dawley rats

|  | Body | Kidney | Liver | Spleen | SEQ ID NO |
|---|---|---|---|---|---|
| PBS | 441 | 3.3 | 11.8 | 0.8 |  |
| ISIS 544145 | 240 | 3.0 | 11.2 | 1.7 | 16 |
| ISIS 544199 | 307 | 2.6 | 10.3 | 2.0 | 20 |
| ISIS 560400 | 294 | 2.8 | 12.3 | 2.0 | 35 |
| ISIS 560401 | 281 | 3.4 | 11.6 | 2.3 | 36 |
| ISIS 560469 | 316 | 3.0 | 11.8 | 2.0 | 38 |
| ISIS 567320 | 312 | 3.1 | 12.4 | 2.5 | 93 |
| ISIS 567321 | 332 | 3.3 | 11.6 | 2.3 | 94 |

Study 2

Male Sprague-Dawley rats were maintained on a 12-hour light/dark cycle and fed ad libitum with Purina normal rat chow, diet 5001. Groups of 4 Sprague-Dawley rats each were injected subcutaneously once a week for 6 weeks with PBS or with 50 mg/kg or 100 mg/kg of 5-10-5 MOE gapmers or deoxy, MOE and cEt oligonucleotides. Forty eight hours after the last dose, rats were euthanized and organs and plasma were harvested for further analysis.

Liver Function

To evaluate the effect of ISIS oligonucleotides on hepatic function, plasma levels of transaminases were measured using an automated clinical chemistry analyzer (Hitachi Olympus AU400e, Melville, N.Y.). Plasma levels of ALT (alanine transaminase) and AST (aspartate transaminase) were measured on day 44 and the results are presented in the Table below expressed in IU/L. Plasma levels of bilirubin were also measured using the same clinical chemistry analyzer and the results are also presented in the Table below expressed in mg/dL. ISIS oligonucleotides that caused changes in the levels of any markers of liver function outside the expected range for antisense oligonucleotides were excluded in further studies.

TABLE 86

Liver function markers in Sprague-Dawley rats

|  | Chemistry | Dose (mg/kg) | ALT (IU/L) | AST (IU/L) | Bilirubin (mg/dL) | SEQ ID NO |
|---|---|---|---|---|---|---|
| PBS | — | — | 22 | 63 | 0.09 |  |
| ISIS 544156 | 5-10-5 MOE | 100 | 153 | 221 | 0.19 | 17 |
| ISIS 560574 | 5-10-5 MOE | 100 | 62 | 128 | 0.24 | 44 |
| ISIS 561010 | Deoxy, MOE and cEt | 50 | 32 | 99 | 0.12 | 113 |
| ISIS 561011 | Deoxy, MOE and cEt | 50 | 56 | 100 | 0.11 | 114 |
| ISIS 563580 | 5-10-5 MOE | 100 | 74 | 89 | 0.09 | 77 |
| ISIS 567233 | 5-10-5 MOE | 100 | 41 | 136 | 0.08 | 90 |

Kidney Function

To evaluate the effect of ISIS oligonucleotides on kidney function, plasma levels of blood urea nitrogen (BUN) and creatinine were measured on day 44 using an automated clinical chemistry analyzer (Hitachi Olympus AU400e, Melville, N.Y.). Results are presented in the Table below, expressed in mg/dL. ISIS oligonucleotides that caused changes in the levels of any of the kidney function markers outside the expected range for antisense oligonucleotides were excluded in further studies. Total urine protein and urine creatinine levels were measured, and the ratio of total urine protein to creatinine was evaluated. The results are presented in the Table below.

TABLE 87

Kidney function plasma markers (mg/dL) in Sprague-Dawley rats

|  | Chemistry | Dose (mg/kg) | BUN | Creatinine | SEQ ID NO |
|---|---|---|---|---|---|
| PBS | — | — | 18 | 0.31 |  |
| ISIS 544156 | 5-10-5 MOE | 100 | 27 | 0.27 | 17 |
| ISIS 560574 | 5-10-5 MOE | 100 | 32 | 0.24 | 44 |
| ISIS 561010 | Deoxy, MOE and cEt | 50 | 24 | 0.31 | 113 |
| ISIS 561011 | Deoxy, MOE and cEt | 50 | 33 | 0.32 | 114 |
| ISIS 563580 | 5-10-5 MOE | 100 | 25 | 0.20 | 77 |
| ISIS 567233 | 5-10-5 MOE | 100 | 37 | 0.23 | 90 |

TABLE 88

Kidney function urine markers in Sprague-Dawley rats

|  | Chemistry | Dose (mg/kg) | Creatinine (mg/dL) | Total protein (mg/dL) | Protein:Creatinine ratio | SEQ ID NO |
|---|---|---|---|---|---|---|
| PBS | — | — | 55 | 66 | 1.2 |  |
| ISIS 544156 | 5-10-5 MOE | 100 | 26 | 166 | 6.2 | 17 |
| ISIS 560574 | 5-10-5 MOE | 100 | 39 | 276 | 6.8 | 44 |
| ISIS 561010 | Deoxy, MOE and cEt | 50 | 54 | 299 | 5.6 | 113 |
| ISIS 561011 | Deoxy, MOE and cEt | 50 | 41 | 525 | 11.7 | 114 |
| ISIS 563580 | 5-10-5 MOE | 100 | 44 | 338 | 8.1 | 77 |
| ISIS 567233 | 5-10-5 MOE | 100 | 46 | 307 | 6.4 | 90 |

Organ Weights

Body weights were measured on day 42 and presented in the Table below. Liver, spleen and kidney weights were measured at the end of the study on day 44, and are presented in the Table below. ISIS oligonucleotides that caused any changes in organ weights outside the expected range for antisense oligonucleotides were excluded from further studies.

TABLE 89

Body and organ weights (g) of Sprague Dawley rats

|  | Chemistry | Dose (mg/kg) | Body | Kidney | Liver | Spleen | SEQ ID NO |
|---|---|---|---|---|---|---|---|
| PBS | — | — | 433 | 3.1 | 10.8 | 0.6 |  |
| ISIS 544156 | 5-10-5 MOE | 100 | 291 | 2.4 | 10.6 | 1.6 | 17 |
| ISIS 560574 | 5-10-5 MOE | 100 | 315 | 3.1 | 10.7 | 2.1 | 44 |
| ISIS 561010 | Deoxy, MOE and cEt | 50 | 386 | 3.0 | 11.9 | 2.1 | 113 |
| ISIS 561011 | Deoxy, MOE and cEt | 50 | 324 | 4.1 | 12.5 | 2.4 | 114 |
| ISIS 563580 | 5-10-5 MOE | 100 | 358 | 3.0 | 12.8 | 1.5 | 77 |
| ISIS 567233 | 5-10-5 MOE | 100 | 286 | 2.9 | 13.0 | 2.9 | 90 |

Study 3

Male Sprague-Dawley rats were maintained on a 12-hour light/dark cycle and fed ad libitum with Purina normal rat chow, diet 5001. Groups of 4 Sprague-Dawley rats each were injected subcutaneously once a week for 6 weeks with PBS or with 50 mg/kg of deoxy, MOE and cEt oligonucleotides. Forty eight hours after the last dose, rats were euthanized and organs and plasma were harvested for further analysis.

Liver Function

To evaluate the effect of ISIS oligonucleotides on hepatic function, plasma levels of transaminases were measured using an automated clinical chemistry analyzer (Hitachi Olympus AU400e, Melville, N.Y.). Plasma levels of ALT (alanine transaminase) and AST (aspartate transaminase) were measured on day 44 and the results are presented in the Table below expressed in IU/L. Plasma levels of bilirubin were also measured using the same clinical chemistry analyzer and the results are also presented in the Table below expressed in mg/dL. ISIS oligonucleotides that caused changes in the levels of any markers of liver function outside the expected range for antisense oligonucleotides were excluded in further studies.

TABLE 90

Liver function markers in Sprague-Dawley rats

|  | ALT (IU/L) | AST (IU/L) | Bilirubin (mg/dL) | SEQ ID NO |
|---|---|---|---|---|
| PBS | 27 | 87 | 0.08 |  |
| ISIS 559277 | 36 | 108 | 0.10 | 110 |
| ISIS 561025 | 150 | 260 | 0.15 | 116 |
| ISIS 561026 | 53 | 105 | 0.08 | 117 |
| ISIS 561079 | 87 | 196 | 0.09 | 160 |
| ISIS 561084 | 62 | 177 | 0.11 | 161 |
| ISIS 561123 | 39 | 94 | 0.07 | 163 |
| ISIS 561436 | 64 | 225 | 0.13 | 170 |

Kidney Function

To evaluate the effect of ISIS oligonucleotides on kidney function, plasma levels of blood urea nitrogen (BUN) and creatinine were measured on day 44 using an automated clinical chemistry analyzer (Hitachi Olympus AU400e, Melville, N.Y.). Results are presented in the Table below, expressed in mg/dL. ISIS oligonucleotides that caused changes in the levels of any of the kidney function markers outside the expected range for antisense oligonucleotides were excluded in further studies. Total urine protein and urine creatinine levels were measured, and the ratio of total urine protein to creatinine was evaluated. The results are presented in the Table below.

TABLE 91

Kidney function plasma markers (mg/dL) in Sprague-Dawley rats

|  | BUN | Creatinine | SEQ ID NO |
|---|---|---|---|
| PBS | 12 | 0.26 |  |
| ISIS 559277 | 16 | 0.30 | 110 |
| ISIS 561025 | 24 | 0.34 | 116 |
| ISIS 561026 | 61 | 0.38 | 117 |
| ISIS 561079 | 87 | 0.67 | 160 |
| ISIS 561084 | 24 | 0.35 | 161 |
| ISIS 561123 | 16 | 0.31 | 163 |
| ISIS 561436 | 39 | 0.37 | 170 |

TABLE 92

Kidney function urine markers in Sprague-Dawley rats

|  | Creatinine (mg/dL) | Total protein (mg/dL) | Protein:Creatinine ratio | SEQ ID NO |
|---|---|---|---|---|
| PBS | 42 | 77 | 1.9 |  |
| ISIS 559277 | 35 | 253 | 7.2 | 110 |

TABLE 92-continued

Kidney function urine markers in Sprague-Dawley rats

|  | Creatinine (mg/dL) | Total protein (mg/dL) | Protein:Creatinine ratio | SEQ ID NO |
|---|---|---|---|---|
| ISIS 561025 | 47 | 583 | 14.3 | 116 |
| ISIS 561026 | 22 | 1993 | 111.4 | 117 |
| ISIS 561079 | 17 | 1313 | 75.5 | 160 |
| ISIS 561084 | 73 | 571 | 7.9 | 161 |
| ISIS 561123 | 33 | 925 | 29.5 | 163 |
| ISIS 561436 | 25 | 789 | 36.6 | 170 |

Organ Weights

Body weights were measured on day 42 and presented in the table below. Liver, spleen and kidney weights were measured at the end of the study on day 44, and are presented in the Table below. ISIS oligonucleotides that caused any changes in organ weights outside the expected range for antisense oligonucleotides were excluded from further studies.

TABLE 93

Body and organ weights (g) of Sprague Dawley rats

|  | Body | Kidney | Liver | Spleen | SEQ ID NO |
|---|---|---|---|---|---|
| PBS | 419 | 3.2 | 10.7 | 0.7 |  |
| ISIS 559277 | 365 | 3.5 | 11.2 | 1.6 | 110 |
| ISIS 561025 | 335 | 3.2 | 12.8 | 2.7 | 116 |
| ISIS 561026 | 334 | 4.9 | 13.9 | 2.3 | 117 |
| ISIS 561079 | 302 | 3.9 | 9.9 | 0.9 | 160 |
| ISIS 561084 | 317 | 3.5 | 12.2 | 1.9 | 161 |
| ISIS 561123 | 367 | 3.3 | 13.5 | 1.5 | 163 |
| ISIS 561436 | 272 | 3.1 | 9.8 | 2.9 | 170 |

Example 15: Effect of ISIS Antisense Oligonucleotides Targeting Human ANGPTL3 in Cynomolgus Monkeys Cynomolgus monkeys were treated with ISIS antisense oligonucleotides selected from studies described in the Examples above. Antisense oligonucleotide efficacy and tolerability, as well as their pharmacokinetic profile in the liver and kidney, were evaluated.

At the time this study was undertaken, the cynomolgus monkey genomic sequence was not available in the National Center for Biotechnology Information (NCBI) database; therefore, cross-reactivity with the cynomolgus monkey gene sequence could not be confirmed. Instead, the sequences of the ISIS antisense oligonucleotides used in the cynomolgus monkeys was compared to a rhesus monkey sequence for homology. It is expected that ISIS oligonucleotides with homology to the rhesus monkey sequence are fully cross-reactive with the cynomolgus monkey sequence as well. The human antisense oligonucleotides tested are cross-reactive with the rhesus genomic sequence (GEN-BANK Accession No. NW_001108682.1 truncated from nucleotides 3049001 to 3062000, designated herein as SEQ ID NO: 3). The greater the complementarity between the human oligonucleotide and the rhesus monkey sequence, the more likely the human oligonucleotide can cross-react with the rhesus monkey sequence. The start and stop sites of each oligonucleotide to SEQ ID NO: 3 is presented in the Table below. "Start site" indicates the 5'-most nucleotide to which the gapmer is targeted in the rhesus monkey gene sequence. 'Mismatches' indicates the number of nucleobases in the human oligonucleotide that are mismatched with the rhesus genomic sequence.

TABLE 94

Antisense oligonucleotides complementary to the rhesus ANGPTL3 genomic sequence (SEQ ID NO: 3)

| ISIS No | Target Start Site | Mismatches | Chemistry | SEQ ID NO |
|---|---|---|---|---|
| 563580 | 9315 | 2 | 5-10-5 MOE | 77 |
| 560400 | 10052 | 1 | 5-10-5 MOE | 35 |
| 567320 | 10232 | 1 | 5-10-5 MOE | 93 |
| 567321 | 10234 | 1 | 5-10-5 MOE | 94 |
| 544199 | 10653 | 0 | 5-10-5 MOE | 20 |
| 567233 | 6834 | 2 | 5-10-5 MOE | 90 |
| 561011 | 3220 | 1 | Deoxy, MOE and (S)-cEt | 114 |
| 559277 | 3265 | 0 | Deoxy, MOE and (S)-cEt | 110 |

Treatment

Prior to the study, the monkeys were kept in quarantine for at least a 30 day period, during which the animals were observed daily for general health. The monkeys were 2-4 years old and weighed between 2 and 4 kg. Nine groups of 5 randomly assigned male cynomolgus monkeys each were injected subcutaneously with ISIS oligonucleotide or PBS at four sites on the back in a clockwise rotation (i.e. left, top, right, and bottom), one site per dose. The monkeys were given loading doses of PBS or 40 mg/kg of ISIS oligonucleotide every two days for the first week (days 1, 3, 5, and 7) and were subsequently dosed once a week for 12 weeks (days 14, 21, 28, 35, 42, 49, 56, 63, 70, 77, and 84) with PBS or 40 mg/kg of ISIS oligonucleotide.

During the study period, the monkeys were observed twice daily for signs of illness or distress. Any animal experiencing more than momentary or slight pain or distress due to the treatment, injury or illness was treated by the veterinary staff with approved analgesics or agents to relieve the pain after consultation with the Study Director. Any animal in poor health or in a possible moribund condition was identified for further monitoring and possible euthanasia. For example, one animal in the ISIS 567321 treatment group was found moribund on day 45 and was terminated. Scheduled euthanasia of the animals was conducted on day 86 (approximately 48 hours after the final dose) by exsanguination after ketamine/xylazine-induced anesthesia and administration of sodium pentobarbital. The protocols described in the Example were approved by the Institutional Animal Care and Use Committee (IACUC).

Hepatic Target Reduction

RNA Analysis

On day 86, RNA was extracted from liver for real-time PCR analysis of measurement of mRNA expression of ANGPTL3. Results are presented as percent change of mRNA, relative to PBS control, normalized with RIBOGREEN®. As shown in the Table below, treatment with ISIS antisense oligonucleotides resulted in significant reduction of ANGPTL3 mRNA in comparison to the PBS control. Analysis of ANGPTL3 mRNA levels revealed that ISIS 544199 and ISIS 559277, which are both fully cross-reactive with the rhesus sequence, significantly reduced expression levels. Other ISIS oligonucleotides, which targeted the monkey sequence with mismatches, were also able to reduce ANGPTL3 mRNA levels.

TABLE 95

Percent inhibition of ANGPTL3 mRNA in the cynomolgus monkey liver relative to the PBS control

| ISIS No | % | SEQ ID NO |
|---|---|---|
| 563580 | 62 | 77 |
| 560400 | 59 | 35 |
| 567320 | 67 | 93 |
| 567321 | 34 | 94 |
| 544199 | 88 | 20 |
| 561011 | 47 | 114 |
| 559277 | 85 | 110 |

Protein Analysis

Approximately 1 mL of blood was collected from all available animals at day 85 and placed in tubes containing the potassium salt of EDTA. The blood samples were placed in ice and centrifuged (3000 rpm for 10 min at 4° C.) to obtain plasma.

Human ANGPTL3 protein levels were quantified using a commercially available ELISA kit (Catalog #DANL30 by R&D Systems, Minneapolis, Minn.) with transgenic plasma samples diluted 1:20,000 using the manufacturer described protocol. The results are presented in the Table below. Analysis of plasman ANGPTL3 revealed that ISIS 563580, 544199 and ISIS 559277 reduced protein levels in a sustained manner. Other ISIS oligonucleotides were also able to reduce ANGPTL3 levels.

TABLE 96

Plasma protein levels (ng/mL) in the cynomolgus monkey

| | Day 1 | Day 3 | Day 16 | Day 30 | Day 44 | Day 58 | Day 72 | Day 86 | SEQ ID NO |
|---|---|---|---|---|---|---|---|---|---|
| PBS | 142 | 113 | 122 | 75 | 147 | 170 | 130 | 158 | |
| ISIS 563580 | 113 | 99 | 102 | 46 | 109 | 93 | 82 | 81 | 77 |
| ISIS 560400 | 92 | 107 | 145 | 63 | 170 | 182 | 157 | 178 | 35 |
| ISIS 567320 | 87 | 72 | 94 | 56 | 176 | 181 | 134 | 166 | 93 |
| ISIS 567321 | 80 | 84 | 98 | 62 | 156 | 116 | 122 | 112 | 94 |
| ISIS 544199 | 114 | 84 | 50 | 34 | 66 | 56 | 81 | 71 | 20 |
| ISIS 567233 | 115 | 111 | 174 | 134 | 162 | 125 | 122 | 109 | 90 |
| ISIS 561011 | 89 | 92 | 111 | 106 | 104 | 100 | 140 | 129 | 114 |
| ISIS 559277 | 86 | 62 | 63 | 54 | 77 | 64 | 68 | 70 | 110 |

Tolerability Studies

Body Weight Measurements

To evaluate the effect of ISIS oligonucleotides on the overall health of the animals, body and weights were measured and are presented in the Table below. The results indicate that effect of treatment with antisense oligonucleotides on body weights was within the expected range for antisense oligonucleotides. Specifically, treatment with ISIS 563580 was well tolerated in terms of the body weights of the monkeys.

TABLE 97

Final body weights (g) in cynomolgus monkey

| | Day 1 | Day 14 | Day 28 | Day 35 | Day 56 | Day 70 | Day 84 | SEQ ID NO |
|---|---|---|---|---|---|---|---|---|
| PBS | 2713 | 2709 | 2721 | 2712 | 2761 | 2754 | 2779 | |
| ISIS 563580 | 2678 | 2669 | 2724 | 2699 | 2797 | 2798 | 2817 | 77 |
| ISIS 560400 | 2713 | 2738 | 2808 | 2767 | 2867 | 2920 | 2976 | 35 |
| ISIS 567320 | 2682 | 2707 | 2741 | 2731 | 2804 | 2830 | 2853 | 93 |
| ISIS 567321 | 2672 | 2745 | 2849 | 2845 | 2995 | 2965 | 3002 | 94 |
| ISIS 544199 | 2760 | 2813 | 2851 | 2897 | 2905 | 2888 | 2871 | 20 |

TABLE 97-continued

Final body weights (g) in cynomolgus monkey

|  | Day 1 | Day 14 | Day 28 | Day 35 | Day 56 | Day 70 | Day 84 | SEQ ID NO |
|---|---|---|---|---|---|---|---|---|
| ISIS 567233 | 2657 | 2668 | 2650 | 2677 | 2907 | 2963 | 2903 | 90 |
| ISIS 561011 | 2753 | 2797 | 2801 | 2811 | 2921 | 2967 | 2941 | 114 |
| ISIS 559277 | 2681 | 2688 | 2701 | 2755 | 2826 | 2831 | 2965 | 110 |

Liver Function

To evaluate the effect of ISIS oligonucleotides on hepatic function, blood samples were collected from all the study groups. The blood samples were collected from the cephalic, saphenous, or femoral veins, 48 hours post-dosing. The monkeys were fasted overnight prior to blood collection. Blood was collected in tubes without anticoagulant for serum separation. The tubes were kept at room temperature for a minimum of 90 minutes and then centrifuged (approximately 3,000 rpm for 10 min) to obtain serum. Levels of various liver function markers were measured using a Toshiba 200FR NEO chemistry analyzer (Toshiba Co., Japan). Plasma levels of ALT and AST were measured and the results are presented in the Table below, expressed in IU/L. Bilirubin, a liver function marker, was similarly measured and is presented in the Table below expressed in mg/dL. The results indicate that most of the antisense oligonucleotides had no effect on liver function outside the expected range for antisense oligonucleotides. Specifically, treatment with ISIS 563580 was well tolerated in terms of the liver function in monkeys.

TABLE 98

ALT levels (IU/L) in cynomolgus monkey plasma

|  | Day 1 | Day 30 | Day 58 | Day 86 | SEQ ID NO |
|---|---|---|---|---|---|
| PBS | 47 | 35 | 32 | 46 |  |
| ISIS 563580 | 56 | 55 | 55 | 83 | 77 |
| ISIS 560400 | 50 | 35 | 47 | 68 | 35 |
| ISIS 567320 | 72 | 44 | 51 | 106 | 93 |
| ISIS 567321 | 53 | 39 | 44 | 75 | 94 |
| ISIS 544199 | 58 | 49 | 51 | 51 | 20 |
| ISIS 567233 | 42 | 38 | 47 | 64 | 90 |
| ISIS 561011 | 48 | 35 | 34 | 43 | 114 |
| ISIS 559277 | 49 | 45 | 53 | 60 | 110 |

TABLE 99

AST levels (IU/L) in cynomolgus monkey plasma

|  | Day 1 | Day 30 | Day 58 | Day 86 | SEQ ID NO |
|---|---|---|---|---|---|
| PBS | 76 | 42 | 39 | 60 |  |
| ISIS 563580 | 75 | 56 | 42 | 81 | 77 |
| ISIS 560400 | 85 | 63 | 59 | 99 | 35 |
| ISIS 567320 | 104 | 64 | 55 | 153 | 93 |
| ISIS 567321 | 83 | 47 | 45 | 66 | 94 |
| ISIS 544199 | 68 | 68 | 70 | 91 | 20 |
| ISIS 567233 | 46 | 80 | 66 | 86 | 90 |
| ISIS 561011 | 48 | 39 | 41 | 51 | 114 |
| ISIS 559277 | 50 | 56 | 55 | 77 | 110 |

TABLE 100

Bilirubin levels (mg/dL) in cynomolgus monkey plasma

|  | Day 1 | Day 30 | Day 58 | Day 86 | SEQ ID NO |
|---|---|---|---|---|---|
| PBS | 0.31 | 0.24 | 0.20 | 0.19 |  |
| ISIS 563580 | 0.34 | 0.23 | 0.17 | 0.18 | 77 |
| ISIS 560400 | 0.29 | 0.19 | 0.14 | 0.13 | 35 |
| ISIS 567320 | 0.38 | 0.24 | 0.16 | 0.19 | 93 |
| ISIS 567321 | 0.35 | 0.20 | 0.16 | 0.17 | 94 |
| ISIS 544199 | 0.23 | 0.16 | 0.17 | 0.15 | 20 |
| ISIS 567233 | 0.26 | 0.17 | 0.15 | 0.12 | 90 |
| ISIS 561011 | 0.20 | 0.13 | 0.16 | 0.13 | 114 |
| ISIS 559277 | 0.22 | 0.15 | 0.16 | 0.15 | 110 |

Kidney Function

To evaluate the effect of ISIS oligonucleotides on kidney function, blood samples were collected from all the study groups. The blood samples were collected from the cephalic, saphenous, or femoral veins, 48 hours post-dosing. The monkeys were fasted overnight prior to blood collection. Blood was collected in tubes without anticoagulant for serum separation. The tubes were kept at room temperature for a minimum of 90 minutes and then centrifuged (approximately 3,000 rpm for 10 min) to obtain serum. Levels of BUN and creatinine were measured using a Toshiba 200FR NEO chemistry analyzer (Toshiba Co., Japan). Results are presented in the Table below, expressed in mg/dL.

The plasma chemistry data indicate that most of the ISIS oligonucleotides did not have any effect on the kidney function outside the expected range for antisense oligonucleotides. Specifically, treatment with ISIS 563580 was well tolerated in terms of the kidney function of the monkeys.

TABLE 101

Plasma BUN levels (mg/dL) in cynomolgus monkeys

|  | Day 1 | Day 30 | Day 58 | Day 86 | SEQ ID NO |
|---|---|---|---|---|---|
| PBS | 28 | 28 | 27 | 29 |  |
| ISIS 563580 | 27 | 27 | 25 | 27 | 77 |
| ISIS 560400 | 25 | 24 | 21 | 27 | 35 |
| ISIS 567320 | 27 | 28 | 26 | 32 | 93 |
| ISIS 567321 | 25 | 24 | 23 | 24 | 94 |
| ISIS 544199 | 23 | 25 | 24 | 23 | 20 |
| ISIS 567233 | 23 | 32 | 30 | 29 | 90 |
| ISIS 561011 | 25 | 24 | 23 | 24 | 114 |
| ISIS 559277 | 26 | 28 | 24 | 26 | 110 |

TABLE 102

Plasma creatinine levels (mg/dL) in cynomolgus monkeys

|  | Day 1 | Day 30 | Day 58 | Day 86 | SEQ ID NO |
|---|---|---|---|---|---|
| PBS | 0.96 | 0.95 | 0.89 | 0.88 |  |
| ISIS 563580 | 0.97 | 1.04 | 0.88 | 0.85 | 77 |
| ISIS 560400 | 0.99 | 1.00 | 0.93 | 0.91 | 35 |
| ISIS 567320 | 0.95 | 0.94 | 0.89 | 0.87 | 93 |
| ISIS 567321 | 0.97 | 0.94 | 0.89 | 0.87 | 94 |
| ISIS 544199 | 0.86 | 0.87 | 0.88 | 0.87 | 20 |
| ISIS 567233 | 0.89 | 1.08 | 1.06 | 1.00 | 90 |
| ISIS 561011 | 0.93 | 0.93 | 0.91 | 0.90 | 114 |
| ISIS 559277 | 0.86 | 0.91 | 0.87 | 0.91 | 110 |

Hematology

To evaluate any effect of ISIS oligonucleotides in cynomolgus monkeys on hematologic parameters, blood samples of approximately 0.5 mL of blood was collected from each of the available study animals in tubes containing $K_2$-EDTA. Samples were analyzed for red blood cell (RBC) count, white blood cells (WBC) count, individual white blood cell counts, such as that of monocytes, neutrophils, lymphocytes, as well as for platelet count, hemoglobin content and hematocrit, using an ADVIA120 hematology analyzer (Bayer, USA). The data is presented in the Tables below.

The data indicate the oligonucleotides did not cause any changes in hematologic parameters outside the expected range for antisense oligonucleotides at this dose. Specifically, treatment with ISIS 563580 was well tolerated in terms of the hematologic parameters of the monkeys.

TABLE 103

Blood cell counts in cynomolgus monkeys

|  | RBC ($\times 10^6$/μL) | Platelets ($\times 10^3$/μL) | WBC ($\times 10^3$/μL) | Neutrophils (% WBC) | Lymphocytes (% total) | Monocytes (% total) | SEQ ID NO |
|---|---|---|---|---|---|---|---|
| PBS | 5.6 | 462 | 12.2 | 58 | 39 | 2 |  |
| ISIS 563580 | 5.5 | 394 | 10.7 | 52 | 44 | 2 | 77 |
| ISIS 560400 | 5.7 | 269 | 10.2 | 44 | 50 | 3 | 35 |
| ISIS 567320 | 5.1 | 329 | 9.1 | 51 | 44 | 3 | 93 |
| ISIS 567321 | 5.3 | 363 | 8.9 | 60 | 36 | 2 | 94 |
| ISIS 544199 | 5.6 | 316 | 9.7 | 34 | 61 | 3 | 20 |
| ISIS 567233 | 5.0 | 298 | 12.1 | 40 | 53 | 4 | 90 |
| ISIS 561011 | 5.5 | 356 | 10.2 | 33 | 62 | 3 | 114 |
| ISIS 559277 | 5.1 | 343 | 8.3 | 45 | 49 | 3 | 110 |

TABLE 104

Hematologic parameters in cynomolgus monkeys

|  | Hemoglobin (g/dL) | HCT (%) | SEQ ID NO |
|---|---|---|---|
| PBS | 13 | 43 |  |
| ISIS 563580 | 12 | 40 | 77 |
| ISIS 560400 | 12 | 41 | 35 |
| ISIS 567320 | 11 | 38 | 93 |
| ISIS 567321 | 12 | 41 | 94 |
| ISIS 544199 | 13 | 44 | 20 |
| ISIS 567233 | 11 | 38 | 90 |
| ISIS 561011 | 13 | 42 | 114 |
| ISIS 559277 | 12 | 40 | 110 |

Effect on Pro-Inflammatory Molecules

To evaluate any inflammatory effect of ISIS oligonucleotides in cynomolgus monkeys, blood samples were taken for analysis of C-reactive protein and C3 levels on day 84 pre-dose. Approximately 1.5 mL of blood was collected from each animal and put into tubes without anticoagulant for serum separation. The tubes were kept at room temperature for a minimum of 90 min and then centrifuged at 3,000 rpm for 10 min at room temperature to obtain serum. C-reactive protein (CRP) and complement C3, which serve as markers of inflammation, were measured using a Toshiba 200FR NEO chemistry analyzer (Toshiba Co., Japan). The results indicate that treatment with ISIS 563580 was tolerable in monkeys.

TABLE 105

C-reactive protein levels (mg/L) in cynomolgus monkey plasma

|  | Day 1 | Day 30 | Day 58 | Day 86 | SEQ ID NO |
|---|---|---|---|---|---|
| PBS | 3.1 | 5.5 | 2.7 | 4.1 |  |
| ISIS 563580 | 2.4 | 2.4 | 4.5 | 3.9 | 77 |
| ISIS 560400 | 3.4 | 7.5 | 9.2 | 14.4 | 35 |
| ISIS 567320 | 2.5 | 1.7 | 2.5 | 4.3 | 93 |
| ISIS 567321 | 3.7 | 3.1 | 5.5 | 7.0 | 94 |
| ISIS 544199 | 1.2 | 1.5 | 8.8 | 8.1 | 20 |
| ISIS 567233 | 1.9 | 12.0 | 6.8 | 6.6 | 90 |
| ISIS 561011 | 1.7 | 1.2 | 2.1 | 3.7 | 114 |
| ISIS 559277 | 1.8 | 2.1 | 10.9 | 5.2 | 110 |

TABLE 106

C3 levels (mg/dL) in cynomolgus monkey plasma

|  | Pre-dose | Day 84 | SEQ ID NO |
|---|---|---|---|
| PBS | 122 | 117 |  |
| ISIS 563580 | 116 | 84 | 77 |
| ISIS 560400 | 120 | 105 | 35 |
| ISIS 567320 | 114 | 100 | 93 |
| ISIS 567321 | 106 | 93 | 94 |
| ISIS 544199 | 113 | 66 | 20 |
| ISIS 567233 | 113 | 63 | 90 |
| ISIS 561011 | 115 | 79 | 114 |
| ISIS 559277 | 119 | 87 | 110 |

Measurement of Oligonucleotide Concentration

The concentration of the full-length oligonucleotide was measured. The method used is a modification of previously published methods (Leeds et al., 1996; Geary et al., 1999) which consist of a phenol-chloroform (liquid-liquid) extraction followed by a solid phase extraction. An internal standard (ISIS 355868, a 27-mer 2'-O-methoxyethyl modified phosphorothioate oligonucleotide, GCGTTTGCTCTTCTTCTTGCGTTTTT, designated herein as SEQ ID NO: 13) was added prior to extraction. Tissue sample concentrations were calculated using calibration curves, with a lower limit of quantitation (LLOQ) of approximately 1.14 µg/g. The results are presented in the Table below, expressed as µg/g liver or kidney tissue. The ratio of full-length oligonucleotide concentrations in the kidney versus the liver was calculated. The ratio of full-length oligonucleotide concentrations in the kidney versus the liver after treatment with ISIS 563580 was found to be most optimal compared to other compounds assessed.

TABLE 107

Oligonucleotide full length concentration

| ISIS No | Kidney | Liver | Kidney/Liver ratio | SEQ ID NO |
|---|---|---|---|---|
| 563580 | 1822 | 1039 | 1.8 | 77 |
| 560400 | 3807 | 1375 | 2.8 | 35 |
| 567320 | 2547 | 569 | 4.5 | 93 |
| 567321 | 2113 | 463 | 4.6 | 94 |
| 544199 | 1547 | 561 | 2.8 | 20 |
| 561011 | 2027 | 477 | 4.3 | 114 |
| 559277 | 2201 | 508 | 4.3 | 110 |

Example 16: ISIS 563580 Clinical Trial

To assess the effect of Study Drug ISIS 563580 a Phase 1, blinded, randomized, placebo-controlled, dose-escalation study was performed on healthy volunteers with a normal lipid profile. The study evaluated the safety, tolerability, pharmacokinetics, effect on plasma levels of ANGPLT3 and the lipoprotein profile of the study subjects after single and multiple doses of the Study Drug ISIS 563580.

The study population was healthy males or females aged 18-65 inclusive. Exclusion criteria included clinically significant abnormalities in the medical history and in the screening laboratory values of any of the subjects. Subjects were randomized 3:1 to receive ISIS 563580 or placebo within each single-dose and multiple-dose cohort. Subjects were administered the study drug or placebo subcutaneously (SC).

Blood and urine samples were collected regularly throughout the study for safety, pharmacokinetic, and pharmacodynamics analyses. The safety and tolerability of ISIS 563580 was assessed by determining the incidence, severity, and dose-relationship of adverse events, vital signs, and clinical laboratory parameters. Safety results in subjects dosed with ISIS 563580 were compared with those in subjects dosed with placebo.

The most frequent adverse events were mild, local reactions at the injection site. Treatment with ISIS 563580 was generally well-tolerated and demonstrated an acceptable safety profile.

Study Drug and Treatment for Single Dose Study

A solution of the Study Drug ISIS 563580 (200 mg/mL, 1.0 mL) contained in 2-mL stoppered glass vials was provided. Vials were for single-use only. ISIS 563580 solution and placebo are prepared by a pharmacist (or qualified delegate). A trained professional administered a single dose of the Study Drug in the abdomen, thigh, or outer area of the upper arm on each dosing day. A total of 16 subjects were enrolled in this study. The study design is presented in the Table below:

TABLE 108

Study design for single dose study with ISIS 563580

| Cohort | Dose (mg) |
|---|---|
| A | 50 |
| B | 100 |
| C | 200 |
| D | 400 |

Subcutaneous injection volumes were 0.25, 0.5, 1.0, and 2.0 mL for cohorts A, B, C, and D, respectively, with the 2.0 mL volume given as 2 non-contiguous 1.0 mL injections. For cohort A, a period of at least 24 hours was required between administering the Study Drug to the first 2 subjects and the remaining 2 subjects in the cohort. Dose escalation proceeded when the subjects in the preceding single-dose cohort had completed dosing and Day 4 safety evaluations demonstrated an acceptable safety profile.

The length of each subject's participation was approximately 8 weeks, including a 4-week screening period, a single dose, and a 4-week post-treatment evaluation period. Subjects had follow-up visits at the Study Center on Days 2, 4, 8, 15, and a telephone contact on Day 30. The effect of the study drug is being assessed.

Study Drug and Treatment for Multiple Dose Study

A solution of the Study Drug ISIS 563580 (200 mg/mL, 1.0 mL) contained in stoppered glass vials was provided. Vials were for single-use only. ISIS 563580 solution and placebo are prepared by a pharmacist (or qualified delegate). A trained professional administered the Study Drug in the abdomen, thigh, or outer area of the upper arm on each dosing day. A total of 32 subjects were enrolled in this study. The study design is presented in the Table below

TABLE 109

Study design for multiple dose study with ISIS 563580

| Cohort | Dose amount | Amount of drug per dose | Total Dose (mg) |
|---|---|---|---|
| AA | 8 | 100 | 800 |
| BB | 8 | 200 | 1600 |
| CC | 8 | 300 | 2400 |
| DD | 8 | 400 | 3200 |

Subcutaneous injection volumes were 0.5, 1.0, 1.5, and 2.0 mL for cohorts AA, BB, CC, and DD, respectively, with the 2.0 mL volume given as 2 non-contiguous 1.0 mL injections. Dosing of the first cohort (Cohort AA) began after at least 4 subjects in the single-dose cohort (Cohort D) had completed dosing and Day 4 safety evaluations demonstrated an acceptable safety profile. Subjects received 3 subcutaneous doses of the Study Drug during week 1 on alternative days (Days 1, 3, and 5) followed by once-weekly SC administrations during the next 5 weeks (Days 8, 15, 22, 29, and 36) for a total of 8 doses.

The length of each subject's participation was approximately 5.5 months, including a 4-week screening period, a 6-week treatment period, and a 13-week post-treatment evaluation period. Subjects had follow-up visits at the Study Center on Days 37, 43, 50, 64, 78, 92, 106, and 127. The results of the lipid profiles of the subjects on Day 36 are presented in the Table below. The asterisks indicate statistically significant changes ($p<0.05$).

Treatment with ISIS 563580 generally produced dose-dependent reductions in plasma ANGPTL3, triglycerides, LDL-cholesterol, non-HDL cholesterol, VLDL-cholesterol, total cholesterol, ApoB and ApoC-III at day 36. In general, the magnitude of the reductions was associated with baseline lipid levels, with larger reductions observed in subjects with higher baselines.

TABLE 110

Mean % change compared the baseline at Day 36

| Parameter | Placebo (N = 8) | 100 mg ISIS 563580 (N = 6) | 200 mg ISIS 563580 (N = 6) | 300 mg ISIS 563580 (N = 6) | 400 mg ISIS 563580 (N = 6) |
|---|---|---|---|---|---|
| ANGPTL3 | −8.1 | −17.3 | −51.6** | −62.4** | −81.9** |
| LDL-cholesterol | −0.9 | −5.3 | −12.8 | −20.4* | −22.4** |
| Triglycerides | −15.3 | −23.8 | −21.0 | −49.1** | −44.3** |
| Non-HDL-cholesterol | −3.2 | −9.0 | −15.4* | −25.4** | −25.6** |
| VLDL-cholesterol | −15.2 | −25.1 | −21.5 | −50.0** | −43.5* |
| Total cholesterol | 0.4 | −2.1 | −12.4* | −22.4** | −28.1** |
| ApoB | −5.1 | −8.2 | −8.8 | −27.1* | −12.5 |
| ApoC-III | 20.6 | 8.2 | −20.3 | −51.3** | −65.0** |

*P < 0.05;
**p < 0.01

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11118183B2). An electronic copy of the "Sequence Listing" will also be available from the USPTO upon request and payment of the fee set forth in 37 CFR 1.19(b)(3).

What is claimed is:

1. A compound comprising a modified oligonucleotide consisting of 19 or 20 linked nucleosides, wherein at least 19 contiguous nucleobases are complementary to an equal length of nucleobases 1140 to 1159 of SEQ ID NO:1 and wherein the modified oligonucleotide comprises at least one modification selected from the group consisting of (i) a modified sugar, (ii) a modified internucleoside linkage, and (iii) a modified nucleobase,
or a salt thereof.

2. The compound or salt of claim 1, wherein the modified oligonucleotide consists of 19 contiguous nucleobases of SEQ ID NO:77.

3. The compound or salt of claim 1, wherein the modified oligonucleotide consists of the 20 contiguous nucleobases of SEQ ID NO:77.

4. The compound or salt of claim 1, wherein the modified oligonucleotide is single-stranded.

5. The compound or salt of claim 1, which comprises the modified internucleoside linkage.

6. The compound or salt of claim 5, wherein the modified internucleoside linkage is a phosphorothioate internucleoside linkage.

7. The compound or salt of claim 1, wherein the modified oligonucleotide comprises the modified sugar.

8. The compound or salt of claim 7, wherein the modified sugar is a bicyclic sugar.

9. The compound or salt of claim 7, wherein the modified sugar comprises a 2'-O-methoxyethyl, a constrained ethyl, a 3'-fluoro-HNA or a 4'-$(CH_2)_n$-O-2' bridge, wherein n is 1 or 2.

10. The compound or salt of claim 1, wherein the modified oligonucleotide comprises the modified nucleobase.

11. The compound or salt of claim 10, wherein the modified nucleobase is a 5-methylcytosine.

12. The compound or salt of claim 1, wherein the modified oligonucleotide comprises:
a gap segment consisting of linked deoxynucleosides;
a 5' wing segment consisting of linked nucleosides;
a 3' wing segment consisting of linked nucleosides;
wherein the gap segment is positioned between the 5' wing segment and the 3' wing segment and
wherein each nucleoside of each wing segment comprises a modified sugar.

13. The compound or salt of claim 12, wherein the modified oligonucleotide consists of 20 linked nucleosides and comprises:
a gap segment consisting of ten linked deoxynucleosides;
a 5' wing segment consisting of five linked nucleosides;
a 3' wing segment consisting of five linked nucleosides;
wherein the gap segment is positioned between the 5' wing segment and the 3' wing segment,
wherein each nucleoside of each wing segment comprises a 2'-O-methoxyethyl sugar, wherein each internucleoside linkage is a phosphorothioate linkage and wherein each cytosine residue is a 5-methylcytosine.

14. The compound or salt of claim 12, wherein the modified oligonucleotide consists of 20 linked nucleosides.

15. A composition comprising the compound or salt of claim 1, and a pharmaceutically acceptable carrier or diluent.

16. The composition of claim 15, wherein the composition comprises the salt of claim 1.

* * * * *